US010759759B2

(12) United States Patent
Kotian et al.

(10) Patent No.: US 10,759,759 B2
(45) Date of Patent: Sep. 1, 2020

(54) PRODRUGS OF KALLIKREIN INHIBITORS

(71) Applicant: BioCryst Pharmaceuticals, Inc., Durham, NC (US)

(72) Inventors: Pravin L. Kotian, Hoover, AL (US); Yarlagadda S. Babu, Birmingham, AL (US); V. Satish Kumar, Birmingham, AL (US); Venkat R. Chintareddy, Vestavia Hills, AL (US); Weihe Zhang, Vestavia, AL (US); Lakshminarayana Vogeti, Lawrence, KS (US)

(73) Assignee: BioCryst Pharmaceuticals, inc., Durham, NC (US)

( * ) Notice: Subject to any disclaimer, the term of this patent is extended or adjusted under 35 U.S.C. 154(b) by 0 days.

(21) Appl. No.: 16/345,503

(22) PCT Filed: Oct. 27, 2017

(86) PCT No.: PCT/US2017/058685
§ 371 (c)(1),
(2) Date: Apr. 26, 2019

(87) PCT Pub. No.: WO2018/081513
PCT Pub. Date: May 3, 2018

(65) Prior Publication Data
US 2019/0382344 A1  Dec. 19, 2019

Related U.S. Application Data

(60) Provisional application No. 62/415,202, filed on Oct. 31, 2016.

(51) Int. Cl.
C07D 213/81 (2006.01)
C07D 401/12 (2006.01)
C07D 405/12 (2006.01)
C07D 413/12 (2006.01)
C07D 495/04 (2006.01)

(52) U.S. Cl.
CPC ......... C07D 213/81 (2013.01); C07D 401/12 (2013.01); C07D 405/12 (2013.01); C07D 413/12 (2013.01); C07D 495/04 (2013.01)

(58) Field of Classification Search
None
See application file for complete search history.

(56) References Cited

U.S. PATENT DOCUMENTS

2019/0382344 A1  12/2019  Kotian et al.

FOREIGN PATENT DOCUMENTS

WO  WO-02/34711 A1  5/2002
WO  WO-2016/029214 A1  2/2016
WO  WO-2016/029216 A2  2/2016
WO  WO-2018/081513 A1  5/2018

OTHER PUBLICATIONS

Partial European Search Report for EP Application No. 17864949.7 dated Mar. 26, 2020.
International Search Report and Written Opinion for International Application No. PCT/US2017/058685 dated Feb. 15, 2018.

Primary Examiner — Zinna Northington Davis
(74) Attorney, Agent, or Firm — Dana M. Gordon; Foley Hoag LLP

(57) ABSTRACT

Disclosed are compounds of formula I, II, and III, and pharmaceutically acceptable salts thereof, which are inhibitors of kallikrein. Also provided are pharmaceutical compositions comprising such a compound, and methods involving use of the compounds and compositions in the treatment and prevention of acquired or hereditary angioedema, or other diseases and conditions characterized by aberrant kallikrein activity.

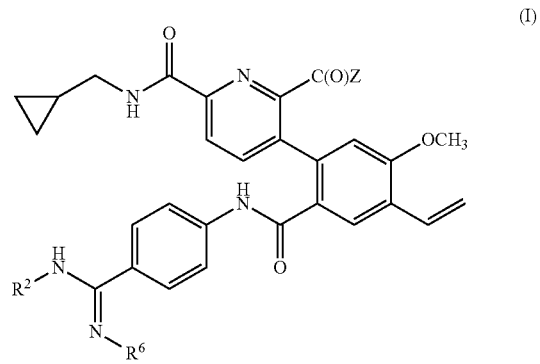

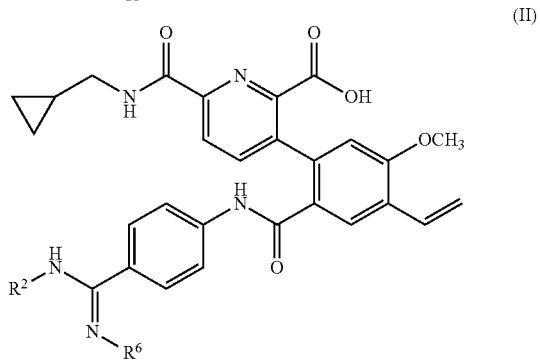

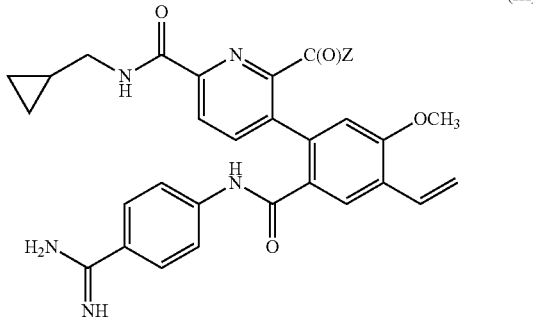

30 Claims, No Drawings

PRODRUGS OF KALLIKREIN INHIBITORS

CROSS-REFERENCES TO RELATED APPLICATIONS

This application is the U.S. national stage of International Patent Application No. PCT/US2017/058685, filed Oct. 27, 2017, which claims the benefit of priority to U.S. Provisional Patent Application Ser. No. 62/415,202, filed Oct. 31, 2016.

BACKGROUND OF THE INVENTION

Hereditary angioedema (HAE) is a serious and potentially life-threatening rare genetic illness, caused by mutations in the C1-esterase inhibitor (C1INH) gene, located on chromosome 11q. HAE is inherited as an autosomal dominant condition, although one quarter of diagnosed cases arise from a new mutation. HAE has been classed as an orphan disease in Europe, with an estimated prevalence of 1 in 50,000. Individuals with HAE experience recurrent acute attacks of painful subcutaneous or submucosal edema of the face, larynx, gastrointestinal tract, limbs or genitalia which, if untreated, may last up to 5 days. Attacks vary in frequency, severity and location and can be life-threatening. Laryngeal attacks, with the potential for asphyxiation, pose the greatest risk. Abdominal attacks are especially painful, and often result in exploratory procedures or unnecessary surgery. Facial and peripheral attacks are disfiguring and debilitating.

HAE has a number of subtypes. HAE type I is defined by C1INH gene mutations which produce low levels of C1-inhibitor, whereas HAE type II is defined by mutations which produce normal levels of ineffective C1 protein. HAE type III has separate pathogenesis, being caused by mutations in the F12 gene which codes for the serine protease known as Factor XII. Diagnostic criteria for distinguishing the subtypes of HAE, and distinguishing HAE from other angioedemas, can be found in *Ann Allergy Asthma Immunol* 2008; 100(Suppl2): S30-S40 and *J Allergy Clin Immunol* 2004; 114: 629-37, incorporated herein by reference.

Current treatments for HAE fall into two main types. Older non-specific treatments including androgens and antifibrinolytics are associated with significant side effects, particularly in females. Newer treatments are based on an understanding of the molecular pathology of the disease, namely that C1INH is the most important inhibitor of kallikrein in human plasma and that C1INH deficiency leads to unopposed activation of the kallikrein-bradykinin cascade, with bradykinin the most important mediator of the locally increased vascular permeability that is the hallmark of an attack.

Approved therapies include purified plasma-derived C1INH (Cinryze®, Berinert), the recombinant peptide kallikrein inhibitor ecallantide (Kalbitor®), and the bradykinin receptor B2 inhibitor icatibant (Firazyr®). All of the currently available targeted therapies are administered by intravenous or subcutaneous injection. There is currently no specific targeted oral chronic therapy for HAE.

There are many delivery routes for active pharmaceutical ingredients (APIs). Generally, the oral route of administration is favored due to advantages, such as, but not limited to, patient convenience, flexibility of timing of administration, location of administration and non-invasiveness. Oral administration also provides more prolonged drug exposure compared with intermittent intravenous infusion, which may be important for drugs with schedule-dependent efficacy. For example, a drug with a short half-life can achieve a greater exposure time by either continuous infusion or by continuous oral dosing. The use of oral therapy further has the potential to reduce the cost of healthcare resources for inpatient and ambulatory patient care services.

In the pharmaceutical arts, it is known that a number of APIs cannot be administered effectively by the oral route. The main reasons why these compounds cannot be administered by the oral route are: a) rapid enzymatic and metabolic degradation; b) chemical and/or biological instability; c) low solubility in aqueous medium; and/or d) limited permeability in the gastrointestinal tract. For such compounds, non-oral routes of delivery, such as parenteral administration, mainly via intramuscular or subcutaneous injections, may be developed. However, non-oral administration poses a disadvantage for the patient as well as healthcare providers, and for this reason, it is important to develop alternative routes of administration for such compounds, such as oral routes of administration.

While the oral route of administration is the most convenient for the patient and the most economical, designing formulations for administration by the oral route involves many complications. Several methods are available to predict the ease by which an API may be formulated into a formulation suitable for administration by the oral route. Such methods include, but are not limited to, the Lipinski rule (also referred to as the Rule of Five) and the Biopharmaceutical Drug Disposition Classification System (BDDCS).

The BDDCS divides APIs into four classifications, depending on their solubility and permeability. Class I APIs have high solubility and high permeability; Class II APIs have low solubility and high permeability; Class III APIs have high solubility and low permeability; and Class IV APIs have low solubility and low permeability. APIs in higher classes in the BDDCS face greater challenges in formulating into an effective, pharmaceutically acceptable product than those in lower classes. Of the four classes, APIs falling into Class IV are the most difficult to formulate into a formulation for administration by the oral route that is capable of delivering an effective amount of the API as problems of both solubility and permeability must be addressed (note the BDDCS does not inherently address chemical stability). The role of BDDCS in drug development is described generally in L. Z. Benet *J. Pharm Sci.* 2013, 102(1), 34-42.

Lipinski's rule (described in Lipinski et al. *Adv. Drug Deliv. Rev.* 46 (1-3): 3-26) states, in general, that in order to develop a successful formulation for administration by the oral route, an API can have no more than one violation of the following criteria:
  i) not more than 5 hydrogen bond donors (nitrogen or oxygen atoms with one or more hydrogen atoms);
  ii) not more than 10 hydrogen bond acceptors (nitrogen or oxygen atoms);
  iii) a molecular mass less than 500 daltons; and
  iv) an octanol-water partition coefficient log P not greater than 5.

Certain kallikrein inhibitors are described in PCT Application Publication No. WO 2016/029214. These compounds have therapeutic potential for treating hereditary angioedema and other disorders associated with dysregulated kallikrein activity. There exists a need to develop further analogs of such kallikrein inhibitors that are amenable to oral dosing, and that exhibit properties such as good bioavailability.

SUMMARY OF THE INVENTION

In certain aspects, the invention provides compounds of formula (I), and pharmaceutically acceptable salts thereof:

(I)

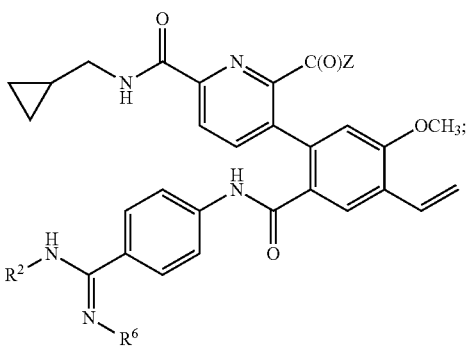

wherein, independently for each occurrence:
Z represents OR¹ or NH(OH);
R¹ represents

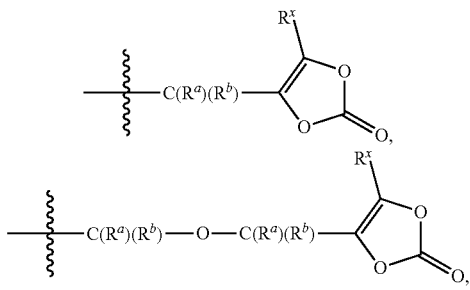

—C(Rᵃ)(Rᵇ)—O—C(O)-M-R³, or (C₂-C₆)alkyl optionally substituted by hydroxyl or heterocycloalkyl;
Rᵃ represents H or (C₁-C₆)alkyl;
Rᵇ represents H or (C₁-C₆)alkyl;
Rˣ represents H or (C₁-C₆)alkyl;
M is a bond or represents O, S, NH, or N(CH₃);
R² represents H, —OH, —C(O)OR⁴, —C(O)SR⁴, —C(O)O—[C(Rᶜ)(Rᵈ)]n-O—C(O)-L-R⁵, or

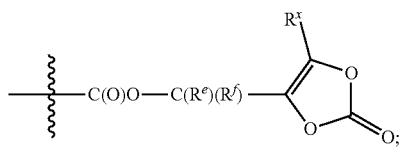

R⁶ represents H, OH, —C(O)OR⁴, —C(O)SR⁴, —C(O)O—[C(Rᶜ)(Rᵈ)]ₙ—O—C(O)-L-R⁵, or

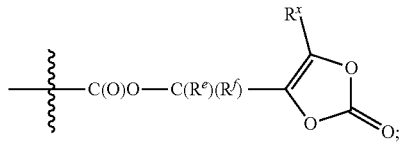

or R² and R⁶, taken together with the atoms to which they are attached, form an optionally substituted 1,2,4-oxadiazol-5-one group;
L, independently for each occurrence, is a bond or represents O, S, NH, or N(CH₃);
Rᶜ, Rᵈ, Rᵉ, and Rᶠ each independently for each occurrence represent H or (C₁-C₆)alkyl;
R³ represents (C₁-C₆)alkyl, aralkyl, or cycloalkyl, optionally substituted with one or more substituents each independently selected from the group consisting of amino, hydroxyl, optionally substituted heterocycloalkyl, —C(O)OH, and —C(O)O((C₁-C₆)alkyl);
R⁴, independently for each occurrence, represents (C₁-C₆) alkyl, cycloalkyl, heterocycloalkyl, aryl, or heteroaryl, optionally substituted with one or more substituents each independently selected from the group consisting of —C(O)OH, —C(O)O((C₁-C₆)alkyl), (C₁-C₆)alkoxy, hydroxyl, oxo, heterocycloalkyl, amino, (C₁-C₆)alkylamino, di((C₁-C₆)alkyl)amino, and silyl ether;
R⁵, independently for each occurrence, represents (C₁-C₆) alkyl, aryl, or heteroaryl, optionally substituted with one or more substituents each independently selected from the group consisting of amino, heterocycloalkyl, (C₁-C₆) alkoxy optionally substituted by (C₁-C₆)alkoxy or a polyether chain; and
n represents 1 or 2;
provided that at least one of R² and R⁶ is not H; and
provided that if Z is OR¹ and R¹ is ethyl or 2-(morpholino) ethyl, then R⁴ is not hexyl or butyl.

In other aspects, the invention provides compounds of formula (II), and pharmaceutically acceptable salts thereof:

(II)

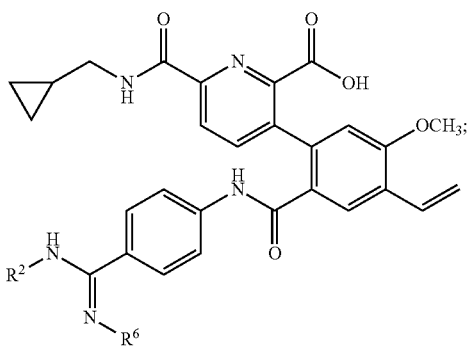

wherein, independently for each occurrence:
R² represents H, —OH, —C(O)OR⁴, —C(O)SR⁴, —C(O)O—[C(Rᶜ)(Rᵈ)]ₙ—O—C(O)-L-R⁵, or

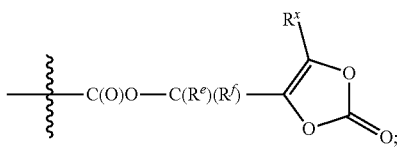

R⁶ represents H, OH, —C(O)OR⁴, —C(O)SR⁴, —C(O)O—[C(Rᶜ)(Rᵈ)]ₙ—O—C(O)-L-R⁵, or

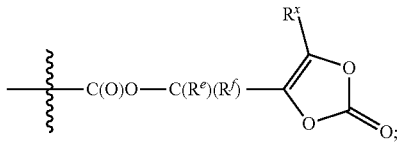

or R² and R⁶, taken together with the atoms to which they are attached, form an optionally substituted 1,2,4-oxadiazol-5-one group;
L, independently for each occurrence, is a bond or represents O, S, NH, or N(CH₃);
Rᶜ, Rᵈ, Rᵉ, and Rᶠ each independently for each occurrence represent H or (C₁-C₆)alkyl;
R⁴, independently for each occurrence, represents (C₁-C₆) alkyl, cycloalkyl, heterocycloalkyl, aryl, or heteroaryl, optionally substituted with one or more substituents each independently selected from the group consisting of —C(O)OH, —C(O)O((C$_1$-C$_6$)alkyl), (C$_1$-C$_6$)alkoxy, hydroxyl, oxo, heterocycloalkyl, amino, (C$_1$-C$_6$)alkylamino, di((C$_1$-C$_6$)alkyl)amino, and silyl ether;

R$^5$, independently for each occurrence, represents (C$_1$-C$_6$) alkyl, aryl, or heteroaryl, optionally substituted with one or more substituents each independently selected from the group consisting of amino, heterocycloalkyl, (C$_1$-C$_6$) alkoxy optionally substituted by (C$_1$-C$_6$)alkoxy or a polyether chain; and n represents 1 or 2;

provided that at least one of R$^2$ and R$^6$ is not H; and the compound of formula (II) is not

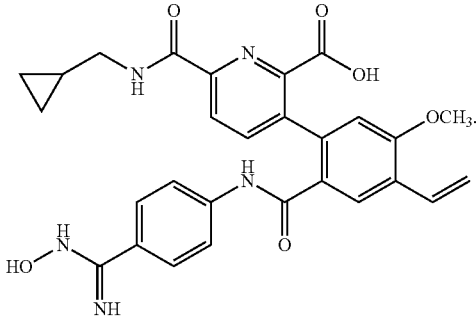 [SMILES: C=Cc1cc(C(=O)Nc2ccc(C(=N)NO)cc2)c(-c2ccc(C(=O)NCC3CC3)nc2C(=O)O)cc1OC]

In further aspects, the invention provides compounds of formula (III), and pharmaceutically acceptable salts thereof:

(III)

wherein, independently for each occurrence:

Z represents OR$^1$ or NH(OH);

R$^1$ represents

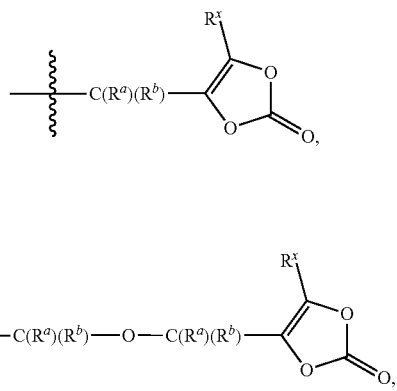

—C(R$^a$)(R$^b$)—O—C(O)-M-R$^3$, or (C$_2$-C$_6$)alkyl optionally substituted by hydroxyl or heterocycloalkyl;

R$^a$ represents H or (C$_1$-C$_6$)alkyl;

R$^b$ represents H or (C$_1$-C$_6$)alkyl;

R$^x$ represents H or (C$_1$-C$_6$)alkyl;

M is a bond or represents O, S, NH, or N(CH$_3$);

R$^3$ represents (C$_1$-C$_6$)alkyl, aralkyl, or cycloalkyl, optionally substituted with one or more substituents each independently selected from the group consisting of amino, hydroxyl, optionally substituted heterocycloalkyl, —C(O)OH, and —C(O)O((C$_1$-C$_6$)alkyl);

provided that the compound of formula (III) is not selected from the following table:

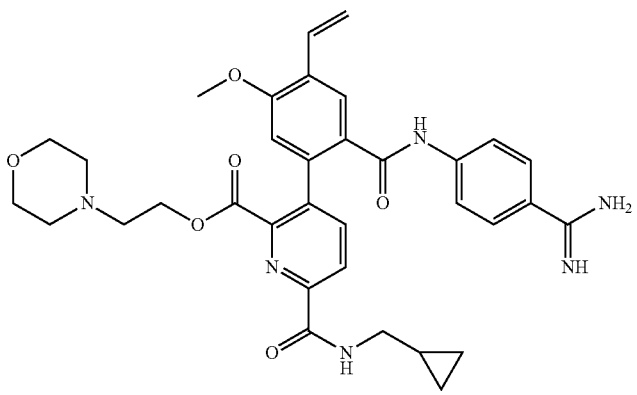 [SMILES: C=Cc1cc(C(=O)Nc2ccc(C(=N)N)cc2)c(-c2ccc(C(=O)NCC3CC3)nc2C(=O)OCCN2CCOCC2)cc1OC]

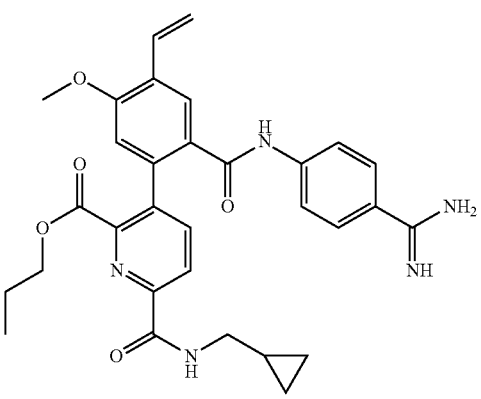 [SMILES: C=Cc1cc(C(=O)Nc2ccc(C(=N)N)cc2)c(-c2ccc(C(=O)NCC3CC3)nc2C(=O)OCCC)cc1OC]
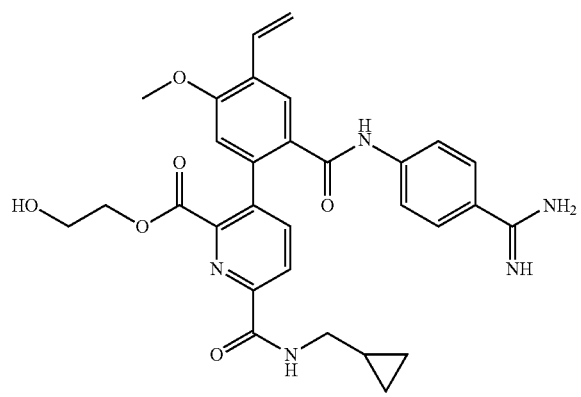 [SMILES: C=Cc1cc(C(=O)Nc2ccc(C(=N)N)cc2)c(-c2ccc(C(=O)NCC3CC3)nc2C(=O)OCCO)cc1OC]
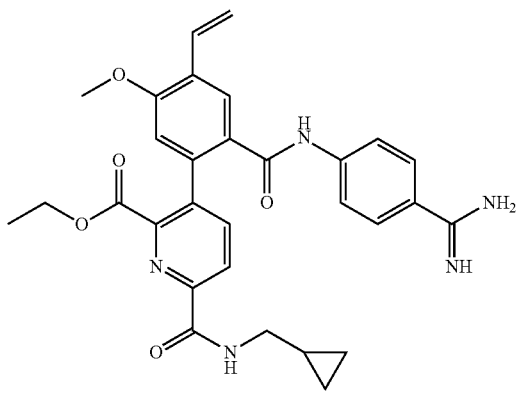 [SMILES: C=Cc1cc(C(=O)Nc2ccc(C(=N)N)cc2)c(-c2ccc(C(=O)NCC3CC3)nc2C(=O)OCC)cc1OC]
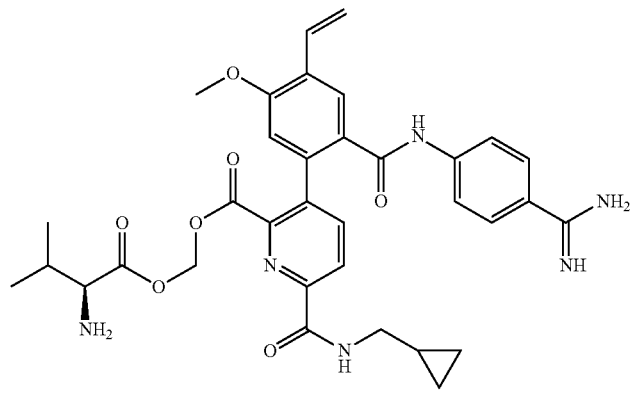 [SMILES: C=Cc1cc(C(=O)Nc2ccc(C(=N)N)cc2)c(-c2ccc(C(=O)NCC3CC3)nc2C(=O)OCOC(=O)[C@@H](N)C(C)C)cc1OC]

-continued
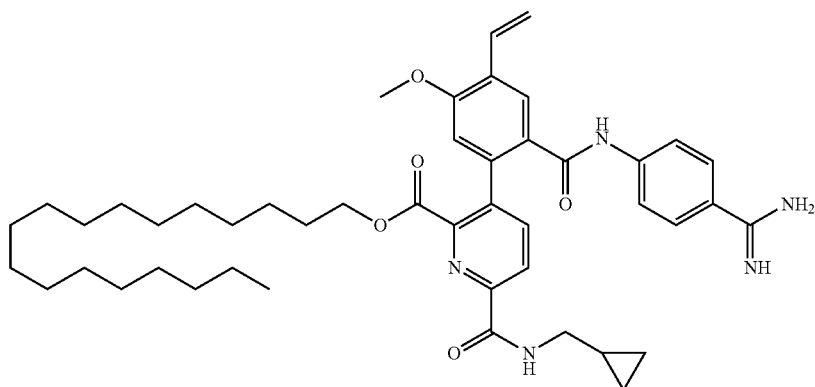
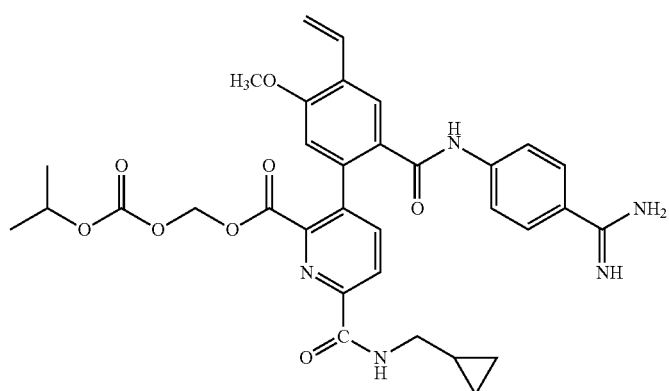
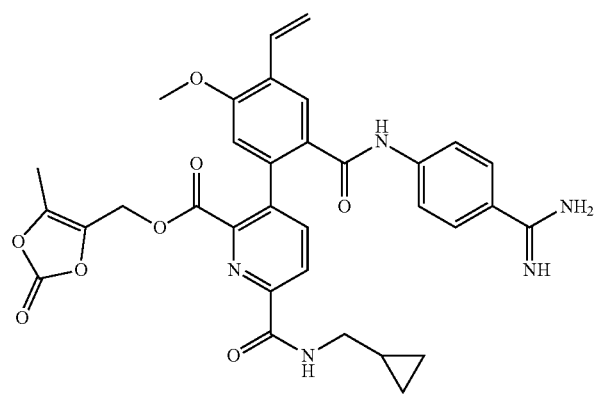 [SMILES: C=Cc1cc(C(=O)Nc2ccc(C(=N)N)cc2)c(-c2ccc(C(=O)NCC3CC3)nc2C(=O)OCc2oc(=O)oc2C)cc1OC]
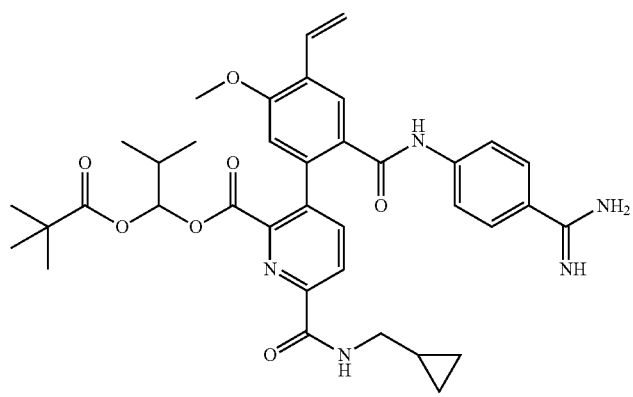 [SMILES: C=Cc1cc(C(=O)Nc2ccc(C(=N)N)cc2)c(-c2ccc(C(=O)NCC3CC3)nc2C(=O)OC(OC(=O)C(C)(C)C)C(C)C)cc1OC]

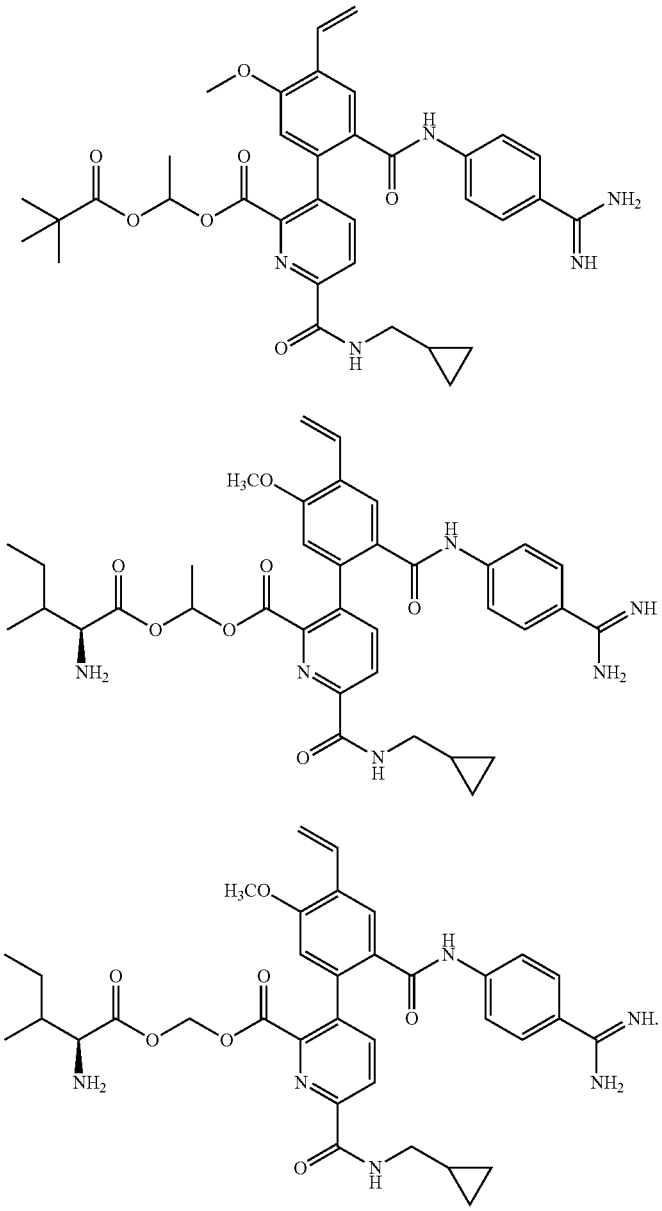

In certain aspects, the invention provides a pharmaceutical composition, comprising a compound of the invention, or a pharmaceutically acceptable salt thereof; and a pharmaceutically acceptable carrier.

In certain aspects, the invention provides methods of treating acquired angioedema or hereditary angioedema, comprising administering to a subject in need thereof a therapeutically effective amount of a compound the invention.

In further aspects, the invention provides methods of treating a disease or condition associated with aberrant activity of kallikrein, comprising administering to a subject in need thereof a therapeutically effective amount of a compound of the invention.

The invention described herein also provides methods of inhibiting blood coagulation, comprising administering to a subject in need thereof an effective amount of a compound of the invention.

DETAILED DESCRIPTION

Inhibitors of kallikrein have been reported and are useful in therapeutic methods and compositions suitable for use in treating acquired angioedema or hereditary angioedema.

Provided herein are compounds of formula (I) that are useful in treating or preventing a disease or condition characterized by aberrant activity of kallikrein.

Definitions

The articles "a" and "an" are used herein to refer to one or more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium, and alternatively oxygen, nitrogen or sulfur.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ alkyl group. In certain embodiments, the term "alkyl" refers to a $C_1$-$C_6$ alkyl group, for example a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "(cycloalkyl)alkyl" as used herein refers to an alkyl group substituted with one or more cycloalkyl groups. An example of cycloalkylalkyl is cyclohexylmethyl group.

The term "heterocycloalkyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocycloalkyl group is optionally substituted by one or more substituents as described below.

The term "(heterocycloalkyl)alkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

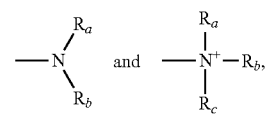

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$.

In certain embodiments, the term "amino" refers to —$NH_2$.

In certain embodiments, the term "alkylamino" refers to —NH(alkyl).

In certain embodiments, the term "dialkylamino" refers to —N(alkyl)$_2$.

The term "amido", as used herein, means —NHC(=O)—, wherein the amido group is bound to the parent molecular moiety through the nitrogen. Examples of amido include alkylamido such as $CH_3C$(=O)N(H)— and $CH_3CH_2C$(=O)N(H)—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

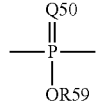

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

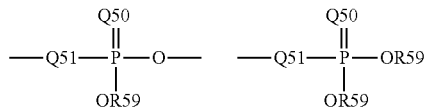

wherein Q50 and R59, each independently, are defined above, and Q51 represents O, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an —$N_3$ group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—. The term "(alkylthio)alkyl" refers to an alkyl group substituted by an alkylthio group.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, and pyrene. Typically, an aryl group contains from 6-10 carbon ring atoms (i.e., ($C_6$-$C_{10}$)aryl). The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group.

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" refers to an alkyl group substituted by an alkoxy group.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH-CH_2-O-$) and vinyloxy (i.e., $CH_2=CH-O-$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl).

Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si-$) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethyl silyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations.

Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in Remington's Pharmaceutical Sciences by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

The present invention provides compounds having the structure of Formula (I), or pharmaceutically acceptable salts thereof:

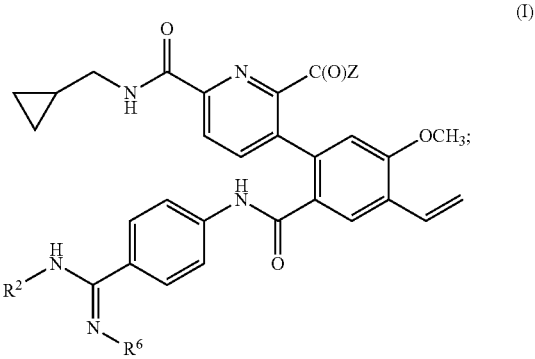

(I)

wherein, independently for each occurrence:

Z represents OR$^1$ or NH(OH);

R$^1$ represents

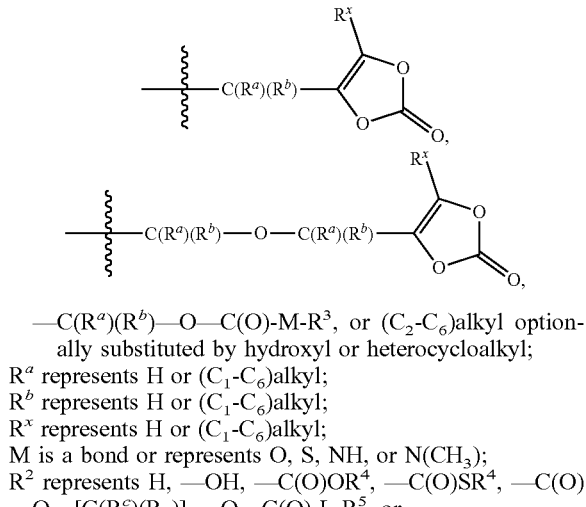

—C(R$^a$)(R$^b$)—O—C(O)-M-R$^3$, or (C$_2$-C$_6$)alkyl optionally substituted by hydroxyl or heterocycloalkyl;

R$^a$ represents H or (C$_1$-C$_6$)alkyl;

R$^b$ represents H or (C$_1$-C$_6$)alkyl;

R$^x$ represents H or (C$_1$-C$_6$)alkyl;

M is a bond or represents O, S, NH, or N(CH$_3$);

R$^2$ represents H, —OH, —C(O)OR$^4$, —C(O)SR$^4$, —C(O)O—[C(R$^c$)(R$_d$)]$_n$—O—C(O)-L-R$^5$, or

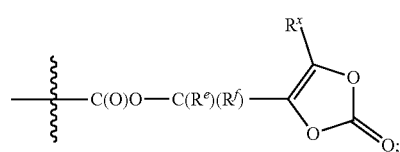

R$^6$ represents H, OH, —C(O)OR$^4$, —C(O)SR$^4$, —C(O)O—[C(R$^c$)(R$_d$)]$_n$—O—C(O)-L-R$^5$, or

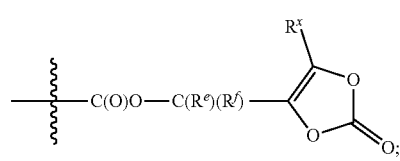

or $R^2$ and $R^6$, taken together with the atoms to which they are attached, form an optionally substituted 1,2,4-oxadiazol-5-one group;

L, independently for each occurrence, is a bond or represents O, S, NH, or $N(CH_3)$;

$R^c$, $R^d$, $R^e$, and $R^f$ each independently for each occurrence represent H or $(C_1-C_6)$alkyl;

$R^3$ represents $(C_1-C_6)$alkyl, aralkyl, or cycloalkyl, optionally substituted with one or more substituents each independently selected from the group consisting of amino, hydroxyl, optionally substituted heterocycloalkyl, —C(O)OH, and —C(O)O$((C_1-C_6)$alkyl);

$R^4$, independently for each occurrence, represents $(C_1-C_6)$ alkyl, cycloalkyl, heterocycloalkyl, aryl, or heteroaryl, optionally substituted with one or more substituents each independently selected from the group consisting of —C(O)OH, —C(O)O$((C_1-C_6)$alkyl), $(C_1-C_6)$alkoxy, hydroxyl, oxo, heterocycloalkyl, amino, $(C_1-C_6)$alkylamino, di$((C_1-C_6)$alkyl)amino, and silyl ether;

$R^5$, independently for each occurrence, represents $(C_1-C_6)$ alkyl, aryl, or heteroaryl, optionally substituted with one or more substituents each independently selected from the group consisting of amino, heterocycloalkyl, $(C_1-C_6)$ alkoxy optionally substituted by $(C_1-C_6)$alkoxy or a polyether chain; and n represents 1 or 2;

provided that at least one of $R^2$ and $R^6$ is not H; and provided that if Z is $OR^1$ and $R^1$ is ethyl or 2-(morpholino) ethyl, then $R^4$ is not hexyl or butyl.

In certain embodiments, Z represents $OR^1$.

In certain embodiments, $R^1$ represents

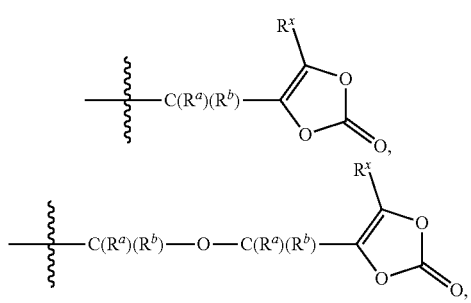

or —C($R^a$)($R^b$)—O—C(O)-M-$R^3$.

In certain embodiments, $R^a$ and $R^b$ each independently represent H or methyl.

In certain embodiments, at least one of $R^a$ and $R^b$ is H.

In certain embodiments, at least one of $R^a$ and $R^b$ is methyl.

In certain embodiments, $R^1$ represents —C($R^a$)($R^b$)—O—C(O)-M-$R^3$. In certain such embodiments, M is a bond. Alternatively, M can be O.

In further such embodiments, $R^3$ represents $(C_1-C_6)$alkyl, for example, $R^3$ may represent $(C_3-C_5)$alkyl.

In yet further such embodiments, $R^3$ represents cycloalkyl.

In still further such embodiments, $R^3$ represents aralkyl, optionally substituted with —$NH_2$.

In certain embodiments, $R^3$ represents $(C_1-C_6)$alkyl, substituted with —$NH_2$ or —OH. For example, $R^3$ may represent $(C_3-C_5)$alkyl, substituted with —$NH_2$ or OH. In further such embodiments, $R^3$ may represent $(C_3-C_5)$alkyl, substituted with —$NH_2$.

In certain embodiments, $R^1$ represents

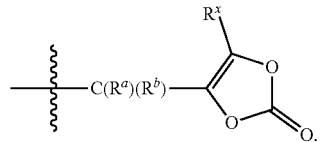

In certain such embodiments, $R^x$ represents H or methyl.

In certain embodiments, $R^1$ represents $(C_2-C_6)$alkyl optionally substituted with hydroxyl.

In certain embodiments, $R^2$ represents H; and $R^6$ represents OH.

Alternatively, in certain embodiments, $R^2$ represents —C(O)$OR^4$ or —C(O)O—[C($R^c$)($R_d$)]$_n$—O—C(O)-L-$R^5$.

For example, $R^2$ may represent —C(O)$OR^4$. In certain such embodiments, $R^4$ represents $(C_1-C_6)$alkyl, substituted with amino, hydroxy, or $(C_1-C_6)$alkoxy.

Alternatively, $R^2$ may represent —C(O)O—[C($R^c$)($R^d$)]$_n$—O—C(O)-L-R, and n is 1. In certain such embodiments, at least one of R and $R^d$ is H. In further such embodiments, at least one of R and $R^d$ is methyl.

In certain such embodiments, L is a bond.

In other such embodiments, $R^5$ represents $(C_1-C_4)$alkyl. Alternatively, $R^5$ may represent $(C_1-C_4)$alkyl, substituted by amino.

In certain embodiments, $R^6$ represents H.

In alternative embodiments, $R^2$ and $R^6$, taken together with the atoms to which they are attached, form a 1,2,4-oxadiazol-5-one group.

In certain embodiments of the compound of formula (I), if $R^1$ is —$CH_2$—O—C(O)—CH(iPr)$NH_2$, then $R^2$ is not —C(O)O(ethyl); and if $R^1$ is —$CH_2$—O—C(O)—CH(iBu)$NH_2$, then $R^2$ is not —C(O)O(hexyl).

In certain embodiments, the compound of formula (I) is selected from the following table:

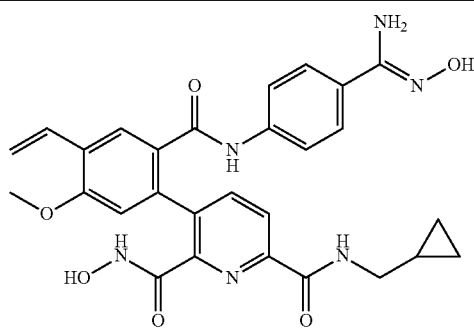

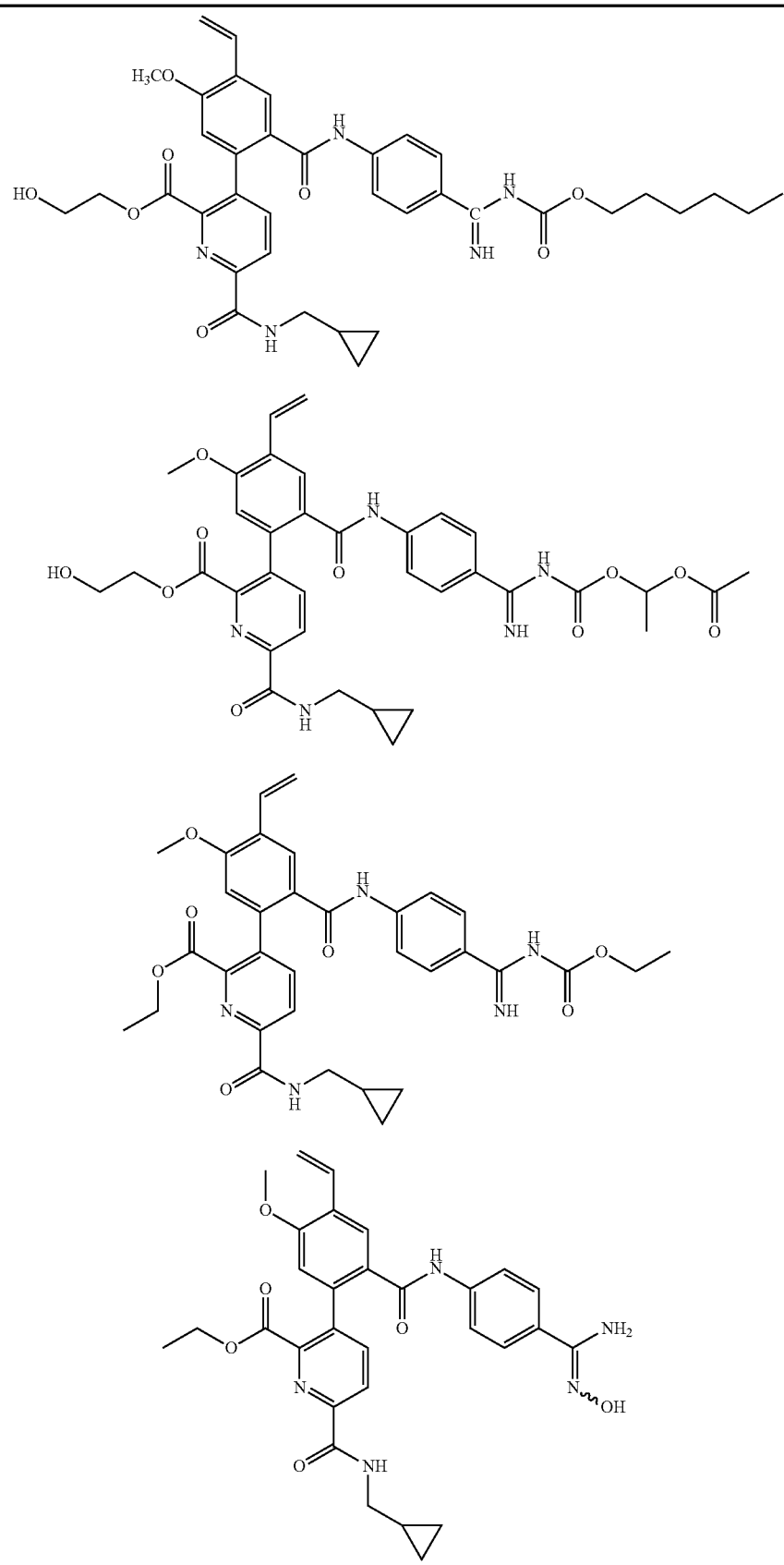

-continued
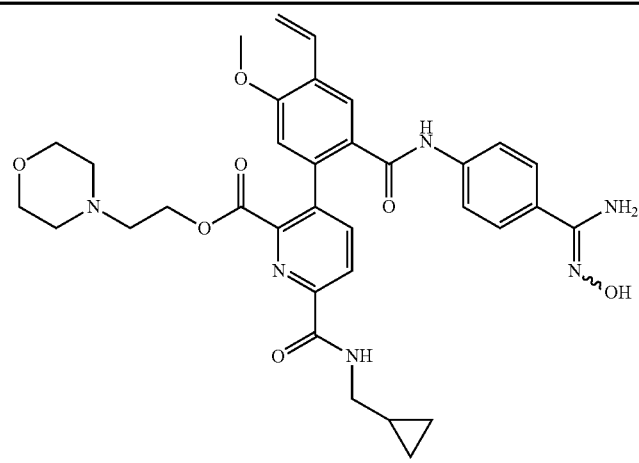

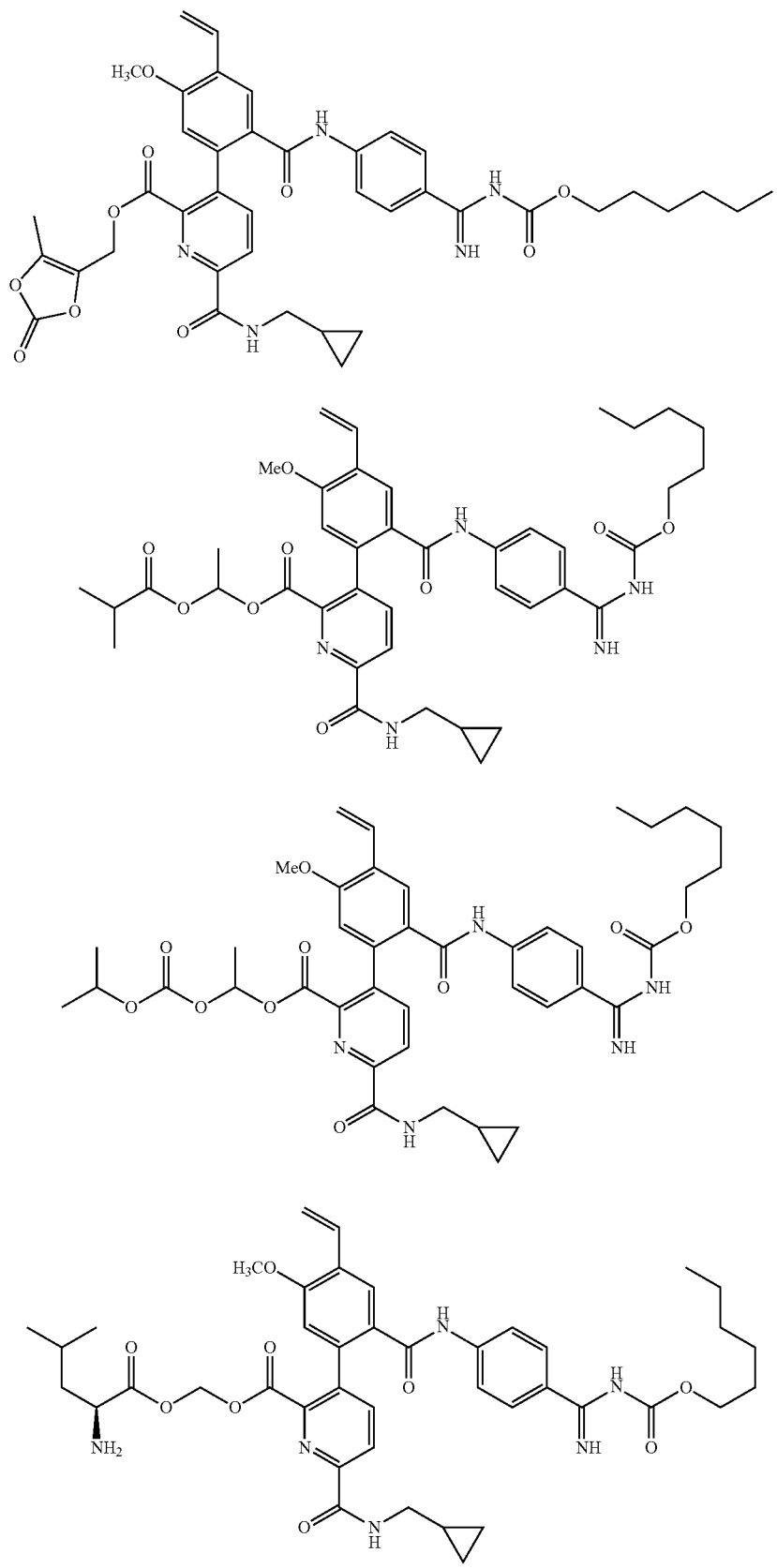

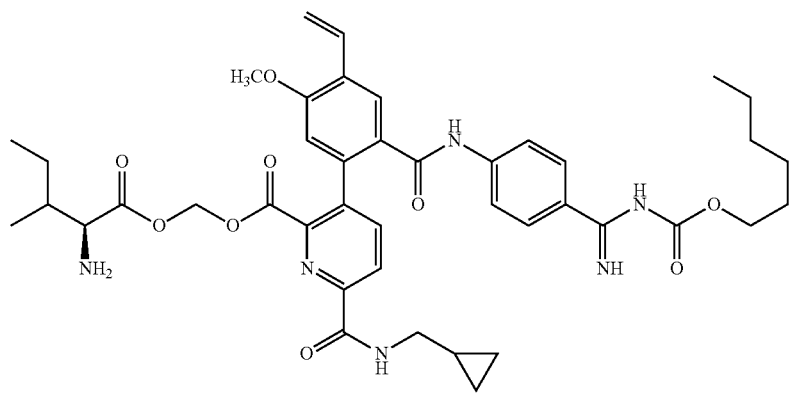 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)C(C)CC)cc1OC]
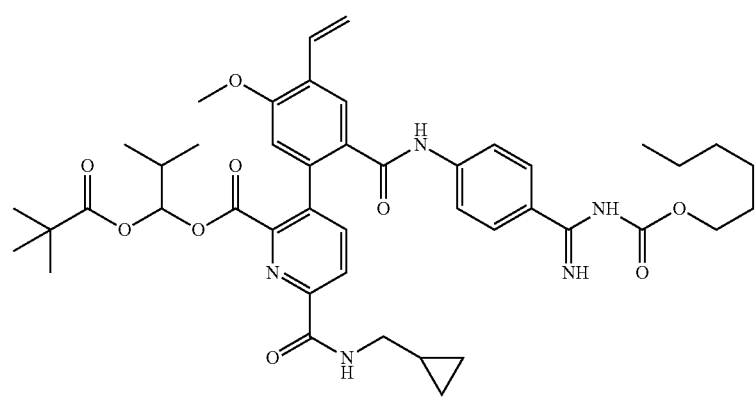 [SMILES: C=Cc1cc(C(=O)Nc2ccc(C(=N)NC(=O)OCCCCCC)cc2)c(-c2ccc(C(=O)NCC3CC3)nc2C(=O)OC(OC(=O)C(C)(C)C)C(C)C)cc1OC]
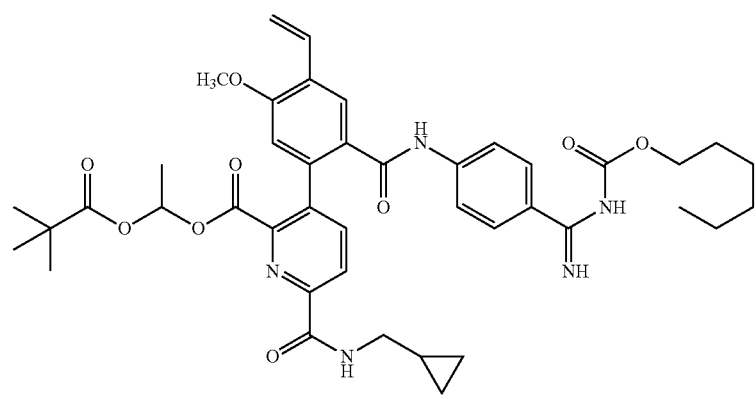 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)C(C)(C)C)cc1OC]
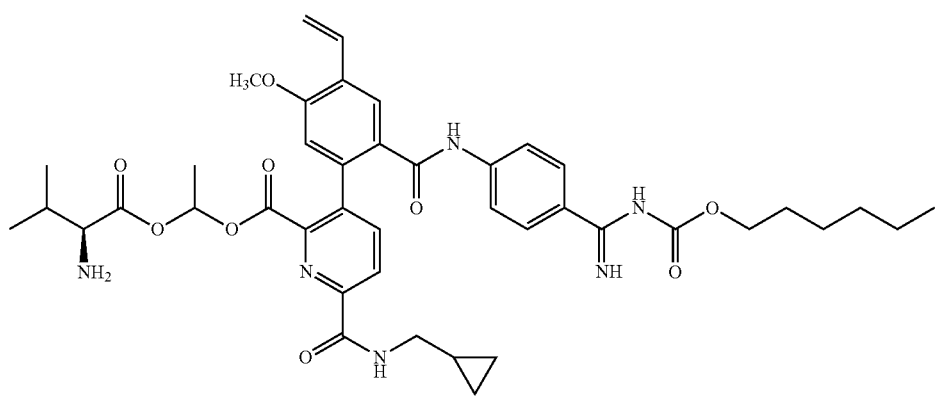 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)[C@@H](N)C(C)C)cc1OC]

-continued
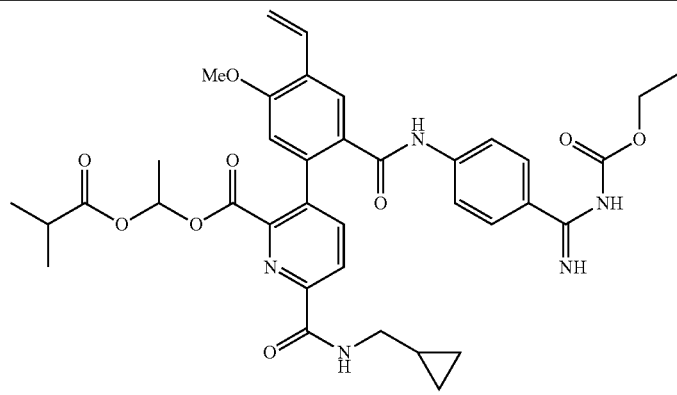
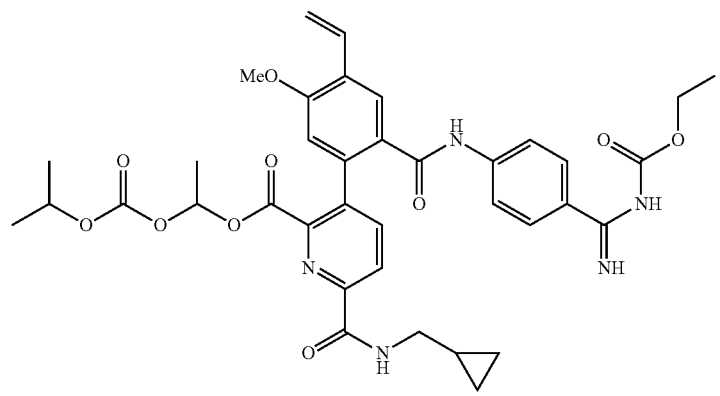 [SMILES: C=Cc1cc(C(=O)Nc2ccc(C(=N)NC(=O)OCC)cc2)c(-c2ccc(C(=O)NCC3CC3)nc2C(=O)OC(C)OC(=O)OC(C)C)cc1OC]
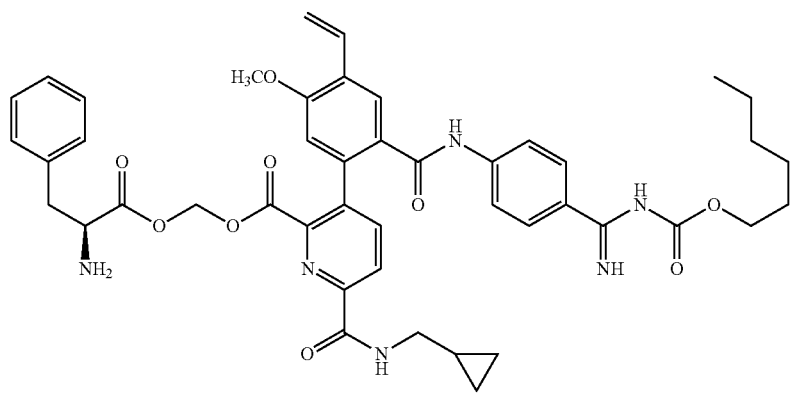 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)Cc2ccccc2)cc1OC]
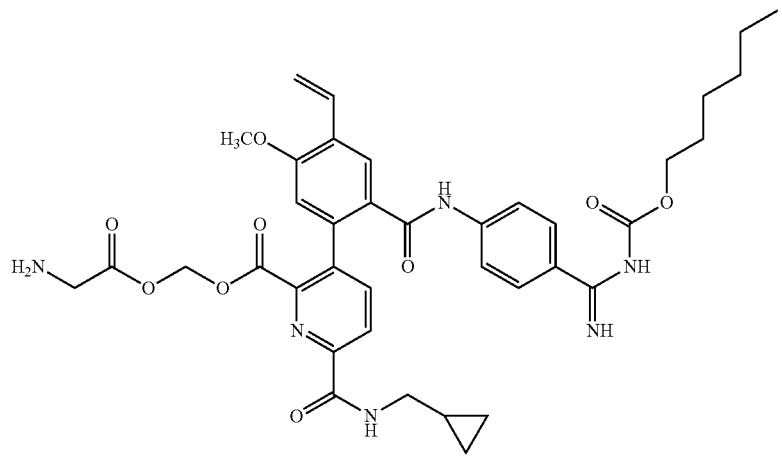 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)CN)cc1OC]

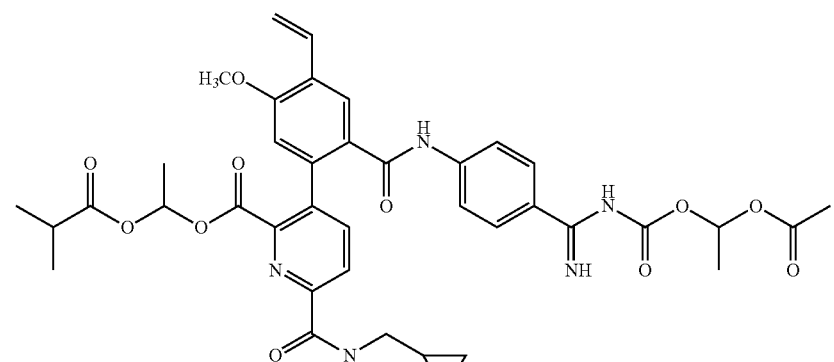
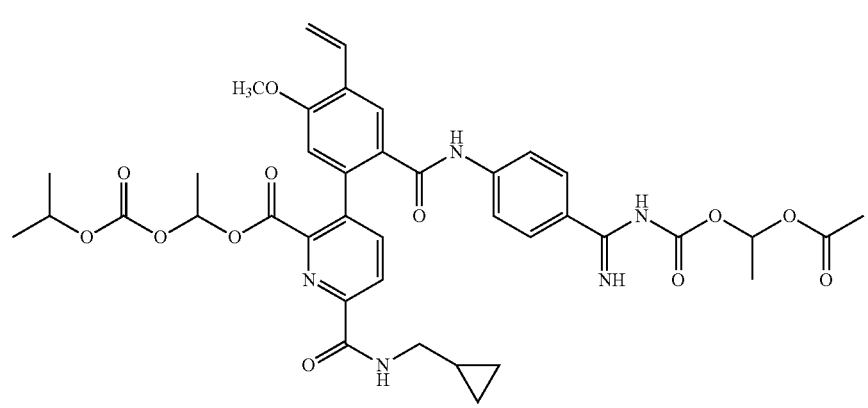 [SMILES: C=Cc1cc(C(=O)Nc2ccc(C(=N)NC(=O)OC(C)OC(C)=O)cc2)c(-c2ccc(C(=O)NCC3CC3)nc2C(=O)OC(C)OC(=O)OC(C)C)cc1OC]
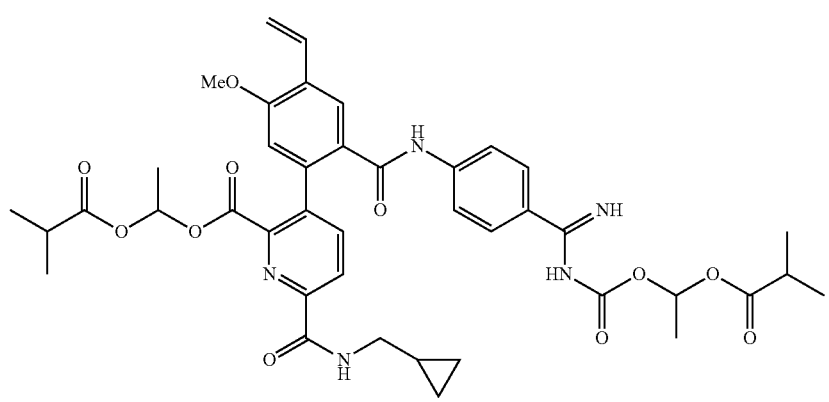 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OC(C)OC(=O)C(C)C)cc1OC]
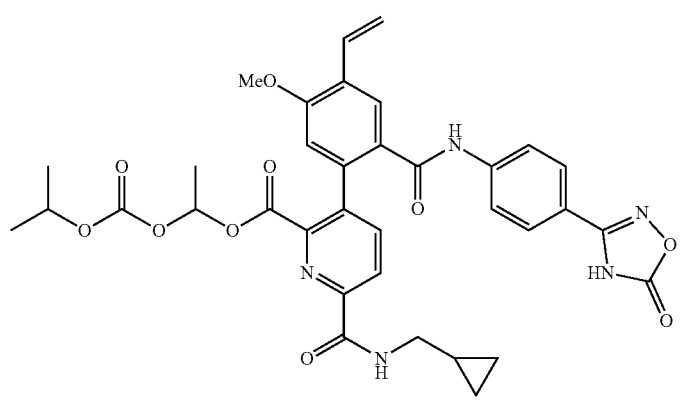 [SMILES: C=Cc1cc(C(=O)Nc2ccc(-c3noc(=O)[nH]3)cc2)c(-c2ccc(C(=O)NCC3CC3)nc2C(=O)OC(C)OC(=O)OC(C)C)cc1OC]

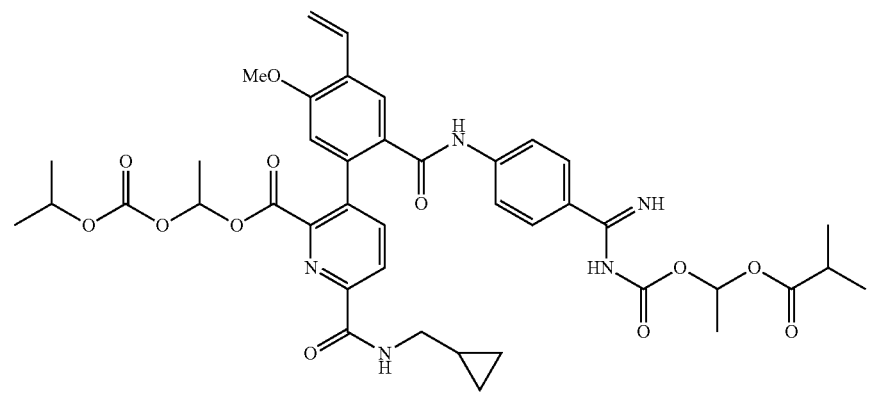 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OC(C)OC(=O)OC(C)C)cc1OC]
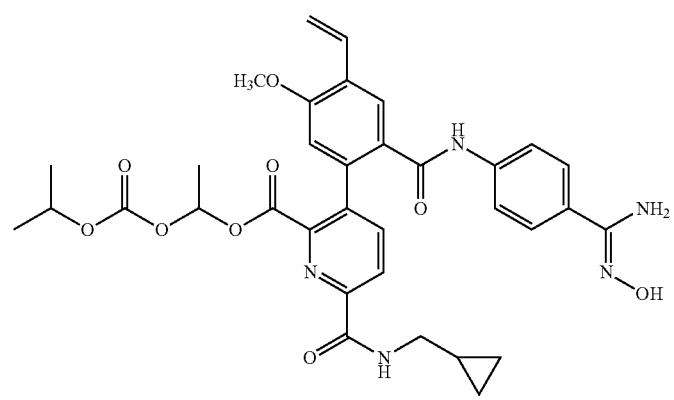 [SMILES: C=Cc1cc(C(=O)Nc2ccc(/C(N)=N/O)cc2)c(-c2ccc(C(=O)NCC3CC3)nc2C(=O)OC(C)OC(=O)OC(C)C)cc1OC]
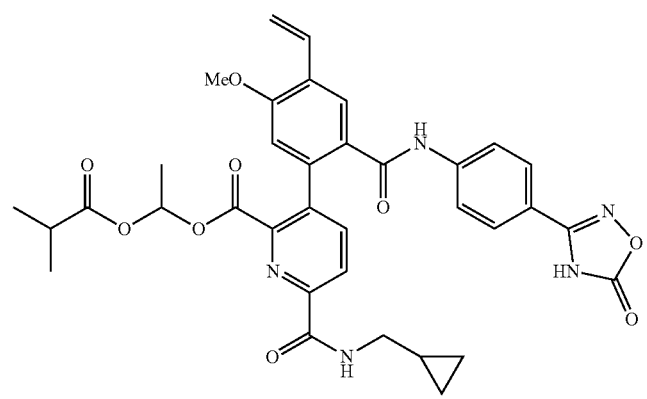 [SMILES: C=Cc1cc(C(=O)Nc2ccc(-c3noc(=O)[nH]3)cc2)c(-c2ccc(C(=O)NCC3CC3)nc2C(=O)OC(C)OC(=O)C(C)C)cc1OC]
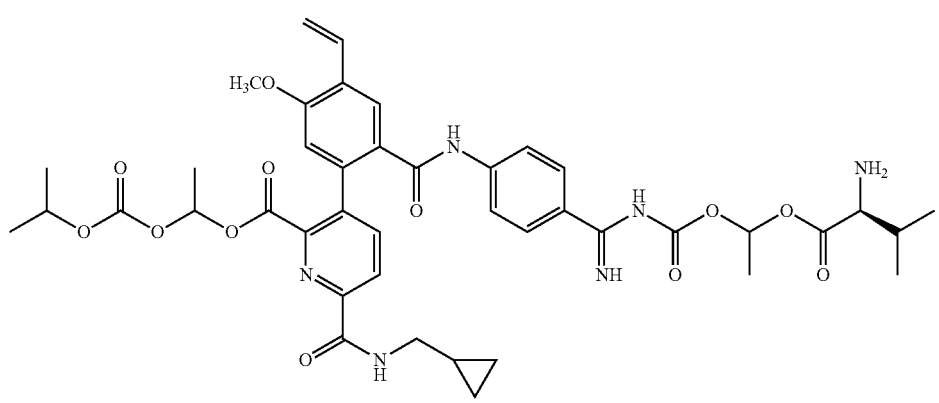 [SMILES: C=Cc1cc(C(=O)Nc2ccc(C(=N)NC(=O)OC(C)OC(=O)[C@@H](N)C(C)C)cc2)c(-c2ccc(C(=O)NCC3CC3)nc2C(=O)OC(C)OC(=O)OC(C)C)cc1OC]

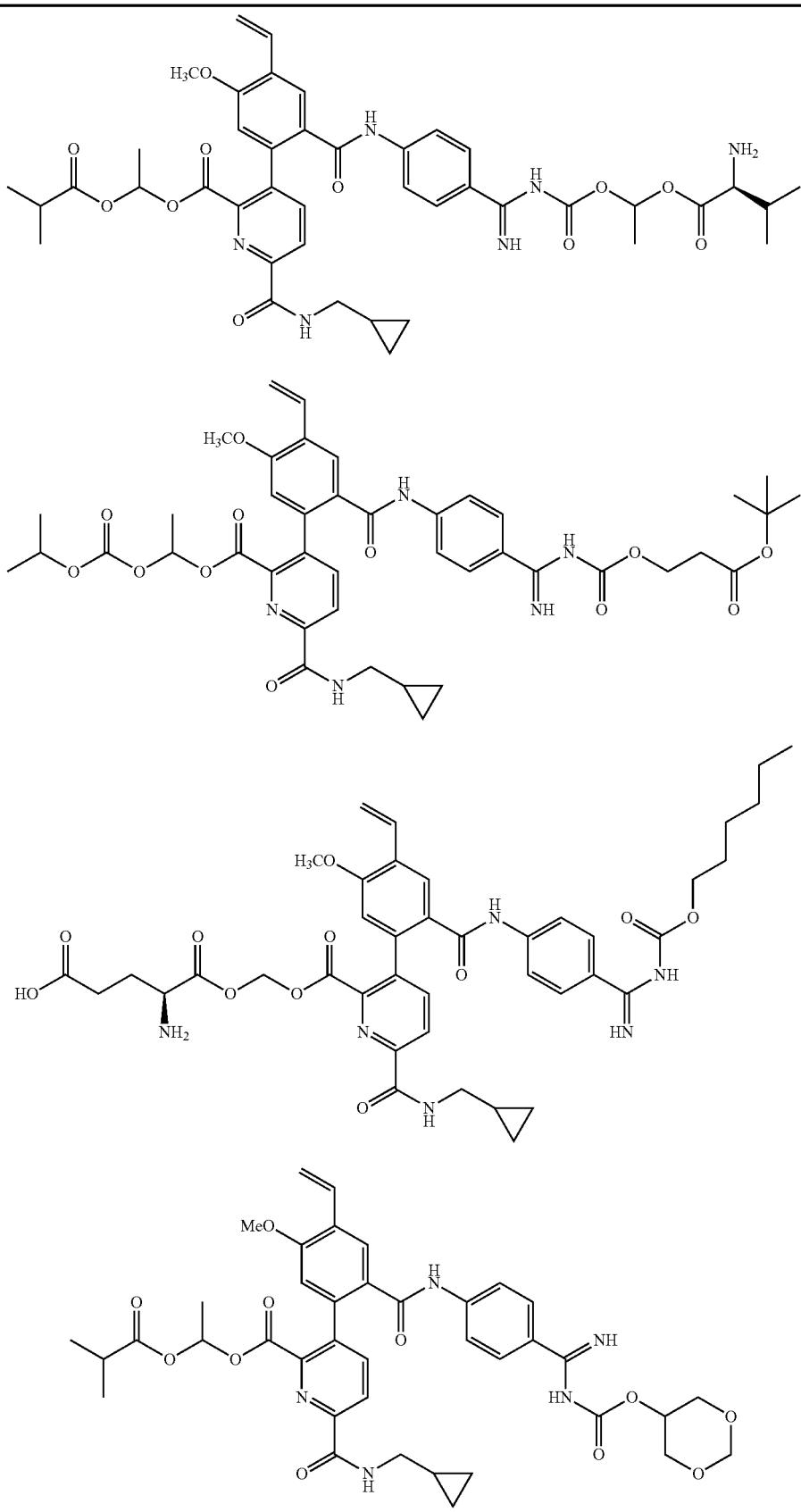

-continued
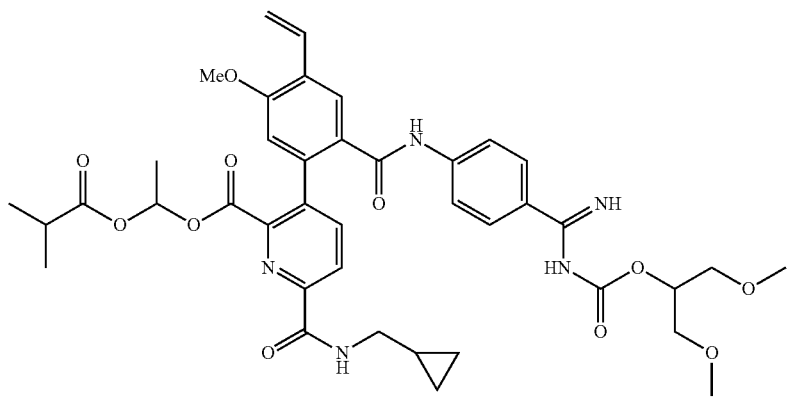 [SMILES: C=Cc1cc(C(=O)Nc2ccc(C(=N)NC(=O)OC(COC)COC)cc2)c(-c2ccc(C(=O)NCC3CC3)nc2C(=O)OC(C)OC(=O)C(C)C)cc1OC]
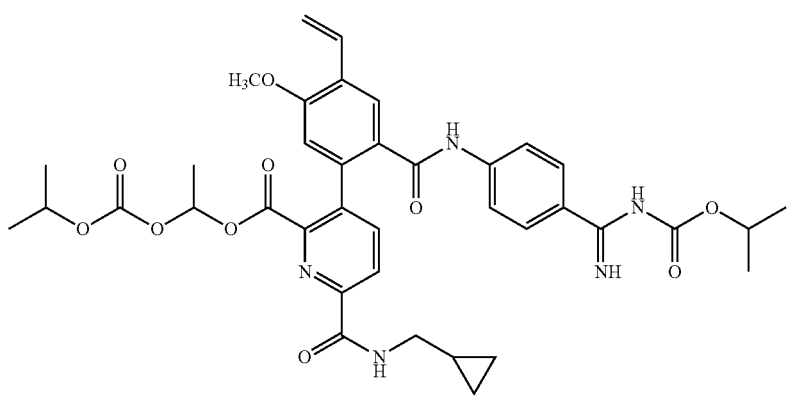 [SMILES: C=Cc1cc(C(=O)Nc2ccc(C(=N)NC(=O)OC(C)C)cc2)c(-c2ccc(C(=O)NCC3CC3)nc2C(=O)OC(C)OC(=O)OC(C)C)cc1OC]
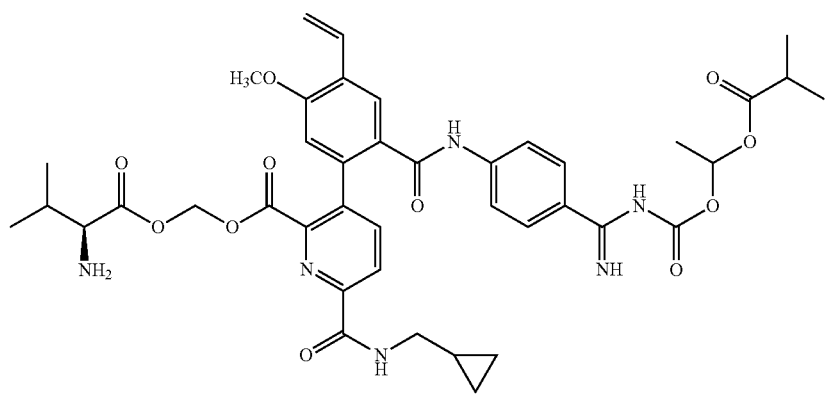 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OCOC(=O)[C@@H](N)C(C)C)cc1OC]
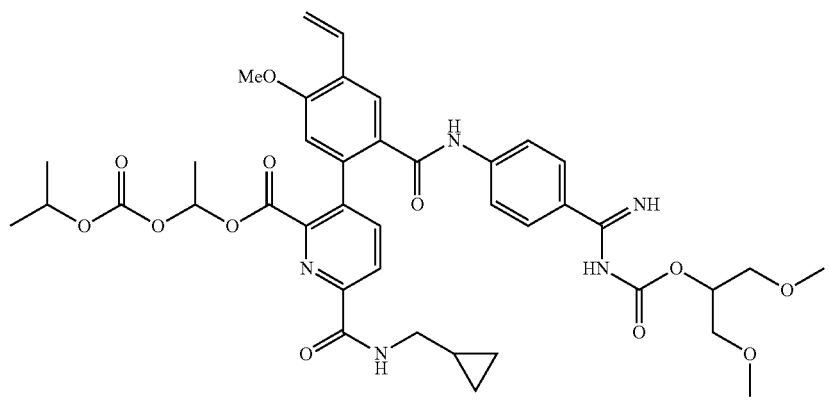 [SMILES: C=Cc1cc(C(=O)Nc2ccc(C(=N)NC(=O)OC(COC)COC)cc2)c(-c2ccc(C(=O)NCC3CC3)nc2C(=O)OC(C)OC(=O)OC(C)C)cc1OC]

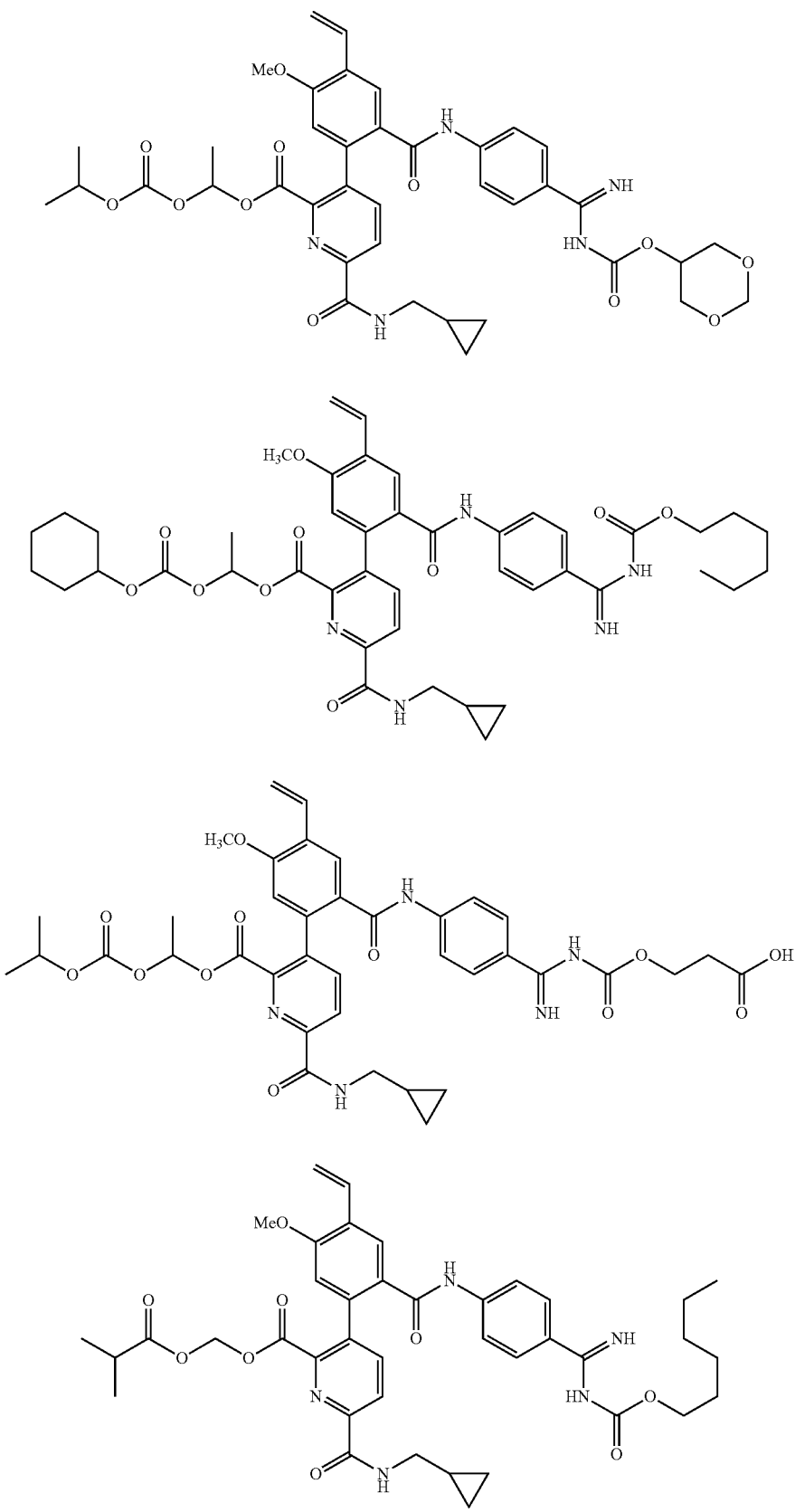

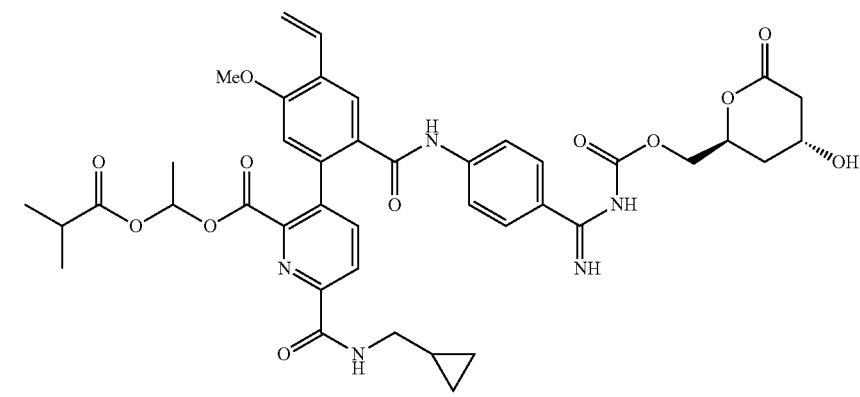 [SMILES: C=Cc1cc(C(=O)Nc2ccc(C(=N)NC(=O)OC[C@@H]3C[C@@H](O)CC(=O)O3)cc2)c(-c2ccc(C(=O)NCC3CC3)nc2C(=O)OC(C)OC(=O)C(C)C)cc1OC]
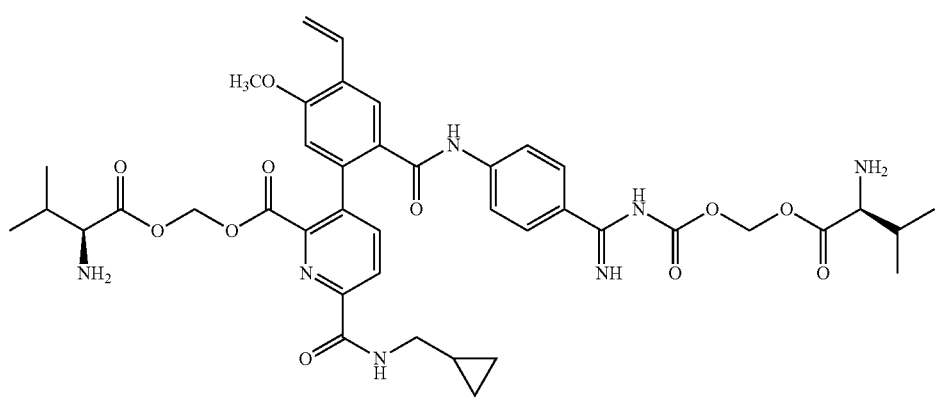 [SMILES: C=Cc1cc(C(=O)Nc2ccc(C(=N)NC(=O)OCOC(=O)[C@@H](N)C(C)C)cc2)c(-c2ccc(C(=O)NCC3CC3)nc2C(=O)OCOC(=O)[C@@H](N)C(C)C)cc1OC]
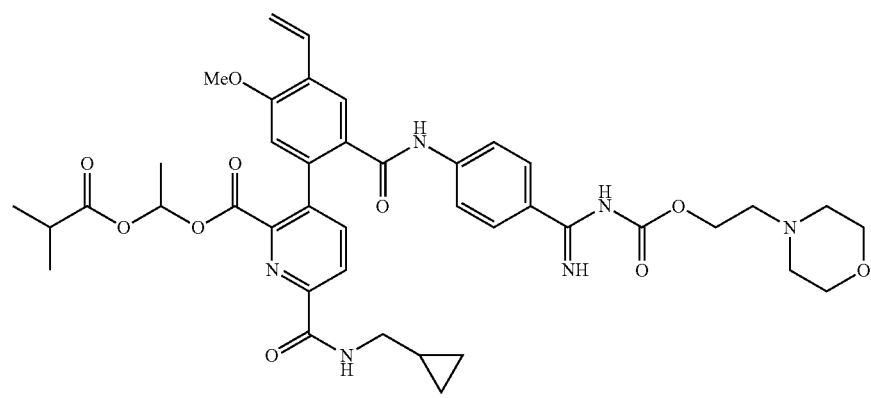 [SMILES: C=Cc1cc(C(=O)Nc2ccc(C(=N)NC(=O)OCCN3CCOCC3)cc2)c(-c2ccc(C(=O)NCC3CC3)nc2C(=O)OC(C)OC(=O)C(C)C)cc1OC]
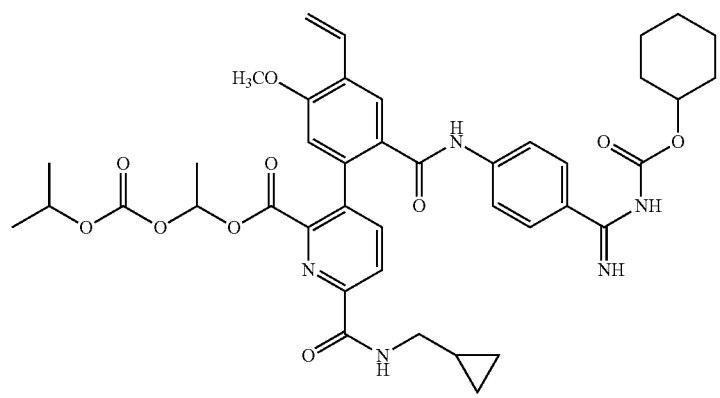 [SMILES: C=Cc1cc(C(=O)Nc2ccc(C(=N)NC(=O)OC3CCCCC3)cc2)c(-c2ccc(C(=O)NCC3CC3)nc2C(=O)OC(C)OC(=O)OC(C)C)cc1OC]

-continued
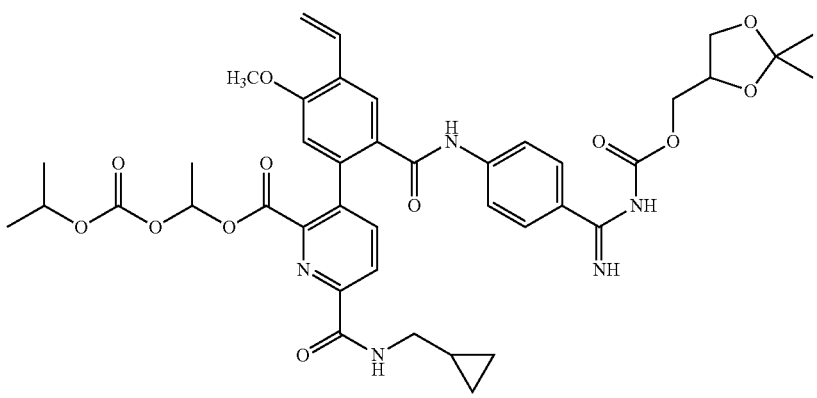 [SMILES: C=Cc1cc(C(=O)Nc2ccc(C(=N)NC(=O)OCC3COC(C)(C)O3)cc2)c(-c2ccc(C(=O)NCC3CC3)nc2C(=O)OC(C)OC(=O)OC(C)C)cc1OC]
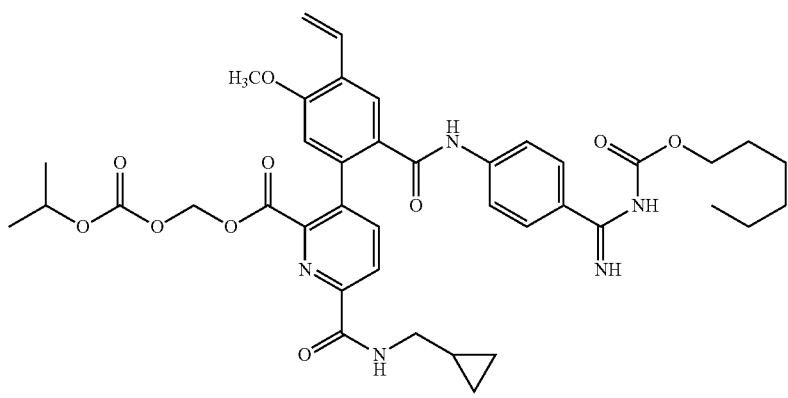 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)OC(C)C)cc1OC]
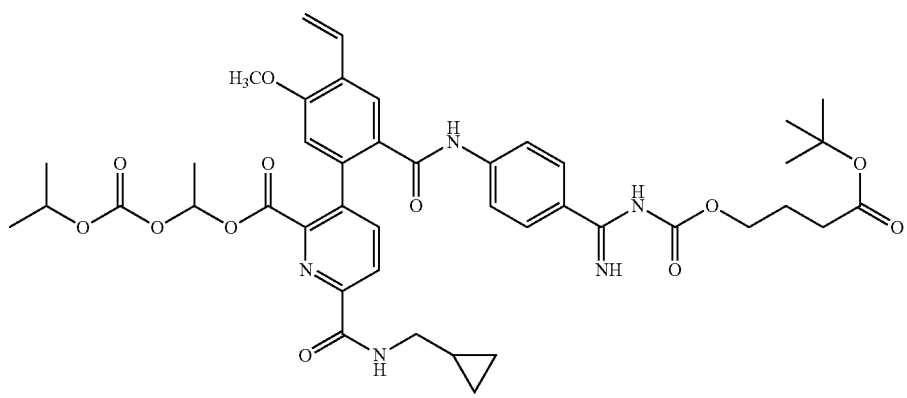 [SMILES: C=Cc1cc(C(=O)Nc2ccc(C(=N)NC(=O)OCCCC(=O)OC(C)(C)C)cc2)c(-c2ccc(C(=O)NCC3CC3)nc2C(=O)OC(C)OC(=O)OC(C)C)cc1OC]
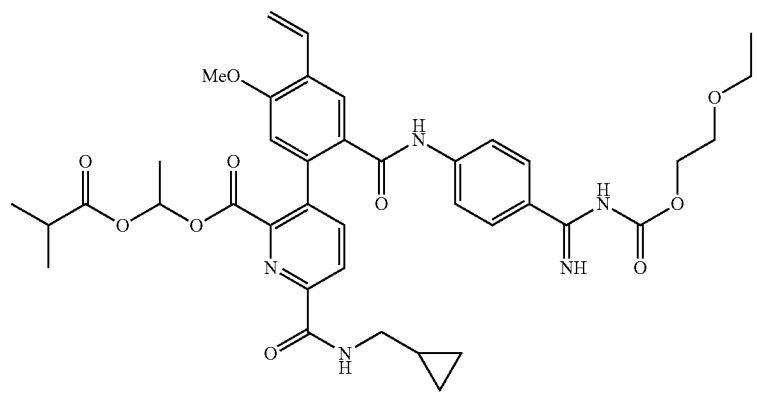 [SMILES: C=Cc1cc(C(=O)Nc2ccc(C(=N)NC(=O)OCCOCC)cc2)c(-c2ccc(C(=O)NCC3CC3)nc2C(=O)OC(C)OC(=O)C(C)C)cc1OC]

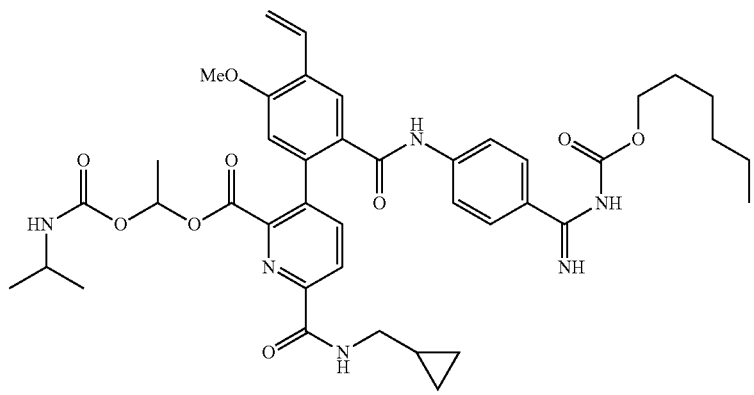 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)NC(C)C)cc1OC]
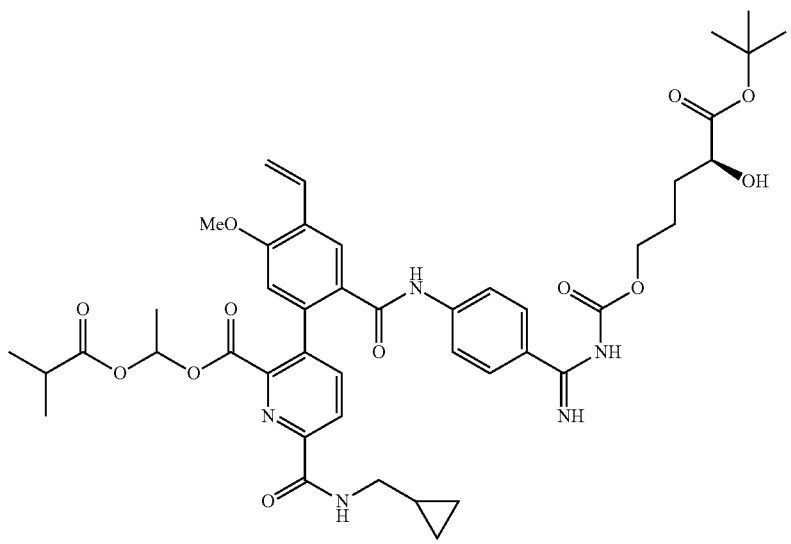 [SMILES: C=Cc1cc(C(=O)Nc2ccc(C(=N)NC(=O)OCCC[C@H](O)C(=O)OC(C)(C)C)cc2)c(-c2ccc(C(=O)NCC3CC3)nc2C(=O)OC(C)OC(=O)C(C)C)cc1OC]
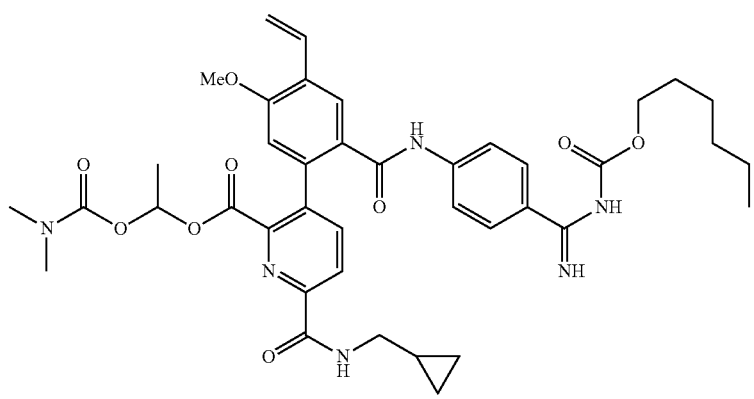 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)N(C)C)cc1OC]

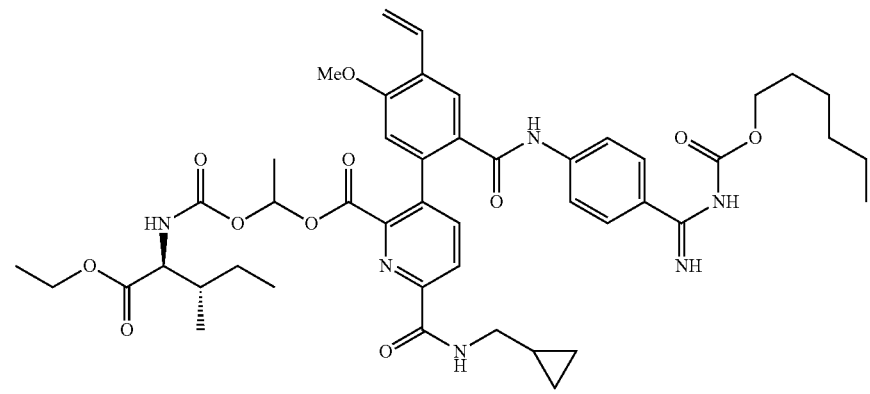 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)N[C@H](C(=O)OCC)[C@@H](C)CC)cc1OC]
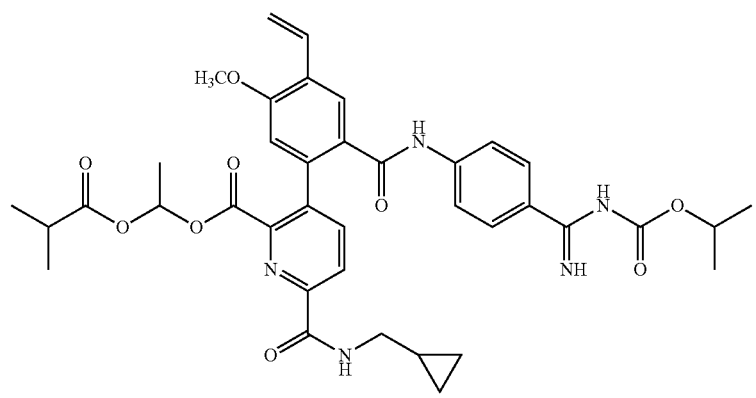 [SMILES: C=Cc1cc(C(=O)Nc2ccc(C(=N)NC(=O)OC(C)C)cc2)c(-c2ccc(C(=O)NCC3CC3)nc2C(=O)OC(C)OC(=O)C(C)C)cc1OC]
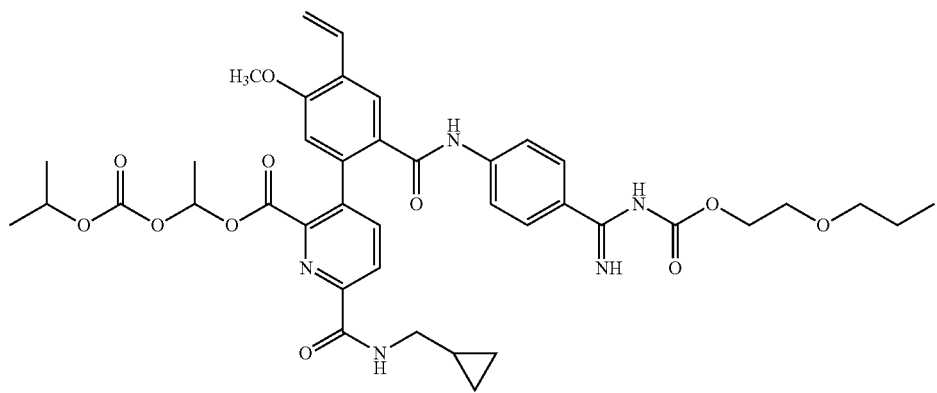 [SMILES: C=Cc1cc(C(=O)Nc2ccc(C(=N)NC(=O)OCCOCCC)cc2)c(-c2ccc(C(=O)NCC3CC3)nc2C(=O)OC(C)OC(=O)OC(C)C)cc1OC]
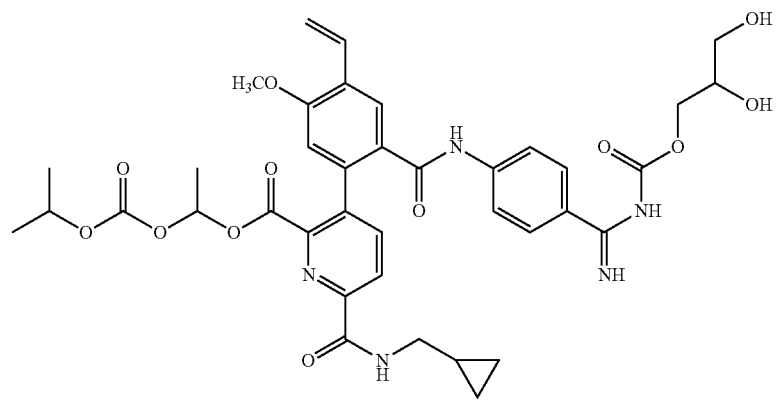 [SMILES: C=Cc1cc(C(=O)Nc2ccc(C(=N)NC(=O)OCC(O)CO)cc2)c(-c2ccc(C(=O)NCC3CC3)nc2C(=O)OC(C)OC(=O)OC(C)C)cc1OC]

-continued
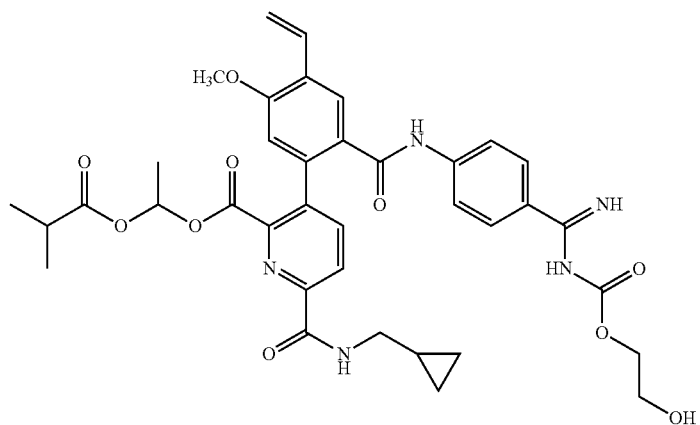 [SMILES: C=Cc1cc(C(=O)Nc2ccc(C(=N)NC(=O)OCCO)cc2)c(-c2ccc(C(=O)NCC3CC3)nc2C(=O)OC(C)OC(=O)C(C)C)cc1OC]
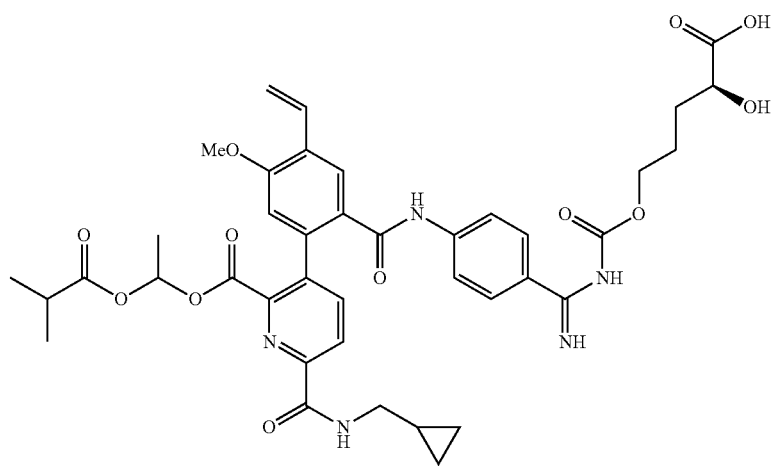 [SMILES: C=Cc1cc(C(=O)Nc2ccc(C(=N)NC(=O)OCCC[C@H](O)C(=O)O)cc2)c(-c2ccc(C(=O)NCC3CC3)nc2C(=O)OC(C)OC(=O)C(C)C)cc1OC]
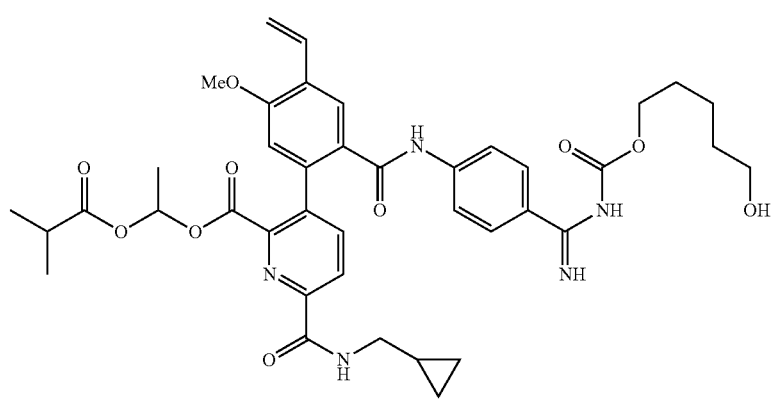 [SMILES: C=Cc1cc(C(=O)Nc2ccc(C(=N)NC(=O)OCCCCCO)cc2)c(-c2ccc(C(=O)NCC3CC3)nc2C(=O)OC(C)OC(=O)C(C)C)cc1OC]

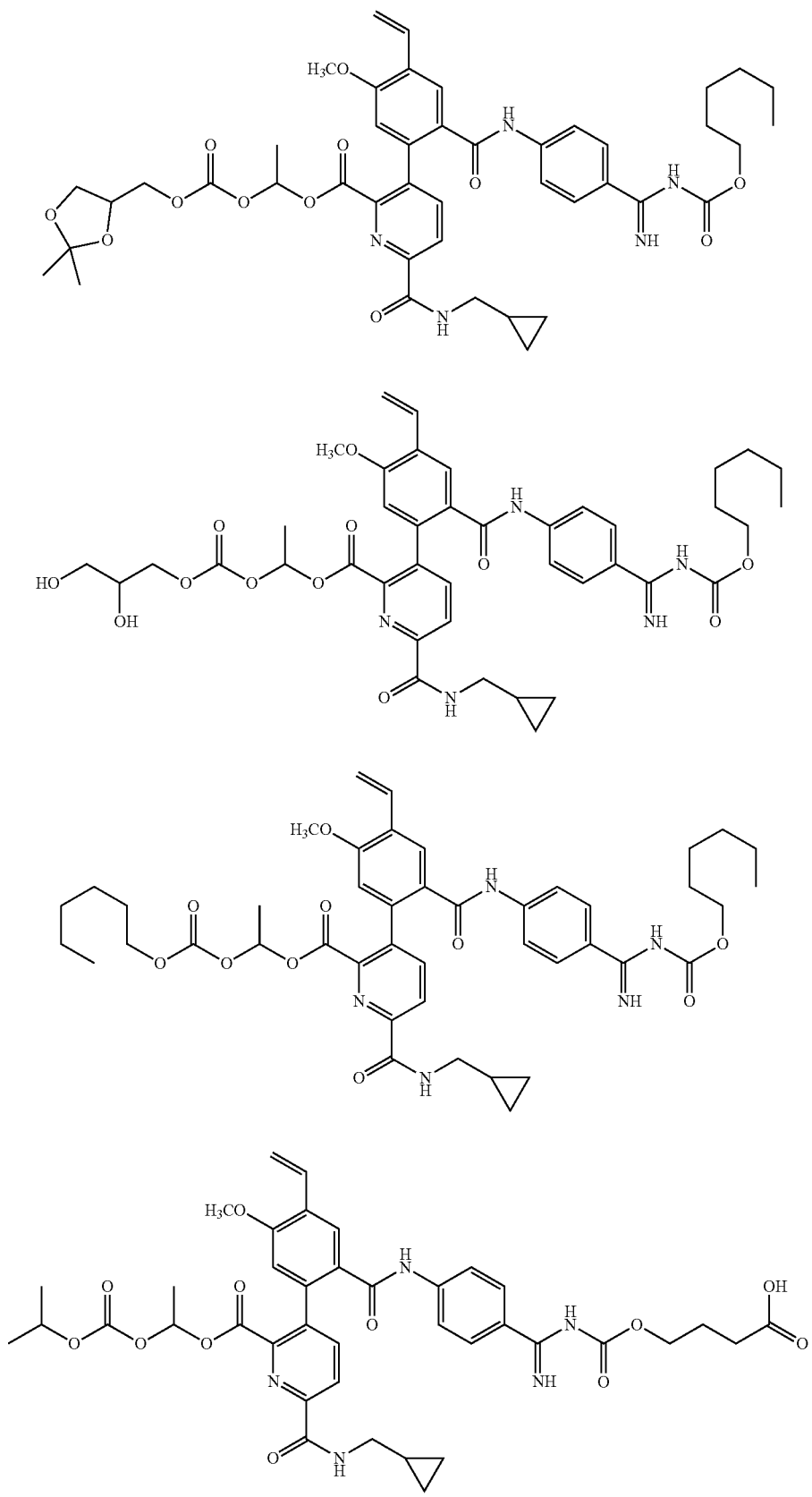

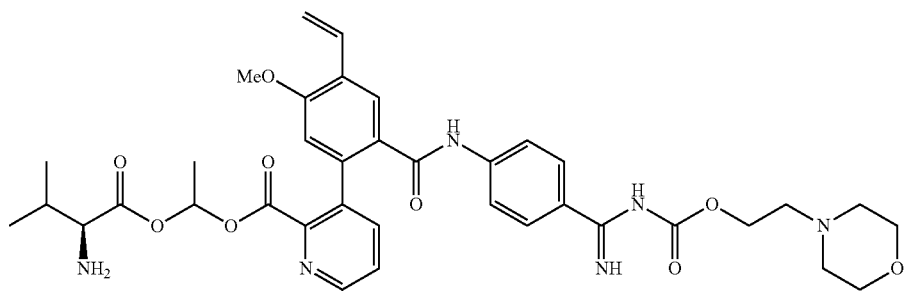
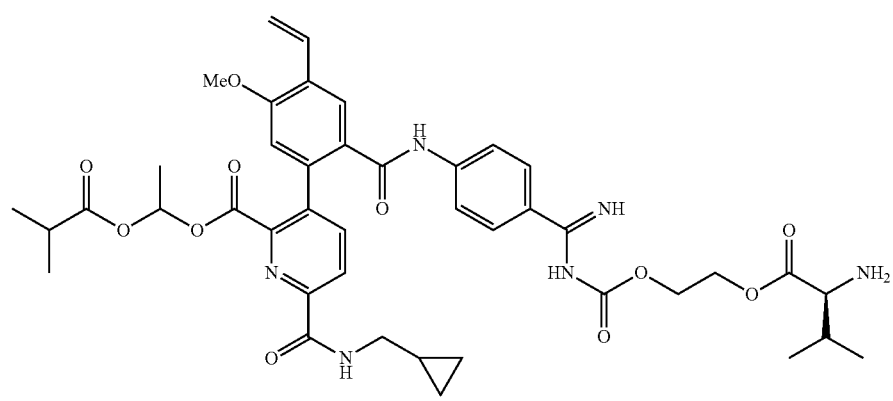 [SMILES: C=Cc1cc(C(=O)Nc2ccc(C(=N)NC(=O)OCCOC(=O)[C@@H](N)C(C)C)cc2)c(-c2ccc(C(=O)NCC3CC3)nc2C(=O)OC(C)OC(=O)C(C)C)cc1OC]
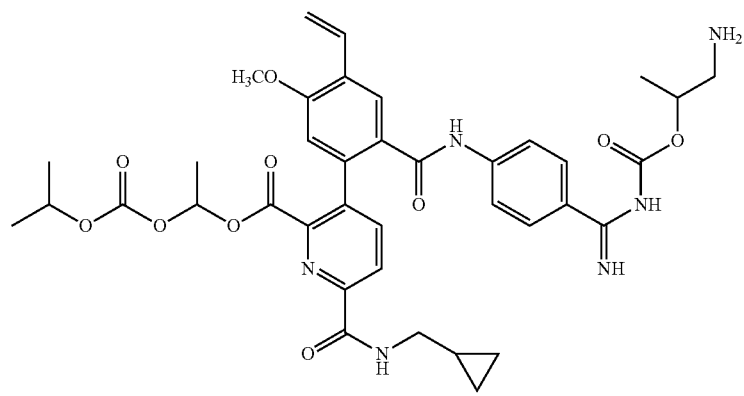 [SMILES: C=Cc1cc(C(=O)Nc2ccc(C(=N)NC(=O)OC(C)CN)cc2)c(-c2ccc(C(=O)NCC3CC3)nc2C(=O)OC(C)OC(=O)OC(C)C)cc1OC]
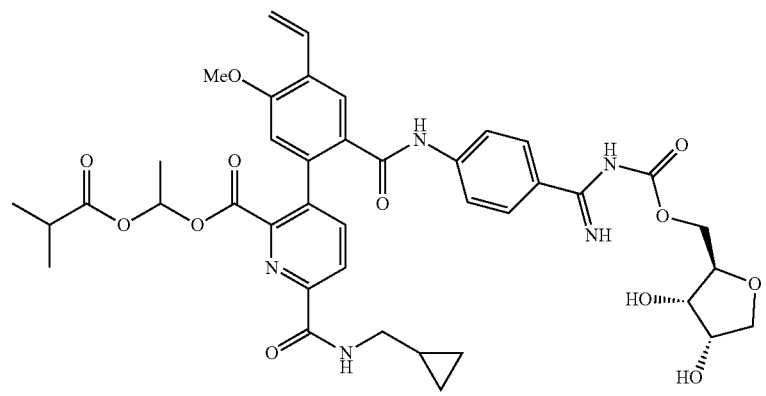 [SMILES: C=Cc1cc(C(=O)Nc2ccc(C(=N)NC(=O)OC[C@H]3OC[C@H](O)[C@@H]3O)cc2)c(-c2ccc(C(=O)NCC3CC3)nc2C(=O)OC(C)OC(=O)C(C)C)cc1OC]

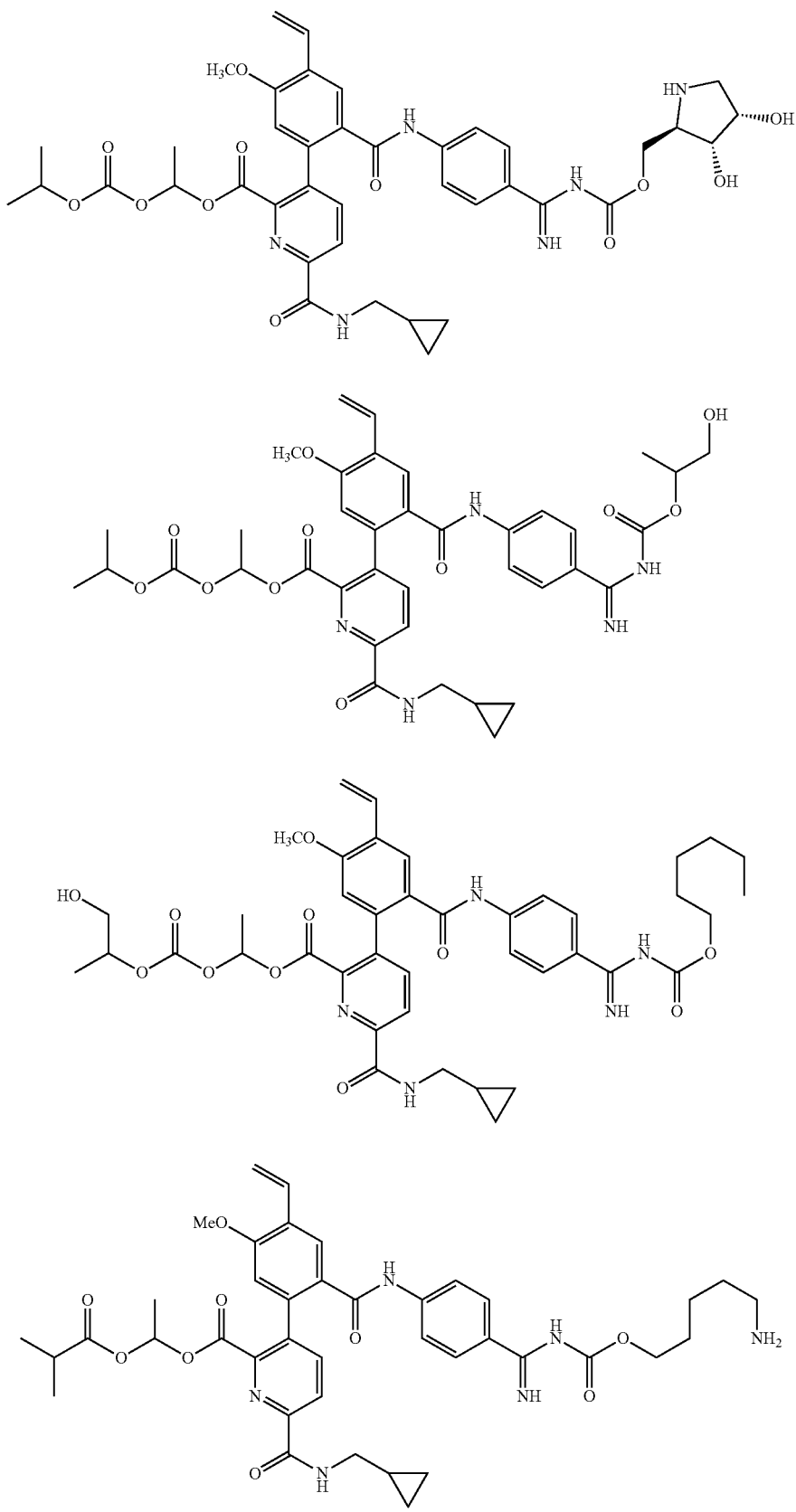

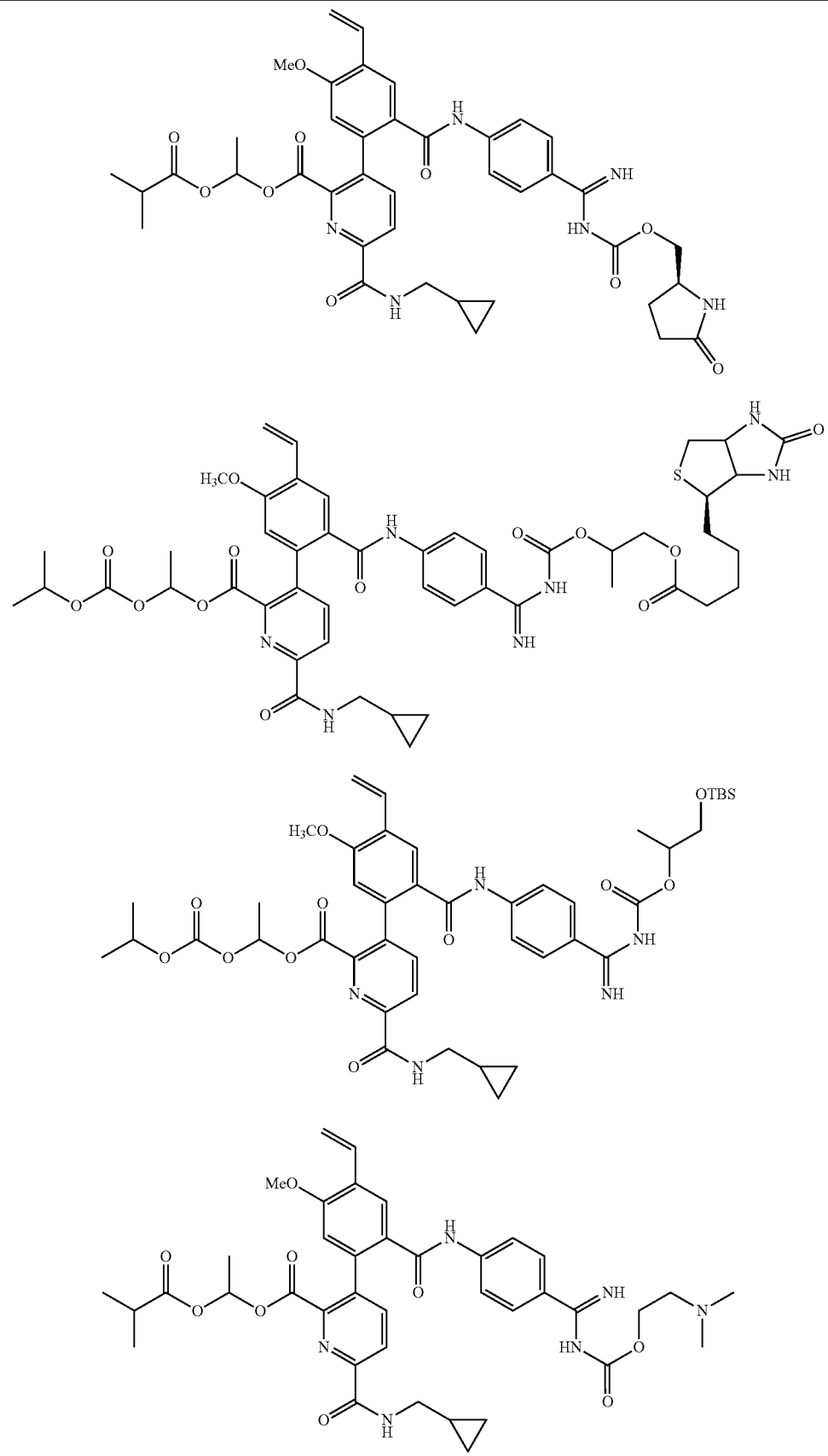

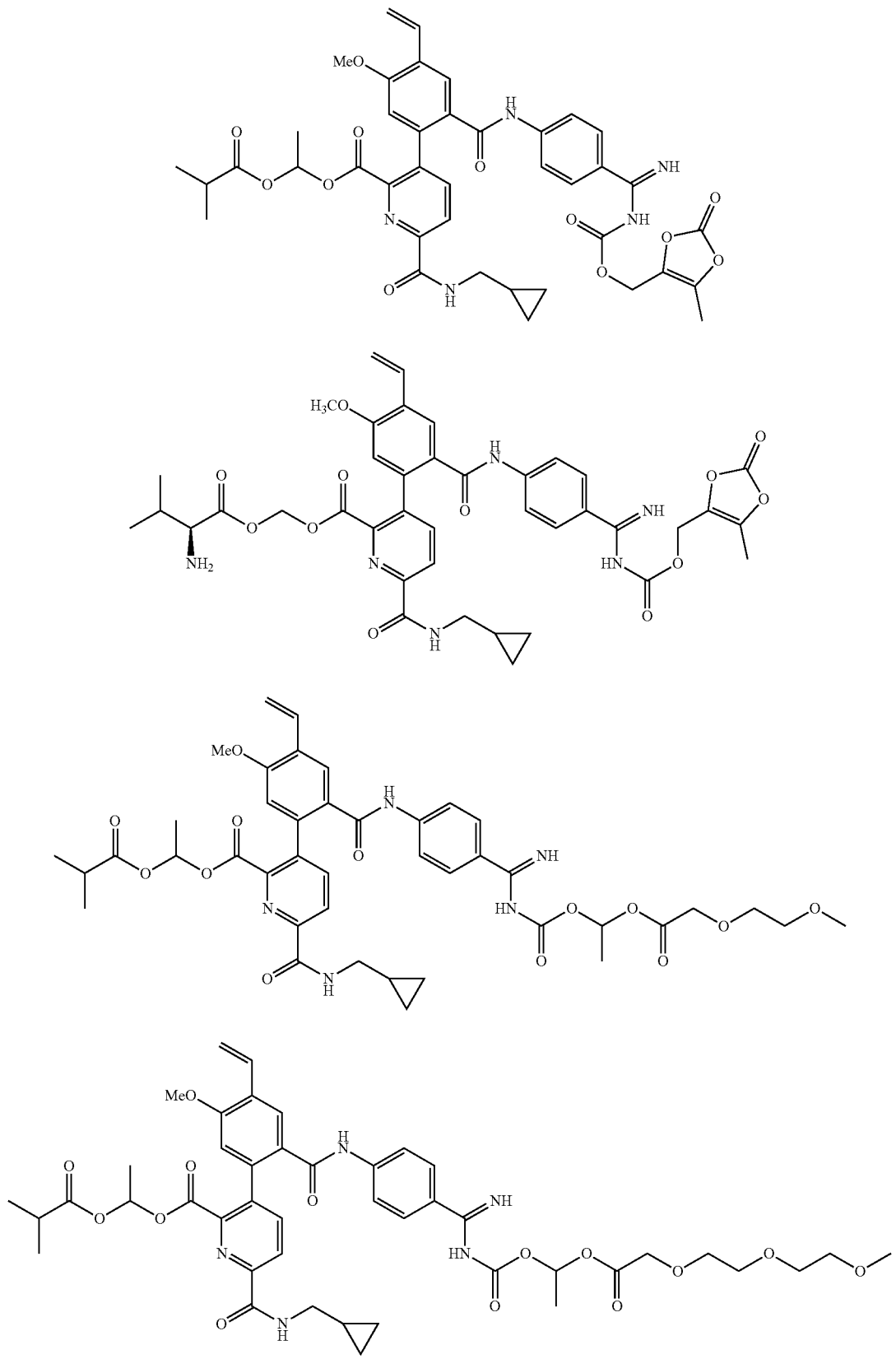

-continued
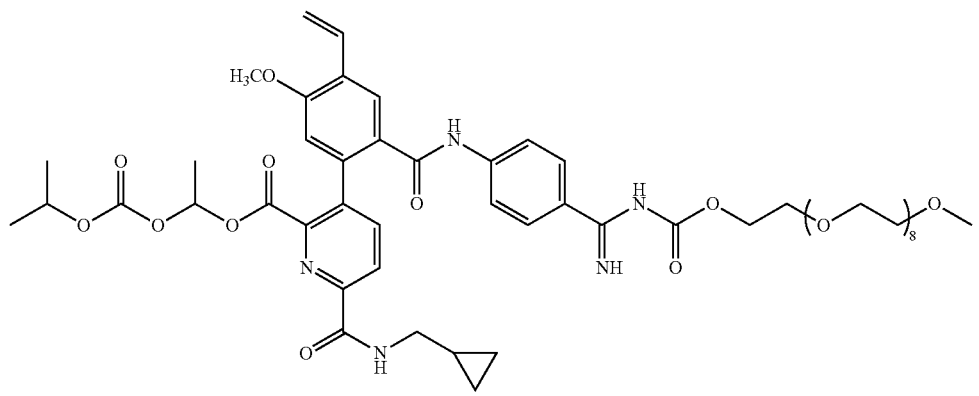
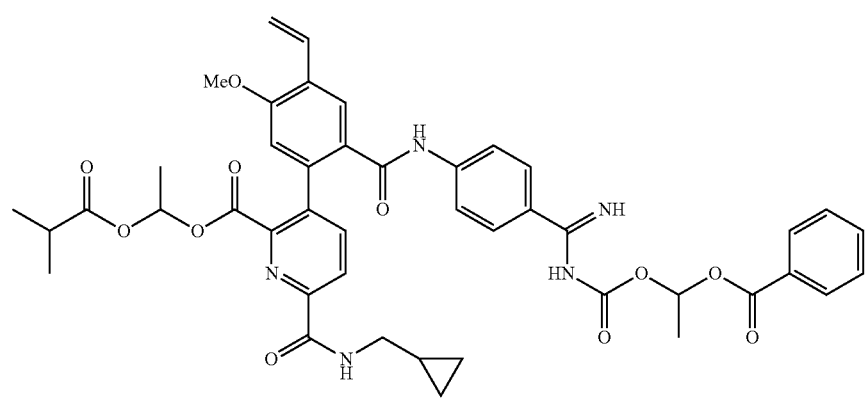 [SMILES: C=Cc1cc(C(=O)Nc2ccc(C(=N)NC(=O)OC(C)OC(=O)c3ccccc3)cc2)c(-c2ccc(C(=O)NCC3CC3)nc2C(=O)OC(C)OC(=O)C(C)C)cc1OC]
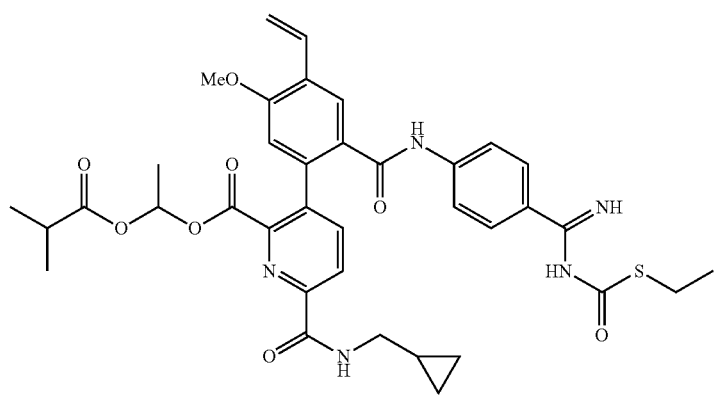 [SMILES: C=Cc1cc(C(=O)Nc2ccc(C(=N)NC(=O)SCC)cc2)c(-c2ccc(C(=O)NCC3CC3)nc2C(=O)OC(C)OC(=O)C(C)C)cc1OC]
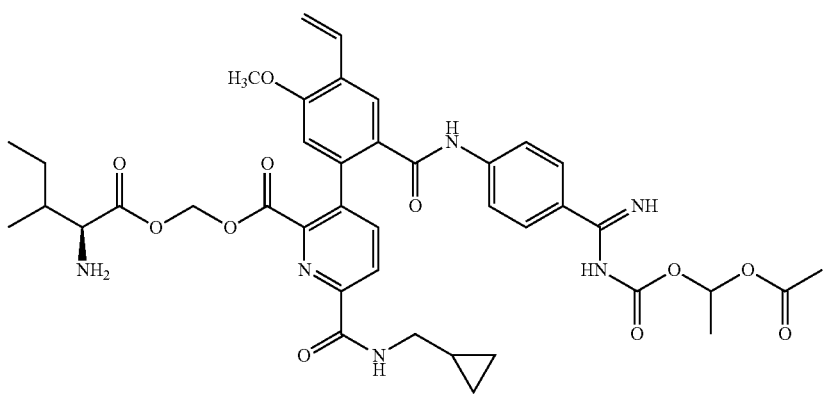 [SMILES: C=Cc1cc(C(=O)Nc2ccc(C(=N)NC(=O)OC(C)OC(C)=O)cc2)c(-c2ccc(C(=O)NCC3CC3)nc2C(=O)OCOC(=O)[C@@H](N)C(C)CC)cc1OC]

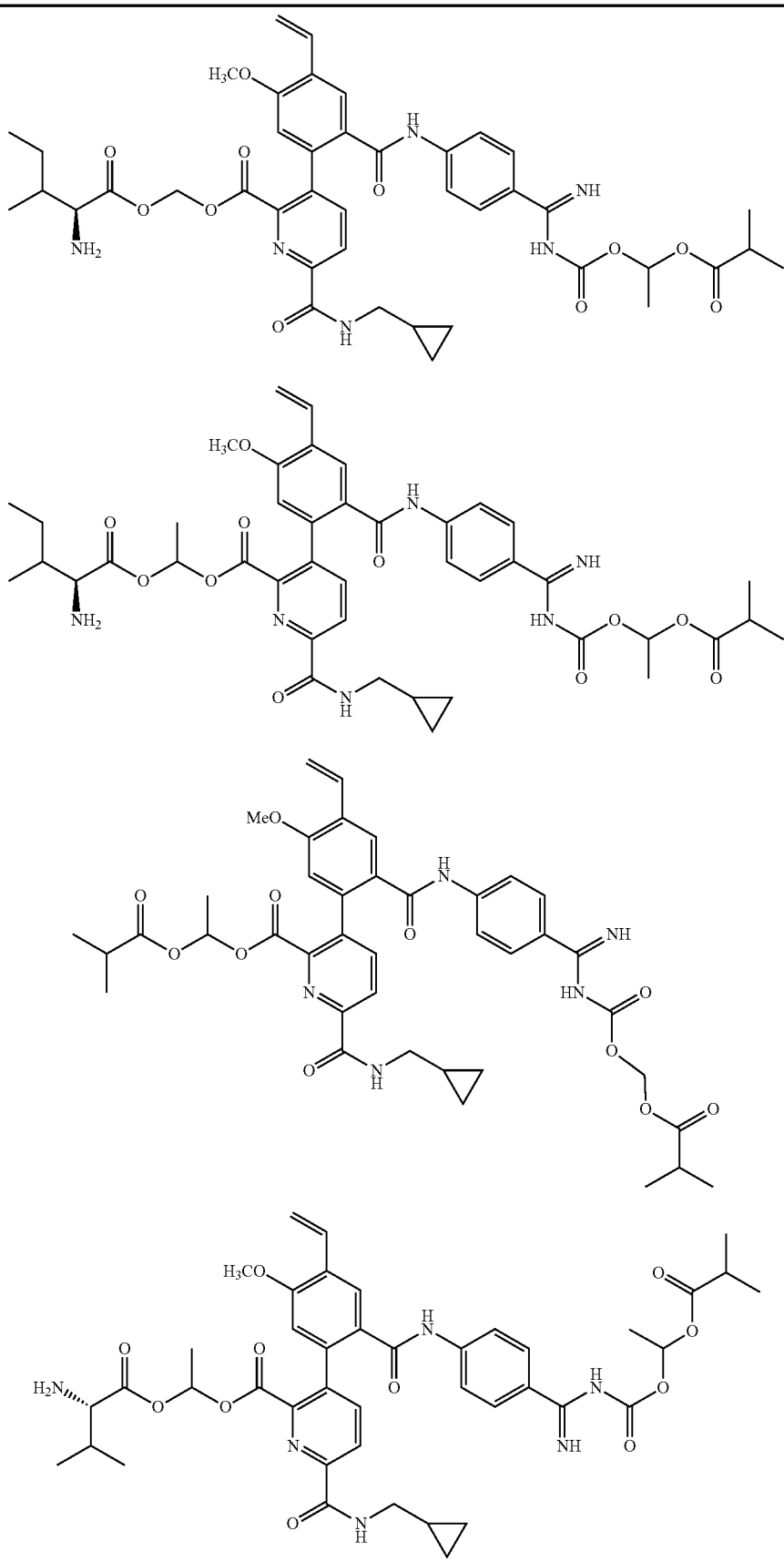

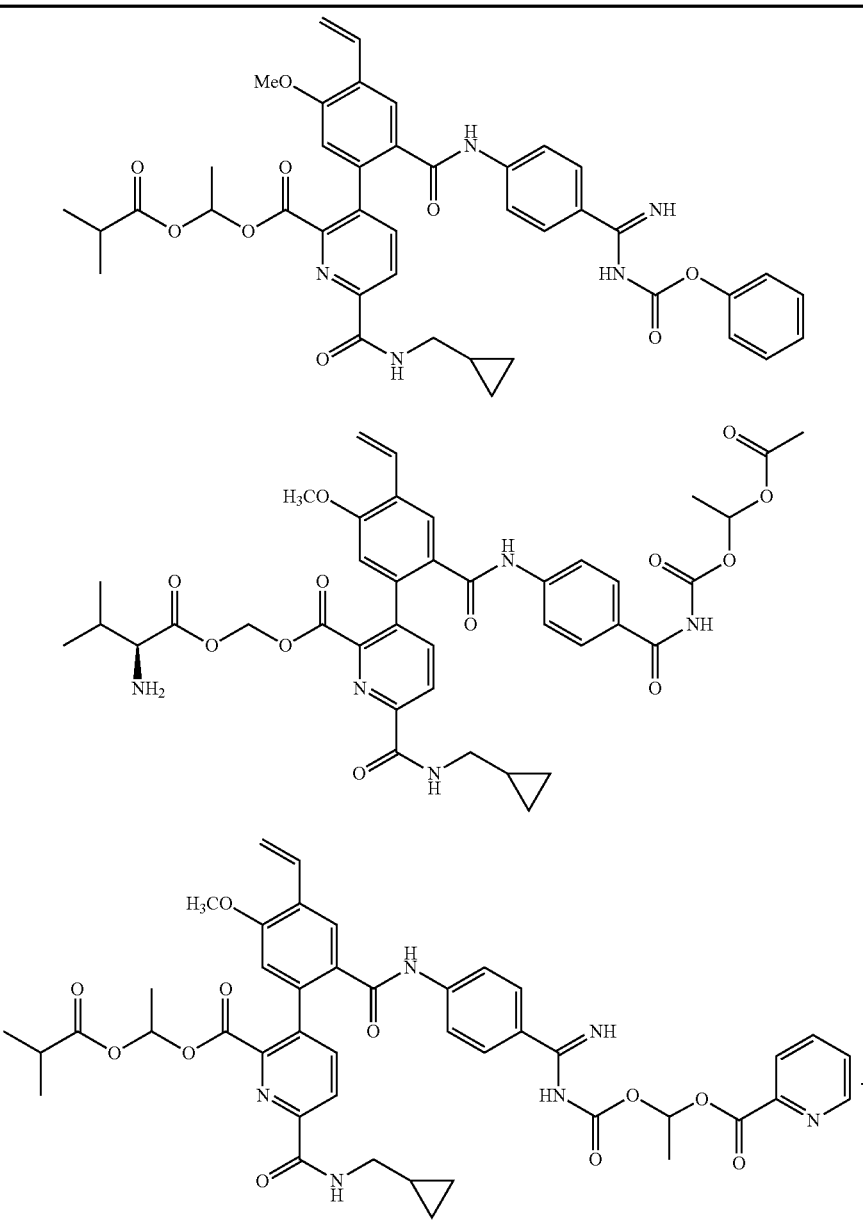
In further embodiments, the compound of formula (I) is selected from the following table:
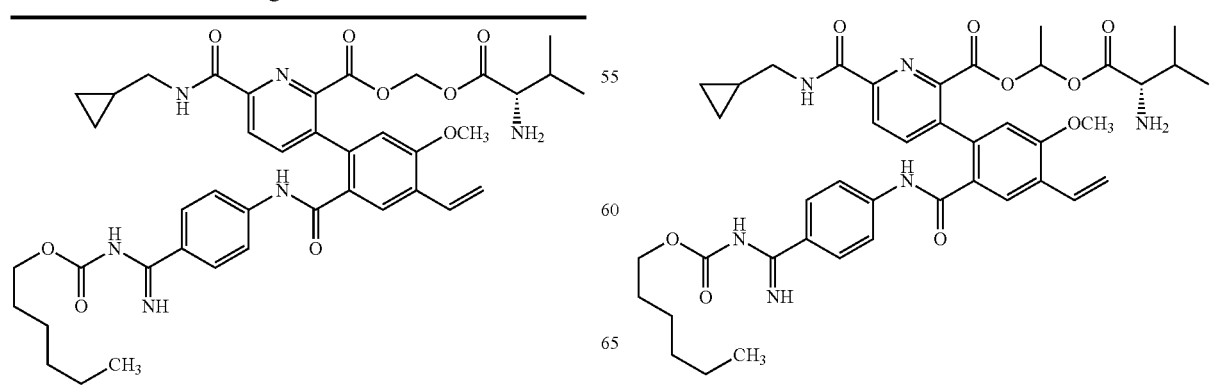

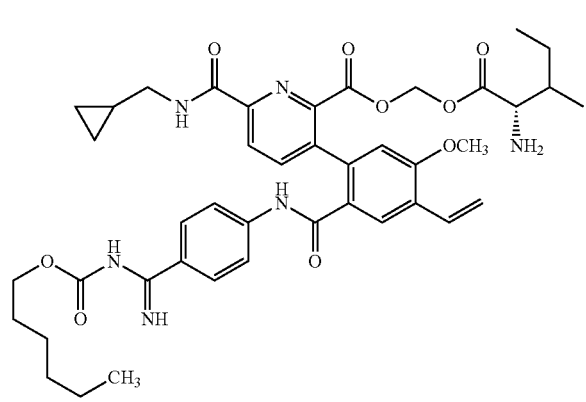 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)C(C)CC)cc1OC]
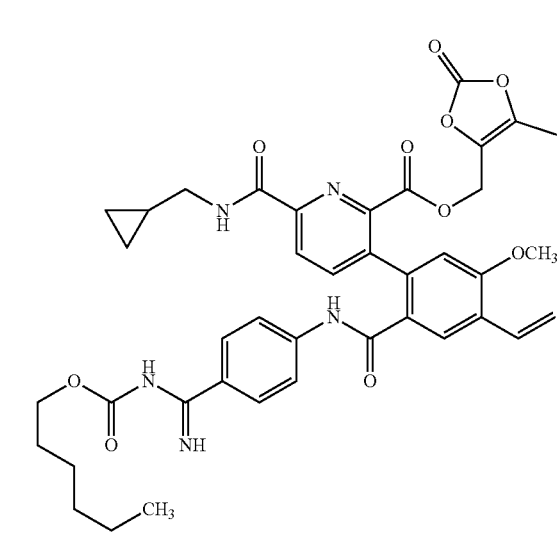 [SMILES: C=Cc1cc(C(=O)Nc2ccc(C(=N)NC(=O)OCCCCCC)cc2)c(-c2ccc(C(=O)NCC3CC3)nc2C(=O)OCc2oc(=O)oc2C)cc1OC]
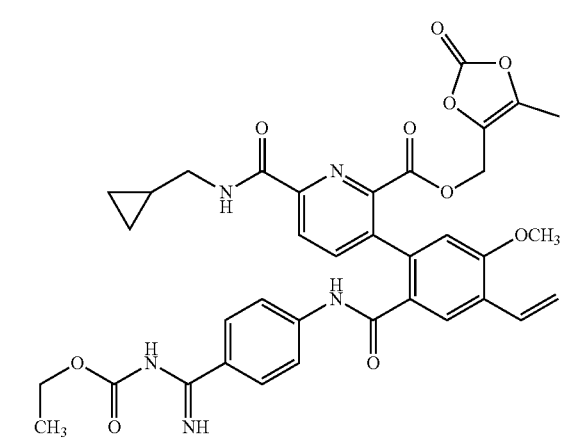 [SMILES: C=Cc1cc(C(=O)Nc2ccc(C(=N)NC(=O)OCC)cc2)c(-c2ccc(C(=O)NCC3CC3)nc2C(=O)OCc2oc(=O)oc2C)cc1OC]
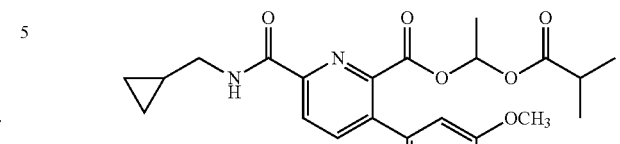
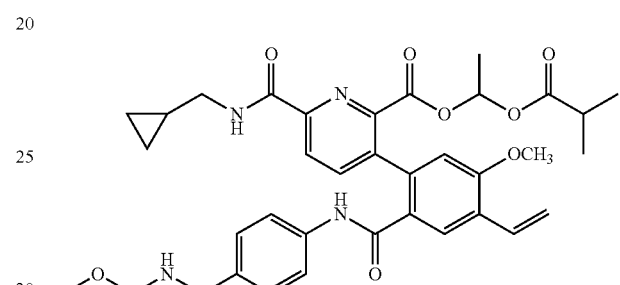

-continued

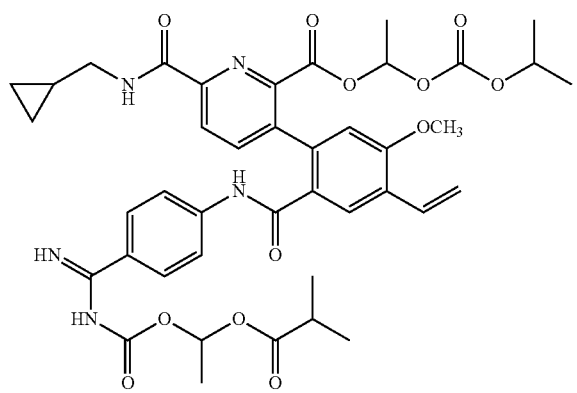 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OC(C)OC(=O)OC(C)C)cc1OC]

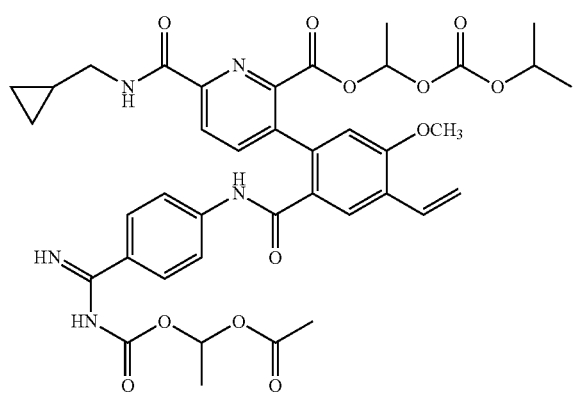 [SMILES: C=Cc1cc(C(=O)Nc2ccc(C(=N)NC(=O)OC(C)OC(C)=O)cc2)c(-c2ccc(C(=O)NCC3CC3)nc2C(=O)OC(C)OC(=O)OC(C)C)cc1OC]

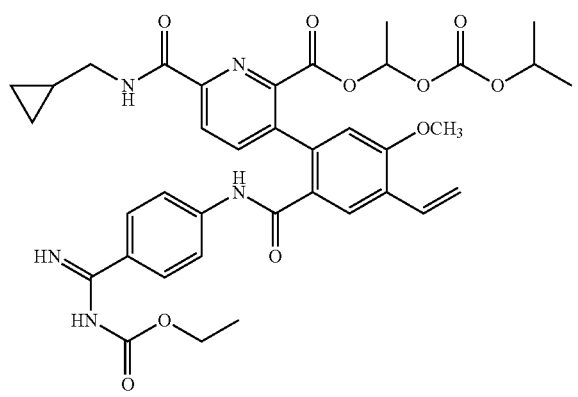 [SMILES: C=Cc1cc(C(=O)Nc2ccc(C(=N)NC(=O)OCC)cc2)c(-c2ccc(C(=O)NCC3CC3)nc2C(=O)OC(C)OC(=O)OC(C)C)cc1OC]

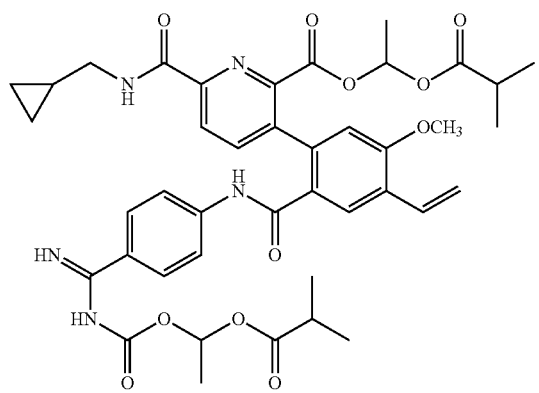 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OC(C)OC(=O)C(C)C)cc1OC]

-continued

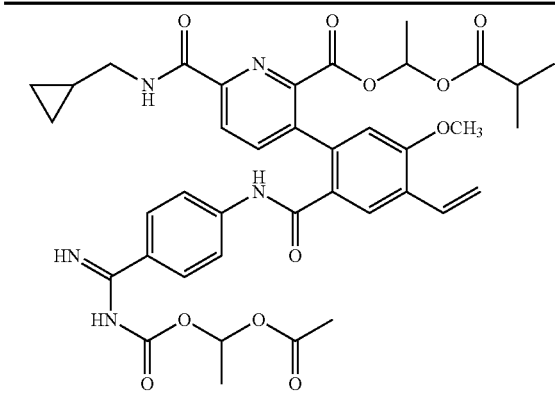

In other aspects, the invention provides compounds having the structure of Formula (II), or pharmaceutically acceptable salts thereof:

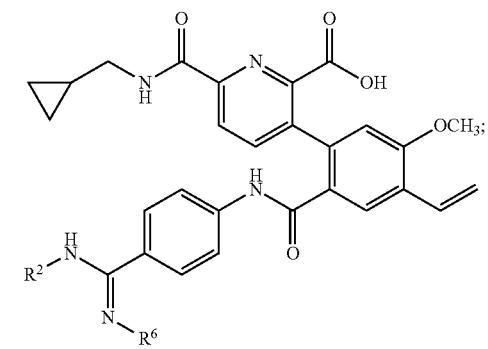

(II)

wherein, independently for each occurrence:

$R^2$ represents H, —OH, —C(O)OR$^4$, —C(O)SR$^4$, —C(O)O—[C(R$^c$)(R$_d$)]$_n$—O—C(O)-L-R$^5$, or

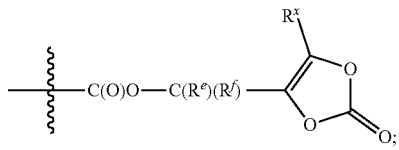

$R^6$ represents H, OH, —C(O)OR$^4$, —C(O)SR$^4$, —C(O)O—[C(R$^c$)(R$^d$)]$_n$—O—C(O)-L-R$^5$, or

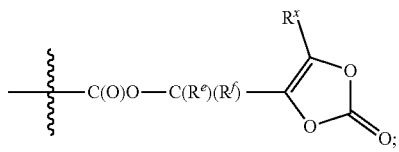

or $R^2$ and $R^6$, taken together with the atoms to which they are attached, form an optionally substituted 1,2,4-oxadiazol-5-one group;

L, independently for each occurrence, is a bond or represents O, S, NH, or N(CH$_3$);

R$^c$, R$^d$, R$^e$, and R$^f$ each independently for each occurrence represent H or (C$_1$-C$_6$)alkyl;

$R^4$, independently for each occurrence, represents (C$_1$-C$_6$)alkyl, cycloalkyl, heterocycloalkyl, aryl, or heteroaryl, optionally substituted with one or more substituents each independently selected from the group consisting of —C(O)OH, —C(O)O((C$_1$-C$_6$)alkyl), (C$_1$-C$_6$)alkoxy, hydroxyl, oxo, heterocycloalkyl, amino, $(C_1-C_6)$alkylamino, di$((C_1-C_6)$alkyl)amino, and silyl ether;

$R^5$, independently for each occurrence, represents $(C_1-C_6)$ alkyl, aryl, or heteroaryl, optionally substituted with one or more substituents each independently selected from the group consisting of amino, heterocycloalkyl, $(C_1-C_6)$ alkoxy optionally substituted by $(C_1-C_6)$alkoxy or a polyether chain; and n represents 1 or 2;

provided that at least one of $R^2$ and $R^6$ is not H; and the compound of formula (II) is not

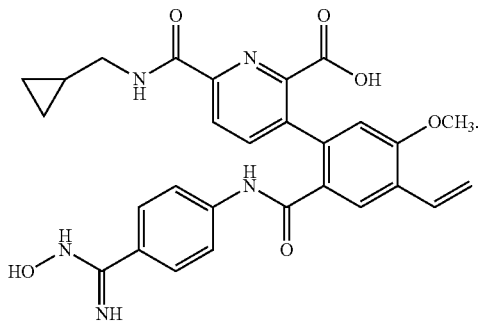 [SMILES: C=Cc1cc(C(=O)Nc2ccc(C(=N)NO)cc2)c(-c2ccc(C(=O)NCC3CC3)nc2C(=O)O)cc1OC]

In certain embodiments, $R^2$ represents —C(O)OR$^4$ or —C(O)O—[C(R$^c$)(R$^d$)]$_n$—O—C(O)-L-R$^5$.

For example, $R^2$ may represent —C(O)OR$^4$. In certain such embodiments, $R^4$ represents ethyl, isopropyl, or hexyl. In alternative such embodiments, $R^4$ represents $(C_1-C_6)$ alkyl, substituted with amino, hydroxy, or $(C_1-C_6)$alkoxy.

Alternatively, $R^2$ represents —C(O)O—[C(R$^c$)(R$_d$)]$_n$—O—C(O)-L-R$^5$, and n is 1. In certain such embodiments, at least one of R and R$^d$ is H. In further certain such embodiments, at least one of R and R$^d$ is methyl.

In certain such embodiments, L is a bond.

In other such embodiments, $R^5$ represents $(C_1-C_4)$alkyl. Alternatively, $R^5$ may represent $(C_1-C_4)$alkyl, substituted by amino.

In certain embodiments, $R^6$ represents H.

Alternatively, $R^2$ and $R^6$, taken together with the atoms to which they are attached, may form a 1,2,4-oxadiazol-5-one group.

In certain embodiments, the compound of formula (II) is selected from the following table:

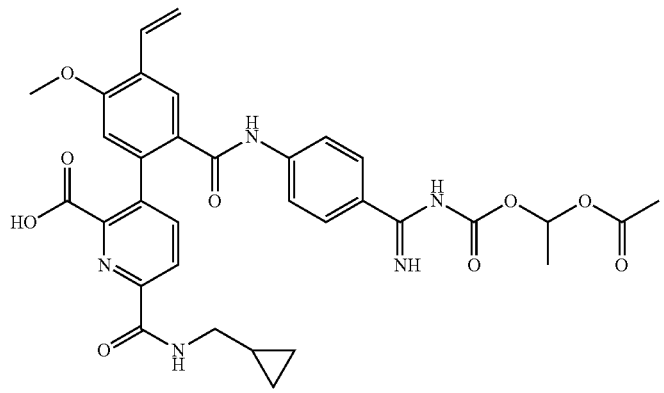 [SMILES: C=Cc1cc(C(=O)Nc2ccc(C(=N)NC(=O)OC(C)OC(C)=O)cc2)c(-c2ccc(C(=O)NCC3CC3)nc2C(=O)O)cc1OC]

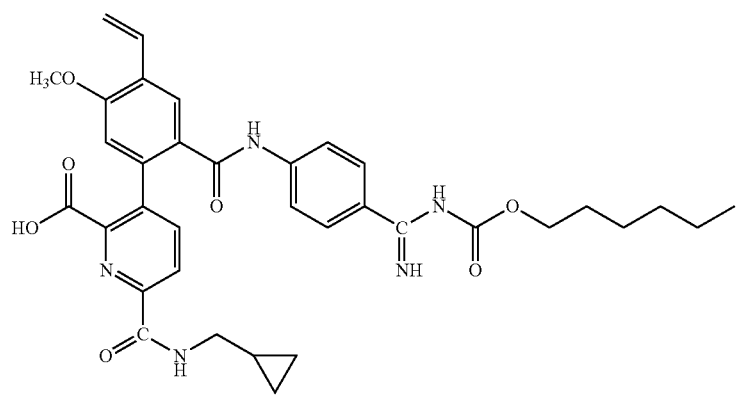 [SMILES: C=Cc1cc(C(=O)Nc2ccc(C(=N)NC(=O)OCCCCCC)cc2)c(-c2ccc(C(=O)NCC3CC3)nc2C(=O)O)cc1OC]

-continued
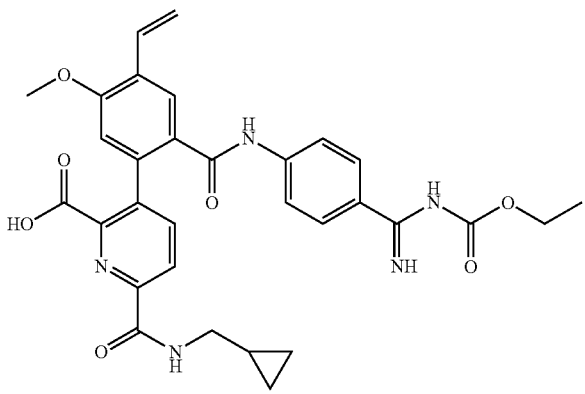 [SMILES: C=Cc1cc(C(=O)Nc2ccc(C(=N)NC(=O)OCC)cc2)c(-c2ccc(C(=O)NCC3CC3)nc2C(=O)O)cc1OC]
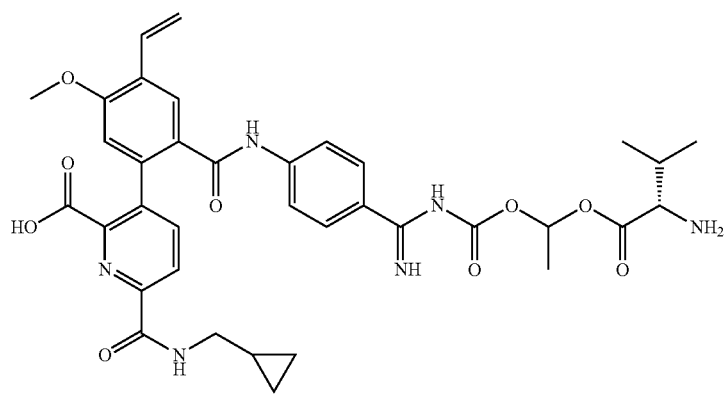 [SMILES: C=Cc1cc(C(=O)Nc2ccc(C(=N)NC(=O)OC(C)OC(=O)[C@@H](N)C(C)C)cc2)c(-c2ccc(C(=O)NCC3CC3)nc2C(=O)O)cc1OC]
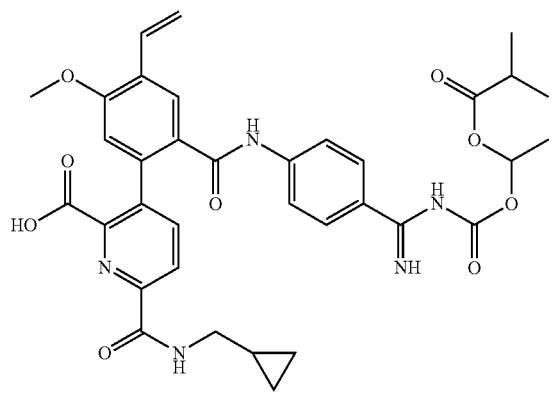 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)O)cc1OC]
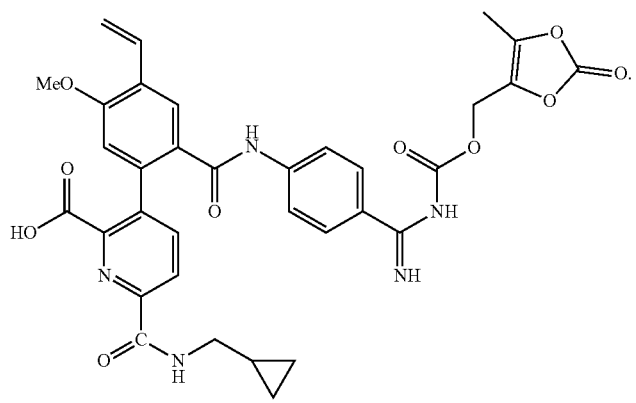 [SMILES: C=Cc1cc(C(=O)Nc2ccc(C(=N)NC(=O)OCc3oc(=O)oc3C)cc2)c(-c2ccc(C(=O)NCC3CC3)nc2C(=O)O)cc1OC]

In other aspects, the invention provides compounds having the structure of Formula (III), or pharmaceutically acceptable salts thereof:

(III)

[Structure of Formula (III)]

wherein, independently for each occurrence:

Z represents OR¹ or NH(OH);

R¹ represents

[Structure]

,

[Structure]

,

—C(Rᵃ)(Rᵇ)—O—C(O)-M-R³, or (C₂-C₆)alkyl optionally substituted by hydroxyl or heterocycloalkyl;

Rᵃ represents H or (C₁-C₆)alkyl;

Rᵇ represents H or (C₁-C₆)alkyl;

Rˣ represents H or (C₁-C₆)alkyl;

M is a bond or represents O, S, NH, or N(CH₃);

R³ represents (C₁-C₆)alkyl, aralkyl, or cycloalkyl, optionally substituted with one or more substituents each independently selected from the group consisting of amino, hydroxyl, optionally substituted heterocycloalkyl, —C(O)OH, and —C(O)O((C₁-C₆)alkyl);

provided that the compound of formula (III) is not selected from the following table:

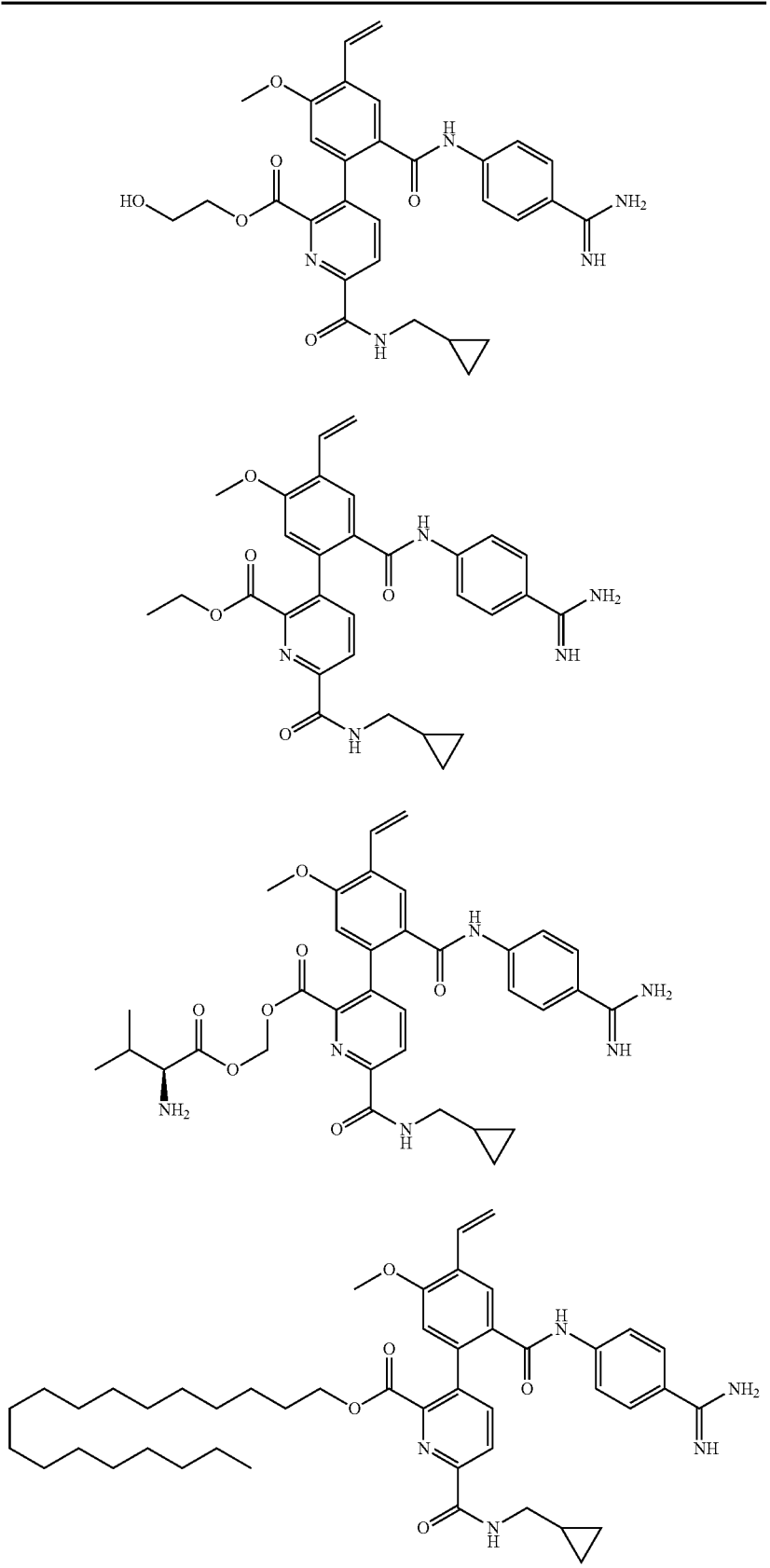

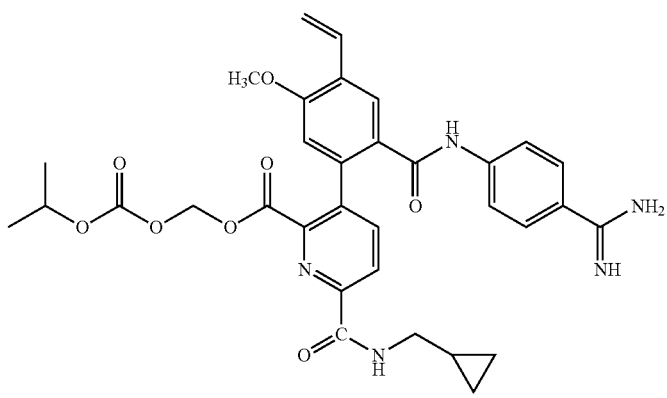 [SMILES: C=Cc1cc(C(=O)Nc2ccc(C(=N)N)cc2)c(-c2ccc(C(=O)NCC3CC3)nc2C(=O)OCOC(=O)OC(C)C)cc1OC]
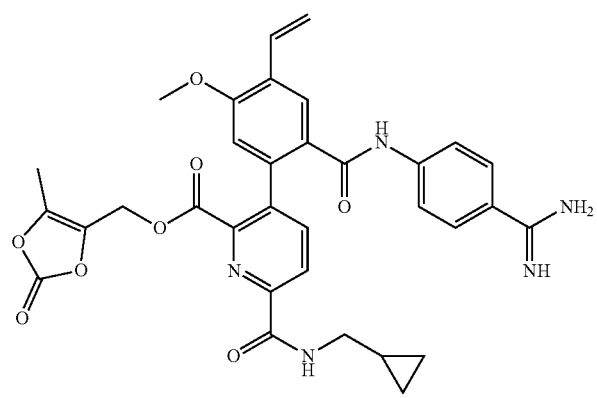 [SMILES: C=Cc1cc(C(=O)Nc2ccc(C(=N)N)cc2)c(-c2ccc(C(=O)NCC3CC3)nc2C(=O)OCc2oc(=O)oc2C)cc1OC]
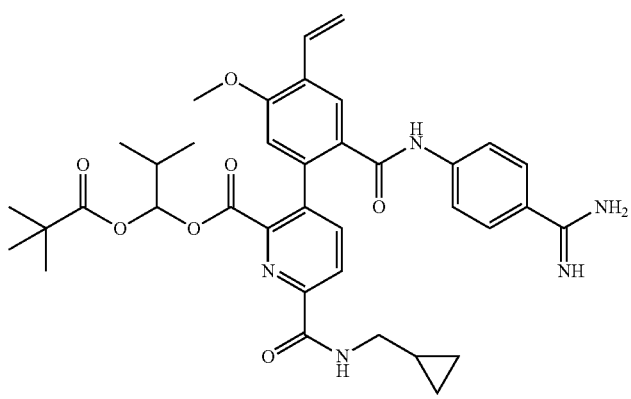 [SMILES: C=Cc1cc(C(=O)Nc2ccc(C(=N)N)cc2)c(-c2ccc(C(=O)NCC3CC3)nc2C(=O)OC(OC(=O)C(C)(C)C)C(C)C)cc1OC]
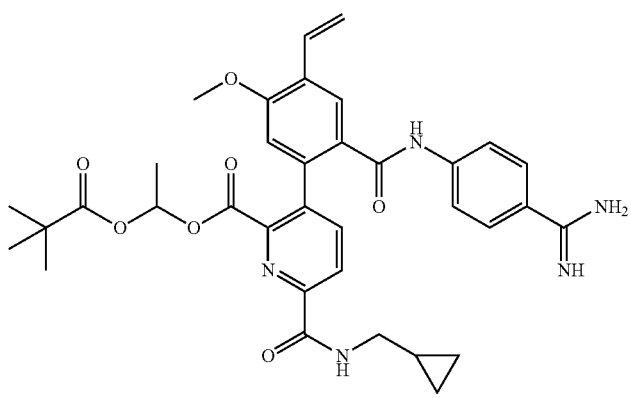 [SMILES: C=Cc1cc(C(=O)Nc2ccc(C(=N)N)cc2)c(-c2ccc(C(=O)NCC3CC3)nc2C(=O)OC(C)OC(=O)C(C)(C)C)cc1OC]

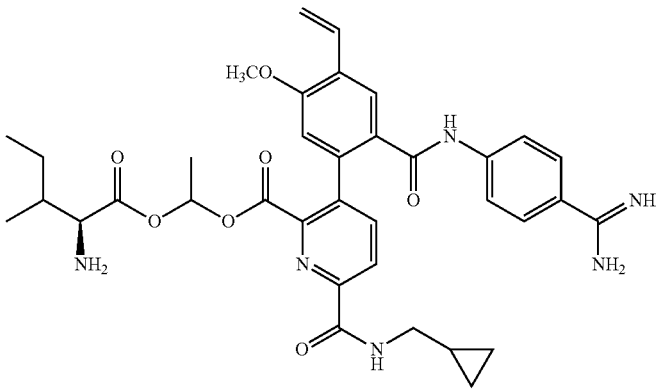 [SMILES: C=Cc1cc(C(=O)Nc2ccc(C(=N)N)cc2)c(-c2ccc(C(=O)NCC3CC3)nc2C(=O)OC(C)OC(=O)[C@@H](N)C(C)CC)cc1OC]

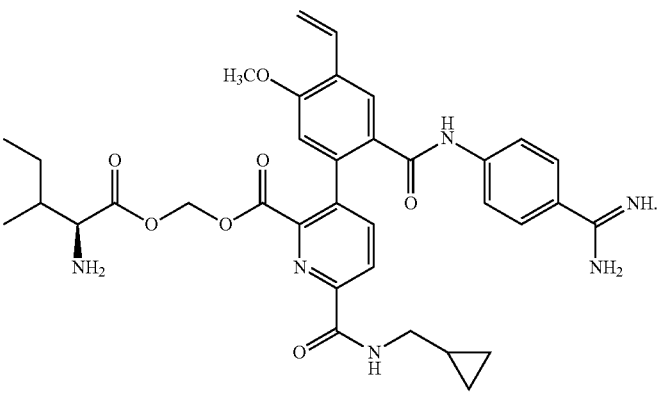 [SMILES: C=Cc1cc(C(=O)Nc2ccc(C(=N)N)cc2)c(-c2ccc(C(=O)NCC3CC3)nc2C(=O)OCOC(=O)[C@@H](N)C(C)CC)cc1OC]

In certain embodiments of the compound of formula (III), Z represents $OR^1$.

In certain embodiments, $R^1$ represents

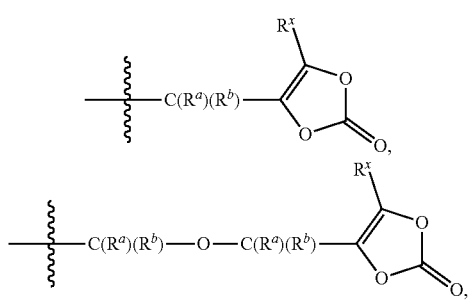

or $-C(R^a)(R^b)-O-C(O)-M-R^3$.

In certain embodiments, $R^a$ and $R^b$ each independently represent H or methyl.

In certain such embodiments, at least one of $R^a$ and $R^b$ is H. In further such embodiments, at least one of $R^a$ and $R^b$ is methyl.

In certain embodiments, $R^1$ represents $-C(R^a)(R^b)-O-C(O)-M-R^3$.

In certain such embodiments, M is a bond. Alternatively, M may be O.

In further such embodiments, $R^3$ represents $(C_1-C_6)$alkyl, for example, $(C_3-C_5)$alkyl.

In alternative embodiments, $R^3$ represents cycloalkyl.

In still further alternative embodiments, $R^3$ represents aralkyl, optionally substituted with $-NH_2$.

In other alternative embodiments, $R^3$ represents $(C_1-C_6)$ alkyl, substituted with $-NH_2$ or $-OH$. For example, $R^3$ may represent $(C_3-C_5)$alkyl, substituted with $-NH_2$ or OH, or $(C_3-C_5)$alkyl, substituted with $-NH_2$.

In certain other embodiments, $R^1$ represents

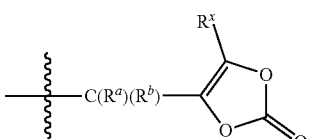

In such embodiments, $R^x$ may represent H or methyl.

Alternatively, $R^1$ represents $(C_3-C_6)$alkyl optionally substituted with hydroxyl.

In some embodiments, the compound of formula (III) may be selected from the following table:

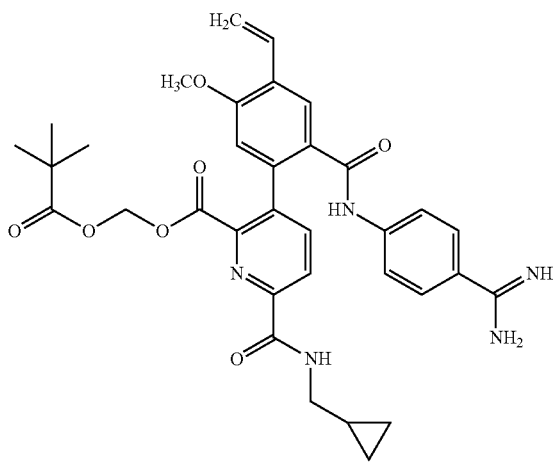 [SMILES: C=Cc1cc(C(=O)Nc2ccc(C(=N)N)cc2)c(-c2ccc(C(=O)NCC3CC3)nc2C(=O)OCOC(=O)C(C)(C)C)cc1OC]
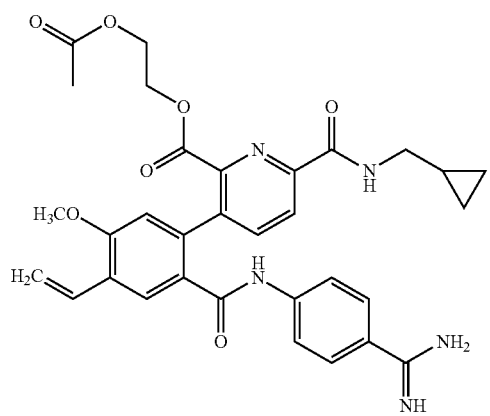 [SMILES: C=Cc1cc(C(=O)Nc2ccc(C(=N)N)cc2)c(-c2ccc(C(=O)NCC3CC3)nc2C(=O)OCCOC(C)=O)cc1OC]
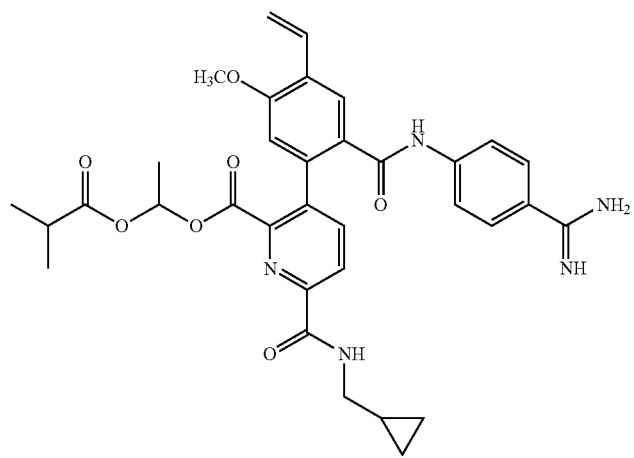 [SMILES: C=Cc1cc(C(=O)Nc2ccc(C(=N)N)cc2)c(-c2ccc(C(=O)NCC3CC3)nc2C(=O)OC(C)OC(=O)C(C)C)cc1OC]

-continued
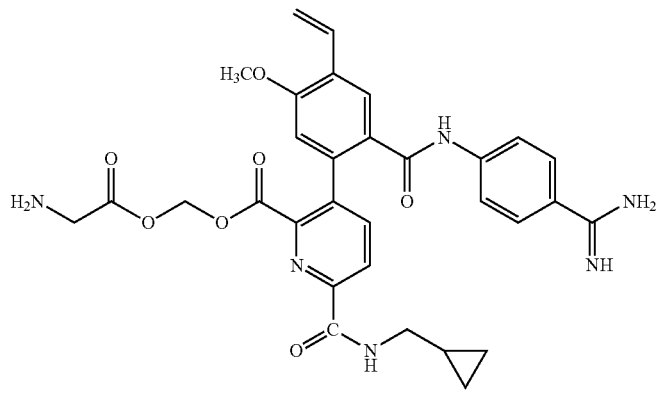 [SMILES: C=Cc1cc(C(=O)Nc2ccc(C(=N)N)cc2)c(-c2ccc(C(=O)NCC3CC3)nc2C(=O)OCOC(=O)CN)cc1OC]
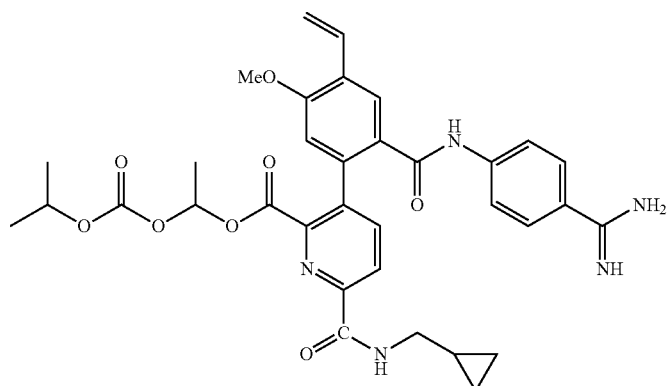
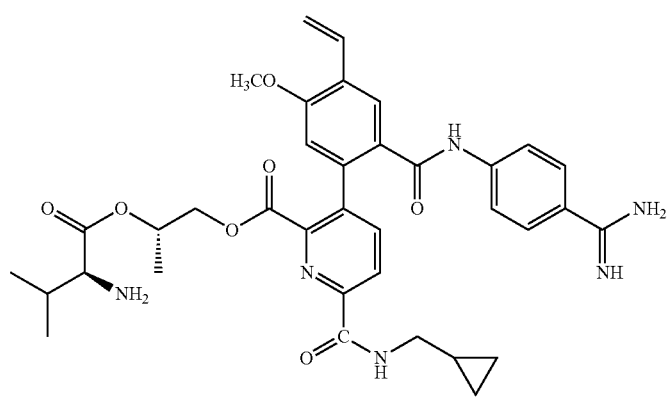 [SMILES: C=Cc1cc(C(=O)Nc2ccc(C(=N)N)cc2)c(-c2ccc(C(=O)NCC3CC3)nc2C(=O)OC[C@H](C)OC(=O)[C@@H](N)C(C)C)cc1OC]
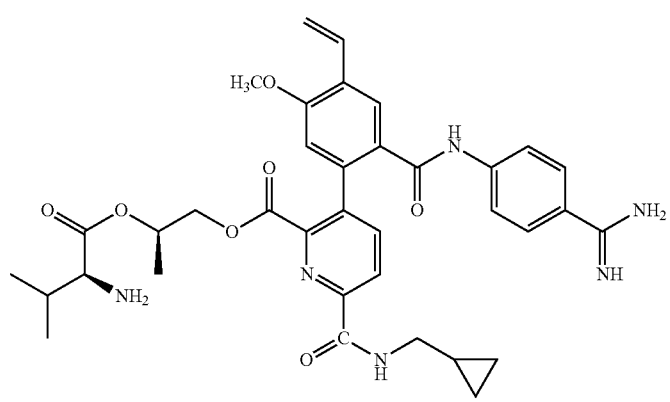 [SMILES: C=Cc1cc(C(=O)Nc2ccc(C(=N)N)cc2)c(-c2ccc(C(=O)NCC3CC3)nc2C(=O)OC[C@@H](C)OC(=O)[C@@H](N)C(C)C)cc1OC]

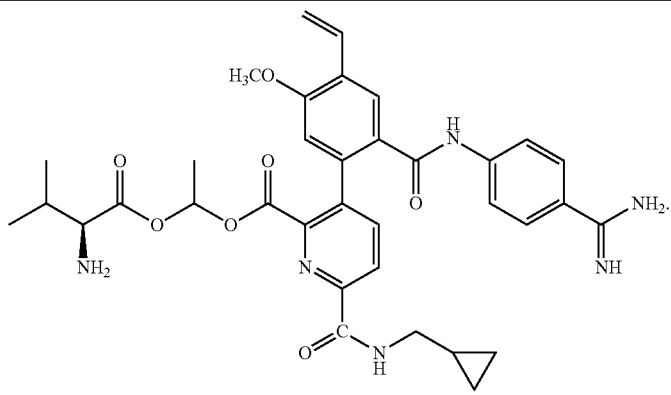

Pharmaceutical Compositions

The invention provides pharmaceutical compositions, each comprising one or more compounds of the invention and a pharmaceutically acceptable carrier. In certain embodiments, the pharmaceutical composition comprises a compound of the invention and a pharmaceutically acceptable carrier. In certain embodiments, the pharmaceutical composition comprises a plurality of compounds of the invention and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of a disease or condition characterized by aberrant kallikrein activity.

Pharmaceutical compositions of the invention can be prepared by combining one or more compounds of the invention with a pharmaceutically acceptable carrier and, optionally, one or more additional pharmaceutically active agents.

Methods of Use

The present invention provides compounds that are useful for treating or preventing a disease or condition characterized by aberrant activity of kallikrein.

In certain aspects, the invention provides a compound of the invention, or a pharmaceutically acceptable salt thereof, for use as a medicament.

In certain aspects, the invention provides methods of treating acquired angioedema or hereditary angioedema. The method includes the step of administering to a subject in need thereof a therapeutically effective amount of a compound of the invention, or a pharmaceutically acceptable salt thereof.

In certain embodiments, the subject has acquired angioedema. In alternative embodiments, the subject has hereditary angioedema.

In certain embodiments, the subject has hereditary angioedema, and the hereditary angioedema is Type I hereditary angioedema. Alternatively, the hereditary angioedema may be Type II hereditary angioedema. Alternatively still, the hereditary angioedema may be Type III hereditary angioedema.

Acquired Angioedema (AAE) (Caldwell J R, et al. Clin Immunol Immunopathol. 1972; 1:39-52) is characterized in several ways, including by acquired deficiency of C1 inhibitor (C1-INH), hyperactivation of the classical pathway of human complement and angioedema symptoms mediated by bradykinin released by inappropriate activation of the contact-kinin system. AAE may be present in two forms, AAE type 1 (which is normally associated with another disease) and AAE type II, which is normally associated with an autoimmune disease. AAE may be caused by a number of factors, including, but not limited to, autoimmune diseases (for example, the production of anti-C1INH antibodies) or by an acquired mutation in C1 INH. Furthermore, the compounds of the invention may be used to treat side effects of angiotensin converting enzyme (ACE) inhibitor treatments. ACE inhibitors block the major pathway for breakdown of bradykinin. Inhibiting kallikrein formation through the use of the compounds of the invention reduces the formation of bradykinin.

In certain aspects, the invention provides methods of treating a disease or condition associated with aberrant activity of kallikrein. The method includes the step of administering to a subject in need thereof a therapeutically effective amount of a compound of the invention, or a pharmaceutically acceptable salt thereof, thereby treating or preventing the disease or condition characterized by aberrant activity of kallikrein. By reducing kallikrein activity in the subject, the disease or condition characterized by aberrant kallikrein activity is treated.

Alternatively, in certain aspects, the invention provides a compound of the invention, or a pharmaceutically acceptable salt thereof, for treatment of a disease or condition characterized by aberrant kallikrein activity.

Alternatively, in certain aspects, the invention provides the use of a compound of the invention, or a pharmaceutically acceptable salt thereof, for the manufacture of a medicament for use in treatment of a disease or condition characterized by aberrant kallikrein activity.

As used herein, a "disease or condition characterized by aberrant kallikrein activity" refers to any disease or condition in which it is desirable to reduce kallikrein activity. For example, it may be desirable to reduce kallikrein activity in the setting of inappropriate activation or hyperactivation of kallikrein.

In some embodiments, the invention provides a method of inhibiting blood coagulation, comprising administering to a subject in need thereof an effective amount of a compound of any one of formulae (I), (II), or (III).

The compounds of the invention may be used to inhibit blood coagulation (particularly by inhibition of factor VIIa without directly inhibiting thrombin). The compounds can therefore be used to prevent intravascular blood clots or for anti-coagulant treatment. Examples of clinical situations in which anti-coagulant therapy would be beneficial are well known and include surgery (such as total hip replacement surgery, transluminal coronary angioplasty and treatment for myocardial infarction or crescendo angina).

Formulations, Routes of Administration, and Dosing

The compounds of the invention can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or an active salt thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention can be conveniently formulated in unit dosage form; for example, containing 5 to 1000 mg, 10 to 750 mg, or 50 to 500 mg of active ingredient per unit dosage form. In one embodiment, the invention provides a composition comprising a compound of the invention formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention can also be administered in combination with other therapeutic agents, for example, other agents that are useful for treating or preventing ischemia, blood loss, or reperfusion injury.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active ingredient for at least 30 days, and preferably 60 days.

In certain embodiments, a compound of the invention is formulated for intraocular administration, for example direct injection or insertion within or in association with an intraocular medical device.

The compounds of the invention may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention to the region of a body which has been treated by interventional technique.

In exemplary embodiment, a compound of the invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the compound is coated, adsorbed, placed, or otherwise incorporated into the device by methods known in the art. For example, the compound may be embedded and released from within ("matrix type") or surrounded by and released through ("reservoir type") polymer materials that coat or span the medical device. In the latter example, the compound may be entrapped within the polymer materials or coupled to the polymer materials using one or more the techniques for generating such materials known in the art. In other formulations, the compound may be linked to the surface of the medical device without the need for a coating, for example by means of detachable bonds, and release with time or can be removed by active mechanical or chemical processes. In other formulations, the compound may be in a permanently immobilized form that presents the compound at the implantation site.

In certain embodiments, the compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D, L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable polymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound is formulated for release from the polymer coating into the environment in which the medical device is placed. Preferably, the compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the compound from the polymer coating can be controlled. For example, the diffusion coefficient of the one or more polymer coatings can be modulated to control the release of the compound from the polymer coating. In a variation on this theme, the diffusion coefficient of the one or more polymer coatings can be controlled to modulate the ability of an analyte that is present in the environment in which the medical device is placed (e.g., an analyte that facilitates the breakdown or hydrolysis of some portion of the polymer) to access one or more components within the polymer composition (and for example, thereby modulate the release of the compound from the polymer coating). Yet another embodiment of the invention includes a device having a plurality of polymer coatings, each having a plurality of diffusion coefficients. In such embodiments of the invention, the release of the compound from the polymer coating can be modulated by the plurality of polymer coatings.

In yet another embodiment of the invention, the release of the compound from the polymer coating is controlled by modulating one or more of the properties of the polymer composition, such as the presence of one or more endogenous or exogenous compounds, or alternatively, the pH of the polymer composition. For example, certain polymer compositions can be designed to release a compound in response to a decrease in the pH of the polymer composition.

Kits

The invention also provides a kit, comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to a mammal to treat or prevent a disease or condition characterized by aberrant kallikrein activity. In one embodiment, the mammal is a human.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

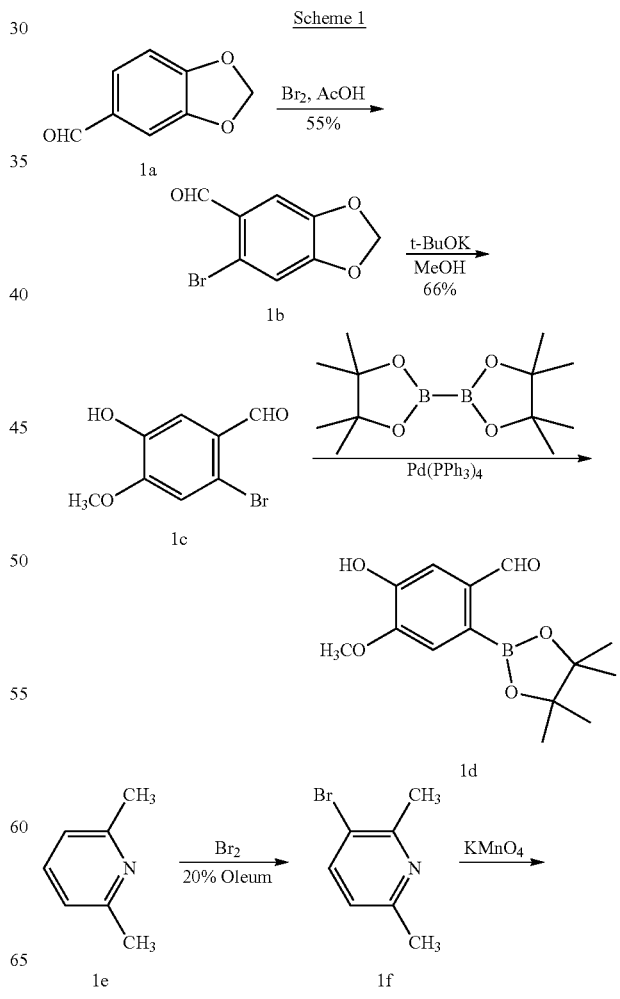

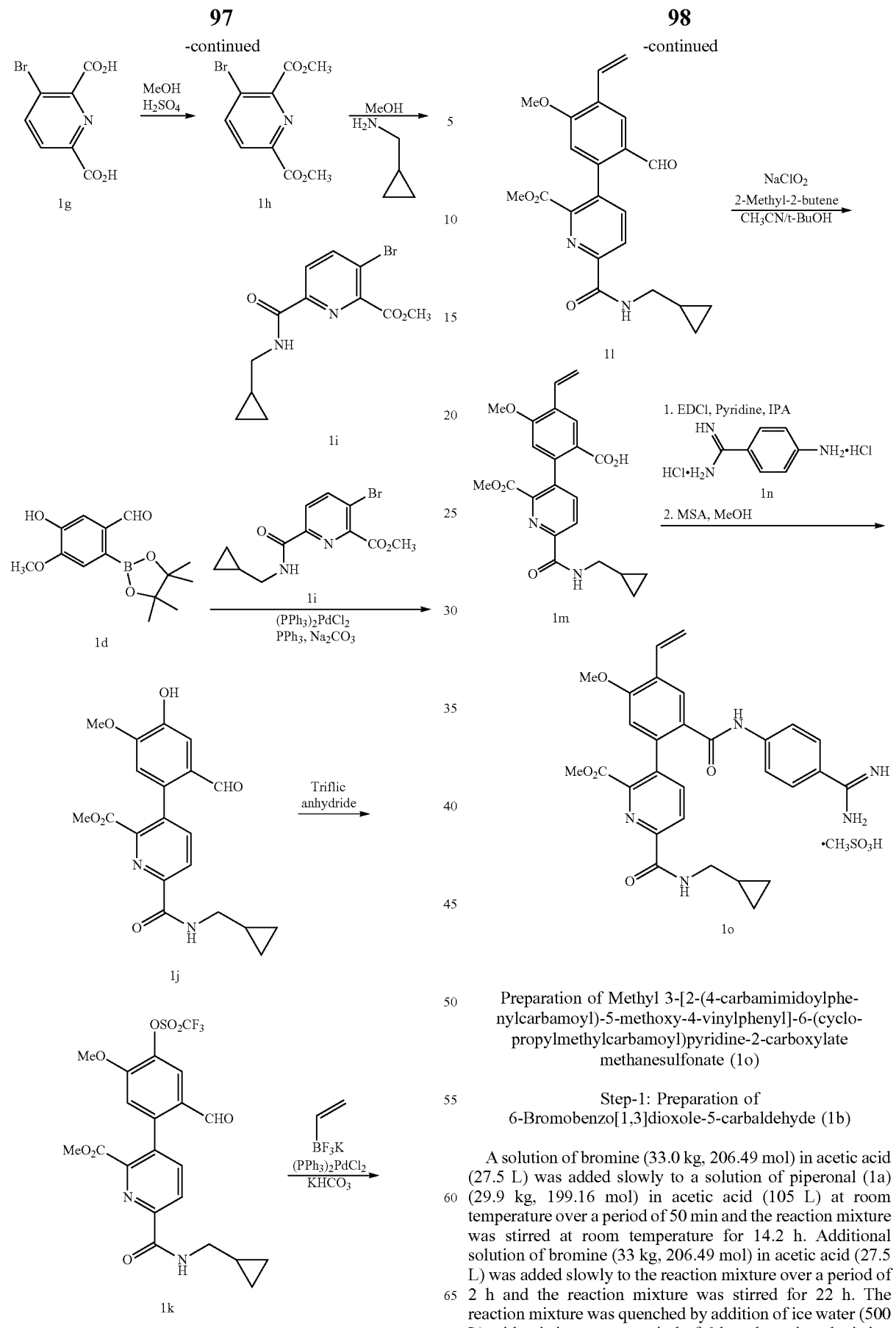

Preparation of Methyl 3-[2-(4-carbamimidoylphenylcarbamoyl)-5-methoxy-4-vinylphenyl]-6-(cyclopropylmethylcarbamoyl)pyridine-2-carboxylate methanesulfonate (1o)

Step-1: Preparation of 6-Bromobenzo[1,3]dioxole-5-carbaldehyde (1b)

A solution of bromine (33.0 kg, 206.49 mol) in acetic acid (27.5 L) was added slowly to a solution of piperonal (1a) (29.9 kg, 199.16 mol) in acetic acid (105 L) at room temperature over a period of 50 min and the reaction mixture was stirred at room temperature for 14.2 h. Additional solution of bromine (33 kg, 206.49 mol) in acetic acid (27.5 L) was added slowly to the reaction mixture over a period of 2 h and the reaction mixture was stirred for 22 h. The reaction mixture was quenched by addition of ice water (500 L) with stirring over a period of 6 h and continued stirring for additional 1.25 h. The mixture was allowed to settle and most of the supernatant liquid was decanted to a waste container using nitrogen pressure. Water (600 L) was added to the solid, stirred, mixture was allowed to settle and then most of the supernatant liquid was decanted to a waste container using nitrogen pressure. Water (100 L) was added to the decanted mixture, stirred for 15 min and the solid obtained was collected by filtration using a centrifuge. The solid was washed with water (2×100 L) and air-dried in a tray drier for 3.75 h to afford the crude product 1b (52 kg). The crude product (51.2 kg) was stirred in n-hexane (178 L) for 3 h, collected by filtration, washed with n-hexane (25 L) and dried to afford 6-Bromobenzo[1,3]dioxole-5-carbaldehyde (1b) (40.11 kg, 87.9%) as a light brown solid. MP: 109-112° C. $^1$H NMR (300 MHz, CDCl$_3$) δ 10.21 (s, 1H), 7.37 (s, 1H), 7.07 (s, 1H), 6.10 (s, 2H); 1HNMR (DMSO-d$_6$): δ 10.06 (s, 1H), 7.42 (s, 1H), 7.29 (s, 1H), 6.20 (d, J=12.3 Hz, 2H).

Step-2: Preparation of
2-Bromo-5-hydroxy-4-methoxy-benzaldehyde (1c)

A solution of potassium tert-butoxide (10.7 kg, 95.36 mol) in DMSO (49 L) was stirred at 50° C. for 30 min. methanol (49 L) was added slowly over a period of 4.25 h and stirred at 50° C. for 30 min. 6-Bromobenzo[1,3]dioxole-5-carbaldehyde (1b) (9.91 kg, 43.27 mol) was added to the reaction mixture in small portions over a period of 45 min and stirred at 50° C. for 1 h. The reaction mixture was cooled to room temperature and split into two equal portions. Each portion was quenched with water (50.9 L) and basified with 50% aqueous NaOH solution (2.4 L). Each portion was extracted with MTBE (4×36 L) to remove impurities. The aqueous layer was acidified with conc. HCl to pH ~3 to obtain product as a yellow solid. The solid was collected by filtration using a centrifuge, washed with water (2×35 L) and air-dried to afford 2-Bromo-5-hydroxy-4-methoxy-benzaldehyde (1c) (4.37 kg, 40.7%, contains 7% water); Mp: 100-102° C.; 1HNMR (300 MHz, DMSO-d$_6$): δ 10.00 (s, 1H), 9.92 (s, 1H), 7.27 (s, 1H), 7.26 (s, 1H), 3.93 (s, 3H).

Step-3: Preparation of 5-Hydroxy-4-methoxy-2-(4,4,5,5-tetramethyl-[1,3,2]dioxaborolan-2-yl)benzaldehyde (1d)

2-Bromo-5-hydroxy-4-methoxy-benzaldehyde (1c) [1.3 kg (93%, 7% water content), 5.25 mol] was dissolved in toluene (13 L) in a reaction flask equipped with a Dean Stark apparatus. The solution was heated at reflux with stirring to distill off about 25% of the toluene along with water (90 mL). The solution was cooled to 90° C. then bis(pinacolato)diboron (1.5 kg, 5.82 mol), KOAc (772.6 g, 7.87 mol) and Pd(PPh$_3$)$_4$ (24.3 g, 0.02 mol) were added and the reaction mixture was heated at reflux for 10 h. After confirming the completion of reaction by TLC (mobile phase: 100% DCM), the reaction mixture was cooled to room temperature and was kept standing overnight. The reaction mixture was filtered through Celite and the Celite cake was washed with toluene (4 L). The filtrate of this batch was mixed with the filtrate of another batch (batch size 1.3 kg obtained from an identical reaction). The mixed filtrate was washed with water (17.5 L), brine (17.5 L), dried over Na$_2$SO$_4$, filtered and the solution was passed through a pad of silica gel (2 kg, mesh size 230-400). The silica gel pad was washed with toluene. The combined filtrate and washing was concentrated under reduced pressure and the residual crude product was stirred with n-hexane (23 L) for 1 h to obtain a solid product. The solid was collected by filtration, washed with n-hexane (5 L) and dried to afford 5-Hydroxy-4-methoxy-2-(4,4,5,5-tetramethyl-[1,3,2]dioxaborolan-2-yl)benzaldehyde (1d) (2.47 kg, 84.6%). $^1$H NMR (300 MHz, CDCl$_3$) δ 10.54 (s, 1H), 7.57 (s, 1H), 7.33 (s, 1H), 5.89 (s, 1H), 4.01 (s, 3H), 1.37 (s, 12H); $^1$H NMR (300 MHz, DMSO-d$_6$) δ 10.35 (s, 1H), 9.95 (s, 1H), 7.33 (s, 1H), 7.23 (s, 1H), 3.87 (s, 3H), 1.33 (s, 12H); MS (ES+) 301.1 (M+Na); 579.1 (2M+Na); Analysis calculated for C$_{14}$H$_{19}$BO$_5$: C, 60.46; H, 6.89. Found: C, 60.60; H, 6.87.

Step-4: Preparation of
3-Bromo-2,6-dimethylpyridine (1f)

2,6-lutidine (1e) (115 kg, 1073.3 mol) was added into pre-chilled Oleum (20-23%, 1015 kg, 2276.7 mol) at 0° C. over a period of 4.5 h (temperature reached 14° C. during the addition). Bromine (88.18 kg, 1103.6 mol) was then added at 5-10° C. over a period of 1 h. The reaction mixture was slowly heated to 150° C. over a period of 12 h. TLC analysis indicated about 40-50% conversion to product and the formation of a dimer by-product (5%). The reaction mixture was cooled to room temperature and then additional bromine (88.18 kg, 1103.6 mol) was added slowly. The reaction mixture was slowly heated to maintain a temperature of 65-75° C. over a period of 15 h. TLC analysis indicated a 65-70% conversion to product and the formation of 5% dimer by product. The reaction mixture was quenched by addition of water (500 L) while maintaining the reaction temperature below 20° C. The mixture was basified with 6.6 M NaOH (3800 L) while maintain the temperature at <40° C. EtOAc (220 L) was added and the mixture was stirred for 1 h then allowed to settle over a period of 2 h. The layers were separated and the aqueous layer was treated with NaOH (10 kg) in water (10 L) and extracted with EtOAc (160 L). The organic extract were combined washed with brine (100 L), dried over Na$_2$SO$_4$ (50.0 kg), filtered and the solvent was evaporated under atmospheric pressure. The residue was vacuum distilled and the desired product 3-Bromo-2,6-dimethylpyridine (1f) was collected at 58-60° C., 2 mm/Hg (98.45 kg, 49.2%) as a colorless liquid.

Step-5: Preparation of
3-Bromopyridine-2,6-dicarboxylic acid (1g)

To a stirred solution of 3-bromo-2,6-dimethylpyridine (1f) (98 kg, 5326.05 mol) in water (1310 L) was added KMnO$_4$ (225 kg, 1423.6 mol) in 5 equal portions in 1 h intervals at 70° C. After stirring for 1 h at 70° C. additional KMnO$_4$ (225 Kg, 1423.6 mol) was added in 5 equal portion in 1 h intervals at 90° C. The reaction mixture was stirred for 12 h at 90° C. The suspension was filtered hot through Celite to obtain a clear solution. The solvent was distilled off to remove about 30% of the total volume. The remaining concentrated solution was chilled to 0° C. and made acidic (to pH 3-4) by the addition of conc. HCl (120 L). The white precipitate obtained was collected by filtration and dried at 70° C. to afford 3-Bromopyridine-2,6-dicarboxylic acid (1g) as a white solid (109 kg, 84%).

Step-6: Preparation of Dimethyl
3-Bromopyridine-2,6-dicarboxylate (1h)

To a stirred solution of 3-bromopyridine-2,6-dicarboxylic acid (1g) (20.0 kg, 81.29 mol) in methanol (100 L) was added conc. H$_2$SO$_4$ (4.4 L) over a period of 30 min. The reaction mixture was heated to 65° C. and maintained at that temperature for 5 h (the reaction was monitored by TLC analysis to determine completion of reaction). The reaction mixture was cooled to room temperature basified by careful addition of aqueous NaHCO$_3$ solution (prepared from 10 kg NaHCO$_3$ in 120 L of water) and further diluted with water (120 L). The white solid obtained was collected by filtration, washed with plenty of water and then oven-dried at 40° C. to obtain dimethyl 3-Bromopyridine-2,6-dicarboxylate (1h) (9.2 kg, 41.3%) as a white solid; 1HNMR (300 MHz, DMSO-d$_6$) δ 8.47 (d, J=8.4, 1H), 8.08 (dd, J=4.5, 8.4, 1H), 3.95 (s, 3H), 3.91 (s, 3H); MS (ES+) 570.6 (2M+Na); Analysis calculated for C$_9$H$_8$BrNO$_4$: C, 39.44; H, 2.94; Br, 29.15N, 5.11. Found: C, 39.52; H, 2.92; Br, 29.28; N, 5.03.

Step-7: Preparation of Methyl 3-bromo-6-(cyclopropylmethylcarbamoyl)pyridine-2-carboxylate (1i)

To a stirred solution of dimethyl 3-Bromopyridine-2,6-dicarboxylate (1h) (9.08 kg, 33.13 mol) in tert-butanol (45.4 L) was added at room temperature cyclopropylmethanamine (3.0 kg, 42.32 mol). The reaction mixture was heated at 65° C. for 17 h. The reaction mixture was cooled to room temperature and then conc. HCl (1.1 L; amount calculated based on 0.25 eq. of cyclopropylmethanamine used in the reaction) was added slowly and the mixture was stirred for 15 min. The reaction mixture was concentrated under reduced pressure to obtain the crude product (~11.8 kg). The crude product was dissolved in hot i-PrOH (20 L) filtered through a Celite pad. The filtrate cooled with stirring to 10° C. to obtain a white precipitate. The solid obtained was collected by filtration, washed with n-heptane (6.0 L) and dried to provide pure methyl 3-bromo-6-(cyclopropylmethylcarbamoyl)pyridine-2-carboxylate (1i) (2.28 kg, 22.0%, HPLC purity: 99.12%). The filtrate was cooled to 10° C. and stirred to give a second crop of compound (1i). The product was collected by filtration, washed with n-heptane (3.0 L) and dried to give compound (1i) (988 g, 9.5%) (HPLC purity: 98.9%). The filtrate was concentrated under reduced pressure to distill off approximately 15 L of i-PrOH. The concentrated filtrate was cooled to 6° C., but no product was formed. The solvent was completely evaporated to provide 7.3 kg of crude product. The crude product can be purified by silica gel column chromatography using tert-butanol and hexanes. An analytical sample was prepared by purification of 3 gm of crude residue by flash column chromatography [silica gel 80 g, eluting with 0-100 (9:1 ethyl acetate in methanol) in hexane] to furnish Methyl 3-bromo-6-(cyclopropylmethylcarbamoyl)pyridine-2-carboxylate (1i) as a white solid. $^1$HNMR (300 MHz, DMSO-d$_6$) δ 8.83 (t, J=5.9, 1H), 8.47-8.41 (m, 1H), 8.06 (d, J=8.4, 1H), 3.96 (s, 3H), 3.16 (t, J=6.5, 2H), 1.14-0.99 (m, 1H), 0.42 (m, 2H), 0.30-0.19 (m, 2H); MS (ES+) 337.0 (M+Na), 650.8 (2M+Na); Analysis calculated for C$_{12}$H$_{13}$BrN$_2$O$_3$: C, 46.03; H, 4.18; N, 8.95; Br, 25.52. Found: C, 46.15; H, 4.17; N, 8.72; Br, 25.26; further elution gave diamide 3-bromo-N$_2$,N$_6$-bis (cyclopropylmethyl)pyridine-2,6-dicarboxamide as a white solid; $^1$HNMR (300 MHz, DMSO-d$_6$) δ 9.05-8.88 (m, 2H), 8.35 (d, J=8.3, 1H), 7.98 (d, J=8.3, 1H), 3.20 (t, J=6.3, 4H), 1.16-0.96 (m, 2H), 0.52-0.36 (m, 4H), 0.34-0.19 (m, 4H); MS (ES+) 354.0 (M+1), 375.9 (M+Na), 727.4 (2M+Na); (ES−) 703.1 (2M−1); Analysis calculated for C$_{15}$H$_{18}$BrN$_3$O$_2$.0.25H$_2$O: C, 50.50; H, 5.23; N, 11.78. Found: C, 50.61; H, 5.03; N, 11.57.

Step-8: Preparation of methyl 6-((cyclopropylmethyl)carbamoyl)-3-(2-formyl-4-hydroxy-5-methoxyphenyl)picolinate (1j)

THF (37.5 L) was charged to a 100 L reactor followed by ethyl 3-bromo-6-(cyclopropylmethyl-carbamoyl)pyridine-2-carboxylate (1i) (2.5 kg, 7.98 mol) under a nitrogen atmosphere. The reaction mixture was degassed twice by applying alternate vacuum and nitrogen. 5-Hydroxy-4-methoxy-2-(4,4,5,5-tetramethyl-[1,3,2]dioxaborolan-2-yl) benzaldehyde (1d) (2.88 kg, 10.36 mol) was added, followed by the addition of PPh$_3$ (53.13 g, 0.20 mol), PdCl$_2$(PPh$_3$)$_2$ (120.4 g, 0.17 mol) and a solution of Na$_2$CO$_3$ (2.12 kg, 20.00 mol) in demineralized water (10.0 L) under nitrogen atmosphere. The reaction mixture was degassed again two times by applying alternate vacuum and nitrogen. The reaction mixture was heated at reflux for 6.5 h, cooled to room temperature and filtered through a Celite bed. Water (75 L) was added to the filtrate and the product was extracted with ethyl acetate (75 L). The aqueous layer was back extracted with ethyl acetate (2×60 L). The combined ethyl acetate extract was divided into two equal portions and each portion was washed with brine (37 L), dried over Na$_2$SO$_4$, filtered and concentrated under reduced pressure to give crude methyl 6-((cyclopropylmethyl)carbamoyl)-3-(2-formyl-4-hydroxy-5-methoxyphenyl)picolinate (1j) as a reddish viscous material (~4.5 Kg) which was used as such for the next step without further purification. An analytical sample was prepared by purification of a small sample by flash column chromatography (silica gel, eluting with 0-100% ethyl acetate in hexane) to furnish methyl 6-((cyclopropylmethyl) carbamoyl)-3-(2-formyl-4-hydroxy-5-methoxyphenyl)picolinate (1j) as an off-white solid; $^1$HNMR (300 MHz, DMSO-d$_6$) δ 9.89 (s, 1H), 9.52 (s, 1H), 8.79 (t, J=6.1 Hz, 1H), 8.23 (d, J=8.0 Hz, 1H), 8.09 (d, J=8.0 Hz, 1H), 7.34 (s, 1H), 6.90 (s, 1H), 3.85 (s, 3H), 3.62 (s, 3H), 3.22 (m, 2H), 1.16-1.02 (m, 1H), 0.49-0.38 (m, 2H), 0.32-0.22 (m, 2H); MS (ES+) 791.0 (2M+Na), (ES−) 382.7 (M−1), 767.3 (2M−1); Analysis calculated for C$_{20}$H$_{20}$N$_2$O$_6$. 0.25H$_2$O: C, 61.77; H, 5.31; N, 7.20. Found: C, 61.54; H, 5.13; N, 7.05.

Step-9: Preparation of methyl 6-((cyclopropylmethyl)carbamoyl)-3-(2-formyl-5-methoxy-4-(((trifluoromethyl)sulfonyl)oxy)phenyl)picolinate (1k)

A solution of methyl 6-((cyclopropylmethyl)carbamoyl)-3-(2-formyl-4-hydroxy-5-methoxyphenyl)picolinate (1j) (2.11 kg, estimated about 3.83 mol from step 8) in dichloromethane (16.0 L) and pyridine (1.4 L, 17.4 mol) cooled to −10° C. and maintained at that temperature for 1 h was added a solution of triflic anhydride (980.0 mL, 5.8 mol) in dichloromethane (6.0 L) drop wise over a period of 3 h at −10° C. The reaction mixture was stirred at −5° C. for 1.3 h, quenched with saturated aqueous NaHCO$_3$ (10.4 L) and stirred for 30 mins. The organic layer was separated, washed successively with saturated aqueous NaHCO$_3$ (10.4 L), 1 N HCl (2×16.6 L), water (13.2 L), brine (13.2 L), dried over MgSO$_4$, filtered and concentrated under reduced pressure to give the crude product. The crude product was stirred with 15% ethyl acetate in n-hexane (7.0 L) for 1 h. The solid obtained was collected by filtration washed with 15% ethyl acetate in n-hexane (3.0 L). The solid was stirred again with 15% ethyl acetate in n-hexane (7.0 L) for 1 h, was collected by filtration and washed with 15% ethyl acetate in n-hexane (3.0 L). The solid was stirred again with 15% ethyl acetate in n-hexane (8.0 L) for 1 h, collected by filtration washed with 15% ethyl acetate in n-hexane (3.0 L). The solid was dried to afford methyl 6-((cyclopropylmethyl)carbamoyl)-3-(2-formyl-5-methoxy-4-(((trifluoromethyl)sulfonyl)oxy) phenyl)picolinate (1k) as a light brown solid (1.7 kg, 86% yield, for combined steps 8 & 9); $^1$H NMR (300 MHz, DMSO-d$_6$): δ 9.64 (s, 1H), 8.78 (t, J=6.1, 1H), 8.29 (d, J=8.0, 1H), 8.16 (d, J=8.0, 1H), 8.03 (s, 1H), 7.39 (s, 1H), 4.00 (s, 3H), 3.63 (s, 3H), 3.22 (m, 2H), 1.11 (m, 1H), 0.52-0.39 (m, 2H), 0.28 (m, 2H); MS (ES+) 538.9 (M+Na).

Step-10: Preparation of methyl 6-((cyclopropylmethyl)carbamoyl)-3-(2-formyl-5-methoxy-4-vinylphenyl)picolinate (1l)

A solution of methyl 6-((cyclopropylmethyl)carbamoyl)-3-(2-formyl-5-methoxy-4-(((trifluoromethyl)sulfonyl)oxy)phenyl)picolinate (1k) (1.7 kg, 3.29 mol) in DME (15 L) was charged into a 50 L reactor under nitrogen. The reaction mixture was degassed twice by applying alternate vacuum and nitrogen. Potassium trifluoro(vinyl)borate (551.2 g, 4.11 mol), $PdCl_2(PPh_3)_2$ (115.52 g, 0.16 mol), $KHCO_3$ (659.14 g, 6.58 mol) and demineralized water (1.7 L) was then added under a $N_2$ atmosphere. The reaction mixture was degassed by applying alternate vacuum and nitrogen. The reaction mixture was heated at reflux for 5 h. The reaction mixture was cooled to room temperature and then filtered through a Celite bed. Demineralized water (16.7 L) was added to the filtrate followed by ethyl acetate (17.6 L). The mixture was stirred for 20 min and then the organic layer was separated. The aqueous layer was back-extracted with ethyl acetate (2×13.5 L). The combined organic extract was washed with brine (13.5 L), dried over $Na_2SO_4$, and filtered. The solvent was evaporated under reduced pressure to give the crude product (1.82 kg). The crude product was purified by column chromatography along with the crude (1.08 kg) (obtained from Batch size 1.0 kg of 1k). Total crude product 1k loaded for column was 2.9 kg, Silica gel (3.0 kg, 230-400 mesh size) was used for slurry and silica gel (32.4 kg, 230-400 mesh size) was used in column, eluting with 25% ethyl acetate in n-hexane was used as. Two fractions were collected.

1. Fractions containing pure product 1l (704.6 g, 34%); $^1$H NMR (300 MHz, $CDCl_3$): δ (ppm) 9.64 (s, 1H), 8.35 (d, J=7.8 Hz, 1H), 8.06-8.03 (m, 2H), 7.78 (d, J=7.8 Hz, 1H), 7.02-6.92 (m, 1H), 6.61 (s, 1H), 5.86 (d, J=17.7 Hz, 1H), 5.38 (d, J=11.4 Hz, 1H), 3.84 (s, 3H), 3.67 (s, 3H), 3.35-3.29 (m, 2H), 1.08-1.03 (m, 1H), 0.55-0.49 (m, 2H), 0.29-0.24 (m, 2H). $^1$HNMR (300 MHz, DMSO-$d_6$) δ 9.68 (s, 1H), 8.77 (t, J=6.1, 1H), 8.35-8.21 (m, 1H), 8.16-8.01 (m, 2H), 7.14-6.87 (m, 2H), 6.01 (dd, J=1.2, 17.8, 1H), 5.45 (dd, J=1.1, 11.3, 1H), 3.91 (s, 3H), 3.64 (s, 3H), 3.23 (m, 2H), 1.21-1.01 (m, 1H), 0.51-0.40 (m, 2H), 0.34-0.20 (m, 2H). MS (ES+) 417.0 (M+Na); Analysis calculated for $C_{22}H_{22}N_2O_5$: C, 66.99; H, 5.62; N, 7.10. Found: C, 66.75; H, 5.52; N, 7.06.

2. Fractions containing product 1l with very slight lower impurity (1012.8 g, 49%).

Step-11: Preparation of 2-(6-((cyclopropylmethyl)carbamoyl)-2-(methoxycarbonyl)pyridin-3-yl)-4-methoxy-5-vinylbenzoic acid (1m)

To a stirred solution of methyl 6-((cyclopropylmethyl)carbamoyl)-3-(2-formyl-5-methoxy-4-vinylphenyl)picolinate (1l) (1.57 kg, 3.80 mol) in acetonitrile (15.4 L) was added tert-butyl alcohol (22.2 L), demineralized water (3.2 L) and sodium dihydrogen phosphate monohydrate (323.74 g, 2.346 mol). The reaction mixture was cooled to 0° C. and added 2-methyl-2-butene (5.3 L, 50.0 mol) and stirred at 0° C. for 30 min. A solution of 80% sodium chlorite (1.36 kg, 12.0 mol) in demineralized water (5.2 L) was added to the reaction mixture over a period of 2.5 h at 0° C. [temperature rises to 7° C. during the addition]. The reaction mixture was stirred at 0° C. for 2 h, diluted with water (40 L) and ethyl acetate (24 L). After stirring the mixture, it was allowed to settle and the organic layer was separated. The aqueous layer was back-extracted with ethyl acetate (2×20 L) then acidified with 5.9% aqueous acetic acid (2 L) and extracted once with ethyl acetate (10 L). The organic extracts were combined washed with water (2×20 L), a solution of acetic acid (125 mL) in water (20.0 L), brine (2×20 L), dried over $Na_2SO_4$, filtered and concentrated under reduced pressure (vapor temperature below 40° C.). The residue obtained was dissolved in acetone (7 L) (residue didn't dissolve completely). The solution was poured slowly into a reactor containing stirred n-hexane (70.0 L) to precipitate the solid product and the mixture was stirred for 2 h. The solid obtained was collected by filtration, washed with 10% acetone in n-hexane (6.3 L), n-hexane (6.3 L), dried to afford 2-(6-((cyclopropylmethyl)carbamoyl)-2-(methoxycarbonyl)pyridin-3-yl)-4-methoxy-5-vinylbenzoic acid (1m) as an off-white solid (1.29 Kg, yield: 79.0%). $^1$H NMR (300 MHz, DMSO-$d_6$): δ (ppm) 12.50 (brs, 1H), 8.69 (t, J=6.0 Hz, 1H, NH), 8.20 (d, J=7.9 Hz, 1H), 8.09 (s, 1H), 7.95 (d, J=8.1 Hz, 1H), 6.97 (dd, J=18.0, 11.3 Hz, 1H), 6.88 (s, 1H), 5.92 (d, J=7.9 Hz, 1H), 5.38 (d, J=11.1 Hz, 1H), 3.85 (s, 3H), 3.63 (s, 3H), 3.27-3.17 (m, 2H), 1.15-1.05 (m, 1H), 0.48-0.40 (m, 2H), 0.31-0.24 (m, 2H); MS (ES+) 433.26, (M+Na); (ES−) 409.28 (M−1).

Step-12: Preparation of Methyl 3-[2-(4-carbamimidoylphenylcarbamoyl)-5-methoxy-4-vinylphenyl]-6-(cyclopropylmethylcarbamoyl)pyridine-2-carboxylate methanesulfonate (1o)

Pyridine (231.6 mL, 2.87 mol) and EDCI (399.3 g, 2.08 mol) were sequentially added to a cooled solution (0° C.) of 2-(6-((cyclopropylmethyl)carbamoyl)-2-(methoxycarbonyl)pyridin-3-yl)-4-methoxy-5-vinylbenzoic acid (1m) (570 g, 1.39 mol] and 4-aminobenzimidamide dihydrochloride (1n) (346.8 g, 1.67 mol) in i-PrOH (5.7 L). The reaction mixture was allowed to warm to room temperature and stirred for 12 h. TLC analysis indicated incomplete reaction. Additional EDCI (133.1 g, 0.69 mol) was added and the reaction mixture was stirred for 11.5 h. The reaction was still incomplete as indicated by TLC analysis, additional EDCI (26.6 g, 0.14 mol) was added and the reaction mixture was stirred for 7.5 h. TLC analysis indicated there was trace amount of unreacted starting material remaining. The reaction mixture was cooled to 0° C. and a solution of methanesulfonic acid (MSA) (378.8 mL, 5.83 mol) in MeOH (2.8 L) was added to the cooled mixture. The reaction mixture was allowed to warm to room temperature and stirred for 1 h. The product was collected by filtration, washed with a mixture of i-PrOH and MeOH (4:1, 2.8 L). The wet cake was slurried in a mixture of i-PrOH and MeOH (2:1, 8.5 L) for 1 h and the product was collected by filtration and washed with a mixture of i-PrOH and MeOH (4:1, 2.8 L). The product was dried in a vacuum oven at 45° C. to afford methyl 3-[2-(4-carbamimidoylphenylcarbamoyl)-5-methoxy-4-vinylphenyl]-6-(cyclopropylmethylcarbamoyl)pyridine-2-carboxylate methanesulfonate (1o) as a pink-colored solid (814 g, 94%). $^1$H NMR (300 MHz, DMSO-$d_6$) δ 10.71 (s, 1H), 9.16 (s, 2H), 8.80 (s, 2H), 8.68 (t, J=6.1 Hz, 1H), 8.22 (d, J=8.0 Hz, 1H), 8.06 (d, J=8.1 Hz, 1H), 7.93 (s, 1H), 7.84-7.72 (m, 4H), 7.12-6.97 (m, 2H), 6.04 (dd, J=17.8, 1.3 Hz, 1H), 5.45 (d, J=12.6 Hz, 1H), 3.91 (s, 3H), 3.60 (s, 3H), 3.25-3.16 (m, 2H), 2.32 (s, 3H), 1.10-1.01 (m, 1H), 0.48-0.37 (m, 2H), 0.30-0.22 (m, 2H); MS (ES+) 528.0 (M+1); Analysis calculated for $C_{29}H_{29}N_5O_5\cdot CH_3SO_3H\cdot 2H_2O$. C, 54.62; H, 5.65; N, 10.62; S, 4.86. Found: C, 54.95; H, 5.55; N, 10.61; S, 4.87.

Scheme 2

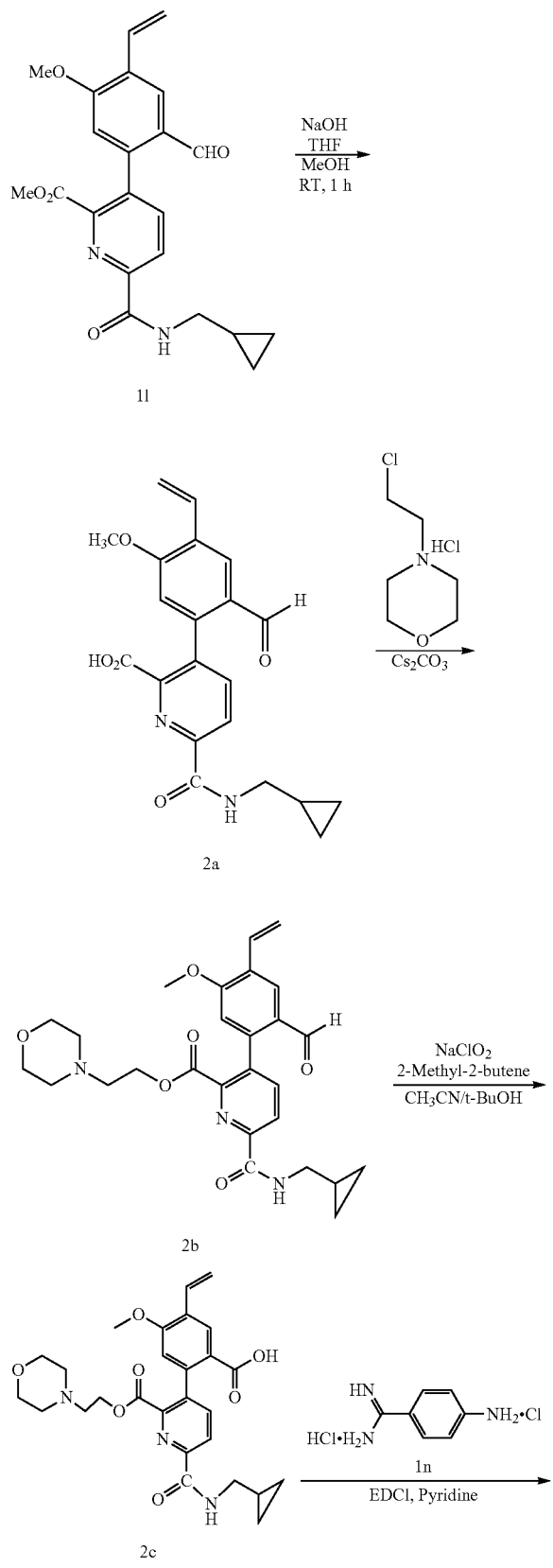

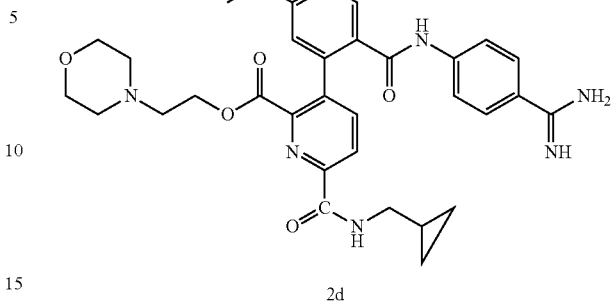

Preparation of 2-morpholinoethyl 3-(2-((4-carbamimidoylphenyl)carbamoyl)-5-methoxy-4-vinylphenyl)-6-((cyclopropylmethyl)carbamoyl)picolinate hydrochloride (2d)

Step-1: Preparation of 6-(Cyclopropylmethylcarbamoyl)-3-(2-formyl-5-methoxy-4-vinylphenyl)picolinic acid (2a)

To a solution of methyl 6-((cyclopropylmethyl)carbamoyl)-3-(2-formyl-5-methoxy-4-vinylphenyl)picolinate (11) (4.37 g, 11.08 mmol) in THF (20 mL) was added 1 N aqueous NaOH (13.85 mL, 13.85 mmol) and stirred at room temperature for 1 h. The reaction mixture was concentrated in vacuum to remove excess THF and methanol. The aqueous layer was acidified using 2.5 N HCl (pH 4.0). The solid obtained was diluted with water (10 mL) dissolved in ethyl acetate (50 mL) and aqueous layer was separated. The aqueous layer was extracted with ethyl acetate (3×50 mL). The organic layer was combined washed with brine and dried in vacuum to furnish 6-(cyclopropylmethylcarbamoyl)-3-(2-formyl-5-methoxy-4-vinylphenyl)picolinic acid (3.51 g, 83% yield) as a pale yellow solid; $^1$H NMR (300 MHz, DMSO) δ 13.07 (bs, 1H), 9.67 (s, 1H), 9.28 (t, J=6.0, 1H), 8.39-8.22 (m, 1H), 8.11 (s, 1H), 8.04 (d, J=8.0, 1H), 7.11-6.92 (m, 2H), 6.08-5.92 (m, 1H), 5.43 (d, J=12.3, 1H), 3.90 (s, 3H), 3.27 (m, 2H), 1.09 (m, 1H), 0.59-0.41 (m, 2H), 0.38-0.22 (m, 2H); MS (ES+) 381.1 (M+1), (ES−) 378.9 (M−1); Analysis: Calculated for: $C_{21}H_{20}ClN_2O_5$ 0.5HCl 0.25H$_2$O: C, 62.57; H, 5.25; N, 6.95. Found: C, 62.86; H, 5.11; N, 6.84.

Step-2: Preparation of 2-morpholinoethyl 6-((cyclopropylmethyl)carbamoyl)-3-(2-formyl-5-methoxy-4-vinylphenyl)picolinate (2b)

To a solution of 6-(Cyclopropylmethylcarbamoyl)-3-(2-formyl-5-methoxy-4-vinylphenyl)picolinic acid (2a)(1 g, 2.63 mmol) in DMF (20 mL) was added cesium carbonate (1.713 g, 5.26 mmol) and 4-(2-chloroethyl)morpholine hydrochloride (0.611 g, 3.29 mmol). The reaction mixture was stirred at room temperature for 72 h. The reaction mixture was quenched with acetic acid (1.5 mL) and neutralized with saturated NaHCO$_3$ solution. The reaction mixture was diluted with water (20 mL) and extracted with ethyl acetate (3×40 mL). The organic layers were combined, dried, concentrated in vacuum and purified by flash column chromatography (silica gel 24 g, eluting with 0-100% CMA80/CHCl$_3$, to furnish 2-morpholinoethyl 6-((cyclopropylmethyl)carbamoyl)-3-(2-formyl-5-methoxy-4-vinylphenyl)picolinate (2b) (0.95 g, 73% yield) as light yellow syrup; $^1$HNMR (300 MHz, DMSO) δ 9.68 (s, 1H), 8.71 (t, J=6.0 Hz, 1H), 8.25 (d, J=8.0 Hz, 1H), 8.16-8.05 (m, 2H), 7.00 (q, J=11.6 Hz, 2H), 6.00 (dd, J=17.8, 1.3 Hz, 1H), 5.45 (dd, J=11.3, 1.2 Hz, 1H), 4.11 (t, J=5.7 Hz, 2H), 3.91 (s, 3H), 3.48-3.41 (m, 4H), 3.24 (dd, J=11.1, 6.6 Hz, 2H), 2.28-2.12 (m, 6H), 1.17-1.00 (m, 1H), 0.54-0.38 (m, 2H), 0.35-0.22 (m, 2H); MS (ES+) 493.98 (M+1), (ES−) 527.97 (M+Cl).

Step-3: Preparation of 2-(6-((cyclopropylmethyl)carbamoyl)-2-((2-morpholinoethoxy)carbonyl)pyridin-3-yl)-4-methoxy-5-vinylbenzoic acid (2c)

Oxidation of 2-morpholinoethyl 6-((cyclopropylmethyl)carbamoyl)-3-(2-formyl-5-methoxy-4-vinylphenyl)picolinate (2b) (0.45 g, 0.912 mmol) using the procedure as reported in step 11 of scheme 1 gave after workup and purification by flash column chromatography (silica gel 25 g, eluting with 0-20% methanol in chloroform) 2-(6-((cyclopropylmethyl)carbamoyl)-2-((2-morpholinoethoxy)carbonyl)pyridin-3-yl)-4-methoxy-5-vinylbenzoic acid (2c) (0.35 g, 75%) as a white solid. $^1$H NMR (300 MHz, DMSO-d$_6$) δ 8.63 (t, J=6.1 Hz, 1H), 8.32 (s, 1H), 8.19 (d, J=8.0 Hz, 1H), 8.11 (s, 1H), 7.96 (d, J=8.0 Hz, 1H), 6.98 (dd, J=17.8, 11.2 Hz, 1H), 6.89 (s, 1H), 5.91 (dd, J=17.8, 1.4 Hz, 1H), 5.39 (dd, J=11.2, 1.4 Hz, 1H), 4.15-4.04 (m, 2H), 3.86 (s, 3H), 3.52-3.44 (m, 4H), 3.23 (td, J=6.6, 3.6 Hz, 2H), 2.29-2.18 (m, 4H), 1.15-1.02 (m, 1H), 0.50-0.40 (m, 2H), 0.32-0.22 (m, 2H); MS (ES+) 510.1 (M+1).

Step-4: Preparation of 2-morpholinoethyl 3-(2-((4-carbamimidoylphenyl)carbamoyl)-5-methoxy-4-vinylphenyl)-6-((cyclopropylmethyl)carbamoyl)picolinate hydrochloride (2d)

To a solution of 2-(6-((cyclopropylmethyl)carbamoyl)-2-((2-morpholinoethoxy)carbonyl)pyridin-3-yl)-4-methoxy-5-vinylbenzoic acid (2c) (0.35 g, 0.68 mmol) in Pyridine (5.0 mL) was added EDCI (0.2 g, 1.02 mmol) followed by 4-aminobenzimidamide dihydrochloride (1n) (0.21 g, 1.02 mmol). The reaction mixture was stirred at room temperature for 2 h and concentrated in vacuum to remove pyridine and DMF. The residue was co-distilled with water (2×10 mL) and dried in high vacuum. The residue was dissolved in methanol and converted into silica gel slurry. The slurry was purified by flash column chromatography (silica gel 40 g, eluting with 0-100% methanol in chloroform) to furnish 2-morpholinoethyl 3-(2-((4-carbamimidoylphenyl)carbamoyl)-5-methoxy-4-vinylphenyl)-6-((cyclopropylmethyl)carbamoyl)picolinate hydrochloride (2d) (0.31 g, 72% yield) as a white solid; $^1$HNMR (300 MHz, DMSO-d$_6$) δ 10.67 (s, 1H), 9.21 (s, 2H), 8.91 (s, 2H), 8.59 (s, 1H), 8.21 (d, J=8.0, 1H), 8.04 (d, J=8.0, 1H), 7.98 (s, 1H), 7.79 (s, 4H), 7.04 (q, J=11.6, 2H), 6.06 (d, J=17.7, 1H), 5.45 (d, J=12.4, 1H), 4.12 (m, 2H), 3.90 (s, 3H), 3.48-3.40 (m, 4H), 3.20 (m, 2H), 2.29-2.15 (m, 6H), 1.08 (m, 1H), 0.44 (m, 2H), 0.26 (m, 2H); MS (ES+) 627.1 (M+1); Analysis calculated for C$_{34}$H$_{38}$N$_6$O$_6$.HCl.1.75H$_2$O: C, 58.78; H, 6.17; Cl, 5.10; N, 12.10. Found: C, 58.59; H, 6.13; Cl, 5.55; N, 12.02.

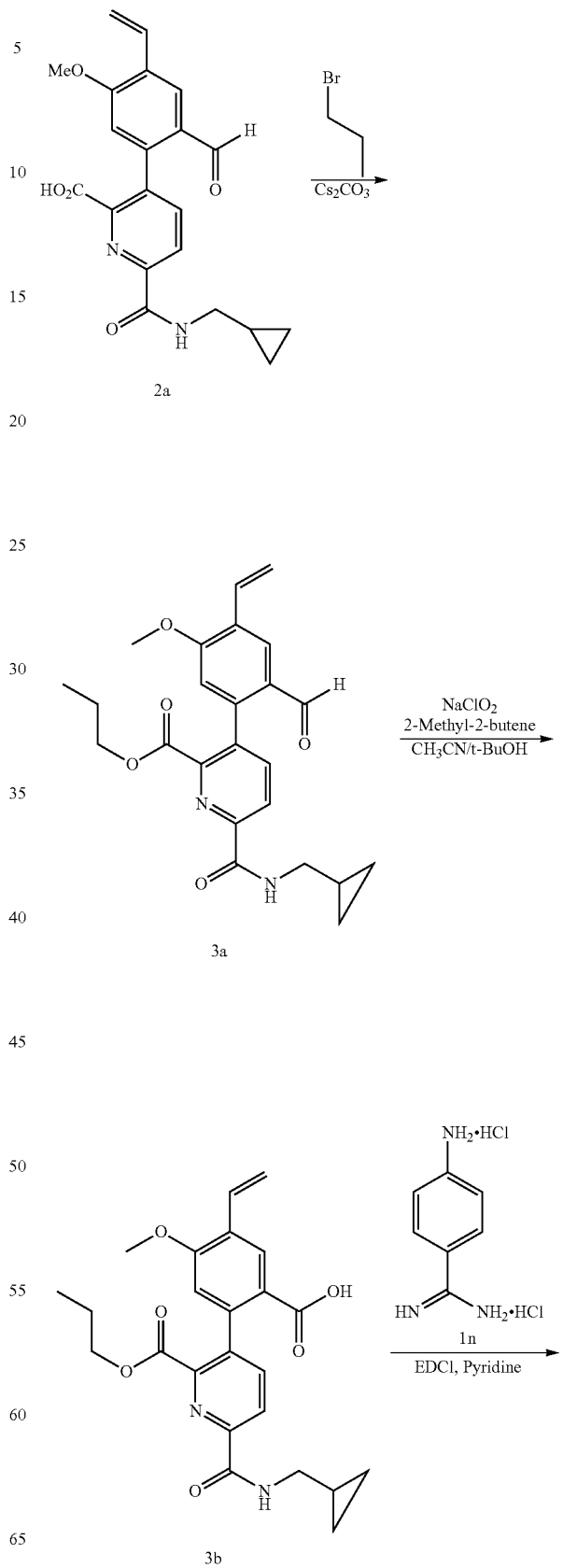

Scheme 3

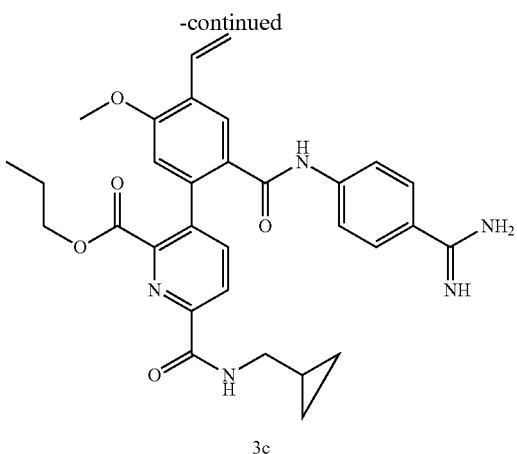

3c

Preparation of propyl 3-(2-((4-carbamimidoylphenyl)carbamoyl)-5-methoxy-4-vinylphenyl)-6-((cyclopropylmethyl)carbamoyl)picolinate hydrochloride (3c)

Step-1: Preparation of propyl 6-((cyclopropylmethyl)carbamoyl)-3-(2-formyl-5-methoxy-4-vinylphenyl)picolinate (3a)

Compound (3a) was prepared from 6-(Cyclopropylmethylcarbamoyl)-3-(2-formyl-5-methoxy-4-vinylphenyl)picolinic acid (2a) (0.44 g, 1.15 mmol) using DMF (10 mL), cesium carbonate (0.47 g, 1.44 mmol) and 1-bromopropane (0.13 mL, 1.44 mmol) according to the procedure reported in step 2 of scheme 2. This gave after workup and purification by flash column chromatography [silica gel, 12 g, eluting ethyl acetate/methanol (9:1) in hexanes 0-100%] propyl 6-((cyclopropylmethyl)carbamoyl)-3-(2-formyl-5-methoxy-4-vinylphenyl)picolinate (3a) (0.42 g, 86% yield) as a colorless oil; MS (ES+) 867.2 (2M+Na).

Step-2: Preparation of 2-(6-((cyclopropylmethyl)carbamoyl)-2-(propoxycarbonyl)pyridin-3-yl)-4-methoxy-5-vinylbenzoic acid (3b)

Oxidation of propyl 6-((cyclopropylmethyl)carbamoyl)-3-(2-formyl-5-methoxy-4-vinylphenyl)picolinate (3a) (0.42 g, 0.98 mmol) using the procedure as reported in step 11 of scheme 1 gave after workup and purification by flash column chromatography [silica gel 12 g, eluting with 0-100% (9:1) ethyl acetate/methanol in hexane] 2-(6-((cyclopropylmethyl)carbamoyl)-2-(propoxycarbonyl)pyridin-3-yl)-4-methoxy-5-vinylbenzoic acid (3b) (0.36 g, 84% yield) as a white solid; ¹HNMR (300 MHz, DMSO) δ 12.56 (s, 1H), 8.65 (t, J=6.0, 1H), 8.19 (d, J=8.0, 1H), 8.11 (s, 1H), 7.96 (d, J=8.0, 1H), 6.98 (dd, J=11.3, 17.8, 1H), 6.89 (s, 1H), 5.90 (dd, J=1.3, 17.8, 1H), 5.38 (d, J=12.5, 1H), 3.95 (t, J=6.4, 2H), 3.85 (s, 3H), 3.23 (m, 2H), 1.33 (m, 2H), 1.10 (m, 1H), 0.67 (t, J=7.4, 3H), 0.45 (m, 2H), 0.28 (m, 2H); MS (ES+) 461.0 (M+Na); 899.0 (2M+Na); (ES−) 437.0 (M−1).

Step-3: Preparation of propyl 3-(2-((4-carbamimidoylphenyl)carbamoyl)-5-methoxy-4-vinylphenyl)-6-((cyclopropylmethyl)carbamoyl)picolinate hydrochloride (3c)

Compound (3c) was prepared from 2-(6-((cyclopropylmethyl)carbamoyl)-2-(propoxycarbonyl)pyridin-3-yl)-4-methoxy-5-vinylbenzoic acid (3b) (0.33 g, 0.75 mmol) using DMF (5 mL), EDCI (0.22 g, 1.13 mmol) and 4-aminobenzimidamide dihydrochloride (1n) (0.2 g, 0.94 mmol) according to the procedure reported in step 4 of scheme 2. This gave after workup and purification by flash column chromatography [silica gel, 24 g, eluting with 0 to 100% methanol in chloroform) propyl 3-(2-((4-carbamimidoylphenyl)carbamoyl)-5-methoxy-4-vinylphenyl)-6-((cyclopropylmethyl)carbamoyl)picolinate hydrochloride (3c) (0.17 g, 41% yield) as white solid; ¹HNMR (300 MHz, DMSO-d₆) δ 10.70 (s, 1H, D₂O exchangeable), 9.38-8.77 (m, 4H, D₂O exchangeable), 8.61 (t, J=6.0, 1H), 8.20 (d, J=8.0, 1H), 8.03 (d, J=8.0, 1H), 7.96 (s, 1H), 7.79 (m, 4H), 7.13-6.94 (m, 2H), 6.05 (d, J=17.7, 1H), 5.44 (d, J=12.5, 1H), 3.96 (m, 2H), 3.89 (s, 3H), 3.21 (s, 2H), 1.32 (m, 2H), 1.09 (m, 1H), 0.67 (t, J=7.4, 3H), 0.44 (m, J=6.4, 2H), 0.26 (m, J=4.9, 2H); MS (ES+) 556.1 (M+1), (ES−) 554.2 (M−1); Analysis: Calculated for: C₃₁H₃₃N₅O₅.1.25 (HCl) 0.0.5H₂O: C, 61.02; H, 5.82; Cl, 7.26; N, 11.48. Found: C, 59.83; H, 5.86; Cl, 6.97; N, 11.20.

Scheme 4

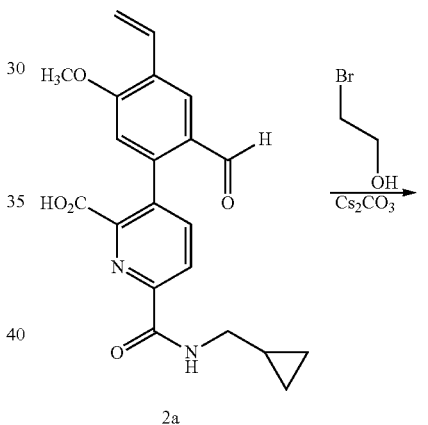

2a

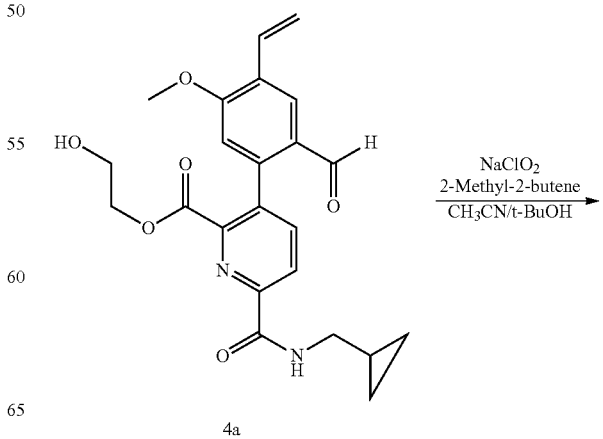

4a

-continued

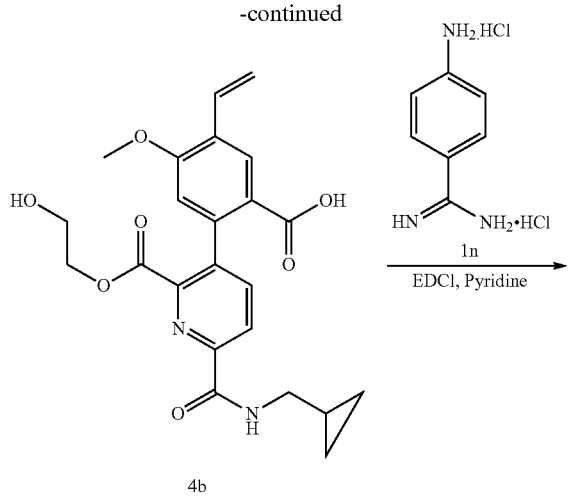

Preparation of 2-hydroxyethyl 3-(2-((4-carbamim-idoylphenyl)carbamoyl)-5-methoxy-4-vinylphenyl)-6-((cyclopropylmethyl)carbamoyl)picolinate hydrochloride (4c)

Step-1: Preparation of 2-hydroxyethyl 6-((cyclopropylmethyl)carbamoyl)-3-(2-formyl-5-methoxy-4-vinylphenyl)picolinate (4a)

Compound (4a) was prepared from 6-(Cyclopropylmethylcarbamoyl)-3-(2-formyl-5-methoxy-4-vinylphenyl)picolinic acid (2a) (0.38 g, 1.00 mmol) using DMF (10 mL), cesium carbonate (0.41 g, 1.25 mmol) and 2-bromoethanol (0.09 mL, 1.25 mmol) according to the procedure reported in step 2 of scheme 2. This gave after workup and purification by flash column chromatography [silica gel, 12 g, eluting ethyl acetate/methanol (9:1) in hexanes 0-100%] 2-hydroxyethyl 6-((cyclopropylmethyl)carbamoyl)-3-(2-formyl-5-methoxy-4-vinylphenyl)picolinate (4a) (0.34 g, 80% yield) as a colorless oil; MS (ES+) 447.0 (M+Na).

Step-2: Preparation of 2-(6-((cyclopropylmethyl)carbamoyl)-2-((2-hydroxyethoxy)carbonyl)pyridin-3-yl)-4-methoxy-5-vinylbenzoic acid (4b)

Oxidation of 2-hydroxyethyl 6-((cyclopropylmethyl)carbamoyl)-3-(2-formyl-5-methoxy-4-vinylphenyl)picolinate (4a) (0.34 g, 0.80 mmol) using the procedure as reported in step 11 of scheme 1 gave after workup and purification by flash column chromatography [silica gel 12 g, eluting with 0-100% (9:1) ethyl acetate/methanol in hexane] 2-(6-((cyclopropylmethyl)carbamoyl)-2-((2-hydroxyethoxy)carbonyl)pyridin-3-yl)-4-methoxy-5-vinylbenzoic acid (4b) (0.24 g, 57% yield) as a white solid; 1HNMR (300 MHz, DMSO-$d_6$) δ 8.69 (d, J=6.1, 1H), 8.19 (d, J=8.0, 1H), 8.09 (s, 1H), 7.95 (d, J=8.0, 1H), 6.98 (dd, J=11.3, 17.8, 1H), 6.87 (s, 1H), 5.91 (d, J=17.8, 1H), 5.39 (d, J=12.5, 1H), 4.01 (t, J=5.5, 2H), 3.85 (s, 3H), 3.37 (m, 2H), 3.23 (m, 2H), 1.13 (m, 1H), 0.44 (m, 2H), 0.29 (m, 2H); MS (ES+) 463.0 (M+Na), (ES−) 438.7 (M−1).

Step-3: Preparation of 2-hydroxyethyl 3-(2-((4-carbamimidoylphenyl)carbamoyl)-5-methoxy-4-vinylphenyl)-6-((cyclopropylmethyl)carbamoyl)picolinate hydrochloride (4c)

Compound (4c) was prepared from 2-(6-((cyclopropylmethyl)carbamoyl)-2-((2-hydroxyethoxy)carbonyl)pyridin-3-yl)-4-methoxy-5-vinylbenzoic acid (4b) (0.23 g, 0.52 mmol) using DMF (5 mL), EDCI (0.15 g, 0.79 mmol) and 4-aminobenzimidamide dihydrochloride (1n) (0.14 g, 0.66 mmol) according to the procedure reported in step 4 of scheme 2. This gave after workup and purification by flash column chromatography [silica gel, 24 g, eluting with 0 to 100% methanol in chloroform) 2-hydroxyethyl 3-(2-((4-carbamimidoylphenyl)carbamoyl)-5-methoxy-4-vinylphenyl)-6-((cyclopropylmethyl)carbamoyl)picolinate hydrochloride (4c) (0.09 g, 32% yield) as white solid; $^1$HNMR (300 MHz, DMSO-$d_6$) δ10.70 (bs, 1H, $D_2O$ exchangeable), 9.19 (bs, 4H, $D_2O$ exchangeable), 8.68 (t, =6.0, 1H), 8.20 (d, J=8.0, 1H), 8.04 (d, J=8.0, 1H), 7.95 (s, 1H), 7.78 (m, 4H), 7.12-6.94 (m, 2H), 6.05 (d, J=17.7, 1H), 5.44 (d, J=12.5, 1H), 4.89 (bs, 1H, $D_2O$ exchangeable), 4.03 (bs, 2H), 3.89 (s, 3H), 3.21 (m, 2H), 1.09 (t, J=7.0, 2H), 0.44 (m, 2H), 0.26 (m, 2H); MS (ES+) 558.1 (M+1), (ES−) 556.0 (M−1); Analysis: Calculated for: $C_{30}H_{31}N_5O_6 \cdot 1.5HCl \cdot 1.5H_2O$: C, 56.36; H, 5.60; Cl, 8.32; N, 10.95. Found: C, 56.26; H, 5.64; Cl, 7.97; N, 10.65.

Scheme 5

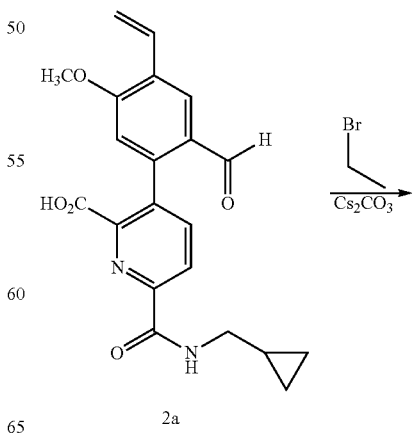

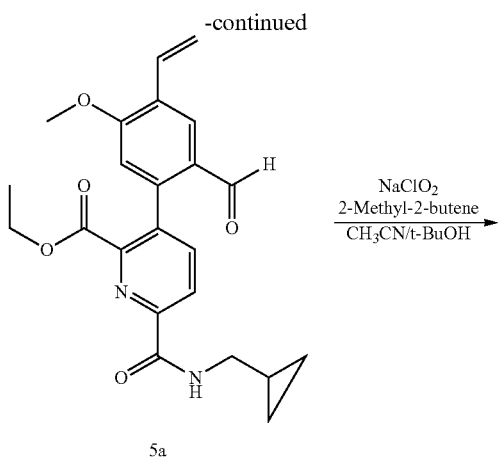

5a

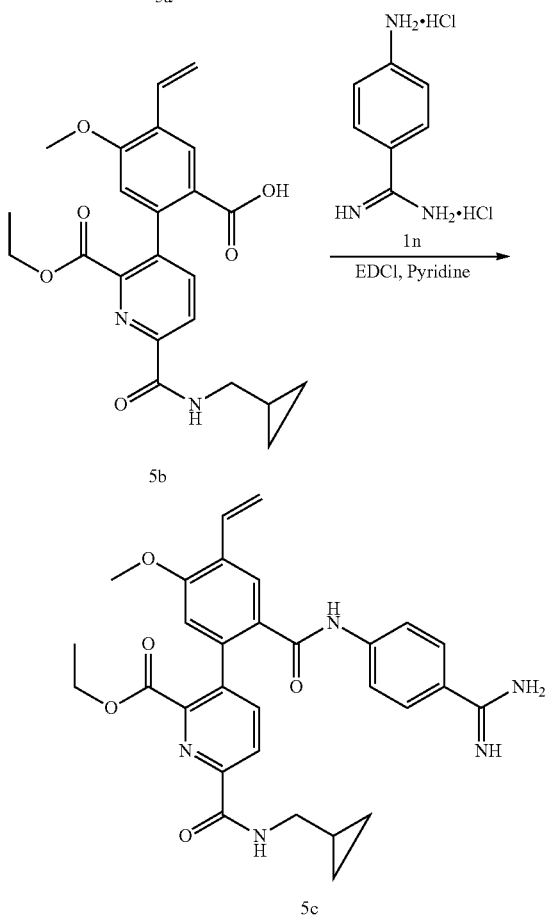

5b

5c

Preparation of ethyl 3-(2-((4-carbamimidoylphenyl)carbamoyl)-5-methoxy-4-vinylphenyl)-6-((cyclopropylmethyl)carbamoyl)picolinate (5c)

Step-1: Preparation of ethyl 6-((cyclopropylmethyl)carbamoyl)-3-(2-formyl-5-methoxy-4-vinylphenyl)picolinate (5a)

Compound (5a) was prepared from 6-(Cyclopropylmethylcarbamoyl)-3-(2-formyl-5-methoxy-4-vinylphenyl)picolinic acid (2a) (0.47 g, 1.22 mmol) using DMF (10 mL), cesium carbonate (0.50 g, 1.53 mmol) and bromoethane (0.114 mL, 1.53 mmol) according to the procedure reported in step 2 of scheme 2. This gave after workup and purification by flash column chromatography [silica gel, 12 g, eluting ethyl acetate/methanol (9:1) in hexanes 0-100%] ethyl 6-((cyclopropylmethyl)carbamoyl)-3-(2-formyl-5-methoxy-4-vinylphenyl)picolinate (5a) (0.95 g, 77% yield) as a colorless oil; $^1$HNMR (300 MHz, DMSO-$d_6$) δ 9.67 (s, 1H), 8.76 (t, J=6.1, 1H), 8.25 (d, J=8.0, 1H), 8.18-8.03 (m, 2H), 7.00 (m, 2H), 6.00 (dd, J=1.3, 17.8, 1H), 5.44 (dd, J=1.2, 11.3, 1H), 4.10-3.99 (m, 2H), 3.91 (s, 3H), 3.23 (m, 2H), 1.11 (s, 1H), 0.92 (t, J=7.1, 3H), 0.52-0.38 (m, 2H), 0.33-0.21 (m, 2H); MS (ES+) 431.1 (M+Na).

Step-2: Preparation of 2-(6-((cyclopropylmethyl)carbamoyl)-2-(ethoxycarbonyl)pyridin-3-yl)-4-methoxy-5-vinylbenzoic acid (5b)

Oxidation of ethyl 6-((cyclopropylmethyl)carbamoyl)-3-(2-formyl-5-methoxy-4-vinylphenyl)picolinate (5a) (0.39 g, 0.95 mmol) using the procedure as reported in step 11 of scheme 1 gave after workup and purification by flash column chromatography [silica gel 12 g, eluting with 0-100% (9:1) ethyl acetate/methanol in hexane] 22-(6-((cyclopropylmethyl)carbamoyl)-2-(ethoxycarbonyl)pyridin-3-yl)-4-methoxy-5-vinylbenzoic acid (5b) (0.23 g, 58% yield) as a white solid; $^1$HNMR (300 MHz, DMSO-$d_6$) δ 12.57 (bs, 1H), 8.68 (t, J=6.1, 1H), 8.19 (d, J=8.0, 1H), 8.11 (s, 1H), 7.96 (d, J=8.0, 1H), 6.98 (dd, J=11.3, 17.8, 1H), 6.89 (s, 1H), 5.91 (dd, J=1.3, 17.8, 1H), 5.39 (m, 1H), 4.04 (q, J=7.1, 2H), 3.86 (s, 3H), 3.22 (m, 2H), 1.10 (m, 1H), 0.94 (t, J=7.1, 3H), 0.50-0.40 (m, 2H), 0.33-0.22 (m, 2H); MS (ES+) 871.1 (2M+Na), (ES−) 422.8 (M−1); Analysis: Calculated for $C_{23}H_{26}N_2O_7$: C, 62.43; H, 5.92; N, 6.33. Found: C, 62.66; H, 5.76; N, 6.38.

Step-3: Preparation of ethyl 3-(2-((4-carbamimidoylphenyl)carbamoyl)-5-methoxy-4-vinylphenyl)-6-((cyclopropylmethyl)carbamoyl)picolinate (5c)

Compound (5c) was prepared from 2-(6-((cyclopropylmethyl)carbamoyl)-2-(ethoxycarbonyl)pyridin-3-yl)-4-methoxy-5-vinylbenzoic acid (5b) (0.23 g, 0.54 mmol) using DMF (5 mL), EDCI (0.16 g, 0.82 mmol) and 4-aminobenzimidamide dihydrochloride (1n) (0.14 g, 0.66 mmol) according to the procedure reported in step 4 of scheme 2. This gave after workup and purification by flash column chromatography [silica gel, 24 g, eluting with 0 to 100% methanol in chloroform) ethyl 3-(2-((4-carbamimidoylphenyl)carbamoyl)-5-methoxy-4-vinylphenyl)-6-((cyclopropylmethyl)carbamoyl)picolinate (5c) (0.097 g, 33% yield) as white solid; $^1$HNMR (300 MHz, DMSO-$d_6$) δ 10.73 (bs, 1H, $D_2O$ exchangeable), 9.25 (bs, 2H, $D_2O$ exchangeable), 9.03 (bs, 2H, $D_2O$ exchangeable), 8.66 (t, J=6.1, 1H), 8.20 (d, J=8.0, 1H), 8.04 (d, J=8.0, 1H), 7.98 (s, 1H), 7.80 (m, 4H), 7.16-6.95 (m, 2H), 6.07 (d, J=17.7, 1H), 5.44 (d, J=12.5, 1H), 4.06 (m, 2H), 3.90 (s, 3H), 3.21 (bs, 2H), 1.09 (m, 1H), 0.93 (t, J=7.1, 3H), 0.43 (m, 2H), 0.27 (m, 2H); MS (ES+) 542.1 (M+1), (ES−) 539.9 (M−1); Analysis: Calculated for: $C_{30}H_{31}N_5O_5 \cdot HCl \cdot 2H_2O$: C, 58.68; H, 5.91; Cl, 5.77; N, 11.40. Found: C, 58.35; H, 5.85; Cl, 5.86; N, 11.06.

Scheme 6

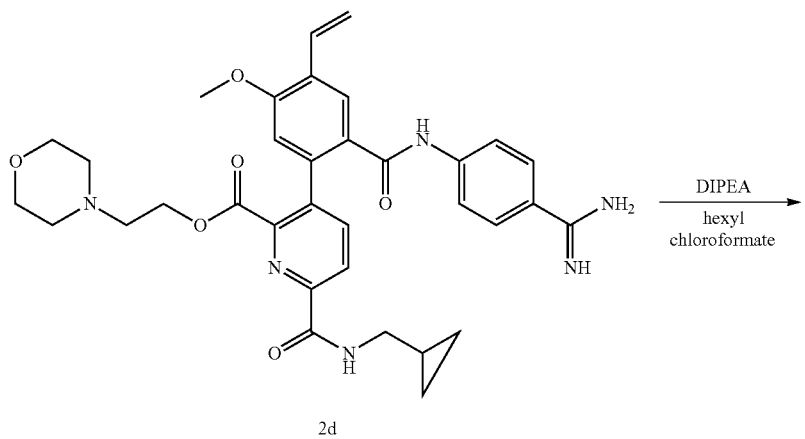

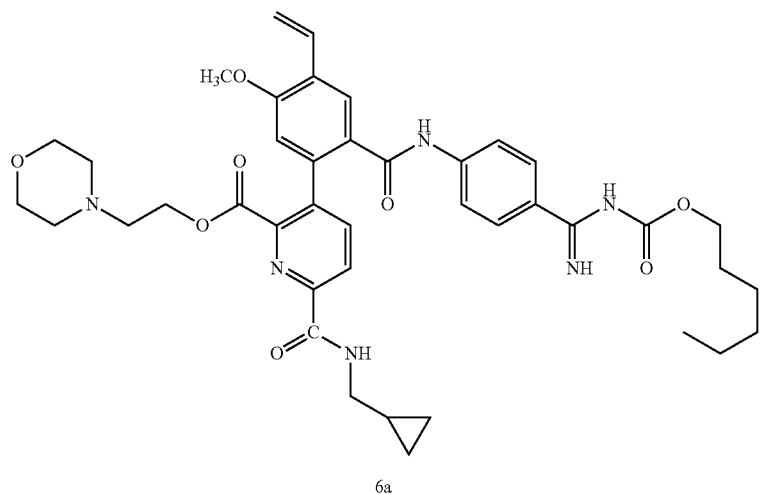

Preparation of 2-morpholinoethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate hydrochloride (6a)

To a solution of 2-morpholinoethyl 3-(2-((4-carbamimidoylphenyl)carbamoyl)-5-methoxy-4-vinylphenyl)-6-((cyclopropylmethyl)carbamoyl)picolinate hydrochloride (2d) (1 g, 1.51 mmol) in Acetonitrile (10 mL) and DMF (4 mL) was added DIPEA (3.95 mL, 22.62 mmol), hexyl chloroformate (2.47 mL, 15.08 mmol) and stirred at room temperature for 10 h. The reaction mixture was triturated twice with MTBE (50 mL) and decanted. The residue obtained was dissolved in acetonitrile (3 mL) and purified by reverse phase flash column chromatography (30 g, C18 column) eluting with 0.1% HCl in water and acetonitrile. The desired fractions were combined and lyophilized to afford 2-morpholinoethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate hydrochloride (6a) (97 mg, 8% yield) as a white solid; $^1$H NMR (300 MHz, DMSO-$d_6$, $D_2O$) δ 8.25 (d, J=8.1 Hz, 1H), 8.08 (d, J=8.0 Hz, 1H), 7.97 (s, 1H), 7.88-7.71 (m, 4H), 7.12-6.96 (m, 2H), 6.07 (dd, J=17.7, 1.4 Hz, 1H), 5.48 (dd, J=11.3, 1.4 Hz, 1H), 4.55-4.32 (m, 2H), 4.25 (t, J=6.6 Hz, 2H), 3.91 (s, 3H), 3.83-3.64 (m, 4H), 3.23 (s, 4H), 3.09 (s, 4H), 1.74-1.57 (m, 2H), 1.43-1.23 (m, 6H), 1.16-1.00 (m, 1H), 0.94-0.80 (m, 3H), 0.51-0.41 (m, 2H), 0.32-0.22 (m, 2H); MS (ES+) 755.7 (M+1), (ES−) 789.8 (M+Cl); Analysis calculated for $C_{41}H_{50}N_6O_8 \cdot 3HCl \cdot 2H_2O$: C, 54.70; H, 6.38; N, 9.33. Found: C, 54.79; H, 6.30; N, 9.27.

Scheme 7

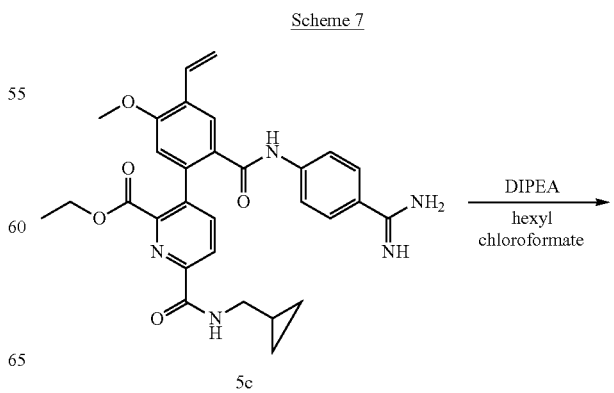

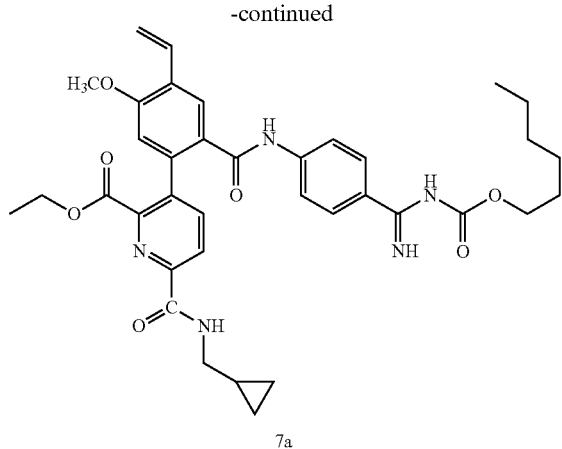

7a

Preparation of ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate hydrochloride (7a)

Compound (7a) was prepared from ethyl 3-(2-((4-carbamimidoylphenyl)carbamoyl)-5-methoxy-4-vinylphenyl)-6-((cyclopropylmethyl)carbamoyl)picolinate hydrochloride (5c) (0.4 g, 0.69 mmol) according to the procedure reported in scheme 6. This gave after workup, purification by reverse phase flash column chromatography (30 g, C18 column) eluting with 0.1% HCl in water and acetonitrile followed by lyophilization ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate hydrochloride (7a) (160 mg, 35% yield) as a white solid; $^1$H NMR (300 MHz, DMSO-$d_6$) δ 10.69 (s, 1H), 8.66 (t, J=6.1 Hz, 1H), 8.21 (d, J=8.0 Hz, 1H), 8.04 (d, J=8.0 Hz, 1H), 7.97 (s, 1H), 7.78 (s, 4H), 7.11-6.98 (m, 2H), 6.05 (dd, J=17.9, 1.6 Hz, 1H), 5.45 (dd, J=11.2, 1.4 Hz, 1H), 4.29-4.16 (m, 2H), 4.12-3.99 (m, 2H), 3.90 (s, 3H), 3.26-3.11 (m, 2H), 1.73-1.59 (m, 2H), 1.44-1.19 (m, 6H), 1.17-1.01 (m, 1H), 0.93 (t, J=7.1 Hz, 3H), 0.93-0.80 (m, 3H), 0.50-0.39 (m, 2H), 0.31-0.20 (m, 2H); MS (ES+) 670.7 (M+1), 692.7 (M+Na), (ES−) 668.7 (M−1); Analysis calculated for $C_{37}H_{43}N_5O_7 \cdot HCl \cdot H_2O$: C, 61.36; H, 6.40; N, 9.67. Found: C, 61.14; H, 6.22; N, 9.68.

Scheme 8

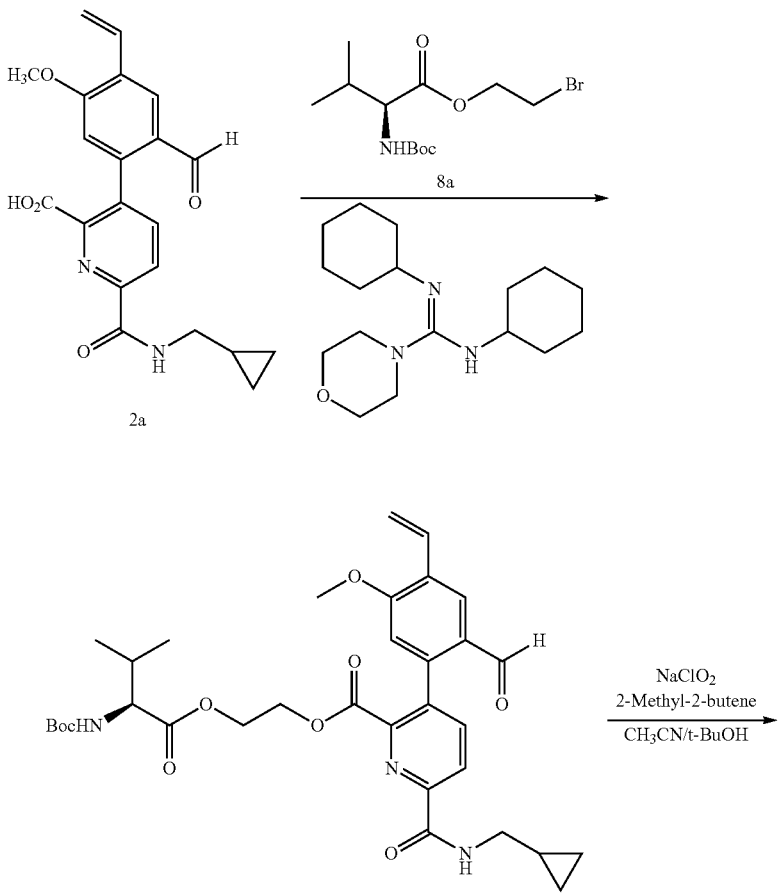

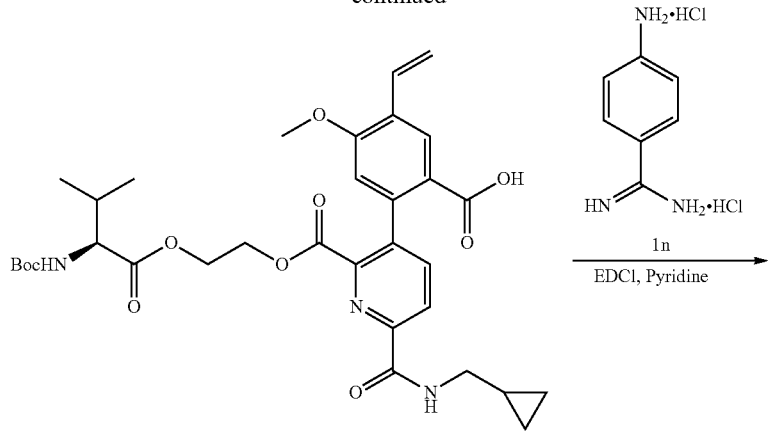

8c

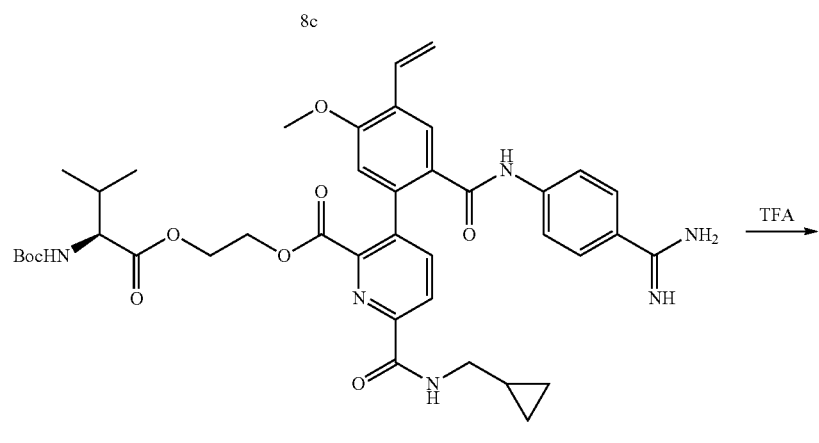

8d

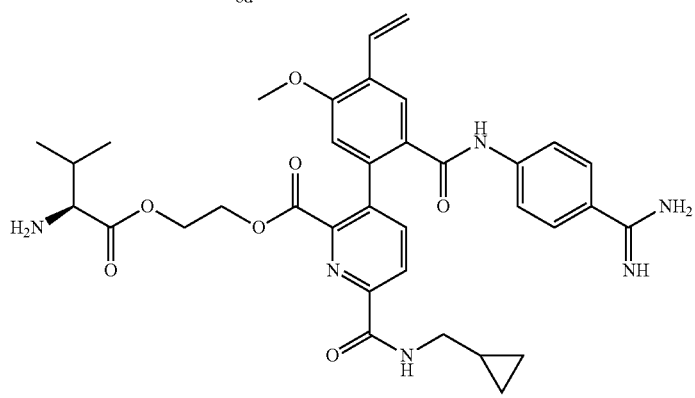

8e

Preparation of (S)-2-((2-amino-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate trifluoroacetate (8e)

Step-1: Preparation of (S)-2-((2-((tert-butoxycarbonyl)amino)-3-methylbutanoyl)oxy)ethyl 6-((cyclopropylmethyl)carbamoyl)-3-(2-formyl-5-methoxy-4-vinylphenyl)picolinate (8b)

To a solution of 6-(Cyclopropylmethylcarbamoyl)-3-(2-formyl-5-methoxy-4-vinylphenyl)picolinic acid (2a) (0.38 g, 1.00 mmol) in DMF (10 mL) was added N,N'-Dicyclohexyl-4-morpholinecarboxamidine (0.37 g, 1.25 mmol), (S)-2-bromoethyl 2-((tert-butoxycarbonyl)amino)-3-methylbutanoate (8a) (0.49 g, 1.50 mmol, prepared according to procedure reported by Fu, Xiaozhong et al. in Bioorganic & Medicinal Chemistry Letters, 17(2), 465-470; 2007) and heated at 80° C. for 5 h. The reaction was quenched with 15 mL of 1% citric acid aqueous solution and extracted with ethyl acetate (3×25 mL). The organic layers were combined washed with water, brine (25 mL), dried, filtered and purified by flash column chromatography (silica gel 25 g, eluting with 0-100% ethyl acetate in hexane), to furnish (S)-2-((2-((tert-butoxycarbonyl)amino)-3-methylbutanoyl)oxy)ethyl 6-((cyclopropylmethyl)carbamoyl)-3-(2-formyl-5-methoxy-4-vinylphenyl)picolinate (8b) (0.51 g, 82% yield) as white foam. $^1$HNMR (300 MHz, DMSO-d$_6$) δ 9.67 (s, 1H), 8.69

(s, 1H), 8.27 (d, J=8.0, 1H), 8.12 (s, 1H), 8.08 (d, J=8.0, 1H), 7.10 (d, J=8.1, 3H), 5.99 (d, J=17.7, 1H), 5.43 (d, J=11.3, 1H), 4.22 (s, 3H), 4.03 (dd, J=7.2, 14.3, 1H), 3.81 (s, 1H), 3.26 (s, 2H), 1.98-1.87 (m, 1H), 1.42-1.24 (m, 11H), 1.15-1.06 (m, 1H), 0.87 (d, J=6.8, 1H), 0.80 (d, J=6.8, 6H), 0.46 (d, J=7.9, 2H), 0.29 (d, J=3.7, 2H); MS (ES+) 624.0 (M+1), (ES−) 657.7 (M+Cl).

Step-2: Preparation of (S)-2-(6-((cyclopropylmethyl)carbamoyl)-2-(7-isopropyl-11,11-dimethyl-6,9-dioxo-2,5,10-trioxa-8-azadodecan-1-oyl)pyridin-3-yl)-4-methoxy-5-vinylbenzoic acid (8c)

Oxidation of (S)-2-((2-((tert-butoxycarbonyl)amino)-3-methylbutanoyl)oxy)ethyl 6-((cyclopropylmethyl)carbamoyl)-3-(2-formyl-5-methoxy-4-vinylphenyl)picolinate (8b) (0.49 g, 0.78 mmol) using the procedure as reported in step 11 of scheme 1 gave after workup and purification by flash column chromatography [silica gel 25 g, eluting with 0-100% methanol/ethyl acetate (1:9) in Hexanes] (S)-2-(6-((cyclopropylmethyl)carbamoyl)-2-(7-isopropyl-11,11-dimethyl-6,9-dioxo-2,5,10-trioxa-8-azadodecan-1-oyl)pyridin-3-yl)-4-methoxy-5-vinylbenzoic acid (8c) (0.43 g, 86% yield) as a white semisolid. $^1$HNMR (300 MHz, DMSO-$d_6$) δ 12.66-12.44 (m, 1H), 8.62 (s, 1H), 8.21 (d, J=8.0, 1H), 8.10 (s, 1H), 7.95 (d, J=8.0, 1H), 7.10 (d, J=8.1, 1H), 6.97 (dd, J=11.3, 17.8, 1H), 6.86 (s, 1H), 5.90 (d, J=17.8, 1H), 5.38 (d, J=12.4, 1H), 4.20 (s, 2H), 3.85 (s, 3H), 3.81 (d, J=8.0, 1H), 3.26 (s, 2H), 1.98-1.90 (m, 1H), 1.36 (d, J=12.7, 9H), 1.27 (d, J=8.0, 2H), 1.13-1.06 (m, 1H), 0.87 (d, J=6.8, 2H), 0.79 (s, 4H), 0.45 (d, J=8.1, 2H), 0.29 (d, J=4.9, 2H); MS (ES+) 662.05 (M+Na), (ES−) 638.23 (M−1).

Step-3: Preparation of (S)-2-((2-((tert-butoxycarbonyl)amino)-3-methylbutanoyl)oxy)ethyl 3-(2-((4-carbamimidoylphenyl)carbamoyl)-5-methoxy-4-vinylphenyl)-6-((cyclopropylmethyl)carbamoyl) picolinate (8d)

Compound (8d) was prepared from (S)-2-(6-((cyclopropylmethyl)carbamoyl)-2-(7-isopropyl-11,11-dimethyl-6,9-dioxo-2,5,10-trioxa-8-azadodecan-1-oyl)pyridin-3-yl)-4-methoxy-5-vinylbenzoic acid (8c) (0.42 mg, 0.66 mmol) using EDCI (0.19 g, 1.0 mmol) and 4-aminobenzimidamide dihydrochloride (1n) (0.17 g, 0.82 mmol) in DMF (5 mL) and Pyridine (5 mL) according to the procedure reported in step 4 of scheme 2. This gave after workup and purification by flash column chromatography [silica gel, 24 g, eluting with 0 to 30% methanol in chloroform] (S)-2-((2-((tert-butoxycarbonyl)amino)-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate (8d) (0.34 g, 69% yield) as white solid. MS (ES+) 757.1 (M+1); (ES−) 790.7 (M+Cl-).

Step-4: Preparation of (S)-2-((2-amino-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate trifluoroacetate (8e)

To a solution of (S)-2-((2-((tert-butoxycarbonyl)amino)-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate (8d) (0.1 g, 0.13 mmol) in dichloromethane (1 mL) was added 2,2,2-trifluoroacetic acid (1.02 mL, 13.21 mmol). The reaction mixture was stirred at room temperature for 1 h and concentrated to dryness. The residue obtained was purified by flash column chromatography [silica gel 4 g, eluting with 0-100% (CMW-80 in CHCl$_3$) followed by, CMW50 in CHCl$_3$), to furnish (S)-2-((2-amino-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate trifluoroacetate (8e) (0.036 g, 42% yield) as a white solid; $^1$HNMR (300 MHz, DMSO-D$_2$O)) δ 8.66 (t, J=5.4, 1H), 8.22 (d, J=8.0, 1H), 8.04 (d, J=8.0, 1H), 7.94 (s, 1H), 7.76 (s, 4H), 7.01 (m, 2H), 6.03 (d, J=8.0, 1H), 5.44 (d, J=4.0, 1H), 4.35-4.14 (m, 2H), 4.09 (m, 2H), 3.89 (s, 3H), 3.22 (m, 3H), 1.89-1.69 (m, 1H), 1.16-0.97 (m, 1H), 0.76 (dd, J=6.8, 10.7, 6H), 0.46 (s, 2H), 0.28 (s, 2H); MS (ES+): 657.0 (M+1); Analysis calculated for C$_{41}$H$_{50}$N$_6$O$_8$.1.5H$_2$O.1.1CF$_3$CO$_2$H: C, 55.22; H, 5.49; N, 10.39; F, 7.75. Found: C, 55.10; H, 5.13; N, 10.25; F, 7.84.

Scheme 9

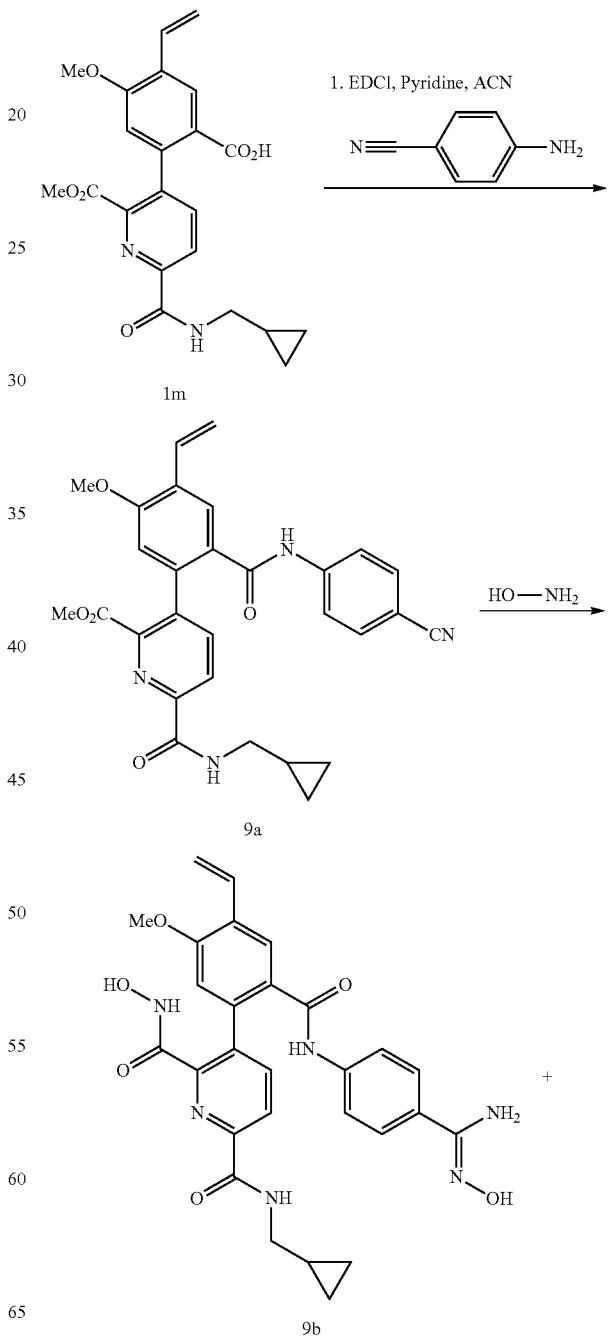

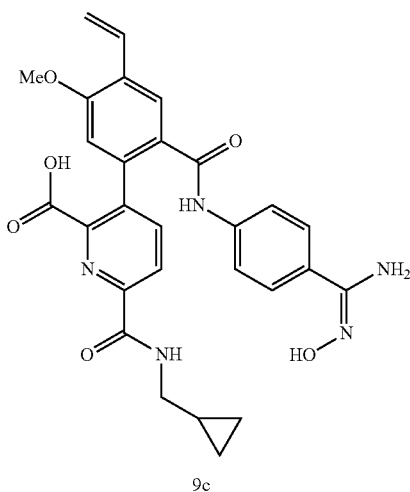 [SMILES: C=Cc1cc(C(=O)Nc2ccc(/C(N)=N\O)cc2)c(-c2ccc(C(=O)NCC3CC3)nc2C(=O)O)cc1OC]

9c

Preparation of N₆-(cyclopropylmethyl)-N₂-hydroxy-3-(2-((4-(N'-hydroxycarbamimidoyl)phenyl)carbamoyl)-5-methoxy-4-vinylphenyl)pyridine-2,6-dicarboxamide (9b) and 6-((cyclopropylmethyl)carbamoyl)-3-(2-((4-(N'-hydroxycarbamimidoyl)phenyl)carbamoyl)-5-methoxy-4-vinylphenyl)picolinic acid (9c)

Step-1: Preparation of methyl 3-(2-((4-cyanophenyl)carbamoyl)-5-methoxy-4-vinylphenyl)-6-((cyclopropylmethyl)carbamoyl)picolinate (9a)

Compound (9a) was prepared from 2-(6-((cyclopropylmethyl)carbamoyl)-2-(methoxycarbonyl)pyridin-3-yl)-4-methoxy-5-vinylbenzoic acid (1m) (0.41 g, 1.0 mmol) using EDCI (0.29 g, 1.5 mmol) and 4-aminobenzonitrile (0.24 g, 2.0 mmol) using acetonitrile (9 mL) and pyridine (1 mL) as solvent, according to the procedure reported in step 4 of scheme 2. This gave after workup and purification by flash column chromatography [silica gel, 24 g, eluting with 0-100% (9:1) EtOAc:MeOH in Hexane] to furnish methyl 3-(2-((4-cyanophenyl)carbamoyl)-5-methoxy-4-vinylphenyl)-6-((cyclopropylmethyl)carbamoyl)picolinate (9a) (0.46 g, 45%) as a white solid; ¹HNMR (300 MHz, DMSO-d₆) δ 10.73 (s, 1H), 8.67 (m, 1H), 8.22 (d, J=8.0, 1H), 8.05 (d, J=8.0, 1H), 7.93 (s, 1H), 7.76 (d, J=3.9, 4H), 7.01 (m, 2H), 6.04 (d, J=17.9, 1H), 5.44 (d, J=11.5, 1H), 3.91 (s, 3H), 3.60 (s, 3H), 3.20 (m, 2H), 1.17 (m, 1H), 0.45 (m, 2H), 0.27 (m, 2H); MS (ES+) 533.0 (M+Na), (ES−) 508.9 (M−1); IR (KBr) 2225 cm-1.

Step-2: Preparation of N₆-(cyclopropylmethyl)-N₂-hydroxy-3-(2-((4-(N'-hydroxycarbamimidoyl)phenyl)carbamoyl)-5-methoxy-4-vinylphenyl)pyridine-2,6-dicarboxamide (9b) and 6-((cyclopropylmethyl)carbamoyl)-3-(2-((4-(N'-hydroxycarbamimidoyl)phenyl)carbamoyl)-5-methoxy-4-vinylphenyl)picolinic acid (9c)

To a solution of methyl 3-(2-((4-cyanophenyl)carbamoyl)-5-methoxy-4-vinylphenyl)-6-((cyclopropylmethyl)carbamoyl)picolinate (9a) (0.44 g, 0.86 mmol) in methanol (10 mL) was added hydroxylamine (0.25 mL, 4.31 mmol) and heated at reflux for 1 h. The reaction mixture was concentrated in vacuum and the residue obtained was purified by column (silica gel 25 g, eluting with 0-100% CMA-80 in chloroform) to furnish N₆-(cyclopropylmethyl)-N₂-hydroxy-3-(2-((4-(N'-hydroxycarbamimidoyl)phenyl)carbamoyl)-5-methoxy-4-vinylphenyl)pyridine-2,6-dicarboxamide (9b) (0.092 g, 20% yield); ¹HNMR (300 MHz, DMSO-d₆) δ 11.73 (s, 1H), 10.31 (s, 1H), 9.50 (m, 1H), 9.28 (s, 1H), 9.16 (s, 1H), 8.12 (d, J=8.0, 1H), 7.93-7.78 (m, 2H), 7.51 (m, 4H), 7.02 (dd, J=11.3, 17.7, 1H), 6.88 (s, 1H), 6.00 (d, J=17.6, 1H), 5.70 (s, 2H), 5.40 (d, J=12.4, 1H), 3.84 (s, 3H), 3.23 (m, 2H), 1.17-1.01 (m, 2H), 0.47 (m, 2H), 0.27 (m, 2H); MS (ES+) 545.0 (M+1), 567.0 (M+Na); (ES−) 543.1 (M−1); Analysis calculated for C₂₈H₂₈N₆O₆: 0.75H₂O: C, 60.26; H, 5.33; N, 15.06. Found: C, 60.34; H, 5.45 N, 14.69; followed by 6-((cyclopropylmethyl)carbamoyl)-3-(2-((4-(N'-hydroxycarbamimidoyl)phenyl)carbamoyl)-5-methoxy-4-vinylphenyl)picolinic acid (9c) (0.35 g, 77% yield) as a white solid; ¹HNMR (300 MHz, DMSO-d₆) δ 9.48 (s, 1H), 8.83-8.66 (m, 1H), 7.89 (m, 1H), 7.77 (s, 1H), 7.64 (m, 1H), 7.45 (m, 4H), 7.21-7.06 (m, 2H), 7.00 (dd, J=11.4, 17.8, 1H), 6.75 (s, 1H), 5.95 (d, J=17.7, 1H), 5.69 (s, 2H), 5.37 (d, J=12.2, 1H), 3.82 (s, 3H), 3.19 (m, 2H), 1.12-1.07 (m, 1H), 0.45 (m, 2H), 0.25 (m, 2H); MS (ES+) 530.0 (M+1), (ES−) 528.0 (M−1).

Scheme 10

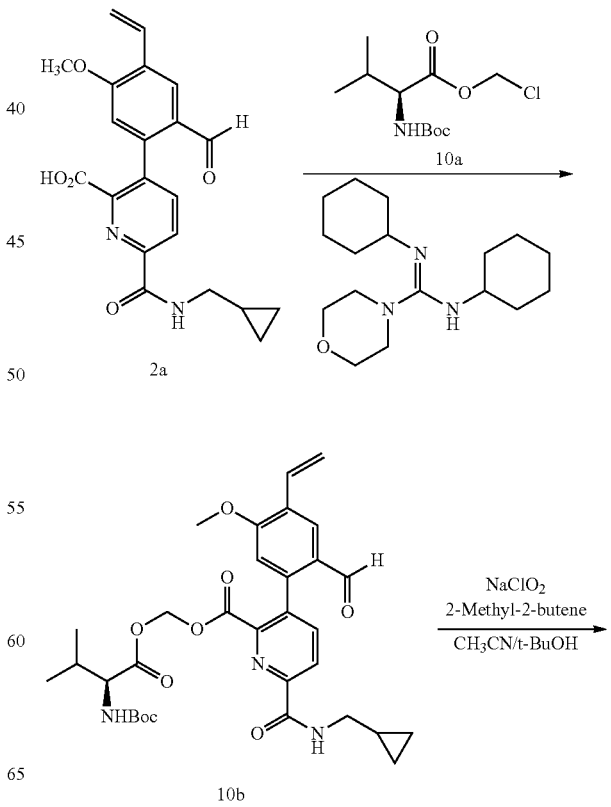

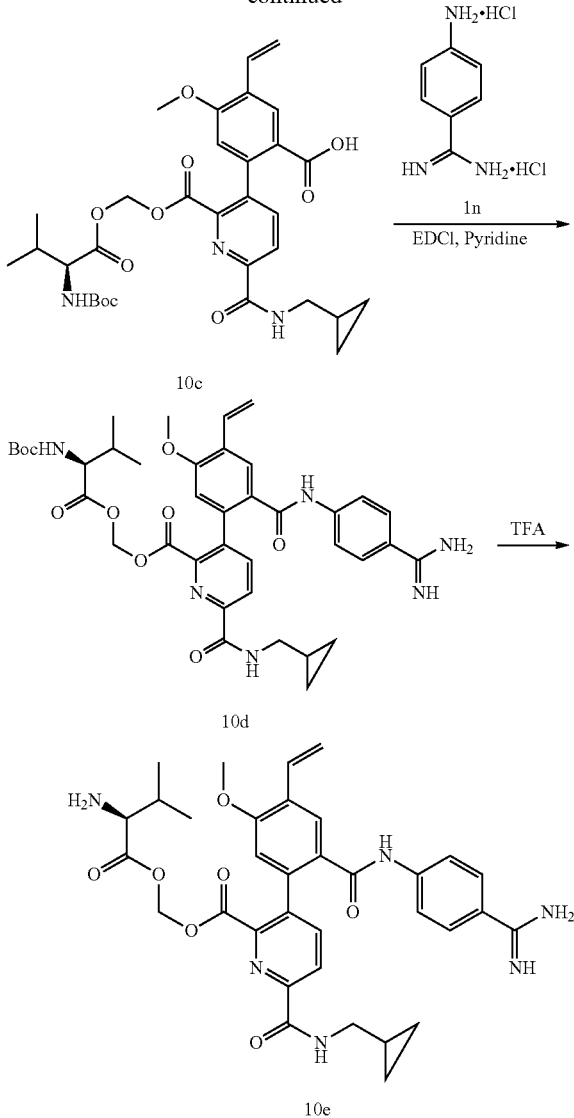

Preparation of (S)-((2-amino-3-methylbutanoyl)oxy)
methyl 3-(2-((4-carbamimidoylphenyl)carbamoyl)-
5-methoxy-4-vinylphenyl)-6-((cyclopropylmethyl)
carbamoyl)picolinate trifluoroacetate (10e)

Step-1: Preparation of (S)-((2-((tert-butoxycarbonyl)
amino)-3-methylbutanoyl)oxy)methyl 6-((cyclopro-
pylmethyl)carbamoyl)-3-(2-formyl-5-methoxy-4-
vinylphenyl)picolinate (10b)

Compound (10b) was prepared according to the procedure reported in step 1 of scheme 8 from 6-(Cyclopropylmethylcarbamoyl)-3-(2-formyl-5-methoxy-4-vinylphenyl)picolinic acid (2a) (0.57 g, 1.5 mmol) in DMF (10 mL) using N,N'-Dicyclohexyl-4-morpholinecarboxamidine (0.55 g, 1.25 mmol) and (S)-chloromethyl 2-((tert-butoxycarbonyl)amino)-3-methylbutanoate (10a) (0.6 g, 2.25 mmol, prepared according to procedure reported by Dousson, Cyril B. and Paparin, Jean-Laurent in PCT Int. Appl., 2015042375, 26 Mar. 2015). This gave after workup and purification by flash column chromatography (silica gel 25 g, eluting with ethyl acetate/Hexanes, 0-100%) (S)-((2-((tert-butoxycarbonyl)amino)-3-methylbutanoyl)oxy)methyl 6-((cyclopropylmethyl)carbamoyl)-3-(2-formyl-5-methoxy-4-vinylphenyl)picolinate (10b) (0.66 g, 72% yield) as a white solid; $^1$HNMR (300 MHz, DMSO-$d_6$) δ 9.69 (s, 1H), 8.67-8.51 (m, 1H), 8.29 (d, J=8.0, 1H), 8.14 (s, 1H), 8.07 (d, J=8.0, 1H), 7.25 (d, J=8.0, 1H), 7.01 (dd, J=11.5, 17.6, 2H), 6.01 (d, J=17.7, 1H), 5.92-5.81 (m, 1H), 5.74 (d, J=6.0, 1H), 5.45 (d, J=12.4, 1H), 3.91 (s, 3H), 3.87-3.79 (m, 1H), 3.24 (d, J=6.0, 2H), 1.97-1.82 (m, 1H), 1.35 (2s, 9H), 1.14-1.05 (m, 1H), 0.80 (dd, J=3.9, 6.7, 6H), 0.53-0.41 (m, 2H), 0.35-0.22 (m, 2H); MS (ES+) 632.0 (M+Na).

Step-2: Preparation of (S)-2-(6-((cyclopropylm-
ethyl)carbamoyl)-2-(6-isopropyl-10,10-dimethyl-5,
8-dioxo-2,4,9-trioxa-7-azaundecan-1-oyl)pyridin-3-
yl)-4-methoxy-5-vinylbenzoic acid (10c)

Oxidation of (S)-((2-((tert-butoxycarbonyl)amino)-3-methylbutanoyl)oxy)methyl 6-((cyclopropylmethyl)carbamoyl)-3-(2-formyl-5-methoxy-4-vinylphenyl)picolinate (10b) (0.63 g, 1.03 mmol) using the procedure as reported in step 11 of scheme 1 gave after workup and purification by flash column chromatography [silica gel 25 g, eluting with 0-100% methanol/ethyl acetate (1:9) in Hexanes] (S)-2-(6-((cyclopropylmethyl)carbamoyl)-2-(6-isopropyl-10,10-dimethyl-5,8-dioxo-2,4,9-trioxa-7-azaundecan-1-oyl)pyridin-3-yl)-4-methoxy-5-vinylbenzoic acid (10c) (0.16 g, 25% yield) as a white semisolid. $^1$HNMR (300 MHz, DMSO-$d_6$) δ 12.53 (s, 1H), 8.50 (t, 1H), 8.23 (d, J=8.0, 1H), 8.11 (s, 1H), 7.96 (d, J=8.0, 1H), 7.24 (d, J=7.9, 1H), 6.98 (dd, J=11.3, 17.8, 2H), 6.88 (s, 1H), 5.96-5.82 (m, J=3.4, 21.1, 2H), 5.73 (d, J=5.9, 1H), 5.39 (d, J=12.5, 1H), 3.85 (s, 3H), 3.82-3.72 (m, 1H), 3.29-3.19 (m, 2H), 2.05-1.90 (m, 1H), 1.35 (s, 9H), 0.92-0.75 (m, 10H). MS (ES+) 626.0 (M+1), 648.0 (M+Na); (ES−) 623.8 (M−1).

Step-3: Preparation of (S)-((2-((tert-butoxycarbonyl)
amino)-3-methylbutanoyl)oxy)methyl 3-(2-((4-car-
bamimidoylphenyl)carbamoyl)-5-methoxy-4-vinyl-
phenyl)-6-((cyclopropylmethyl)carbamoyl)picolinate
(10d)

Compound (8d) was prepared from (S)-2-(6-((cyclopropylmethyl)carbamoyl)-2-(6-isopropyl-10,10-dimethyl-5,8-dioxo-2,4,9-trioxa-7-azaundecan-1-oyl)pyridin-3-yl)-4-methoxy-5-vinylbenzoic acid (10c) (0.162 g, 0.26 mmol) using EDCI (0.075 g, 0.34 mmol) and 4-aminobenzimidamide dihydrochloride (1n) (0.08 g, 0.34 mmol) in DMF (2 mL) and Pyridine (2 mL) according to the procedure reported in step 4 of scheme 2. This gave after workup and purification by flash column chromatography [silica gel, 24 g, eluting with 0 to 30% methanol in chloroform) (S)-((2-((tert-butoxycarbonyl)amino)-3-methylbutanoyl)oxy)
methyl 3-(2-((4-carbamimidoylphenyl)carbamoyl)-5-methoxy-4-vinylphenyl)-6-((cyclopropylmethyl)carbamoyl)picolinate (10d) (0.098 g, 51% yield) as white solid; 1HNMR (300 MHz, DMSO-$d_6$) δ 10.72 (s, 1H), 9.27-9.02 (m, 2H), 9.00-8.77 (m, 2H), 8.50-8.35 (m, 1H), 8.24 (d, J=8.0, 1H), 8.04 (d, J=8.0, 1H), 7.97 (s, 1H), 7.83-7.71 (m, 4H), 7.24 (d, 1H), 7.11-6.98 (m, 2H), 6.05 (d, J=17.7, 1H), 5.95-5.62 (m, 2H), 5.45 (d, J=12.6, 1H), 3.89 (s, 3H), 3.86-3.77 (m, 1H), 3.28-3.13 (m, 2H), 1.99-1.84 (m, 1H), 1.34 (s, 9H), 1.07 (d, J=7.0, 1H), 0.79 (d, J=6.8, 6H), 0.52-0.40 (m, 2H), 0.31-0.23 (m, 2H); MS (ES+) 742.9 (M+1); (ES−): 776.4 (M+Cl-).

Step-4: Preparation of (S)-((2-amino-3-methylbutanoyl)oxy)methyl 3-(2-((4-carbamimidoylphenyl)carbamoyl)-5-methoxy-4-vinylphenyl)-6-((cyclopropylmethyl)carbamoyl)picolinate trifluoroacetate (10e)

Compound (10e) was prepared from (S)-((2-((tert-butoxycarbonyl)amino)-3-methylbutanoyl)oxy)methyl 3-(2-((4-carbamimidoylphenyl)carbamoyl)-5-methoxy-4-vinylphenyl)-6-((cyclopropylmethyl)carbamoyl)picolinate (10d) (0.07 g, 0.11 mmol) in dichloromethane (1 mL) using 2,2,2-trifluoroacetic acid (0.82 mL, 10.64 mmol) according to the procedure reported in Step-4 of scheme 8. This gave after workup and purification by flash column chromatography [silica gel 4 g, eluting with 0-100% (CMW-80 in CHCl$_3$) followed by, CMW50 in CMW-80), to furnish ((S)-((2-amino-3-methylbutanoyl)oxy)methyl 3-(2-((4-carbamimidoylphenyl)carbamoyl)-5-methoxy-4-vinylphenyl)-6-((cyclopropylmethyl)carbamoyl)picolinate trifluoroacetate (10e) (0.024 g, 35% yield) as a light brown solid; $^1$HNMR (300 MHz, DMSO-d$_6$) δ 10.75 (s, 1H), 9.18 (s, 5H), 8.52-8.29 (m, 3H), 8.25 (d, J=8.0, 2H), 8.04 (d, J=8.0, 1H), 7.99 (s, 1H), 7.81-7.74 (m, 4H), 7.10-6.96 (m, 2H), 6.06 (d, J=17.8, 1H), 6.01-5.70 (m, 2H), 5.46 (d, J=12.0, 1H), 3.92-3.86 (m, 4H), 3.27-3.20 (m, 2H), 2.16-1.97 (m, 1H), 1.13-1.07 (m, 1H), 0.87 (d, J=6.8, 6H), 0.48-0.42 (m, 2H), 0.31-0.26 (m, 2H); MS (ES+) 643.00 (M+1); Analysis calculated for C$_{34}$H$_{38}$N$_6$O$_7$.HCl.1.8 CF$_3$CO$_2$H: C, 51.06; H, 4.65; F, 11.60; N, 9.50. Found: C, 51.41; H, 4.78; F, 11.95; N, 9.33.

Scheme 11

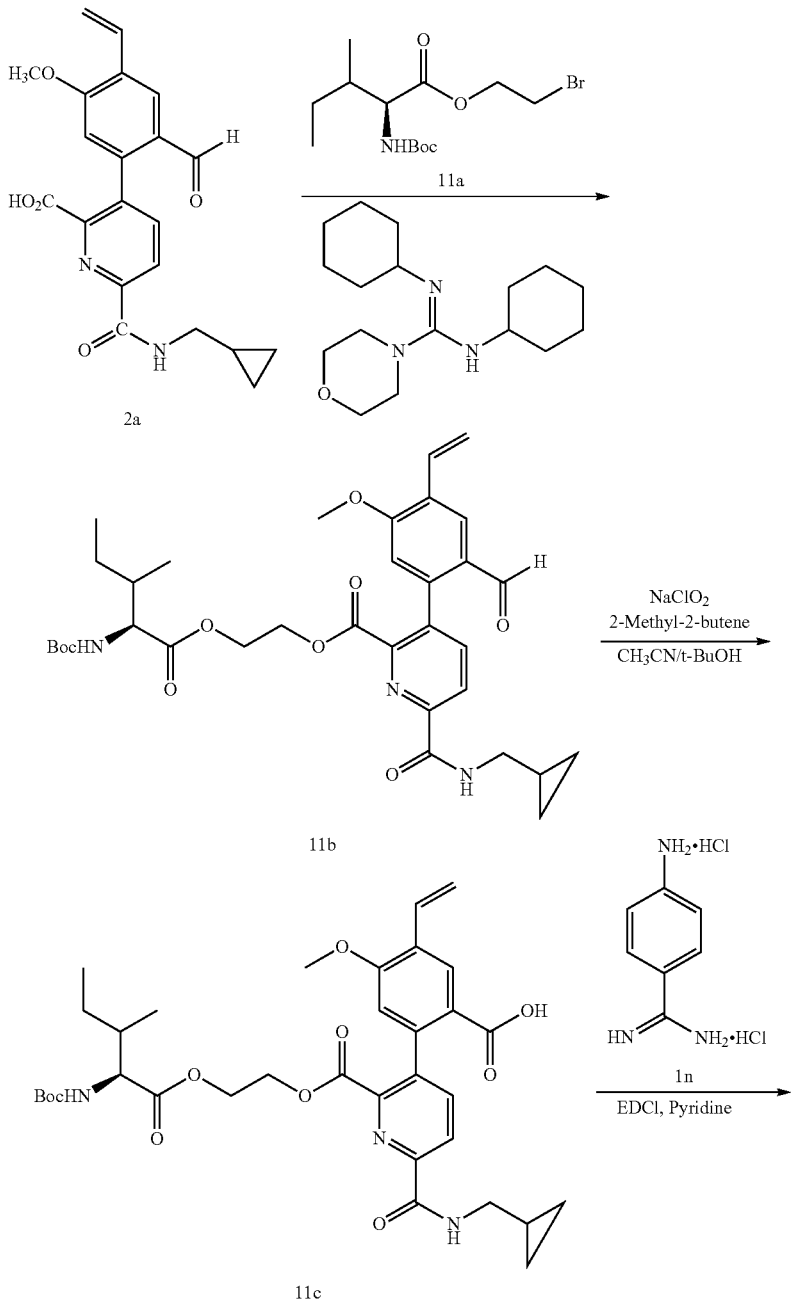

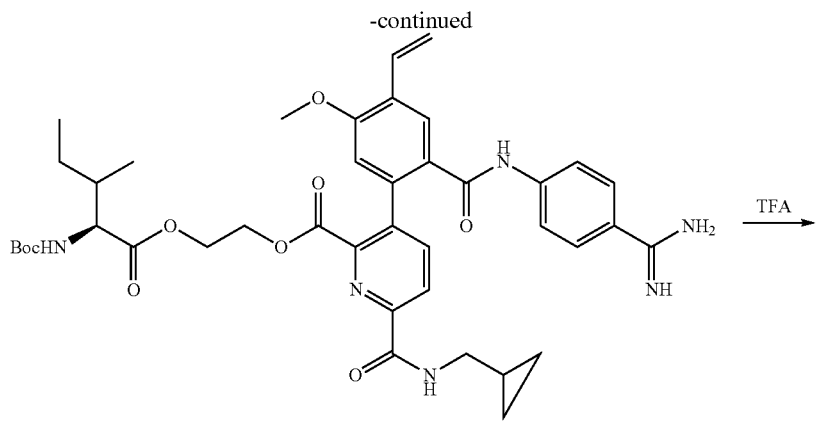

11d

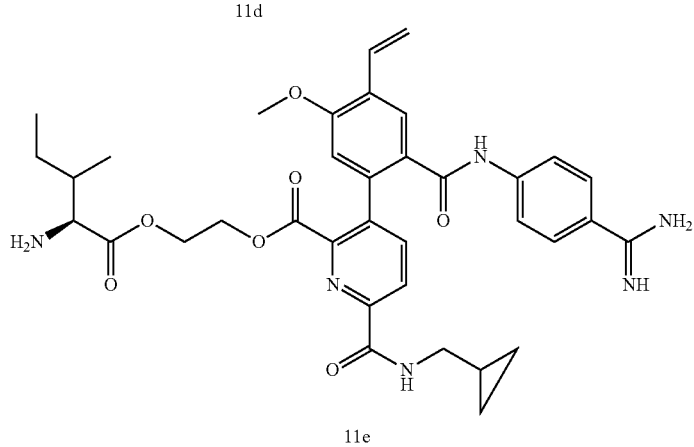

11e

Preparation of 2-(((2S)-2-amino-3-methylpentanoyl)oxy)ethyl 3-(2-((4-carbamimidoylphenyl)carbamoyl)-5-methoxy-4-vinylphenyl)-6-((cyclopropylmethyl)carbamoyl)picolinate trifluoroacetate (11e)

Step-1: Preparation of 2-(((2S)-2-((tert-butoxycarbonyl)amino)-3-methylpentanoyl)oxy)ethyl 6-((cyclopropylmethyl)carbamoyl)-3-(2-formyl-5-methoxy-4-vinylphenyl)picolinate (11b)

Compound (10b) was prepared according to the procedure reported in step 1 of scheme 8 from 6-(Cyclopropylmethylcarbamoyl)-3-(2-formyl-5-methoxy-4-vinylphenyl)picolinic acid (2a) (0.57 g, 1.5 mmol) in DMF (15 mL) using N,N'-Dicyclohexyl-4-morpholinecarboxamidine (0.55 g, 1.88 mmol) and (2S)-2-bromoethyl 2-((tert-butoxycarbonyl)amino)-3-methylpentanoate (11a) (0.76 g, 2.25 mmol, prepared according to procedure reported by Fu, Xiaozhong et al. in Bioorganic & Medicinal Chemistry Letters, 17(2), 465-470; 2007). This gave after workup and purification by flash column chromatography (silica gel 25 g, eluting with ethyl acetate/Hexanes, 0-100%) 2-(((2S,3R)-2-((tert-butoxycarbonyl)amino)-3-methylpentanoyl)oxy)ethyl 6-((cyclopropylmethyl)carbamoyl)-3-(2-formyl-5-methoxy-4-vinylphenyl)picolinate (11b) (0.75 g, 78% yield) as a white solid; $^1$HNMR (300 MHz, DMSO-$d_6$) δ 9.68 (2s, J=3.5, 1H), 8.69 (t, J=5.9, 1H), 8.26 (d, J=8.0, 1H), 8.12 (s, 1H), 8.08 (d, J=8.0, 1H), 7.17-6.94 (m, 3H), 5.99 (d, J=16.6, 1H), 5.43 (d, J=11.3, 1H), 4.21 (m, 2H), 4.03 (m, 2H), 3.90 (s, 3H), 3.89-3.83 (m, 1H), 3.31-3.21 (m, 2H), 1.75-1.61 (m, 1H), 1.33 (2s, J=3.8, 9H), 1.28-1.24 (m, 1H), 1.15-1.05 (m, 2H), 0.72 (dd, J=7.1, 18.2, 6H), 0.46 (m, 2H), 0.29 (m, 2H); MS (ES+) 638.1 (M+1); 660.1 (M+Na); (ES−) 636.2 (M−1).

Step-2: Preparation of 2-(2-((S)-7-((R)-sec-butyl)-11,11-dimethyl-6,9-dioxo-2,5,10-trioxa-8-azadodecan-1-oyl)-6-((cyclopropylmethyl)carbamoyl)pyridin-3-yl)-4-methoxy-5-vinylbenzoic acid (11c)

Oxidation of 2-(((2S)-2-((tert-butoxycarbonyl)amino)-3-methylpentanoyl)oxy)ethyl 6-((cyclopropylmethyl)carbamoyl)-3-(2-formyl-5-methoxy-4-vinylphenyl)picolinate (11b) (0.69 g, 1.08 mmol) using the procedure as reported in step 11 of scheme 1 gave after workup and purification by flash column chromatography [silica gel 25 g, eluting with 0-100% methanol/ethyl acetate (1:9) in Hexanes] 2-(2-((7S)-7-(sec-butyl)-11,11-dimethyl-6,9-dioxo-2,5,10-trioxa-8-azadodecan-1-oyl)-6-((cyclopropylmethyl)carbamoyl)pyridin-3-yl)-4-methoxy-5-vinylbenzoic acid (11c) (0.61 g, 86% yield) as an off-white semisolid. $^1$HNMR (300 MHz, DMSO-$d_6$) δ 12.55 (s, 1H), 8.62 (t, J=6.0, 1H), 8.21 (d, J=8.0, 1H), 8.11 (s, 1H), 7.96 (d, J=8.0, 1H), 7.10 (d, J=8.3, 1H), 6.97 (dd, J=11.3, 17.8, 1H), 6.85 (s, 1H), 5.91 (d, J=17.9, 1H), 5.38 (d, J=12.4, 1H), 4.43-4.30 (m, 1H), 4.24-4.16 (m, 2H), 3.85 (s, 3H), 3.45 (s, 2H), 3.29-3.20 (m, 2H), 1.76-1.59 (m, 1H), 1.34 (s, 9H), 1.07 (d, J=7.0, 3H), 0.78-0.67 (m, 6H), 0.51-0.40 (m, 2H), 0.34-0.25 (m, 2H). MS (ES−) 651.5 (M−1);

Step-3: Preparation of 2-(((2S)-2-((tert-butoxycarbonyl)amino)-3-methylpentanoyl)oxy)ethyl 3-(2-((4-carbamimidoylphenyl)carbamoyl)-5-methoxy-4-vinylphenyl)-6-((cyclopropylmethyl)carbamoyl) picolinate (11d)

Compound (11d) was prepared from 2-(2-((7S)-7-(sec-butyl)-11,11-dimethyl-6,9-dioxo-2,5,10-trioxa-8-azadodecan-1-oyl)-6-((cyclopropylmethyl)carbamoyl)pyridin-3-yl)-4-methoxy-5-vinylbenzoic acid (11c) (0.6 g, 0.91 mmol) using EDCI (0.26 g, 1.37 mmol) and 4-aminobenzimidamide dihydrochloride (1n) (0.29 g, 1.37 mmol) in DMF (5 mL) and Pyridine (5 mL) according to the procedure reported in step 4 of scheme 2. This gave after workup and purification by flash column chromatography [silica gel, 24 g, eluting with 0 to 30% methanol in chloroform) 2-(((2S)-2-((tert-butoxycarbonyl)amino)-3-methylpentanoyl)oxy) ethyl 3-(2-((4-carbamimidoylphenyl)carbamoyl)-5-methoxy-4-vinylphenyl)-6-((cyclopropylmethyl)carbamoyl)picolinate (11d) (0.41 g, 58% yield) as white solid; $^1$HNMR (300 MHz, DMSO-$d_6$) δ 10.68 (bs, 1H), 9.01 (s, 4H), 8.67-8.53 (m, 1H), 8.22 (d, J=8.0, 1H), 8.04 (d, J=8.0, 1H), 7.96 (s, 1H), 7.77 (s, 4H), 7.12-7.02 (m, 1H), 6.99 (s, 1H), 6.04 (d, J=17.6, 1H), 5.44 (d, J=12.3, 1H), 4.32-3.96 (m, 4H), 3.89 (s, 3H), 3.87-3.76 (m, 1H), 3.28-3.17 (m, 2H), 1.72-1.57 (m, 1H), 1.32 (s, 9H), 1.27-1.19 (m, 2H), 1.14-1.08 (m, 1H), 0.76-0.62 (m, 6H), 0.45 (M, 2H), 0.28 (M, 2H); MS (ES+) 771.1 (M+1); (ES−) 804.9 (M+Cl−).

Step-4: Preparation of 2-(((2S)-2-amino-3-methylpentanoyl)oxy)ethyl 3-(2-((4-carbamimidoylphenyl)carbamoyl)-5-methoxy-4-vinylphenyl)-6-((cyclopropylmethyl)carbamoyl)picolinate trifluoroacetate (11e)

Compound (11e) was prepared 2-(((2S)-2-((tert-butoxycarbonyl)amino)-3-methylpentanoyl)oxy)ethyl 3-(2-((4-carbamimidoylphenyl)carbamoyl)-5-methoxy-4-vinylphenyl)-6-((cyclopropylmethyl)carbamoyl)picolinate (111d) (0.39 g, 0.5 mmol) in dichloromethane (5 mL) using 2,2,2-trifluoroacetic acid (3.85 mL, 49.9 mmol) according to the procedure reported in Step-4 of scheme 8. This gave after workup and purification by flash column chromatography [silica gel 4 g, eluting with 0-100% (CMW-80 in CHCl$_3$) followed by, CMW50 in CMW-80), to furnish 2-(((2S)-2-amino-3-methylpentanoyl)oxy)ethyl 3-(2-((4-carbamimidoylphenyl)carbamoyl)-5-methoxy-4-vinylphenyl)-6-((cyclopropylmethyl)carbamoyl)picolinate trifluoroacetate (11e) (0.25 g, 73% yield) as a white solid; $^1$HNMR (300 MHz, DMSO-$d_6$) δ 10.71 (s, 1H), 9.14 (d, J=20.9, 4H), 8.56 (s, 1H), 8.35 (s, 3H), 8.23 (d, J=8.0, 1H), 8.05 (d, J=8.0, 1H), 7.97 (s, 1H), 7.77 (s, 4H), 7.32-7.11 (m, 1H), 7.03 (s, 1H), 6.99 (s, 1H), 6.05 (d, J=17.7, 1H), 5.45 (d, J=12.2, 1H), 4.26 (s, 4H), 3.90 (s, 3H), 3.38 (d, J=7.0, 1H), 3.22 (s, 2H), 1.76 (s, 1H), 1.31 (s, 1H), 1.08 (d, J=7.0, 2H), 0.79 (d, J=6.8, 3H), 0.70 (t, J=7.3, 3H), 0.51-0.39 (m, 2H), 0.32-0.20 (m, 2H); MS (ES+) 671.09 (M+1); Analysis calculated for: $C_{36}H_{42}N_6O_7 \cdot 0.5HCl \cdot 2CF_3CO_2H$: C, 52.39; H, 4.89; F, 12.43; N, 9.16. Found: C, 52.55; H, 5.01; F, 12.50; N, 8.91.

Scheme 12

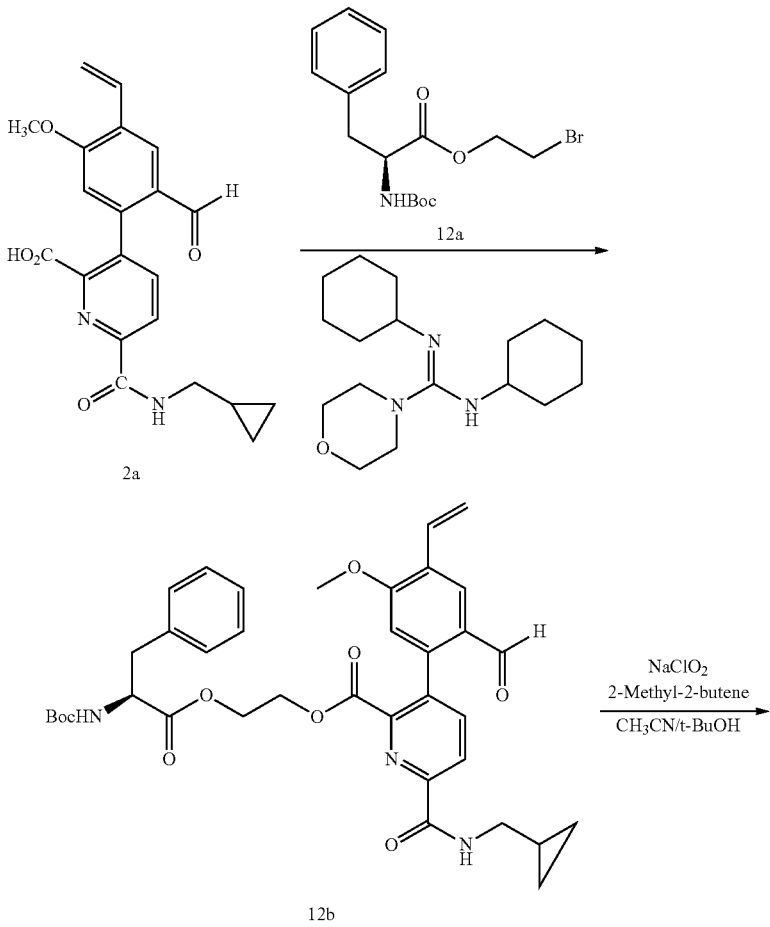

12b

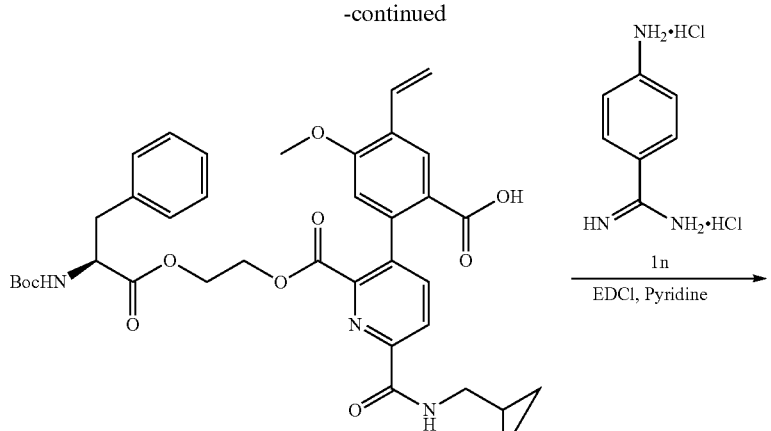

12c

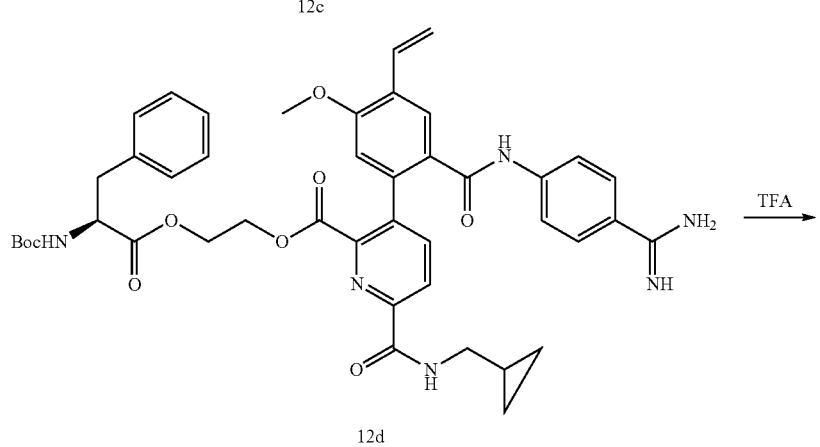

12d

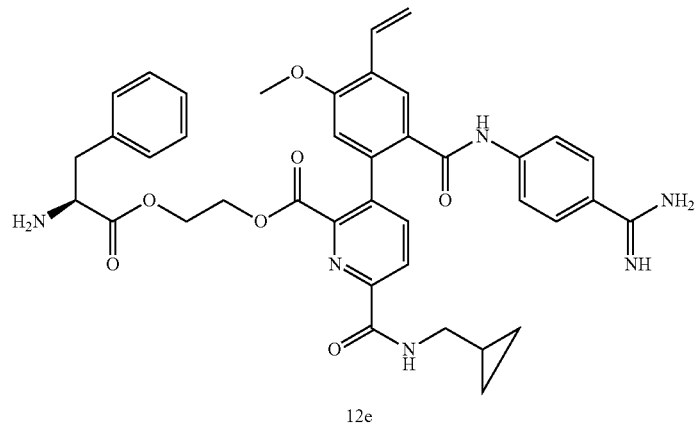

12e

Preparation of (S)-2-((2-amino-3-phenylpropanoyl) oxy)ethyl 3-(2-(((4-carbamimidoylphenyl)carbamoyl)-5-methoxy-4-vinylphenyl)-6-((cyclopropylmethyl)carbamoyl)picolinate trifluoroacetate (12e)

Step-1: Preparation of (S)-2-((2-(((tert-butoxycarbonyl)amino)-3-phenylpropanoyl)oxy)ethyl 6-((cyclopropylmethyl)carbamoyl)-3-(2-formyl-5-methoxy-4-vinylphenyl)picolinate (12b)

Compound (12b) was prepared according to the procedure reported in step 1 of scheme 8 from 6-(Cyclopropylmethylcarbamoyl)-3-(2-formyl-5-methoxy-4-vinylphenyl)picolinic acid (2a) (0.52 g, 1.34 mmol) in DMF (15 mL) using N,N'-Dicyclohexyl-4-morpholinecarboxamidine (0.5 g, 1.7 mmol) and (S)-2-bromoethyl 2-((tert-butoxycarbonyl)amino)-3-phenylpropanoate (12a) (0.76 g, 2.03 mmol, prepared according to procedure reported by Fu, Xiaozhong et al. in Bioorganic & Medicinal Chemistry Letters, 17(2), 465-470; 2007). This gave after workup and purification by flash column chromatography (silica gel 25 g, eluting with ethyl acetate/Hexanes, 0-100%) S)-2-((2-((tert-butoxycarbonyl)amino)-3-phenylpropanoyl)oxy)ethyl 6-((cyclopropylmethyl)carbamoyl)-3-(2-formyl-5-methoxy-4-vinylphenyl)picolinate (12b) (0.75 g, 82% yield) as a white solid; $^1$HNMR (300 MHz, DMSO-$d_6$) δ 9.69 (2s, J=5.6, 1H), 8.72 (t, J=6.0, 1H), 8.27 (d, J=8.0, 1H), 8.12 (s, 1H), 8.08 (d, J=8.0, 1H), 7.23 (dd, J=5.8, 20.9, 7H), 7.06-6.93 (m, 2H), 5.98 (d, J=17.7, 1H), 5.43 (d, J=12.4, 1H), 4.21-4.08 (m, 4H), 3.89 (s, 3H), 3.28-3.17 (m, 2H), 3.00-2.75 (m, 2H), 1.28 (s, 9H), 1.08 (m, 1H), 0.49-0.39 (m, 2H), 0.30-0.24 (m, 2H); MS (ES+) 694.0 (M+Na); MS (ES−) 669.8 (M−1)

Step-2: Preparation of (S)-2-(2-(7-benzyl-11,11-dimethyl-6,9-dioxo-2,5,10-trioxa-8-azadodecan-1-oyl)-6-((cyclopropylmethyl)carbamoyl)pyridin-3-yl)-4-methoxy-5-vinylbenzoic acid (12c)

Oxidation of (S)-2-((2-((tert-butoxycarbonyl)amino)-3-phenylpropanoyl)oxy)ethyl 6-((cyclopropylmethyl)carbamoyl)-3-(2-formyl-5-methoxy-4-vinylphenyl)picolinate (12b) (0.67 g, 1.00 mmol) using the procedure as reported in step 11 of scheme 1 gave after workup and purification by flash column chromatography [silica gel 25 g, eluting with 0-100% methanol/ethyl acetate (1:9) in Hexanes] (S)-2-(2-(7-benzyl-11,11-dimethyl-6,9-dioxo-2,5,10-trioxa-8-azadodecan-1-oyl)-6-((cyclopropylmethyl)carbamoyl)pyridin-3-yl)-4-methoxy-5-vinylbenzoic acid (12c) (0.45 g, 66% yield) as an off-white semisolid. $^1$HNMR (300 MHz, DMSO-$d_6$) δ 12.59 (s, 1H), 8.64 (t, J=6.0, 1H), 8.21 (d, J=8.0, 1H), 8.10 (s, 1H), 7.96 (d, J=8.0, 1H), 7.22 (dd, J=7.9, 15.0, 6H), 6.97 (dd, J=11.3, 17.8, 1H), 6.86 (s, 1H), 5.90 (d, J=17.7, 1H), 5.38 (d, J=12.5, 1H), 4.15 (s, 5H), 3.83 (s, 3H), 3.22 (s, 2H), 3.00-2.72 (m, 2H), 1.28 (s, 9H), 1.07 (s, 1H), 0.42 (d, J=8.0, 2H), 0.25 (d, J=3.7, 2H); MS (ES+) 710.0 (M+Na), MS (ES−) 686.0 (M−1).

Step-3: Preparation of (S)-2-((2-((tert-butoxycarbonyl)amino)-3-phenylpropanoyl)oxy)ethyl 3-(2-((4-carbamimidoylphenyl)carbamoyl)-5-methoxy-4-vinylphenyl)-6-((cyclopropylmethyl)carbamoyl) picolinate (12d)

Compound (12d) was prepared from (S)-2-(2-(7-benzyl-11,11-dimethyl-6,9-dioxo-2,5,10-trioxa-8-azadodecan-1-oyl)-6-((cyclopropylmethyl)carbamoyl)pyridin-3-yl)-4-methoxy-5-vinylbenzoic acid (12c) (0.45 g, 0.66 mmol) using EDCI (0.19 g, 1.00 mmol) and 4-aminobenzimidamide dihydrochloride (1n) (0.21 g, 1.00 mmol) in DMF (5 mL) and Pyridine (5 mL) according to the procedure reported in step 4 of scheme 2. This gave after workup and purification by flash column chromatography [silica gel, 24 g, eluting with 0 to 30% methanol in chloroform] (S)-2-((2-((tert-butoxycarbonyl)amino)-3-phenylpropanoyl)oxy)ethyl 3-(2-((4-carbamimidoylphenyl)carbamoyl)-5-methoxy-4-vinylphenyl)-6-((cyclopropylmethyl)carbamoyl)picolinate (12d) (0.43 g, 54% yield) as white solid; $^1$HNMR (300 MHz, DMSO-$d_6$) δ 10.48 (bs, 1H), 8.86 (s, 4H), 8.44-8.35 (m, 1H), 7.98 (d, J=8.0, 1H), 7.80 (d, J=8.0, 1H), 7.72 (s, 1H), 7.59-7.49 (m, 4H), 7.06-6.99 (m, J=7.9, 1H), 6.97-6.89 (m, J=6.4, 12.3, 4H), 6.85-6.73 (m, 2H), 5.80 (d, J=17.0, 1H), 5.20 (d, J=12.5, 1H), 4.05-3.94 (m, 1H), 3.92-3.77 (m, 4H), 3.63 (s, 3H), 3.00-2.94 (m, 2H), 2.74-2.47 (m, 2H), 1.03 (s, 9H), 0.94-0.92 (m, 1H), 0.22-0.11 (m, J=8.1, 2H), 0.02-−0.04 (m, 2H); MS (ES+) 805.1 (M+1); MS (ES−) 802.9 (M+Cl).

Step-4: Preparation of (S)-2-((2-amino-3-phenylpropanoyl)oxy)ethyl 3-(2-((4-carbamimidoylphenyl) carbamoyl)-5-methoxy-4-vinylphenyl)-6-((cyclopropylmethyl)carbamoyl)picolinate trifluoroacetate (12e)

Compound (12e) was prepared from (S)-2-((2-((tert-butoxycarbonyl)amino)-3-phenylpropanoyl)oxy)ethyl 3-(2-((4-carbamimidoylphenyl)carbamoyl)-5-methoxy-4-vinylphenyl)-6-((cyclopropylmethyl)carbamoyl)picolinate (12d) (0.4 g, 0.49 mmol) in dichloromethane (5 mL) using 2,2,2-trifluoroacetic acid (3.78 mL, 49.1 mmol) according to the procedure reported in Step-4 of scheme 8. This gave after workup and purification by flash column chromatography [silica gel 4 g, eluting with 0-100% (CMW-80 in CHCl$_3$) followed by, CMW50 in CMW-80), to furnish 2-(((2S)-2-amino-3-methylpentanoyl)oxy)ethyl 3-(2-((4-carbamimidoylphenyl)carbamoyl)-5-methoxy-4-vinylphenyl)-6-((cyclopropylmethyl)carbamoyl)picolinate trifluoroacetate (12e) (0.19 g, 56% yield) as a white solid; 10.69 (s, 1H), 9.38-9.01 (m, 1H), 8.92 (s, 2H), 8.63-8.56 (m, 1H), 8.22 (d, J=8.0, 1H), 8.04 (d, J=8.0, 1H), 7.94 (s, 1H), 7.80-7.71 (m, 4H), 7.22-7.07 (m, J=7.0, 6H), 7.01 (t, J=8.9, 2H), 6.03 (d, J=17.7, 1H), 5.44 (d, J=12.4, 1H), 4.29-4.09 (m, 2H), 4.07-3.97 (m, 2H), 3.87 (s, 3H), 3.70-3.59 (m, 1H), 3.22-3.12 (m, 2H), 2.92-2.71 (m, 2H), 1.11-0.98 (m, 1H), 0.47-0.34 (m, J=8.1, 2H), 0.31-0.18 (m, J=4.9, 2H); MS (ES+) 705.0 (M+1); Analysis calculated for: C$_{39}$H$_{40}$N$_6$O$_7$.0.5HCl.1.3CF$_3$CO$_2$H: C, 57.35; H, 4.84; F, 850; N, 9.65. Found: C, 57.01; H, 5.03; F, 8.52; N, 9.27.

Scheme 13

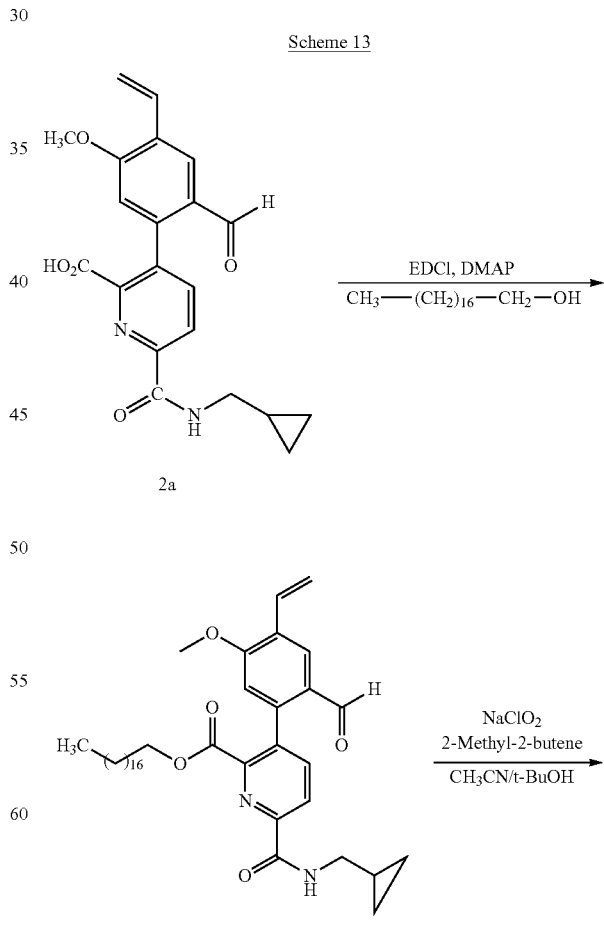

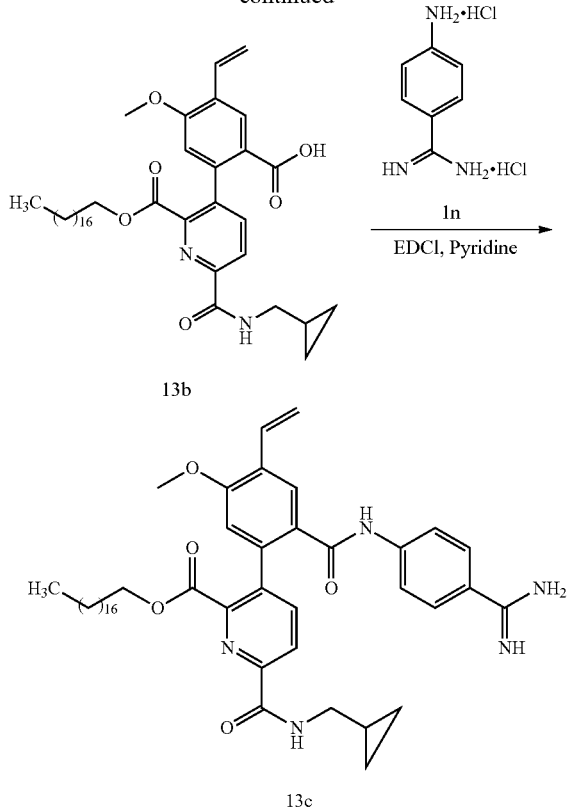

13b

13c

Preparation of Octadecyl 3-(2-(4-carbamimidoyl-phenylcarbamoyl)-5-methoxy-4-vinylphenyl)-6-(cyclopropylmethylcarbamoyl)picolinate (13c)

Step-1: Preparation of octadecyl 6-(cyclopropylmethylcarbamoyl)-3-(2-formyl-5-methoxy-4-vinylphenyl)picolinate (13a)

Compound (13a) was prepared according to the procedure reported in step 4 of scheme 2 from 6-(Cyclopropylmethylcarbamoyl)-3-(2-formyl-5-methoxy-4-vinylphenyl)picolinic acid (2a) (0.57 g, 1.5 mmol) in DMF (10 mL) using EDCI (0.43 g, 2.25 mmol) and DMAP (0.28 g, 2.25 mmol). This gave after workup and purification by flash column chromatography (silica gel 40 g, eluting with ethyl acetate/Hexanes, 0-100%) octadecyl 6-(cyclopropylmethylcarbamoyl)-3-(2-formyl-5-methoxy-4-vinylphenyl)picolinate (13a) (0.32 g, 33% yield) as a colorless oil; MS (ES+) 632.91 (M+1), 655.05 (M+Na).

Step-2: Preparation of 2-(6-(cyclopropylmethylcarbamoyl)-2-(octadecyloxycarbonyl)pyridin-3-yl)-4-methoxy-5-vinylbenzoic acid (13b)

Oxidation of octadecyl 6-(cyclopropylmethylcarbamoyl)-3-(2-formyl-5-methoxy-4-vinylphenyl)picolinate (13a) (0.31 g, 0.49 mmol) using the procedure as reported in step 11 of scheme 1 gave after workup and purification by flash column chromatography [silica gel 12 g, eluting with 0-100% methanol/ethyl acetate (1:9) in Hexanes] 2-(6-(cyclopropylmethylcarbamoyl)-2-(octadecyloxycarbonyl) pyridin-3-yl)-4-methoxy-5-vinylbenzoic acid (13b) as a white semisolid. $^1$HNMR (300 MHz, DMSO-$d_6$) δ 12.57 (s, 1H), 8.65 (t, J=6.1 Hz, 1H), 8.18 (d, J=8.0 Hz, 1H), 8.10 (s, 1H), 7.95 (d, J=8.0 Hz, 1H), 6.97 (dd, J=17.8, 11.3 Hz, 1H), 6.88 (s, 1H), 5.89 (d, J=16.5 Hz, 1H), 5.37 (d, J=12.5 Hz, 1H), 3.97 (t, J=5.9 Hz, 2H), 3.84 (s, 3H), 3.22 (t, J=6.6 Hz, 2H), 1.22 (d, J=12.4 Hz, 26H), 1.10 (s, 5H), 0.97 (s, 2H), 0.84 (d, J=6.9 Hz, 3H), 0.44 (dd, J=5.2, 2.9 Hz, 2H), 0.32-0.22 (m, 2H). MS (ES−) 647.50 (M−1).

Step-3: Preparation of octadecyl 3-(2-(4-carbamimidoylphenylcarbamoyl)-5-methoxy-4-vinylphenyl)-6-(cyclopropylmethylcarbamoyl)picolinate (13c)

Compound (13c) was prepared from 2-(6-(cyclopropylmethylcarbamoyl)-2-(octadecyloxycarbonyl)pyridin-3-yl)-4-methoxy-5-vinylbenzoic acid (13b) (0.09 g, 0.13 mmol) using EDCI (0.04 g, 0.20 mmol) and 4-aminobenzimidamide dihydrochloride (1n) (0.034 g, 0.16 mmol) in DMF (5 mL) and Pyridine (5 mL) according to the procedure reported in step 4 of scheme 2. This gave after workup and purification by flash column chromatography [silica gel, 24 g, eluting with 0 to 100% methanol in chloroform) octadecyl 3-(2-(4-carbamimidoylphenylcarbamoyl)-5-methoxy-4-vinylphenyl)-6-(cyclopropylmethylcarbamoyl)picolinate (13c) (0.008 g, 8% yield) as pale yellow solid; $^1$HNMR (300 MHz, DMSO-$d_6$) δ 10.67 (s, 1H, $D_2O$ exchangeable), 9.19 (s, 2H, $D_2O$ exchangeable), 8.83 (s, 2H, $D_2O$ exchangeable), 8.68-8.56 (m, 1H), 8.19 (d, J=8.1, 1H), 8.01 (d, J=8.0, 1H), 7.96 (s, 1H), 7.78 m, 4H), 7.02 (m, 2H), 6.10-5.97 (m, 1H), 5.49-5.37 (m, 1H), 4.03-3.95 (m, 2H), 3.89 (s, 3H), 3.24-3.19 (m, 2H), 1.23 (bm, 29H), 1.11-1.06 (m, 3H), 0.85 (m, 3H), 0.45 (m, 2H), 0.27 (m, 2H); MS (ES+) 767.4 (M+1).

Scheme 14

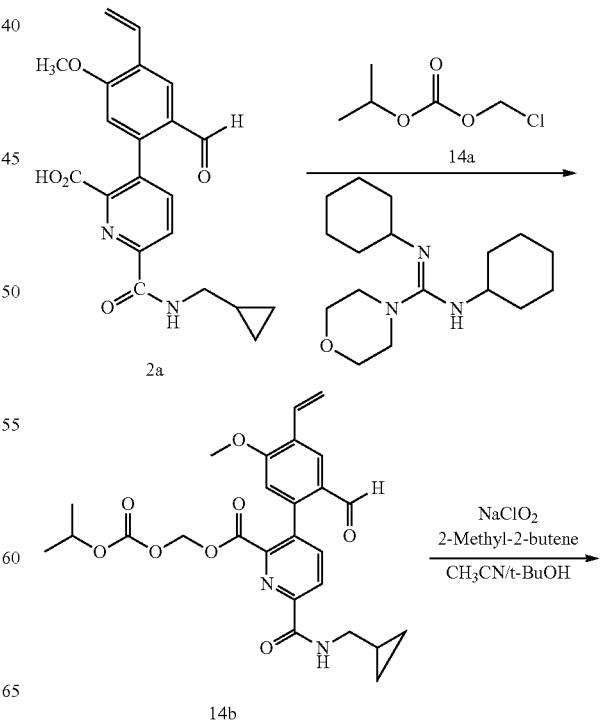

2a

14b

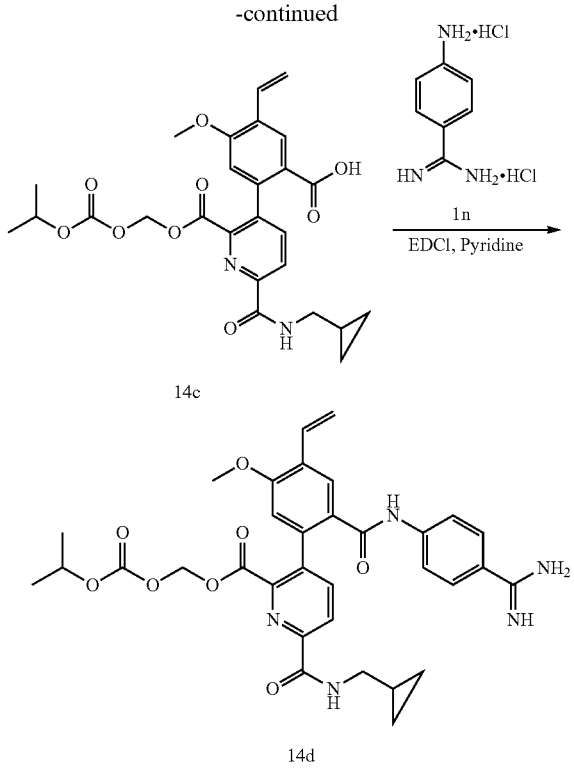

Preparation of ((isopropoxycarbonyl)oxy)methyl 3-(2-((4-carbamimidoylphenyl)carbamoyl)-5-methoxy-4-vinylphenyl)-6-((cyclopropylmethyl) carbamoyl)picolinate (14d)

Step-1: Preparation of ((isopropoxycarbonyl)oxy) methyl 6-((cyclopropylmethyl)carbamoyl)-3-(2-formyl-5-methoxy-4-vinylphenyl)picolinate (14b)

Compound (14b) was prepared according to the procedure reported in step 1 of scheme 8 from 6-(Cyclopropylmethylcarbamoyl)-3-(2-formyl-5-methoxy-4-vinylphenyl)picolinic acid (2a) (0.87 g, 2.25 mmol) in DMF (10 mL) using N,N'-Dicyclohexyl-4-morpholinecarboxamidine (0.83 g, 2.25 mmol) and chloromethyl isopropyl carbonate (14a) (0.52 g, 3.38.25 mmol). This gave after workup and purification by flash column chromatography (silica gel 25 g, eluting with ethyl acetate/Hexanes, 0-100%) ((isopropoxycarbonyl)oxy)methyl 6-((cyclopropylmethyl)carbamoyl)-3-(2-formyl-5-methoxy-4-vinylphenyl)picolinate (14b) (0.73 g, 65% yield) as a white solid; $^1$H NMR (300 MHz, DMSO-$d_6$) δ 9.69 (s, 1H), 8.70 (q, J=6.4 Hz, 1H), 8.27 (d, J=8.0 Hz, 1H), 8.13 (s, 1H), 8.08 (d, J=8.0 Hz, 1H), 7.08-6.91 (m, 2H), 6.06-5.95 (m, 1H), 5.73 (s, 2H), 5.42 (t, J=13.6 Hz, 1H), 4.81-4.66 (m, 1H), 3.90 (s, 3H), 3.24 (dd, J=10.2, 6.6 Hz, 2H), 1.22 (d, J=6.3 Hz, 6H), 1.09 (d, J=7.0 Hz, 1H), 0.49-0.42 (m, 2H), 0.29 (q, J=4.9 Hz, 2H); MS (ES+): MS (ES+) 519.0 (M+Na); Analysis calculated for: $C_{26}H_{28}N_2O_8$: C, 62.89; H, 5.68; N, 5.64. Found: C, 62.59; H, 5.62; N, 5.52.

Step-2: Preparation of 2-(6-((cyclopropylmethyl) carbamoyl)-2-((((isopropoxycarbonyl)oxy)methoxy) carbonyl)pyridin-3-yl)-4-methoxy-5-vinylbenzoic acid (14c)

Oxidation of ((isopropoxycarbonyl)oxy)methyl 6-((cyclopropylmethyl)carbamoyl)-3-(2-formyl-5-methoxy-4-vinylphenyl)picolinate (14b) (0.71 g, 1.43 mmol) using the procedure as reported in step 11 of scheme 1 gave after workup and purification by flash column chromatography [silica gel 12 g, eluting with 0-100% methanol/ethyl acetate (1:9) in Hexanes] 2-(6-((cyclopropylmethyl)carbamoyl)-2-((((isopropoxycarbonyl)oxy)methoxy) carbonyl)pyridin-3-yl)-4-methoxy-5-vinylbenzoic acid (14c) (0.19 g, 26% yield) as a white solid. $^1$HNMR (300 MHz, DMSO-$d_6$) δ 12.57 (s, 1H), 8.64 (t, J=6.1 Hz, 1H), 8.22 (d, J=8.0 Hz, 1H), 7.95 (d, J=8.1 Hz, 1H), 6.98 (dd, J=17.8, 11.3 Hz, 1H), 6.88 (s, 1H), 5.90 (dd, J=17.7, 1.4 Hz, 1H), 5.77-5.66 (m, 2H), 5.39 (dd, J=11.2, 1.4 Hz, 1H), 4.80-4.65 (m, 1H), 3.85 (s, 3H), 3.33-3.14 (m, 2H), 1.34-1.15 (m, 6H), 1.16-1.09 (m, 1H), 0.52-0.39 (m, 2H), 0.34-0.22 (m, 2H).

Step-3: Preparation of ((isopropoxycarbonyl)oxy) methyl 3-(2-((4-carbamimidoylphenyl)carbamoyl)-5-methoxy-4-vinylphenyl)-6-((cyclopropylmethyl) carbamoyl)picolinate (14d)

Compound (14d) was prepared from 2-(6-((cyclopropylmethyl)carbamoyl)-2-((((isopropoxycarbonyl)oxy) methoxy) carbonyl)pyridin-3-yl)-4-methoxy-5-vinylbenzoic acid (14c) (0.18 g, 0.35 mmol) using EDCI (0.14 g, 0.71 mmol) and 4-aminobenzimidamide dihydrochloride (1n) (0.18 g, 0.88 mmol) in DMF (5 mL) and Pyridine (5 mL) according to the procedure reported in step 4 of scheme 2. This gave after workup and purification by flash column chromatography [silica gel, 24 g, eluting with 0 to 30% methanol in chloroform) ((isopropoxycarbonyl)oxy)methyl 3-(2-((4-carbamimidoylphenyl)carbamoyl)-5-methoxy-4-vinylphenyl)-6-((cyclopropylmethyl)carbamoyl)picolinate (14d) (0.081 g, 36% yield) as white solid; $^1$HNMR (300 MHz, DMSO-$d_6$) δ 10.72 (s, 1H), 9.20 (s, 2H), 8.89 (s, 2H), 8.62 (t, J=6.1 Hz, 1H), 8.22 (d, J=8.0 Hz, 1H), 8.01 (d, J=8.1 Hz, 1H), 7.98 (s, 1H), 7.78 (s, 4H), 7.10-6.96 (m, 2H), 6.04 (t, J=14.9 Hz, 1H), 5.72 (s, 2H), 5.45 (d, J=12.5 Hz, 1H), 4.72 (m, 1H), 3.89 (s, 3H), 3.21 (s, 2H), 1.19 (d, J=6.2 Hz, 6H), 1.08 (m, 1H), 0.44 (m, 2H), 0.27 (m, 2H); MS (ES+) 630.0 (M+1), (ES−) 664.2 (M+Cl); Analysis calculated for $C_{35}H_{35}N_5O_8$.(HCl).($H_2O$): C, 57.93; H, 5.60; N, 10.24; Cl, 5.18. Found: C, 58.08; H, 5.58; N, 9.84; Cl, 4.95.

Scheme 15

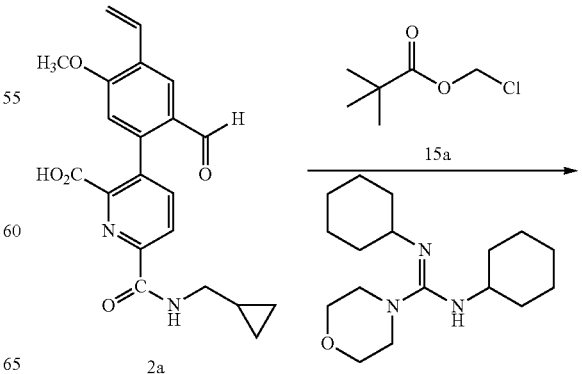

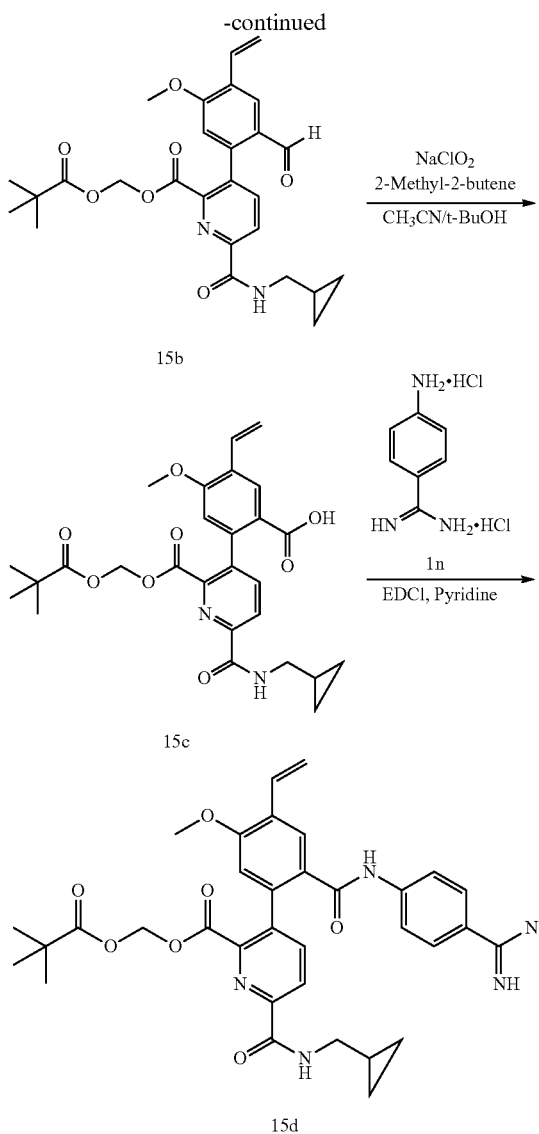

Preparation of (pivaloyloxy)methyl 3-(2-((4-carbamimidoylphenyl)carbamoyl)-5-methoxy-4-vinylphenyl)-6-((cyclopropylmethyl)carbamoyl)picolinate (15d)

Step-1: Preparation of (pivaloyloxy)methyl 6-((cyclopropylmethyl)carbamoyl)-3-(2-formyl-5-methoxy-4-vinylphenyl)picolinate (15b)

Compound (15b) was prepared according to the procedure reported in step 1 of scheme 8 from 6-(Cyclopropylmethylcarbamoyl)-3-(2-formyl-5-methoxy-4-vinylphenyl)picolinic acid (2a) (0.87 g, 2.25 mmol) in DMF (10 mL) using N,N'-Dicyclohexyl-4-morpholinecarboxamidine (0.83 g, 2.25 mmol) and chloromethyl pivalate (15a) (0.49 mL, 3.38 mmol). This gave after workup and purification by flash column chromatography (silica gel 25 g, eluting with ethyl acetate/Hexanes, 0-100%) ((isopropoxycarbonyl)oxy)methyl (pivaloyloxy)methyl 6-((cyclopropylmethyl)carbamoyl)-3-(2-formyl-5-methoxy-4-vinylphenyl)picolinate (15b) (0.95 g, 80% yield) as a white solid; $^1$H NMR (300 MHz, MeOD) δ 9.68 (s, 1H), 8.67 (t, J=5.9 Hz, 1H), 8.27 (d, J=8.0 Hz, 1H), 8.12 (s, 1H), 8.07 (d, J=8.0 Hz, 1H), 7.08-6.91 (m, 2H), 5.99 (dd, J=17.8, 1.3 Hz, 1H), 5.74 (q, J=5.8 Hz, 2H), 5.44 (dd, J=11.2, 1.2 Hz, 1H), 3.90 (s, 3H), 3.24 (dd, J=10.2, 6.7 Hz, 2H), 1.13-1.06 (m, 1H), 1.04 (s, 9H), 0.50-0.39 (m, 2H), 0.34-0.22 (m, 2H); MS (ES+) 494.96 (M+1); 516.93 (M+Na);

Step-2: Preparation of 2-(6-((cyclopropylmethyl)carbamoyl)-2-(((pivaloyloxy)methoxy)carbonyl)pyridin-3-yl)-4-methoxy-5-vinylbenzoic acid (15c)

Oxidation of ((isopropoxycarbonyl)oxy)methyl (pivaloyloxy)methyl 6-((cyclopropylmethyl)carbamoyl)-3-(2-formyl-5-methoxy-4-vinylphenyl)picolinate (15b) (0.95 g, 1.93 mmol) using the procedure as reported in step 11 of scheme 1 gave after workup and purification by flash column chromatography [silica gel 25 g, eluting with 0-20% methanol in chloroform] 2-(6-((cyclopropylmethyl)carbamoyl)-2-(((pivaloyloxy)methoxy)carbonyl)pyridin-3-yl)-4-methoxy-5-vinylbenzoic acid (15c) (0.73 g, 70% yield) as a white solid. $^1$HNMR (300 MHz, DMSO-d$_6$) δ 12.53 (s, 1H), 8.60 (t, J=6.0 Hz, 1H), 8.22 (d, J=8.0 Hz, 1H), 8.10 (s, 1H), 7.94 (d, J=8.0 Hz, 1H), 6.97 (dd, J=17.8, 11.3 Hz, 1H), 6.89 (s, 1H), 5.89 (dd, J=17.8, 1.2 Hz, 1H), 5.74 (s, 2H), 5.39 (dd, J=11.3, 1.2 Hz, 1H), 3.83 (s, 3H), 3.24 (dd, J=9.4, 6.6 Hz, 2H), 1.30-1.24 (m, 1H), 1.05 (s, 9H), 0.53-0.40 (m, 2H), 0.32-0.23 (m, 2H); MS (ES+) 533.0 (M+Na); (ES−) 509.4 (M−1)

Step-3: Preparation of (pivaloyloxy)methyl 3-(2-((4-carbamimidoylphenyl)carbamoyl)-5-methoxy-4-vinylphenyl)-6-((cyclopropylmethyl)carbamoyl)picolinate (15d)

Compound (15d) was prepared from 2-(6-((cyclopropylmethyl)carbamoyl)-2-(((pivaloyloxy)methoxy)carbonyl)pyridin-3-yl)-4-methoxy-5-vinylbenzoic acid (15c) (0.7 g, 1.37 mmol) using EDCI (0.33 g, 1.71 mmol) and 4-aminobenzimidamide dihydrochloride (1n) (0.36 g, 1.71 mmol) in DMF (5 mL) and Pyridine (5 mL) according to the procedure reported in step 4 of scheme 2. This gave after workup and purification by flash column chromatography [silica gel, 40 g, eluting with 0 to 30% methanol in chloroform) (pivaloyloxy)methyl 3-(2-((4-carbamimidoylphenyl)carbamoyl)-5-methoxy-4-vinylphenyl)-6-((cyclopropylmethyl)carbamoyl)picolinate (15d) (0.5 g, 58% yield) as white solid; $^1$HNMR (300 MHz, DMSO-d$_6$) δ 10.69 (s, 1H), 9.17 (s, 2H), 8.85 (s, 2H), 8.53 (t, J=6.0 Hz, 1H), 8.23 (d, J=8.0 Hz, 1H), 8.03-7.97 (m, 2H), 7.85-7.68 (m, 4H), 7.12-6.94 (m, 2H), 6.05 (d, J=17.7 Hz, 1H), 5.73 (s, 2H), 5.45 (d, J=12.6 Hz, 1H), 3.88 (s, 3H), 3.26-3.15 (m, 2H), 1.15-1.06 (m, 1H), 1.03 (s, 9H), 0.51-0.40 (m, 2H), 0.33-0.23 (m, 2H); MS (ES+): 628.0 (M+1), MS (ES−) 662.2 (M+Cl); Analysis calculated for $C_{34}H_{37}N_5O_7HCl.H_2O$: C, 59.86; H, 5.91; Cl, 5.20; N, 10.27. Found: C, 60.08; H, 5.60; Cl, 4.95; N, 10.19.

Scheme 16

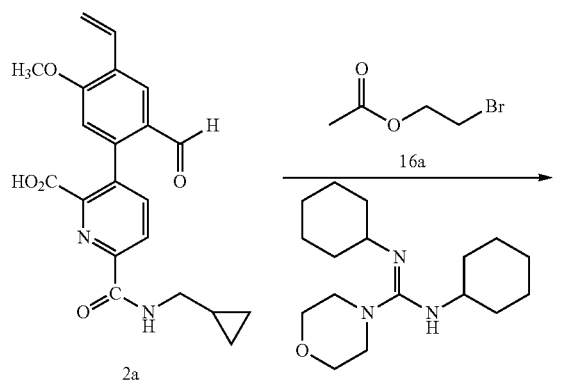

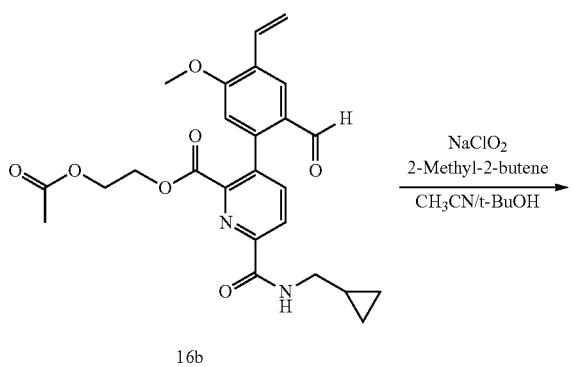

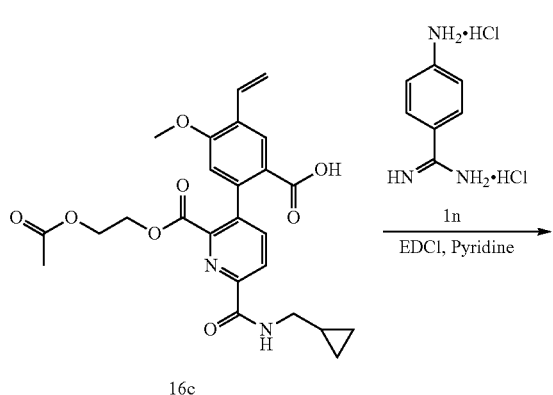

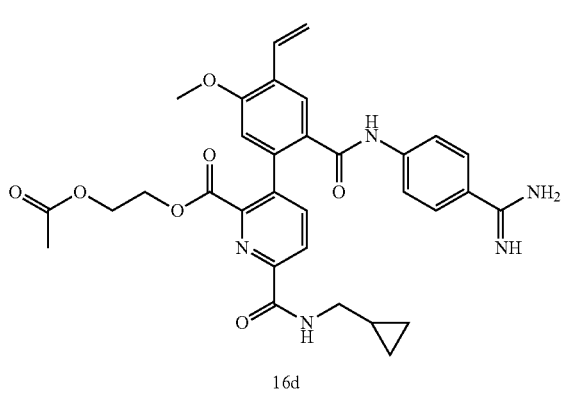

Preparation of 2-acetoxyethyl 3-(2-((4-carbamimidoylphenyl)carbamoyl)-5-methoxy-4-vinylphenyl)-6-((cyclopropylmethyl)carbamoyl)picolinate (16d)

Step-1: Preparation of 2-acetoxyethyl 6-((cyclopropylmethyl)carbamoyl)-3-(2-formyl-5-methoxy-4-vinylphenyl)picolinate (16b)

Compound (16b) was prepared according to the procedure reported in step 1 of scheme 8 from 6-(Cyclopropylmethylcarbamoyl)-3-(2-formyl-5-methoxy-4-vinylphenyl)picolinic acid (2a) (0.87 g, 2.25 mmol) in DMF (10 mL) using N,N'-Dicyclohexyl-4-morpholinecarboxamidine (0.83 g, 2.25 mmol) and 2-bromoethyl acetate (16a) (0.37 mL, 3.38 mmol). This gave after workup and purification by flash column chromatography (silica gel 25 g, eluting with ethyl acetate/Hexanes, 0-100%) 2-acetoxyethyl 6-((cyclopropylmethyl)carbamoyl)-3-(2-formyl-5-methoxy-4-vinylphenyl)picolinate (16b) (0.63 g, 55% yield) as a yellow semisolid; $^1$H NMR (300 MHz, DMSO-$d_6$) δ 9.68 (s, 1H), 8.74 (t, J=6.1 Hz, 1H), 8.26 (d, J=8.0 Hz, 1H), 8.11 (s, 1H), 8.09 (d, J=8.0 Hz, 1H), 7.07-6.91 (m, 2H), 5.99 (dd, J=17.8, 1.3 Hz, 1H), 5.44 (dd, J=11.3, 1.2 Hz, 1H), 4.24 (t, J=4.4 Hz, 2H), 4.00-3.94 (m, 2H), 3.90 (s, 3H), 3.29-3.21 (m, 2H), 1.92 (s, 3H), 1.15-1.06 (m, 1H), 0.53-0.40 (m, 2H), 0.35-0.23 (m, 2H); MS (ES+) 489.0 (M+Na); (ES−) 465.1 (M−1).

Step-2: Preparation of 2-(2-((2-acetoxyethoxy)carbonyl)-6-((cyclopropylmethyl)carbamoyl)pyridin-3-yl)-4-methoxy-5-vinylbenzoic acid (16c)

Oxidation of 2-acetoxyethyl 6-((cyclopropylmethyl)carbamoyl)-3-(2-formyl-5-methoxy-4-vinylphenyl)picolinate (16b) (0.63 g, 1.35 mmol) using the procedure as reported in step 11 of scheme 1 gave after workup and purification by flash column chromatography [silica gel 25 g, eluting with 0-20% methanol in chloroform] 2-(2-((2-acetoxyethoxy)carbonyl)-6-((cyclopropylmethyl)carbamoyl)pyridin-3-yl)-4-methoxy-5-vinylbenzoic acid (16c) (0.43 g, 58% yield) as a white solid. $^1$HNMR (300 MHz, DMSO-$d_6$) δ 12.59 (s, 1H), 8.67 (t, J=6.1 Hz, 1H), 8.20 (d, J=8.0 Hz, 1H), 8.11 (d, J=11.6 Hz, 1H), 7.97 (t, J=10.2 Hz, 1H), 6.96 (dd, J=17.8, 11.3 Hz, 1H), 6.88 (s, 1H), 5.89 (dd, J=17.8, 1.3 Hz, 1H), 5.38 (dd, J=11.3, 1.2 Hz, 1H), 4.29-4.16 (m, 2H), 4.00-3.93 (m, 2H), 3.85 (s, 3H), 3.24 (t, J=6.4 Hz, 2H), 1.93 (s, 3H), 1.15-1.05 (m, 1H), 0.52-0.38 (m, 2H), 0.34-0.21 (m, 2H); MS (ES+) 483.0 (M+1); 505.0 (M+Na); (ES−) 481.4 (M−1).

Step-3: Preparation of 2-acetoxyethyl 3-(2-((4-carbamimidoylphenyl)carbamoyl)-5-methoxy-4-vinylphenyl)-6-((cyclopropylmethyl)carbamoyl)picolinate (16d)

Compound (16d) was prepared from 2-(2-((2-acetoxyethoxy)carbonyl)-6-((cyclopropylmethyl)carbamoyl)pyridin-3-yl)-4-methoxy-5-vinylbenzoic acid (16c) (0.4 g, 0.83 mmol) using EDCI (0.2 g, 1.04 mmol) and 4-aminobenzimidamide dihydrochloride (1n) (0.22 g, 1.04 mmol) in DMF (5 mL) and Pyridine (5 mL) according to the procedure reported in step 4 of scheme 2. This gave after workup and purification by flash column chromatography [silica gel, 40 g, eluting with 0 to 30% methanol in chloroform) 2-acetoxyethyl 3-(2-((4-carbamimidoylphenyl)carbamoyl)-5-methoxy-4-vinylphenyl)-6-((cyclopropylmethyl)carbamoyl)picolinate (16d) (0.14 g, 28% yield) as white solid; $^1$HNMR (300 MHz, DMSO-d$_6$) δ 10.68 (s, 1H), 9.27 (s, 4H), 8.63 (t, J=6.0 Hz, 1H), 8.22 (d, J=8.0 Hz, 1H), 8.03 (d, J=8.0 Hz, 1H), 7.96 (s, 1H), 7.77 (s, 4H), 7.14-6.96 (m, 2H), 6.05 (d, J=17.7 Hz, 1H), 5.44 (d, J=12.5 Hz, 1H), 4.33-4.11 (m, 2H), 4.04-3.96 (m, 2H), 3.89 (s, 3H), 3.25-3.12 (m, 2H), 1.90 (s, 3H), 1.14-1.07 (m, 1H), 0.50-0.40 (m, 2H), 0.31-0.21 (m, 2H); MS (ES+) 600.0 (M+1); (ES−) 633.3 (M+Cl); Analysis calculated for C$_{32}$H$_{33}$N$_5$O$_7$·HCl·H$_2$O: C, 58.76; H, 5.55; Cl, 5.42; N, 10.71. Found: C, 58.74; H, 5.54; Cl, 4.72; N, 10.40.

Scheme 17

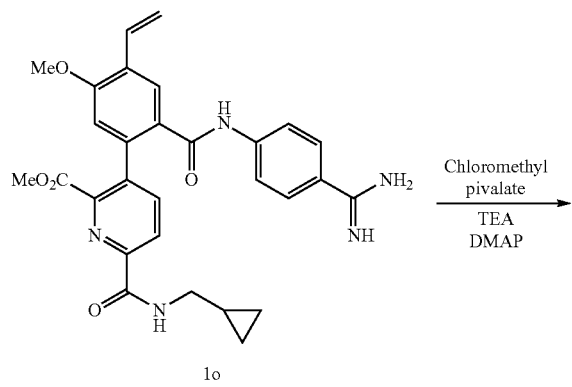

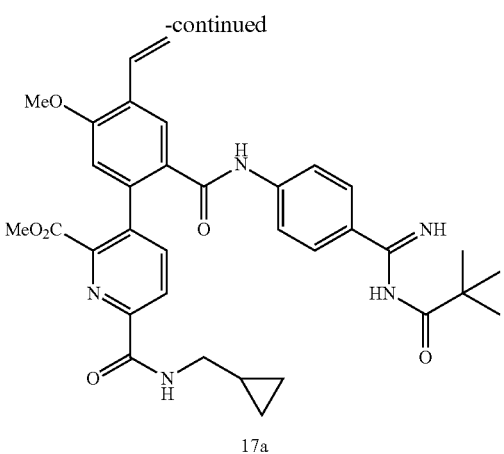

Preparation of methyl 6-((cyclopropylmethyl)carbamoyl)-3-(5-methoxy-2-((4-(N-pivaloylcarbamimidoyl)phenyl)carbamoyl)-4-vinylphenyl)picolinate (17a)

Compound (17a) was prepared from methyl 3-(2-((4-carbamimidoylphenyl)carbamoyl)-5-methoxy-4-vinylphenyl)-6-((cyclopropylmethyl)picolinate (1o) (0.28 g, 0.5 mmol) according to the procedure reported in scheme 6. This gave after workup, purification by flash column chromatography methyl 6-((cyclopropylmethyl)carbamoyl)-3-(5-methoxy-2-((4-(N-pivaloylcarbamimidoyl)phenyl) carbamoyl)-4-vinylphenyl)picolinate (17a) (72 mg, 21% yield) as a white solid; $^1$H NMR (300 MHz, DMSO-d$_6$) δ 10.57 (s, 1H, D$_2$O exchangeable), 10.23-9.69 (m, 1H, D$_2$O exchangeable), 9.29-8.73 (m, 1H, D$_2$O exchangeable), 8.66 (t, J=6.3 Hz, 1H), 8.22 (d, J=8.0 Hz, 1H), 8.05 (d, J=8.0 Hz, 1H), 8.00 (d, J=8.8 Hz, 2H), 7.92 (s, 1H), 7.69 (d, J=8.9 Hz, 2H), 7.04 (q, J=11.6 Hz, 2H), 6.05 (d, J=17.7 Hz, 1H), 5.44 (d, J=12.5 Hz, 1H), 3.90 (s, 3H), 3.61 (s, 3H), 3.20 (t, J=6.2 Hz, 2H), 1.18 (s, 9H), 1.13-1.01 (m, 1H), 0.43 (dt, J=5.5, 5.0 Hz, 2H), 0.26 (q, J=4.9 Hz, 2H); MS (ES+) 612.0 (M+1), 634.0 (M+Na), MS (ES−) 610.3 (M−1), 646.5 (M+Cl); Analysis calculated for C$_{34}$H$_{37}$N$_5$O$_6$(H$_2$O)$_{0.5}$: C, 65.77; H, 6.17; N, 11.28 Found: C, 65.66; H, 5.98; N, 11.16.

Scheme 18

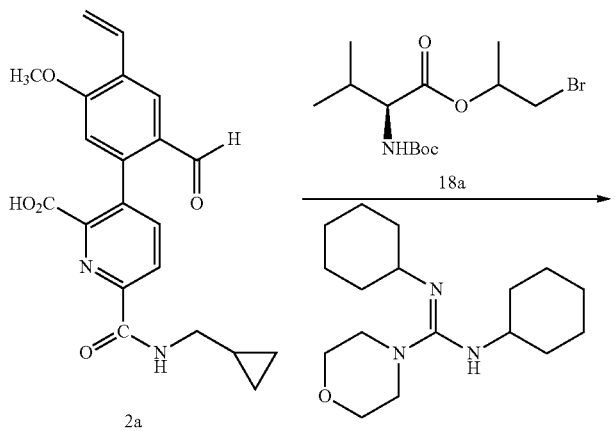

-continued
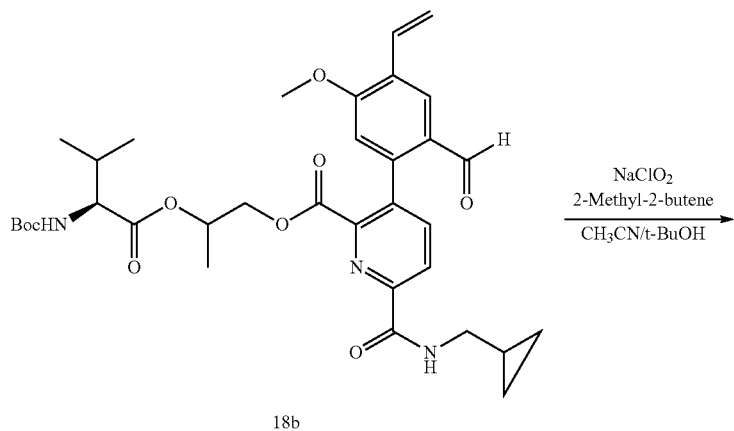
18b
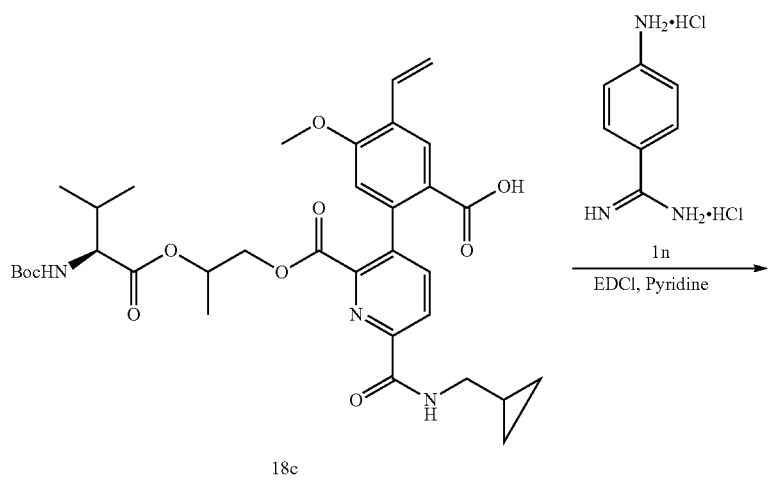
18c
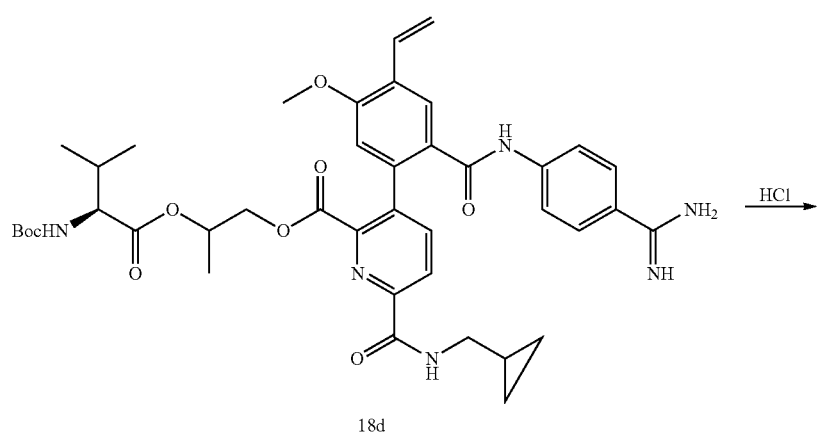
18d

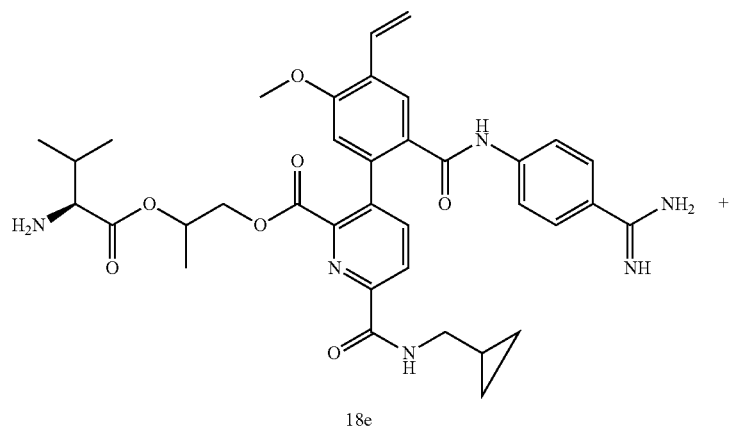
18e
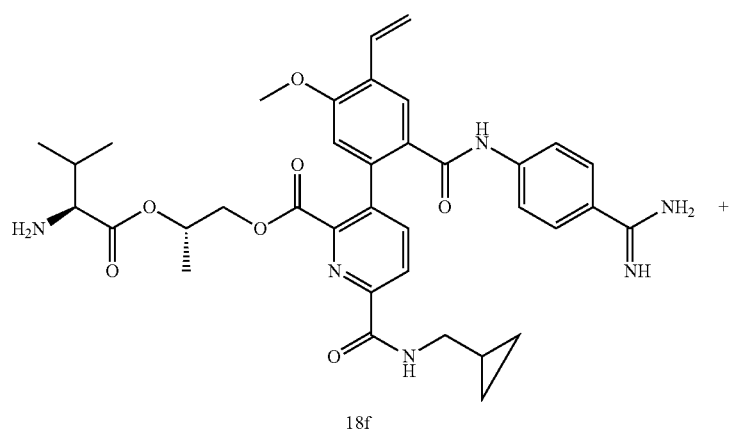
18f
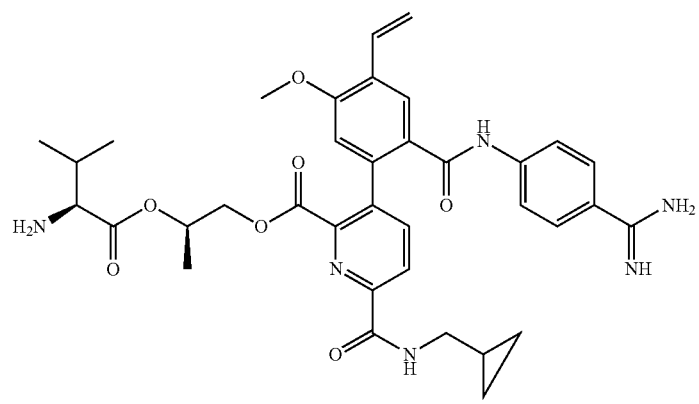
18g

Preparation of 2-(((S)-2-amino-3-methylbutanoyl) oxy)propyl 3-(2-((4-carbamimidoylphenyl)carbamoyl)-5-methoxy-4-vinylphenyl)-6-((cyclopropylmethyl)carbamoyl)picolinate (18e), (S)-2-(((S)-2-amino-3-methylbutanoyl)oxy)propyl 3-(2-((4-carbamimidoylphenyl)carbamoyl)-5-methoxy-4-vinylphenyl)-6-((cyclopropylmethyl)carbamoyl) picolinate (18f), (R)-2-(((S)-2-amino-3-methylbutanoyl)oxy)propyl 3-(2-((4-carbamimidoylphenyl)carbamoyl)-5-methoxy-4-vinylphenyl)-6-((cyclopropylmethyl)carbamoyl) picolinate (18g)

Step-1: Preparation of 2-((S)-2-(tert-butoxycarbonylamino)-3-methylbutanoyloxy)propyl6-(cyclopropylmethylcarbamoyl)-3-(2-formyl-5-methoxy-4-vinylphenyl)picolinate (18b)

Compound (18b) was prepared according to the procedure reported in step 1 of scheme 8 from 6-(Cyclopropylmethylcarbamoyl)-3-(2-formyl-5-methoxy-4-vinylphenyl)picolinic acid (2a) (0.95 g, 2.5 mmol) in DMF (10 mL) using N,N'-Dicyclohexyl-4-morpholinecarboxamidine (0.92 g, 3.12 mmol) and (2S)-1-bromopropan-2-yl 2-(tert-butoxycarbonylamino)-3-methylbutanoate (18a) (1.48 g, 4.37 mmol). This gave after workup and purification by flash column chromatography (silica gel 25 g, eluting with ethyl acetate/Hexanes, 0-100%) 2-((S)-2-(tert-butoxycarbonylamino)-3-methylbutanoyloxy)propyl6-(cyclopropylmethylcarbamoyl)-3-(2-formyl-5-methoxy-4-vinylphenyl)picolinate (18b) (1.13 g, 71% yield) as a white solid; $^1$H NMR (300 MHz, DMSO-$d_6$) δ 9.75-9.60 (m, 1H), 8.70-8.58 (m, 1H), 8.26 (d, J=8.0 Hz, 1H), 8.10 (dd, J=11.8, 6.5 Hz, 2H), 7.16-6.90 (m, 3H), 5.99 (d, J=17.8 Hz, 1H), 5.44 (d, J=12.3 Hz, 1H), 4.95 (s, 1H), 4.16-4.07 (m, 1H), 3.91 (s, 3H), 3.81-3.68 (m, 1H), 3.30-3.18 (m, 2H), 1.97-1.84 (m, 1H), 1.33 (s, 9H), 1.28-1.21 (m, 1H), 1.12-0.96 (m, 3H), 0.95-0.68 (m, 7H), 0.54-0.39 (m, 2H), 0.36-0.23 (m, 2H); MS (ES+) 637.94 (M+1), 659.91 (M+Na); (ES−) 636.02 (M−1).

Step-2: Preparation of 2-(6-((cyclopropylmethyl)carbamoyl)-2-((7S)-7-isopropyl-4,11,11-trimethyl-6,9-dioxo-2,5,10-trioxa-8-azadodecan-1-oyl)pyridin-3-yl)-4-methoxy-5-vinylbenzoic acid (18c)

Oxidation of 2-((S)-2-(tert-butoxycarbonylamino)-3-methylbutanoyloxy)propyl6-(cyclopropylmethylcarbamoyl)-3-(2-formyl-5-methoxy-4-vinylphenyl)picolinate (18b) (2.6 g, 4.08 mmol) using the procedure as reported in step 11 of scheme 1 gave after workup and purification by flash column chromatography [silica gel 40 g, eluting with 0-100% methanol/ethyl acetate (1:9) in Hexanes] 2-(6-((cyclopropylmethyl)carbamoyl)-2-((7S)-7-isopropyl-4,11,11-trimethyl-6,9-dioxo-2,5,10-trioxa-8-azadodecan-1-oyl)pyridin-3-yl)-4-methoxy-5-vinylbenzoic acid (18c) (01.1 g, 41% yield) as a white solid. $^1$HNMR (300 MHz, DMSO-$d_6$) δ 12.55 (s, 1H), 8.59 (s, 1H), 8.21 (d, J=8.0 Hz, 1H), 8.11 (s, 1H), 7.95 (d, J=8.0 Hz, 1H), 7.14-7.04 (m, 1H), 6.97 (dd, J=17.8, 11.2 Hz, 1H), 6.90-6.82 (m, 1H), 5.90 (d, J=17.8 Hz, 1H), 5.38 (d, J=12.3 Hz, 1H), 5.07-4.85 (m, 1H), 4.14-4.03 (m, 2H), 3.85 (s, 3H), 3.81-3.72 (m, 1H), 3.29-3.18 (m, 2H), 1.98-1.84 (m, 1H), 1.39-1.31 (m, 9H), 1.12-0.96 (m, 4H), 0.83-0.74 (m, 6H), 0.51-0.40 (m, 2H), 0.35-0.24 (m, 2H); MS (ES+) 676.1 (M+Na); (ES−) 652.01 (M−1).

Step-3: Preparation of 2-(((S)-2-((tert-butoxycarbonyl)amino)-3-methylbutanoyl)oxy)propyl 3-(2-((4-carbamimidoylphenyl)carbamoyl)-5-methoxy-4-vinylphenyl)-6-((cyclopropylmethyl)carbamoyl) picolinate (18d)

Compound (18d) was prepared from 2-(6-((cyclopropylmethyl)carbamoyl)-2-((7S)-7-isopropyl-4,11,11-trimethyl-6,9-dioxo-2,5,10-trioxa-8-azadodecan-1-oyl)pyridin-3-yl)-4-methoxy-5-vinylbenzoic acid (18c) (1.00 g, 1.53 mmol) using EDCI (0.44 g, 2.3 mmol) and 4-aminobenzimidamide dihydrochloride (1n) (0.48 g, 2.3 mmol) in DMF (5 mL) and Pyridine (5 mL) according to the procedure reported in step 4 of scheme 2. This gave after workup and purification by flash column chromatography [silica gel, 25 g, eluting with 0 to 50% methanol in chloroform) 2-(((S)-2-((tert-butoxycarbonyl)amino)-3-methylbutanoyl)oxy)propyl 3-(2-((4-carbamimidoylphenyl)carbamoyl)-5-methoxy-4-vinylphenyl)-6-((cyclopropylmethyl)carbamoyl)picolinate (18d) (0.81 g, 63% yield) as white solid. $^1$HNMR (300 MHz, DMSO-$d_6$) δ 10.70 (s, 1H), 9.03 (bs, 4H), 8.63-8.49 (m, 1H), 8.21 (dd, J=7.9, 4.8 Hz, 1H), 8.00 (dd, J=15.2, 7.8 Hz, 2H), 7.78 (s, 4H), 7.13-6.94 (m, 3H), 6.04 (d, J=17.8 Hz, 1H), 5.40 (d, J=19.3 Hz, 1H), 5.06-4.83 (m, 1H), 4.22-3.96 (m, 2H), 3.89 (s, 3H), 3.78-3.68 (m, 1H), 3.30-3.16 (m, 2H), 2.00-1.81 (m, 1H), 1.33 (s, 9H), 1.26-1.18 (m, 1H), 1.04-0.88 (m, 3H), 0.81-0.72 (m, 6H), 0.50-0.41 (m, 2H), 0.32-0.22 (m, 2H); MS (ES+) 771.1 (M+1); (ES−) 805.1 (M+Cl).

Step-4: Preparation of 2-(((S)-2-amino-3-methylbutanoyl)oxy)propyl 3-(2-((4-carbamimidoylphenyl)carbamoyl)-5-methoxy-4-vinylphenyl)-6-((cyclopropylmethyl)carbamoyl)picolinate (18e)

To a solution of 2-(((S)-2-((tert-butoxycarbonyl)amino)-3-methylbutanoyl)oxy)propyl 3-(2-((4-carbamimidoylphenyl)carbamoyl)-5-methoxy-4-vinylphenyl)-6-((cyclopropylmethyl)carbamoyl)picolinate (18d) (0.78 g, 1.01 mmol) in dioxane (5 mL) was added hydrogen chloride (4M in dioxane) (4.22 mL, 16.90 mmol). The resulting mixture was stirred at room temperature for 4 h and concentrated in vacuum to dryness. The resulting mixture was purified by flash column chromatography [silica gel 40 g, eluting with 0-100% (CMW80/CHCl$_3$) followed by 0-100% CMW50/CMW80)] to furnish 2-(((S)-2-amino-3-methylbutanoyl)oxy)propyl 3-(2-((4-carbamimidoylphenyl)carbamoyl)-5-methoxy-4-vinylphenyl)-6-((cyclopropylmethyl)carbamoyl)picolinate (18e) (0.285 g, 42% yield) as a white solid. $^1$HNMR (300 MHz, DMSO-$d_6$) δ 10.68 (s, 1H), 8.97 (s, 2H), 8.66-8.45 (m, 1H), 8.21 (dd, J=8.0, 4.3 Hz, 1H), 8.10-7.87 (m, 2H), 7.85-7.66 (m, 5H), 7.01 (m, 2H), 6.06 (d, J=17.7 Hz, 1H), 5.44 (d, J=12.4 Hz, 1H), 4.89 (m, 1H), 4.11 (s, 2H), 3.99-3.73 (m, 4H), 3.23 (s, 4H), 1.95-1.70 (m, 1H), 1.35 (m, 1H), 1.16-0.91 (m, 4H), 0.87-0.66 (m, 6H), 0.45 (m, 2H), 0.27 (m, 2H); MS (ES+) 671.1 (M+1); (ES−) 669.0 (M−1); Analysis calculated for $C_{36}H_{42}N_6O_7$·HCl·2.5H$_2$O: C, 57.48; H, 6.43; N, 11.17; Cl, 4.71. Found: C, 57.53; H, 6.23; N, 10.95; Cl, 5.21.

Step-5: Preparation of (S)-2-(((S)-2-amino-3-methylbutanoyl)oxy)propyl 3-(2-((4-carbamimidoylphenyl)carbamoyl)-5-methoxy-4-vinylphenyl)-6-((cyclopropylmethyl)carbamoyl)picolinate (18f), (R)-2-(((S)-2-amino-3-methylbutanoyl)oxy)propyl 3-(2-((4-carbamimidoylphenyl)carbamoyl)-5-methoxy-4-vinylphenyl)-6-((cyclopropylmethyl)carbamoyl) picolinate (18g)

Compound (18e) was re-purified by preparative-HPLC (eluting with acetonitrile in water [containing 0.1% HCL)

from 0-100%) to give compounds (18f and 18g), structure was assigned randomly. Data for isomer-A: 1HNMR (300 MHz, DMSO-d$_6$) δ 10.78 (s, 1H, D$_2$O exchangeable), 9.24 (s, 2H, D$_2$O exchangeable), 8.96 (s, 2H, D$_2$O exchangeable), 8.60-8.45 (m, 1H), 8.41 (s, 3H, D$_2$O exchangeable), 8.26-8.12 (m, 1H), 8.09-7.96 (m, 2H), 7.88-7.65 (m, 4H), 7.10-6.91 (m, 2H), 6.08 (d, J=17.5 Hz, 1H), 5.45 (d, J=11.4 Hz, 1H), 5.14-4.82 (m, 1H), 4.26-4.03 (m, 2H), 3.89 (s, 3H), 3.75 (s, 1H), 3.26-3.17 (m, 2H), 2.16-1.96 (m, 1H), 1.17-0.97 (m, 3H), 0.93-0.71 (m, 7H), 0.50-0.40 (m, 2H), 0.32-0.21 (m, 2H); MS (ES$^+$) 671.7 (M+1); (ES$^-$) 705.7 (M+Cl); Analysis calculated for C$_{36}$H$_{42}$N$_6$O$_7$.2.25HCl.3H$_2$O: C, 53.59; H, 6.28; N, 10.42. Found: C, 53.62; H, 6.37; N, 10.31; Data for isomer-B: $^1$HNMR (300 MHz, DMSO-d$_6$) δ 10.77 (s, 1H, D$_2$O exchangeable), 9.23 (s, 2H, D$_2$O exchangeable), 8.94 (s, 2H, D$_2$O exchangeable), 8.58 (t, J=6.1 Hz, 1H), 8.47-8.25 (m, 3H, D$_2$O exchangeable), 8.21 (t, J=6.5 Hz, 1H), 8.08-7.94 (m, 2H), 7.89-7.69 (m, 4H), 7.11-6.95 (m, 2H), 6.07 (d, J=17.8 Hz, 1H), 5.44 (d, J=11.4 Hz, 1H), 5.07-4.76 (m, 1H), 4.28-4.03 (m, 2H), 3.90 (s, 3H), 3.77-3.58 (m, 1H), 3.27-3.12 (m, 2H), 2.15-2.00 (m, 1H), 1.13-0.97 (m, 3H), 0.94-0.74 (m, 7H), 0.49-0.37 (m, 2H), 0.32-0.22 (m, 2H); MS (ES$^+$) 671.7 (M+1); (ES$^-$) 705.7 (M+Cl).

Scheme 19

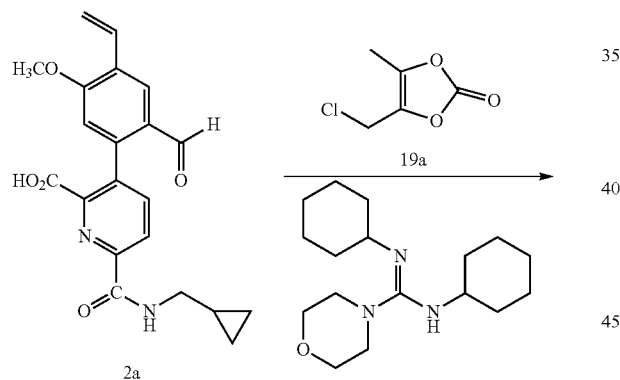

2a

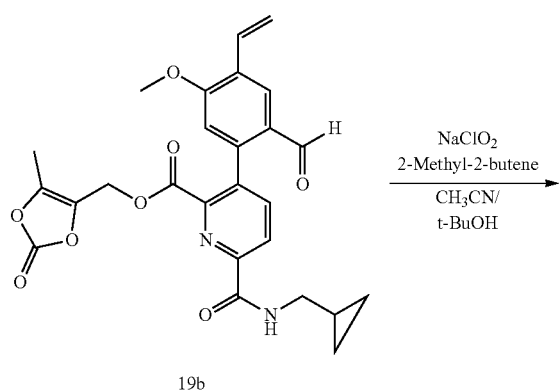

19b

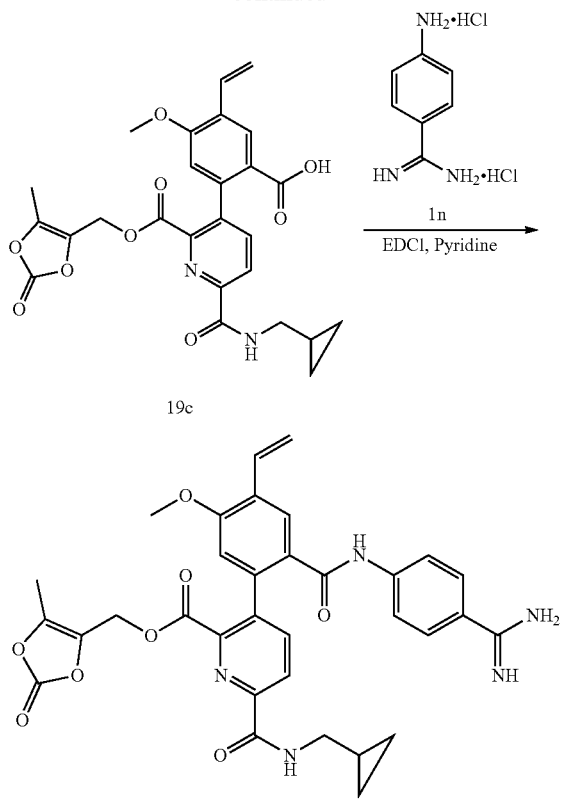

19c

19d

Preparation of (5-methyl-2-oxo-1,3-dioxol-4-yl)methyl 3-(2-((4-carbamimidoylphenyl)carbamoyl)-5-methoxy-4-vinylphenyl)-6-((cyclopropylmethyl)carbamoyl)picolinate (19d)

Step-1: Preparation of (5-methyl-2-oxo-1,3-dioxol-4-yl)methyl 6-((cyclopropylmethyl)carbamoyl)-3-(2-formyl-5-methoxy-4-vinylphenyl)picolinate (19b)

Compound (19b) was prepared according to the procedure reported in step 1 of scheme 8 from 6-(Cyclopropylmethylcarbamoyl)-3-(2-formyl-5-methoxy-4-vinylphenyl)picolinic acid (2a) (0.87 g, 2.25 mmol) in DMF (10 mL) using N,N'-Dicyclohexyl-4-morpholinecarboxamidine (0.83 g, 2.25 mmol) and 4-(chloromethyl)-5-methyl-1,3-dioxol-2-one (19a) (0.5 g, 3.38 mmol). This gave after workup and purification by flash column chromatography (silica gel 25 g, eluting with ethyl acetate/Hexanes, 0-100%) (5-methyl-2-oxo-1,3-dioxol-4-yl)methyl 6-((cyclopropylmethyl)carbamoyl)-3-(2-formyl-5-methoxy-4-vinylphenyl)picolinate (19b) (0.76 g, 64% yield) as a yellow solid; $^1$H NMR (300 MHz, DMSO-d$_6$) δ 9.63 (s, 1H), 8.75 (t, J=6.1 Hz, 1H), 8.26 (m, 1H), 8.10 (d, J=8.0 Hz, 1H), 8.06 (s, 1H), 6.98 (m, 2H), 5.97 (m, 1H), 5.44 (dd, J=11.3, 1.2 Hz, 1H), 5.00 (q, J=14.1 Hz, 2H), 3.87 (s, 3H), 3.30-3.14 (m, 2H), 1.99 (s, 3H), 1.15-1.04 (m, 1H), 0.51-0.39 (m, 2H), 0.32-0.21 (m, 2H); MS (ES+) 514.9 (M+Na); Analysis calculated for C$_{26}$H$_{24}$N$_2$O$_8$: C, 63.41; H, 4.91; N, 5.69. Found: C, 63.06; H, 4.87; N, 5.54.

Step-2: Preparation of 2-(6-((cyclopropylmethyl)carbamoyl)-2-(((5-methyl-2-oxo-1,3-dioxol-4-yl)methoxy)carbonyl)pyridin-3-yl)-4-methoxy-5-vinylbenzoic acid (19c)

Oxidation of (5-methyl-2-oxo-1,3-dioxol-4-yl)methyl 6-((cyclopropylmethyl)carbamoyl)-3-(2-formyl-5-methoxy-4-vinylphenyl)picolinate (19b) (0.78 g, 1.56 mmol) using the procedure as reported in step 11 of scheme 1 gave after workup and purification by flash column chromatography [silica gel 12 g, eluting with 0-20% methanol in chloroform] 2-(6-((cyclopropylmethyl)carbamoyl)-2-(((5-methyl-2-oxo-1,3-dioxol-4-yl)methoxy)carbonyl)pyridin-3-yl)-4-methoxy-5-vinylbenzoic acid (19c) (0.75 g, 95% yield) as a white solid MS (ES+) 531.0 (M+Na), (ES−) 506.7 (M−1).

Step-3: Preparation of (5-methyl-2-oxo-1,3-dioxol-4-yl)methyl 3-(2-((4-carbamimidoylphenyl)carbamoyl)-5-methoxy-4-vinylphenyl)-6-((cyclopropylmethyl)carbamoyl)picolinate (19d) Compound (19d) was prepared from 2-(6-((cyclopropylmethyl)carbamoyl)-2-(((5-methyl-2-oxo-1,3-dioxol-4-yl)methoxy)carbonyl)pyridin-3-yl)-4-methoxy-5-vinylbenzoic acid (19c) (0.7 g, 1.4 mmol) using EDCI (0.54 g, 2.8 mmol) and 4-aminobenzimidamide dihydrochloride (1n) (0.73 g, 3.51 mmol) in DMF (5 mL) and Pyridine (5 mL) according to the procedure reported in step 4 of scheme 2. This gave after workup and purification by flash column chromatography (silica gel, 12 g, eluting with 0 to 100% CMW80 (CHCl$_3$-MeOH—H$_2$O) in chloroform) (5-methyl-2-oxo-1,3-dioxol-4-yl)methyl 3-(2-((4-carbamimidoylphenyl)carbamoyl)-5-methoxy-4-vinylphenyl)-6-((cyclopropylmethyl)carbamoyl)picolinate (19d) (0.46 g, 52% yield) as white solid; $^1$HNMR (300 MHz, DMSO-d$_6$) δ 10.61 (s, 1H), 9.19 (s, 2H, D$_2$O exchangeable), 8.88 (s, 2H, D$_2$O exchangeable), 8.64 (t, J=6.0 Hz, 1H), 8.20 (d, J=8.0 Hz, 1H), 8.00 (d, J=8.0 Hz, 1H), 7.94 (s, 1H), 7.75 (s, 4H), 7.13-6.93 (m, 2H), 6.14-5.95 (m, 1H), 5.44 (d, J=12.6 Hz, 1H), 4.98 (d, J=3.4 Hz, 2H), 3.86 (s, 3H), 3.20 (s, 2H), 2.02 (s, 3H), 1.09 (m, 1H), 0.50-0.38 (m, 2H), 0.31-0.22 (m, 2H); MS (ES+) 626.0 (M+1), (ES−) 659.6 (M+Cl); Analysis calculated for C$_{33}$H$_{31}$N$_5$O$_8$.HCl.1.5 (H$_2$O): C, 57.52; H, 5.12; Cl, 5.14; N, 10.16. Found: C, 57.31; H, 5.06; Cl, 5.31; N, 10.05.

Scheme 20

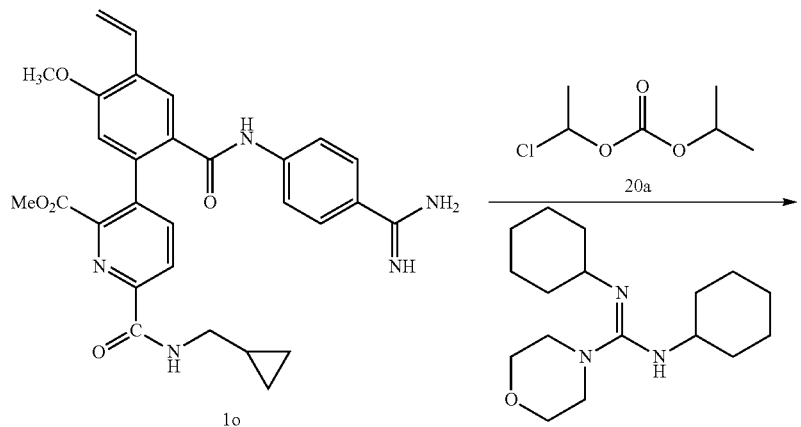

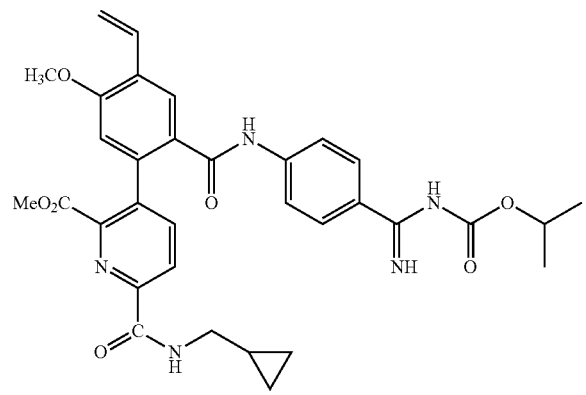

Preparation of methyl 6-((cyclopropylmethyl)carbamoyl)-3-(2-((4-(N-(isopropoxycarbonyl)carbamimidoyl)phenyl)carbamoyl)-5-methoxy-4-vinylphenyl)picolinate (20b)

Compound (20b) was prepared according to the procedure reported in step 1 of scheme 8 from methyl 3-(2-((4-carbamimidoylphenyl)carbamoyl)-5-methoxy-4-vinylphenyl)-6-((cyclopropylmethyl)carbamoyl)picolinate (1o) (0.15 g, 0.29 mmol) in DMF (10 mL) using N,N'-Dicyclohexyl-4-morpholinecarboxamidine (0.11 g, 0.36 mmol) and 1-chloroethyl isopropyl carbonate (20a) (0.07 g, 0.43 mmol). This gave after workup and purification by flash column chromatography (silica gel 25 g, eluting with ethyl acetate in Hexanes, 0-100%) methyl 6-((cyclopropylmethyl)carbamoyl)-3-(2-((4-(N-(isopropoxycarbonyl)carbamimidoyl)phenyl)carbamoyl)-5-methoxy-4-vinylphenyl)picolinate (20b) (0.09 g, 53% yield) as a yellow solid; $^1$H NMR (300 MHz, DMSO-$d_6$) δ 10.56 (s, 1H, $D_2O$ exchangeable), 9.07 (s, 2H, $D_2O$ exchangeable), 8.67 (t, J=6.1 Hz, 1H), 8.22 (d, J=8.0 Hz, 1H), 8.04 (d, J=8.1 Hz, 1H), 7.98-7.89 (m, 3H), 7.68 (d, J=8.9 Hz, 2H), 7.04 (q, J=10.9 Hz, 2H), 6.05 (d, J=17.7 Hz, 1H), 5.44 (d, J=12.5 Hz, 1H), 4.89-4.76 (m, 1H), 3.90 (s, 3H), 3.60 (s, 3H), 3.20 (t, J=6.6 Hz, 2H), 1.21 (d, J=6.2 Hz, 7H), 1.09 (s, 1H), 0.43 (dt, J=5.5, 5.0 Hz, 2H), 0.26 (q, J=4.8 Hz, 2H). MS (ES−) 612.0 (M−1); Analysis calculated for $C_{33}H_{35}N_5O_7$: C, 64.59; H, 5.75; N, 11.41. Found: C, 64.29; H, 5.93; N, 11.24.

Scheme 21

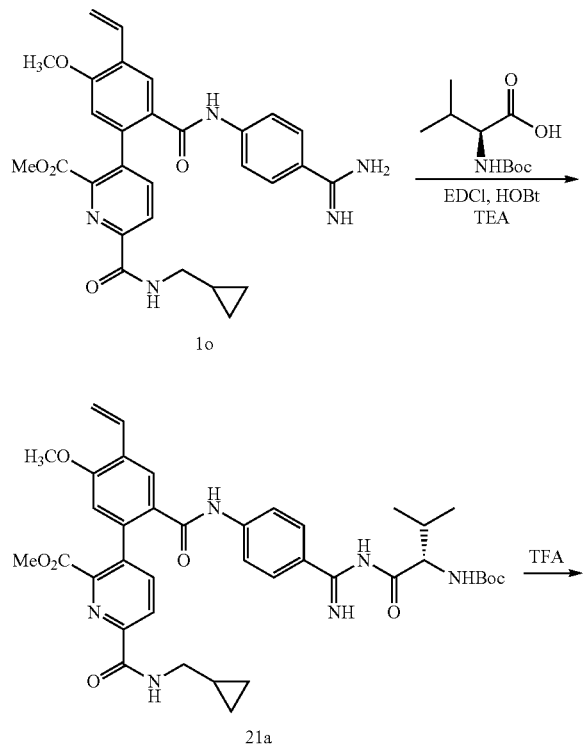

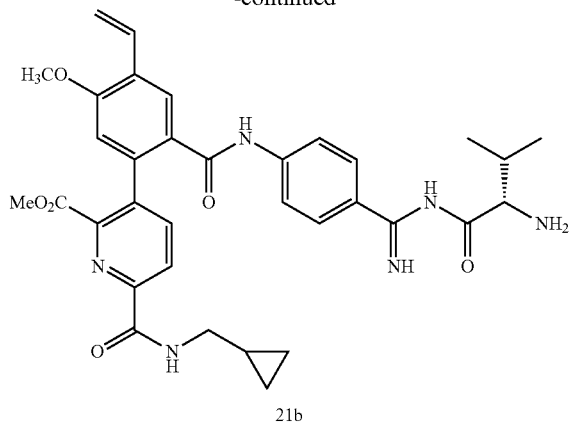

Preparation of (S)-methyl 3-(2-((4-(N-(2-amino-3-methylbutanoyl)carbamimidoyl)phenyl)carbamoyl)-5-methoxy-4-vinylphenyl)-6-((cyclopropylmethyl)carbamoyl)picolinate (21b)

Step-1: Preparation of (S)-methyl 3-(2-((4-(N-(2-((tert-butoxycarbonyl)amino)-3-methylbutanoyl)carbamimidoyl)phenyl)carbamoyl)-5-methoxy-4-vinylphenyl)-6-((cyclopropylmethyl)carbamoyl)picolinate (21a)

Compound (21a) was prepared according to the procedure reported in step 1 of scheme 8 from methyl 3-(2-((4-carbamimidoylphenyl)carbamoyl)-5-methoxy-4-vinylphenyl)-6-((cyclopropylmethyl)carbamoyl)picolinate (1o) (0.5 g, 0.95 mmol) in DMF (10 mL) using EDCI (0.83 g, 2.25 mmol), HOBt (0.15 g, 1.14 mmol), TEA (0.34 mL, 2.44 mmol) and (S)-2-((tert-butoxycarbonyl)amino)-3-methylbutanoic acid (0.21 g, 0.95 mmol). This gave after workup and purification by flash column chromatography (silica gel 12g, eluting with 0-10% methanol in chloroform) (S)-methyl 3-(2-((4-(N-(2-((tert-butoxycarbonyl)amino)-3-methylbutanoyl)carbamimidoyl)phenyl) carbamoyl)-5-methoxy-4-vinylphenyl)-6-((cyclopropylmethyl)carbamoyl)picolinate (21a) (0.48 g, 69% yield) as a yellow solid; $^1$H NMR (300 MHz, DMSO-$d_6$) δ10.58 (s, 1H), 10.03 (s, 1H), 9.07 (s, 1H), 8.66 (t, J=6.1 Hz, 1H), 8.22 (d, J=8.0 Hz, 1H), 8.08-7.99 (m, 3H), 7.92 (s, 1H), 7.70 (d, J=8.8 Hz, 2H), 7.11-6.96 (m, 2H), 6.46 (d, J=9.0 Hz, 1H), 6.05 (d, J=17.7 Hz, 1H), 5.44 (d, J=12.5 Hz, 1H), 4.00-3.91 (m, 1H), 3.91 (s, 3H), 3.60 (s, 3H), 3.20 (t, J=6.4 Hz, 2H), 2.30-2.10 (m, 1H), 1.38 (s, 9H), 1.13-1.01 (m, 1H), 0.89 (d, J=6.8 Hz, 3H), 0.82 (d, J=6.8 Hz, 3H), 0.47-0.38 (m, 2H), 0.32-0.22 (m, 2H); MS (ES+) 749.1 (M+Na); Analysis calculated for $C_{39}H_{46}N_6O_8\cdot(H_2O)_{0.5}$: C, 63.66; H, 6.44; N, 11.42. Found: C, 63.43; H, 6.42; N, 11.18.

Step-2: Preparation of (S)-methyl 3-(2-((4-(N-(2-amino-3-methylbutanoyl)carbamimidoyl)phenyl)carbamoyl)-5-methoxy-4-vinylphenyl)-6-((cyclopropylmethyl)carbamoyl)picolinate (21b)

Compound (21b) was prepared from (S)-methyl 3-(2-((4-(N-(2-((tert-butoxycarbonyl)amino)-3-methylbutanoyl)carbamimidoyl)phenyl)carbamoyl)-5-methoxy-4-vinylphenyl)-6-((cyclopropylmethyl)carbamoyl)picolinate (21a) (0.12 g, 0.16 mmol) in dichloromethane (4 mL) using 2,2,2-trifluoroacetic acid (0.5 mL, 6.36 mmol) according to the procedure reported in Step-4 of scheme 8. This gave after workup and purification by flash column chromatography [silica gel 4 g, eluting with 0-10% methanol in chloroform) to furnish (S)-methyl 3-(2-((4-(N-(2-amino-3-methylbutanoyl)carbamimidoyl)phenyl)carbamoyl)-5-methoxy-4-vinylphenyl)-6-((cyclopropylmethyl)carbamoyl)picolinate (21b) (0.028 g, 24% yield) as a yellow solid; $^1$HNMR (300 MHz, DMSO-$d_6$) δ 11.41 (s, 1H), 10.56 (s, 1H), 9.78 (s, 1H), 8.66 (t, J=6.0 Hz, 1H), 8.22 (d, J=8.0 Hz, 1H), 8.09-7.84 (m, 4H), 7.79 (d, J=8.9 Hz, 1H), 7.71 (d, J=8.8 Hz, 1H), 7.10-6.98 (m, 2H), 6.05 (d, J=17.7 Hz, 1H), 5.45 (d, J=11.3 Hz, 1H), 4.06 (d, J=4.2 Hz, 1H), 3.90 (s, 3H), 3.61 (s, 3H), 3.20 (t, J=6.4 Hz, 2H), 2.24-2.05 (m, 1H), 1.15-0.73 (m, 7H), 0.49-0.20 (m, 4H).

Scheme 22

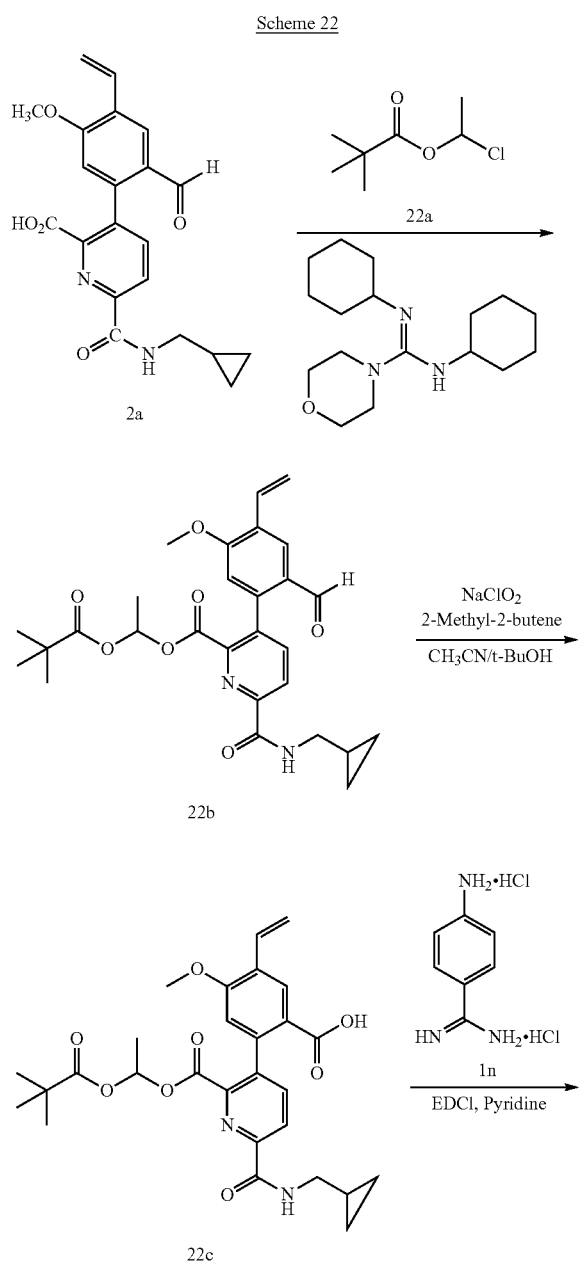

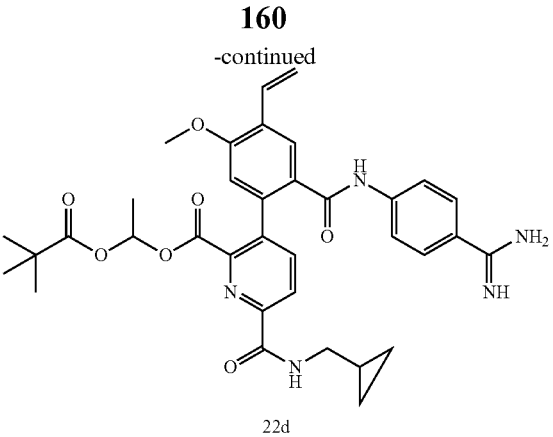

Preparation of 1-(pivaloyloxy)ethyl 3-(2-((4-carbamimidoylphenyl)carbamoyl)-5-methoxy-4-vinylphenyl)-6-((cyclopropylmethyl)carbamoyl)picolinate (22d)

Step-1: Preparation of 1-(pivaloyloxy)ethyl 6-((cyclopropylmethyl)carbamoyl)-3-(2-formyl-5-methoxy-4-vinylphenyl)picolinate (22b)

Compound (22b) was prepared according to the procedure reported in step 1 of scheme 8 from 6-(Cyclopropylmethylcarbamoyl)-3-(2-formyl-5-methoxy-4-vinylphenyl)picolinic acid (2a) (0.76 g, 2.00 mmol) in DMF (10 mL) using N,N'-Dicyclohexyl-4-morpholinecarboxamidine (0.59 g, 2.00 mmol) and 1-chloroethyl pivalate (22a) (0.82 mL, 5.00 mmol). This gave after workup and purification by flash column chromatography (silica gel 12 g, eluting with ethyl acetate/Hexanes, 0-100%) 1-(pivaloyloxy)ethyl 6-((cyclopropylmethyl)carbamoyl)-3-(2-formyl-5-methoxy-4-vinylphenyl)picolinate (22b) (0.67 g, 65% yield) as a yellow solid; $^1$H NMR (300 MHz, DMSO-$d_6$) δ 9.69 (d, J=0.8 Hz, 1H), 8.65 (d, J=3.1 Hz, 1H), 8.27 (d, J=8.0 Hz, 1H), 8.14 (s, 1H), 8.07 (dd, J=8.0, 1.7 Hz, 1H), 7.09-6.92 (m, 2H), 6.74-6.62 (m, 1H), 5.99 (d, J=17.8 Hz, 1H), 5.44 (dd, J=11.3, 1.1 Hz, 1H), 3.90 (d, J=4.6 Hz, 3H), 3.24 (m, 2H), 1.21 (3, 3H), 1.10 (m, J=12.6, 6.4 Hz, 1H), 1.01 (d, J=5.4 Hz, 9H), 0.52-0.42 (m, 2H), 0.33-0.23 (m, 2H); MS (ES-): 543.3 (M+Cl); Analysis calculated for $C_{28}H_{32}N_2O_7 \cdot 0.75H_2O$: C, 66.13; H, 6.34; N, 5.51. Found: C, 65.75; H, 6.20; N, 5.37.

Step-2: Preparation of 2-(6-((cyclopropylmethyl)carbamoyl)-2-((1-(pivaloyloxy)ethoxy)carbonyl)pyridin-3-yl)-4-methoxy-5-vinylbenzoic acid (22c)

Oxidation of 1-(pivaloyloxy)ethyl 6-((cyclopropylmethyl)carbamoyl)-3-(2-formyl-5-methoxy-4-vinylphenyl)picolinate (22b) (0.60 g, 1.19 mmol) using the procedure as reported in step 11 of scheme 1 gave after workup and purification by flash column chromatography [silica gel 12 g, eluting with 0-100% methanol in chloroform] 2-(6-((cyclopropylmethyl)carbamoyl)-2-((1-(pivaloyloxy)ethoxy)carbonyl)pyridin-3-yl)-4-methoxy-5-vinylbenzoic acid (22c) (0.5 g, 80% yield) as a white solid. $^1$HNMR (300 MHz, DMSO-$d_6$) δ 12.57 (s, 1H, $D_2O$ exchangeable), 8.69-8.50 (m, 1H), 8.22 (d, J=8.0 Hz, 1H), 8.13 (s, 1H), 7.95 (d, J=8.0 Hz, 1H), 7.06-6.85 (m, 2H), 6.69 (d, J=5.3 Hz, 1H), 5.90 (dd, J=17.8, 1.3 Hz, 1H), 5.39 (dd, J=11.3, 1.2 Hz, 1H), 3.84 (d, J=4.1 Hz, 3H), 3.29-3.19 (m, 2H), 1.21 (d, J=2.4 Hz, 3H), 1.10 (dd, J=5.7, 3.2 Hz, 1H), 1.02 (d, J=13.3 Hz, 9H), 0.50-0.42 (m, 2H), 0.32-0.25 (m, 2H); MS (ES+): MS (ES+) 525.1 (M+1), (ES−) 559.3 (M+Cl); Analysis calculated for $C_{28}H_{32}N_2O_8 \cdot 0.75H_2O$: C, 62.50; H, 6.28; N, 5.21. Found: C, 62.68; H, 6.36; N, 5.11.

Step-3: Preparation of 1-(pivaloyloxy)ethyl 3-(2-((4-carbamimidoylphenyl)carbamoyl)-5-methoxy-4-vinylphenyl)-6-((cyclopropylmethyl)carbamoyl) picolinate (22d)

Compound (22d) was prepared from 2-(6-((cyclopropylmethyl)carbamoyl)-2-((1-(pivaloyloxy)ethoxy)carbonyl)pyridin-3-yl)-4-methoxy-5-vinylbenzoic acid (22c) (0.47 g, 0.89 mmol) using EDCI (0.26 g, 1.34 mmol) and 4-aminobenzimidamide dihydrochloride (1n) (0.22 g, 1.07 mmol) in DMF (2.5 mL) and Pyridine (2.5 mL) according to the procedure reported in step 4 of scheme 2. This gave after workup and purification by flash column chromatography [silica gel, 12 g, eluting with 0 to 100% methanol in chloroform) 1-(pivaloyloxy)ethyl 3-(2-((4-carbamimidoylphenyl)carbamoyl)-5-methoxy-4-vinylphenyl)-6-((cyclopropylmethyl)carbamoyl)picolinate (22d) (0.21 g, 35% yield) as an off-white solid; $^1$HNMR (300 MHz, DMSO-$d_6$) δ 10.72 (d, J=16.9 Hz, 1H, D$_2$O exchangeable), 9.15 (d, J=53.7 Hz, 4H, D$_2$O exchangeable), 8.52 (d, J=28.1 Hz, 1H), 8.22 (d, J=8.0 Hz, 1H), 8.00 (bs, 2H), 7.80 (s, 4H), 7.14-6.91 (m, 2H), 6.72 (q, J=5.3 Hz, 1H), 6.07 (d, J=17.8 Hz, 1H), 5.45 (d, J=12.3 Hz, 1H), 3.88 (s, 3H), 3.24 (bs, 2H), 1.19 (d, J=5.2 Hz, 3H), 1.12-1.08 (m, 1H), 1.04 (s, 9H), 0.52-0.39 (m, 2H), 0.34-0.20 (m, 2H). MS (ES+): MS (ES+) 642.3 (M+1), (ES−) 676.1 (M+Cl); Analysis calculated for $C_{28}H_{32}N_2O_7 \cdot H_2O \cdot HCl$: C, 60.38; H, 6.08; N, 10.06; Cl, 5.09. Found: C, 60.11; H, 6.22; N, 10.05; Cl, 5.11.

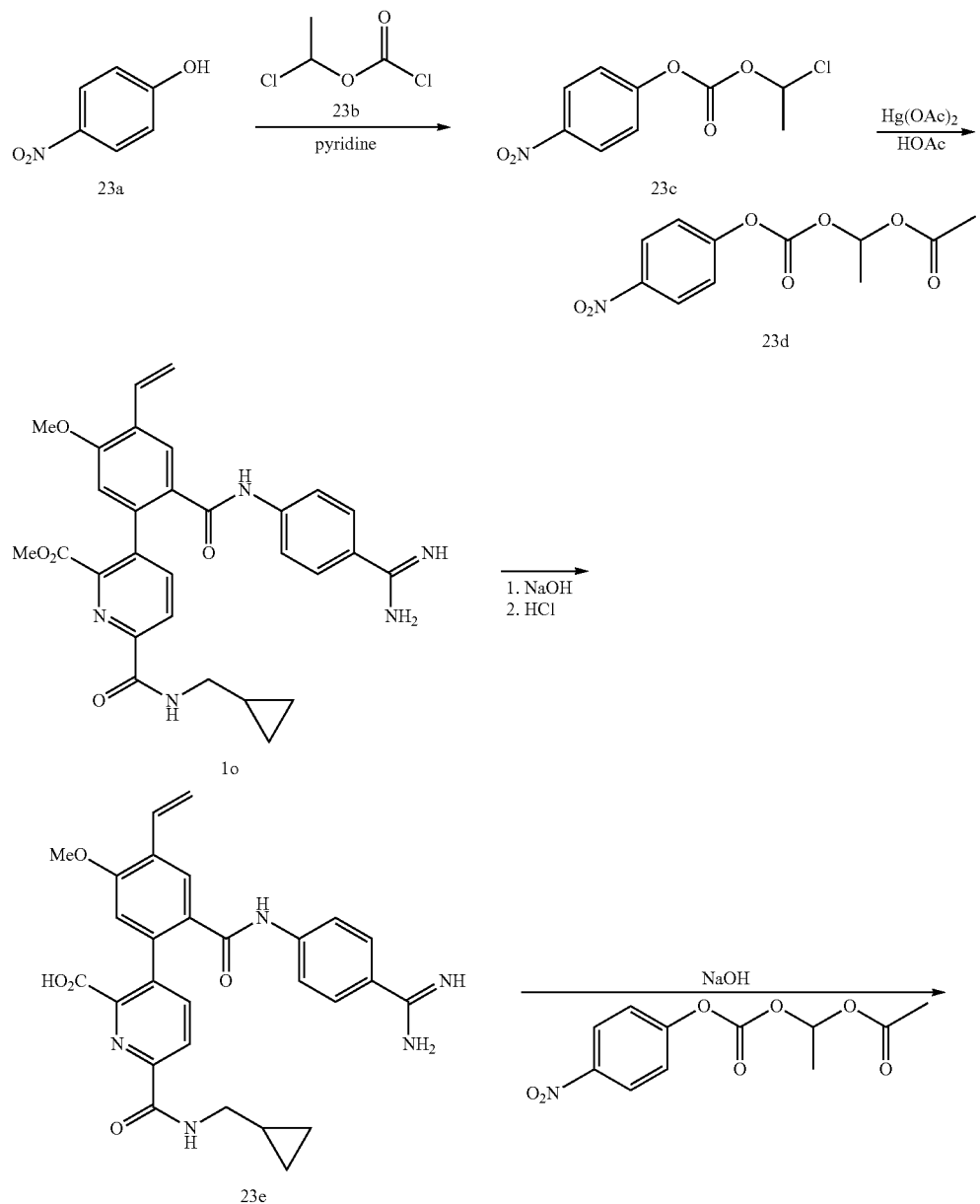

Scheme 23

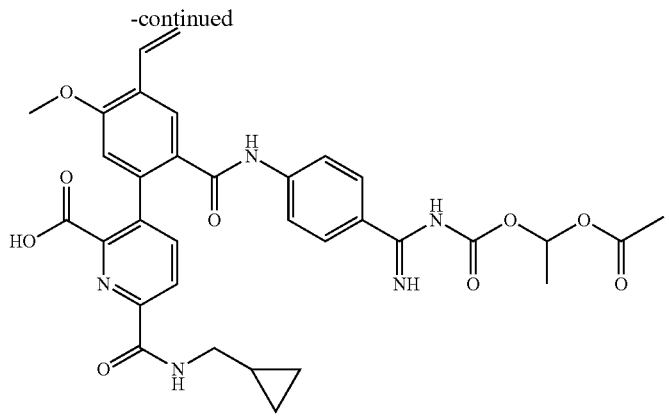

23f

Preparation of 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinic acid (23f)

Step-1: Preparation of 1-chloroethyl (4-nitrophenyl) carbonate (23c)

To an ice-cold reaction mixture of 4-nitrophenol (23a) (5 g, 35.9 mmol) and pyridine (2.91 mL, 35.9 mmol) in DCM (300 mL) was added 1-chloroethyl chloroformate (23b) (5.65 g, 39.5 mmol). The reaction was allowed warm to room temperature overnight washed with water, 0.5% aqueous NaOH and water. The organic layer was dried and concentrated to give 1-chloroethyl 4-nitrophenyl carbonate (23c) (7.6 g, 86% yield) as an off white solid, which was used in next step without further purification. $^1$H NMR (300 MHz, DMSO-$d_6$) δ 8.40-8.30 (m, 2H), 7.67-7.58 (m, 2H), 6.62 (q, J=5.7 Hz, 1H), 1.87 (d, J=5.7 Hz, 3H).

Step-2: Preparation of 1-((4-nitrophenoxy)carbonyloxy)ethyl acetate (23d)

To a solution of 1-chloroethyl (4-nitrophenyl) carbonate (23c) (6.5 g, 26.5 mmol) in HOAc (50 mL) was added mercuric acetate (10.29 g, 32.3 mmol). The resulting mixture was stirred overnight at room temperature and concentrated in vacuum to dryness. The residue was taken up in EtOAc/Hexane (200 mL, 1:3, v/v), filtered and filtrate was concentrated in vacuum to dryness. The residue obtained was purified by flash column chromatography [silica gel, eluting with EtOAc in hexane from 0-30%] to give 1-((4-nitrophenoxy)carbonyloxy)ethyl acetate (23d) (4.2 g, 15.60 mmol, 59.0% yield) as a clear oil. $^1$H NMR (300 MHz, DMSO-$d_6$) δ 8.40-8.26 (m, 2H), 7.64-7.51 (m, 2H), 6.74 (q, J=5.5 Hz, 1H), 2.10 (s, 3H), 1.55 (d, J=5.5 Hz, 3H).

Step-3: Preparation of 3-(2-((4-carbamimidoylphenyl)carbamoyl)-5-methoxy-4-vinylphenyl)-6-((cyclopropylmethyl)carbamoyl)picolinic acid (23e)

To a solution of methyl 3-(2-((4-carbamimidoylphenyl)carbamoyl)-5-methoxy-4-vinylphenyl)-6-((cyclopropylmethyl)carbamoyl)picolinate (1o) (1 g, 1.9 mmol) in methanol (10 mL) and THF (10 mL) was added 2 N NaOH (10 mL). The reaction mixture was stirred at room temperature for 3 h, and concentrated in vacuum to remove methanol and THF. The aqueous layer was acidified with 6N HCl to pH 6-7 and the solid obtained was collected by filtration washed with water and ether to furnish on drying 3-(2-((4-carbamimidoylphenyl)carbamoyl)-5-methoxy-4-vinylphenyl)-6-((cyclopropylmethyl)carbamoyl)picolinic acid (23e) (0.78 g, 80%) as a off white solid; $^1$H NMR (300 MHz, DMSO-$d_6$) δ 12.67 (s, 1H), 9.11 (s, 2H), 8.97 (s, 2H), 8.74 (s, 1H), 7.90 (d, J=7.8, 1H), 7.80 (s, 1H), 7.72-7.58 (m, 4H), 6.99 (dd, J=11.3, 17.7, 1H), 6.78 (s, 1H), 5.95 (d, J=17.2, 1H), 5.38 (d, J=11.9, 1H), 3.82 (s, 3H), 3.18 (s, 2H), 1.06 (s, 1H), 0.43 (d, J=7.9, 2H), 0.25 (d, J=4.7, 2H); MS (ES+) 514.0 (M+1); Analysis calculated for $C_{28}H_{27}N_5O_5$·HCl·H$_2$O: C, 59.21; H, 5.32; N, 12.33. Found: C, 59.43; H, 5.21; N, 12.06.

Step-4: Preparation of 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinic acid (23f)

To a solution of NaOH (75 mg, 1.881 mmol) in acetone/H$_2$O (13 mL, Ratio: 12:1) was added 3-(2-((4-carbamimidoylphenyl)carbamoyl)-5-methoxy-4-vinylphenyl)-6-((cyclopropylmethyl)carbamoyl)picolinic acid (23e) (0.5 g, 0.94 mmol), the mixture was stirred for 10 min at RT. Then 1-((4-nitrophenoxy)carbonyloxy)ethyl acetate (23d) (0.76 mg, 2.82 mmol) was added and the resulting mixture was stirred overnight at room temperature. The reaction was diluted with HOAc (5.0 mL), concentrated in vacuum to remove acetone and diluted with EtOAc and water. The mixture was extracted with EtOAc (3×), the combined organic layers were washed with brine, dried, filtered and concentrated in vacuum. The residue obtained was purified by flash column chromatography [silica gel 24 g, eluting with DMA80 in DCM from 0 to 60%] to give 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinic acid (23f) (0.47 mg, 77% yield) as a white solid. $^1$H NMR (300 MHz, DMSO-$d_6$) δ 12.61 (brs, 1H, D$_2$O exchangeable), 9.17 (d, J=31.6 Hz, 2H, D$_2$O exchangeable), 8.78 (t, J=6.6 Hz, 1H, D$_2$O exchangeable), 7.92 (d, J=7.8 Hz, 1H), 7.88-7.81 (m, 2H), 7.78 (brs, 1H, D$_2$O exchangeable), 7.64 (d, J=7.9 Hz, 1H), 7.54 (d, J=8.9 Hz, 2H), 7.13 (s, 1H), 7.07-6.94 (m, 1H), 6.77-6.70 (m, 2H), 5.95 (dd, J=17.8, 1.5 Hz, 1H), 5.37 (dd, J=11.2, 1.5 Hz, 1H), 3.81 (s, 3H), 3.19 (t, J=6.2 Hz, 2H), 2.01 (s, 3H), 1.41 (d, J=5.4 Hz, 3H), 1.11-0.99 (m, 1H), 0.50-0.38 (m, 2H), 0.30-0.20 (m, 2H); MS (ES$^+$) 644.6 (M+1); (ES$^-$) 642.6 (M−1); Analysis calculated for $C_{33}H_{33}N_5O_9$·0.5NH$_4$Cl·0.5H$_2$O: C, 58.34; H, 5.34; N, 11.34. Found: C, 58.08; H, 5.49; N, 11.50.

Scheme 24
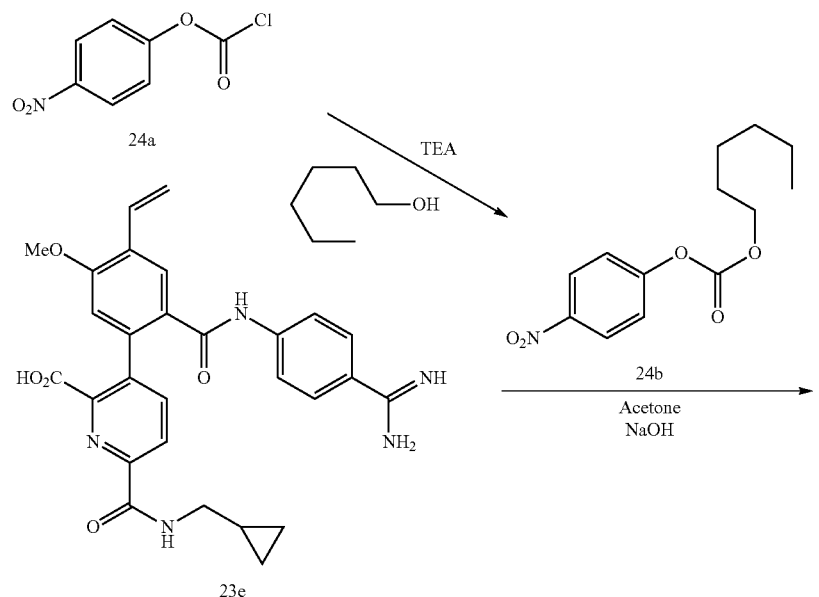
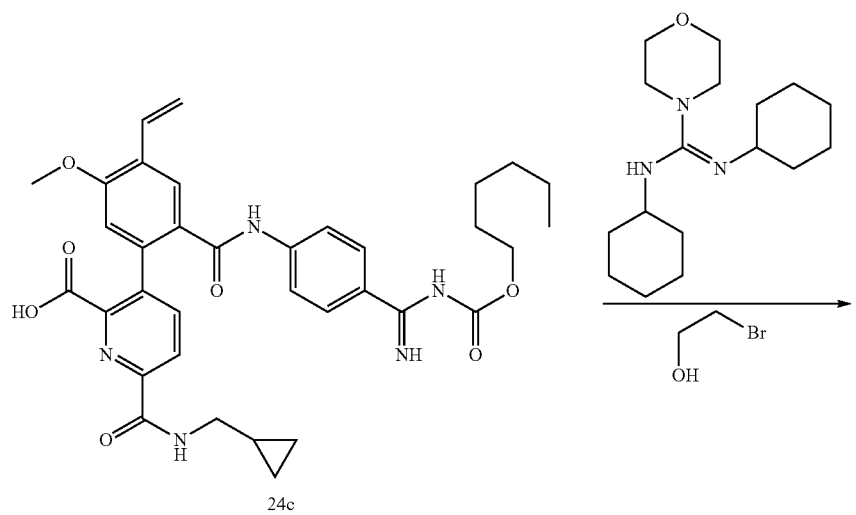
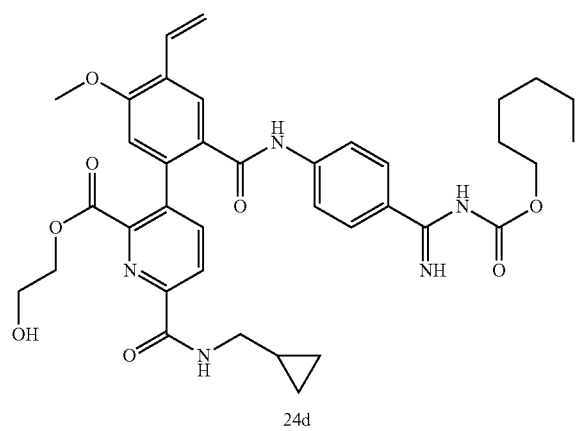

Preparation of 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinic acid (24c) and 2-hydroxyethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (24d)

Step-1: Preparation of hexyl (4-nitrophenyl) carbonate (24b)

To a stirred solution of hexan-1-ol (6.14 mL, 48.9 mmol) in THF (50 mL) cooled to 0° C. was added TEA (15.01 mL, 108 mmol), 4-nitrophenyl carbonochloridate (24a) (9.66 g, 46.5 mmol) and allowed to warm to room temperature overnight. The reaction mixture was diluted with ethyl acetate (100 mL) and the solid separated was removed by filtration washed with ethyl acetate (100 mL). The filtrate was washed with brine (2×50 mL), dried, filtered and concentrated in vacuum to afford hexyl (4-nitrophenyl) carbonate (24b) (10.5 g, 80% yield) as a yellow syrup; $^1$H NMR (300 MHz, DMSO-$d_6$) δ 8.36-8.24 (m, 2H), 7.63-7.49 (m, 2H), 4.24 (t, J=6.6 Hz, 2H), 1.67 (dq, J=8.2, 6.5 Hz, 2H), 1.45-1.14 (m, 6H), 0.98-0.76 (m, 3H).

Step-2: Preparation of 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinic acid (24c)

Compound (24c) was prepared from added 3-(2-((4-carbamimidoylphenyl)carbamoyl)-5-methoxy-4-vinylphenyl)-6-((cyclopropylmethyl)carbamoyl)picolinic acid (23e) (0.5 g, 0.94 mmol) in acetone (20 mL), water (2 mL), using NaOH (94 mg, 2.35 mmol) and hexyl (4-nitrophenyl) carbonate (24b) (0.38 g, 1.41 mmol) according to the procedure reported in step 4 of scheme 23. This gave after workup and purification by flash column chromatography (silica gel 25 g, eluting with 0-100% DMA 80 in dichloromethane) 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinic acid (24c) (0.54 g, 89% yield) as a white solid; $^1$H NMR (300 MHz, DMSO-$d_6$) δ 11.25 (s, 1H), 9.08 (d, J=6.8 Hz, 1H), 8.24-8.05 (m, 1H), 7.98-7.75 (m, 4H), 7.75-7.53 (m, 2H), 7.10-6.91 (m, 1H), 6.89 (s, 1H), 6.00 (dd, J=17.9, 1.6 Hz, 1H), 5.41 (dd, J=11.2, 1.6 Hz, 1H), 3.99 (t, J=6.7 Hz, 2H), 3.85 (s, 3H), 3.51-3.28 (m, 2H), 1.57 (q, J=6.8 Hz, 2H), 1.40-1.17 (m, 6H), 1.18-0.98 (m, 1H), 0.93-0.78 (m, 3H), 0.54-0.39 (m, 2H), 0.33-0.19 (m, 2H); MS (ES+) 642.6 (M+1), (ES−) 640.7 (M−1).

Step-3: Preparation of 2-hydroxyethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (24d)

Compound (24d) was prepared according to the procedure reported in step 1 of scheme 8 from 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinic acid (24c) (0.2 g, 0.39 mmol) in DMF (5 mL) using N,N'-Dicyclohexyl-4-morpholinecarboxamidine (0.11 g, 0.39 mmol) and 2-bromoethanol (42.8 mg, 0.34 mmol). This gave after workup and purification by flash column chromatography (silica gel 12 g, eluting with 0-100% DMA 80 in dichloromethane) 2-hydroxyethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (24d) (110 mg, 52% yield) as a white solid; $^1$H NMR (300 MHz, DMSO-$d_6$) δ 10.52 (s, 1H), 9.06 (d, J=59.1 Hz, 2H, $D_2O$ exchangeable), 8.68 (t, J=6.1 Hz, 1H), 8.21 (d, J=8.0 Hz, 1H), 8.04 (d, J=8.0 Hz, 1H), 7.98-7.86 (m, 3H), 7.73-7.61 (m, 2H), 7.11-6.96 (m, 2H), 6.04 (dd, J=17.8, 1.6 Hz, 1H), 5.43 (dd, J=11.2, 1.6 Hz, 1H), 4.87 (t, J=5.7 Hz, 1H, $D_2O$ exchangeable), 4.20-3.90 (m, 4H), 3.89 (s, 3H), 3.46-3.24 (m, 2H), 3.21 (t, J=6.6 Hz, 2H), 1.58 (dt, J=12.8, 6.3 Hz, 2H), 1.44-1.18 (m, 6H), 1.16-0.99 (m, 1H), 0.94-0.78 (m, 3H), 0.49-0.37 (m, 2H), 0.32-0.20 (m, 2H); MS (ES+) 686.6 (M+1), 708.5 (M+Na), (ES−) 720.7 (M+Cl).

Scheme 25

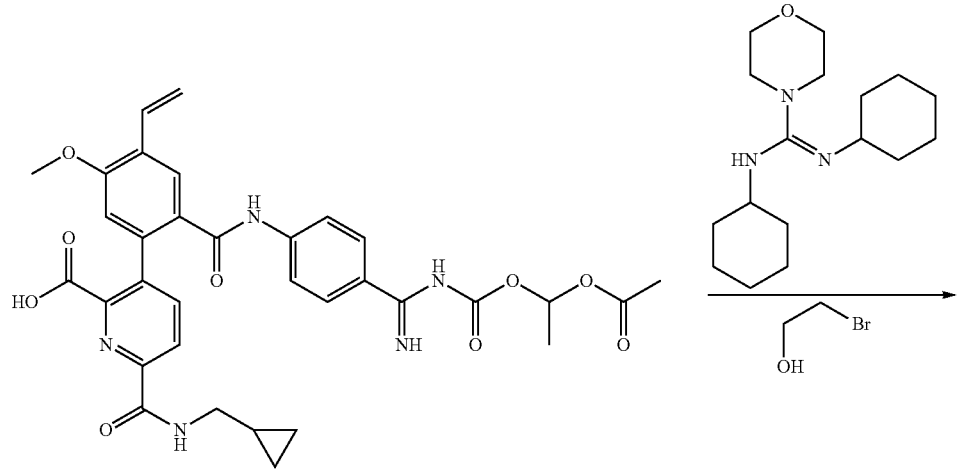

23f

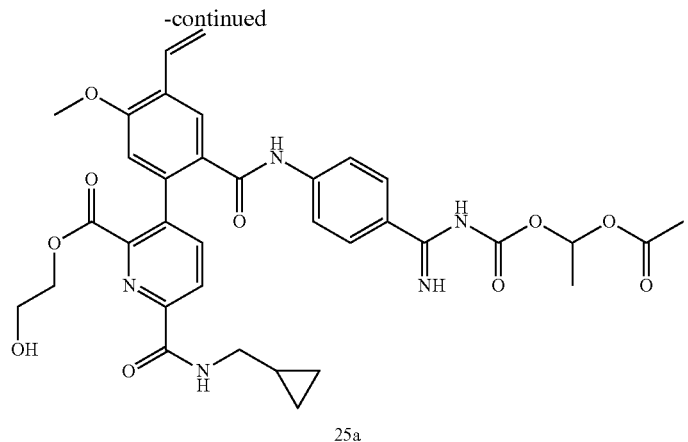

25a

Preparation of 2-hydroxyethyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (25a)

Compound (25a) was prepared according to the procedure reported in step 1 of scheme 8 from 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinic acid (23f) (0.38 g, 0.58 mmol) in DMF (15 mL) using N,N'-Dicyclohexyl-4-morpholinecarboxamidine (0.21 g, 0.73 mmol) and 2-bromoethanol (80 mg, 0.64 mmol). This gave after workup and purification by flash column chromatography (silica gel 12 g, eluting with a 9:1 mixture of ethyl acetate and methanol in hexanes from 0-70%) 2-hydroxyethyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (25a) (46 mg, 12% yield) as a white solid; $^1$H NMR (300 MHz, DMSO-$d_6$) δ 10.54 (s, 1H, $D_2O$ exchangeable), 9.21 (d, J=23.5 Hz, 2H, $D_2O$ exchangeable), 8.67 (t, J=6.1 Hz, 1H, $D_2O$ exchangeable), 8.20 (d, J=8.0 Hz, 1H), 8.03 (d, J=8.0 Hz, 1H), 7.99-7.89 (m, 3H), 7.67 (d, J=8.9 Hz, 2H), 7.10-6.96 (m, 2H), 6.76 (q, J=5.4 Hz, 1H), 6.04 (dd, J=17.8, 1.5 Hz, 1H), 5.43 (dd, J=11.2, 1.5 Hz, 1H), 4.86 (t, J=5.6 Hz, 1H, $D_2O$ exchangeable), 4.03 (s, 2H), 3.89 (s, 3H), 3.34-3.28 (m, 2H), 3.21 (t, J=6.5 Hz, 2H), 2.02 (s, 3H), 1.43 (d, J=5.5 Hz, 3H), 1.13-1.02 (m, 1H), 0.48-0.39 (m, 2H), 0.30-0.23 (m, 2H); MS (ES+) 688.5 (M+1); 710.6 (M+Na); (ES−) 686.7 (M−1).

Scheme 26

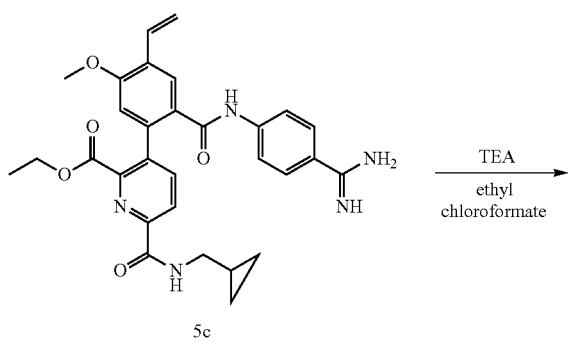

5c

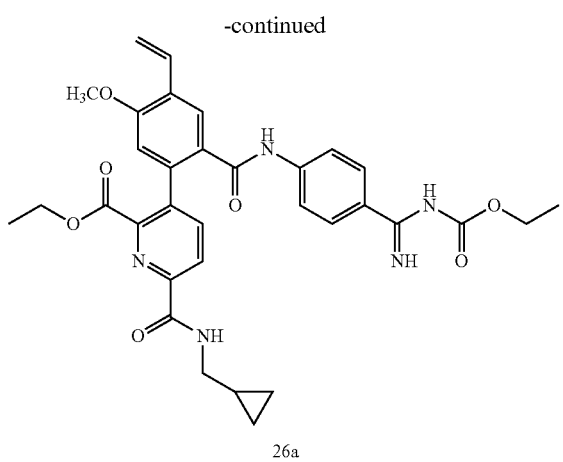

26a

Preparation of ethyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (26a)

Compound (26a) was prepared from ethyl 3-(2-((4-carbamimidoylphenyl)carbamoyl)-5-methoxy-4-vinylphenyl)-6-((cyclopropylmethyl)carbamoyl)picolinate hydrochloride (5c) (0.2 g, 0.37 mmol) according to the procedure reported in scheme 6. This gave after workup, purification by flash column chromatography (silica gel 12 g, eluting with DMA80 in DCM from 0-40%) ethyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (26a) (75 mg, 33% yield) as a white solid; $^1$H NMR (300 MHz, DMSO-$d_6$) δ 10.52 (s, 1H, $D_2O$ exchangeable), 9.05 (d, J=61.8 Hz, 2H, $D_2O$ exchangeable), 8.65 (t, J=6.1 Hz, 1H, $D_2O$ exchangeable), 8.20 (d, J=8.0 Hz, 1H), 8.03 (d, J=8.1 Hz, 1H), 7.93 (d, J=9.5 Hz, 3H), 7.68 (d, J=8.6 Hz, 2H), 7.09-6.94 (m, 2H), 6.11-5.93 (m, 1H), 5.49-5.38 (m, 1H), 4.04 (q, J=7.2 Hz, 4H), 3.89 (s, 3H), 3.20 (t, J=6.3 Hz, 2H), 1.21 (t, J=7.1 Hz, 3H), 1.15-1.02 (m, 1H), 0.91 (t, J=7.1 Hz, 3H), 0.48-0.38 (m, 2H), 0.31-0.21 (m, 2H); MS (ES+) 636.5 (M+Na); (ES−) 612.7 (M−1); Analysis calculated for $C_{33}H_{35}N_5O_7 \cdot 0.5H_2O$. C, 63.65; H, 5.83; N, 11.25; found: C, 63.60; H, 6.09; N, 10.95.

Scheme 27

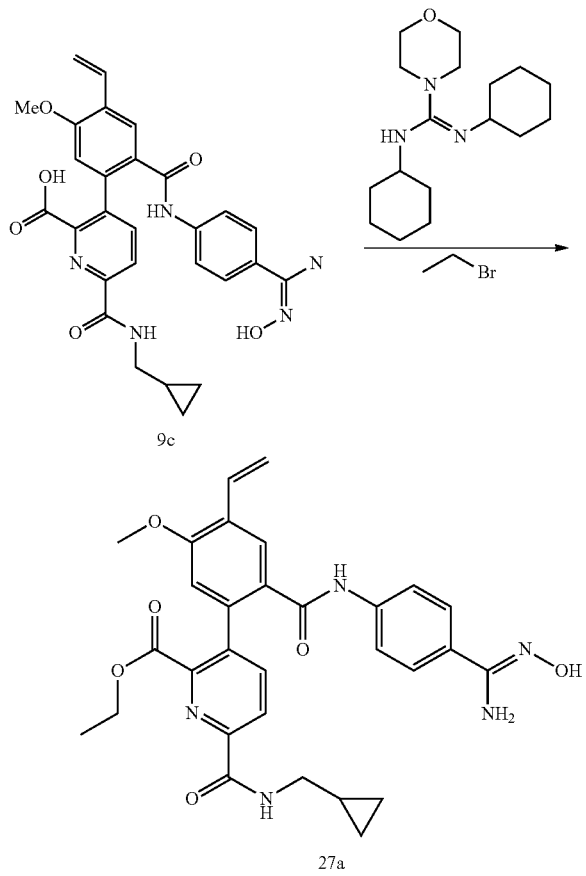

Preparation of ethyl 6-((cyclopropylmethyl)carbamoyl)-3-(2-((4-(N'-hydroxycarbamimidoyl)phenyl)carbamoyl)-5-methoxy-4-vinylphenyl)picolinate (27a)

Compound (27a) was prepared according to the procedure reported in step 1 of scheme 8 from 6-((cyclopropylmethyl)carbamoyl)-3-(2-((4-(N'-hydroxycarbamimidoyl)phenyl)carbamoyl)-5-methoxy-4-vinylphenyl)picolinic acid (9c) (0.5 g, 0.94 mmol) in DMF (15 mL) using N,N'-Dicyclohexyl-4-morpholinecarboxamidine (0.35 g, 1.18 mmol) and bromoethane (0.11 mL, 1.42 mmol). This gave after workup and purification by flash column chromatography (First column: silica gel 24 g, eluting with methanol in DCM from 0-100%; second column: silica gel 24 g, eluting with methanol/ethyl acetate (1/9) in hexanes from 0-100%) ethyl 6-((cyclopropylmethyl)carbamoyl)-3-(2-((4-(N'-hydroxycarbamimidoyl)phenyl)carbamoyl)-5-methoxy-4-vinylphenyl)picolinate (27a) (29 mg, 6% yield) as a white solid; $^1$H NMR (300 MHz, DMSO-$d_6$) δ 10.32 (s, 1H), 9.53 (s, 1H, $D_2O$ exchangeable), 8.66 (t, J=6.0 Hz, 1H), 8.20 (d, J=8.0 Hz, 1H), 8.02 (d, J=8.0 Hz, 1H), 7.92 (s, 1H), 7.57 (s, 4H), 7.15-6.92 (m, 2H), 6.03 (d, J=17.8 Hz, 1H), 5.73 (bs, 2H, $D_2O$ exchangeable), 5.43 (d, J=11.4 Hz, 1H), 4.15-3.97 (m, 2H), 3.88 (s, 3H), 3.27-3.12 (m, 2H), 1.18-1.01 (m, 1H), 0.92 (t, J=7.1 Hz, 3H), 0.52-0.37 (m, 2H), 0.32-0.20 (m, 2H); MS (ES+): 580.5 (M+Na); MS (ES−): 592.5 (M+Cl); Analysis calculated for $C_{30}H_{31}N_5O_6 \cdot H_2O$: C, 62.60; H, 5.78; N, 12.17; found: C, 62.84; H, 5.63; N, 12.10.

Scheme 28

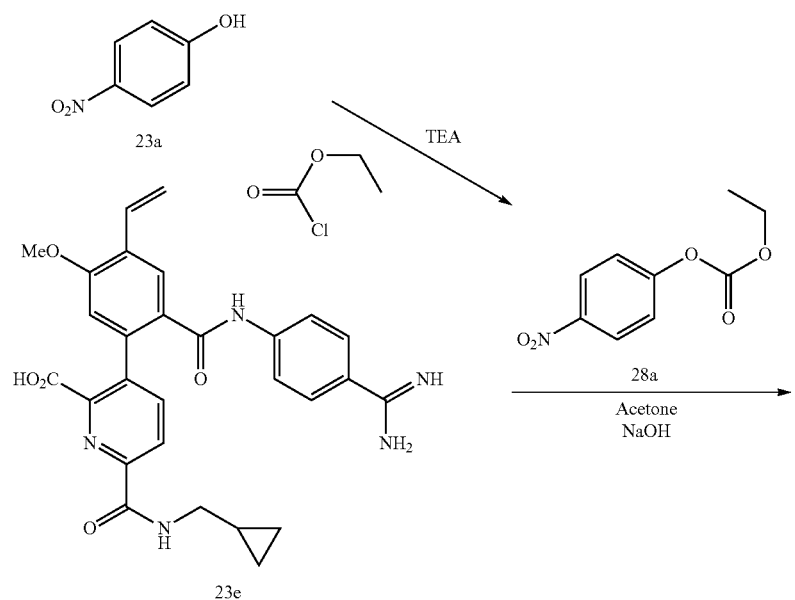

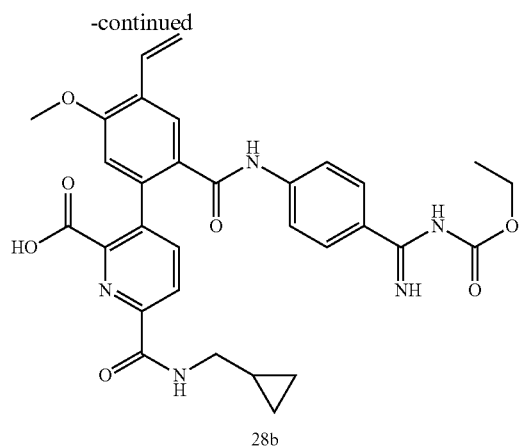

28b

Step-2: Preparation of 6-((cyclopropylmethyl)carbamoyl)-3-(2-((4-(N-(ethoxycarbonyl)carbamimidoyl)phenyl)carbamoyl)-5-methoxy-4-vinylphenyl)picolinic acid (28b)

Compound (28b) was prepared from 3-(2-((4-carbamimidoylphenyl)carbamoyl)-5-methoxy-4-vinylphenyl)-6-((cyclopropylmethyl)carbamoyl)picolinic acid (23e) (1.68 g, 3.16 mmol) in acetone/water (12 mL, 2:1), using NaOH (0.28 g, 6.95 mmol) and ethyl (4-nitrophenyl) carbonate (28a) (2 g, 9.47 mmol) according to the procedure reported in step 4 of scheme 23. This gave after workup and purification by flash column chromatography (silica gel 25 g, eluting with 0-100% DMA 60 in dichloromethane) 6-((cyclopropylmethyl)carbamoyl)-3-(2-((4-(N-(ethoxycarbonyl)carbamimidoyl)phenyl)carbamoyl)-5-methoxy-4-vinylphenyl)picolinic acid (28b) (1.2 g, 65% yield) as a white solid. $^1$H NMR (300 MHz, DMSO-$d_6$) δ 12.75 (brs, 1H, $D_2O$ exchangeable), 10.77 (s, 1H, $D_2O$ exchangeable), 9.48-8.88 (m, 3H, $D_2O$ exchangeable), 8.20 (d, J=8.0 Hz, 1H), 8.00-7.81 (m, 4H), 7.72-7.59 (m, 2H), 7.10-6.92 (m, 2H), 6.02 (dd, J=17.7, 1.5 Hz, 1H), 5.42 (dd, J=11.2, 1.5 Hz, 1H), 4.05 (q, J=7.1 Hz, 2H), 3.87 (s, 3H), 3.23 (t, J=6.4 Hz, 2H), 1.21 (t, J=7.1 Hz, 3H), 1.14-1.01 (m, 1H), 0.52-0.40 (m, 2H), 0.34-0.21 (m, 2H); MS (ES+) 586.5 (M+1); (ES−) 584.5 (M−1).

Scheme 29

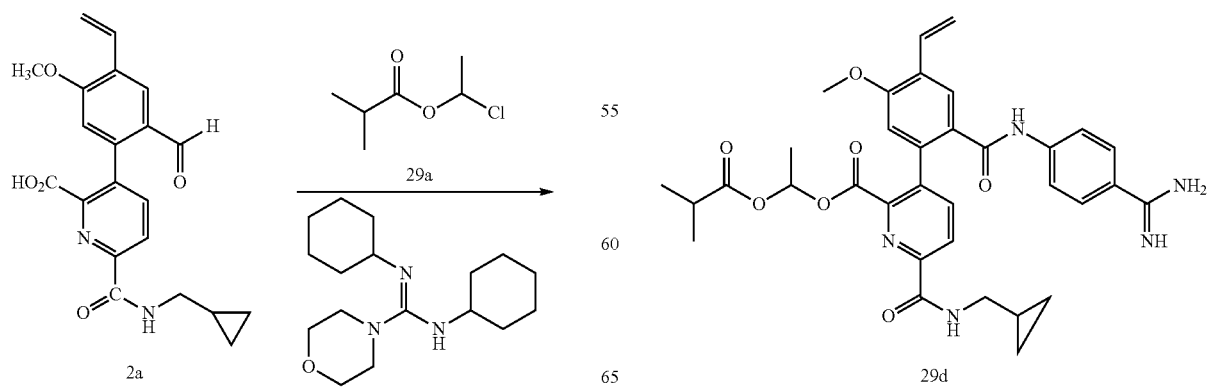

Preparation of 1-(isobutyryloxy)ethyl 3-(2-((4-carbamimidoylphenyl)carbamoyl)-5-methoxy-4-vinylphenyl)-6-((cyclopropylmethyl)carbamoyl)picolinate (29d)

Step-1: Preparation of 1-(isobutyryloxy)ethyl 6-((cyclopropylmethyl)carbamoyl)-3-(2-formyl-5-methoxy-4-vinylphenyl)picolinate (29b)

Compound (29b) was prepared according to the procedure reported in step 1 of scheme 8 from 6-(Cyclopropylmethylcarbamoyl)-3-(2-formyl-5-methoxy-4-vinylphenyl)picolinic acid (2a) (1.72 g, 4.52 mmol) in DMF (20 mL) using N,N'-Dicyclohexyl-4-morpholinecarboxamidine (1.33 g, 4.52 mmol) and 1-chloroethyl isobutyrate (29a) (1.7 g, 4.52 mmol). This gave after workup and purification by flash column chromatography (silica gel 40 g, eluting with ethyl acetate/Hexanes, 0-100%) 1-(isobutyryloxy)ethyl 6-((cyclopropylmethyl)carbamoyl)-3-(2-formyl-5-methoxy-4-vinylphenyl)picolinate (29b) (1.777 g, 79% yield) as a yellow syrup; $^1$H NMR (300 MHz, DMSO-d$_6$) δ 9.69 (d, J=1.6 Hz, 1H), 8.77-8.59 (m, 1H), 8.27 (dd, J=8.1, 0.7 Hz, 1H), 8.14 (s, 1H), 8.08 (dd, J=8.0, 2.1 Hz, 1H), 7.08-6.93 (m, 2H), 6.72 (p, J=5.4 Hz, 1H), 6.00 (dt, J=17.9, 1.3 Hz, 1H), 5.44 (dd, J=11.3, 1.4 Hz, 1H), 3.90 (d, J=5.9 Hz, 3H), 3.29-3.17 (m, 2H), 2.36 (dp, J=15.6, 6.9 Hz, 1H), 1.21 (dd, J=11.5, 5.5 Hz, 3H), 1.19-1.02 (m, 1H), 1.02-0.92 (m, 6H), 0.50-0.41 (m, 2H), 0.32-0.22 (m, 2H); MS (ES+) 495.4 (M+1), 517.4 (M+Na).

Step-2: Preparation of 2-(6-((cyclopropylmethyl)carbamoyl)-2-((1-(isobutyryloxy)ethoxy)carbonyl)pyridin-3-yl)-4-methoxy-5-vinylbenzoic acid (29c)

Oxidation of 1-(isobutyryloxy)ethyl 6-((cyclopropylmethyl)carbamoyl)-3-(2-formyl-5-methoxy-4-vinylphenyl)picolinate (29b) (11.9 g, 24.06 mmol) using the procedure as reported in step 11 of scheme 1 gave after workup 2-(6-((cyclopropylmethyl)carbamoyl)-2-((1-(isobutyryloxy)ethoxy)carbonyl)pyridin-3-yl)-4-methoxy-5-vinylbenzoic acid (29c) (12.25 g, 100% yield) as a yellow solid. $^1$H NMR (300 MHz, DMSO-d$_6$) δ 12.57 (s, 1H, D$_2$O exchangeable), 8.62 (dt, J=12.7, 6.1 Hz, 1H), 8.22 (dd, J=8.0, 1.5 Hz, 1H), 8.13 (d, J=1.1 Hz, 1H), 7.96 (d, J=8.0 Hz, 1H), 6.98 (ddd, J=17.9, 11.3, 1.4 Hz, 1H), 6.89 (d, J=1.1 Hz, 1H), 6.71 (tt, J=5.4, 3.1 Hz, 1H), 5.91 (dd, J=17.8, 1.5 Hz, 1H), 5.39 (dd, J=11.2, 1.4 Hz, 1H), 3.85 (d, J=5.9 Hz, 3H), 3.27-3.20 (m, 2H), 2.37 (dq, J=20.7, 6.9 Hz, 1H), 1.20 (d, J=5.4 Hz, 3H), 1.18-1.01 (m, 1H), 1.03-0.92 (m, 6H), 0.50-0.41 (m, 2H), 0.32-0.24 (m, 2H); MS (ES+) 511.5 (M+1), 533.5 (M+Na), (ES-) 509.5 (M-1).

Step-3: Preparation of 1-(isobutyryloxy)ethyl 3-(2-((4-carbamimidoylphenyl)carbamoyl)-5-methoxy-4-vinylphenyl)-6-((cyclopropylmethyl)carbamoyl)picolinate (29d)

Compound (29d) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (1.5 g, 2.94 mmol) using EDCI (0.85 g, 4.41 mmol) and 4-aminobenzimidamide dihydrochloride (1n) (0.73 g, 3.53 mmol) in DMF (10 mL) and Pyridine (4 mL) according to the procedure reported in step 4 of scheme 2. This gave after workup and purification by reverse phase column chromatography [C-18, 30 g, eluting with acetonitrile-water 10 to 80%) 1-(isobutyryloxy)ethyl 3-(2-((4-carbamimidoylphenyl)carbamoyl)-5-methoxy-4-vinylphenyl)-6-((cyclopropylmethyl)carbamoyl)picolinate (29d) (0.45 g, 23% yield) as a white solid; $^1$HNMR (300 MHz, DMSO-d$_6$) δ 10.80-10.61 (m, 1H), 9.22 (s, 2H), 8.94 (s, 2H), 8.67-8.46 (m, 1H), 8.22 (d, J=8.0 Hz, 1H), 8.01 (s, 2H), 7.78 (s, 4H), 7.11-6.97 (m, 2H), 6.80-6.66 (m, 1H), 6.06 (d, J=17.9 Hz, 1H), 5.45 (dd, J=11.2, 1.5 Hz, 1H), 3.89 (s, 3H), 3.29-3.17 (m, 2H), 2.47-2.27 (m, 1H), 1.18 (d, J=5.4 Hz, 3H), 1.14-0.89 (m, 7H), 0.49-0.39 (m, 2H), 0.32-0.22 (m, 2H); MS (ES+) 628.7 (M+1).

Scheme 30

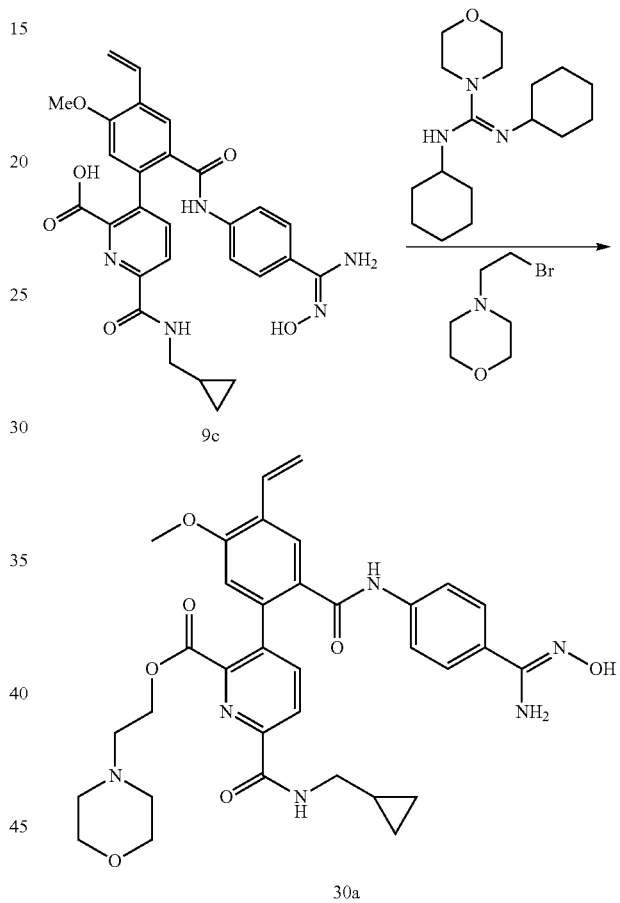

9c

30a

Preparation of 2-morpholinoethyl 6-((cyclopropylmethyl)carbamoyl)-3-(2-((4-(N'-hydroxycarbamimidoyl)phenyl)carbamoyl)-5-methoxy-4-vinylphenyl)picolinate (30a)

Compound (30a) was prepared according to the procedure reported in step 1 of scheme 8 from 6-((cyclopropylmethyl)carbamoyl)-3-(2-((4-(N'-hydroxycarbamimidoyl)phenyl)carbamoyl)-5-methoxy-4-vinylphenyl)picolinic acid (9c) (0.52 g, 0.98 mmol) in DMF (10 mL) using N,N'-Dicyclohexyl-4-morpholinecarboxamidine (0.36 g, 1.23 mmol) and 4-(2-chloroethyl)morpholine hydrochloride (0.183 g, 0.984 mmol). This gave after workup and purification by flash column chromatography [EZ-PREP, C-18 column, 50 g, eluting with 0.1% aqueous HCl in water and in acetonitrile from 0-100%], followed by lyophilization 2-morpholinoethyl 6-((cyclopropylmethyl)carbamoyl)-3-(2-((4-(N'-hydroxycarbamimidoyl)phenyl)carbamoyl)-5-methoxy-4-vinylphenyl)picolinate (30a) (54 mg, 9% yield) as a white solid; $^1$H NMR (300 MHz, DMSO-d$_6$) δ 12.83 (s, 1H, D$_2$O exchangeable), 11.72 (s, 1H, D$_2$O exchangeable), 11.13 (s, 1H, D$_2$O exchangeable), 10.95 (s, 1H), 8.90 (s, 3H, D$_2$O exchangeable), 8.79 (t, J=6.1 Hz, 1H), 8.21 (d, J=8.0 Hz, 1H), 8.07 (d, J=8.0 Hz, 1H), 7.96 (s, 1H), 7.89-7.78 (m, 2H), 7.72-7.61 (m, 2H), 7.09-6.93 (m, 2H), 6.10 (dd, J=17.8, 1.6 Hz, 1H), 5.51-5.35 (m, 1H), 4.68-4.33 (m, 2H), 3.90 (s, 3H), 3.81-3.69 (m, 4H), 3.27-2.88 (m, 8H), 1.16-0.93 (m, 1H), 0.46-0.37 (m, 2H), 0.29-0.20 (m, 2H); $^1$H NMR (300 MHz, DMSO-d$_6$ D$_2$O) δ 10.92 (s, 1H), 8.82 (t, J=6.1 Hz, 1H), 8.23 (d, J=8.1 Hz, 1H), 8.08 (d, J=8.0 Hz, 1H), 7.97 (s, 1H), 7.89-7.79 (m, 2H), 7.74-7.62 (m, 2H), 7.19-6.82 (m, 2H), 6.10 (d, J=17.9 Hz, 1H), 5.45 (d, J=11.4 Hz, 1H), 4.67-4.31 (m, 2H), 3.91 (s, 3H), 3.76 (s, 4H), 3.33-2.89 (m, 8H), 1.17-0.95 (m, 1H), 0.48-0.38 (m, 2H), 0.32-0.18 (m, 2H); MS (ES+): 643.6 (M+1); MS (ES−): 641.8 (M−1), 677.6 (M+Cl); Analysis calculated for C$_{34}$H$_{38}$N$_6$O$_7$.2.5H$_2$O.2HCl: C, 53.69; H, 5.96; Cl, 9.32; N, 11.05; found: C, 53.63; H, 5.95; Cl, 9.32; N, 10.99.

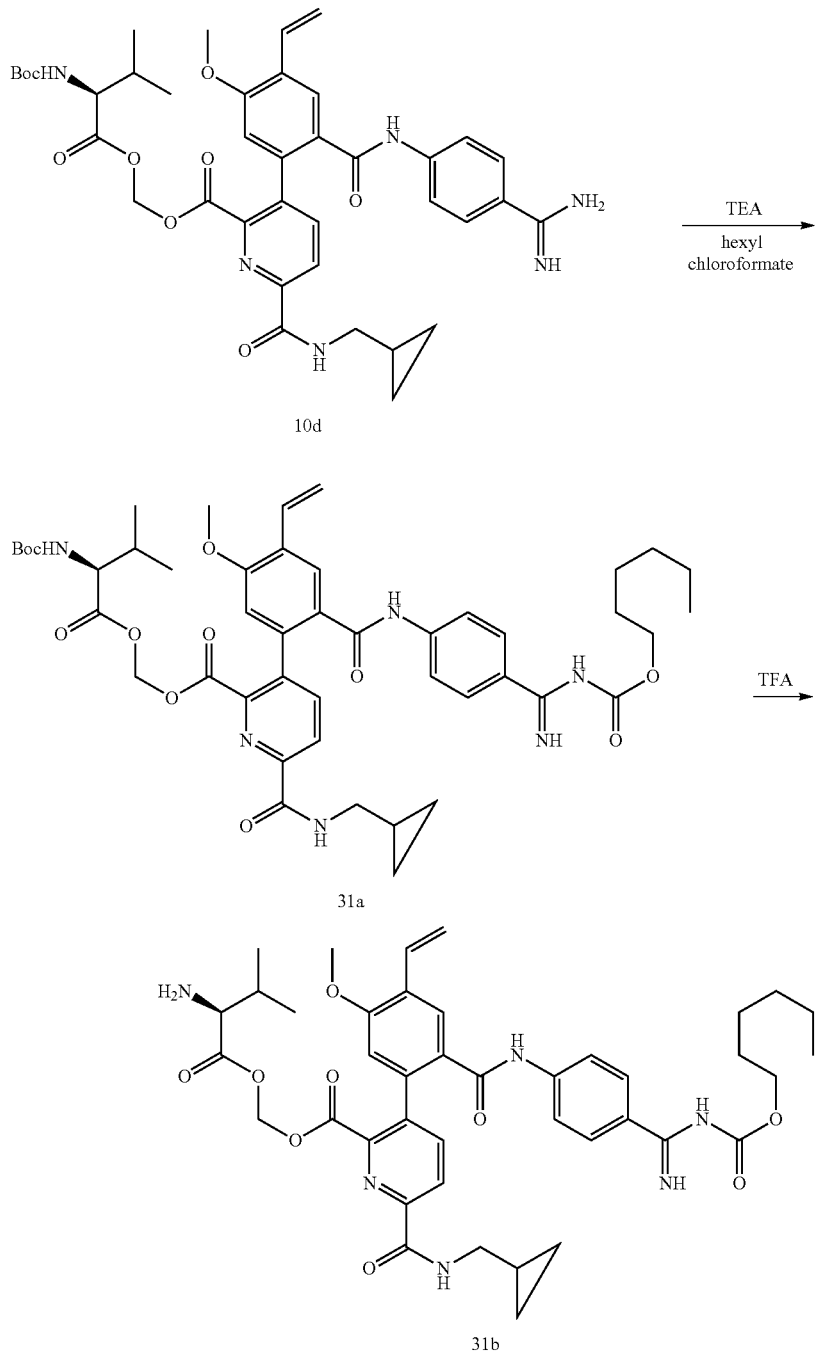

Scheme 31

Preparation of (S)-((2-amino-3-methylbutanoyl)oxy) methyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate (31b)

Step-1: Preparation of (S)-((2-((tert-butoxycarbonyl) amino)-3-methylbutanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (31a)

Compound (31a) was prepared from (S)-((2-((tert-butoxycarbonyl)amino)-3-methylbutanoyl)oxy)methyl 3-(2-((4-carbamimidoylphenyl)carbamoyl)-5-methoxy-4-vinylphenyl)-6-((cyclopropylmethyl)carbamoyl)picolinate (10d) (0.7 g, 0.94 mmol) and hexyl chloroformate (1.541 mL, 9.42 mmol) followed according to the procedure reported in scheme 6. This gave after workup, purification by reverse phase flash column chromatography [silica gel 24 g, eluting with ethyl acetate/methanol (9:1) in hexanes from 0-100%] (S)-((2-((tert-butoxycarbonyl)amino)-3-methylbutanoyl) oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (31a) (115 mg, 14% yield) as an off white solid; MS (ES+): 871.81 (M+1).

Step-2: Preparation of (S)-((2-amino-3-methylbutanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl) picolinate (31b)

Compound (31b) was prepared from (S)-((2-((tert-butoxycarbonyl)amino)-3-methylbutanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (31a) (0.11 g, 0.14 mmol) in dichloromethane (5 mL) using 2,2,2-trifluoroacetic acid (0.22 mL, 2.88 mmol) according to the procedure reported in Step-4 of scheme 8. This gave after workup and purification by flash column chromatography (EZ-PREP, C-18 column, 50 g, eluting with 0.1% aqueous HCl in water and acetonitrile from 0-60%), followed by lyophilization (S)-((2-amino-3-methylbutanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl) picolinate (31b) (0.031 g, 32% yield) as a white solid; $^1$H NMR (300 MHz, DMSO-$d_6$) δ 12.37 (bs, 1H, $D_2O$ exchangeable), 10.86 (s, 1H, $D_2O$ exchangeable), 10.30 (bs, 1H, $D_2O$ exchangeable), 8.65 (bs, 4H, $D_2O$ exchangeable), 8.56-8.44 (m, 1H), 8.25 (d, J=8.0 Hz, 1H), 8.09-7.96 (m, 2H), 7.91-7.69 (m, 4H), 7.15-6.94 (m, 2H), 6.10 (dd, J=17.6, 1.5 Hz, 1H), 6.03-5.69 (m, 2H), 5.56-5.35 (m, 1H), 4.24 (t, J=6.5 Hz, 2H), 3.89 (s, 3H), 3.87-3.84 (m, 1H), 3.31-3.19 (m, 2H), 2.20-1.95 (m, 1H), 1.75-1.60 (m, 2H), 1.46-1.21 (m, 6H), 1.14-1.02 (m, 1H), 0.98-0.77 (m, 9H), 0.56-0.37 (m, 2H), 0.36-0.20 (m, 2H); MS (ES+): 771.7 (M+1), 772.7 (M+2), 793.6 (M+Na); MS (ES−): 805.8 (M+Cl); Analysis calculated for $C_{41}H_{50}N_6O_9 \cdot 3H_2O \cdot 2HCl$: C, 54.85; H, 6.51; N, 9.36; Cl, 7.90. Found: C, 54.83; H, 6.15; N, 9.29; Cl, 7.68.

Scheme 32

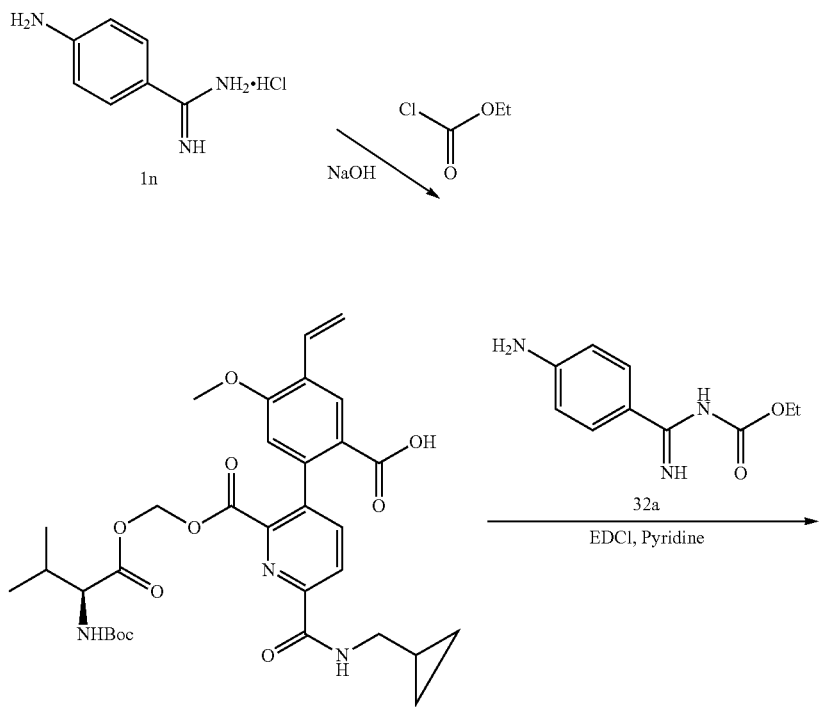

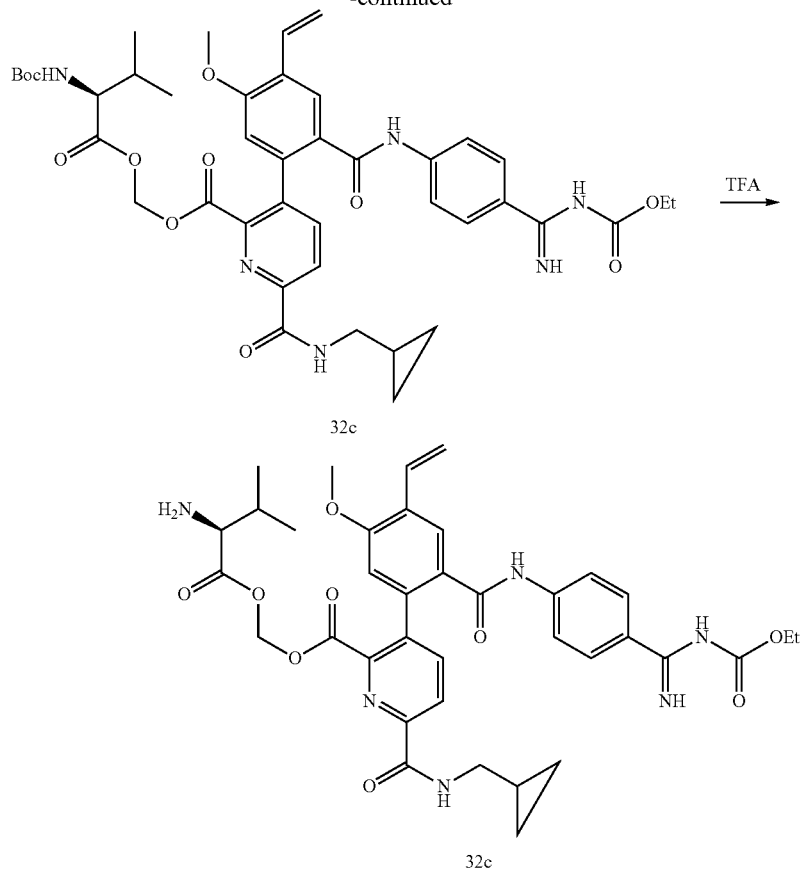

Preparation of (S)-((2-amino-3-methylbutanoyl)oxy)methyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (32c)

Step-1: Preparation of ethyl ((4-aminophenyl)(imino)methyl)carbamate (32a)

To a solution of 4-aminobenzimidamide (1n) (4 g, 19.22 mmol) in acetone-water (90 mL, Ratio: 2:1), was added a solution of NaOH (2.69 g, 67.3 mmol) in water (30 mL) and cooled to 0° C. To this solution was added ethyl chloroformate (2.09 g, 19.22 mmol) at 0° C. and stirred for additional 20 min at 5-10° C. The reaction was diluted with EtOAc (100 mL) and phases were separated. The organic phase was concentrated in vacuum. The residue was taken up with EtOAc (50 mL) and diluted a solution of with HCl (3 mL) in EtOAc (20 mL). The solid obtained was collected by filtration to give ethyl (4-aminophenyl)(imino)methylcarbamate hydrochloride salt (32a) (3.5 g, 75% yield) as a yellow solid; $^1$H NMR (300 MHz, DMSO-$d_6$) δ 11.86 (s, 1H, $D_2O$ exchangeable), 10.91 (s, 1H, $D_2O$ exchangeable), 9.96 (s, 1H, $D_2O$ exchangeable), 7.75-7.52 (m, 2H), 6.79-6.56 (m, 2H), 5.16 (brs, 3H, $D_2O$ exchangeable), 4.32 (q, J=7.1 Hz, 2H), 1.32 (t, J=7.1 Hz, 3H); MS (ES$^+$) 208.3 (M+1); (ES$^-$) 242.3 (M+Cl).

Step-2: Preparation of (S)-((2-((tert-butoxycarbonyl)amino)-3-methylbutanoyl)oxy)methyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (32c)

Compound (32c) was prepared from (S)-2-(6-((cyclopropylmethyl)carbamoyl)-2-(6-isopropyl-10,10-dimethyl-5,8-dioxo-2,4,9-trioxa-7-azaundecan-1-oyl)pyridin-3-yl)-4-methoxy-5-vinylbenzoic acid (10c) (0.5 g, 0.8 mmol) using EDCI (0.23 g, 1.2 mmol) and ethyl ((4-aminophenyl)(imino)methyl)carbamate (32a) (0.21 g, 1.00 mmol) in Pyridine (3 mL) according to the procedure reported in step 4 of scheme 2. This gave after workup and purification by flash column chromatography [silica gel, 12 g, with DMA80 in DCM from 0-40%) (S)-((2-((tert-butoxycarbonyl)amino)-3-methylbutanoyl)oxy)methyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (32c) (0.27 g, 41% yield) as white solid; MS (ES−) 813.9 (M−1);

Step-3: Preparation of (S)-((2-amino-3-methylbutanoyl)oxy)methyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (32c)

Compound (32c) was prepared from (S)-((2-((tert-butoxycarbonyl)amino)-3-methylbutanoyl)oxy)methyl 6-((cyclopropylmethyl)carbamoyl)-3-(2-((4-(N-(ethoxycarbonyl)

carbamimidoyl)phenyl)carbamoyl)-5-methoxy-4-vinylphenyl)picolinate (32c) (0.16 g, 0.2 mmol) in dichloromethane (10 mL) using 2,2,2-trifluoroacetic acid (0.303 mL, 3.93 mmol) according to the procedure reported in Step-4 of scheme 8. This gave after workup and purification by prep-HPLC [C18 column, eluting with ACN in water (containing 0.1% HCl) from 0-100%], followed by lyophilization (S)-((2-amino-3-methylbutanoyl)oxy)methyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (32c) (0.046 g, 31% yield) as a white solid; $^1$H NMR (300 MHz, DMSO-d$_6$) δ 12.36 (brs, 1H, D$_2$O exchangeable), 11.21 (brs, 1H, D$_2$O exchangeable), 10.85 (s, 1H, D$_2$O exchangeable), 10.39 br (s, 1H, D$_2$O exchangeable), 8.62 (s, 2H, D$_2$O exchangeable), 8.49 (t, J=6.0 Hz, 1H, D$_2$O exchangeable), 8.25 (d, J=8.0 Hz, 1H), 8.04 (d, J=7.0 Hz, 2H), 7.85-7.71 (m, 4H), 7.12-6.94 (m, 2H), 6.16-6.03 (m, 1H), 5.94 (d, J=21.2 Hz, 1H), 5.87-5.73 (m, 1H), 5.51-5.40 (m, 1H), 4.32 (q, J=7.1 Hz, 2H), 3.89 (s, 4H), 3.28-3.17 (m, 2H), 2.15-2.00 (m, 1H), 1.31 (t, J=7.1 Hz, 3H), 1.14-1.00 (m, 1H), 0.93-0.82 (m, 6H), 0.52-0.39 (m, 2H), 0.33-0.22 (m, 2H); MS (ES$^+$) 715.7 (M+1); (ES$^-$) 749.7 (M+Cl).

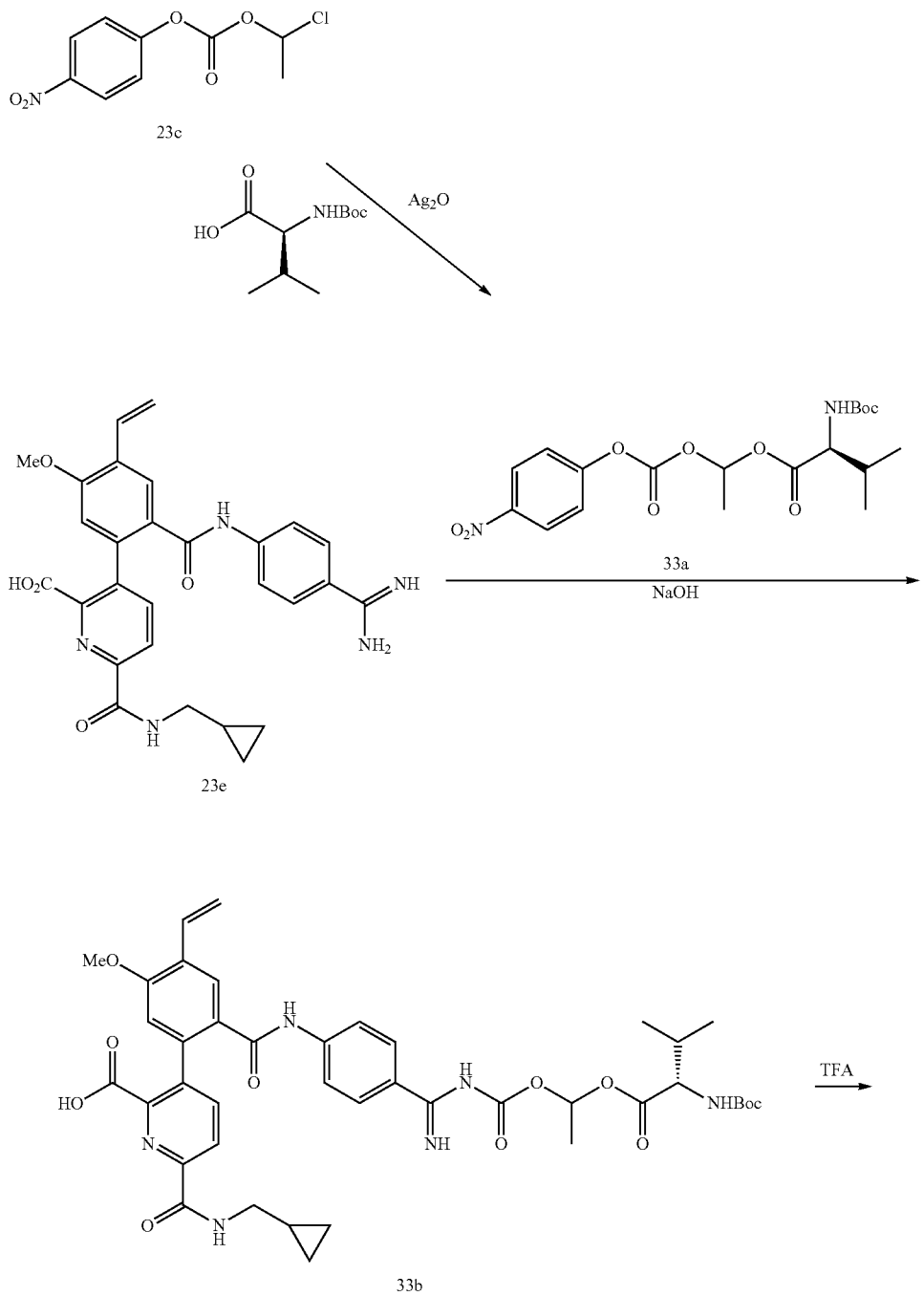

Scheme 33

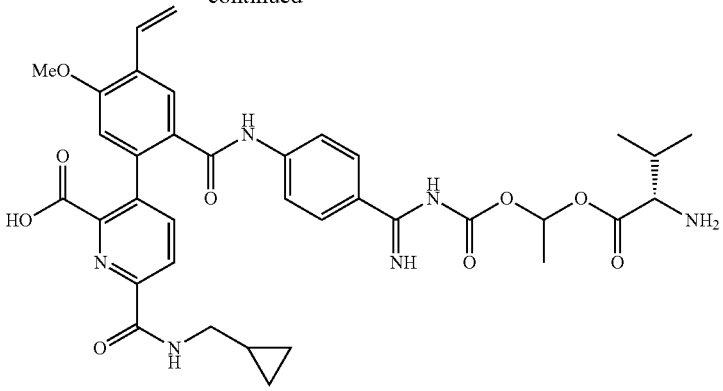

33c

Preparation of 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinic acid (33c)

Step-1: Preparation of (2S)-1-(((4-nitrophenoxy)carbonyl)oxy)ethyl 2-((tert-butoxycarbonyl)amino)-3-methylbutanoate (33a)

A mixture of 1-chloroethyl 4-nitrophenyl carbonate (0.5 g, 2.04 mmol), Boc-L-valine (0.89 g, 4.07 mmol) and silver oxide (0.47 g, 2.04 mmol) were mixed and heated in a pre-heated oil bath at 90° C. for 15 min. The reaction mixture was cooled to room temperature and triturated with EtOAc. The inorganic solids were separated by filtration, washed with EtOAc (3×s). The filtrate was washed with water (4×s), aqueous saturated NaHCO$_3$, dried, filtered and concentrated in vacuum. The crude was purified by flash column chromatography [silica gel 24 g, eluting with EtOAc in hexane 0-40%] to give (2S)-1-(((4-nitrophenoxy)carbonyl)oxy)ethyl 2-((tert-butoxycarbonyl)amino)-3-methylbutanoate (33a) (0.31 g, 35% yield). $^1$H NMR (300 MHz, DMSO-d$_6$) δ 8.39-8.29 (m, 2H), 7.61-7.49 (m, 2H), 7.32 (dd, J=11.9, 7.8 Hz, 1H), 6.79 (q, J=5.3 Hz, 1H), 3.93-3.80 (m, 1H), 2.12-1.91 (m, 1H), 1.61-1.50 (m, 3H), 1.38 (d, J=4.3 Hz, 9H), 0.96-0.83 (m, 6H); MS (ES+) 449.4 (M+Na)

Step-2: Preparation of 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinic acid (33b)

Compound (33b) was prepared from 3-(2-((4-carbamimidoylphenyl)carbamoyl)-5-methoxy-4-vinylphenyl)-6-((cyclopropylmethyl)carbamoyl)picolinic acid (23e) (0.5 g, 0.94 mmol) according to the procedure reported in step 4 of scheme 23. This gave after workup and purification by flash column chromatography [silica gel 24 g, eluting with DMA80 in DCM from 0 to 60%] 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinic acid (33b) (0.42 g, 56% yield) as a white solid. $^1$H NMR (300 MHz, DMSO-d$_6$) δ 12.42 (s, 1H, D$_2$O exchangeable), 9.18 (d, J=19.3 Hz, 2H, D$_2$O exchangeable), 8.77 (t, J=5.2 Hz, 1H, D$_2$O exchangeable), 7.99-7.75 (m, 4H), 7.66 (d, J=7.9 Hz, 1H), 7.60-7.51 (m, 2H), 7.24-7.13 (m, 2H, D$_2$O exchangeable), 7.00 (dd, J=17.8, 11.3 Hz, 1H), 6.86-6.79 (m, 1H), 6.77 (s, 1H, D$_2$O exchangeable), 5.96 (dd, J=17.8, 1.5 Hz, 1H), 5.38 (dd, J=11.3, 1.3 Hz, 1H), 3.89-3.73 (m, 4H), 3.18 (t, J=6.5 Hz, 2H), 2.05-1.85 (m, 1H), 1.45-1.30 (m, 12H), 1.14-0.98 (m, 1H), 0.93-0.77 (m, 6H), 0.53-0.38 (m, 2H), 0.32-0.20 (m, 2H); MS (ES+) 801.7 (M+1); (ES−) 799.8 (M−1).

Step-3: Preparation of 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinic acid (33c)

Compound (33c) was prepared from 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinic acid (33b) (0.3 g, 0.38 mmol) in dichloromethane (10 mL) using 2,2,2-trifluoroacetic acid (0.303 mL, 3.93 mmol) according to the procedure reported in step 4 of scheme 8. This gave after workup and purification by prep-HPLC [C18 column, eluting with ACN in water (containing 0.1% HCl) from 0-100%], followed by lyophilization 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinic acid (33c) (56 mg, 21% yield) as a white solid. $^1$H NMR (300 MHz, DMSO-d$_6$) δ 12.88 (brs, 1H, D$_2$O exchangeable), 10.65 (d, J=22.9 Hz, 1H, D$_2$O exchangeable), 9.85 (s, 1H, D$_2$O exchangeable), 9.28 (t, J=5.9 Hz, 1H, D$_2$O exchangeable), 8.70-8.34 (m, 4H, D$_2$O exchangeable), 8.24 (d, J=8.0 Hz, 1H), 8.02-7.93 (m, 2H), 7.92-7.80 (m, 2H), 7.80-7.65 (m, 2H), 7.11-6.90 (m, 3H), 6.05 (dd, J=17.8, 1.7 Hz, 1H), 5.44 (dd, J=11.3, 1.5 Hz, 1H), 4.04-3.94 (m, 1H), 3.88 (s, 3H), 3.24 (t, J=6.4 Hz, 2H), 2.24-2.10 (m, 1H), 1.56 (d, J=5.4 Hz, 3H), 1.17-1.03 (m, 1H), 1.03-0.85 (m, 6H), 0.54-0.42 (m, 2H), 0.34-0.23 (m, 2H); MS (ES+) 701.6 (M+1); (ES−) 699.7 (M−1); Analysis calculated for: $C_{36}H_{40}N_6O_9 \cdot 3.5H_2O \cdot 1.75HCl$: C, 52.25; H, 5.94; N, 10.15; Cl, 7.50. Found: C, 52.26; H, 5.75; N, 10.14; Cl, 7.65.

Scheme 34

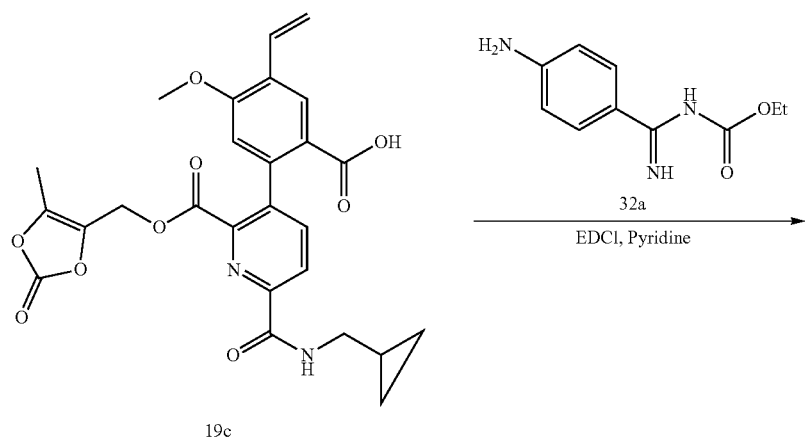

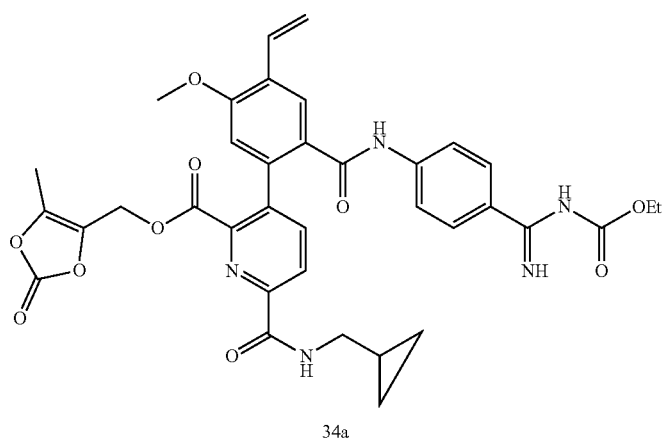

Preparation of (5-methyl-2-oxo-1,3-dioxol-4-yl) methyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (34a)

Compound (34a) was prepared from 2-(6-((cyclopropylmethyl)carbamoyl)-2-(((5-methyl-2-oxo-1,3-dioxol-4-yl)methoxy)carbonyl)pyridin-3-yl)-4-methoxy-5-vinylbenzoic acid (19c) (0.38 g, 0.75 mmol) using EDCI (0.22 g, 1.12 mmol) and ethyl ((4-aminophenyl)(imino)methyl)carbamate (32a) (0.19 g, 0.9 mmol) in DMF (20 mL) and Pyridine (1 mL) according to the procedure reported in step 4 of scheme 2. This gave after workup and purification by flash column chromatography [silica gel (12 g), eluting with EtOAc in hexane 0-100%) (5-methyl-2-oxo-1,3-dioxol-4-yl)methyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (34a) (0.13 mg, 25% yield) as an off white solid; $^1$H NMR (300 MHz, DMSO-$d_6$) δ 10.41 (s, 1H, $D_2O$ exchangeable), 9.05 (d, J=69.2 Hz, 2H, $D_2O$ exchangeable), 8.63 (t, J=6.1 Hz, 1H, $D_2O$ exchangeable), 8.20 (d, J=8.0 Hz, 1H), 8.05-7.83 (m, 4H), 7.63 (d, J=8.8 Hz, 2H), 7.08-6.98 (m, 1H), 6.97 (s, 1H), 6.04 (dd, J=17.8, 1.6 Hz, 1H), 5.43 (dd, J=11.1, 1.5 Hz, 1H), 4.97 (d, J=2.7 Hz, 2H), 4.04 (q, J=7.1 Hz, 2H), 3.85 (s, 3H), 3.28-3.13 (m, 2H), 2.01 (s, 3H), 1.21 (t, J=7.1 Hz, 3H), 1.14-0.99 (m, 1H), 0.50-0.39 (m, 2H), 0.32-0.22 (m, 2H); MS (ES$^+$) 720.5 (M+Na); (ES$^-$) 696.5 (M−1); Analysis calculated for $C_{36}H_{35}N_5O_{10}$: C, 61.97; H, 5.06; N, 10.04; found: C, 61.81; H, 5.41; N, 9.99.

Scheme 35

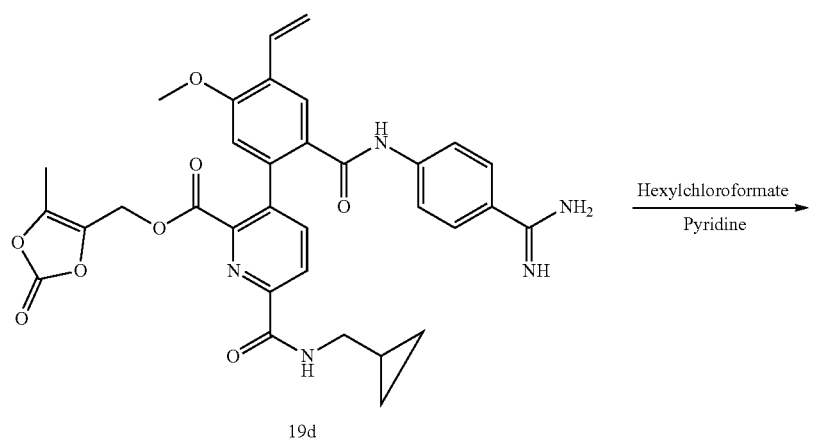

Preparation of (5-methyl-2-oxo-1,3-dioxol-4-yl) methyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate (35a)

Compound (35a) was prepared from (5-methyl-2-oxo-1,3-dioxol-4-yl)methyl 3-(2-((4-carbamimidoylphenyl)carbamoyl)-5-methoxy-4-vinylphenyl)-6-((cyclopropylmethyl)carbamoyl)picolinate (19d) (0.93 g, 1.5 mmol) according to the procedure reported in scheme 6. This gave after workup, purification by reverse phase flash column chromatography [silica gel 24 g, MeOH-EtOAc (9:1) in hexanes 0 to 100%] (5-methyl-2-oxo-1,3-dioxol-4-yl)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (35a) (0.07 g, 6% yield) as a white solid; $^1$H NMR (300 MHz, DMSO-$d_6$) δ 10.41 (s, 1H), 9.31-8.81 (m, 2H), 8.64 (t, J=6.1 Hz, 1H), 8.20 (d, J=8.0 Hz, 1H), 7.99 (d, J=8.0 Hz, 1H), 7.96-7.85 (m, 3H), 7.63 (d, J=8.7 Hz, 2H), 7.09-6.93 (m, 2H), 6.04 (dd, J=17.8, 1.6 Hz, 1H), 5.47-5.38 (m, 1H), 4.97 (d, J=3.1 Hz, 2H), 3.99 (t, J=6.7 Hz, 2H), 3.85 (s, 3H), 3.25-3.16 (m, 2H), 2.01 (s, 3H), 1.66-1.50 (m, 2H), 1.40-1.16 (m, 6H), 1.16-1.01 (m, 1H), 0.93-0.80 (m, 3H), 0.49-0.38 (m, 2H), 0.31-0.21 (m, 2H); MS (ES+) 754.7 (M+1).

Scheme 36

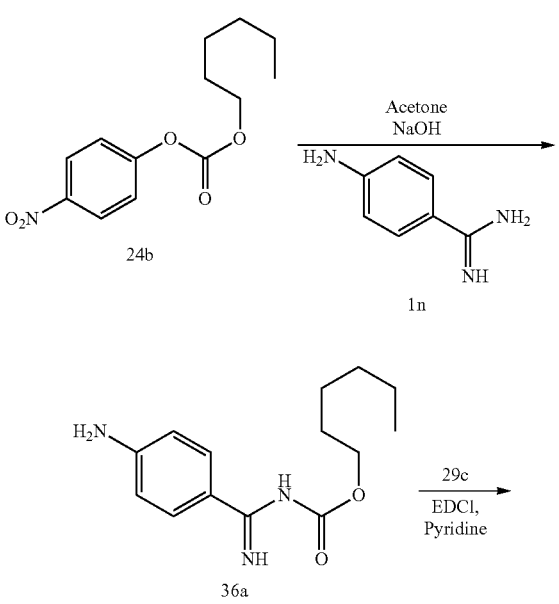

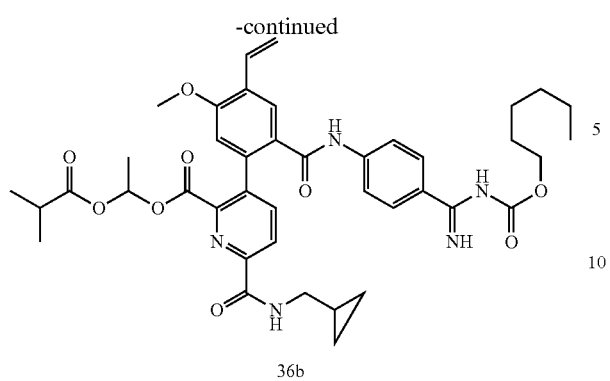

36b

Preparation of 1-(isobutyryloxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (36b)

Step-1: Preparation of hexyl ((4-aminophenyl)(imino)methyl)carbamate (36a)

Compound (36a) was prepared from 4-aminobenzimidamide dihydrochloride (1n) (5.98 g, 28.7 mmol) in acetone (225 mL), using 1 M aqueous NaOH solution (60.3 mL, 60.3 mmol) and hexyl (4-nitrophenyl) carbonate (24b) (10.75 g, 40.2 mmol) according to the procedure reported in step 4 of scheme 23. This gave after workup and purification by flash column chromatography (silica gel 80 g, eluting with 0-100% ethyl acetate in hexanes) hexyl ((4-aminophenyl)(imino)methyl)carbamate (36a) (5.24 g, 69% yield) as a semi solid; $^1$H NMR (300 MHz, DMSO-$d_6$) δ 9.15 (s, 1H), 8.61 (s, 1H), 7.80-7.69 (m, 2H), 6.58-6.52 (m, 2H), 5.85 (s, 2H), 3.97 (t, J=6.7 Hz, 2H), 1.65-1.50 (m, 2H), 1.39-1.21 (m, 6H), 0.94-0.79 (m, 3H); MS (ES+) 264.3 (M+1), 286.4 (M+23), 527.6 (2M+1), (ES−) 262.4 (M−1).

Step-2: Preparation of 1-(isobutyryloxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (36b)

Compound (36b) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (2.23 g, 4.37 mmol) using EDCI (1.01 g, 5.24 mmol) and hexyl ((4-aminophenyl)(imino)methyl)carbamate (36a) (1.15 g, 4.37 mmol) in Pyridine (2 mL) according to the procedure reported in step 4 of scheme 2. This gave after workup and purification by flash column chromatography [silica gel 120 g, eluting with EtOAc in hexane 0-100%) 1-(isobutyryloxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (36b) (1.7 g, 51.5% yield) as a white powder. $^1$H NMR (300 MHz, DMSO-$d_6$) δ 10.67-10.31 (m, 1H), 9.33-8.70 (m, 2H, D$_2$O exchangeable), 8.68-8.42 (m, 1H), 8.22 (d, J=8.0 Hz, 1H), 8.05-7.95 (m, 2H), 7.92 (d, J=8.5 Hz, 2H), 7.77-7.54 (m, 2H), 7.15-6.91 (m, 2H), 6.80-6.63 (m, 1H), 6.05 (d, J=17.8 Hz, 1H), 5.44 (d, J=11.5 Hz, 1H), 3.99 (t, J=6.6 Hz, 2H), 3.88 (s, 3H), 3.30-3.18 (m, 2H), 2.47-2.28 (m, 1H), 1.67-1.49 (m, 2H), 1.41-1.22 (m, 6H), 1.17 (d, J=5.2 Hz, 3H), 1.14-1.03 (m, 1H), 1.07-0.89 (m, 6H), 0.92-0.77 (m, 3H), 0.53-0.37 (m, 2H), 0.34-0.22 (m, 2H); Analysis calculated for $C_{41}H_{49}N_5O_9 \cdot 2.25H_2O$: C, 61.83; H, 6.77; N, 8.79. Found: C, 61.77; H, 6.60; N, 8.82.

Scheme 37

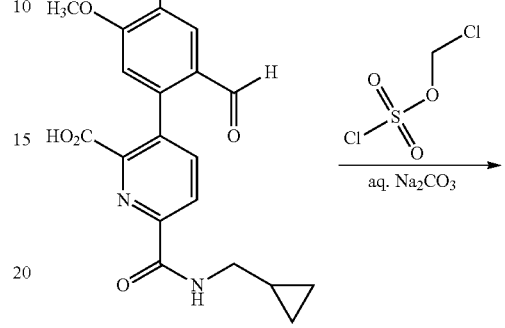

2a

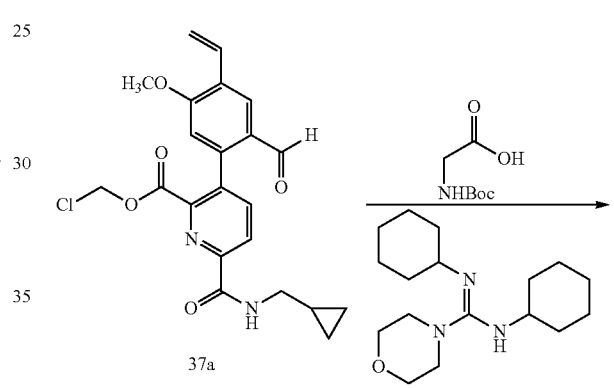

37a

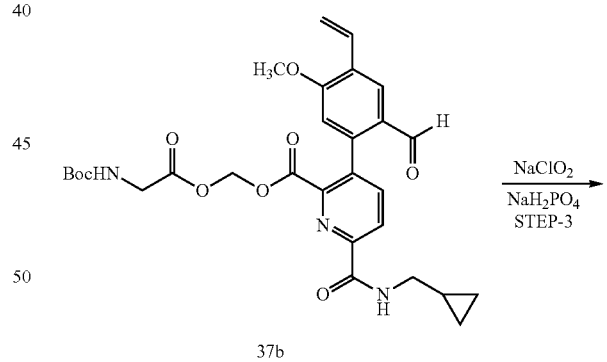

37b

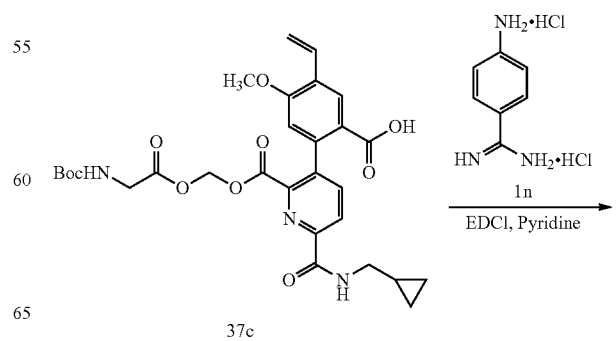

37c

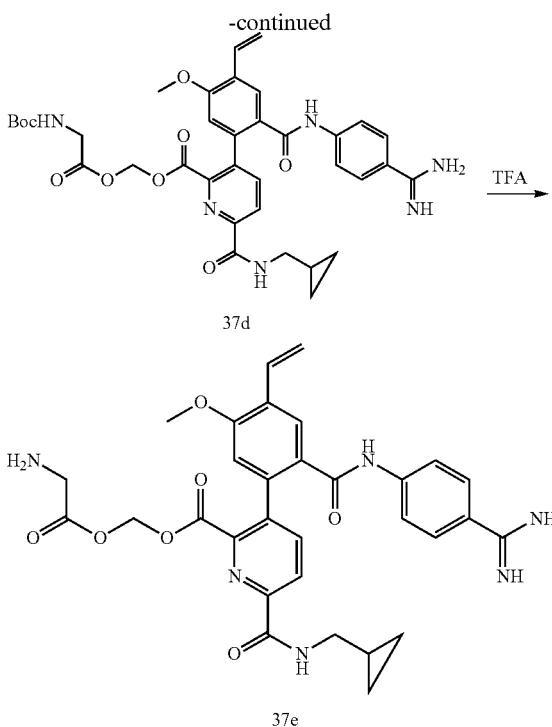

Preparation of (2-aminoacetoxy)methyl 3-(2-((4-carbamimidoylphenyl)carbamoyl)-5-methoxy-4-vinylphenyl)-6-((cyclopropylmethyl)carbamoyl) picolinate Hydrochloride (37e)

Step-1: Preparation of chloromethyl 6-((cyclopropylmethyl)carbamoyl)-3-(2-formyl-5-methoxy-4-vinylphenyl)picolinate (37a)

To a vigorously stirred solution of 6-(cyclopropylmethylcarbamoyl)-3-(2-formyl-5-methoxy-4-vinylphenyl)picolinic acid (2a) (2 g, 5.26 mmol) in EtOAc (40 mL), Water (40 mL) was added tetra butyl ammonium hydrogen sulfate (0.18 g, 0.53 mmol), chloromethyl sulfochloridate (0.64 mL, 6.31 mmol) and mixture was stirred at room temperature for 3 h. Layers were separated and aqueous layer was extracted with ethyl acetate (2×70 mL). The combined organic layer was washed with water (80 mL), brine, dried (MgSO$_4$), filtered and concentrated in vacuum to dryness to furnish crude product. The resultant crude product was suspended in hexane (80 mL) and sonicated for few minutes. The hexane layer was decanted and resultant solid was dried under vacuum to afford chloromethyl 6-((cyclopropylmethyl)carbamoyl)-3-(2-formyl-5-methoxy-4-vinylphenyl)picolinate (37a) (2.4 g, 106% yield) as a white solid; $^1$H NMR (300 MHz, DMSO-d$_6$) δ 9.71 (s, 1H), 8.75 (t, J=6.1 Hz, 1H), 8.29 (d, J=8.0 Hz, 1H), 8.21-8.05 (m, 2H), 7.09-6.94 (m, 2H), 6.01 (dd, J=17.8, 1.4 Hz, 1H), 5.94-5.86 (m, 2H), 5.44 (dd, J=11.3, 1.4 Hz, 1H), 3.90 (s, 3H), 3.24 (h, J=6.7 Hz, 2H), 1.17-1.03 (m, 1H), 0.52-0.40 (m, 2H), 0.34-0.22 (m, 2H).

Step-2: Preparation of (2-((tert-butoxycarbonyl)amino)acetoxy)methyl 6-((cyclopropylmethyl)carbamoyl)-3-(2-formyl-5-methoxy-4-vinylphenyl)picolinate (37b)

Compound (37b) was prepared according to the procedure reported in step 1 of scheme 8 from chloromethyl 6-((cyclopropylmethyl)carbamoyl)-3-(2-formyl-5-methoxy-4-vinylphenyl)picolinate (37a) in DMF (15 mL) using N,N'-Dicyclohexyl-4-morpholinecarboxamidine (1.07 g, 3.64 mmol) and Bocglycine (0.74 g, 4.20 mmol). This gave after workup and purification by flash column chromatography (silica gel 25 g, eluting with ethyl acetate/Hexanes, 0-100%) (2-((tert-butoxycarbonyl)amino)acetoxy)methyl 6-((cyclopropylmethyl)carbamoyl)-3-(2-formyl-5-methoxy-4-vinylphenyl)picolinate (37b) (0.42 g, 26% yield) as a colorless foam; $^1$H NMR (300 MHz, DMSO-d$_6$) δ 9.69 (s, 1H), 8.70 (t, J=6.0 Hz, 1H), 8.28 (d, J=8.0 Hz, 1H), 8.15 (s, 1H), 8.08 (d, J=8.0 Hz, 1H), 7.29 (t, J=6.1 Hz, 1H), 7.09-6.93 (m, 2H), 6.02 (dd, J=17.8, 1.4 Hz, 1H), 5.77 (q, J=6.1 Hz, 2H), 5.45 (d, J=11.3 Hz, 1H), 3.91 (s, 3H), 3.70-3.62 (m, 2H), 3.30-3.18 (m, 2H), 1.36 (s, 9H), 1.20-1.02 (m, 1H), 0.51-0.40 (m, 2H), 0.33-0.24 (m, 2H); MS (ES+) 590.5 (M+Na).

Step-3: Preparation of 2-(6-((cyclopropylmethyl)carbamoyl)-2-(10,10-dimethyl-5,8-dioxo-2,4,9-trioxa-7-azaundecan-1-oyl)pyridin-3-yl)-4-methoxy-5-vinylbenzoic acid (37c)

Oxidation of (2-((tert-butoxycarbonyl)amino)acetoxy)methyl 6-((cyclopropylmethyl)carbamoyl)-3-(2-formyl-5-methoxy-4-vinylphenyl)picolinate (37b) (0.4 g, 0.71 mmol) using the procedure as reported in step 11 of scheme 1 gave after workup 2-(6-((cyclopropylmethyl)carbamoyl)-2-(10,10-dimethyl-5,8-dioxo-2,4,9-trioxa-7-azaundecan-1-oyl)pyridin-3-yl)-4-methoxy-5-vinylbenzoic acid (37c) (0.4 g, 97% yield) as a light yellow solid; $^1$H NMR (300 MHz, DMSO-d$_6$) δ 12.57 (s, 1H), 8.63 (t, J=6.1 Hz, 1H), 8.23 (d, J=8.0 Hz, 1H), 8.12 (s, 1H), 7.97 (d, J=8.0 Hz, 1H), 7.25 (t, J=6.0 Hz, 1H), 6.98 (dd, J=17.8, 11.3 Hz, 1H), 6.89 (s, 1H), 5.98-5.86 (m, 1H), 5.83-5.71 (m, 2H), 5.39 (dd, J=11.3, 1.4 Hz, 1H), 3.86 (s, 3H), 3.68 (d, J=6.1 Hz, 2H), 3.24 (q, J=7.5, 6.3 Hz, 2H), 1.36 (s, 9H), 1.18-0.99 (m, 1H), 0.52-0.41 (m, 2H), 0.33-0.24 (m, 2H); MS (ES+) 606.5 (M+Na), MS (ES−) 582.6 (M−1).

Step-4: Preparation of (2-((tert-butoxycarbonyl)amino)acetoxy)methyl 3-(2-((4-carbamimidoylphenyl)carbamoyl)-5-methoxy-4-vinylphenyl)-6-((cyclopropylmethyl)carbamoyl)picolinate (37d)

Compound (37d) was prepared from 2-(6-((cyclopropylmethyl)carbamoyl)-2-(10,10-dimethyl-5,8-dioxo-2,4,9-trioxa-7-azaundecan-1-oyl)pyridin-3-yl)-4-methoxy-5-vinylbenzoic acid (37c) (0.58 mg, 1.00 mmol) using EDCI (0.29 g, 1.5 mmol) and 4-aminobenzimidamide dihydrochloride (1n) (0.26 g, 1.25 mmol) in Pyridine (5 mL) according to the procedure reported in step 4 of scheme 2. This gave after workup (2-((tert-butoxycarbonyl)amino)acetoxy)methyl 3-(2-((4-carbamimidoylphenyl)carbamoyl)-5-methoxy-4-vinylphenyl)-6-((cyclopropylmethyl)carbamoyl)picolinate (37d) (0.7 g, 100% yield) which was used in next step without further purification. MS (ES+) 701.6 (M+1), (ES−) 735.7 (M+Cl).

Step-5: Preparation of (2-aminoacetoxy)methyl 3-(2-((4-carbamimidoylphenyl)carbamoyl)-5-methoxy-4-vinylphenyl)-6-((cyclopropylmethyl)carbamoyl)picolinate Hydrochloride (37e)

Compound (37e) was prepared from (2-((tert-butoxycarbonyl)amino)acetoxy)methyl 3-(2-((4-carbamimidoylphenyl)carbamoyl)-5-methoxy-4-vinylphenyl)-6-((cyclopropylmethyl)carbamoyl)picolinate (37d) (0.7 g, 1.0 mmol) in dichloromethane (20 mL) using 2,2,2-trifluoroacetic acid (1.54 mL, 20.00 mmol) according to the procedure reported in Step-4 of scheme 8. This gave after workup and purification by flash column chromatography (C18, 100 g) eluting with 0.1% HCl and acetonitrile followed by lyophilization (2-aminoacetoxy)methyl 3-(2-((4-carbamimidoylphenyl)carbamoyl)-5-methoxy-4-vinylphenyl)-6-((cyclopropylmethyl)carbamoyl)picolinate Hydrochloride (37e) (65 mg, 10% yield) as a white solid. ¹H NMR (300 MHz, DMSO-d₆) δ 10.74 (s, 1H, D₂O exchangeable), 9.33-9.07 (m, 2H, D₂O exchangeable), 8.96-8.76 (m, 3H, D₂O exchangeable), 8.61 (s, 1H), 8.24 (dd, J=8.1, 3.8 Hz, 1H), 8.08-7.97 (m, 2H), 7.77 (d, J=3.8 Hz, 4H), 7.10-6.93 (m, 2H), 6.08 (d, J=18.0 Hz, 1H), 5.84 (s, 2H), 5.45 (d, J=11.4 Hz, 1H), 3.94-3.86 (m, 3H), 3.79-3.70 (m, 2H), 3.22 (s, 4H), 1.16-0.99 (m, 1H), 0.51-0.40 (m, 2H), 0.33-0.22 (m, 2H); MS (ES+) 601.5 (M+1); (ES−) 635.6 (M+Cl); Analysis calculated for: $C_{31}H_{32}N_6O_7 \cdot 2.75HCl \cdot 1.25H_2O$: C, 51.47; H, 5.19; N, 11.62; found: C, 51.20; H, 5.44; N, 11.65.

Scheme 38

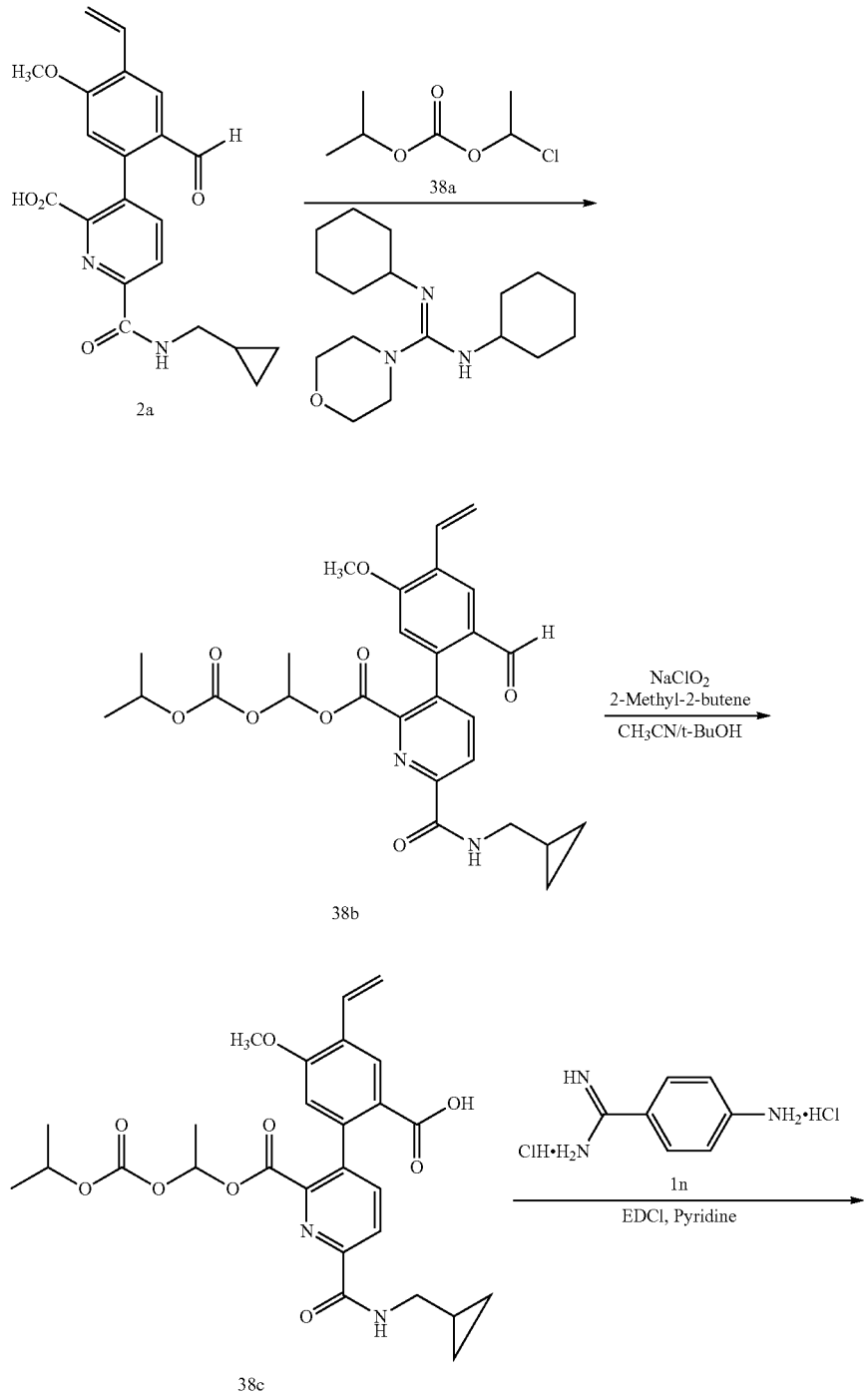

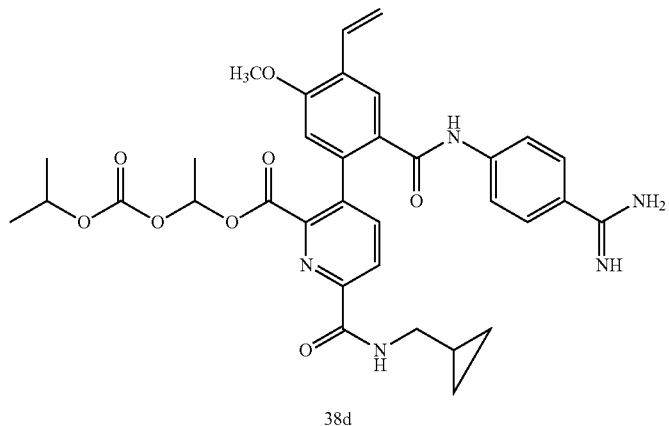

38d

Preparation of 1-((isopropoxycarbonyl)oxy)ethyl 3-(2-((4-carbamimidoylphenyl)carbamoyl)-5-methoxy-4-vinylphenyl)-6-((cyclopropylmethyl)carbamoyl)picolinate (38d)

Step-1: Preparation of 1-((isopropoxycarbonyl)oxy)ethyl 6-((cyclopropylmethyl)carbamoyl)-3-(2-formyl-5-methoxy-4-vinylphenyl)picolinate (38b)

Compound (38b) was prepared according to the procedure reported in step 1 of scheme 8 from 6-(Cyclopropylmethylcarbamoyl)-3-(2-formyl-5-methoxy-4-vinylphenyl)picolinic acid (2a) (1.33 g, 3.5 mmol) in DMF (15 mL) using N,N'-Dicyclohexyl-4-morpholinecarboxamidine (1.28 g, 4.38 mmol) and 1-chloroethyl isopropyl carbonate (38a) (0.875 g, 5.25 mmol). This gave after workup and purification by flash column chromatography (silica gel 40 g, eluting with ethyl acetate/Hexanes, 0-100%) 1-((isopropoxycarbonyl)oxy)ethyl 6-((cyclopropylmethyl)carbamoyl)-3-(2-formyl-5-methoxy-4-vinylphenyl)picolinate (38b) (1.23 g, 69% yield) as a yellow solid; $^1$H NMR (300 MHz, DMSO-$d_6$) δ 9.69 (d, J=3.6 Hz, 1H), 8.69 (dt, J=6.3, 3.1 Hz, 1H), 8.27 (dd, J=8.0, 2.5 Hz, 1H), 8.14 (s, 1H), 8.08 (d, J=8.0 Hz, 1H), 7.12-6.89 (m, 2H), 6.72-6.51 (m, 1H), 6.11-5.94 (m, 1H), 5.44 (dd, J=11.2, 1.3 Hz, 1H), 4.69 (h, J=6.2 Hz, 1H), 3.90 (d, J=1.5 Hz, 3H), 3.31-3.16 (m, 2H), 1.32-0.96 (m, 10H), 0.54-0.39 (m, 2H), 0.35-0.20 (m, 2H); MS (ES+): 511.5 (M+1), 533.5 (M+Na); MS (ES−): 509.5 (M−1).

Step-2: Preparation of 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c)

Oxidation of 1-((isopropoxycarbonyl)oxy)ethyl 6-((cyclopropylmethyl)carbamoyl)-3-(2-formyl-5-methoxy-4-vinylphenyl)picolinate (38b) (1.15 g, 2.26 mmol) using the procedure as reported in step 11 of scheme 1 gave after workup 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (1.13 g, 95% yield) as a white solid; $^1$H NMR (300 MHz, DMSO-$d_6$) δ 12.60 (s, 1H), 8.73-8.55 (m, 1H), 8.22 (d, J=8.1 Hz, 1H), 8.12 (s, 1H), 7.96 (d, J=8.1 Hz, 1H), 6.98 (dd, J=17.7, 11.3 Hz, 1H), 6.88 (d, J=10.2 Hz, 1H), 6.72-6.53 (m, 1H), 5.91 (dd, J=17.8, 1.5 Hz, 1H), 5.39 (dd, J=11.3, 1.4 Hz, 1H), 4.84-4.59 (m, 1H), 3.86 (s, 3H), 3.33-3.13 (m, 2H), 1.31-1.08 (m, 10H), 0.51-0.42 (m, 2H), 0.34-0.24 (m, 2H); MS (ES+): 527.5 (M+1), 549.4 (M+Na); MS (ES−): 525.5 (M−1).

Step-3: Preparation of 1-((isopropoxycarbonyl)oxy)ethyl 3-(2-((4-carbamimidoylphenyl)carbamoyl)-5-methoxy-4-vinylphenyl)-6-((cyclopropylmethyl)carbamoyl)picolinate (38d)

Compound (38d) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.7 g, 1.33 mmol) using EDCI (0.38 g, 2.0 mmol) and 4-aminobenzimidamide dihydrochloride (1n) (0.42 g, 2.00 mmol) in DMF (12 mL) and Pyridine (4 mL) according to the procedure reported in step 4 of scheme 2. This gave after workup and purification by flash column chromatography (silica gel, 40 g, eluting with methanol in chloroform from 0 to 100%) 1-((isopropoxycarbonyl)oxy)ethyl 3-(2-((4-carbamimidoylphenyl)carbamoyl)-5-methoxy-4-vinylphenyl)-6-((cyclopropylmethyl)carbamoyl)picolinate (38d) (0.33 g, 39.0% yield) as an off-white solid; $^1$H NMR (300 MHz, DMSO-$d_6$) δ 10.97-10.50 (bs, 1H, $D_2O$ exchangeable), 9.22 (bs, 2H, $D_2O$ exchangeable), 8.96 (bs, 2H, $D_2O$ exchangeable), 8.75-8.44 (bs, 1H, $D_2O$ exchangeable), 8.22 (d, J=8.0 Hz, 1H), 8.08-7.93 (m, 2H), 7.78 (d, J=8.1 Hz, 4H), 7.04 (dd, J=17.9, 11.2 Hz, 2H), 6.63 (q, J=5.3 Hz, 1H), 6.07 (dd, J=17.9, 1.5 Hz, 1H), 5.45 (d, J=11.4 Hz, 1H), 4.70 (s, 1H), 3.89 (s, 3H), 3.32-3.16 (m, 2H), 1.35-0.91 (m, 10H), 0.57-0.37 (m, 2H), 0.34-0.20 (m, 2H). MS (ES+): 644.6 (M+1); MS (ES−): 678.6 (M+Cl); Analysis calculated for: $C_{34}H_{37}N_5O_8 \cdot 1.75$ HCl·0.75$H_2O$: C, 56.64; H, 5.63; Cl, 8.61; N, 9.71. Found: C, 56.62; H, 5.49; Cl, 8.77; N, 9.80.

Scheme 39

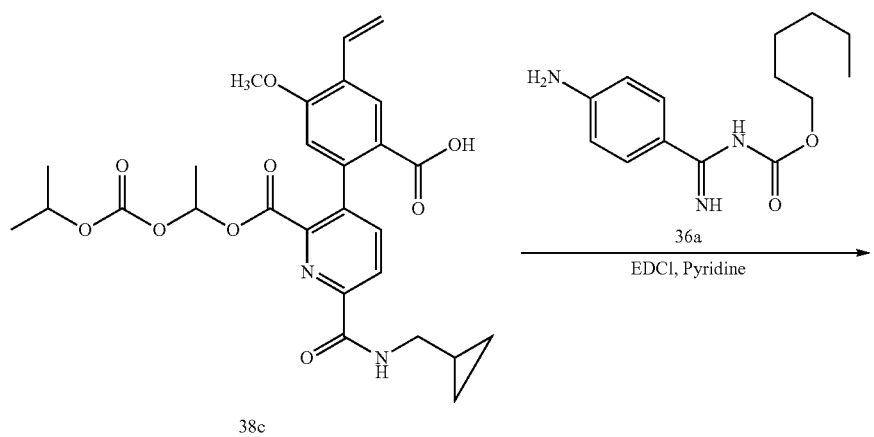

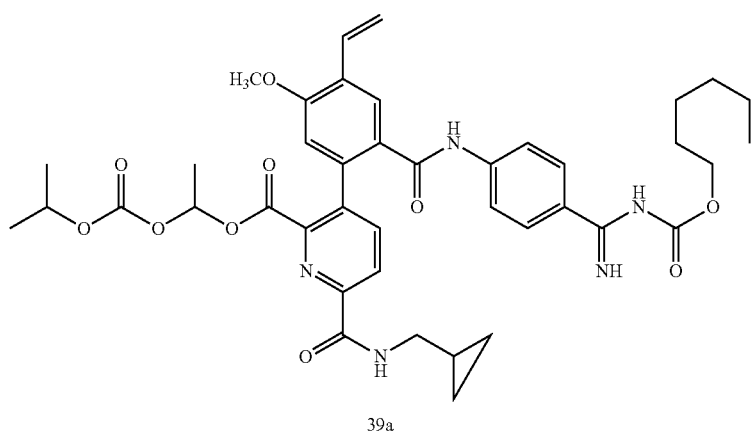

Preparation of 1-((isopropoxycarbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (39a)

Compound (39a) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.4 g, 0.76 mmol) using EDCI (0.22 g, 1.14 mmol) and hexyl (4-aminophenyl)(imino)methylcarbamate (36a) (0.3 g, 1.14 mmol) in DMF (12 mL) and Pyridine (4 mL) according to the procedure reported in step 4 of scheme 2. This gave after workup and purification by flash column chromatography (First column: silica gel, 40 g, eluting with methanol in chloroform from 0 to 100%; second column: silica gel, 24 g, eluting with ethyl acetate in hexanes from 0 to 100%) 1-((isopropoxycarbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (39a) (0.15 g, 26% yield) as a white solid; $^1$H NMR (300 MHz, DMSO-$d_6$) δ 10.64-10.38 (2bs, 1H, $D_2O$ exchangeable), 8.95 (s, 3H, $D_2O$ exchangeable), 8.71-8.49 (m, 1H), 8.22 (d, J=8.1 Hz, 1H), 8.04-7.97 (m, 2H), 7.96-7.89 (m, 2H), 7.78-7.56 (m, 2H), 7.15-6.93 (m, 2H), 6.63 (q, J=5.3 Hz, 1H), 6.05 (dd, J=17.8, 1.6 Hz, 1H), 5.54-5.32 (m, 1H), 4.87-4.55 (m, 1H), 3.99 (t, J=6.7 Hz, 2H), 3.89 (s, 3H), 3.26-3.20 (m, 2H), 1.57 (s, 2H), 1.41-1.23 (m, 6H), 1.23-0.93 (m, 10H), 0.94-0.78 (m, 3H), 0.50-0.38 (m, 2H), 0.35-0.21 (m, 2H); MS (ES+): 772.6 (M+1), 794.6 (M+Na); (ES−): 806.8 (M+Cl); Analysis calculated for $C_{41}H_{49}N_5O_{10}$·5$H_2O$: C, 63.06; H, 6.45; N, 8.97. Found: C, 62.93; H, 6.43; N, 9.21.

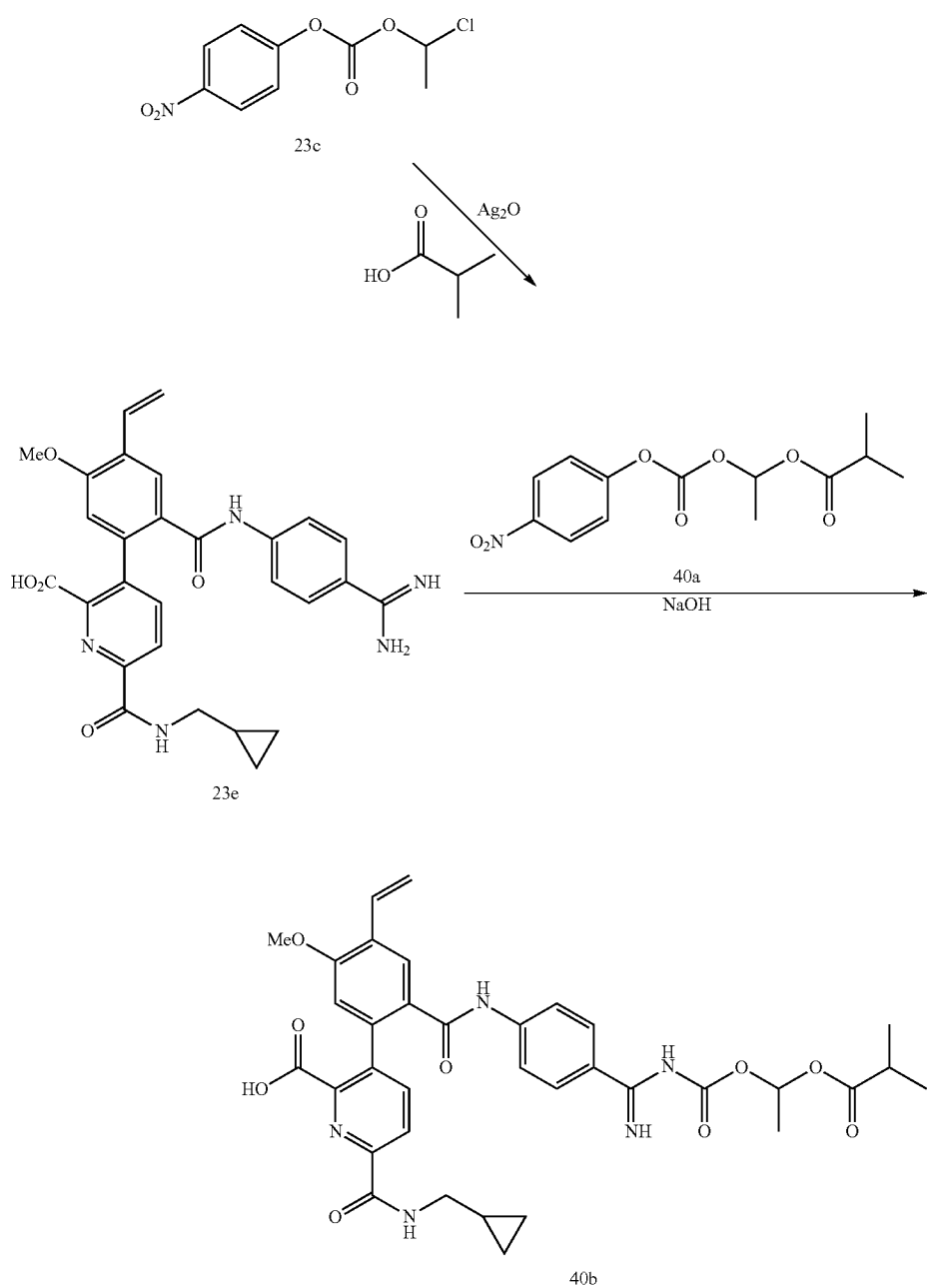

Preparation of 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinic acid (40a)

Step-1: Preparation of 1-(((4-nitrophenoxy)carbonyl)oxy)ethyl isobutyrate (40a)

Compound (40a) was prepared from 1-chloroethyl 4-nitrophenyl carbonate (23c) (10 g, 40.7 mmol), isobutyric acid (11.33 mL, 122 mmol) and silver oxide (9.43 g, 40.7 mmol) according to the procedure reported in step 1 of scheme 33. This gave after workup and purification by flash column chromatography [silica gel 120 g, eluting with EtOAc in hexane 0-100%] 1-(((4-nitrophenoxy)carbonyl)oxy)ethyl isobutyrate (40a) (6.16 g, 51% yield) as a clear oil; $^1$H NMR (300 MHz, DMSO-d$_6$) δ 8.40-8.26 (m, 2H), 7.62-7.51 (m, 2H), 6.74 (q, J=5.4 Hz, 1H), 2.61 (dt, J=14.0, 7.0 Hz, 1H), 1.55 (d, J=5.4 Hz, 3H), 1.10 (dd, J=6.9, 0.7 Hz, 6H).

Step-2: Preparation of 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinic acid (40a)

Compound (40a) was prepared from 3-(2-((4-carbamimidoylphenyl)carbamoyl)-5-methoxy-4-vinylphenyl)-6-((cyclopropylmethyl)carbamoyl)picolinic acid (23e) (3.0 g, 5.64 mmol) according to the procedure reported in step 4 of scheme 23. This gave after workup and purification by flash column chromatography [silica gel 80 g, eluting with DMA80 in DCM from 0 to 100%] 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinic acid (40a) (0.40 g, 11% yield) as a white solid; $^1$H NMR (300 MHz, DMSO-d$_6$) δ 12.47 (s, 1H, D$_2$O exchangeable), 9.23 (s, 1H), 9.13 (s, 1H, D$_2$O exchangeable), 8.77 (s, 1H, D$_2$O exchangeable), 7.92 (d, J=7.9 Hz, 1H), 7.88-7.78 (m, 3H), 7.65 (d, J=7.8 Hz, 1H), 7.56 (d, J=8.6 Hz, 2H), 7.23-7.05 (m, 1H, D$_2$O exchangeable), 7.01 (dd, J=17.7, 11.3 Hz, 1H), 6.84-6.65 (m, 2H), 5.96 (d, J=17.8 Hz, 1H), 5.38 (d, J=11.4 Hz, 1H), 3.82 (s, 3H), 3.18 (t, J=6.6 Hz, 2H), 2.56-2.45 (m, 1H), 1.42 (d, J=5.4 Hz, 3H), 1.14-0.95 (m, 7H), 0.50-0.37 (m, 2H), 0.30-0.18 (m, 2H); MS (ES+) 672.4 (M+1) 694.4, (ES−) 670.5 (M−1).

vinylphenyl)-6-((cyclopropylmethyl)carbamoyl)picolinate (22d) (0.41 g, 0.77 mmol) using EDCI (0.22 g, 1.16 mmol) and hexyl (4-aminophenyl)(imino)methylcarbamate (36a) (0.31 g, 1.16 mmol) in DMF (12 mL) and Pyridine (4 mL) according to the procedure reported in step 4 of scheme 2. This gave after workup and purification by flash column chromatography ((silica gel, 40 g, eluting with ethyl acetate in hexanes from 0-100%) 1-((tert-butoxycarbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (41a) (0.19 g, 31% yield) as a white solid; $^1$H NMR (300 MHz, DMSO-d$_6$) δ 10.70-10.34 (2bs, 1H, D$_2$O exchangeable), 9.13 (bs, 1H, D$_2$O exchangeable), 8.94 (bs, 1H, D$_2$O exchangeable), 8.68-8.37 (m, 1H), 8.23 (d, J=8.0 Hz, 1H), 8.09-7.83 (m, 4H), 7.81-7.53 (m, 3H),

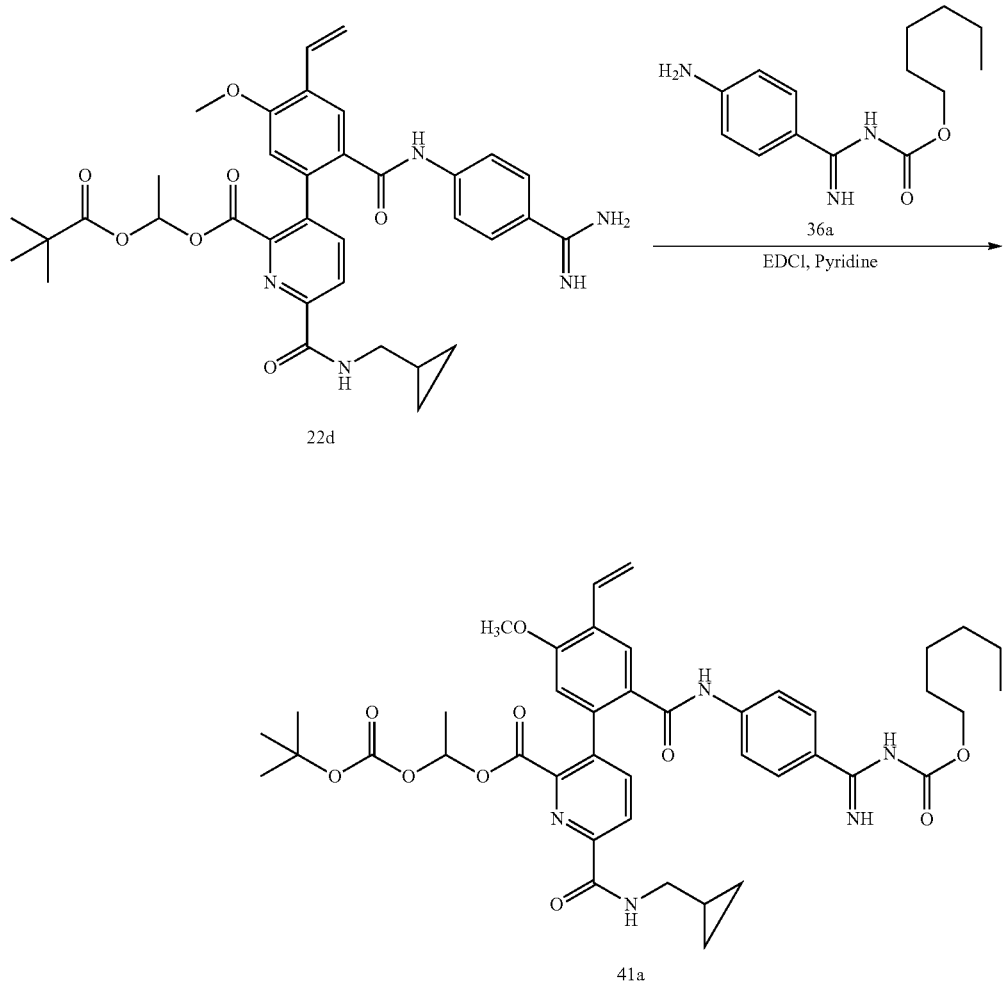

Preparation of 1-((tert-butoxycarbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (41a)

Compound (41a) was prepared from 1-(pivaloyloxy)ethyl 3-(2-((4-carbamimidoylphenyl)carbamoyl)-5-methoxy-4-

7.14-6.91 (m, 2H), 6.78-6.64 (m, 1H), 6.05 (dd, J=17.7, 1.5 Hz, 1H), 5.44 (dd, J=11.2, 1.5 Hz, 1H), 3.99 (t, J=6.7 Hz, 2H), 3.88 (s, 3H), 3.31-3.17 (m, 2H), 1.68-1.49 (m, 2H), 1.42-0.74 (m, 22H), 0.52-0.40 (m, 2H), 0.34-0.21 (m, 2H); MS (ES+): 770.7 (M+1); MS (ES−): 768.7 (M−1); Analysis calculated for C$_{42}$H$_{51}$N$_5$O$_9$·0.25H$_2$O: C, 65.14; H, 6.70; N, 9.04. Found: C, 65.02; H, 6.78; N, 9.09.

Scheme 42

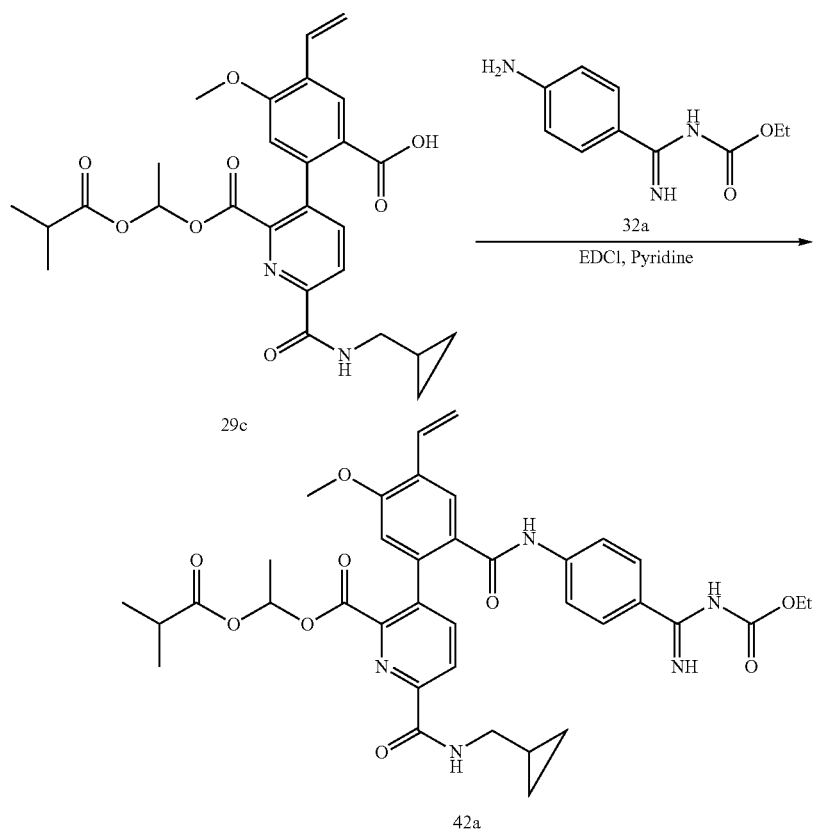

Preparation of 1-(isobutyryloxy)ethyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (42a)

Compound (42a) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.2 g, 0.39 mmol) using EDCI (0.083 g, 0.43 mmol) and ethyl ((4-aminophenyl)(imino)methyl)carbamate (32a) (0.095 g, 0.39 mmol) in DMF (2 mL) and Pyridine (1 mL) according to the procedure reported in step 4 of scheme 2. This gave after workup and purification by flash column chromatography ((silica gel 4 g, eluting with ethyl acetate in DCM from 0-60%) 1-(isobutyryloxy)ethyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (42a) (0.045 g, 16% yield) as a white solid; $^1$H NMR (300 MHz, DMSO-$d_6$) δ 10.60-10.40 (m, 1H), 9.28-8.78 (m, 2H), 8.68-8.44 (m, 1H), 8.22 (d, J=8.1 Hz, 1H), 8.06-7.86 (m, 3H), 7.75-7.56 (m, 3H), 7.12-6.95 (m, 2H), 6.73 (brs, 1H), 6.05 (dd, J=17.7, 1.5 Hz, 1H), 5.50-5.38 (m, 1H), 4.04 (q, J=7.1 Hz, 2H), 3.88 (s, 3H), 3.30-3.16 (m, 2H), 2.47-2.30 (m, 1H), 1.32-0.76 (m, 13H), 0.49-0.40 (m, 2H), 0.31-0.24 (m, 2H); MS (ES+) 700.5 (M+1), 722.5 (M+Na), MS (ES−): 698.5 (M−1).

Scheme 43

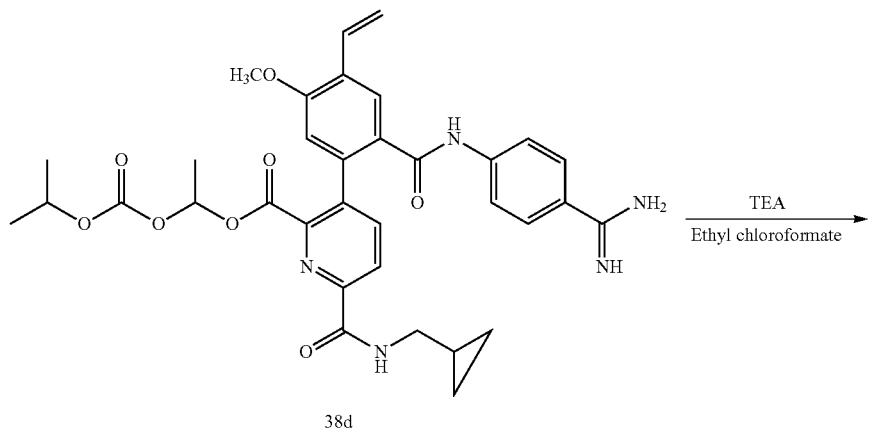

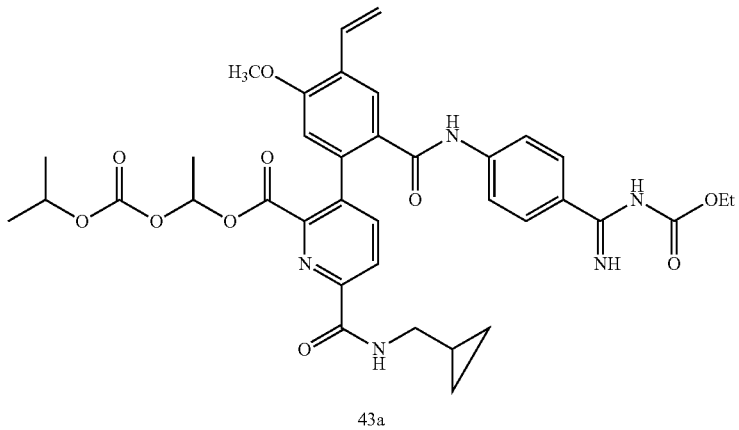

43a

Preparation of 1-((isopropoxycarbonyl)oxy)ethyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (43a)

Compound (43a) was prepared from 1-((isopropoxycarbonyl)oxy)ethyl 3-(2-((4-carbamimidoylphenyl)carbamoyl)-5-methoxy-4-vinylphenyl)-6-((cyclopropylmethyl)carbamoyl)picolinate (38d) (3.0 g, 4.66 mmol) according to the procedure reported in scheme 6. This gave after workup, purification by flash column chromatography [silica gel 80 g, eluting with ethyl acetate in hexanes from 0-100%; Second column: EZ-PREP, C-18 column, 30 g, eluting with 0.1% aqueous HCl in water and acetonitrile from 0-50%], followed by lyophilization 1-((isopropoxycarbonyl)oxy) ethyl 6-((cyclopropylmethyl)carbamoyl)-3-(2-((4-(N-(ethoxycarbonyl)carbamimidoyl)phenyl)carbamoyl)-5-methoxy-4-vinylphenyl)picolinate (43a) (0.42 g, 13% yield) as a white solid; $^1$H NMR (300 MHz, DMSO-d$_6$) δ 12.34 & 11.07 (2bs, 1H, D$_2$O exchangeable), 10.81 & 10.74 (2bs, 1H), 10.34 (bs, 1H, D$_2$O exchangeable), 8.65 & 8.56 (2bs, 1H), 8.22 (d, J=8.0 Hz, 1H), 8.10-7.93 (m, 2H), 7.89-7.65 (m, 5H), 7.16-6.87 (m, 2H), 6.63 (q, J=5.3 Hz, 1H), 6.08 (dd, J=17.7, 1.6 Hz, 1H), 5.58-5.30 (m, 1H), 4.87-4.55 (m, 1H), 4.31 (q, J=7.1 Hz, 2H), 3.89 (s, 3H), 3.31-3.14 (m, 2H), 1.31 (t, J=7.1 Hz, 3H), 1.16 (h, J=7.1 Hz, 10H), 0.54-0.37 (m, 2H), 0.35-0.19 (m, 2H); MS (ES+): 716.7 (M+1); MS (ES−): 750.7 (M+Cl); Analysis calculated for $C_{37}H_{41}N_5O_{10}·1.75H_2O·1.0HCl$: C, 56.70; H, 5.85; N, 8.94; found: C, 56.94; H, 5.66; N, 9.08.

Scheme 44

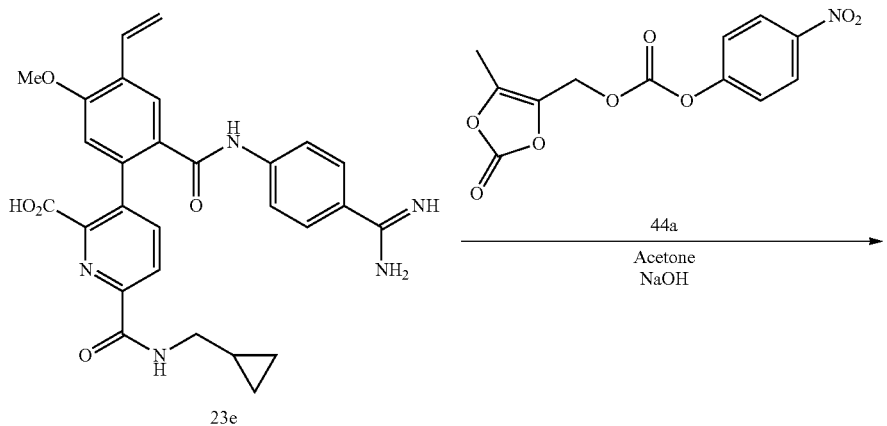

23e

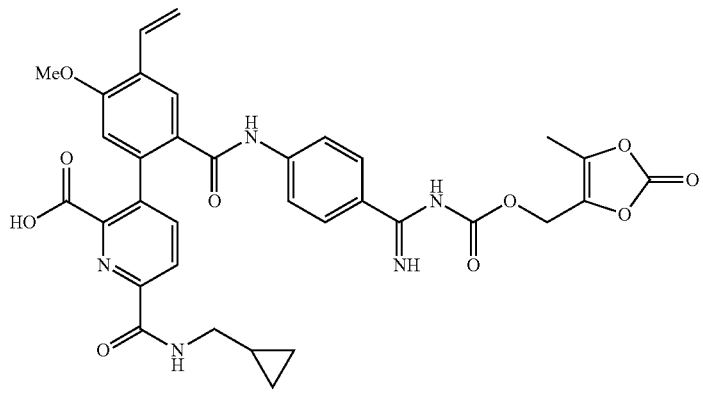

44b

Preparation of 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinic acid (44b)

Compound (44b) was prepared according to the procedure reported in step 4 of scheme 23 from 3-(2-((4-carbamimidoylphenyl)carbamoyl)-5-methoxy-4-vinylphenyl)-6-((cyclopropylmethyl)carbamoyl)picolinic acid (23e) (0.28 g, 0.52 mmol) in acetone/water (13 mL, 12:1), using NaOH (46 mg, 1.15 mmol) and (5-methyl-2-oxo-1,3-dioxol-4-yl) methyl (4-nitrophenyl) carbonate (44a) (0.385 g, 1.30 mmol, prepared according to procedure reported by Rahmathullah, Syed M. et al; in Journal of Medicinal Chemistry, 42(19), 3994-4000; 1999). This gave after workup and purification by flash column chromatography [C18 column, eluting with CH$_3$CN in water (containing 0.1% HCl) from 0-100%] followed by lyophilization 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinic acid (44b) (85 mg, 24% yield) as a white solid; $^1$H NMR (300 MHz, DMSO-d$_6$) δ 12.88 (s, 1H, D$_2$O exchangeable), 10.72 (s, 1H, D$_2$O exchangeable), 10.21 (s, 1H, D$_2$O exchangeable), 9.27 (t, J=6.0 Hz, 1H, D$_2$O exchangeable), 8.24 (d, J=8.0 Hz, 1H), 8.02-7.93 (m, 2H), 7.84-7.70 (m, 4H), 7.10-6.94 (m, 2H), 6.04 (dd, J=17.7, 1.6 Hz, 1H), 5.44 (dd, J=11.2, 1.6 Hz, 1H), 5.19 (s, 2H), 5.06 (s, 1H), 3.88 (s, 3H), 3.24 (t, J=6.4 Hz, 2H), 2.22 (s, 3H), 1.16-1.00 (m, 1H), 0.55-0.41 (m, 2H), 0.34-0.22 (m, 2H); MS (ES+) 670.5 (M+1); (ES−) 668.6 (M−1); Analysis Calculated for C$_{34}$H$_{31}$N$_5$O$_{10}$·HCl·2.5H$_2$O: C, 54.37; H, 4.96; N, 9.32; found: C, 54.52; H, 4.74; N, 8.97.

Scheme 45

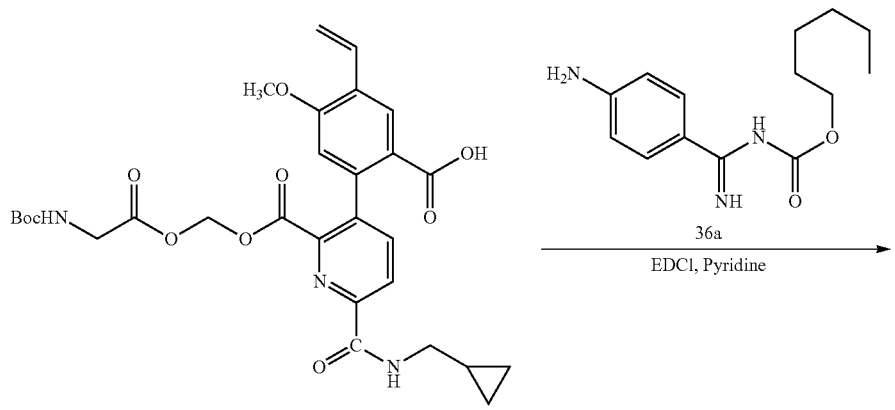

37c

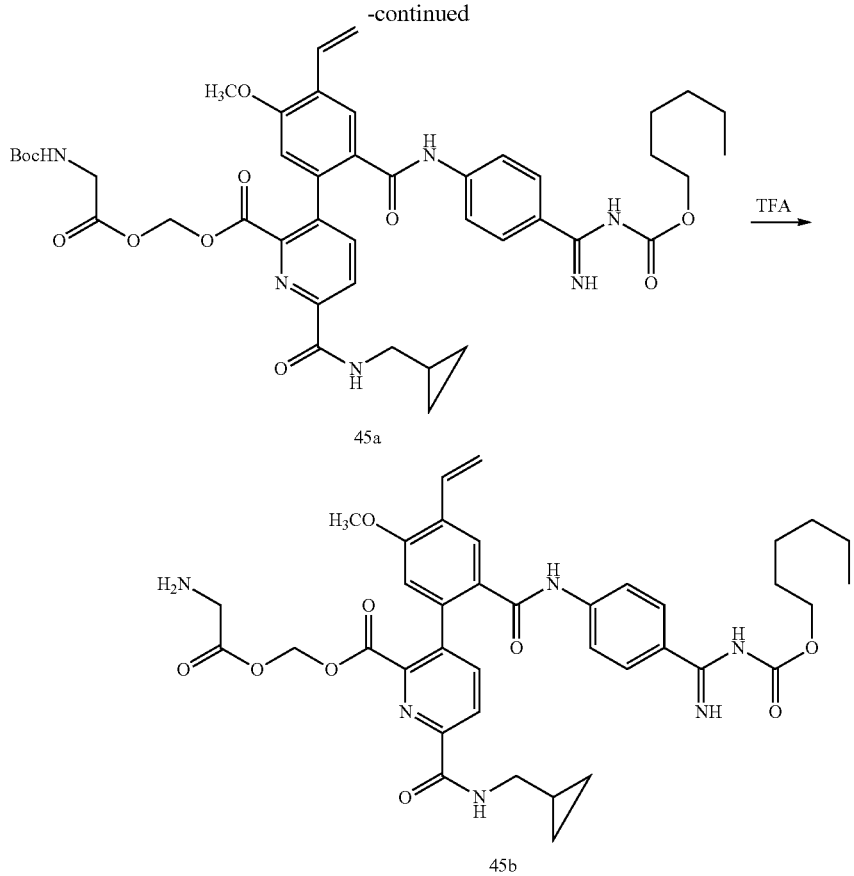

45a

45b

Preparation of (2-aminoacetoxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (45b)

Step-1: Preparation of (2-((tert-butoxycarbonyl)amino)acetoxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (45a)

Compound (45a) was prepared from 2-(6-((cyclopropylmethyl)carbamoyl)-2-(10,10-dimethyl-5,8-dioxo-2,4,9-trioxa-7-azaundecan-1-oyl)pyridin-3-yl)-4-methoxy-5-vinylbenzoic acid (37c) (0.3 g, 0.51 mmol) using EDCI (0.12 g, 0.62 mmol) and hexyl (4-aminophenyl)(imino)methylcarbamate (36a) (0.15 g, 0.57 mmol) in Pyridine (1 mL) according to the procedure reported in step 4 of scheme 2. This gave after workup and purification by flash column chromatography (silica gel, 12 g, eluting with methanol/EtOAc (9:1) in hexanes from 0 to 100%) (2-((tert-butoxycarbonyl)amino)acetoxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (45a) (0.23 g, 53% yield) as a white solid; $^1$H NMR (300 MHz, DMSO-$d_6$) δ 10.63 (s, 1H), 8.60 (t, J=6.1 Hz, 1H), 8.23 (d, J=8.0 Hz, 1H), 8.03 (d, J=8.0 Hz, 1H), 7.98 (s, 1H), 7.83 (d, J=8.6 Hz, 2H), 7.72 (d, J=8.7 Hz, 2H), 7.26 (t, J=6.1 Hz, 1H), 7.11-6.95 (m, 2H), 6.13-6.00 (m, 1H), 5.85-5.64 (m, 2H), 5.49-5.39 (m, 1H), 4.23-4.07 (m, 2H), 3.89 (s, 3H), 3.62 (d, J=6.0 Hz, 2H), 3.29-3.14 (m, 2H), 1.73-1.55 (m, 2H), 1.46-0.76 (m, 19H), 0.51-0.40 (m, 2H), 0.32-0.22 (m, 2H); MS (ES+) 829.8 (M+1), MS (ES−) 863.8 (M+Cl).

Step-2: Preparation of (2-aminoacetoxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (45b)

Compound (45b) was prepared from (2-((tert-butoxycarbonyl)amino)acetoxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (45a) (0.21 g, 0.25 mmol) in dichloromethane (4 mL) using 2,2,2-trifluoroacetic acid (0.4 mL, 0.58 mmol) according to the procedure reported in Step-4 of scheme 8. This gave after workup and purification by reverse phase preparative flash column chromatography (C18, 26 g, eluting with 0.1% aqueous HCl and acetonitrile 0 to 50%) followed by lyophilization (2-aminoacetoxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (45b) (0.095 g, 51% yield) as a white solid; $^1$H NMR (300 MHz, DMSO-$d_6$) δ 12.33 (brs, 1H), 10.82 (s, 1H), 10.35 (brs, 1H), 8.62 (t, J=6.1 Hz, 1H), 8.48 (brs, 3H), 8.25 (d, J=8.0 Hz, 1H), 8.05 (d, J=8.0 Hz, 2H), 7.85-7.69 (m, 4H), 7.12-6.94 (m, 2H), 6.16-6.04 (m, 1H), 5.92-5.76 (m, 2H), 5.51-5.40 (m, 1H), 4.32-4.19 (m, 2H), 3.90 (s, 3H), 3.82-3.67 (m, 2H), 3.30-3.15 (m, 2H), 1.74-1.59 (m, 2H), 1.44-1.21 (m, 6H), 1.18-1.01 (m, 1H), 0.94-0.81 (m, 3H), 0.50-0.39 (m, 2H), 0.33-0.23 (m, 2H); MS (ES+): 729.7 (M+1).

Scheme 46

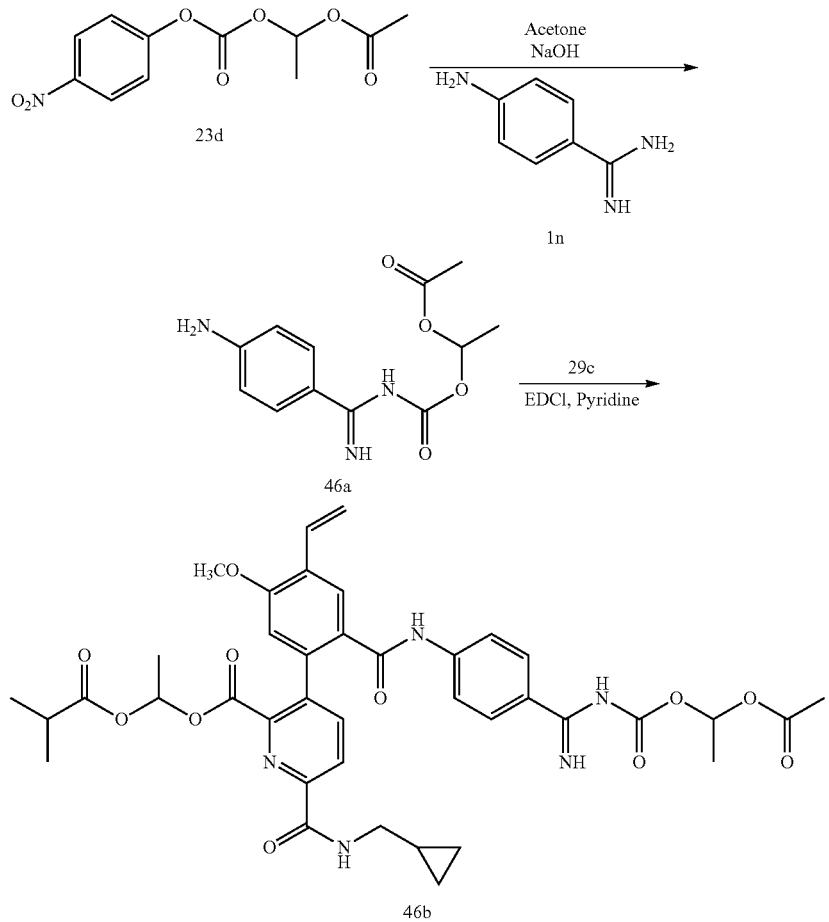

Preparation of 1-(isobutyryloxy)ethyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (46b)

Step-1: Preparation of 1-((((4-aminophenyl)(imino)methyl)carbamoyl)oxy)ethyl acetate (46a)

Compound (46a) was prepared from 4-aminobenzimidamide dihydrochloride (1n) (1.33 g, 6.37 mmol) in acetone/water (26 mL, 12:1), using NaOH solution (0.54 g, 13.37 mmol) and 1-(((4-nitrophenoxy)carbonyl)oxy)ethyl acetate (23d) (2.4 g, 8.92 mmol) according to the procedure reported in step 4 of scheme 23. This gave after workup and purification by flash column chromatography (silica gel 80 g, eluting with 0-70% ethyl acetate/methanol (9:1) in hexanes) 1-((((4-aminophenyl)(imino)methyl)carbamoyl)oxy)ethyl acetate (46a) (1.2 g, 71% yield) as a yellow solid; $^1$H NMR (300 MHz, DMSO-$d_6$) δ 9.18 (s, 1H, D$_2$O exchangeable), 8.85 (s, 1H, D$_2$O exchangeable), 7.81-7.69 (m, 2H), 6.76 (q, J=5.4 Hz, 1H), 6.60-6.48 (m, 2H), 5.93 (s, 2H, D$_2$O exchangeable), 2.01 (s, 3H), 1.42 (d, J=5.4 Hz, 3H); MS (ES+) 266.4 (M+1); (ES+) 264.4 (M−1).

Step-2: Preparation of 1-(isobutyryloxy)ethyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (46b)

Compound (46b) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (1.6 g, 3.13 mmol) using EDCI (0.78 g, 4.07 mmol) and 1-((((4-aminophenyl)(imino)methyl)carbamoyl)oxy)ethyl acetate (46a) (0.91 g, 3.45 mmol) in Pyridine (4 mL) according to the procedure reported in step 4 of scheme 2. This gave after workup and purification by reverse phase chromatography [C18, 100 g, Acetonitrile-water (0.1% HCl), 10% to 80% as eluents] followed by lyophilization 1-(isobutyryloxy)ethyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (46b) (0.62 g, 26% yield) HCl salt as a white solid; $^1$H NMR (300 MHz, DMSO-$d_6$) δ 10.76-10.56 (m, 1H), 8.67-8.46 (m, 1H), 8.22 (d, J=8.0 Hz, 1H), 8.00 (s, 2H), 7.88-7.64 (m, 4H), 7.19-6.95 (m, 2H), 6.89-6.79 (m, 1H), 6.81-6.67 (m, 1H), 6.06 (d, J=17.8 Hz, 1H), 5.49-5.40 (m, 1H), 3.88 (s, 3H), 3.29-3.17 (m, 2H), 2.47-2.29 (m, 1H), 2.06 (s, 3H), 1.49 (t, J=5.4 Hz, 3H), 1.17 (d, J=5.4 Hz, 3H), 1.16-0.98 (m, 1H), 1.03-0.89 (m, 6H), 0.49-0.40 (m, 2H), 0.33-0.24 (m, 2H); MS (ES+): 758.7 (M+1).

Scheme 47

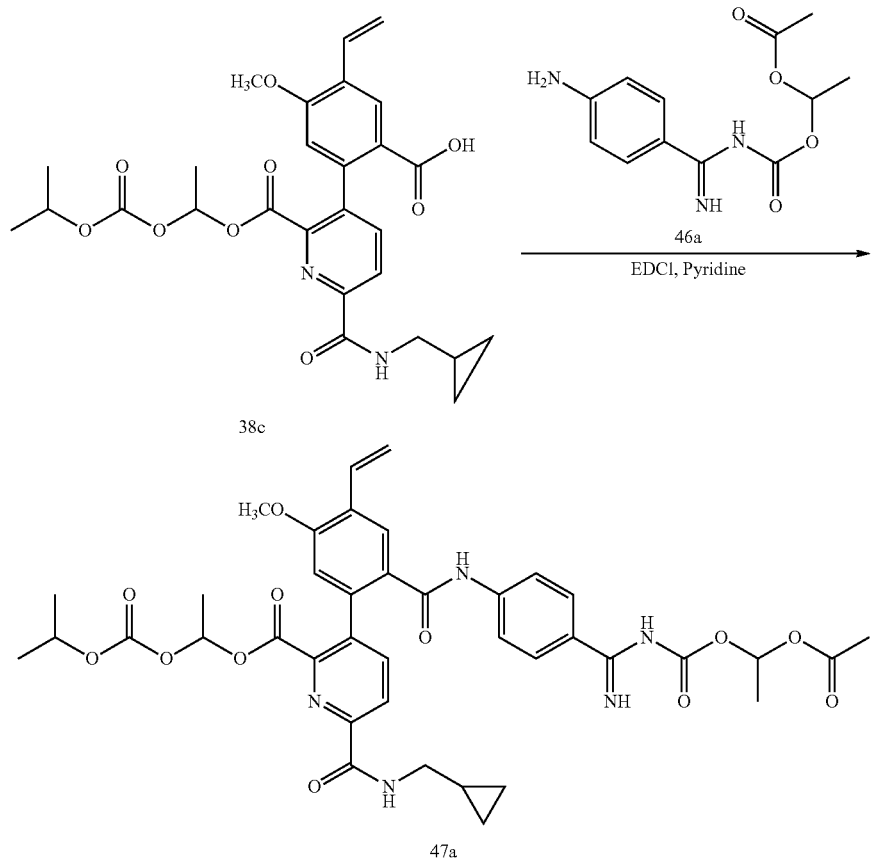

Preparation of 1-((isopropoxycarbonyl)oxy)ethyl 3-(2-((4-(N-((1-acetoxyethoxy)carbonyl) carbamimidoyl)phenyl)carbamoyl)-5-methoxy-4-vinylphenyl)-6-((cyclopropylmethyl)carbamoyl) picolinate (47a)

Compound (47a) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (2.5 g, 4.75 mmol) using EDCI (1.09 g, 5.70 mmol) and 1-((((4-aminophenyl)(imino)methyl)carbamoyl)oxy) ethyl acetate (46a) (1.32 g, 5 mmol) in DMF (10 mL) and Pyridine (5 mL) according to the procedure reported in step 4 of scheme 2. This gave after workup and purification by flash column chromatography [silica gel 40 g, eluting with MeOH-EtOAc (9:1) in hexanes 0 to 100%] 1-((isopropoxycarbonyl)oxy)ethyl 3-(2-((4-(N-((1-acetoxyethoxy)carbonyl)carbamimidoyl)phenyl) carbamoyl)-5-methoxy-4-vinylphenyl)-6-((cyclopropylmethyl)carbamoyl)picolinate (47a) (1.84 g, 50% yield) as a white powder; $^1$H NMR (300 MHz, DMSO-$d_6$) δ 10.66-10.44 (m, 1H), 9.34-9.09 (m, 2H), 8.70-8.48 (m, 1H), 8.22 (d, J=8.0 Hz, 1H), 8.07-7.89 (m, 3H), 7.77-7.59 (m, 3H), 7.13-6.95 (m, 2H), 6.76 (q, J=5.4 Hz, 1H), 6.63 (q, J=5.3 Hz, 1H), 6.06 (d, J=17.8 Hz, 1H), 5.44 (d, J=11.4 Hz, 1H), 4.79-4.62 (m, 1H), 3.89 (s, 3H), 3.28-3.16 (m, 2H), 2.02 (s, 3H), 1.42 (d, J=5.4 Hz, 3H), 1.24-1.03 (m, 10H), 0.51-0.38 (m, 2H), 0.31-0.23 (m, 2H); MS (ES+) 774.7 (M+1).

Scheme 48

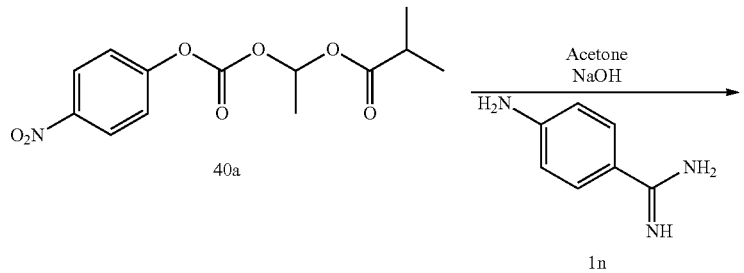

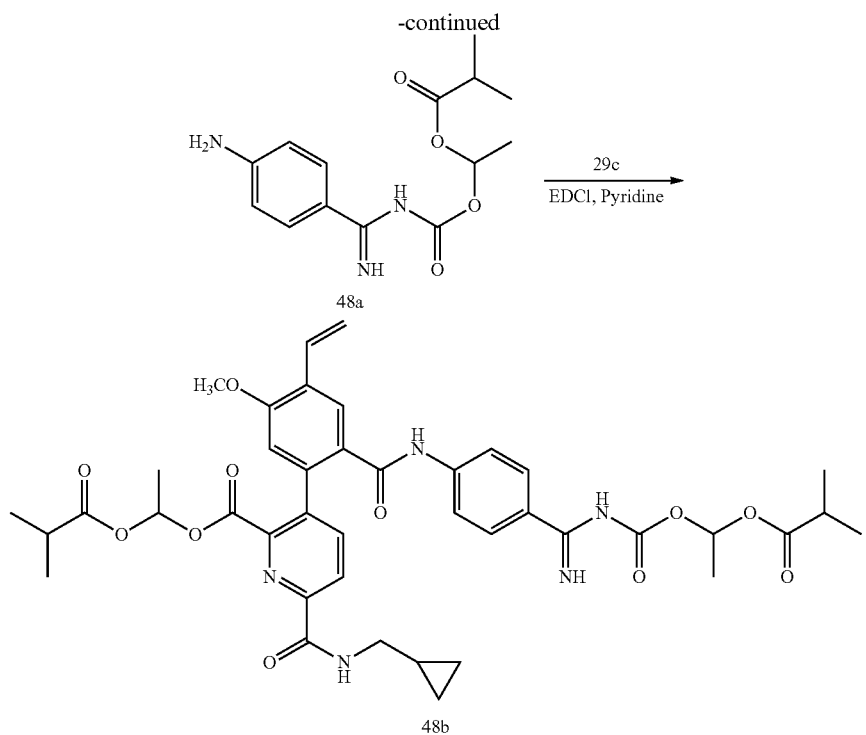

Step-2: Preparation of 1-(isobutyryloxy)ethyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (48b)

Compound (48b) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.51 g, 1.0 mmol) using EDCI (0.24 g, 1.24 mmol) and 1-((((4-aminophenyl)(imino)methyl)carbamoyl)oxy)ethyl isobutyrate (48a) (0.32 g, 1.1 mmol) in DMF (3 mL) and Pyridine (3 mL) according to the procedure reported in step 4 of scheme 2. This gave after workup and purification by flash column chromatography [silica gel, 25 g eluting with a (9:1) mixture of ethyl acetate and methanol in hexanes 0 to 100%]

1-(isobutyryloxy)ethyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (48b) (0.21 g, 26% yield) as a white solid; $^1$H NMR (300 MHz, DMSO-$d_6$) δ 10.53 (d, J=25.5 Hz, 1H, $D_2O$ exchangeable), 9.22 (d, J=25.3 Hz, 2H, $D_2O$ exchangeable), 8.57 (d, J=28.1 Hz, 1H), 8.23 (d, J=8.0 Hz, 1H), 7.97 (d, J=17.7 Hz, 4H), 7.80-7.56 (m, 2H), 7.10-6.95 (m, 2H), 6.83-6.68 (m, 2H), 6.17-5.94 (m, 1H), 5.44 (d, J=11.4 Hz, 1H), 3.89 (s, 3H), 3.22 (d, J=6.4 Hz, 2H), 2.61-2.30 (m, 2H), 1.43 (d, J=5.4 Hz, 3H), 1.17 (s, 3H), 1.05 (dd, J=7.0, 5.3 Hz, 6H), 1.05-0.88 (m, 7H), 0.50-0.40 (m, 2H), 0.32-0.23 (m, 2H); MS (ES+) 786.7 (M+1), 808.7 (M+Na), (ES−) 784.8 (M−1); Analysis calculated for $C_{41}H_{47}N_5O_{11}$·0.5$H_2O$: C, 61.95; H, 6.09; N, 8.81. Found: C, 61.98; H, 6.16; N, 8.81.

Scheme 49

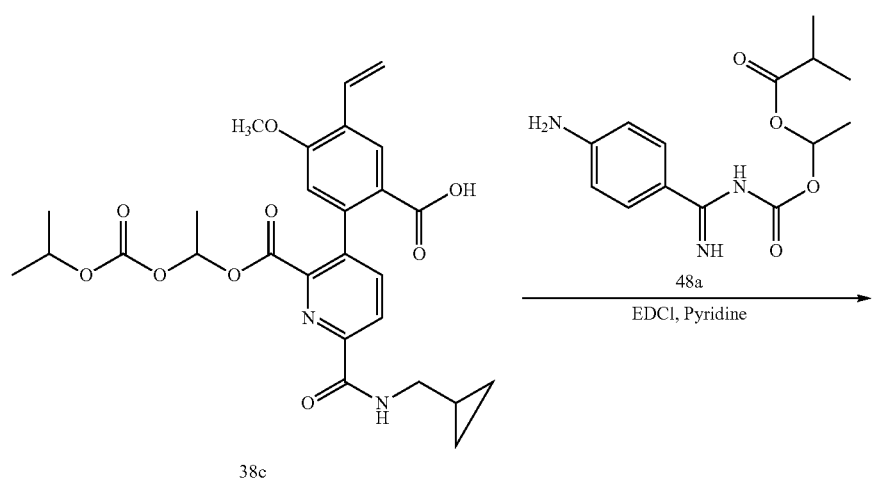

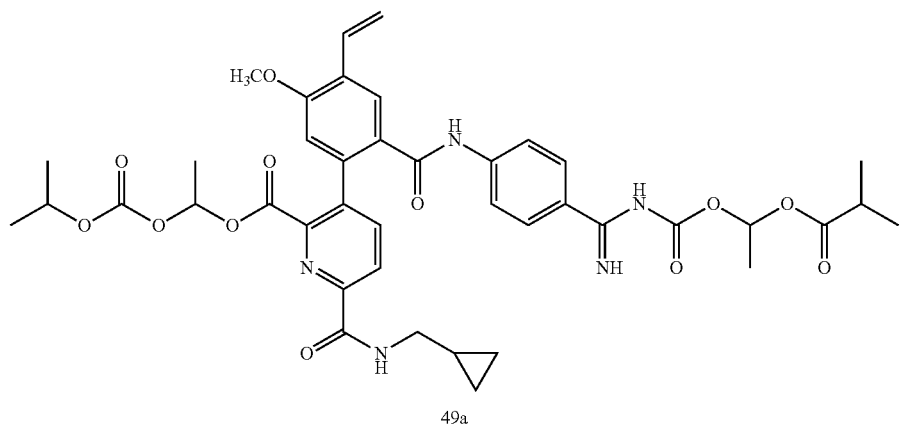

49a

Preparation of 1-((isopropoxycarbonyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (49a)

Compound (49a) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.51 g, 0.96 mmol) using EDCI (0.28 g, 1.44 mmol) and 1-((((4-aminophenyl)(imino)methyl)carbamoyl)oxy)ethyl isobutyrate (48a) (0.31 g, 1.06 mmol) in DMF (3 mL) and Pyridine (3 mL) according to the procedure reported in step 4 of scheme 2. This gave after workup and purification by flash column chromatography [silica gel 25 g, eluting with MeOH-EtOAc (9:1) in hexanes 0 to 100%]

1-((isopropoxycarbonyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (49a) (0.22 g, 29% yield) as a white solid; $^1$H NMR (300 MHz, DMSO-d$_6$) δ 10.55 (d, J=28.4 Hz, 1H, D$_2$O exchangeable), 9.23 (d, J=23.0 Hz, 2H, D$_2$O exchangeable), 8.61 (d, J=25.5 Hz, 1H), 8.23 (d, J=8.1 Hz, 1H), 8.11-7.89 (m, 5H), 7.77-7.60 (m, 1H), 7.10-6.96 (m, 2H), 6.77 (q, J=5.4 Hz, 1H), 6.63 (q, J=5.3 Hz, 1H), 6.06 (dd, J=17.8, 1.6 Hz, 1H), 5.44 (dd, J=11.2, 1.5 Hz, 1H), 4.71 (s, 1H), 3.89 (s, 3H), 3.24 (t, J=6.4 Hz, 2H), 2.61-2.38 (m, 1H), 1.43 (d, J=5.4 Hz, 3H), 1.32-0.96 (m, 16H), 0.52-0.39 (m, 2H), 0.34-0.21 (m, 2H); MS (ES+) 802.7 (M+1), (ES−) 836.9 (M+Cl); Analysis calculated for C$_{41}$H$_{47}$N$_5$O$_{12}$ (H$_2$O)$_{0.75}$: C, 60.73; H, 5.97; N, 8.64; found; C, 60.75; H, 6.07; N, 8.57.

Scheme 50

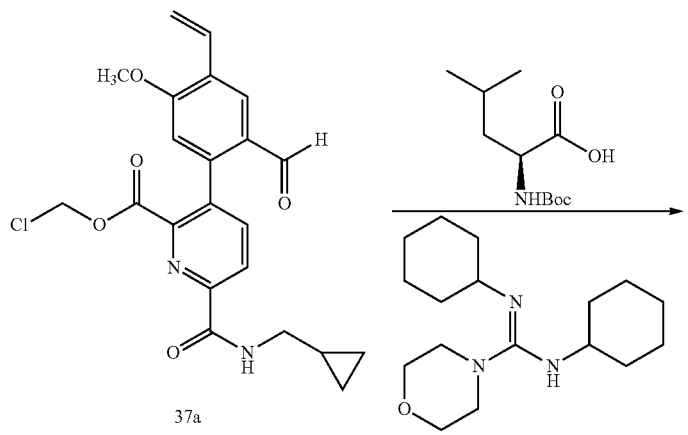

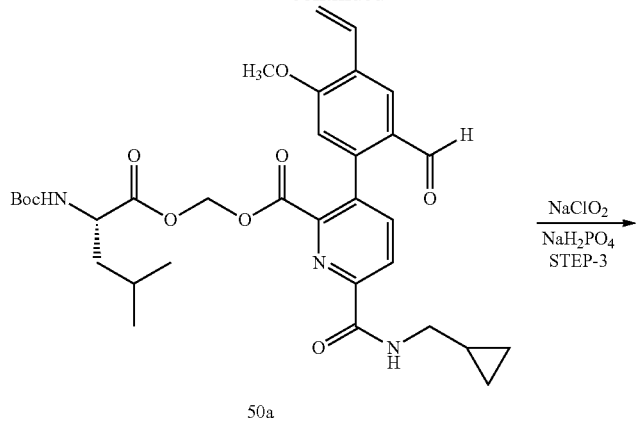
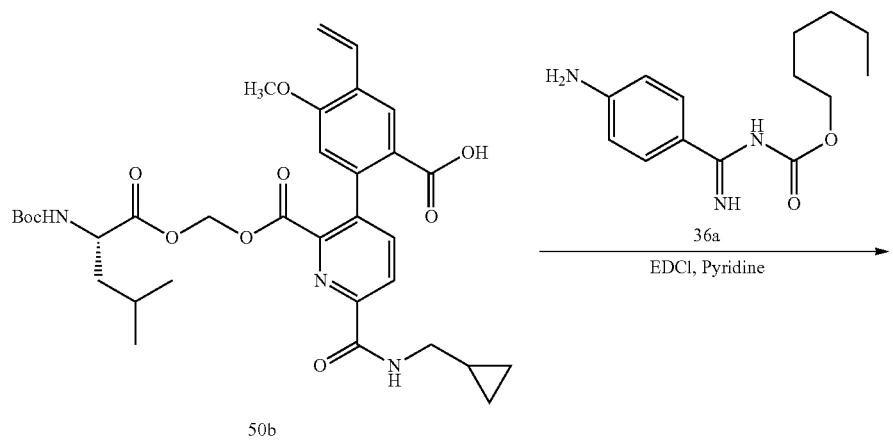
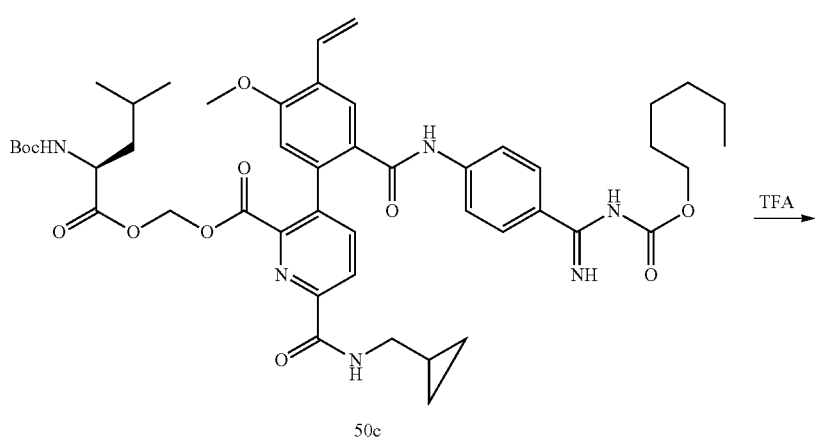

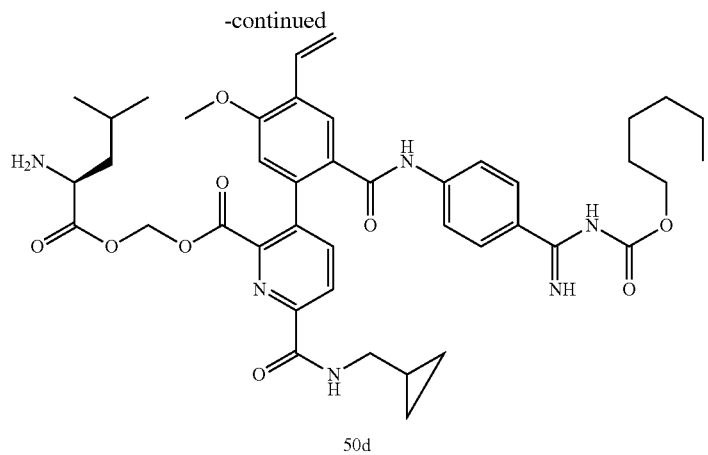

50d

Preparation of (S)-((2-amino-4-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (50d)

Step-1: Preparation of (S)-((2-(((tert-butoxycarbonyl)amino)-4-methylpentanoyl)oxy)methyl 6-((cyclopropylmethyl)carbamoyl)-3-(2-formyl-5-methoxy-4-vinylphenyl)picolinate (50a)

Compound (50a) was prepared according to the procedure reported in step 1 of scheme 8 from chloromethyl 6-((cyclopropylmethyl)carbamoyl)-3-(2-formyl-5-methoxy-4-vinylphenyl)picolinate (37a) (1.25 g, 2.91 mmol) in DMF (10 mL) using N,N'-Dicyclohexyl-4-morpholinecarboxamidine (1.07 g, 3.64 mmol) and (S)-2-((tert-butoxycarbonyl)amino)-4-methylpentanoic acid (0.87 g, 3.5 mmol). This gave after workup and purification by flash column chromatography (silica gel 40 g, eluting with ethyl acetate/Hexanes, 0-100%) (S)-((2-(((tert-butoxycarbonyl)amino)-4-methylpentanoyl)oxy)methyl 6-((cyclopropylmethyl)carbamoyl)-3-(2-formyl-5-methoxy-4-vinylphenyl)picolinate (50a) (0.77 g, 43% yield) as a yellow thick syrup; $^1$H NMR (300 MHz, DMSO-$d_6$) δ 9.69 (s, 1H), 8.66 (t, J=5.9 Hz, 1H), 8.28 (dd, J=7.9, 0.9 Hz, 1H), 8.13 (d, J=2.3 Hz, 1H), 8.07 (d, J=8.1 Hz, 1H), 7.33 (dd, J=7.8, 3.5 Hz, 1H), 7.08-6.93 (m, 2H), 6.01 (dd, J=17.8, 1.3 Hz, 1H), 5.81 (dd, J=8.5, 5.9 Hz, 1H), 5.73 (dd, J=5.9, 1.4 Hz, 1H), 5.45 (dd, J=11.2, 1.4 Hz, 1H), 3.95 (dd, J=8.2, 3.8 Hz, 1H), 3.91 (d, J=1.1 Hz, 3H), 3.25 (p, J=7.0 Hz, 2H), 1.65-1.39 (m, 2H), 1.34 (s, 9H), 1.25 (dq, J=7.1, 4.0, 3.0 Hz, 1H), 1.14-0.98 (m, 1H), 0.84 (d, J=6.5 Hz, 3H), 0.81 (d, J=6.4 Hz, 3H), 0.52-0.42 (m, 2H), 0.33-0.23 (m, 2H); MS (ES+) 624.4 (M+1), 646.6 (M+Na), (ES−) 658.8 (M+Cl).

Step-2: Preparation of (S)-2-(6-((cyclopropylmethyl)carbamoyl)-2-(6-isobutyl-10,10-dimethyl-5,8-dioxo-2,4,9-trioxa-7-azaundecan-1-oyl)pyridin-3-yl)-4-methoxy-5-vinylbenzoic acid (50b)

Oxidation of (S)-((2-(((tert-butoxycarbonyl)amino)-4-methylpentanoyl)oxy)methyl 6-((cyclopropylmethyl)carbamoyl)-3-(2-formyl-5-methoxy-4-vinylphenyl)picolinate (50a) (0.75 g, 1.20 mmol) using the procedure as reported in step 11 of scheme 1 gave after workup (S)-2-(6-((cyclopropylmethyl)carbamoyl)-2-(6-isobutyl-10,10-dimethyl-5,8-dioxo-2,4,9-trioxa-7-azaundecan-1-oyl)pyridin-3-yl)-4-methoxy-5-vinylbenzoic acid (50b) (0.85 g, 111% yield) as a yellow solid; $^1$H NMR (300 MHz, DMSO-$d_6$) δ 12.57 (s, 1H, $D_2O$ exchangeable), 8.68-8.50 (m, 1H), 8.23 (d, J=8.0 Hz, 1H), 8.11 (s, 1H), 7.96 (d, J=8.0 Hz, 1H), 7.32 (d, J=7.8 Hz, 1H), 7.05-6.82 (m, 2H), 5.98-5.68 (m, 3H), 5.39 (d, J=11.4 Hz, 1H), 4.03-3.89 (m, 1H), 3.86 (s, 3H), 3.31-3.19 (m, 2H), 1.40-1.31 (m, 10H), 1.29-1.19 (m, 1H), 0.89-0.76 (m, 8H), 0.53-0.42 (m, 2H), 0.33-0.23 (m, 2H); MS (ES+) 662.6 (M+Na), (ES−) 638.6 (M−1).

Step-3: Preparation of (S)-((2-(((tert-butoxycarbonyl)amino)-4-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (50c)

Compound (50c) was prepared from (S)-2-(6-((cyclopropylmethyl)carbamoyl)-2-(6-isobutyl-10,10-dimethyl-5,8-dioxo-2,4,9-trioxa-7-azaundecan-1-oyl)pyridin-3-yl)-4-methoxy-5-vinylbenzoic acid (50b) (0.32 mg, 0.5 mmol) using EDCI (1.5 equiv.) and hexyl ((4-aminophenyl)(imino)methyl)carbamate (36a) (0.17 g, 0.63 mmol) in DMF (3 mL) and Pyridine (3 mL) according to the procedure reported in step 4 of scheme 2. This gave after workup (S)-((2-(((tert-butoxycarbonyl)amino)-4-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (50c) (0.44 g, 99% yield) which was used in next step without further purification. $^1$H NMR (300 MHz, DMSO-$d_6$) δ 10.55 (s, 1H, $D_2O$ exchangeable), 9.05 (d, J=59.7 Hz, 2H, $D_2O$ exchangeable), 8.54 (t, J=6.1 Hz, 1H), 8.31-8.14 (m, 1H), 8.02 (d, J=8.0 Hz, 1H), 7.99-7.82 (m, 3H), 7.67 (d, J=8.7 Hz, 3H), 7.32 (d, J=7.9 Hz, 1H), 7.11-6.91 (m, 2H), 6.12-5.99 (m, 1H), 5.81 (dd, J=38.6, 24.4 Hz, 3H), 5.50-5.37 (m, 1H), 3.89 (s, 3H), 3.29-3.15 (m, 2H), 2.62 (t, J=15.3 Hz, 1H), 1.58 (d, J=7.0 Hz, 2H), 1.30 (d, J=8.7 Hz, 16H), 0.96-0.70 (m, 12H), 0.52-0.39 (m, 2H), 0.33-0.21 (m, 2H); MS (ES+) 908.5 (M+Na), (ES−) 920.6 (M+Cl).

Step-4: Preparation of (S)-((2-amino-4-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (50d)

Compound (50d) was prepared from (S)-((2-(((tert-butoxycarbonyl)amino)-4-methylpentanoyl)oxy)methyl 6-((cyclopropylmethyl)carbamoyl)-3-(2-((4-(N-((hexyloxy) carbonyl)carbamimidoyl)phenyl)carbamoyl)-5-methoxy-4-vinylphenyl)picolinate (50c) (0.43 g, 0.49 mmol) in dichloromethane (10 mL) using 2,2,2-trifluoroacetic acid (0.75 mL, 9.72 mmol) according to the procedure reported in Step-4 of scheme 8. This gave after workup and purification by flash column chromatography (C18, 26 g) eluting with 0.1% HCl and acetonitrile followed by lyophilization (S)-((2-amino-4-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl) picolinate (50d) (0.15 g, 38% yield) as a white solid. $^1$H NMR (300 MHz, DMSO-d$_6$) δ 10.74 (s, 1H, D$_2$O exchangeable), 10.47-9.87 (m, 2H, D$_2$O exchangeable), 8.71-8.29 (m, 4H, 3H D$_2$O exchangeable), 8.23 (s, 1H), 8.03 (d, J=8.1 Hz, 1H), 7.98 (s, 1H), 7.83-7.69 (m, 4H), 7.12-6.97 (m, 2H), 6.05 (dd, J=17.8, 1.5 Hz, 1H), 5.90 (s, 1H), 5.82 (s, 1H), 5.46 (dd, J=11.2, 1.5 Hz, 1H), 4.22 (t, J=6.6 Hz, 2H), 3.99 (t, J=6.8 Hz, 1H), 3.89 (s, 3H), 3.22 (d, J=8.3 Hz, 2H), 1.76-1.58 (m, 2H), 1.54 (t, J=7.1 Hz, 2H), 1.44-1.19 (m, 7H), 1.17-0.99 (m, 1H), 0.93-0.84 (m, 3H), 0.84-0.73 (m, 6H), 0.51-0.38 (m, 2H), 0.32-0.21 (m, 2H); MS (ES+) 785.7 (M+1), 807.7 (M+Na); Analysis calculated for: $C_{42}H_{52}N_6O_9 \cdot 2CF_3CO_2H \cdot 2H_2O$: C, 52.42; H, 5.55; N, 7.97. Found: C, 52.57; H, 5.30; N, 7.85.

Preparation of 1-((isopropoxycarbonyl)oxy)ethyl 6-((cyclopropylmethyl)carbamoyl)-3-(2-((4-(N-hydroxycarbamimidoyl)phenyl)carbamoyl)-5-methoxy-4-vinylphenyl)picolinate (51b)

Compound (51b) was prepared according to the procedure reported in step 4 of scheme 2 from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (1.21 g, 2.29 mmol) using EDCI (0.53 g, 2.75 mmol) and 4-amino-N'-hydroxybenzimidamide (51a) (0.35 g, 2.29 mmol, prepared according to the procedure reported by Lin, Chia-Chi et al; in Organic Letters, 16(3), 892-895; 2014) in DMF (15 mL) and Pyridine (5 mL). This gave after workup and purification by flash column chromatography (silica gel, 40 g, eluting with ethyl acetate/methanol (9:1) in hexanes from 0 to 100%) 1-((isopropoxycarbonyl)oxy)ethyl6-((cyclopropylmethyl)carbamoyl)-3-(2-((4-(N-hydroxycarbamimidoyl)phenyl)carbamoyl)-5-methoxy-4-vinylphenyl)picolinate (51b) (0.14 g, 9% yield) as an off-white solid; $^1$H NMR (300 MHz, DMSO-d$_6$) δ 8.71-8.55 (m, 1H), 8.29 (s, 1H), 8.22 (d, J=8.0 Hz, 1H), 8.06-7.93 (m, 1H), 7.35 (d, J=8.6 Hz, 2H), 7.00 (dd, J=17.9, 11.4 Hz, 1H), 6.93 (d, J=6.4 Hz, 1H), 6.63 (t, J=5.2 Hz, 1H), 6.56-6.46 (m, 2H), 6.34 (s, 2H), 6.09 (dd, J=17.8, 1.6 Hz, 1H), 5.50 (s, 2H, D$_2$O exchangeable), 5.44 (dd, J=11.3, 1.5 Hz, 1H), 4.87-4.61 (m, 1H), 3.88 & 3.87 (2s, 3H), 3.24 (t, J=6.5 Hz, 2H), 1.34-1.02 (m, 10H), 0.53-0.39 (m, 2H), 0.32-0.22 (m, 2H); MS (ES+): 660.57 (M+1), 682.57 (M+Na); MS (ES−): 658.6 (M−1), 694.5 (M+Cl); Analysis calculated for: $C_{34}H_{37}N_5O_9 \cdot 0.75H_2O$: C, 60.66; H, 5.76; N, 10.40; found: C, 60.67; H, 5.78; N, 10.38.

Scheme 51

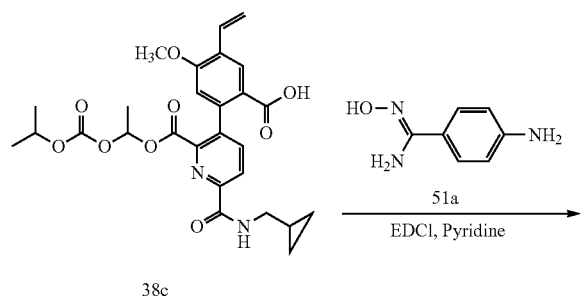

38c

Scheme 52

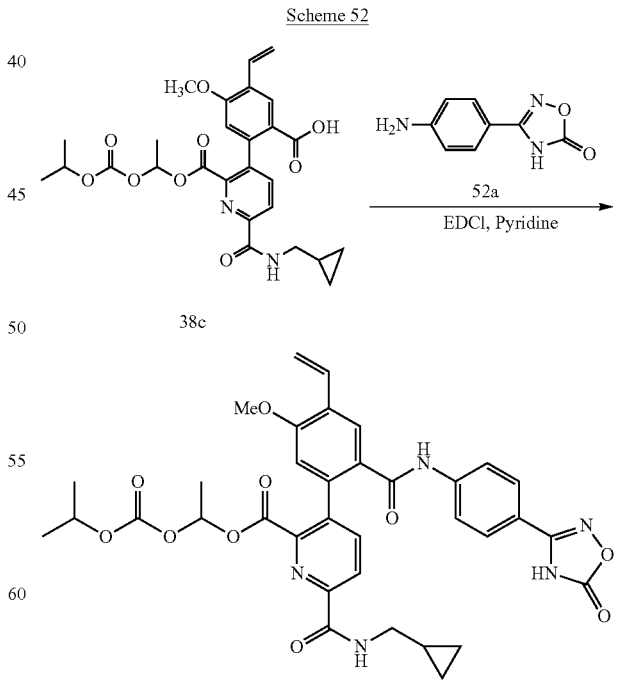

51b

52b

Preparation of 1-((isopropoxycarbonyl)oxy)ethyl 6-((cyclopropylmethyl)carbamoyl)-3-(5-methoxy-2-((4-(5-oxo-4,5-dihydro-1,2,4-oxadiazol-3-yl)phenyl)carbamoyl)-4-vinylphenyl)picolinate (52b)

Compound (52b) was prepared according to the procedure reported in step 4 of scheme 2 from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.5 g, 0.95 mmol) using EDCI (0.27 g, 1.42 mmol) and 3-(4-aminophenyl)-1,2,4-oxadiazol-5(4H)-one (52a) (0.18 g, 1.04 mmol, CAS #864680-71-7) in DMF (3 mL) and Pyridine (3 mL). This gave after workup and purification by flash column chromatography (silica gel, 25 g, eluting with ethyl acetate/methanol (9:1) in hexanes in hexanes from 0 to 100%) 1-((isopropoxycarbonyl)oxy)ethyl 6-((cyclopropylmethyl)carbamoyl)-3-(5-methoxy-2-((4-(5-oxo-4,5-dihydro-1,2,4-oxadiazol-3-yl)phenyl)carbamoyl)-4-vinylphenyl)picolinate (52b) (0.17 g, 26% yield) as a white solid; $^1$H NMR (300 MHz, DMSO-$d_6$) δ 12.88 (s, 1H, $D_2O$ exchangeable), 10.61 (d, J=26.7 Hz, 1H), 8.61 (d, J=24.1 Hz, 1H), 8.23 (d, J=8.0 Hz, 1H), 8.07-7.93 (m, 2H), 7.85-7.64 (m, 4H), 7.13-6.94 (m, 2H), 6.64 (q, J=5.3 Hz, 1H), 6.06 (dd, J=17.8, 1.6 Hz, 1H), 5.51-5.37 (m, 1H), 4.81-4.56 (m, 1H), 3.89 (s, 3H), 3.24 (t, J=6.7 Hz, 2H), 1.17 (t, J=7.0 Hz, 9H), 1.08 (dq, J=8.0, 4.8, 4.1 Hz, 1H), 0.44 (dt, J=8.1, 2.9 Hz, 2H), 0.33-0.23 (m, 2H); MS (ES+) 686.5 (M+1), 708.6 (M+Na), (ES−) 684.7 (M−1), 720.6 (M+Cl); Analysis calculated for $C_{35}H_{35}N_5O_{10} \cdot H_2O$: C, 59.74; H, 5.30; N, 9.95. Found: C, 60.15; H, 5.32; N, 10.02.

Scheme 53

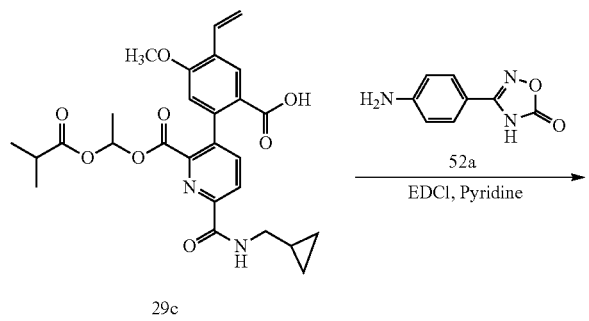

Preparation of 1-(isobutyryloxy)ethyl 6-((cyclopropylmethyl)carbamoyl)-3-(5-methoxy-2-((4-(5-oxo-4,5-dihydro-1,2,4-oxadiazol-3-yl)phenyl)carbamoyl)-4-vinylphenyl)picolinate (53a)

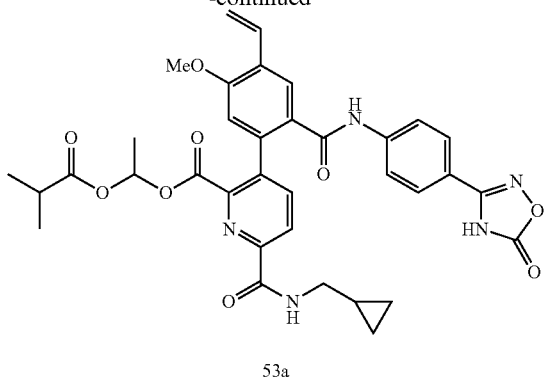

53a

Compound (53a) was prepared according to the procedure reported in step 4 of scheme 2 from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.4 g, 0.78 mmol) using EDCI (0.19 g, 0.98 mmol) and 3-(4-aminophenyl)-1,2,4-oxadiazol-5(4H)-one (52a) (0.21 g, 1.18 mmol, CAS #864680-71-7) in DMF (3 mL) and Pyridine (3 mL). This gave after workup and purification by flash column chromatography (silica gel, 25 g, eluting with ethyl acetate/methanol (9:1) in hexanes in hexanes from 0 to 100%) 1-(isobutyryloxy)ethyl 6-((cyclopropylmethyl)carbamoyl)-3-(5-methoxy-2-((4-(5-oxo-4,5-dihydro-1,2,4-oxadiazol-3-yl)phenyl)carbamoyl)-4-vinylphenyl)picolinate (53a) (0.21 g, 40% yield) as a white solid; $^1$H NMR (300 MHz, DMSO-$d_6$) δ 12.88 (s, 1H, $D_2O$ exchangeable), 10.59 (d, J=23.7 Hz, 1H), 8.57 (d, J=26.5 Hz, 1H), 8.23 (d, J=8.0 Hz, 1H), 8.00 (s, 2H), 7.75 (d, J=11.5 Hz, 4H), 7.11-6.96 (m, 2H), 6.74 (s, 1H), 6.06 (dd, J=17.8, 1.5 Hz, 1H), 5.45 (dd, J=11.2, 1.5 Hz, 1H), 3.89 (s, 3H), 3.28-3.19 (m, 2H), 2.49-2.32 (m, 1H), 1.22-1.15 (m, 3H), 1.14-1.04 (m, 1H), 1.05-0.92 (m, 6H), 0.50-0.41 (m, 2H), 0.32-0.23 (m, 2H); MS (ES+) 692.7 (M+Na), (ES−) 668.6 (M−1).

Scheme 54

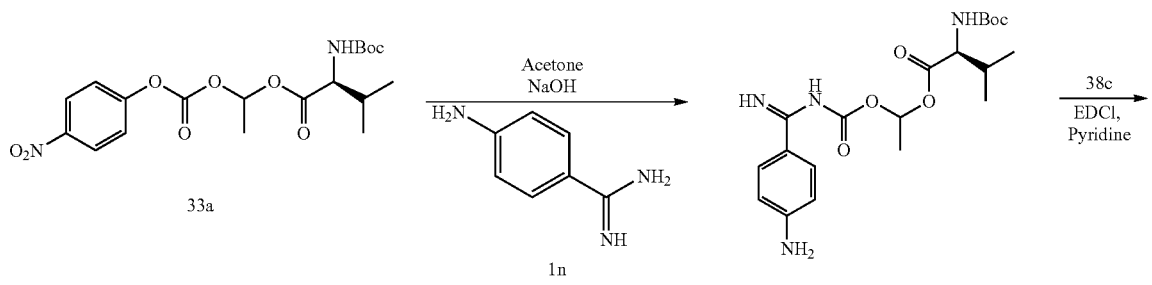

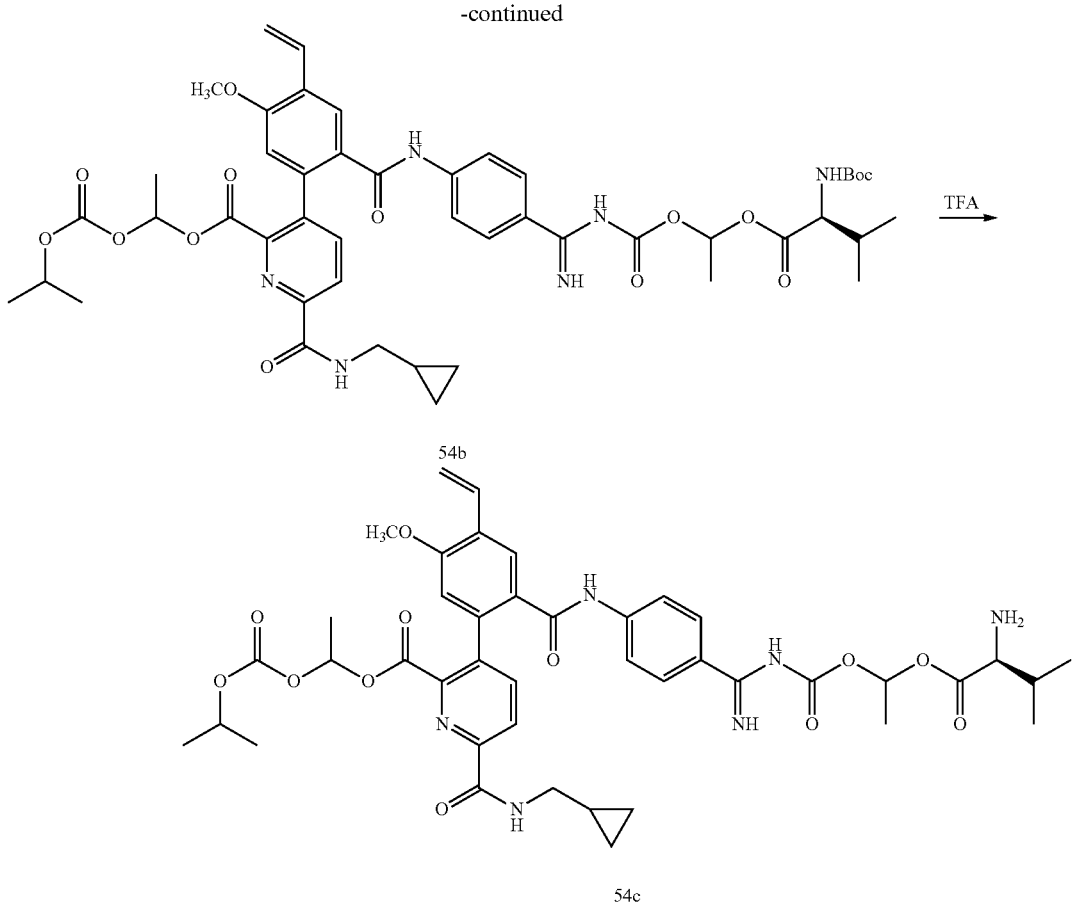

Preparation of 1-((isopropoxycarbonyl)oxy)ethyl 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinate (54c)

Step-1: Preparation of (2S)-1-((((4-aminophenyl)(imino)methyl)carbamoyl)oxy)ethyl 2-((tert-butoxycarbonyl)amino)-3-methylbutanoate (54a)

Compound (54a) was prepared from 4-aminobenzimidamide dihydrochloride (1n) (1.72 g, 8.28 mmol) in acetone/water (26 mL, 12:1), using NaOH (0.68 g, 16.98 mmol) and (2S)-1-(((4-nitrophenoxy)carbonyl)oxy)ethyl 2-((tert-butoxycarbonyl)amino)-3-methylbutanoate (33a) (3.89 g, 9.11 mmol) according to the procedure reported in step 4 of scheme 23. This gave after workup and purification by flash column chromatography (2S)-1-((((4-aminophenyl)(imino)methyl)carbamoyl)oxy)ethyl 2-((tert-butoxycarbonyl)amino)-3-methylbutanoate (54a) (2.84 g, 81% yield) as a white solid. $^1$H NMR (300 MHz, DMSO-$d_6$) δ 9.17 (s, 1H, $D_2O$ exchangeable), 8.86 (s, 1H, $D_2O$ exchangeable), 7.77 (dd, J=8.8, 2.4 Hz, 2H), 7.18 (dd, J=11.5, 8.1 Hz, 1H), 6.83 (dd, J=5.5, 3.0 Hz, 1H), 6.55 (d, J=8.7 Hz, 2H), 5.94 (s, 2H, $D_2O$ exchangeable), 3.80 (ddd, J=8.1, 6.2, 3.1 Hz, 1H), 1.47-1.28 (m, 13H), 0.85 (td, J=4.1, 2.0 Hz, 6H); MS (ES−) 457.5 (M+Cl)

Step-2: Preparation of 1-((isopropoxycarbonyl)oxy)ethyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinate (54b)

Compound (54b) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.6 g, 1.14 mmol) using EDCI (0.33 g, 1.71 mmol) and (2S)-1-((((4-aminophenyl)(imino)methyl)carbamoyl)oxy)ethyl 2-((tert-butoxycarbonyl)amino)-3-methylbutanoate (54a) (0.58 g, 1.37 mmol) in DMF (10 mL) and Pyridine (2 mL) according to the procedure reported in step 4 of scheme 2. This gave after workup and purification by flash column chromatography [silica gel, 12 g eluting with a (9:1) mixture of ethyl acetate and methanol in hexanes 0 to 60%] 1-((isopropoxycarbonyl)oxy)ethyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinate (54b) (0.29 g, 28% yield) as an off white solid; $^1$H NMR (300 MHz, DMSO-$d_6$) δ 10.55 (d, J=27.1 Hz, 1H), 9.33-9.10 (m, 2H, $D_2O$ exchangeable), 8.60 (d, J=25.9 Hz, 1H, $D_2O$ exchangeable), 8.22 (d, J=8.0 Hz, 1H), 8.02-7.90 (m, 4H), 7.70 (d, J=10.2 Hz, 2H), 7.20 (dd, J=11.4, 8.2 Hz, 1H), 7.09-6.96 (m, 2H), 6.83 (s, 1H), 6.63 (q, J=5.3 Hz, 1H), 6.15-5.99 (m, 1H), 5.44 (d, J=11.6 Hz, 1H), 4.78-4.62 (m, 1H), 3.89 (s, 3H), 3.80 (t, J=7.2 Hz, 1H), 3.35 (s, 32H), 2.07-1.89 (m, 1H), 1.47-1.41 (m, 3H), 1.38-1.35 (m, 7H), 1.20-1.13 (m, 9H), 0.90-0.81 (m, 9H), 0.51-0.39 (m, 2H), 0.32-0.21 (m, 2H); MS (ES$^+$) 932.8 (M+1); 954.8 (M+Na).

Step-3: Preparation of 1-((isopropoxycarbonyl)oxy) ethyl 3-(2-((4-(N-((1-(((S)-2-amino-3-methylbutanoyl)oxy)ethoxy)carbonyl)carbamimidoyl)phenyl) carbamoyl)-5-methoxy-4-vinylphenyl)-6-((cyclopropylmethyl)carbamoyl)picolinate (54c)

Compound (54c) was prepared from 1-((isopropoxycarbonyl)oxy)ethyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl) carbamoyl)-5-methoxy-4-vinylphenyl)picolinate (54b) (0.29 g, 0.31 mmol) in dichloromethane (12 mL) using 2,2,2-trifluoroacetic acid (0.47 mL, 6.14 mmol) according to the procedure reported in Step-4 of scheme 8. This gave after workup and purification by prep-HPLC [C18 column, eluting with CH$_3$CN in water (containing 0.1% HCl) from 0-100%] followed by lyophilization 1-((isopropoxycarbonyl)oxy)ethyl 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl) carbamoyl)picolinate (54c) (0.04 g, 16% yield) as a white solid. $^1$H NMR (300 MHz, DMSO-d$_6$) δ 10.71 (d, J=22.8 Hz, 1H), 8.71-8.42 (m, 4H, D$_2$O exchangeable), 8.22 (d, J=8.0 Hz, 1H), 8.07-7.95 (m, 2H), 7.91-7.80 (m, 2H), 7.80-7.66 (m, 2H), 7.27-6.89 (m, 4H), 6.63 (q, J=5.2 Hz, 1H), 6.07 (d, J=18.1 Hz, 1H), 5.44 (d, J=11.6 Hz, 1H), 4.78-4.63 (m, 1H), 4.09-3.94 (m, 2H), 3.89 (s, 3H), 3.31-3.12 (m, 2H), 2.26-2.06 (m, 1H), 1.56 (d, J=5.4 Hz, 3H), 1.23-1.09 (m, 10H), 1.02-0.92 (m, 6H), 0.51-0.38 (m, 2H), 0.32-0.20 (m, 2H); MS (ES$^+$) 831.7 (M+1); (ES$^-$) 865.8 (M+Cl); Analysis calculated for C$_{42}$H$_{50}$N$_6$O$_{12}$.2HCl.3.5H$_2$O: C, 52.17; H, 6.15; N, 8.69; found: C, 52.12; H, 5.97; N, 8.67.

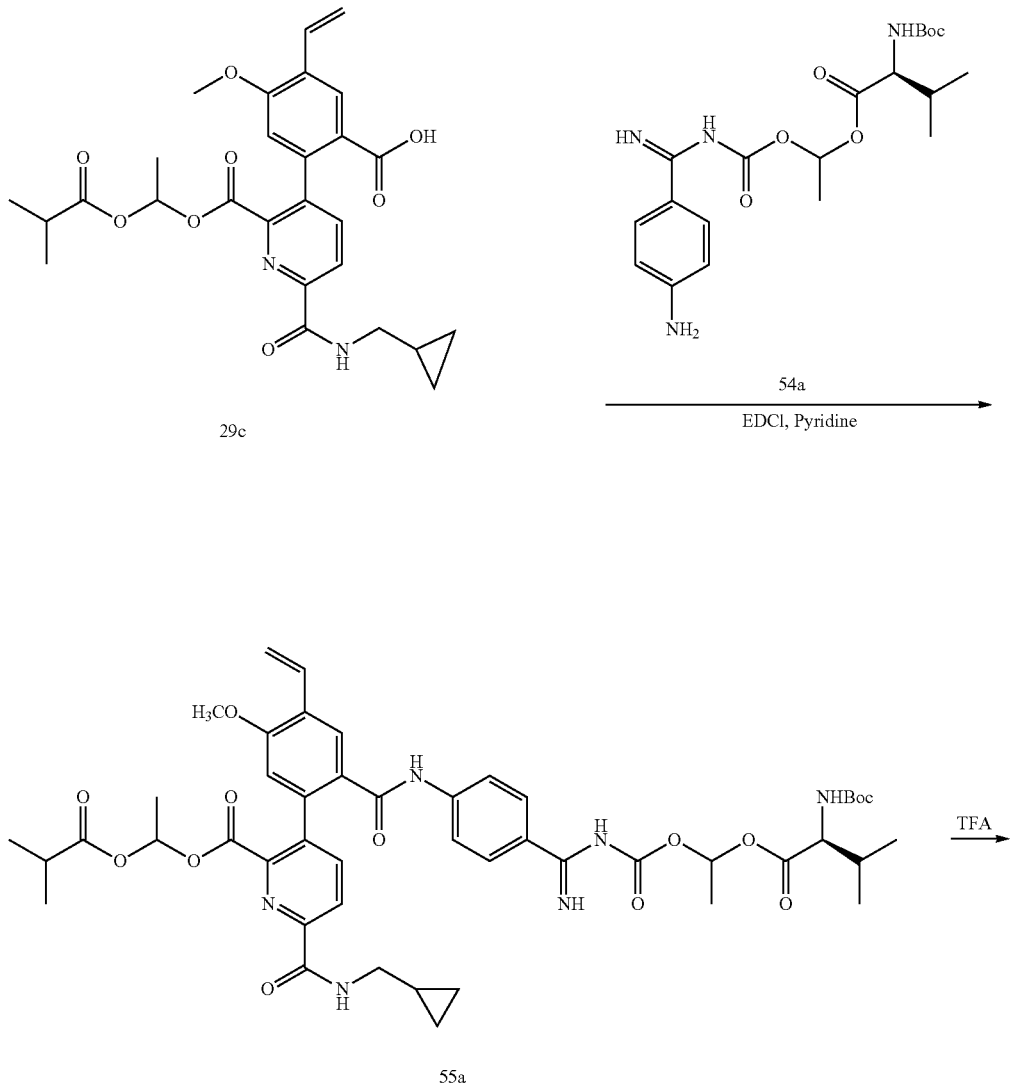

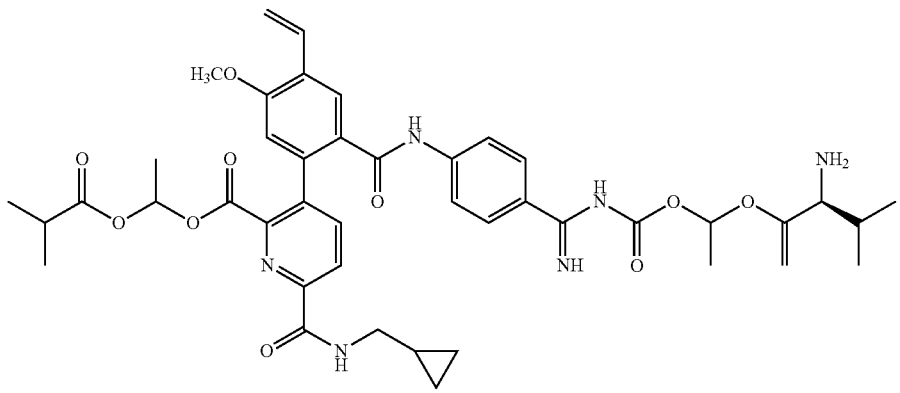

55b

Preparation of 1-(isobutyryloxy)ethyl 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinate (55b)

Step-1: Preparation of 1-(isobutyryloxy)ethyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinate (55a)

Compound (55a) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.65 g, 1.27 mmol) using EDCI (0.37 g, 1.91 mmol) and (2S)-1-((((4-aminophenyl)(imino)methyl)carbamoyl)oxy)ethyl 2-((tert-butoxycarbonyl)amino)-3-methylbutanoate (54a) (0.65 g, 1.53 mmol) in DMF (10 mL) and Pyridine (2 mL) according to the procedure reported in step 4 of scheme 2. This gave after workup and purification by flash column chromatography [silica gel, 12 g eluting with a (9:1) mixture of ethyl acetate and methanol in hexanes 0 to 60%] followed by prep HPLC [eluting with CH$_3$CN in water (containing with 0.1% HCl) from 0-100%] 1-(isobutyryloxy)ethyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinate (55a) (0.27 g, 23% yield) as an off white solid; $^1$H NMR (300 MHz, DMSO-d$_6$) δ 10.53 (d, J=23.7 Hz, 1H, D$_2$O exchangeable), 9.22 (d, J=9.7 Hz, 2H, D$_2$O exchangeable), 8.56 (d, J=27.5 Hz, 1H, D$_2$O exchangeable), 8.32-8.18 (m, 1H), 8.07-7.89 (m, 4H), 7.77-7.58 (m, 2H), 7.26-7.12 (m, 1H), 7.12-6.94 (m, 2H), 6.90-6.78 (m, 1H), 6.74 (s, 1H), 6.05 (dd, J=17.8, 1.6 Hz, 1H), 5.44 (dd, J=11.2, 1.5 Hz, 1H), 3.88 (s, 3H), 3.83-3.76 (m, 1H), 3.23 (t, J=6.3 Hz, 2H), 2.46-2.31 (m, 1H), 2.03-1.88 (m, 1H), 1.48-1.40 (m, 3H), 1.38-1.33 (m, 9H), 1.21-1.14 (m, 3H), 1.12-1.05 (m, 1H), 1.03-0.94 (m, 6H), 0.89-0.82 (m, 6H), 0.50-0.39 (m, 2H), 0.32-0.21 (m, 2H); MS (ES$^+$) 916.8 (M+1); 937.8 (M+Na); (ES$^-$) 914.8 (M-1).

Step-2: Preparation of 1-(isobutyryloxy)ethyl 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinate (55b)

Compound (55b) was prepared from 1-(isobutyryloxy)ethyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinate (55a) (0.27 g, 0.29 mmol) in dichloromethane (12 mL) using 2,2,2-trifluoroacetic acid (0.45 mL, 5.79 mmol) according to the procedure reported in Step-4 of scheme 8. This gave after workup and purification by prep-HPLC [C18 column, eluting with CH$_3$CN in water (containing 0.1% HCl) from 0-100%] followed by lyophilization 1-(isobutyryloxy)ethyl 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinate (55b) (0.09 g, 37% yield) as a white solid. $^1$H NMR (300 MHz, DMSO-d$_6$) δ 10.76 (d, J=14.8 Hz, 1H, D$_2$O exchangeable), 10.13 (s, 1H, D$_2$O exchangeable), 8.79-8.46 (m, 4H, D$_2$O exchangeable), 8.22 (d, J=8.0 Hz, 1H), 8.10-7.94 (m, 2H), 7.89-7.66 (m, 4H), 7.12-6.89 (m, 3H), 6.73 (d, J=5.6 Hz, 1H), 6.17-5.99 (m, 1H), 5.44 (d, J=12.6 Hz, 1H), 3.92 (dd, J=19.8, 4.6 Hz, 5H), 3.24 (t, J=6.6 Hz, 2H), 2.45-2.33 (m, 1H), 2.26-2.13 (m, 1H), 1.58 (dd, J=5.5, 2.3 Hz, 3H), 1.17 (d, J=5.4 Hz, 3H), 1.12-1.05 (m, 1H), 1.02-0.95 (m, 12H), 0.52-0.40 (m, 2H), 0.34-0.23 (m, 2H); MS (ES$^+$) 815.8 (M+1).

Scheme 56

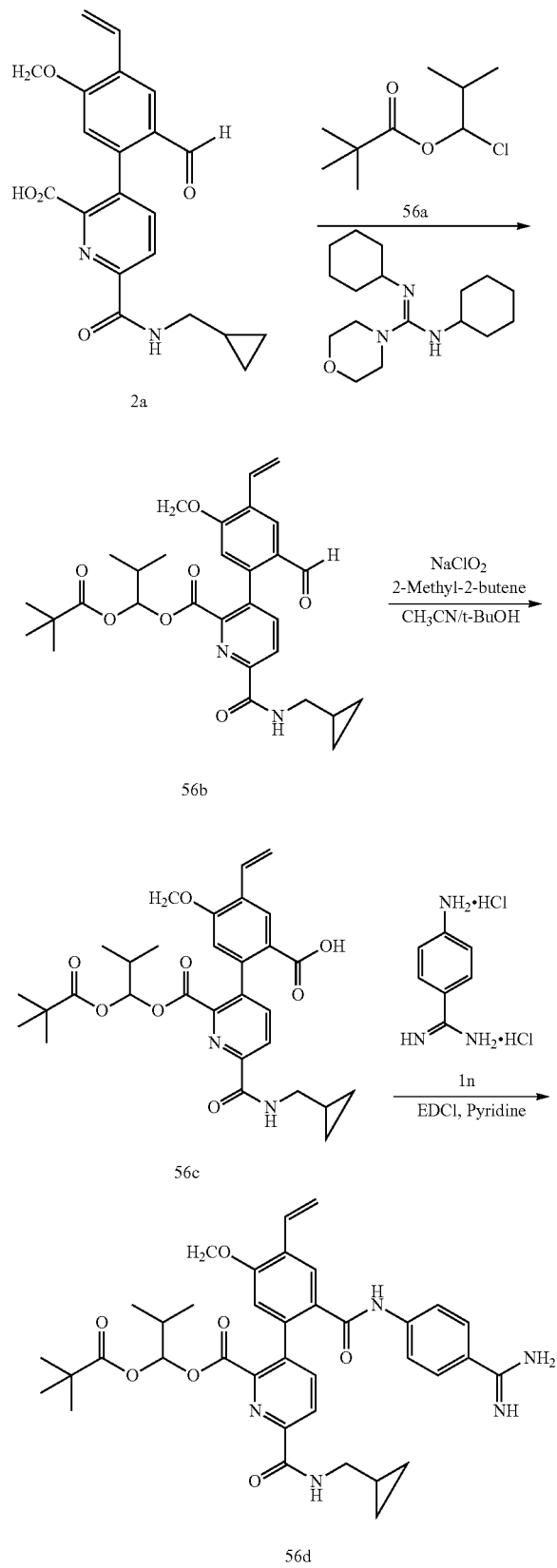

Preparation of 2-methyl-1-(pivaloyloxy)propyl 3-(2-((4-carbamimidoylphenyl)carbamoyl)-5-methoxy-4-vinylphenyl)-6-((cyclopropylmethyl)carbamoyl)picolinate (56d)

Step-1: Preparation of 2-methyl-1-(pivaloyloxy)propyl 6-((cyclopropylmethyl)carbamoyl)-3-(2-formyl-5-methoxy-4-vinylphenyl)picolinate (56b)

Compound (56b) was prepared according to the procedure reported in step 1 of scheme 8 from 6-(Cyclopropylmethylcarbamoyl)-3-(2-formyl-5-methoxy-4-vinylphenyl)picolinic acid (2a) (0.86 g, 2.25 mmol) in DMF (5 mL) using N,N'-Dicyclohexyl-4-morpholinecarboxamidine (0.83 g, 2.81 mmol) and 1-chloro-2-methylpropyl pivalate (56a) (0.43 g, 2.25 mmol). This gave after workup and purification by flash column chromatography (silica gel 40 g, eluting with ethyl acetate/hexanes, 0-100%) 2-methyl-1-(pivaloyloxy)propyl 6-((cyclopropylmethyl)carbamoyl)-3-(2-formyl-5-methoxy-4-vinylphenyl)picolinate (56b) (0.68 g, 57% yield) as a white solid; $^1$H NMR (300 MHz, DMSO-$d_6$) δ 9.69 (d, J=2.6 Hz, 1H), 8.51 (t, J=5.9 Hz, 1H), 8.27 (d, J=8.0 Hz, 1H), 8.13 (s, 1H), 8.06 (d, J=8.0 Hz, 1H), 7.08-6.93 (m, 2H), 6.51 (dd, J=7.0, 4.9 Hz, 1H), 5.98 (d, J=17.7 Hz, 1H), 5.44 (d, J=11.5 Hz, 1H), 3.89 (d, J=4.8 Hz, 3H), 3.26 (t, J=6.5 Hz, 2H), 1.83 (dt, J=11.3, 6.8 Hz, 1H), 1.13-1.00 (m, 10H), 0.85-0.72 (m, 6H), 0.52-0.42 (m, 2H), 0.28 (q, J=4.9 Hz, 2H); Analysis calculated for $C_{30}H_{36}N_2O_7$: C, 67.15; H, 6.76; N, 5.22; found: C, 66.74; H, 6.81; N, 5.19.

Step-2: Preparation of 2-(6-((cyclopropylmethyl)carbamoyl)-2-((2-methyl-1-(pivaloyloxy)propoxy)carbonyl)pyridin-3-yl)-4-methoxy-5-vinylbenzoic acid (56c)

Oxidation of 2-methyl-1-(pivaloyloxy)propyl 6-((cyclopropylmethyl)carbamoyl)-3-(2-formyl-5-methoxy-4-vinylphenyl)picolinate (56b) (0.65 g, 1.21 mmol) using the procedure as reported in step 11 of scheme 1 gave after workup and purification by flash column chromatography (Silica gel, 12 g column, eluting with methanol in chloroform 0-100%) 2-(6-((cyclopropylmethyl)carbamoyl)-2-((2-methyl-1-(pivaloyloxy)propoxy)carbonyl)pyridin-3-yl)-4-methoxy-5-vinylbenzoic acid (56c) (0.45, 0.81 mmol, 66.8% yield) as white solid; $^1$H NMR (300 MHz, DMSO-$d_6$) δ 12.53 (s, 1H), 8.47 (dd, J=14.2, 6.1 Hz, 1H), 8.22 (d, J=8.0 Hz, 1H), 8.13 (s, 1H), 7.93 (d, J=8.0 Hz, 1H), 7.04-6.85 (m, 2H), 6.51 (d, J=4.7 Hz, 1H), 5.88 (d, J=16.8 Hz, 1H), 5.38 (dd, J=11.3, 1.2 Hz, 1H), 3.84 (d, J=6.2 Hz, 3H), 3.25 (t, J=6.5 Hz, 2H), 1.89-1.73 (m, 1H), 1.05 (d, J=8.1 Hz, 10H), 0.83-0.71 (m, 6H), 0.51-0.43 (m, 2H), 0.32-0.24 (m, 2H); MS (ES+) 553.1 (M+1), (ES−) 550.9 (M−1).

Step-3: Preparation of 2-methyl-1-(pivaloyloxy)propyl 3-(2-((4-carbamimidoylphenyl)carbamoyl)-5-methoxy-4-vinylphenyl)-6-((cyclopropylmethyl)carbamoyl)picolinate (56d)

Compound (56d) was prepared from 2-(6-((cyclopropylmethyl)carbamoyl)-2-((2-methyl-1-(pivaloyloxy)propoxy)carbonyl)pyridin-3-yl)-4-methoxy-5-vinylbenzoic acid (56c) (0.4 g, 0.73 mmol) using EDCI (0.28 g, 1.46 mmol) and 4-aminobenzimidamide dihydrochloride (1n) (0.38 g, 1.82 mmol) in DMF (10 mL) and Pyridine (10 mL) according to the procedure reported in step 4 of scheme 2. This gave after workup and purification by flash column chromatography (silica gel, 12 g, eluting with 0 to 100% CMW80 (CHCl$_3$-MeOH—H$_2$O) in chloroform) 2-methyl-1-(pivaloyloxy)propyl 3-(2-((4-carbamimidoylphenyl)carbamoyl)-5-methoxy-4-vinylphenyl)-6-((cyclopropylmethyl)

carbamoyl)picolinate (56d) (0.32 g, 65% yield) as white solid; ¹HNMR (300 MHz, DMSO-d₆) δ 10.71 (bs, 1H, D₂O exchangeable), 9.09 (bs, 4H, D₂O exchangeable), 8.36 (s, 1H), 8.21 (d, J=7.7 Hz, 1H), 8.10-7.89 (m, 2H), 7.79 (s, 4H), 7.03 (m, 2H), 6.54 (s, 1H), 6.05 (d, J=17.7 Hz, 1H), 5.44 (d, J=12.3 Hz, 1H), 3.87 (s, 3H), 3.24 (m, 2H), 1.80 (bs, 1H), 1.08 (m, 10H), 0.76 (d, J=6.5 Hz, 6H), 0.47 (m, 2H), 0.27 (m, 2H); MS (ES+) 670.0 (M+1), (ES−) 704.2 (M+Cl); Analysis calculated for $C_{37}H_{43}N_5O_7 \cdot HCl \cdot H_2O$: C, 61.36; H, 6.40; Cl, 4.90; N, 9.67; found: C, 61.06; H, 6.37; Cl, 4.55; N, 9.55.

Preparation of 2-methyl-1-(pivaloyloxy)propyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (57a)

Compound (57a) was prepared from 2-methyl-1-(pivaloyloxy)propyl 3-(2-((4-carbamimidoylphenyl)carbamoyl)-5-methoxy-4-vinylphenyl)-6-((cyclopropylmethyl)carbamoyl)picolinate (56d) (0.14 g, 0.21 mmol), and hexyl chloroformate (0.339 mL, 2.075 mmol), using TEA (0.29 mL, 2.08 mmol) as base in acetonitrile (10 mL) according to the procedure reported in scheme 6. This gave after workup, purification by flash column chromatography [silica gel 24 g, eluting with ethyl acetate in hexanes from 0-100%] 2-methyl-1-(pivaloyloxy)propyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (57a) (0.086 g, 52% yield) as an off-white solid; ¹H NMR (300 MHz, DMSO-d₆) δ 10.64-10.39 (2bs, 1H, D₂O exchangeable), 9.36-8.72 (2bs, 2H, D₂O exchangeable), 8.53-8.30 (m, 1H), 8.27-8.16 (m, 1H), 8.07-7.84 (m, 4H), 7.77-7.56 (m, 2H), 7.15-6.91 (m, 2H), 6.69-6.39 (m, 1H), 6.03 (dd, J=17.8, 1.6 Hz, 1H), 5.51-5.34 (m, 1H), 3.99 (t, J=6.6 Hz, 2H), 3.87 (s, 3H), 3.30-3.19 (m, 2H), 1.79 (s, 1H), 1.65-1.49 (m, 2H), 1.43-1.17 (m, 6H), 1.16-0.95 (m, 10H), 0.92-0.83 (m, 2H), 0.82-0.68 (m, 7H), 0.54-0.38 (m, 2H), 0.34-0.19 (m, 2H); MS (ES+): 798.7 (M+1), 820.7 (M+Na); MS (ES−): 796.7 (M−1); Analysis calculated for $C_{44}H_{55}N_5O_9 \cdot 0.25H_2O$: C, 65.86; H, 6.97; N, 8.73; found: C, 65.73; H, 6.98; N, 8.52.

Scheme 57

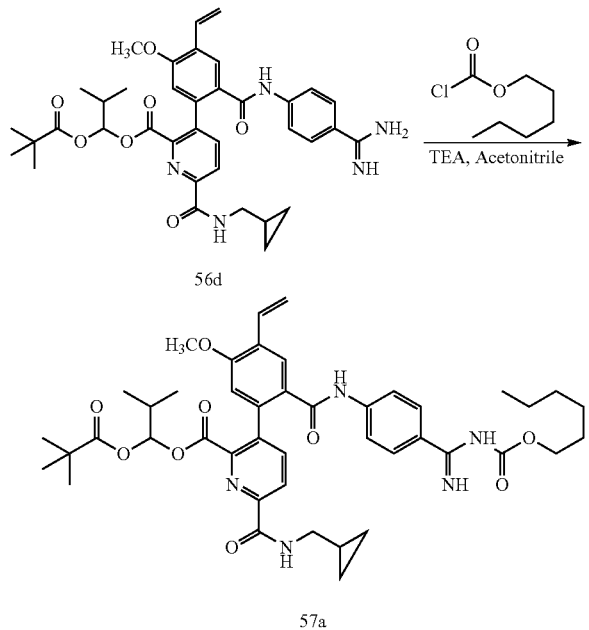

Scheme 58

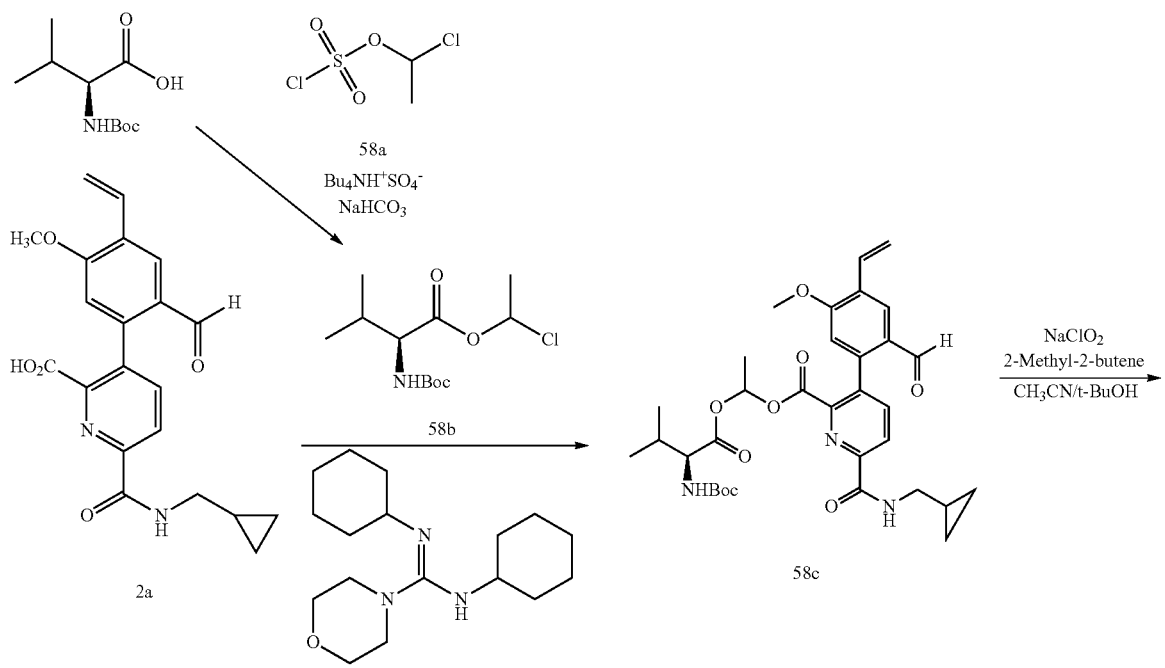

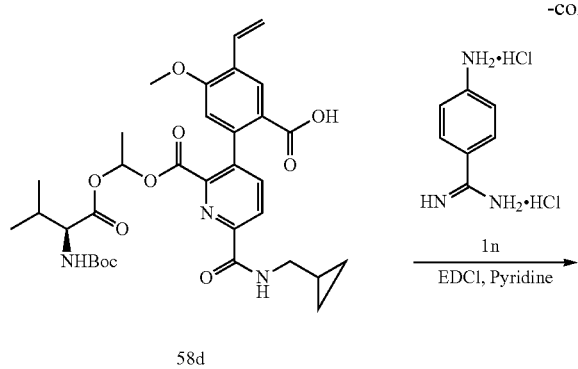

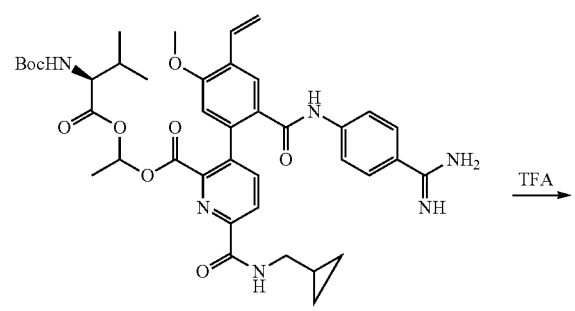

58d

58e

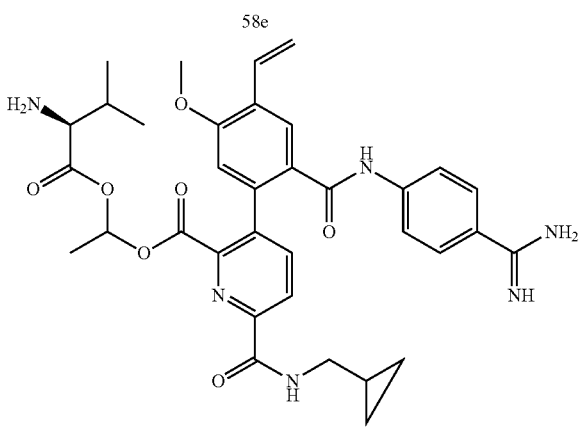

58f

Preparation of 1-(((S)-2-amino-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate Hydrochloride (58f)

Step-1: Preparation of (2S)-1-chloroethyl 2-((tert-butoxycarbonyl)amino)-3-methylbutanoate (58b)

To a vigorously stirred ice cold solution of L-Boc-Valine (5.2 g, 23.93 mmol), sodium bicarbonate (8.04 g, 96 mmol), tetrabutylammonium hydrogen sulfate (0.813 g, 2.39 mmol) in water (75 mL) and $CH_2Cl_2$ (75 mL) was added a solution of 1-chloroethyl sulfochloridate (58a) (6.0 g, 33.5 mmol, prepared from 1-chloroethyl chloroformate and chlorosulfonic acid according to procedure reported in U.S. Pat. Appl. Publ., 20140056849) in dichloromethane (20 mL). The reaction mixture was allowed to warm to room temperature over a period of 16 h. The organic layer was separated washed with brine (2×100 mL), dried, filtered and concentrated in vacuum to dryness. The residue was purified by flash column chromatography (silica gel 80 g, eluting with 0-50% ethyl acetate in hexane) to furnish ((2S)-1-chloroethyl 2-((tert-butoxycarbonyl)amino)-3-methylbutanoate (58b) (3.5 g, 52% yield) as a colorless oil. MS (ES−) 314.2 (M+Cl).

Step-2: Preparation of 1-(((S)-2-((tert-butoxycarbonyl)amino)-3-methylbutanoyl)oxy)ethyl 6-((cyclopropylmethyl)carbamoyl)-3-(2-formyl-5-methoxy-4-vinylphenyl)picolinate (58c)

Compound (58c) was prepared according to the procedure reported in step 1 of scheme 8 from 6-((cyclopropylmethyl)carbamoyl)-3-(2-formyl-5-methoxy-4-vinylphenyl)picolinic acid (2a) (2.45 g, 6.43 mmol) in DMF (15 mL) using N,N'-Dicyclohexyl-4-morpholinecarboxamidine (2.36 g, 8.04 mmol) and (2S)-1-chloroethyl 2-((tert-butoxycarbonyl)amino)-3-methylbutanoate (58b) (2.7 g, 9.65 mmol). This gave after workup and purification by flash column chromatography (silica gel 25 g, eluting with ethyl acetate/Hexanes, 0-100%) 1-(((S)-2-((tert-butoxycarbonyl)amino)-3-methylbutanoyl)oxy)ethyl 6-((cyclopropylmethyl)carbamoyl)-3-(2-formyl-5-methoxy-4-vinylphenyl)picolinate (58c) (3 g, 75% yield) as a yellow solid. MS (ES+) 624.8 (M+1), 646.7 (M+Na)

Step-3: Preparation of 2-(6-((cyclopropylmethyl)carbamoyl)-2-((6S)-6-isopropyl-3,10,10-trimethyl-5,8-dioxo-2,4,9-trioxa-7-azaundecan-1-oyl)pyridin-3-yl)-4-methoxy-5-vinylbenzoic acid (58d)

Oxidation of 1-(((S)-2-((tert-butoxycarbonyl)amino)-3-methylbutanoyl)oxy)ethyl 6-((cyclopropylmethyl)carbamoyl)-3-(2-formyl-5-methoxy-4-vinylphenyl)picolinate (58c) (2.0 g, 3.21 mmol) using the procedure as reported in step 11 of scheme 1 gave after workup 2-(6-((cyclopropylmethyl)carbamoyl)-2-((6S)-6-isopropyl-3,10,10-trimethyl-5,8-dioxo-2,4,9-trioxa-7-azaundecan-1-oyl)pyridin-3-yl)-4-methoxy-5-vinylbenzoic acid (58d) (2 g, 97% yield) as a yellow solid, which was used as such in next step without further purification. MS (ES+) 662.6 (M+Na); (ES−) 638.6 (M−1).

Step-4: Preparation of 1-(((S)-2-((tert-butoxycarbonyl)amino)-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate (58e)

Compound (58e) was prepared 2-(6-((cyclopropylmethyl)carbamoyl)-2-((6S)-6-isopropyl-3,10,10-trimethyl-5,8-dioxo-2,4,9-trioxa-7-azaundecan-1-oyl)pyridin-3-yl)-4-methoxy-5-vinylbenzoic acid (58d) (0.92 g, 1.43 mmol) using EDCI (0.41 g, 2.15 mmol) and 4-aminobenzimidamide dihydrochloride (1n) (0.36 g, 1.72 mmol) in DMF (20 mL) and Pyridine (5 mL) according to the procedure reported in step 4 of scheme 2. This gave after workup and purification by flash column chromatography [silica gel (12 g), eluting with EtOAc in hexane from 0-100%] 1-(((S)-2-((tert-butoxycarbonyl)amino)-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate (58e) (0.14 g, 13% yield) as an off white solid. MS (ES$^+$) 757.8 (M+1).

Step-5: Preparation of 1-(((S)-2-amino-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate Hydrochloride (58f)

Compound (58f) was prepared from 1-(((S)-2-((tert-butoxycarbonyl)amino)-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate (58e) (0.14 g, 0.19 mmol) in dichloromethane (10 mL) using 2,2,2-trifluoroacetic acid (0.29 mL, 3.7 mmol) according to the procedure reported in Step-4 of scheme 8. This gave after workup and purification by preparative HPLC [eluting with CH$_3$CN in water (containing with 0.1% HCl) from 0-100%] followed by lyophilization 1-(((S)-2-amino-3-methylbutanoyl)oxy)ethyl 3-(2-((4-carbamimidoylphenyl)carbamoyl)-5-methoxy-4-vinylphenyl)-6-((cyclopropylmethyl)carbamoyl)picolinate Hydrochloride (58f) (26 mg, 0.040 mmol, 21.40% yield) as a white solid; $^1$H NMR (300 MHz, DMSO-d$_6$) δ 10.78 (d, J=22.3 Hz, 1H), 9.28 (s, 2H, D$_2$O exchangeable), 9.04 (s, 2H, D$_2$O exchangeable), 8.58 (s, 3H, D$_2$O exchangeable), 8.52-8.41 (m, 1H), 8.29-8.19 (m, 1H), 8.09-7.95 (m, 2H), 7.80 (d, J=5.9 Hz, 4H), 7.10-6.94 (m, 2H), 6.91-6.82 (m, 1H), 6.10 (d, J=18.0 Hz, 1H), 5.45 (dd, J=11.2, 1.5 Hz, 1H), 3.91-3.84 (m, 4H), 3.27-3.21 (m, 2H), 2.14-1.96 (m, 1H), 1.34-1.18 (m, 3H), 1.13-1.00 (m, 1H), 0.92-0.81 (m, 6H), 0.49-0.37 (m, 2H), 0.30-0.21 (m, 2H); MS (ES+) 657.7 (M+1); (ES−) 691.8 (M+Cl).

Scheme 59

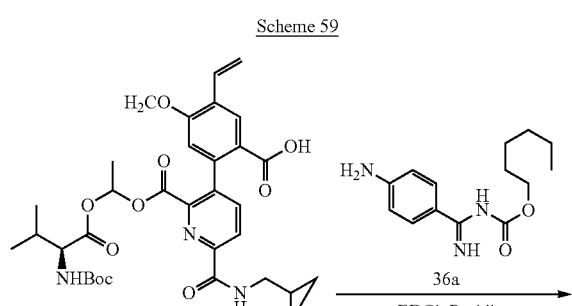

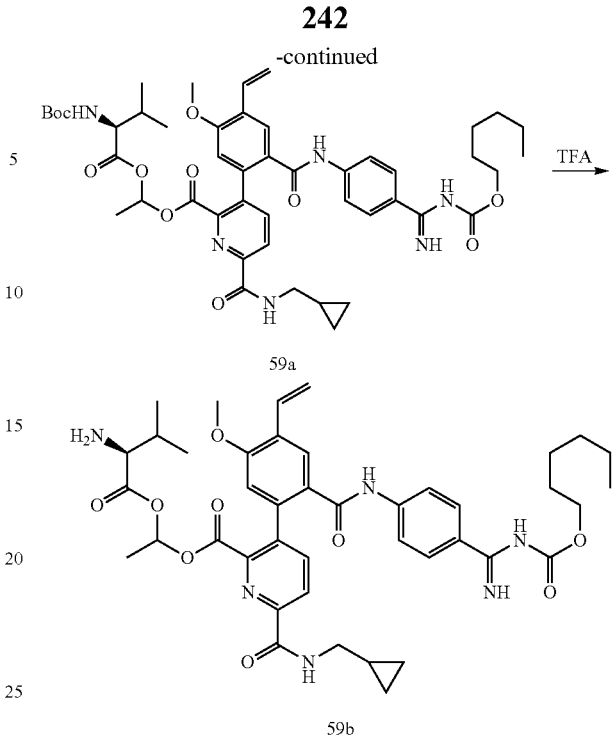

Preparation of 1-(((S)-2-amino-3-methylbutanoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate Hydrochloride (59b)

Step-1: Preparation of 1-(((S)-2-((tert-butoxycarbonyl)amino)-3-methylbutanoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (59a)

Compound (59a) was prepared 2-(6-((cyclopropylmethyl)carbamoyl)-2-((6S)-6-isopropyl-3,10,10-trimethyl-5,8-dioxo-2,4,9-trioxa-7-azaundecan-1-oyl)pyridin-3-yl)-4-methoxy-5-vinylbenzoic acid (58d) (0.49 g, 0.77 mmol) using EDCI (0.22 g, 1.15 mmol) and hexyl ((4-aminophenyl)(imino)methyl)carbamate (36a) (0.24 g, 0.92 mmol) in DMF (20 mL) and Pyridine (4 mL) according to the procedure reported in step 4 of scheme 2. This gave after workup and purification by flash column chromatography [silica gel (12 g), eluting with EtOAc in hexane from 0-100%] 1-(((S)-2-((tert-butoxycarbonyl)amino)-3-methylbutanoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (59a) (0.23 g, 33% yield) as an off white solid; MS (ES+) 885.8 (M+1), 907.8 (M+Na).

Step-2: Preparation of 1-(((S)-2-amino-3-methylbutanoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate Hydrochloride (59b)

Compound (59b) was prepared 1-(((S)-2-((tert-butoxycarbonyl)amino)-3-methylbutanoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl) picolinate (59a) (0.23 g, 0.25 mmol) in dichloromethane (5 mL) using 2,2,2-trifluoroacetic acid (0.39 mL, 5.1 mmol) according to the procedure reported in Step-4 of scheme 8. This gave after workup and purification by preparative HPLC [C18 column, eluting with $CH_3CN$ in water (containing with 0.1% HCl) from 0-100%] followed by lyophilization 1-(((S)-2-amino-3-methylbutanoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate Hydrochloride (59b) (0.06 g, 29% yield) as a white solid; $^1$H NMR (300 MHz, DMSO-$d_6$) δ 12.33 (s, 1H, $D_2O$ exchangeable), 10.85-10.70 (m, 1H, $D_2O$ exchangeable), 10.33 (s, 1H, $D_2O$ exchangeable), 8.55 (m, 4H, $D_2O$ exchangeable), 8.30-8.16 (m, 1H), 8.10-7.93 (m, 2H), 7.78 (s, 4H), 7.13-6.95 (m, 2H), 6.88 (q, J=5.3 Hz, 1H), 6.10 (dd, J=16.9, 5.6 Hz, 1H), 5.45 (d, J=11.5 Hz, 1H), 4.26 (t, J=5.9 Hz, 2H), 3.94-3.79 (m, 4H), 3.29-3.18 (m, 2H), 2.14-1.99 (m, 1H), 1.74-1.58 (m, 2H), 1.38-1.24 (m, 9H), 0.95-0.78 (m, 10H), 0.50-0.37 (m, 2H), 0.28 (d, J=4.6 Hz, 2H); MS (ES$^+$) 785.6 (M+1); (ES) 819.6 (M+Cl).

Preparation of 1-((isopropoxycarbonyl)oxy)ethyl 3-(2-((4-(N-((3-(tert-butoxy)-3-oxopropoxy)carbonyl)carbamimidoyl)phenyl)carbamoyl)-5-methoxy-4-vinylphenyl)-6-((cyclopropylmethyl)carbamoyl) picolinate (60c)

Step-1: Preparation of tert-butyl 3-(((4-nitrophenoxy)carbonyl)oxy)propanoate (60a)

Compound (60a) was prepared according to the procedure described in step 1 of scheme 24 from 4-nitrophenyl chloroformate (2.84 g, 13.68 mmol) in THF (50 mL) using tert-butyl 3-hydroxypropanoate (2 g, 13.68 mmol) and triethylamine (4.20 mL, 30.1 mmol). This gave after workup tert-butyl 3-(((4-nitrophenoxy)carbonyl)oxy)propanoate (60a) (3.5 g, 82% yield) as a clear oil; $^1$H NMR (300 MHz, DMSO-$d_6$) δ 8.35-8.28 (m, 2H), 7.59-7.50 (m, 2H), 4.42 (t, J=6.0 Hz, 2H), 2.70 (t, J=6.0 Hz, 2H), 1.42 (s, 9H); MS (ES+) 334.4 (M+Na).

Scheme 60

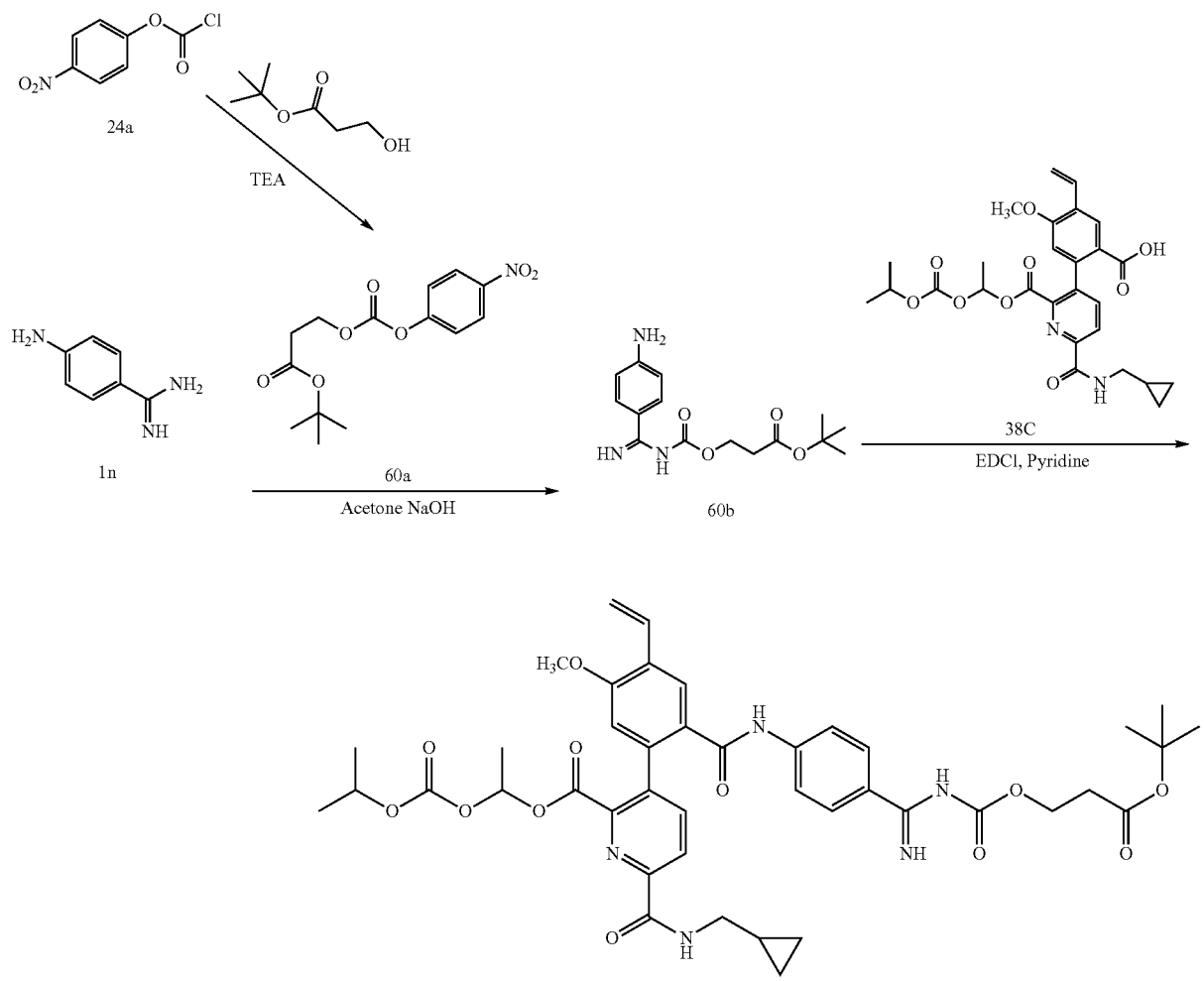

Step-2: Preparation of tert-butyl 3-((((4-aminophenyl)(imino)methyl)carbamoyl)oxy)propanoate (60b)

Compound (60b) was prepared from 4-aminobenzimidamide dihydrochloride (1n) (1.85 g, 8.87 mmol) in acetone/water (20 mL, 4:1 ratio), using NaOH (0.75 g, 18.64 mmol) and hexyl tert-butyl 3-(((4-nitrophenoxy)carbonyl)oxy)propanoate (60a) (3.32 g, 10.65 mmol) according to the procedure reported in step 4 of scheme 23. This gave after workup and purification by flash column chromatography (silica gel 12 g, eluting with 0-100% ethyl acetate/MeOH (9:1) in hexanes) tert-butyl 3-((((4-aminophenyl)(imino)methyl)carbamoyl)oxy)propanoate (60b) (1.65 g, 61% yield) as a semisolid. $^1$H NMR (300 MHz, DMSO-$d_6$) δ 9.14 (s, 1H, $D_2O$ exchangeable), 8.65 (s, 1H, $D_2O$ exchangeable), 7.83-7.68 (m, 2H), 6.62-6.47 (m, 2H), 5.86 (s, 2H, $D_2O$ exchangeable), 4.15 (t, J=6.2 Hz, 2H), 2.56 (t, J=6.2 Hz, 2H), 1.41 (s, 9H); MS (ES−) 306.5 (M−1)

Step-3: Preparation of 1-((isopropoxycarbonyl)oxy)ethyl 3-(2-((4-(N-((3-(tert-butoxy)-3-oxopropoxy)carbonyl)carbamimidoyl)phenyl)carbamoyl)-5-methoxy-4-vinylphenyl)-6-((cyclopropylmethyl)carbamoyl)picolinate (60c)

Compound (60c) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.5 g, 1.42 mmol) using EDCI (0.27 g, 1.42 mmol) and tert-butyl 3-((((4-aminophenyl)(imino)methyl)carbamoyl)oxy)propanoate (60b) (0.35 g, 1.14 mmol) in DMF (10 mL) and Pyridine (2 mL) according to the procedure reported in step 4 of scheme 2. This gave after workup and purification by flash column chromatography [silica gel (12 g), eluting with EtOAc/MeOH (9:1) in hexane from 0-60%] then prep HPLC [C18 column, eluting with $CH_3CN$ in water (containing with 0.1% HCl) from 0-100%] followed by lyophilization 1-((isopropoxycarbonyl)oxy)ethyl 3-(2-((4-(N-((3-(tert-butoxy)-3-oxopropoxy)carbonyl)carbamimidoyl)phenyl)carbamoyl)-5-methoxy-4-vinylphenyl)-6-((cyclopropylmethyl)carbamoyl)picolinate (60c) (85 mg, 11% yield) as a white solid; $^1$H NMR (300 MHz, DMSO-$d_6$) δ 10.69 (d, J=24.8 Hz, 1H, $D_2O$ exchangeable), 8.61 (d, J=28.9 Hz, 1H, $D_2O$ exchangeable), 8.22 (d, J=8.0 Hz, 1H), 8.06-7.95 (m, 2H), 7.87-7.66 (m, 4H), 7.10-6.93 (m, 2H), 6.63 (q, J=5.3 Hz, 1H), 6.06 (dd, J=17.8, 1.4 Hz, 1H), 5.45 (d, J=11.6 Hz, 1H), 4.79-4.62 (m, 1H), 4.48-4.30 (m, 2H), 3.89 (s, 3H), 3.29-3.14 (m, 2H), 2.76-2.62 (m, 2H), 1.41 (s, 9H), 1.28-1.00 (m, 12H), 0.51-0.39 (m, 2H), 0.31-0.21 (m, 2H); MS (ES+) 816.7 (M+1); 838.79 (M+Na); (ES−) 850.9 (M+Cl); Analysis calculated for $C_{42}H_{49}N_5O_{12}$·HCl·1.5$H_2O$: C, 57.37; H, 6.08; N, 7.96; found: C, 57.35; H, 6.13; N, 7.96.

Scheme 61

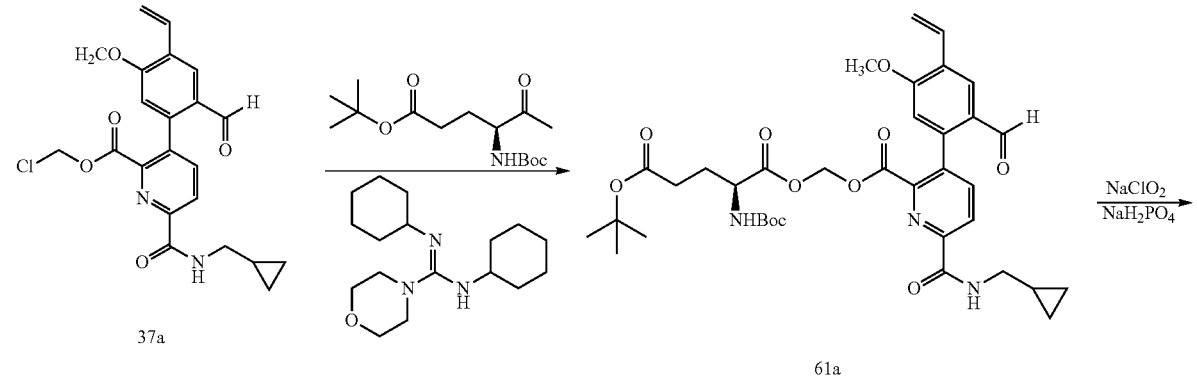

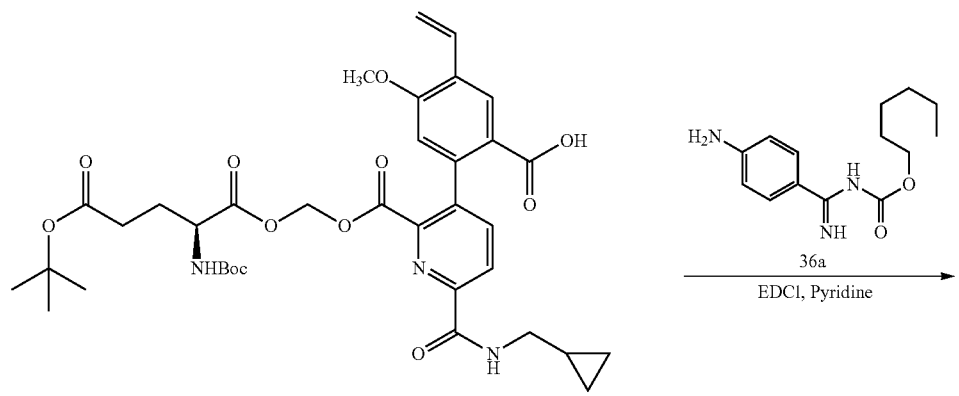

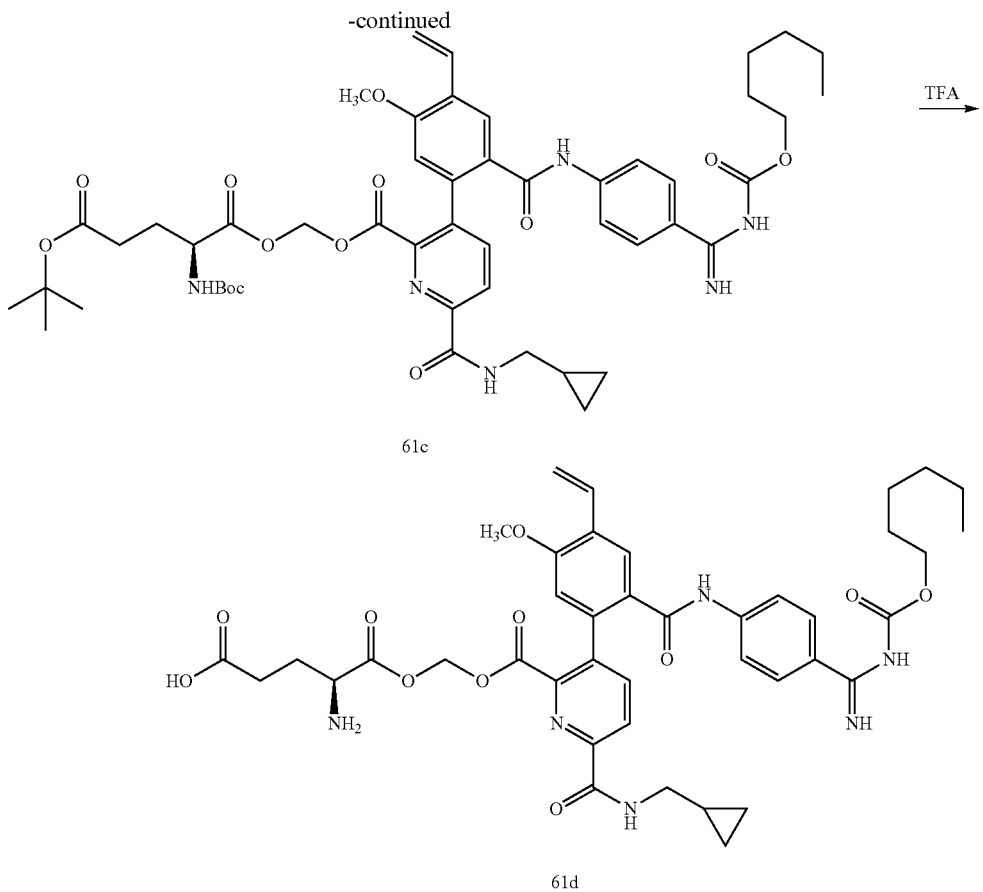

Preparation of (S)-4-amino-5-((((6-((cyclopropylmethyl)carbamoyl)-3-(2-((4-(N-((hexyloxy)carbonyl)carbamimidoyl)phenyl)carbamoyl)-5-methoxy-4-vinylphenyl)picolinoyl)oxy)methoxy)-5-oxopentanoic acid (61d)

Step-1: Preparation of (S)-5-tert-butyl 1-(((6-((cyclopropylmethyl)carbamoyl)-3-(2-formyl-5-methoxy-4-vinylphenyl)picolinoyl)oxy)methyl) 2-((tert-butoxycarbonyl)amino)pentanedioate (61a)

Compound (61a) was prepared according to the procedure reported in step 1 of scheme 8 from chloromethyl 6-((cyclopropylmethyl)carbamoyl)-3-(2-formyl-5-methoxy-4-vinylphenyl)picolinate (37a) (2.0 g, 4.66 mmol) in DMF (15 mL) using N,N'-Dicyclohexyl-4-morpholinecarboxamidine (2.05 g, 7.0 mmol) and (S)-5-(tert-butoxy)-2-((tert-butoxycarbonyl)amino)-5-oxopentanoic acid (1.84 g, 6.06 mmol). This gave after workup and purification by flash column chromatography (silica gel 25 g, eluting with ethyl acetate/Hexanes, 0-100%) (S)-5-tert-butyl 1-(((6-((cyclopropylmethyl)carbamoyl)-3-(2-formyl-5-methoxy-4-vinylphenyl)picolinoyl)oxy)methyl) 2-((tert-butoxycarbonyl)amino) pentanedioate (61a) (2.25 g, 69% yield) as a colorless foam; $^1$H NMR (300 MHz, DMSO-$d_6$) δ 9.68 (s, 1H), 8.70-8.56 (m, 1H), 8.36-8.24 (m, 1H), 8.13 (d, J=3.8 Hz, 1H), 8.07 (d, J=8.0 Hz, 1H), 7.34 (dd, J=7.9, 3.5 Hz, 1H), 7.08-6.92 (m, 2H), 6.00 (dt, J=17.8, 1.3 Hz, 1H), 5.86-5.70 (m, 2H), 5.44 (dd, J=11.2, 1.4 Hz, 1H), 4.02-3.94 (m, 1H), 3.90 (s, 3H), 3.31-3.18 (m, 2H), 2.24 (t, J=7.4 Hz, 2H), 1.91-1.57 (m, 2H), 1.48-1.00 (m, 19H), 0.51-0.41 (m, 2H), 0.33-0.24 (m, 2H).

Step-2: Preparation of (S)-2-(2-(6-(3-(tert-butoxy)-3-oxopropyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (61b)

Oxidation of (S)-5-tert-butyl 1-(((6-((cyclopropylmethyl)carbamoyl)-3-(2-formyl-5-methoxy-4-vinylphenyl)picolinoyl)oxy)methyl) 2-((tert-butoxycarbonyl)amino)pentanedioate (61a) (2.2 g, 3.16 mmol) using the procedure as reported in step 11 of scheme 1 gave after workup (S)-2-(2-(6-(3-(tert-butoxy)-3-oxopropyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (61b) (2.2 g, 98% yield) as a light yellow solid; $^1$H NMR (300 MHz, DMSO-$d_6$) δ 12.57 (s, 1H), 8.56 (s, 1H), 8.23 (d, J=8.0 Hz, 1H), 8.11 (s, 1H), 7.96 (d, J=8.0 Hz, 1H), 7.33 (d, J=7.9 Hz, 1H), 6.97 (dd, J=17.8, 11.3 Hz, 1H), 6.87 (s, 1H), 5.91 (d, J=17.9 Hz, 1H), 5.85-5.68 (m, 2H), 5.39 (d, J=11.2 Hz, 1H), 4.08-3.92 (m, 1H), 3.85 (s, 3H), 3.31-3.16 (m, 2H), 2.31-2.18 (m, 2H), 1.93-1.76 (m, 1H), 1.76-1.60 (m, 1H), 1.45-1.25 (m, 19H), 0.52-0.39 (m, 2H), 0.34-0.21 (m, 2H).

Step-3: Preparation of (S)-5-tert-butyl 1-(((6-((cyclopropylmethyl)carbamoyl)-3-(2-((4-(N-((hexyloxy)carbonyl)carbamimidoyl)phenyl)carbamoyl)-5-methoxy-4-vinylphenyl)picolinoyl)oxy)methyl) 2-((tert-butoxycarbonyl)amino)pentanedioate (61c)

Compound (61c) was prepared from (S)-2-(2-(6-(3-(tert-butoxy)-3-oxopropyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (61b) (0.48 g, 0.67 mmol) using EDCI (0.16 g, 0.81 mmol) and hexyl ((4-aminophenyl)(imino)methyl)carbamate (36a) (0.18 g, 0.67 mmol) in DMF (6 mL) and Pyridine (5 mL) according to the procedure reported in step 4 of scheme 2. This gave after workup and purification by flash column chromatography [silica gel 12 g, eluting with MeOH:EtOAc (9:1) in hexanes 0 to 100%] (S)-5-tert-butyl 1-(((6-((cyclopropylmethyl)carbamoyl)-3-(2-((4-(N-((hexyloxy)carbonyl)carbamimidoyl)phenyl)carbamoyl)-5-methoxy-4-vinylphenyl)picolinoyl)oxy)methyl) 2-((tert-butoxycarbonyl)amino)pentanedioate (61c) (0.31 g, 48.0% yield) as a gummy solid; MS (ES+) 957.8 (M+1) & 979.8 (M+Na).

Step-4: Preparation of (S)-4-amino-5-(((6-((cyclopropylmethyl)carbamoyl)-3-(2-((4-(N-((hexyloxy)carbonyl)carbamimidoyl)phenyl)carbamoyl)-5-methoxy-4-vinylphenyl)picolinoyl)oxy)methoxy)-5-oxopentanoic acid (61d)

Compound (61d) was prepared from ((S)-5-tert-butyl 1-(((6-((cyclopropylmethyl)carbamoyl)-3-(2-((4-(N-((hexyloxy)carbonyl)carbamimidoyl)phenyl)carbamoyl)-5-methoxy-4-vinylphenyl)picolinoyl)oxy)methyl) 2-((tert-butoxycarbonyl)amino)pentanedioate (61c) (0.3 g, 0.31 mmol) in dichloromethane (2 mL) using 2,2,2-trifluoroacetic acid (1.0 mL, 12.6 mmol) according to the procedure reported in Step-4 of scheme 8. This gave after workup and purification by reverse phase column chromatography (C18, 26 g) eluting with 0-100% 0.1% aqueous HCl and acetonitrile followed by lyophilization (S)-4-amino-5-(((6-((cyclopropylmethyl)carbamoyl)-3-(2-((4-(N-((hexyloxy)carbonyl)carbamimidoyl)phenyl)carbamoyl)-5-methoxy-4-vinylphenyl)picolinoyl)oxy)methoxy)-5-oxopentanoic acid (61d) (0.048 g, 19% yield) as a white powder; $^1$H NMR (300 MHz, DMSO-$d_6$) δ 12.55-12.12 (m, 2H), 10.77 (s, 1H), 8.81-8.41 (m, 3H), 8.25 (d, J=8.1 Hz, 1H), 8.10-7.97 (m, 2H), 7.77 (s, 4H), 7.15-6.92 (m, 2H), 6.15-6.08 (m, 1H), 5.96-5.73 (m, 2H), 5.52-5.39 (m, 1H), 4.31-4.16 (m, 2H), 4.13-4.00 (m, 1H), 3.89 (s, 3H), 3.29-3.16 (m, 2H), 2.61-2.20 (m, 2H), 2.03-1.87 (m, 2H), 1.74-1.56 (m, 2H), 1.46-1.20 (m, 6H), 1.17-1.00 (m, 1H), 0.91-0.84 (m, 3H), 0.49-0.39 (m, 2H), 0.31-0.23 (m, 2H); MS (ES+) 801.7 (M+1), MS (ES−) 835.8 (M+Cl).

Scheme 62

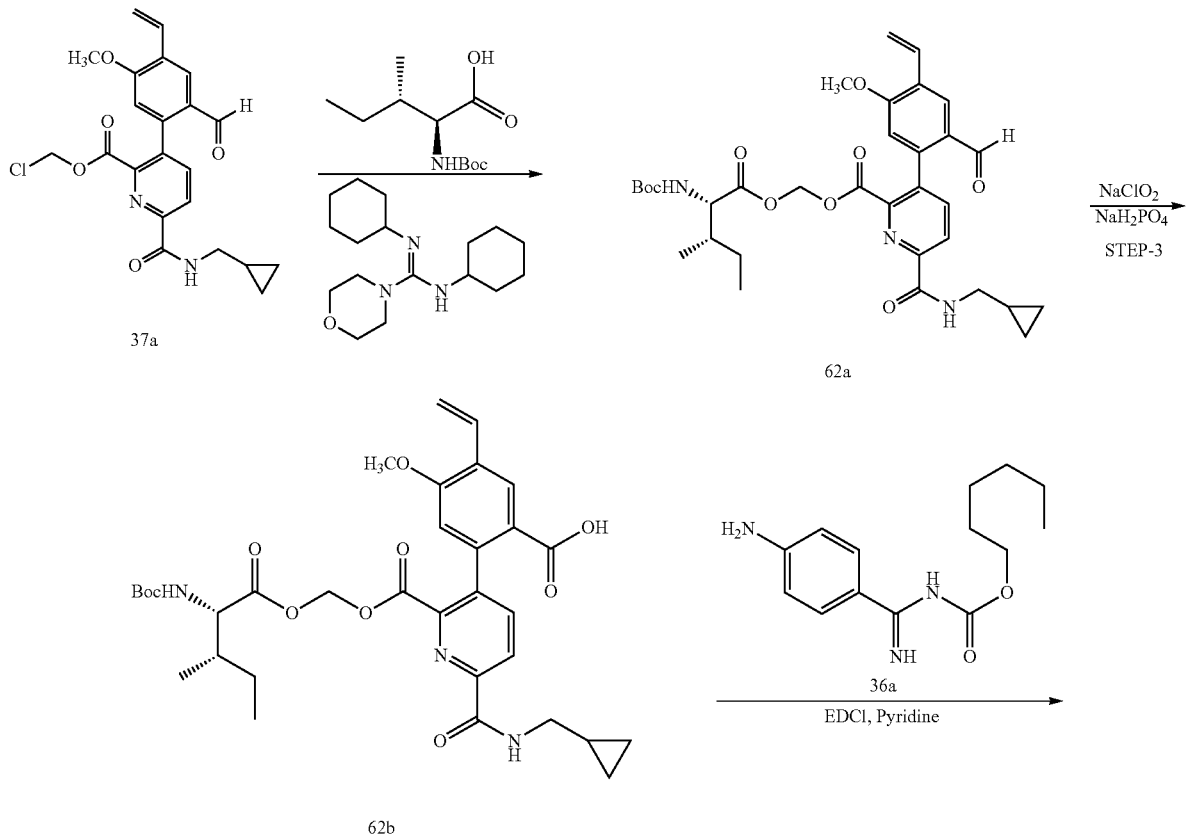

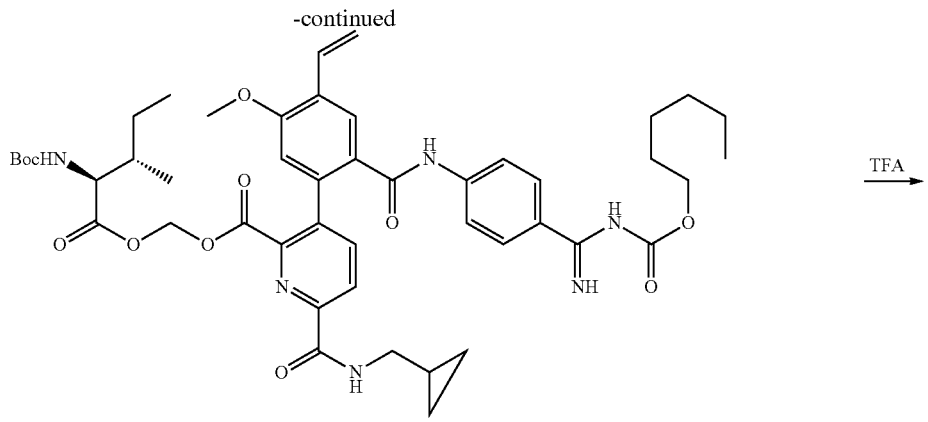

62c

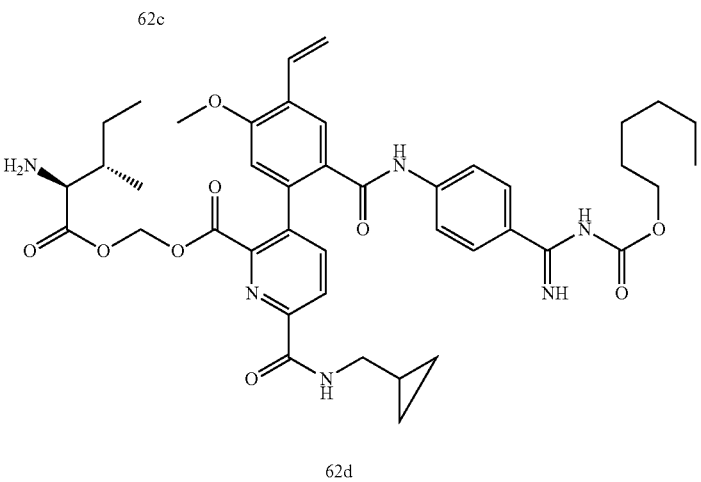

62d

Preparation of (((2S,3S)-2-amino-3-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (62d)

Step-1: Preparation of (((2S,3S)-2-((tert-butoxycarbonyl)amino)-3-methylpentanoyl)oxy)methyl 6-((cyclopropylmethyl)carbamoyl)-3-(2-formyl-5-methoxy-4-vinylphenyl)picolinate (62a)

Compound (62a) was prepared according to the procedure reported in step 1 of scheme 8 from chloromethyl 6-((cyclopropylmethyl)carbamoyl)-3-(2-formyl-5-methoxy-4-vinylphenyl)picolinate (37a) (1.3 g, 3.03 mmol) in DMF (10 mL) using N,N'-Dicyclohexyl-4-morpholinecarboxamidine (1.1 g, 3.8 mmol) and Boc-L isoleucine (0.84 g, 3.64 mmol). This gave after workup and purification by flash column chromatography (silica gel 40 g, eluting with ethyl acetate/Hexanes, 0-100%) (((2S,3S)-2-((tert-butoxycarbonyl)amino)-3-methylpentanoyl)oxy)methyl 6-((cyclopropylmethyl)carbamoyl)-3-(2-formyl-5-methoxy-4-vinylphenyl)picolinate (62a) (0.67 g, 36% yield) as a light yellow solid; $^1$H NMR (300 MHz, DMSO-d$_6$) δ 9.69 (d, J=1.2 Hz, 1H), 8.57 (t, J=5.8 Hz, 1H), 8.29 (dt, J=8.0, 2.4 Hz, 1H), 8.17-8.11 (m, 1H), 8.07 (d, J=8.1 Hz, 1H), 7.28 (d, J=7.8 Hz, 1H), 7.09-6.89 (m, 2H), 6.01 (dt, J=17.8, 1.5 Hz, 1H), 5.84 (dd, J=11.2, 5.9 Hz, 1H), 5.75 (dd, J=6.0, 2.2 Hz, 1H), 5.45 (dd, J=11.2, 1.4 Hz, 1H), 3.91 (s, 3H), 3.89-3.81 (m, 1H), 3.25 (p, J=6.4 Hz, 2H), 1.86-1.51 (m, 1H), 1.34 (d, J=4.3 Hz, 9H), 1.33-1.22 (m, 2H), 1.17-1.02 (m, 1H), 0.80-0.67 (m, 6H), 0.53-0.41 (m, 2H), 0.34-0.22 (m, 2H); MS (ES+) 646.6 (M+Na).

Step-2: Preparation of 2-(2-((S)-6-((S)-sec-butyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (62b)

Oxidation of (((2S,3S)-2-((tert-butoxycarbonyl)amino)-3-methylpentanoyl)oxy)methyl 6-((cyclopropylmethyl)carbamoyl)-3-(2-formyl-5-methoxy-4-vinylphenyl)picolinate (62a) (0.64 g, 99% yield) using the procedure as reported in step 11 of scheme 1 gave after workup 2-(2-((S)-6-((S)-sec-butyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (62b) (0.84 g, 129% yield) as a yellow solid; $^1$H NMR (300 MHz, DMSO-d$_6$) δ 12.56 (s, 1H, D$_2$O exchangeable), 8.56-8.43 (m, 1H), 8.27-8.19 (m, 1H), 8.12 (s, 1H), 7.99-7.93 (m, 1H), 7.27 (d, J=7.8 Hz, 1H), 6.98 (dd, J=17.8, 11.3 Hz, 1H), 6.88 (s, 1H), 5.96-5.81 (m, 2H), 5.74 (d, J=6.0 Hz, 1H), 5.39 (dd, J=11.2, 1.4 Hz, 1H), 3.86 (s, 3H), 3.25 (t, J=6.3 Hz, 2H), 1.76-1.54 (m, 1H), 1.41-1.31 (m, 9H), 1.32-1.20 (m, 2H), 1.19-1.04 (m, 1H), 0.74 (q, J=7.3, 6.6 Hz, 6H), 0.53-0.43 (m, 2H), 0.34-0.23 (m, 2H); MS (ES+) 662.6 (M+Na), 638.6 (M−1).

Step-3: Preparation of (((2S,3S)-2-((tert-butoxycarbonyl)amino)-3-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (62c)

Compound (62c) was prepared from 2-(2-((S)-6-((S)-sec-butyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (62b) (0.32 g, 0.5 mmol) using EDCI (1.5 equiv.) and hexyl ((4-aminophenyl)(imino)methyl)carbamate (36a) (0.17 g, 0.63 mmol) in DMF (3 mL) and Pyridine (3 mL) according to the procedure reported in step 4 of scheme 2. This gave after workup (((2S,3S)-2-((tert-butoxycarbonyl)amino)-3-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (62c) (0.39 g, 86% yield) which was used in next step without further purification; $^1$H NMR (300 MHz, DMSO-$d_6$) δ 10.55 (s, 1H), 9.41-8.75 (m, 2H, $D_2O$ exchangeable), 8.42 (s, 1H), 8.24 (d, J=8.0 Hz, 1H), 8.11-7.99 (m, 1H), 8.00-7.87 (m, 3H), 7.74-7.59 (m, 2H), 7.38-7.22 (m, 1H), 7.15-6.89 (m, 2H), 6.05 (d, J=17.8 Hz, 1H), 5.92-5.57 (m, 2H), 5.44 (d, J=11.6 Hz, 1H), 3.87 (d, J=12.4 Hz, 4H), 3.28-3.18 (m, 2H), 1.58 (d, J=7.3 Hz, 2H), 1.31 (d, J=12.2 Hz, 20H), 0.92-0.82 (m, 3H), 0.81-0.62 (m, 6H), 0.51-0.38 (m, 2H), 0.32-0.19 (m, 3H); MS (ES+) 886.60 (M+1), 908.53 (M+Na).

Step-4: Preparation of (((2S,3S)-2-amino-3-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (62d)

Compound (62d) was prepared from (((2S,3S)-2-((tert-butoxycarbonyl)amino)-3-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (62c) (0.38 g, 0.42 mmol) in dichloromethane (20 mL) using 2,2,2-trifluoroacetic acid (0.65 mL, 8.47 mmol) according to the procedure reported in Step-4 of scheme 8. This gave after workup and purification by flash column chromatography (C18, 26 g) eluting with 0.1% HCl and acetonitrile followed by lyophilization (((2S,3S)-2-amino-3-methylpentanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (62d) (0.13 g, 37% yield) as a white solid. $^1$H NMR (300 MHz, DMSO-$d_6$) δ 10.75 (s, 1H, $D_2O$ exchangeable), 10.46-10.14 (m, 2H, $D_2O$ exchangeable), 8.66-8.33 (m, 4H, 3H $D_2O$ exchangeable), 8.25 (d, J=8.1 Hz, 1H), 8.04 (d, J=8.2 Hz, 1H), 7.99 (s, 1H), 7.76 (d, J=1.7 Hz, 4H), 7.11-6.96 (m, 2H), 6.06 (dd, J=17.8, 1.5 Hz, 1H), 6.02-5.87 (m, 1H), 5.80 (s, 1H), 5.46 (dd, J=11.2, 1.4 Hz, 1H), 4.24 (t, J=6.5 Hz, 2H), 4.00 (s, 1H), 3.89 (s, 3H), 3.31-3.17 (m, 2H), 1.86-1.74 (m, 1H), 1.74-1.57 (m, 2H), 1.47-1.10 (m, 8H), 1.15-0.99 (m, 1H), 0.93-0.71 (m, 9H), 0.51-0.41 (m, 2H), 0.31-0.21 (m, 2H); MS (ES+) 785.7 (M+1), 807.7 (M+Na); Calculated for: $C_{42}H_{52}N_6O_9$ $(CF_3COOH)_2(H_2O)_{2.25}$. C; 52.20; H, 5.57; N, 7.98; found: C, 52.17; H, 5.26; N, 7.81.

Scheme 63

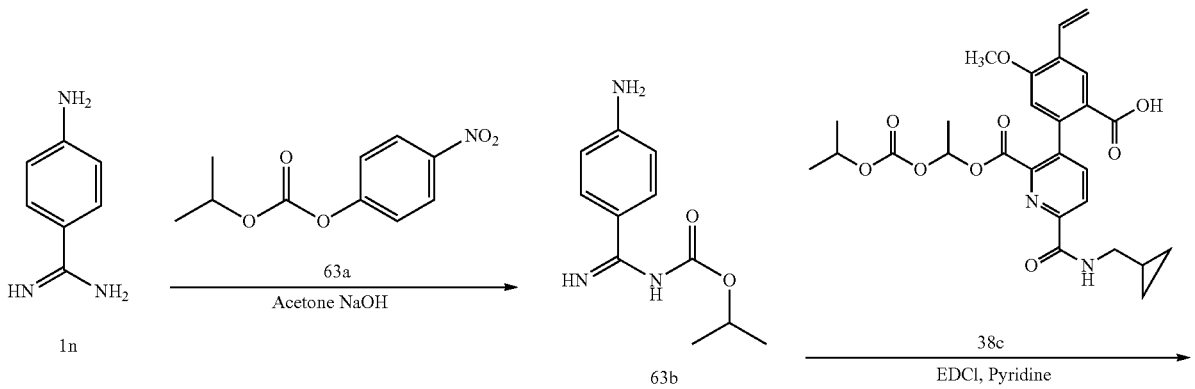

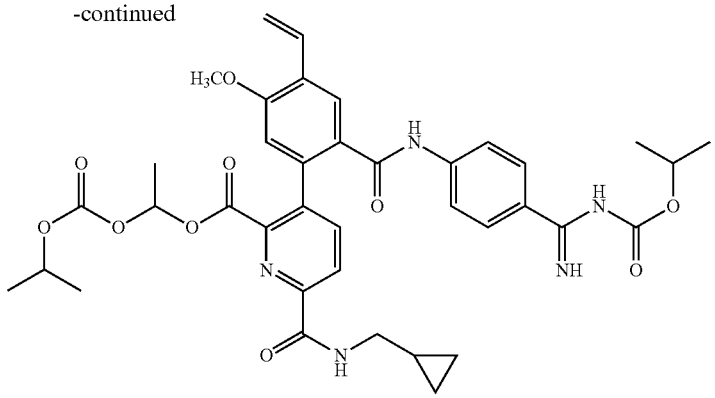

63c

Preparation of 1-((isopropoxycarbonyl)oxy)ethyl 6-((cyclopropylmethyl)carbamoyl)-3-(2-((4-(N-(isopropoxycarbonyl)carbamimidoyl)phenyl)carbamoyl)-5-methoxy-4-vinylphenyl)picolinate (63c)

Step-1: Preparation of isopropyl ((4-aminophenyl)(imino)methyl)carbamate (63b)

Compound (63b) was prepared according to the procedure reported in step 4 of scheme 23 from 4-aminobenzimidamide dihydrochloride (1n) (4.82 g, 23.15 mmol) in acetone/water (60 mL, 11:1 ratio), using NaOH (1.95 g, 48.6 mmol) and isopropyl (4-nitrophenyl) carbonate (63a) (7.3 g, 32.4 mmol, prepared according to the procedure reported by Nishikawa., Hiroshi in PCT Int. Appl., 2008044562). This gave after workup and purification by flash column chromatography (silica gel 12 g, eluting with ethyl acetate in hexanes from 0 to 100%) ((4-aminophenyl)(imino)methyl)carbamate (63b) (2.73 g, 12.34 mmol, 53.3% yield) as a white solid; $^1$H NMR (300 MHz, DMSO-$d_6$) δ 9.17 (s, 1H, $D_2O$ exchangeable), 8.60 (s, 1H, $D_2O$ exchangeable), 7.80-7.64 (m, 2H), 6.63-6.47 (m, 2H), 5.84 (s, 2H, $D_2O$ exchangeable), 4.87-4.68 (m, 1H), 1.20 (d, J=6.2 Hz, 6H); MS (ES+) 222.4 (M+1); (ES−) 220.4 (M−1).

Step-2: Preparation of 1-((isopropoxycarbonyl)oxy) ethyl 6-((cyclopropylmethyl)carbamoyl)-3-(2-((4-(N-(isopropoxycarbonyl)carbamimidoyl)phenyl) carbamoyl)-5-methoxy-4-vinylphenyl)picolinate (63c)

Compound (63c) was prepared from 2-(6-((cyclopropylmethyl)carbamoyl)-2-((1-((isopropoxycarbonyl)oxy) ethoxy)carbonyl)pyridin-3-yl)-4-methoxy-5-vinylbenzoic acid (38c) (0.5 g, 0.95 mmol) using EDCI (0.27 g, 1.42 mmol) and isopropyl ((4-aminophenyl)(imino)methyl)carbamate (63b) (0.25 g, 1.14 mmol) in DMF (8 mL) and Pyridine (4 mL) according to the procedure reported in step 4 of scheme 2. This gave after workup and purification by flash column chromatography [silica gel (12 g), eluting with EtOAc/MeOH (9:1) in hexane from 0-60%] then prep HPLC [eluting with $CH_3CN$ in water (containing with 0.1% HCl) from 0-100%] followed by lyophilization 1-((isopropoxycarbonyl)oxy)ethyl 6-((cyclopropylmethyl)carbamoyl)-3-(2-((4-(N-(isopropoxycarbonyl)carbamimidoyl)phenyl)carbamoyl)-5-methoxy-4-vinylphenyl)picolinate (63c) (52 mg, 8% yield) as an off white solid; $^1$H NMR (300 MHz, DMSO-$d_6$) δ 12.32 (s, 1H, $D_2O$ exchangeable), 10.72 (d, J=24.4 Hz, 1H, $D_2O$ exchangeable), 8.61 (d, J=30.3 Hz, 1H, $D_2O$ exchangeable), 8.22 (d, J=8.0 Hz, 1H), 8.01 (d, J=7.4 Hz, 2H), 7.77 (s, 4H), 7.09-6.93 (m, 2H), 6.63 (q, J=5.3 Hz, 1H), 6.06 (d, J=18.1 Hz, 1H), 5.45 (d, J=11.6 Hz, 1H), 5.10-4.94 (m, 1H), 4.78-4.63 (m, 1H), 3.89 (s, 3H), 3.28-3.14 (m, 2H), 1.32 (d, J=6.3 Hz, 6H), 1.26-1.02 (m, 11H), 0.52-0.39 (m, 2H), 0.32-0.20 (m, 2H); MS (ES+) 730.7 (M+1); (ES−) 764.7 (M+Cl); Analysis calculated for $C_{38}H_{43}N_5O_{10}\cdot HCl\cdot 4.5H_2O$: C, 53.87; H, 6.30; Cl, 4.18; N, 8.27; found: C, 53.75; H, 5.68; Cl, 3.93; N, 8.17.

Scheme 64

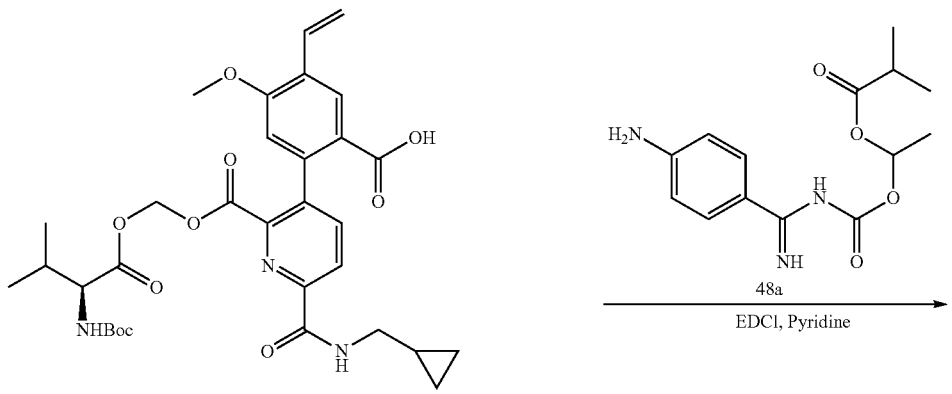

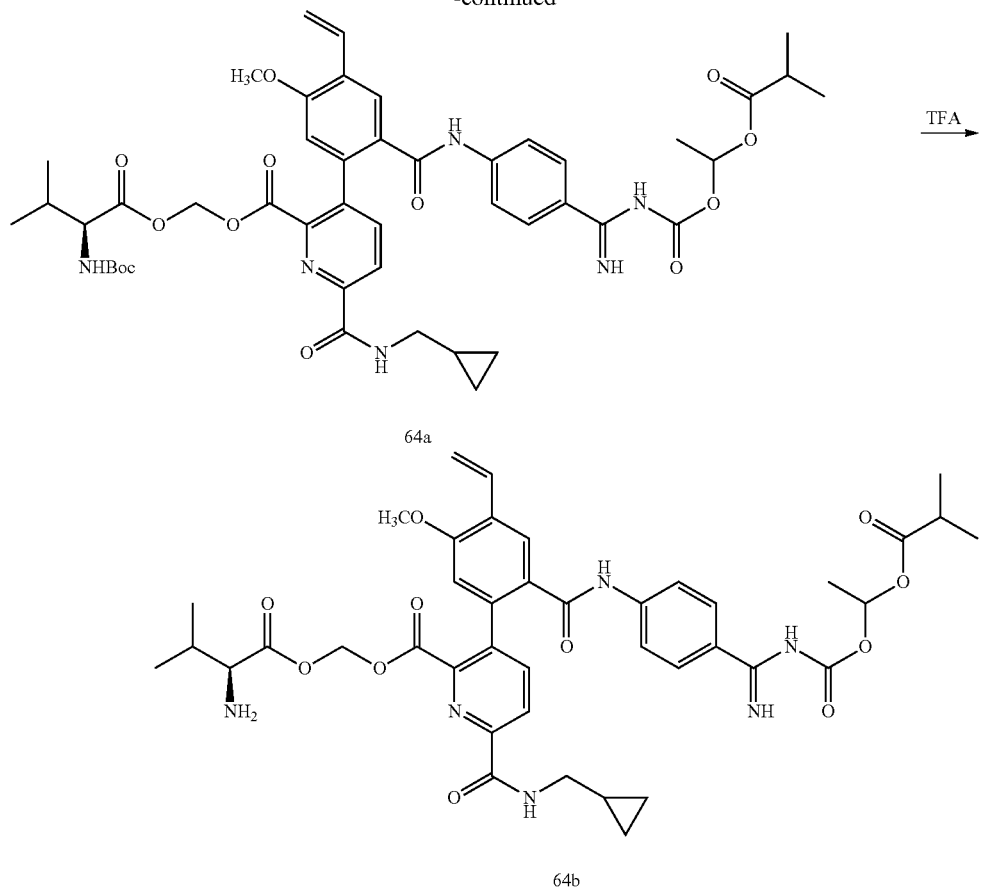

Preparation of (((S)-2-amino-3-methylbutanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (64b)

Step-1: Preparation of (((S)-2-((tert-butoxycarbonyl)amino)-3-methylbutanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (64a)

Compound (64a) was prepared from (S)-2-(6-((cyclopropylmethyl)carbamoyl)-2-(6-isopropyl-10,10-dimethyl-5,8-dioxo-2,4,9-trioxa-7-azaundecan-1-oyl)pyridin-3-yl)-4-methoxy-5-vinylbenzoic acid (10c) (0.5 g, 0.8 mmol) using EDCI (0.23 g, 1.2 mmol) and 1-((((4-aminophenyl)(imino)methyl)carbamoyl)oxy)ethyl isobutyrate (48a) (0.26 g, 0.88 mmol) in DMF (3 mL) and Pyridine (3 mL) according to the procedure reported in step 4 of scheme 2. This gave after workup (((S)-2-((tert-butoxycarbonyl)amino)-3-methylbutanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (64a) (0.51 g, 71% yield) as a white solid; 1H NMR (300 MHz, DMSO-$d_6$) δ 10.57 (s, 1H), 9.38-9.04 (m, 2H), 8.44 (s, 1H), 8.24 (d, J=8.0 Hz, 1H), 8.03 (d, J=8.0 Hz, 1H), 7.95 (d, J=9.1 Hz, 3H), 7.68 (d, J=8.8 Hz, 2H), 7.25 (d, J=7.9 Hz, 1H), 7.10-6.97 (m, 2H), 6.77 (q, J=5.3 Hz, 1H), 6.11-5.99 (m, 1H), 5.82-5.62 (m, 2H), 5.44 (d, J=11.5 Hz, 1H), 3.86-3.75 (m, 1H), 3.27-3.17 (m, 2H), 2.54 (s, 1H), 1.99-1.81 (m, 1H), 1.43 (d, J=5.4 Hz, 3H), 1.33 (s, 9H), 1.17-0.96 (m, 7H), 0.79 (d, J=6.8 Hz, 6H), 0.51-0.41 (m, 2H), 0.33-0.20 (m, 2H); MS (ES+) 901.7 (M+1), 923.8 (M+Na).

Step-2: Preparation of (((S)-2-amino-3-methylbutanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (64b)

Compound (64b) was prepared from (((S)-2-((tert-butoxycarbonyl)amino)-3-methylbutanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (64a) (0.5 g, 0.56 mmol) in dichloromethane (10 mL) using 2,2,2-trifluoroacetic acid (0.86 mL, 11.10 mmol) according to the procedure reported in Step-4 of scheme 8. This gave after workup and purification by reverse phase column chromatography [silica gel 26 g, acetonitrile in 0.1% HCl in water as eluents, 0 to 50%] followed by lyophilization(((S)-2-amino-3-methylbutanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (64b) (125 mg, 27% yield) as a light pink powder; 1H NMR (300 MHz, DMSO-$d_6$) δ 10.76 (s, 1H, $D_2O$ exchangeable), 8.70-8.38 (m, 4H, 3H, $D_2O$ exchangeable), 8.25 (d, J=8.1 Hz, 1H), 8.10-7.96 (m, 2H), 7.90-7.78 (m, 2H), 7.78-7.67 (m, 2H), 7.11-6.94 (m, 2H), 6.89-6.75 (m, 1H), 6.09 (dd, J=17.7, 1.6 Hz, 1H), 6.02-5.71 (m, 3H), 5.45 (dd, J=11.2, 1.5 Hz, 1H), 3.89 (s, 3H), 3.29-3.15 (m, 2H), 2.48-2.39 (m, 1H), 2.17-2.00 (m, 1H), 1.50 (d, J=5.4 Hz, 3H), 1.09 (dd, J=7.0, 3.3 Hz, 6H), 1.09-0.98 (m, 1H), 0.87 (d, J=6.9 Hz, 6H), 0.51-0.38 (m, 2H), 0.33-0.20 (m, 2H); MS (ES+) 801.7 (M+1), (ES−) 835.8 (M+Cl); Analysis calculated for $C_{41}H_{48}N_6O_{11} \cdot 1.5HCl \cdot 0.5CF_3CO_2H \cdot 2H_2O$: C, 53.18; H, 5.74; Cl, 5.61; N, 8.86; found: C, 52.86; H, 5.86; Cl, 5.82; N, 9.07.

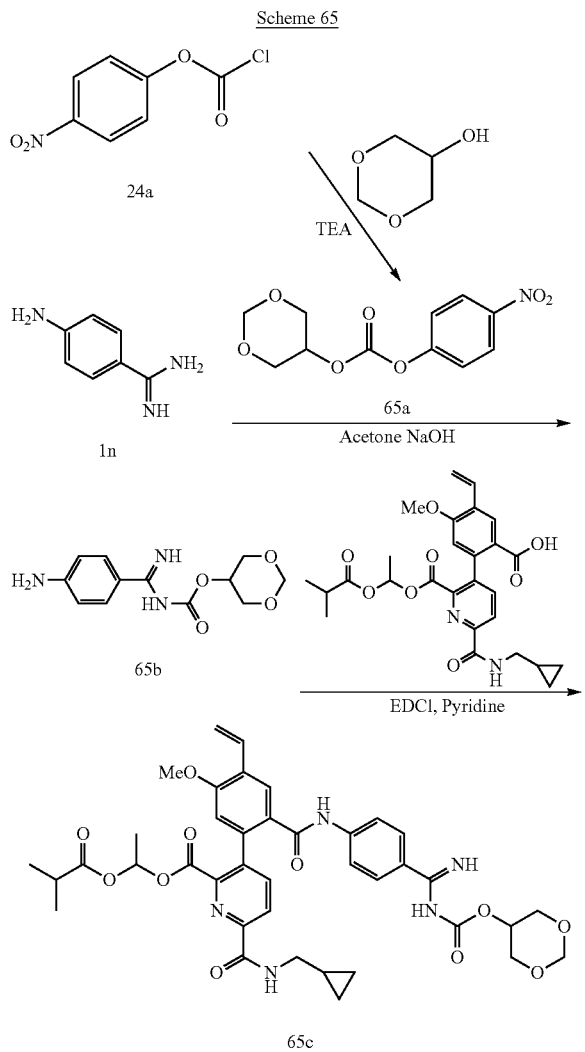

Scheme 65

Preparation of 1-(isobutyryloxy)ethyl 3-(2-((4-(N-(((1,3-dioxan-5-yl)oxy)carbonyl)carbamimidoyl)phenyl)carbamoyl)-5-methoxy-4-vinylphenyl)-6-((cyclopropylmethyl)carbamoyl)picolinate (65c)

Step-1: Preparation of 1,3-dioxan-5-yl (4-nitrophenyl) carbonate (65a)

Compound (65a) was prepared according to the procedure described in step 1 of scheme 24 from 4-nitrophenyl chloroformate (5.76 g, 27.7 mmol) in THF (50 mL) using 1,3-dioxan-5-ol (2.5 mL, 29.2 mmol) and triethylamine (8.95 mL, 64.2 mmol). This gave after workup and purification by flash column chromatography[(silica gel, 80 g) eluting with ethyl acetate in hexanes 0-100%] 1,3-dioxan-5-yl (4-nitrophenyl) carbonate (65a) (3.06 g, 39% yield) as a white solid which can be used as such in next step without further purification; $^1$H NMR (300 MHz, DMSO-$d_6$) δ 8.39-8.27 (m, 2H), 7.66-7.55 (m, 2H), 4.93 (d, J=6.1 Hz, 1H), 4.77 (d, J=6.2 Hz, 1H), 4.68 (p, J=2.4 Hz, 1H), 4.04 (d, J=2.4 Hz, 4H).

Step-2: Preparation of 1,3-dioxan-5-yl ((4-aminophenyl)(imino)methyl)carbamate (65b)

Compound (65b) was prepared from 4-aminobenzimidamide dihydrochloride (1n) (2.32 g, 11.14 mmol) in acetone (50 mL), using 1 N aqueous NaOH solution (27.9 mL, 27.9 mmol) and 1,3-dioxan-5-yl (4-nitrophenyl) carbonate (65a) (3 g, 11.14 mmol) according to the procedure reported in step 4 of scheme 23. This gave after workup 1,3-dioxan-5-yl ((4-aminophenyl)(imino)methyl)carbamate (65b) (0.62 g, 21% yield) as a yellow solid which can be used as such in next step without further purification; $^1$H NMR (300 MHz, DMSO-$d_6$) δ9.14 (s, 1H), 8.73 (s, 1H), 7.93-7.65 (m, 2H), 6.67-6.39 (m, 2H), 5.89 (s, 2H), 4.79 (d, J=2.0 Hz, 2H), 4.64-4.41 (m, 1H), 4.06-3.98 (m, 2H), 3.79 (dd, J=11.8, 4.5 Hz, 2H).

Step-3: Preparation of 1-(isobutyryloxy)ethyl 3-(2-((4-(N-(((1,3-dioxan-5-yl)oxy)carbonyl)carbamimidoyl)phenyl)carbamoyl)-5-methoxy-4-vinylphenyl)-6-((cyclopropylmethyl)carbamoyl)picolinate (65c)

Compound (65c) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.5 g, 0.98 mmol) using EDCI (0.28 g, 1.47 mmol) and 1,3-dioxan-5-yl ((4-aminophenyl)(imino)methyl)carbamate (65b) (0.33 g, 1.22 mmol) in DMF (3 mL) and Pyridine (3 mL) according to the procedure reported in step 4 of scheme 2. This gave after workup and purification by flash column chromatography [silica gel, 25 g eluting with EtOAc/MeOH (9:1) in hexane from 0-60%] followed by lyophilization 1-(isobutyryloxy)ethyl 3-(2-((4-(N-(((1,3-dioxan-5-yl)oxy)carbonyl)carbamimidoyl)phenyl)carbamoyl)-5-methoxy-4-vinylphenyl)-6-((cyclopropylmethyl)carbamoyl)picolinate (65c) (125 mg, 17% yield) as a white solid; $^1$H NMR (300 MHz, DMSO-$d_6$) δ 10.49 (d, J=23.3 Hz, 1H, $D_2O$ exchangeable), 9.07 (s, 2H, $D_2O$ exchangeable), 8.55 (d, J=27.9 Hz, 1H), 8.20 (d, J=8.0 Hz, 1H), 8.06-7.85 (m, 4H), 7.66 (m, 2H), 7.09-6.91 (m, 2H), 6.71 (m, 1H), 6.03 (d, J=17.5 Hz, 1H), 5.41 (d, J=11.4 Hz, 1H), 4.77 (q, J=6.2 Hz, 2H), 4.51 (m, 1H), 3.99 (dd, J=11.8, 2.8 Hz, 2H), 3.86 (s, 3H), 3.79 (dd, J=11.7, 4.2 Hz, 2H), 3.26-3.16 (m, 2H), 2.45-2.26 (m, 1H), 1.14 (d, J=5.3 Hz, 3H), 1.12-1.00 (m, 1H), 0.94 (d, J=7.9 Hz, 6H), 0.50-0.37 (m, 2H), 0.30-0.17 (m, 2H); MS (ES+) 758.6 (M+1), 780.7 (M+Na), (ES−) 756.8 (M−1); Analysis calculated for $C_{39}H_{43}N_5O_{11} \cdot H_2O$: C, 60.38; H, 5.85; N, 9.03. Found: C, 60.46; H, 5.84; N, 9.09.

Scheme 66
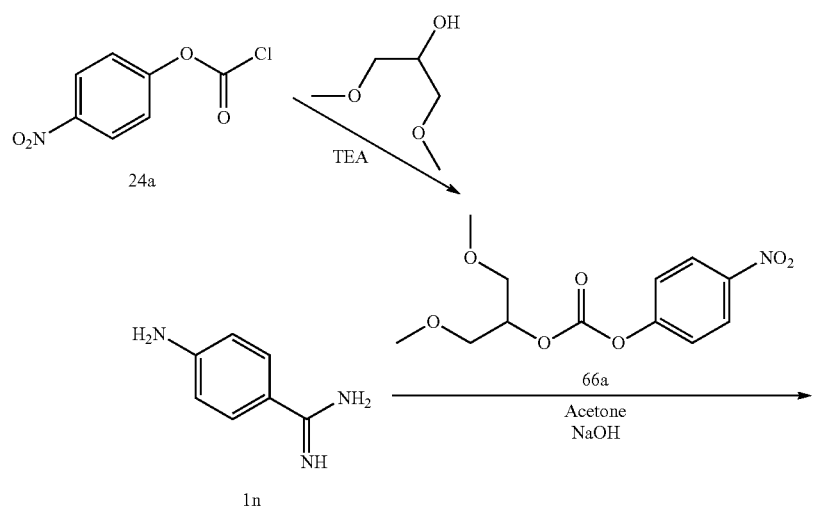
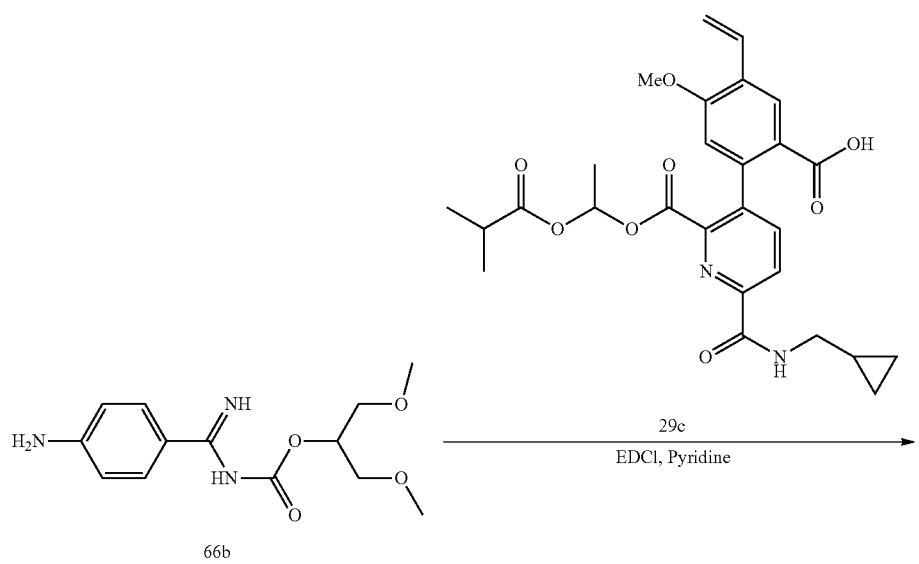
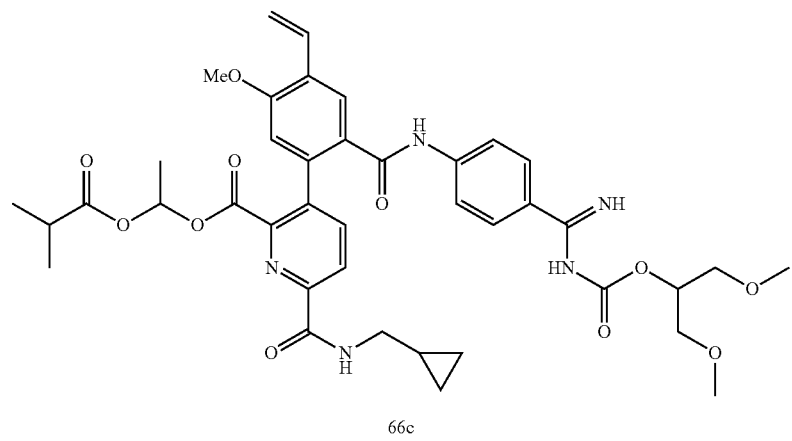

Preparation of 1-(isobutyryloxy)ethyl 6-((cyclopropylmethyl)carbamoyl)-3-(2-((4-(N-(((1,3-dimethoxypropan-2-yl)oxy)carbonyl)carbamimidoyl)phenyl)carbamoyl)-5-methoxy-4-vinylphenyl) picolinate (66c)

Step-1: Preparation of 1,3-dimethoxypropan-2-yl (4-nitrophenyl) carbonate (66a)

Compound (66a) was prepared according to the procedure described in step 1 of scheme 24 from 4-nitrophenyl chloroformate (4.97 g, 23.93 mmol) in THF (50 mL) using 1,3-dimethoxypropan-2-ol (3.03 mL, 25.2 mmol) and triethylamine (7.73 mL, 55.4 mmol). This gave after workup 1,3-dimethoxypropan-2-yl (4-nitrophenyl) carbonate (66a) (5.05 g, 70% yield) as a yellow syrup which can be used as such in next step without further purification; $^1$H NMR (300 MHz, DMSO-$d_6$) δ 8.40-8.26 (m, 2H), 7.57 (d, J=9.2 Hz, 2H), 5.03 (p, J=5.0 Hz, 1H), 3.59 (s, 2H), 3.57 (s, 2H), 3.30 (s, 6H).

Step-2: Preparation of 1,3-dimethoxypropan-2-yl ((4-aminophenyl)(imino)methyl)carbamate (66b)

Compound (65b) was prepared from 4-aminobenzimidamide dihydrochloride (1n) (3.65 g, 17.53 mmol) in acetone (100 mL), using NaOH solution (1.75 g, 43.8 mmol) and a solution of 1,3-dimethoxypropan-2-yl (4-nitrophenyl) carbonate (66a) (5 g, 17.53 mmol) in acetone (25 mL) according to the procedure reported in step 4 of scheme 23. This gave after workup and purification by flash column chromatography (silica gel, 12 g eluting with ethyl acetate and hexanes 0 to 100%) 1,3-dimethoxypropan-2-yl ((4-aminophenyl)(imino)methyl)carbamate (66b) (0.5 g, 10% yield) as a brown solid; $^1$H NMR (300 MHz, DMSO-$d_6$) δ 9.13 (s, 1H, D$_2$O exchangeable), 8.67 (s, 1H, D$_2$O exchangeable), 7.88-7.65 (m, 2H), 6.66-6.46 (m, 2H), 5.87 (s, 2H, D$_2$O exchangeable), 4.94 (p, J=5.2 Hz, 1H), 3.46 (dd, J=5.1, 1.4 Hz, 4H), 3.26 (s, 6H).

Step-3: Preparation of 1-(isobutyryloxy)ethyl 6-((cyclopropylmethyl)carbamoyl)-3-(2-((4-(N-(((1,3-dimethoxypropan-2-yl)oxy)carbonyl)carbamimidoyl)phenyl)carbamoyl)-5-methoxy-4-vinylphenyl) picolinate (66c)

Compound (66c) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.5 g, 0.98 mmol) using EDCI (0.28 g, 1.47 mmol) and 1,3-dimethoxypropan-2-yl ((4-aminophenyl)(imino)methyl)carbamate (66b) (0.34 g, 1.22 mmol) in DMF (3 mL) and Pyridine (3 mL) according to the procedure reported in step 4 of scheme 2. This gave after workup and purification by flash column chromatography [silica gel 25 g, eluting with EtOAc/MeOH (9:1) in hexane from 0-60%] followed by lyophilization 1-(isobutyryloxy)ethyl 6-((cyclopropylmethyl)carbamoyl)-3-(2-((4-(N-(((1,3-dimethoxypropan-2-yl)oxy)carbonyl)carbamimidoyl)phenyl)carbamoyl)-5-methoxy-4-vinylphenyl)picolinate (66c) (160 mg, 21% yield) as a white solid; $^1$H NMR (300 MHz, DMSO-$d_6$) δ 10.51 (d, J=24.1 Hz, 1H, D$_2$O exchangeable), 9.14 (s, 1H, D$_2$O exchangeable), 8.98 (s, 1H, D$_2$O exchangeable), 8.57 (d, J=28.0 Hz, 1H), 8.22 (d, J=8.0 Hz, 1H), 8.06-7.85 (m, 4H), 7.70 (m, 2H), 7.11-6.94 (m, 2H), 6.74 (m, 1H), 6.06 (dd, J=17.8, 1.5 Hz, 1H), 5.44 (dd, J=11.3, 1.5 Hz, 1H), 4.96 (p, J=5.2 Hz, 1H), 3.95-3.78 (m, 3H), 3.50-3.43 (m, 4H), 3.35 (s, 6H), 3.28-3.15 (m, 2H), 2.47-2.28 (m, 1H), 1.17 (d, J=5.2 Hz, 3H), 1.15-1.04 (m, 1H), 1.05-0.91 (m, 6H), 0.50-0.39 (m, 2H), 0.31-0.23 (m, 2H); MS (ES+) 774.7 (M+1), 796.7 (M+Na), (ES−) 772.8 (M−1); Analysis calculated for: $C_{40}H_{47}N_5O_{11}$ (H$_2$O) 0.75. C, 61.02; H, 6.21; N, 8.89. Found: C, 61.00; H, 6.20; N, 8.80.

Scheme 67

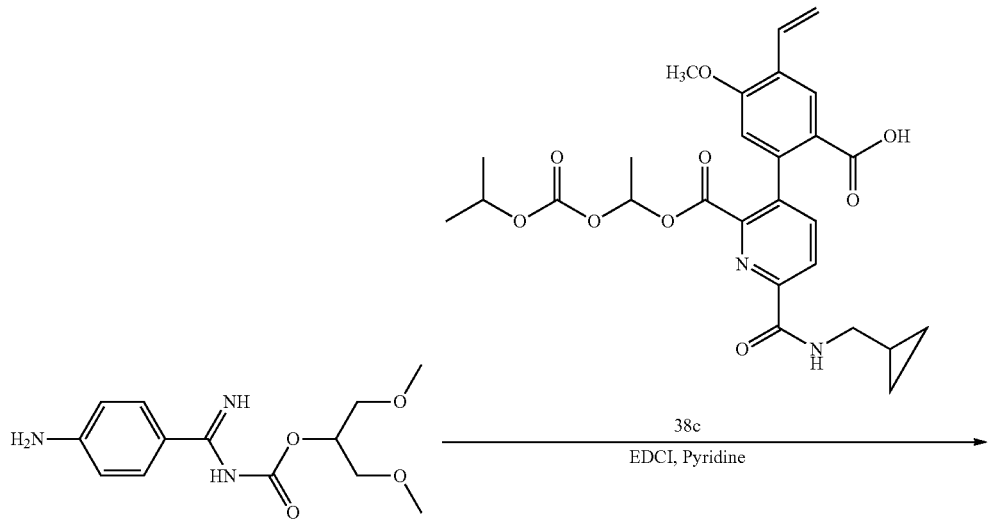

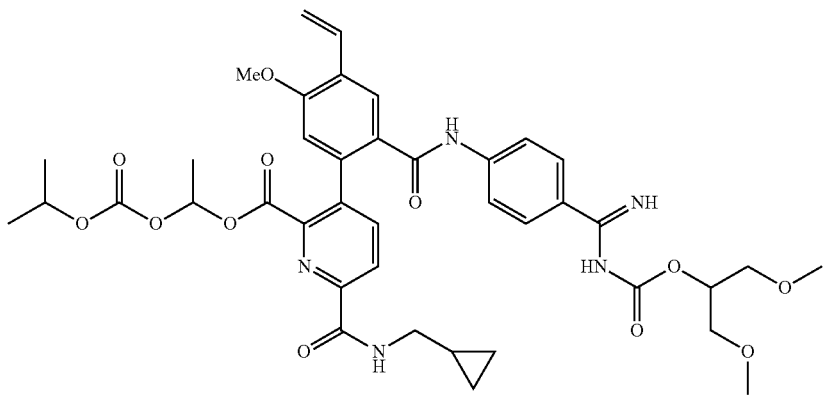

67a

Preparation of 1-((isopropoxycarbonyl)oxy)ethyl 6-((cyclopropylmethyl)carbamoyl)-3-(2-((4-(N-(((1,3-dimethoxypropan-2-yl)oxy)carbonyl)carbamimidoyl)phenyl)carbamoyl)-5-methoxy-4-vinylphenyl)picolinate (67a)

Compound (67a) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.5 g, 0.95 mmol) using EDCI (0.27 g, 1.42 mmol) and 1,3-dimethoxypropan-2-yl ((4-aminophenyl)(imino)methyl)carbamate (66b) (0.33 g, 1.19 mmol) in DMF (3 mL) and Pyridine (3 mL) according to the procedure reported in step 4 of scheme 2. This gave after workup and purification by flash column chromatography [silica gel 25 g, eluting with EtOAc/MeOH (9:1) in hexane from 0-60%] 1-((isopropoxycarbonyl)oxy)ethyl 6-((cyclopropylmethyl)carbamoyl)-3-(2-((4-(N-(((1,3-dimethoxypropan-2-yl)oxy)carbonyl)carbamimidoyl)phenyl)carbamoyl)-5-methoxy-4-vinylphenyl)picolinate (67a) (115 mg, 0.146 mmol, 15.33% yield) as a white solid; $^1$H NMR (300 MHz, DMSO-$d_6$) δ 10.53 (d, J=26.8 Hz, 1H), 9.28-9.05 (m, 1H, D$_2$O exchangeable), 9.05-8.85 (m, 1H, D$_2$O exchangeable), 8.61 (d, J=25.2 Hz, 1H), 8.23 (d, J=8.0 Hz, 1H), 8.08-7.84 (m, 4H), 7.77-7.60 (m, 2H), 7.17-6.91 (m, 2H), 6.70-6.53 (m, 1H), 6.06 (d, J=17.8 Hz, 1H), 5.44 (d, J=11.3 Hz, 1H), 4.96 (t, J=5.2 Hz, 1H), 4.78-4.61 (m, 1H), 3.89 (s, 3H), 3.51-3.41 (m, 4H), 3.32-3.20 (m, 8H), 1.24-1.04 (m, 10H), 0.52-0.36 (m, 2H), 0.33-0.17 (m, 2H); MS (ES+) 790.8 (M+1), 812.7 (M+Na).

Scheme 68

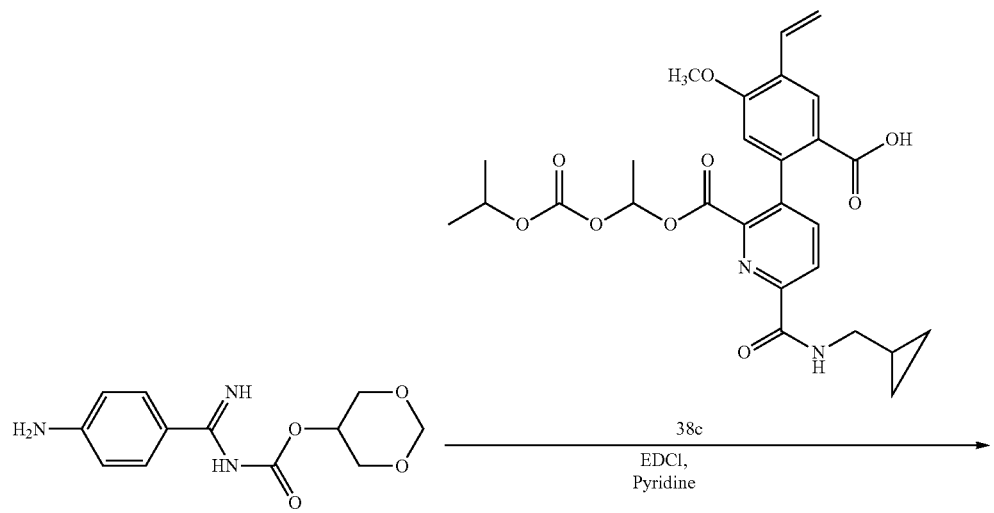

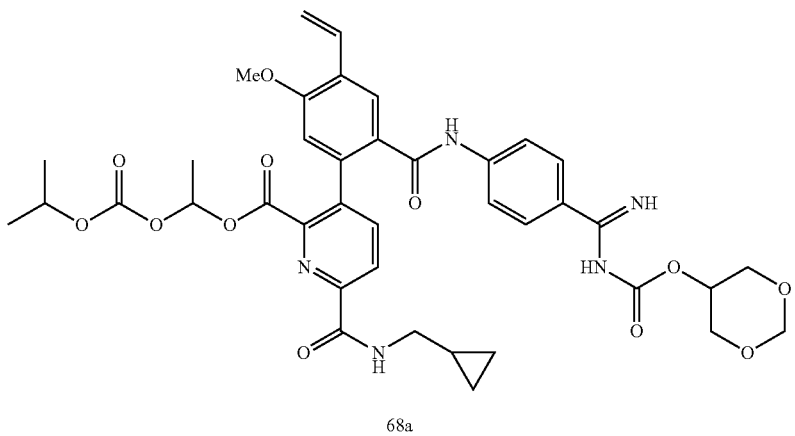

68a

Preparation of 1-((isopropoxycarbonyl)oxy)ethyl 3-(2-((4-(N-(((1,3-dioxan-5-yl)oxy)carbonyl)carbamimidoyl)phenyl)carbamoyl)-5-methoxy-4-vinylphenyl)-6-((cyclopropylmethyl)carbamoyl)picolinate (68a)

Compound (68a) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.5 g, 0.95 mmol) using EDCI (0.27 g, 1.42 mmol) and 1,3-dioxan-5-yl ((4-aminophenyl)(imino)methyl)carbamate (65b) (0.32 g, 1.19 mmol) in DMF (3 mL) and Pyridine (3 mL) according to the procedure reported in step 4 of scheme 2. This gave after workup and purification by flash column chromatography [silica gel 25 g, eluting with EtOAc/MeOH (9:1) in hexane from 0-100%] 1-((isopropoxycarbonyl)oxy)ethyl 3-(2-((4-(N-(((1,3-dioxan-5-yl)oxy)carbonyl)carbamimidoyl)phenyl)carbamoyl)-5-methoxy-4-vinylphenyl)-6-((cyclopropylmethyl)carbamoyl)picolinate (68a) (110 mg, 15% yield) as a white solid; $^1$H NMR (300 MHz, DMSO-$d_6$) δ 10.54 (d, J=26.2 Hz, 1H), 9.31-8.88 (m, 2H, $D_2O$ exchangeable), 8.69-8.47 (m, 1H), 8.23 (d, J=8.0 Hz, 1H), 8.08-7.86 (m, 4H), 7.76-7.57 (m, 2H), 7.11-6.95 (m, 2H), 6.69-6.57 (m, 1H), 6.14-5.96 (m, 1H), 5.44 (d, J=11.5 Hz, 1H), 4.79 (q, J=6.1 Hz, 2H), 4.76-4.64 (m, 1H), 4.60-4.48 (m, 1H), 4.02 (dd, J=12.1, 2.9 Hz, 2H), 3.89 (s, 3H), 3.82 (dd, J=11.8, 4.3 Hz, 2H), 3.28-3.18 (m, 2H), 1.28-1.02 (m, 10H), 0.50-0.39 (m, 2H), 0.33-0.22 (m, 2H); MS (ES+) 774.3 (M+1), 796.6 (M+Na); Analysis calculated for; $C_{39}H_{43}N_5O_{12} \cdot H_2O$: C, 59.16; H, 5.73; N, 8.84; found: C, 59.42; H, 5.50; N, 8.73.

Scheme 69

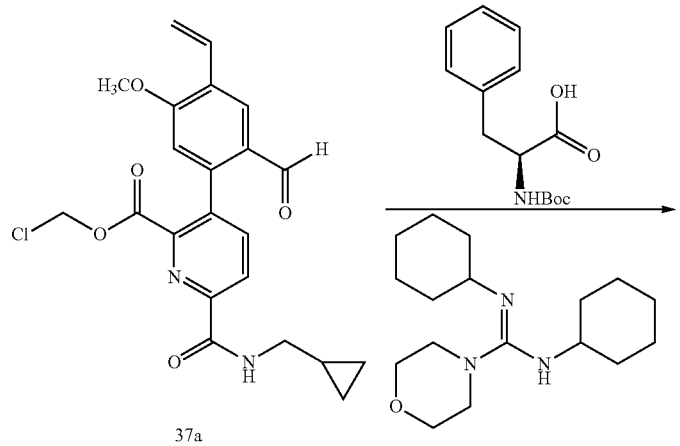

37a

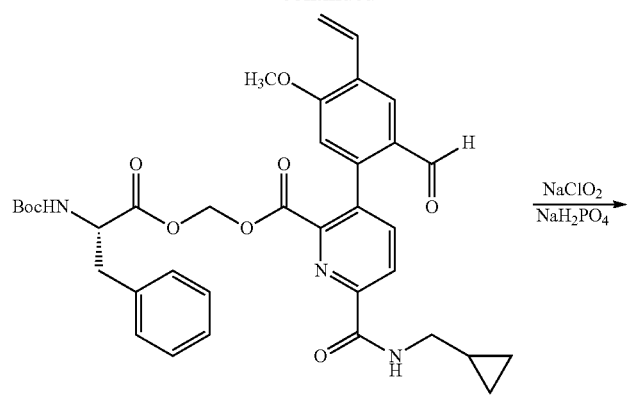
69a
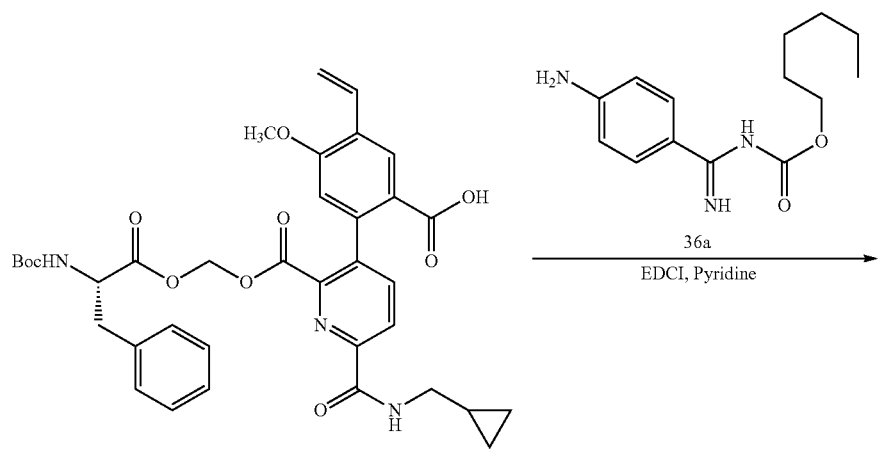
69b
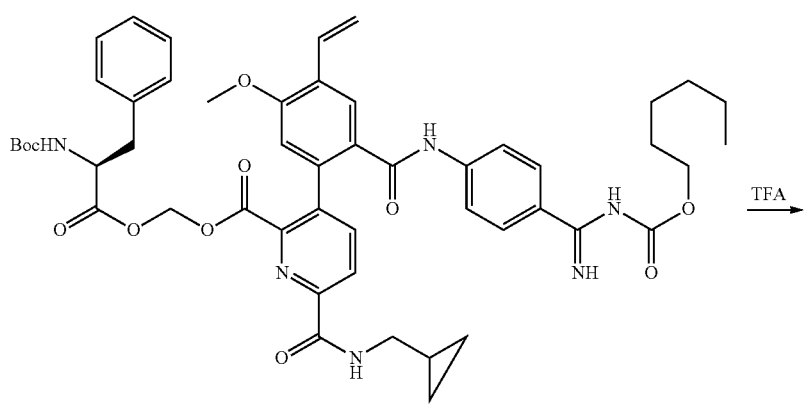
69c

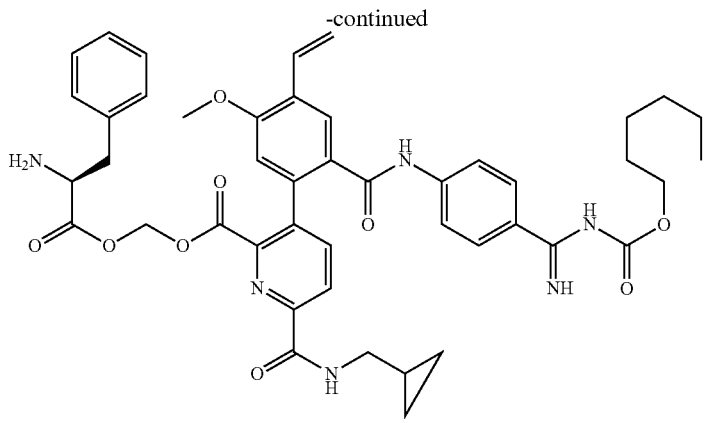

69d

Preparation of (S)-((2-amino-3-phenylpropanoyl) oxy)methyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate (69d)

Step-1: Preparation of (S)-((2-(((tert-butoxycarbonyl) amino)-3-phenylpropanoyl)oxy)methyl 6-((cyclopropylmethyl)carbamoyl)-3-(2-formyl-5-methoxy-4-vinylphenyl)picolinate (69a)

Compound (69a) was prepared according to the procedure reported in step 1 of scheme 8 from chloromethyl 6-((cyclopropylmethyl)carbamoyl)-3-(2-formyl-5-methoxy-4-vinylphenyl)picolinate (37a) (1.25 g, 2.91 mmol) in DMF (10 mL) using N,N'-Dicyclohexyl-4-morpholinecarboxamidine (1.07 g, 3.64 mmol) and (S)-2-((tert-butoxycarbonyl) amino)-3-phenylpropanoic acid (0.93 g, 3.5 mmol). This gave after workup and purification by flash column chromatography (silica gel 40 g, eluting with ethyl acetate/ Hexanes, 0-100%) (S)-((2-((tert-butoxycarbonyl)amino)-3-phenylpropanoyl)oxy)methyl 6-((cyclopropylmethyl) carbamoyl)-3-(2-formyl-5-methoxy-4-vinylphenyl) picolinate (69a) (1.09 g, 57% yield) as a white solid; $^1$H NMR (300 MHz, DMSO-d$_6$) δ 9.68 (s, 1H), 8.67 (t, J=6.1 Hz, 1H), 8.29 (dd, J=7.9, 1.5 Hz, 1H), 8.16-8.02 (m, 2H), 7.36 (d, J=8.0 Hz, 1H), 7.22 (t, J=3.5 Hz, 4H), 7.08-6.83 (m, 2H), 6.01-5.89 (m, 1H), 5.85 (t, J=6.3 Hz, 1H), 5.77 (dd, J=6.0, 1.5 Hz, 1H), 5.45-5.36 (m, 1H), 4.20-4.08 (m, 1H), 3.88 (d, J=2.4 Hz, 3H), 3.25 (q, J=6.4, 4.9 Hz, 2H), 2.96-2.68 (m, 2H), 1.27 (d, J=2.1 Hz, 9H), 1.23-1.10 (m, 1H), 1.15-1.01 (m, 1H), 0.49-0.41 (m, 2H), 0.32-0.22 (m, 2H); MS (ES+) 680.6 (M+Na).

Step-2: Preparation of (S)-2-(2-(6-benzyl-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (69b)

Oxidation of S)-((2-((tert-butoxycarbonyl)amino)-3-phenylpropanoyl)oxy)methyl 6-((cyclopropylmethyl)carbamoyl)-3-(2-formyl-5-methoxy-4-vinylphenyl)picolinate (69a) (1.07 g, 1.62 mmol) using the procedure as reported in step 11 of scheme 1 gave after workup (S)-2-(2-(6-benzyl-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (69b) (1.35 g, 124% yield) as a yellow solid; $^1$H NMR (300 MHz, DMSO-d$_6$) δ 12.59 (s, 1H, D$_2$O exchangeable), 8.61 (t, J=6.1 Hz, 1H), 8.24 (d, J=8.0 Hz, 1H), 8.09 (s, 1H), 7.96 (d, J=8.1 Hz, 1H), 7.35 (d, J=8.0 Hz, 1H), 7.22 (d, J=1.9 Hz, 3H), 6.96 (dd, J=11.1, 4.9 Hz, 2H), 6.88 (s, 1H), 5.92-5.68 (m, 4H), 5.36 (d, J=9.9 Hz, 1H), 4.15 (s, 1H), 3.82 (s, 3H), 3.29-3.17 (m, 2H), 2.89 (s, 1H), 2.85-2.69 (m, 1H), 1.27 (s, 10H), 0.48-0.40 (m, 2H), 0.27 (dd, J=5.0, 1.6 Hz, 2H); MS (ES+) 696.6 (M+Na), (ES−) 672.6 (M−1).

Step-3: Preparation of (S)-((2-(((tert-butoxycarbonyl) amino)-3-phenylpropanoyl)oxy)methyl 6-((cyclopropylmethyl)carbamoyl)-3-(2-((4-(N-((hexyloxy) carbonyl)carbamimidoyl)phenyl)carbamoyl)-5-methoxy-4-vinylphenyl)picolinate (69c)

Compound (69c) was prepared from ((S)-2-(2-(6-benzyl-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (69b) (0.46 mg, 0.68 mmol) using EDCI (1.5 equiv.) and hexyl ((4-aminophenyl)(imino) methyl)carbamate (36a) (0.22 g, 0.85 mmol) in DMF (4 mL) and Pyridine (4 mL) according to the procedure reported in step 4 of scheme 2. This gave after workup (S)-((2-((tert-butoxycarbonyl)amino)-3-phenylpropanoyl)oxy)methyl 6-((cyclopropylmethyl)carbamoyl)-3-(2-((4-(N-((hexyloxy) carbonyl)carbamimidoyl)phenyl)carbamoyl)-5-methoxy-4-vinylphenyl)picolinate (69c) (0.52 g, 84% yield) which was used in next step without further purification; $^1$H NMR (300 MHz, DMSO-d$_6$) δ 10.53 (s, 1H, D$_2$O exchangeable), 9.30-8.75 (m, 2H, D$_2$O exchangeable), 8.56 (t, J=6.0 Hz, 1H), 8.24 (d, J=8.0 Hz, 1H), 8.02 (d, J=8.1 Hz, 1H), 7.96-7.87 (m, 3H), 7.66 (d, J=8.7 Hz, 2H), 7.35 (d, J=8.1 Hz, 1H), 7.17 (d, J=5.0 Hz, 3H), 7.04-6.96 (m, 1H), 6.00 (d, J=17.9 Hz, 1H), 5.77 (s, 3H), 5.41 (d, J=11.7 Hz, 1H), 4.11 (s, 1H), 3.86 (s, 3H), 3.21 (s, 3H), 2.99-2.62 (m, 2H), 1.69-1.50 (m, 2H), 1.35-1.25 (m, 14H), 1.25-1.17 (m, 1H), 1.17-0.98 (m, 4H), 0.91-0.83 (m, 3H), 0.47-0.39 (m, 2H), 0.29-0.20 (m, 2H); MS (ES+) 942.52 (M+Na).

Step-4: Preparation of (S)-((2-amino-3-phenylpropanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl) picolinate (69d)

Compound (69d) was prepared from (S)-((2-((tert-butoxycarbonyl)amino)-3-phenylpropanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (69c) (0.51 g, 0.56 mmol) in dichloromethane (10 mL) using 2,2,2-trifluoroacetic acid (0.86 mL, 11.21 mmol) according to the procedure reported in Step-4 of scheme 8. This gave after workup and purification by flash column chromatography (C18, 26 g) eluting with 0.1% HCl and acetonitrile followed by lyophilization (S)-((2-amino-3-phenylpropanoyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl) picolinate hydrochloride salt (69d) (0.025 g, 5% yield) as a white solid. $^1$H NMR (300 MHz, DMSO-d$_6$) δ 10.77 (s, 1H, D$_2$O exchangeable), 8.84-8.47 (m, 4H, 3H D$_2$O exchangeable), 8.27 (d, J=8.0 Hz, 1H), 8.04 (d, J=8.0 Hz, 1H), 7.96 (s, 1H), 7.76 (s, 4H), 7.34-7.12 (m, 5H), 7.01 (d, J=5.1 Hz, 1H), 6.04 (d, J=17.9 Hz, 1H), 5.89 (d, J=6.0 Hz, 1H), 5.85-5.72 (m, 2H), 5.44 (d, J=11.4 Hz, 1H), 4.36-4.13 (m, 4H), 3.86 (s, 3H), 3.29-3.18 (m, 2H), 3.10-2.94 (m, 1H), 1.67 (t, J=7.3 Hz, 2H), 1.44-1.21 (m, 6H), 1.14-0.97 (m, 1H), 0.93-0.76 (m, 3H), 0.51-0.33 (m, 2H), 0.29-0.19 (m, 2H); MS (ES+) 819.7 (M+1), 841.8 (M+Na).

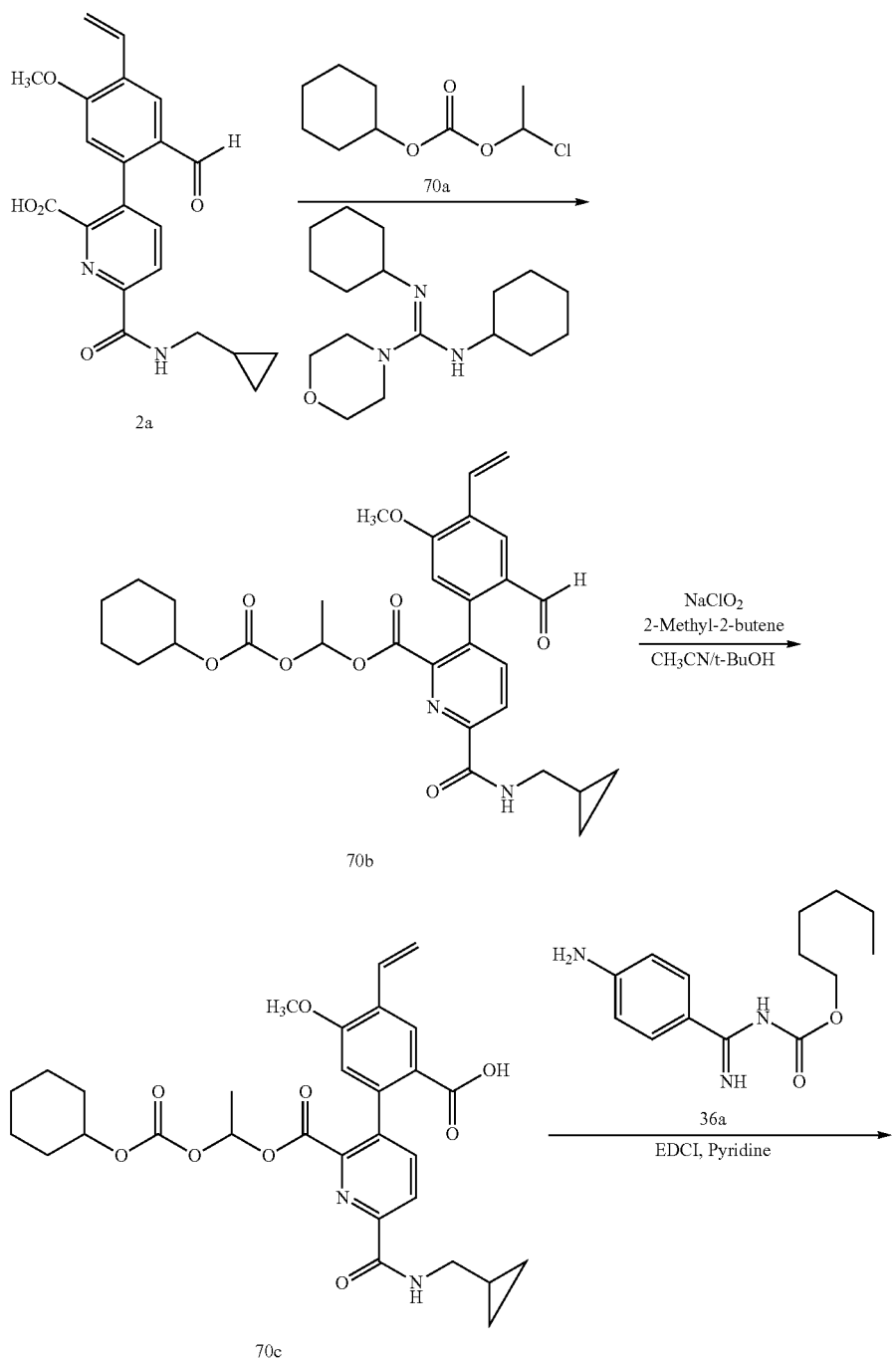

Scheme 70

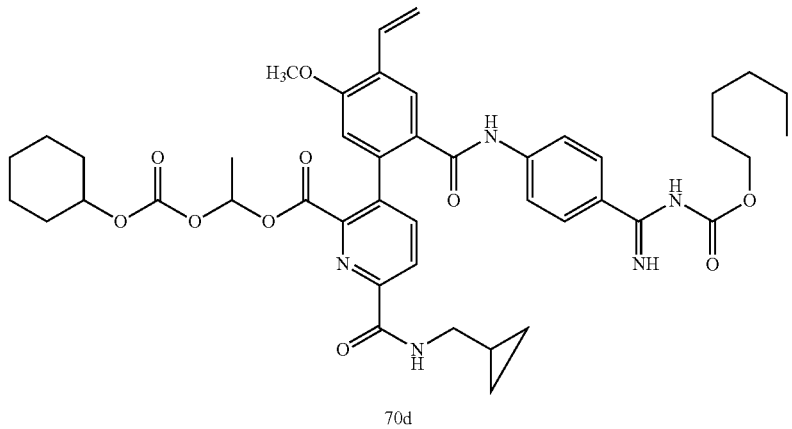

70d

Preparation of 1-(((cyclohexyloxy)carbonyl)oxy) ethyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate (70d)

Step-1: Preparation of 1-(((cyclohexyloxy)carbonyl) oxy)ethyl 6-((cyclopropylmethyl)carbamoyl)-3-(2-formyl-5-methoxy-4-vinylphenyl)picolinate (70b)

Compound (70b) was prepared according to the procedure reported in step 1 of scheme 8 from 6-(Cyclopropylmethylcarbamoyl)-3-(2-formyl-5-methoxy-4-vinylphenyl)picolinic acid (2a) (1.9 g, 5.0 mmol) in DMF (30 mL) using N,N'-Dicyclohexyl-4-morpholinecarboxamidine (1.83 g, 6.25 mmol) and 1-chloroethyl cyclohexyl carbonate (70a) (1.55 g, 7.50 mmol). This gave after workup and purification by flash column chromatography (silica gel 40 g, eluting with ethyl acetate/Hexanes, 0-100%) 1-(((cyclohexyloxy) carbonyl)oxy)ethyl 6-((cyclopropylmethyl)carbamoyl)-3-(2-formyl-5-methoxy-4-vinylphenyl)picolinate (70b) (2.41 g, 88% yield) as a yellow solid; $^1$H NMR (300 MHz, DMSO-d$_6$) δ 9.69 (d, J=4.0 Hz, 1H), 8.76-8.64 (m, 1H), 8.27 (dd, J=8.0, 2.4 Hz, 1H), 8.14 (d, J=2.2 Hz, 1H), 8.08 (dd, J=8.0, 0.7 Hz, 1H), 7.11-6.90 (m, 2H), 6.68-6.54 (m, 1H), 6.01 (dt, J=17.8, 1.2 Hz, 1H), 5.44 (dd, J=11.2, 1.4 Hz, 1H), 4.55-4.38 (m, 1H), 3.91 (d, J=1.5 Hz, 3H), 3.30-3.17 (m, 2H), 1.87-1.72 (m, 2H), 1.69-1.55 (m, 2H), 1.51-1.03 (m, 10H), 0.53-0.38 (m, 2H), 0.35-0.20 (m, 2H); MS (ES+): 551.5 (M+1), 573.3 (M+Na).

Step-2: Preparation of 2-(2-((1-(((cyclohexyloxy) carbonyl)oxy)ethoxy)carbonyl)-6-((cyclopropylmethyl)carbamoyl)pyridin-3-yl)-4-methoxy-5-vinylbenzoic acid (70c)

Oxidation of 1-(((cyclohexyloxy)carbonyl)oxy)ethyl 6-((cyclopropylmethyl)carbamoyl)-3-(2-formyl-5-methoxy-4-vinylphenyl)picolinate (70b) (2.31 g, 4.19 mmol) using the procedure as reported in step 11 of scheme 1 gave after workup 2-(2-((1-(((cyclohexyloxy)carbonyl)oxy)ethoxy) carbonyl)-6-((cyclopropylmethyl)carbamoyl)pyridin-3-yl)-4-methoxy-5-vinylbenzoic acid (70c) (2.21 g, 93% yield) as a yellow solid; $^1$H NMR (300 MHz, DMSO-d$_6$) δ 12.62 (s, 1H, D$_2$O exchangeable), 8.75-8.54 (m, 1H), 8.22 (d, J=8.1 Hz, 1H), 8.12 (s, 1H), 7.96 (d, J=8.0 Hz, 1H), 6.98 (dd, J=17.8, 11.3 Hz, 1H), 6.92-6.83 (m, 1H), 6.71-6.53 (m, 1H), 5.91 (dd, J=17.8, 1.4 Hz, 1H), 5.39 (dd, J=11.2, 1.4 Hz, 1H), 4.48 (s, 1H), 3.86 (s, 3H), 3.30-3.17 (m, 2H), 1.89-0.87 (m, 14H), 0.56-0.39 (m, 2H), 0.34-0.21 (m, 2H); MS (ES+): 567.5 (M+1), 589.5 (M+Na); MS (ES−): 565.6 (M−1).

Step-3: Preparation of 1-(((cyclohexyloxy)carbonyl) oxy)ethyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate (70d)

Compound (70d) was prepared from 2-(2-((1-(((cyclohexyloxy)carbonyl)oxy)ethoxy)carbonyl)-6-((cyclopropylmethyl)carbamoyl)pyridin-3-yl)-4-methoxy-5-vinylbenzoic acid (70c) (0.47 g, 0.83 mmol) using EDCI (0.24 g, 1.24 mmol) and hexyl ((4-aminophenyl)(imino)methyl)carbamate (36a) (0.33 g, 1.24 mmol) in DMF (15 mL) and Pyridine (5 mL) according to the procedure reported in step 4 of scheme 2. This gave after workup and purification by flash column chromatography (Two separate columns: silica gel, 40 g, eluting with ethyl acetate in hexanes from 0 to 100%) 1-(((cyclohexyloxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (70d) (0.32 g, 48% yield) as a white solid; $^1$H NMR (300 MHz, DMSO-d$_6$) δ 10.56 & 10.48 (2s, 1H, D$_2$O exchangeable), 9.36-8.73 (m, 2H, D$_2$O exchangeable), 8.64 & 8.57 (2s, 1H), 8.22 (d, J=8.1 Hz, 1H), 8.05-7.97 (m, 2H), 7.96-7.85 (m, 2H), 7.75-7.60 (m, 2H), 7.14-6.89 (m, 2H), 6.63 (q, J=5.3 Hz, 1H), 6.06 (dd, J=17.8, 1.5 Hz, 1H), 5.44 (d, J=11.3 Hz, 1H), 4.57-4.36 (m, 1H), 3.99 (t, J=6.7 Hz, 2H), 3.89 (s, 3H), 3.27-3.19 (m, 2H), 1.90-1.01 (m, 23H), 0.91-0.83 (m, 2H), 0.54-0.38 (m, 2H), 0.33-0.19 (m, 2H); MS (ES+): 812.78 (M+1); MS (ES−): 810.89 (M−1); Analysis calculated for $C_{44}H_{53}N_5O_{10} \cdot 0.5H_2O$: C, 64.37; H, 6.63; N, 8.53; found: C, 64.24; H, 6.68; N, 8.31.

Scheme 71

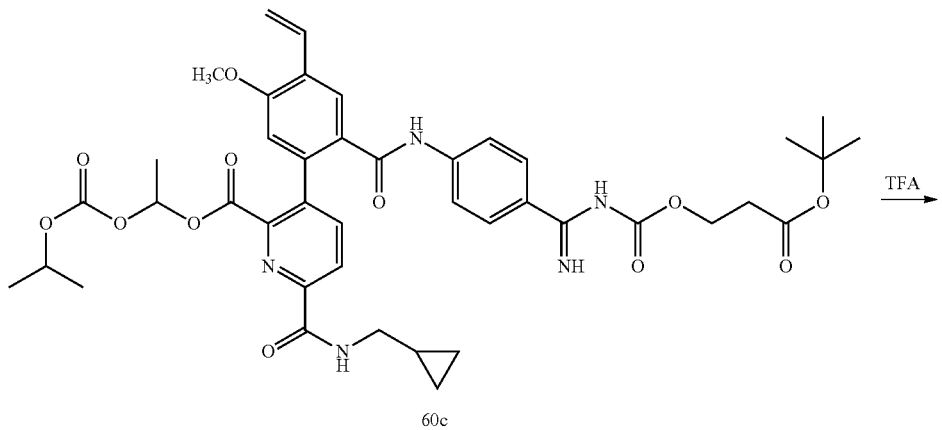

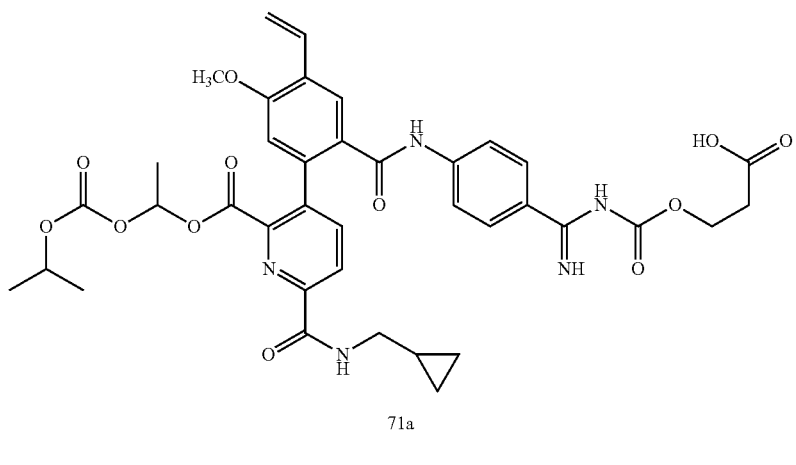

Preparation of 3-(((((4-(2-(6-((cyclopropylmethyl) carbamoyl)-2-((1-((isopropoxycarbonyl)oxy)ethoxy) carbonyl)pyridin-3-yl)-4-methoxy-5-vinylbenzamido)phenyl)(imino)methyl)carbamoyl)oxy)propanoic acid (71a)

Compound (71a) was prepared from 1-((isopropoxycarbonyl)oxy)ethyl 3-(2-((4-(N-((3-(tert-butoxy)-3-oxopropoxy)carbonyl)carbamimidoyl)phenyl)carbamoyl)-5-methoxy-4-vinylphenyl)-6-((cyclopropylmethyl) carbamoyl)picolinate (60c) (60 mg, 0.074 mmol) in dichloromethane (20 mL) using 2,2,2-trifluoroacetic acid (0.113 mL, 1.47 mmol) according to the procedure reported in Step-4 of scheme 8. This gave after workup and purification by flash column prep-HPLC [C18 column, eluting with $CH_3CN$ in water (containing 0.1% HCl) from 0-100%], followed by lyophilization 3-(((((4-(2-(6-((cyclopropylmethyl)carbamoyl)-2-((1-((isopropoxycarbonyl)oxy)ethoxy) carbonyl)pyridin-3-yl)-4-methoxy-5-vinylbenzamido)phenyl)(imino)methyl)carbamoyl)oxy)propanoic acid (71a) (29 mg, 52% yield) as a white solid; $^1$H NMR (300 MHz, DMSO-$d_6$) δ 12.54 (brs, 1H, $D_2O$ exchangeable), 11.23 (brs, 1H, $D_2O$ exchangeable), 10.77 (d, J=19.8 Hz, 1H), 10.34 (brs, 1H, $D_2O$ exchangeable), 8.61 (d, J=29.5 Hz, 1H), 8.22 (d, J=8.0 Hz, 1H), 8.06-7.95 (m, 2H), 7.87-7.68 (m, 4H), 7.11-6.93 (m, 2H), 6.63 (q, J=5.3 Hz, 1H), 6.07 (d, J=17.8 Hz, 1H), 5.44 (d, J=11.4 Hz, 1H), 4.78-4.63 (m, 1H), 4.44 (t, J=5.9 Hz, 2H), 3.89 (s, 3H), 3.26-3.18 (m, 2H), 2.72 (t, J=6.0 Hz, 2H), 1.26-1.00 (m, 11H), 0.51-0.37 (m, 2H), 0.33-0.20 (m, 2H); MS (ES+) 760.6 (M+1); 782.6 (M+Na); MS (ES−): 794.7 (M+Cl); Analysis calculated for $C_{38}H_{41}N_5O_{12}$·HCl·3$H_2O$: C, 53.68; H, 5.69; N, 8.24; found: C, 53.63; H, 5.60; N, 8.25.

Scheme 72

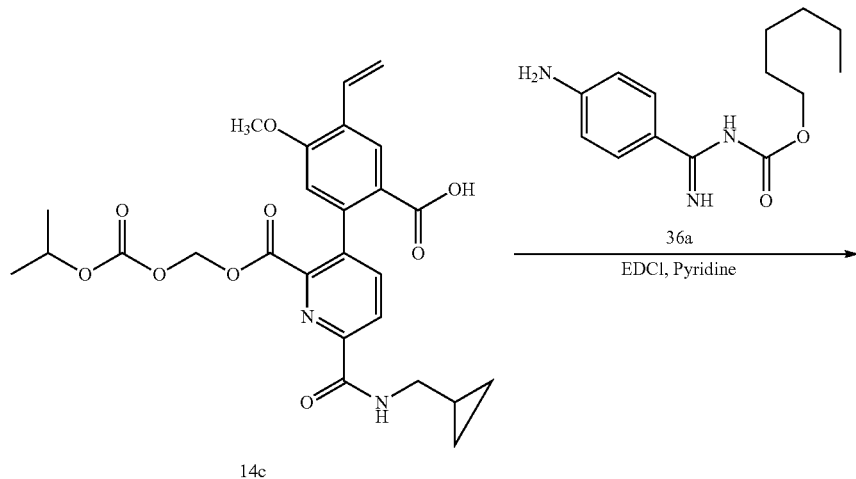

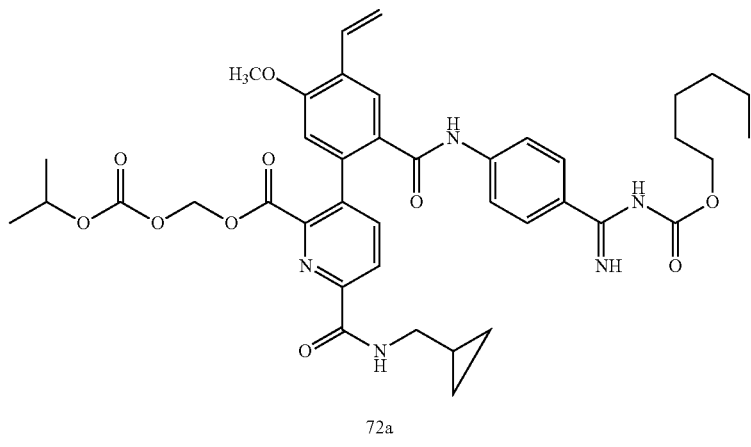

Preparation of (((isopropoxycarbonyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (72a)

Compound (72a) was prepared from 2-(6-((cyclopropylmethyl)carbamoyl)-2-((((isopropoxycarbonyl)oxy)methoxy) carbonyl)pyridin-3-yl)-4-methoxy-5-vinylbenzoic acid (14c) (0.47 g, 0.94 mmol) using EDCI (0.27 g, 1.41 mmol) and hexyl ((4-aminophenyl)(imino)methyl)carbamate (36a) (0.29 g, 1.10 mmol) in DMF (3 mL) and Pyridine (3 mL) according to the procedure reported in step 4 of scheme 2. This gave after workup and purification by flash column chromatography [(silica gel, 24 g), eluting with a 9:1 mixture of ethyl acetate and methanol in hexanes (0 to 100%)] followed by lyophilization ((isopropoxycarbonyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (72a) (0.23 g, 33% yield) as a white solid; $^1$H NMR (300 MHz, DMSO-d$_6$) δ 10.52 (s, 1H), 9.34-8.73 (m, 2H, D$_2$O exchangeable), 8.57 (t, J=6.1 Hz, 1H), 8.23 (d, J=8.0 Hz, 1H), 8.06-7.82 (m, 4H), 7.67 (d, J=8.5 Hz, 2H), 7.14-6.94 (m, 2H), 6.05 (d, J=17.8 Hz, 1H), 5.73 (s, 2H), 5.44 (d, J=11.4 Hz, 1H), 3.99 (t, J=6.6 Hz, 2H), 3.88 (s, 3H), 3.27-3.17 (m, 2H), 2.46-2.33 (m, 1H), 1.67-1.50 (m, 2H), 1.40-1.20 (m, 6H), 1.15-1.03 (m, 1H), 0.99 (d, J=7.0 Hz, 6H), 0.91-0.80 (m, 3H), 0.44 (dt, J=8.0, 2.9 Hz, 2H), 0.27 (d, J=4.9 Hz, 2H); MS (ES+) 742.8 (M+1), 764.8 (M+Na); Analysis calculated for: C$_{40}$H$_{47}$N$_5$O$_9$(H$_2$O)$_{0.5}$: C, 63.99; H, 6.44; N, 9.33; found: C, 63.99; H, 6.41; N, 9.35.

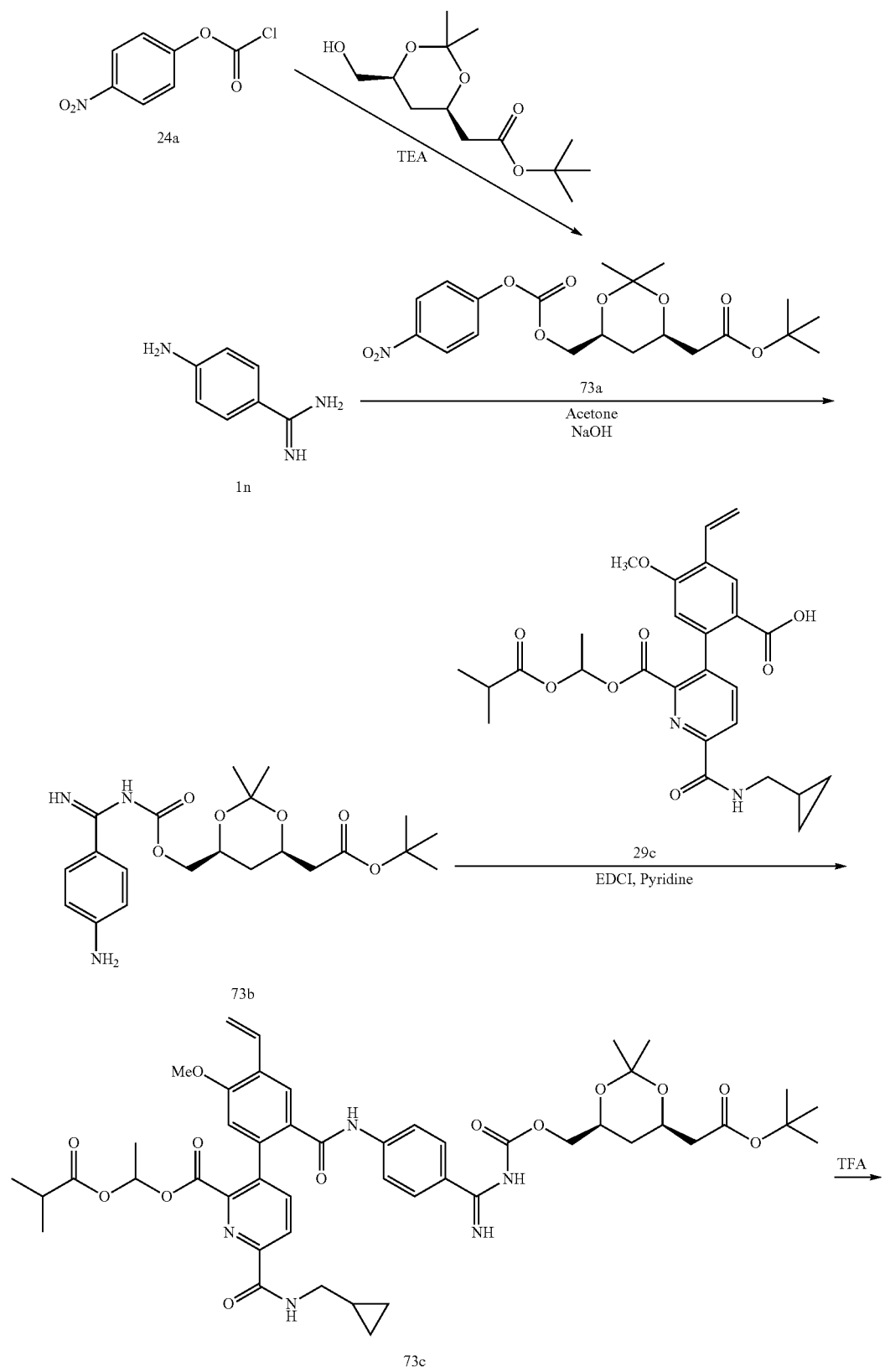

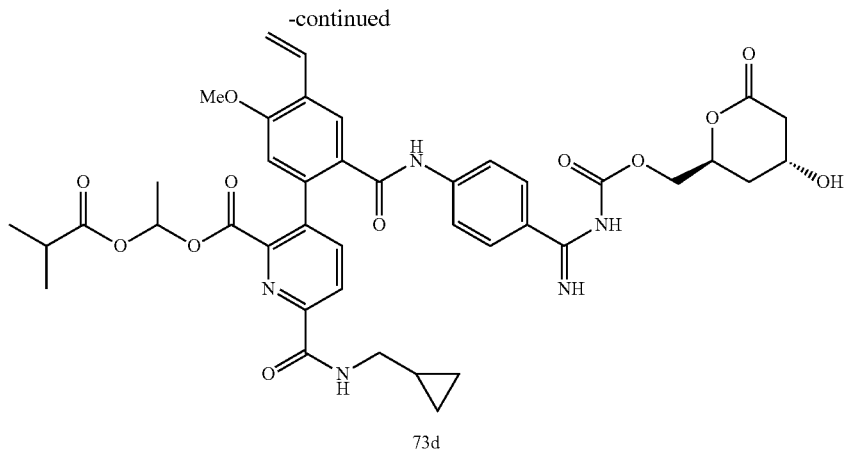

73d

Preparation of 1-(isobutyryloxy)ethyl 6-((cyclopropylmethyl)carbamoyl)-3-(2-((4-(N-(((((2S,4R)-4-hydroxy-6-oxotetrahydro-2H-pyran-2-yl)methoxy)carbonyl)carbamimidoyl)phenyl)carbamoyl)-5-methoxy-4-vinylphenyl)picolinate (73d)

Step-1: Preparation of tert-butyl 2-((4R,6S)-2,2-dimethyl-6-((((4-nitrophenoxy)carbonyl)oxy)methyl)-1,3-dioxan-4-yl)acetate (73a)

Compound (73a) was prepared according to the procedure described in step 1 of scheme 24 from 4-nitrophenyl chloroformate (0.43 g, 2.11 mmol) in THF (20 mL) using tert-butyl 2-((4R,6S)-6-(hydroxymethyl)-2,2-dimethyl-1,3-dioxan-4-yl)acetate (0.55 g, 2.11 mmol) and triethylamine (0.65 mL, 4.65 mmol). This gave after workup tert-butyl 2-((4R,6S)-2,2-dimethyl-6-((((4-nitrophenoxy)carbonyl)oxy)methyl)-1,3-dioxan-4-yl)acetate (73a) (0.82 g, 91% yield) as thick dark orange syrup which can be used as such in next step without further purification.

Step-2: Preparation of tert-butyl 2-((4R,6S)-6-(((((4-aminophenyl)(imino)methyl)carbamoyl)oxy)methyl)-2,2-dimethyl-1,3-dioxan-4-yl)acetate (73b)

Compound (73b) was prepared from 4-aminobenzimidamide dihydrochloride (1n) (0.3 g, 1.45 mmol) in acetone (10 mL), using 1 N aqueous NaOH solution (3.18 mL, 3.18 mmol) and tert-butyl 2-((4R,6S)-2,2-dimethyl-6-((((4-nitrophenoxy)carbonyl)oxy)methyl)-1,3-dioxan-4-yl)acetate (73a) (0.8 g, 1.88 mmol) according to the procedure reported in step 4 of scheme 23. This gave after workup and purification by flash column chromatography (silica gel, 12 g eluting with ethyl acetate and hexanes 0 to 100%) tert-butyl 2-((4R,6S)-6-(((((4-aminophenyl)(imino)methyl)carbamoyl)oxy)methyl)-2,2-dimethyl-1,3-dioxan-4-yl)acetate (73b) (0.4 g, 66% yield) as a colorless foam; $^1$H NMR (300 MHz, DMSO-$d_6$) δ 9.12 (s, 1H), 8.67 (s, 1H), 7.80-7.70 (m, 2H), 6.60-6.50 (m, 2H), 5.87 (s, 2H), 4.32-4.11 (m, 2H), 3.92 (d, J=5.0 Hz, 2H), 2.41 (dd, J=15.1, 4.8 Hz, 1H), 2.24 (dd, J=15.1, 8.1 Hz, 1H), 1.61-1.11 (m, 17H); MS (ES+) 422.5 (M+1), 444.5 (M+Na).

Step-3: Preparation of 1-(isobutyryloxy)ethyl 3-(2-((4-(N-(((((4S,6R)-6-(2-(tert-butoxy)-2-oxoethyl)-2,2-dimethyl-1,3-dioxan-4-yl)methoxy)carbonyl)carbamimidoyl)phenyl)carbamoyl)-5-methoxy-4-vinylphenyl)-6-((cyclopropylmethyl)carbamoyl) picolinate (73c)

Compound (73c) was prepared from 2-(6-((cyclopropylmethyl)carbamoyl)-2-((1-(isobutyryloxy)ethoxy) carbonyl) pyridine-3-yl)-4-methoxy-5-vinylbenzoic acid (29c) (0.3 g, 0.59 mmol) using EDCI (0.14 g, 0.71 mmol) and tert-butyl 2-((4R,6S)-6-(((((4-aminophenyl)(imino)methyl)carbamoyl)oxy)methyl)-2,2-dimethyl-1,3-dioxan-4-yl)acetate (73b) (0.25 g, 0.59 mmol) in DMF (3 mL) and Pyridine (1 mL) according to the procedure reported in step 4 of scheme 2. This gave after workup and purification by flash column chromatography [silica gel 12 g, eluting with EtOAc/MeOH (9:1) in hexane from 0-60%] 1-(isobutyryloxy)ethyl 3-(2-((4-(N-(((((4S,6R)-6-(2-(tert-butoxy)-2-oxoethyl)-2,2-dimethyl-1,3-dioxan-4-yl)methoxy)carbonyl)carbamimidoyl)phenyl)carbamoyl)-5-methoxy-4-vinylphenyl)-6-((cyclopropylmethyl)carbamoyl)picolinate (73c) (0.315 g, 59% yield) as a foam.

Step-4: Preparation of 1-(isobutyryloxy)ethyl 6-((cyclopropylmethyl)carbamoyl)-3-(2-((4-(N-(((((2S,4R)-4-hydroxy-6-oxotetrahydro-2H-pyran-2-yl)methoxy)carbonyl)carbamimidoyl)phenyl)carbamoyl)-5-methoxy-4-vinylphenyl)picolinate (73d)

Compound (73d) was prepared from 1-(isobutyryloxy) ethyl 3-(2-((4-(N-(((((4S,6R)-6-(2-(tert-butoxy)-2-oxoethyl)-2,2-dimethyl-1,3-dioxan-4-yl)methoxy)carbonyl)carbamimidoyl)phenyl)carbamoyl)-5-methoxy-4-vinylphenyl)-6-((cyclopropylmethyl)carbamoyl)picolinate (73c) (0.26 g, 0.28 mmol) in dichloromethane (2 mL) using 2,2,2-trifluoroacetic acid (0.66 mL, 8.53 mmol) according to the procedure reported in Step-4 of scheme 8. This gave after workup and purification by flash column prep-HPLC [C18 column, 26 g eluting with CH$_3$CN in water (containing 0.1% HCl) from 0-100%], followed by lyophilization 1-(isobutyryloxy)ethyl 6-((cyclopropylmethyl)carbamoyl)-3-(2-((4-(N-(((((2S,4R)-4-hydroxy-6-oxotetrahydro-2H-pyran-2-yl)methoxy)carbonyl)carbamimidoyl)phenyl)carbamoyl)-5-methoxy-4-vinylphenyl)picolinate (73d) (47 mg, 20%) as a white solid; $^1$H NMR (300 MHz, DMSO-$d_6$) δ 10.81-10.56 (m, 1H), 8.69-8.46 (m, 1H), 8.22 (d, J=8.0 Hz, 1H), 8.00 (s, 2H), 7.78 (s, 4H), 7.11-6.97 (m, 2H), 6.80-6.67 (m, 1H), 6.05 (d, J=17.8 Hz, 1H), 5.45 (d, J=11.4 Hz, 1H), 5.41-5.25 (m, 1H), 4.97-4.81 (m, 1H), 4.51-4.28 (m, 1H), 4.25-4.16 (m, 1H), 3.89 (s, 3H), 3.29-3.17 (m, 2H), 2.74-2.54 (m, 1H), 1.90-1.79 (m, 2H), 1.66-1.54 (m, 1H), 1.17 (d, J=5.4 Hz, 3H), 1.15-0.98 (m, 1H), 1.04-0.91 (m, 8H), 0.51-0.38 (m, 2H), 0.33-0.21 (m, 2H); MS (ES+) 800.7 (M+1), 822.7 (M+Na), MS (ES−) 834.8 (M+Cl).
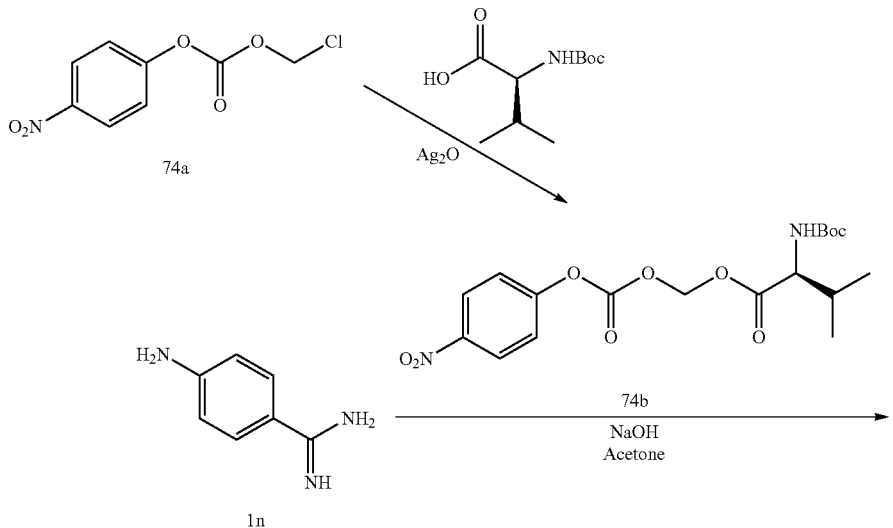
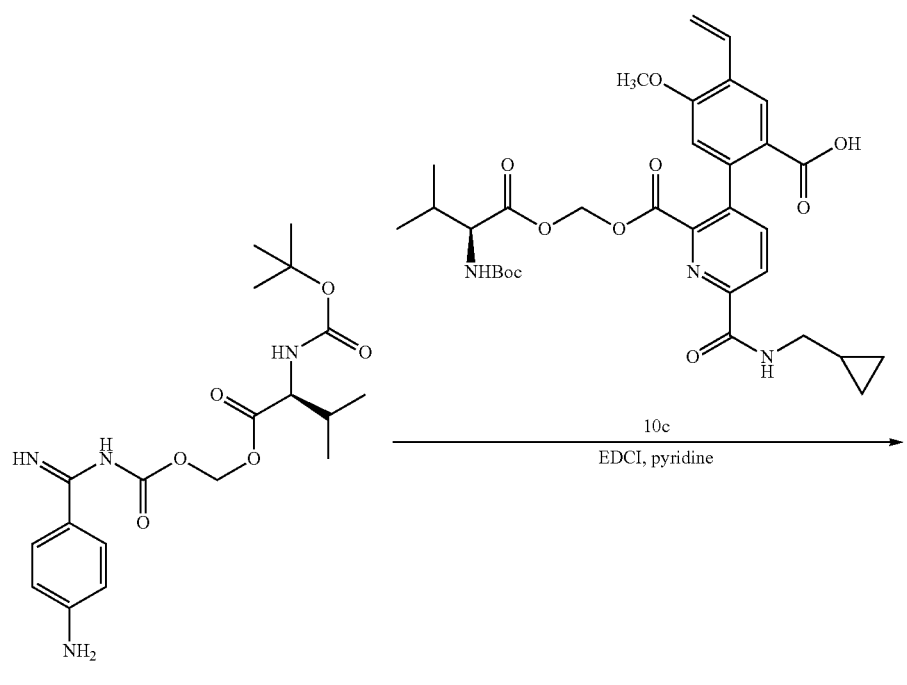

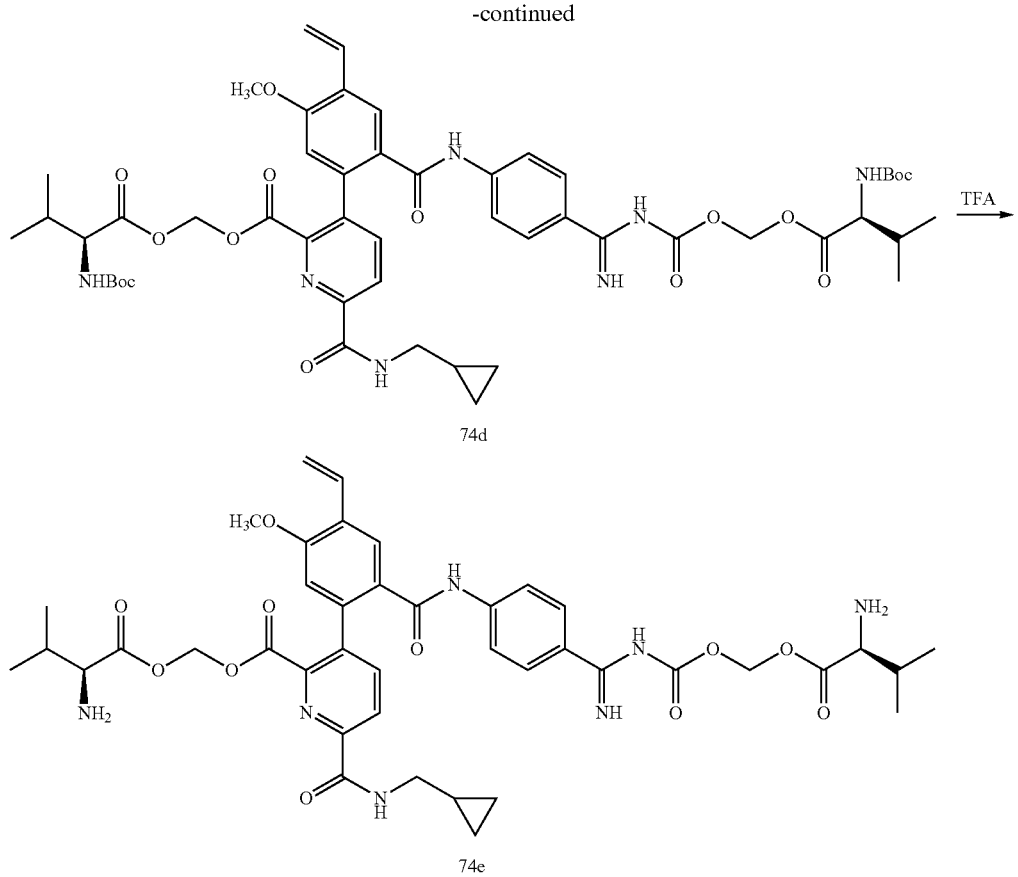

Preparation of (((S)-2-amino-3-methylbutanoyl)oxy)methyl 3-(2-((4-(N—(((((S)-2-amino-3-methylbutanoyl)oxy)methoxy)carbonyl)carbamimidoyl)phenyl)carbamoyl)-5-methoxy-4-vinylphenyl)-6-((cyclopropylmethyl)carbamoyl)picolinate (74e)

Step-1: Preparation of (S)-(((4-nitrophenoxy)carbonyl)oxy)methyl 2-((tert-butoxycarbonyl)amino)-3-methylbutanoate (74b)

Compound (74b) was prepared according to the procedure reported in step 1 of scheme 33 from chloromethyl 4-nitrophenyl carbonate (74a) (6 g, 25.9 mmol), Boc-L-valine (11.26 g, 51.8 mmol) and silver oxide (6.00 g, 25.9 mmol). This gave after workup and purification by flash column chromatography [silica gel 24 g, eluting with EtOAc in hexane 0-40%] (S)-(((4-nitrophenoxy)carbonyl)oxy)methyl 2-((tert-butoxycarbonyl)amino)-3-methylbutanoate (74b) (2.2 g, 21% yield). $^1$H NMR (300 MHz, DMSO-$d_6$) δ 8.41-8.31 (m, 2H), 7.61-7.51 (m, 2H), 7.39 (d, J=7.7 Hz, 1H), 5.93 (d, J=6.2 Hz, 1H), 5.85 (d, J=6.1 Hz, 1H), 3.93 (dd, J=7.7, 6.4 Hz, 1H), 2.11-2.02 (m, 1H), 1.38 (s, 9H), 0.91 (dd, J=6.9, 1.8 Hz, 6H).

Step-2: Preparation of (S)-((((4-aminophenyl)(imino)methyl)carbamoyl)oxy)methyl 2-((tert-butoxycarbonyl)amino)-3-methylbutanoate (74c)

Compound (74c) was prepared from 4-aminobenzimidamide dihydrochloride (1n) (1.24 g, 5.95 mmol) in acetone/water (26 mL, 12:1), NaOH (0.49 g, 12.20 mmol) and (S)-(((4-nitrophenoxy)carbonyl)oxy)methyl 2-((tert-butoxycarbonyl)amino)-3-methylbutanoate (74b) (2.7 g, 6.55 mmol) according to the procedure reported in step 4 of scheme 23. This gave after workup and purification by flash column chromatography [silica gel (24 g), eluting with EtOAc/MeOH (9:1) in hexane from 0-70%] (S)-((((4-aminophenyl)(imino)methyl)carbamoyl)oxy)methyl 2-((tert-butoxycarbonyl)amino)-3-methylbutanoate (74c) (1.01 g, 42% yield) as a yellow solid. MS (ES+): 409.5 (M+1); MS (ES−) 407.6 (M−1).

Step-3: Preparation of (((S)-2-((tert-butoxycarbonyl)amino)-3-methylbutanoyl)oxy)methyl 6-((cyclopropylmethyl)carbamoyl)-3-(2-((4-(N—((S)-6-isopropyl-10,10-dimethyl-5,8-dioxo-2,4,9-trioxa-7-azaundecan-1-oyl)carbamimidoyl)phenyl)carbamoyl)-5-methoxy-4-vinylphenyl)picolinate (74d)

Compound (74d) was prepared from (S)-2-(6-((cyclopropylmethyl)carbamoyl)-2-(6-isopropyl-10,10-dimethyl-5,8-dioxo-2,4,9-trioxa-7-azaundecan-1-oyl)pyridin-3-yl)-4-methoxy-5-vinylbenzoic acid (10c) (0.6 g, 0.96 mmol) using EDCI (0.28 g, 1.44 mmol) and (S)-((((4-aminophenyl)(imino)methyl)carbamoyl)oxy)methyl 2-((tert-butoxycarbonyl)amino)-3-methylbutanoate (74c) (0.47 g, 1.15 mmol) in DMF (10 mL) and pyridine (2 mL) according to the procedure reported in step 4 of scheme 2. This gave after workup and purification by flash column chromatography [silica gel (12 g), eluting with EtOAc/MeOH (9:1) in hexane from 0-60%] then prep HPLC [eluting with CH$_3$CN in water (containing with 0.1% HCl) from 0-100%] followed by lyophilization (((S)-2-((tert-butoxycarbonyl)amino)-3-methylbutanoyl)oxy)methyl 6-((cyclopropylmethyl)carbamoyl)-3-(2-((4-(N—((S)-6-isopropyl-10,10-dimethyl-5,8-dioxo-2,4,9-trioxa-7-azaundecan-1-oyl)carbamimidoyl)phenyl)carbamoyl)-5-methoxy-4-vinylphenyl)picolinate (74d) (0.22 mg, 23% yield) as a white solid. MS (ES+) 1016.8 (M+1).

Step-4: Preparation of (((S)-2-amino-3-methylbutanoyl)oxy)methyl 3-(2-((4-(N—(((((S)-2-amino-3-methylbutanoyl)oxy)methoxy)carbonyl)carbamimidoyl)phenyl)carbamoyl)-5-methoxy-4-vinylphenyl)-6-((cyclopropylmethyl)carbamoyl)picolinate (74e)

Compound (74e) was prepared from (((S)-2-((tert-butoxycarbonyl)amino)-3-methylbutanoyl)oxy)methyl 6-((cyclopropylmethyl)carbamoyl)-3-(2-((4-(N—((S)-6-isopropyl-10,10-dimethyl-5,8-dioxo-2,4,9-trioxa-7-azaundecan-1-oyl)carbamimidoyl)phenyl)carbamoyl)-5-methoxy-4-vinylphenyl)picolinate (74d) (0.22 g, 0.22 mmol) in dichloromethane (20 mL) using 2,2,2-trifluoroacetic acid (0.67 mL, 8.66 mmol) according to the procedure reported in Step-4 of scheme 8. This gave after workup and purification by prep-HPLC [C18 column, eluting with ACN in water (containing 0.1% HCl) from 0-100%], followed by lyophilization (((S)-2-amino-3-methylbutanoyl)oxy)methyl 3-(2-((4-(N—(((((S)-2-amino-3-methylbutanoyl)oxy)methoxy)carbonyl)carbamimidoyl)phenyl)carbamoyl)-5-methoxy-4-vinylphenyl)-6-((cyclopropylmethyl)carbamoyl)picolinate (74e) (75 mg, 43% yield) as an off white solid; $^1$H NMR (300 MHz, DMSO-d$_6$) δ 10.83 (s, 1H, D$_2$O exchangeable), 10.21-9.47 (m, 1H, D$_2$O exchangeable), 8.79-8.55 (m, 6H, D$_2$O exchangeable), 8.53-8.42 (m, 1H), 8.25 (d, J=8.0 Hz, 1H), 8.07-8.01 (m, 2H), 7.88 (d, J=8.7 Hz, 2H), 7.79 (d, J=8.7 Hz, 2H), 7.10-6.97 (m, 2H), 6.11 (dd, J=17.8, 1.6 Hz, 1H), 6.02-5.68 (m, 4H), 5.50-5.31 (m, 1H), 4.05-3.93 (m, 1H), 3.94-3.81 (m, 4H), 3.30-3.15 (m, 2H), 2.22 (dt, J=12.1, 6.4 Hz, 1H), 2.16-1.96 (m, 2H), 1.16-1.01 (m, 1H), 0.98 (dd, J=9.5, 6.9 Hz, 6H), 0.87 (dd, J=6.9, 2.0 Hz, 6H), 0.50-0.39 (m, 2H), 0.32-0.23 (m, 2H); MS (ES+) 816.7 (M+1); 838.7 (M+Na); Analysis calculated for: C$_{41}$H$_{49}$N$_7$O$_{11}$·2.75HCl·3.75H$_2$O. 0.25TFA: C, 49.24; H, 5.92; Cl, 9.63; N, 9.74; found: C, 49.29; H, 5.99; Cl, 9.93; N, 9.76.

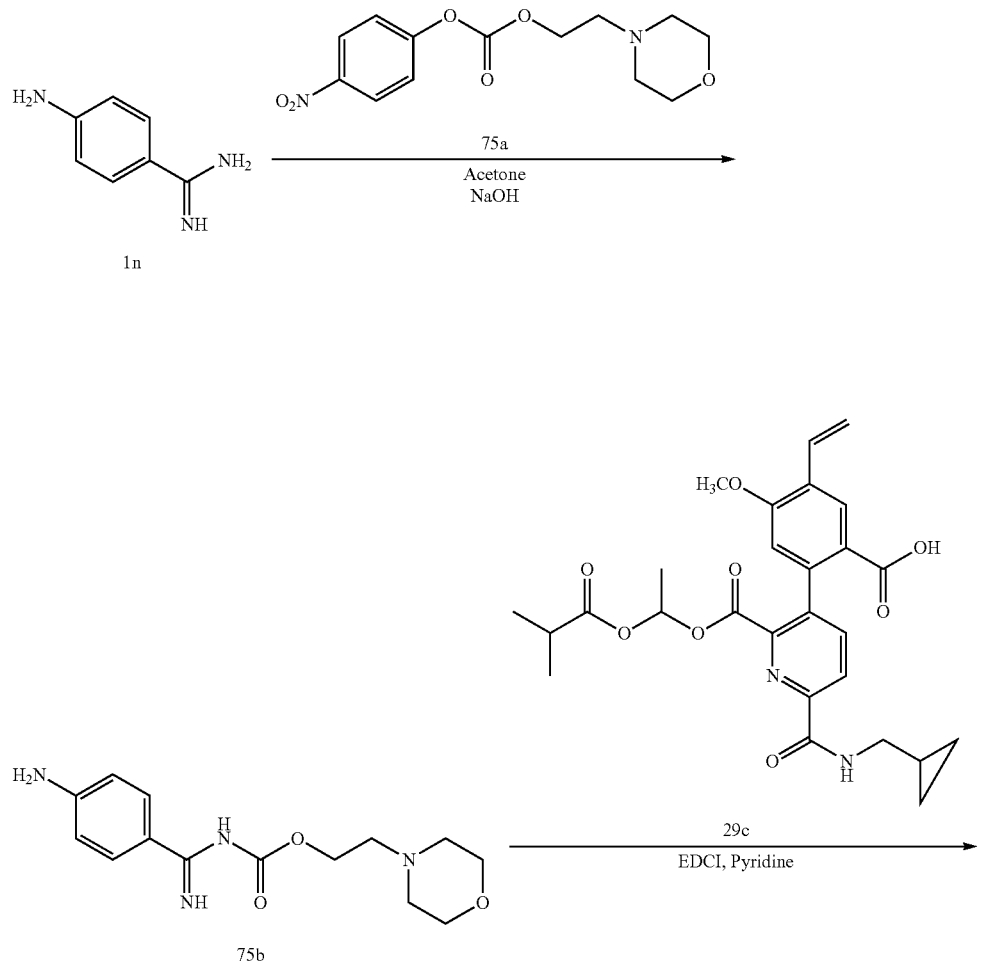

-continued

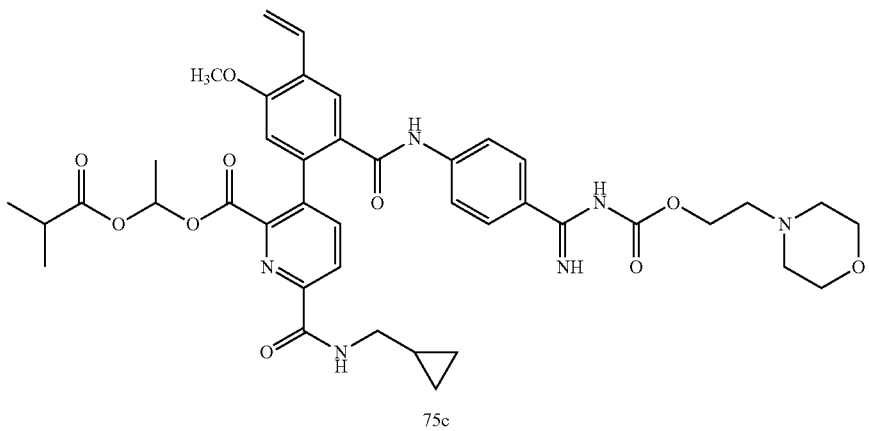

75c

Preparation of 1-(isobutyryloxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (75c)

Step-1: Preparation of 2-morpholinoethyl ((4-aminophenyl)(imino)methyl)carbamate (75b)

Compound (75b) was prepared according to the procedure described in step 4 of scheme 23 from 4-aminobenzimidamide dihydrochloride (1n) (1.5 g, 7.21 mmol) in acetone (30 mL), using a solution of NaOH (0.63 g, 15.86 mmol) in water (10 mL) and 2-morpholinoethyl (4-nitrophenyl) carbonate (75a) (0.8 g, 1.88 mmol, prepared according to the procedure reported by Yoon, Suk Kyoon et al; in PCT Int. Appl, 2004002985). This gave after workup and purification by flash column chromatography (silica gel, 12 g eluting with ethyl acetate and hexanes 0 to 100%) 2-morpholinoethyl ((4-aminophenyl)(imino)methyl)carbamate (75b) (0.7 g, 2.395 mmol, 33.2% yield) as a light orange solid. 1H NMR (300 MHz, DMSO-$d_6$) δ 9.09 (s, 1H), 8.61 (s, 1H), 7.79-7.69 (m, 2H), 6.60-6.51 (m, 2H), 5.85 (s, 2H), 4.09 (t, J=5.9 Hz, 2H), 3.61-3.52 (m, 4H), 2.54 (t, J=6.0 Hz, 2H), 2.46-2.35 (m, 4H); MS (ES+) 585.6 (2M+1), MS (ES−) 291.4 (M−1), 327.5 (M+Cl).

Step-2: Preparation of 1-(isobutyryloxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (75c)

Compound (75c) was prepared from 2-(6-((cyclopropylmethyl)carbamoyl)-2-((1-(isobutyryloxy)ethoxy) carbonyl)pyridine-3-yl)-4-methoxy-5-vinylbenzoic acid (29c) (0.2 g, 0.39 mmol) using EDCI (0.09 g, 0.47 mmol) and 2-morpholinoethyl ((4-aminophenyl)(imino)methyl)carbamate (75b) (0.12 g, 0.39 mmol) in DMF (3 mL) and Pyridine (1 mL) according to the procedure reported in step 4 of scheme 2. This gave after workup and purification by reverse phase column chromatography [C18, 26 g, Acetonitrile in water (with 0.1% HCl) 0 to 60% as eluents] followed by lyophilization 1-(isobutyryloxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (75c) (0.08 g, 0.102 mmol, 26.0% yield) as a white powder; $^1$H NMR (300 MHz, DMSO-$d_6$) δ 10.87-10.61 (m, 1H), 8.69-8.45 (m, 1H), 8.22 (d, J=8.0 Hz, 1H), 8.08-7.94 (m, 2H), 7.88-7.70 (m, 4H), 7.11-6.96 (m, 2H), 6.80-6.68 (m, 1H), 6.06 (d, J=17.8 Hz, 1H), 5.49-5.39 (m, 1H), 4.72-4.55 (m, 2H), 4.07-3.58 (m, 9H), 3.59-3.35 (m, 2H), 3.30-3.16 (m, 4H), 2.49-2.35 (m, 1H), 1.25-0.89 (m, 10H), 0.50-0.39 (m, 2H), 0.31-0.23 (m, 2H); MS (ES+) 785.8 (M+1), MS (ES−) 819.8 (M+Cl).

Scheme 76

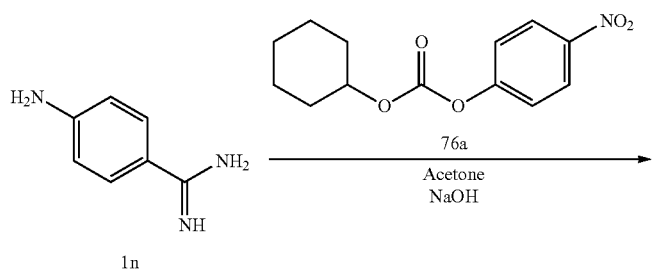

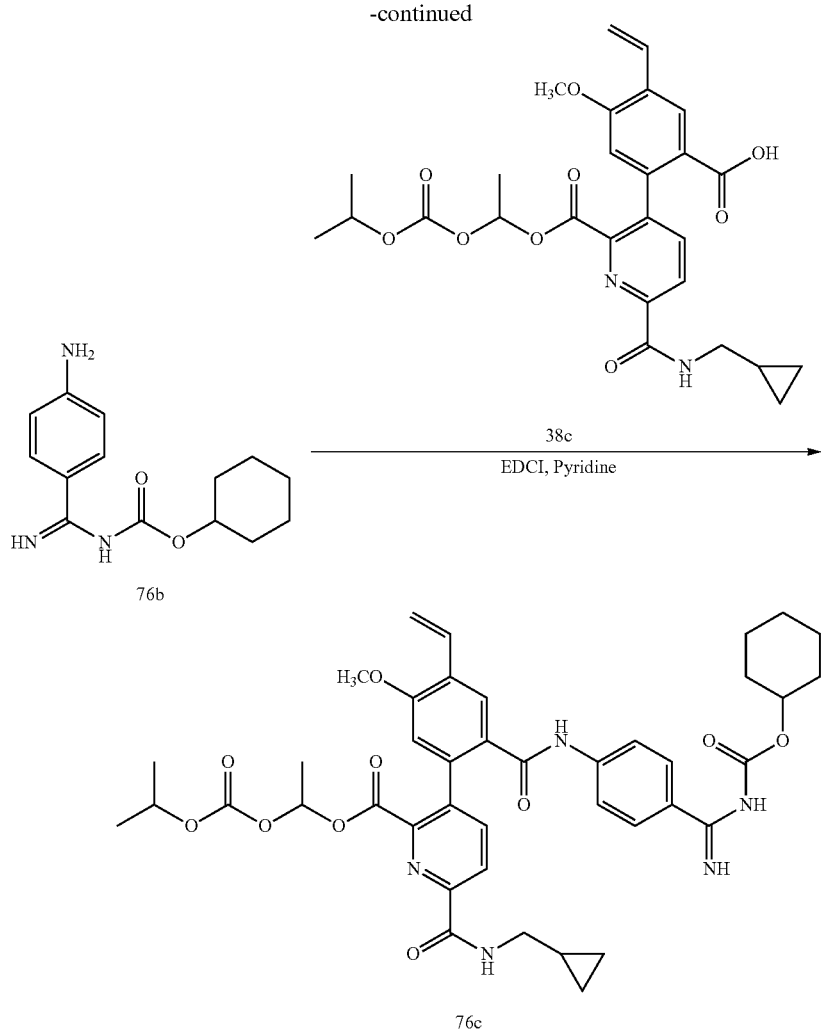

Preparation of 1-((isopropoxycarbonyl)oxy)ethyl 3-(2-((4-(N-((cyclohexyloxy)carbonyl)carbamimidoyl)phenyl)carbamoyl)-5-methoxy-4-vinylphenyl)-6-((cyclopropylmethyl)carbamoyl)picolinate (76c)

Step-1: Preparation of cyclohexyl ((4-aminophenyl)(imino)methyl)carbamate (76b)

Compound (76b) was prepared according to the procedure described in step 4 of scheme 23 from 4-aminobenzimidamide dihydrochloride (1n) (1.96 g, 9.42 mmol) in acetone/water (40 mL, 4:1), using NaOH (0.79 g, 19.79 mmol) and cyclohexyl (4-nitrophenyl) carbonate (76a) (3.0 g, 11.31 mmol, prepared according to the procedure reported by Yoo, Moohi et al in PCT Int. Appl., 2010024586). This gave after workup and purification by flash column chromatography (silica gel, 80 g eluting with ethyl acetate and hexanes 0 to 100%) cyclohexyl ((4-aminophenyl)(imino)methyl)carbamate (76b) (1.59 g, 6.08 mmol, 65% yield) as a white solid; $^1$H NMR (300 MHz, DMSO-$d_6$) δ 9.14 (bs, 1H, D$_2$O exchangeable), 8.59 (bs, 1H, D$_2$O exchangeable), 7.85-7.58 (m, 2H), 6.63-6.41 (m, 2H), 5.84 (s, 2H, D$_2$O exchangeable), 4.66-4.39 (m, 1H), 1.94-1.78 (m, 2H), 1.76-1.62 (m, 2H), 1.58-1.46 (m, 1H), 1.42-1.15 (m, 5H); MS (ES+): 262.4 (M+1), 284.4 (M+Na); MS (ES−): 296.6 (M+Cl).

Step-2: Preparation of 1-((isopropoxycarbonyl)oxy)ethyl 3-(2-((4-(N-((cyclohexyloxy)carbonyl)carbamimidoyl)phenyl)carbamoyl)-5-methoxy-4-vinylphenyl)-6-((cyclopropylmethyl)carbamoyl)picolinate (76c)

Compound (76c) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (1.01 g, 1.91 mmol) using EDCI (0.55 g, 2.87 mmol) and cyclohexyl ((4-aminophenyl)(imino)methyl)carbamate (76b) (0.5 g, 1.91 mmol) in DMF (15 mL) and Pyridine (5 mL) according to the procedure reported in step 4 of scheme 2. This gave after workup and purification flash column chromatography (silica gel, 40 g, eluting with ethyl acetate in hexanes from 0 to 100%) 1-((isopropoxycarbonyl)oxy)ethyl 3-(2-((4-(N-((cyclohexyloxy)carbonyl)carbamimidoyl)phenyl)carbamoyl)-5-methoxy-4-vinylphenyl)-6-((cyclopropylmethyl)carbamoyl)picolinate (76c) (0.28 g, 19% yield) as a white solid; $^1$H NMR (300 MHz, DMSO-$d_6$) δ 10.56 & 10.47 (2bs, 1H), 9.13 & 8.94 (2bs, 2H, D$_2$O exchangeable), 8.64 & 8.55 (2bs, 1H), 8.22 (d, J=8.0 Hz, 1H), 8.07-7.83 (m, 4H), 7.70-7.61 (m, 2H), 7.16-6.88 (m, 2H), 6.63 (q, J=5.3 Hz, 1H), 6.06 (d, J=17.8 Hz, 1H), 5.44 (d, J=11.5 Hz, 1H), 4.79-4.63 (m, 1H), 4.61-4.45 (m, 1H), 3.89 (s, 3H), 3.30-3.07 (m, 2H), 1.96-1.80 (m, 2H), 1.75-1.62 (m, 2H), 1.60-1.46 (m, 1H), 1.45-0.98 (m, 15H), 0.52-0.39 (m, 2H), 0.34-0.21 (m, 2H); MS (ES+): 770.7 (M+1), 792.8 (M+Na); Analysis calculated for: $C_{41}H_{47}N_5O_{10} \cdot 5H_2O$: C, 63.23; H, 6.21; N, 8.99; found: C, 63.13; H, 6.20; N, 8.79.
Scheme 77
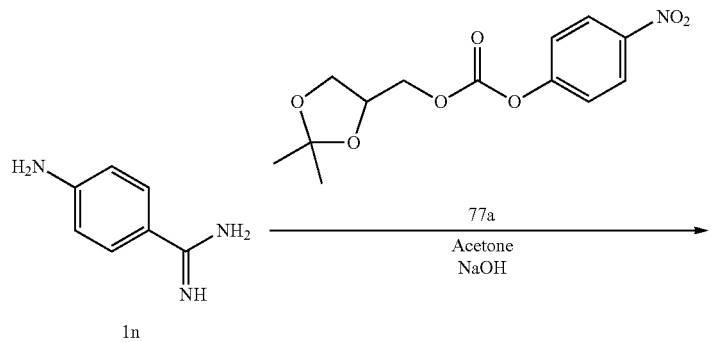
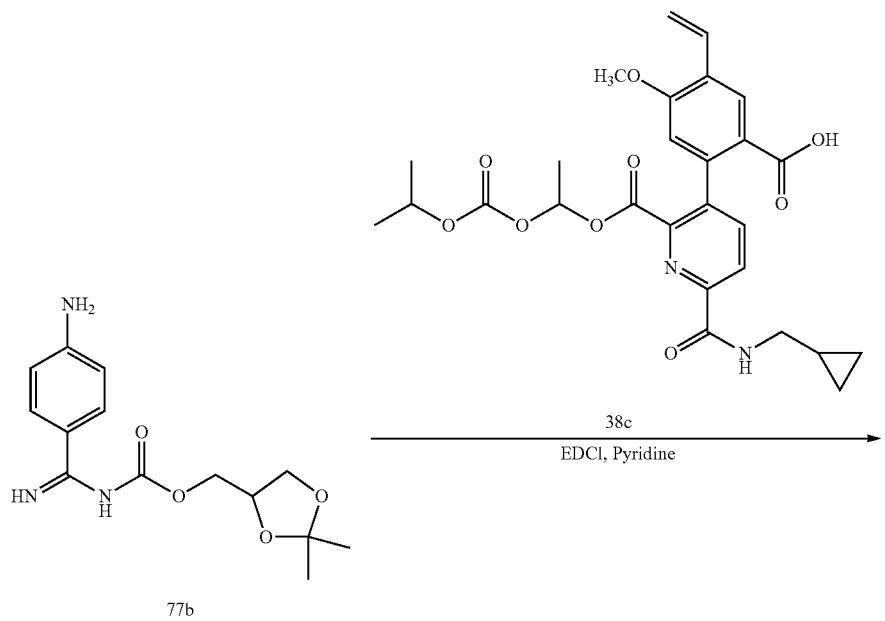
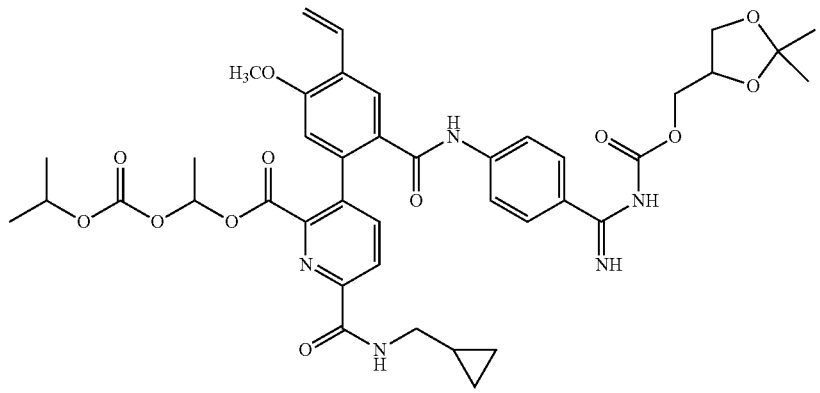

Preparation of 1-((isopropoxycarbonyl)oxy)ethyl 6-((cyclopropylmethyl)carbamoyl)-3-(2-((4-(N-(((2,2-dimethyl-1,3-dioxolan-4-yl)methoxy)carbonyl)carbamimidoyl)phenyl)carbamoyl)-5-methoxy-4-vinylphenyl)picolinate (77c)

Step-1: Preparation of (2,2-dimethyl-1,3-dioxolan-4-yl)methyl ((4-aminophenyl)(imino)methyl)carbamate (77b)

Compound (77b) was prepared according to the procedure described in step 4 of scheme 23 from 4-aminobenzimidamide dihydrochloride (1n) (2.80 g, 13.46 mmol) in acetone/water (40 mL, 4:1), using NaOH (1.13 g, 28.3 mmol) and (2,2-dimethyl-1,3-dioxolan-4-yl)methyl (4-nitrophenyl) carbonate (77a) (4.00 g, 13.46 mmol, prepared according to the procedure reported by Guenther, Sven et al; in PCT Int. Appl., 2013016668). This gave after workup and purification by flash column chromatography (silica gel, 80 g eluting with ethyl acetate and hexanes 0 to 100%) (2,2-dimethyl-1,3-dioxolan-4-yl)methyl ((4-aminophenyl)(imino)methyl) carbamate (77b) (2.78 g, 71% yield) as a yellow wax. $^1$H NMR (300 MHz, DMSO-$d_6$) δ 9.12 (bs, 1H, D$_2$O exchangeable), 8.68 (bs, 1H, D$_2$O exchangeable), 7.86-7.62 (m, 2H), 6.67-6.40 (m, 2H), 5.88 (bs, 2H, D$_2$O exchangeable), 4.35-4.19 (m, 1H), 4.14-3.90 (m, 3H), 3.67 (dd, J=8.4, 6.2 Hz, 1H), 1.37-1.31 (m, 3H), 1.30-1.25 (m, 3H); MS (ES+): 294.3 (M+1), 316.4 (M+Na); MS (ES−): 292.5 (M−1); 328.5 (M+Cl).

Step-2: Preparation of 1-((isopropoxycarbonyl)oxy)ethyl 6-((cyclopropylmethyl)carbamoyl)-3-(2-((4-(N-(((2,2-dimethyl-1,3-dioxolan-4-yl)methoxy)carbonyl)carbamimidoyl)phenyl)carbamoyl)-5-methoxy-4-vinylphenyl)picolinate (77c)

Compound (77c) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (1.08 g, 2.05 mmol) using EDCI (0.59 g, 3.07 mmol) and (2,2-dimethyl-1,3-dioxolan-4-yl)methyl ((4-aminophenyl)(imino)methyl)carbamate (77b) (0.6 g, 2.05 mmol) in DMF (15 mL) and Pyridine (5 mL) according to the procedure reported in step 4 of scheme 2. This gave after workup and purification flash column chromatography [EZ-PREP, C-18 column, 50 g, eluting with 0.1% aq HCl in water and acetonitrile from 0-100%], followed by lypholization 1-((isopropoxycarbonyl)oxy)ethyl 6-((cyclopropylmethyl)carbamoyl)-3-(2-((4-(N-(((2,2-dimethyl-1,3-dioxolan-4-yl)methoxy)carbonyl)carbamimidoyl)phenyl)carbamoyl)-5-methoxy-4-vinylphenyl)picolinate (77c) (0.37 g, 22% yield) as a white solid; $^1$H NMR (300 MHz, DMSO-$d_6$) δ 12.40 (bs, 1H, D$_2$O exchangeable), 10.80 & 10.72 (2s, 1H), 10.34 (bs, 1H, D$_2$O exchangeable), 8.69 & 8.56 (2s, 1H), 8.23 (d, J=8.0 Hz, 1H), 8.08-7.94 (m, 2H), 7.89-7.67 (m, 4H), 7.13-6.95 (m, 2H), 6.63 (q, J=5.3 Hz, 1H), 6.07 (d, J=17.8 Hz, 1H), 5.45 (d, J=11.5 Hz, 1H), 4.83-4.61 (m, 1H), 4.49-4.29 (m, 2H), 4.28-4.13 (m, 1H), 4.07 (dd, J=8.5, 6.3 Hz, 1H), 3.89 (s, 3H), 3.76 (dd, J=8.6, 5.8 Hz, 1H), 3.38-3.09 (m, 2H), 1.45-1.00 (m, 16H), 0.53-0.37 (m, 2H), 0.34-0.17 (m, 2H); MS (ES+): 802.7 (M+1); MS (ES−): 836.8 (M+Cl); Analysis calculated for: C$_{41}$H$_{47}$N$_5$O$_{12}$.2.0H$_2$O.1.0HCl: C, 56.32; H, 5.99; Cl, 4.05; N, 8.01; found: C, 56.31; H, 5.98; Cl, 4.31; N, 8.03.

Scheme 78

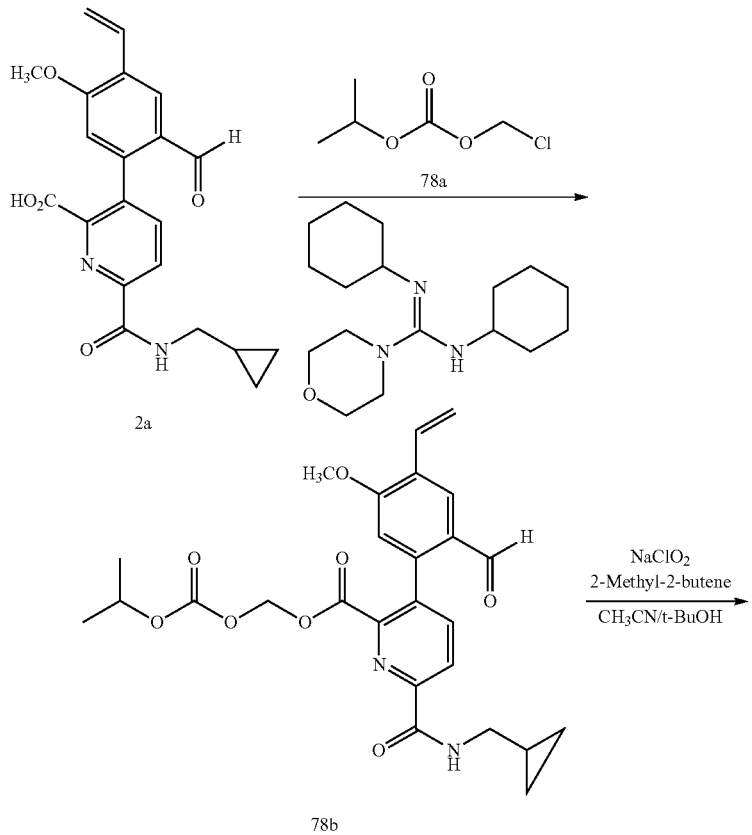

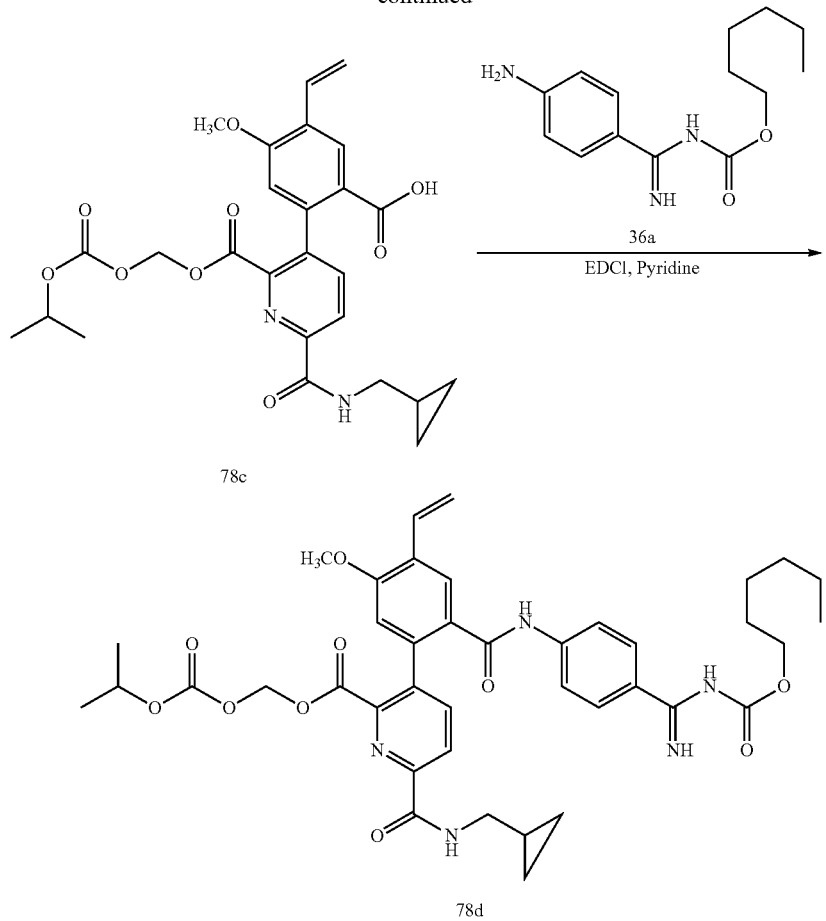

Preparation of ((isopropoxycarbonyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (78d)

Step-1: Preparation of ((isopropoxycarbonyl)oxy) methyl 6-((cyclopropylmethyl)carbamoyl)-3-(2-formyl-5-methoxy-4-vinylphenyl)picolinate (78b)

Compound (70b) was prepared according to the procedure reported in step 1 of scheme 8 from 6-(Cyclopropylmethylcarbamoyl)-3-(2-formyl-5-methoxy-4-vinylphenyl)picolinic acid (2a) (2.66 g, 7.00 mmol) in DMF (30 mL) using N,N'-Dicyclohexyl-4-morpholinecarboxamidine (2.57 g, 8.75 mmol) and chloromethyl isopropyl carbonate (78a) (1.60 g, 10.50 mmol). This gave after workup and purification by flash column chromatography (silica gel 40 g, eluting with ethyl acetate/Hexanes, 0-100%) 1-(((cyclohexyloxy)carbonyl)oxy)ethyl ((isopropoxycarbonyl)oxy)methyl 6-((cyclopropylmethyl)carbamoyl)-3-(2-formyl-5-methoxy-4-vinylphenyl)picolinate (78b) (2.77 g, 5.57 mmol, 80% yield) as an off-white solid; $^1$H NMR (300 MHz, DMSO-$d_6$) δ 9.69 (s, 1H), 8.73 (t, J=6.1 Hz, 1H), 8.28 (d, J=8.0 Hz, 1H), 8.14 (s, 1H), 8.08 (d, J=8.0 Hz, 1H), 7.14-6.88 (m, 2H), 6.01 (dd, J=17.8, 1.4 Hz, 1H), 5.73 (s, 2H), 5.45 (dd, J=11.2, 1.4 Hz, 1H), 4.86-4.61 (m, 1H), 3.90 (s, 3H), 3.30-3.17 (m, 2H), 1.25-1.19 (m, 6H), 1.17-1.05 (m, 1H), 0.53-0.39 (m, 2H), 0.34-0.23 (m, 2H); MS (ES+): 497.5 (M+1).

Step-2: Preparation of 2-(6-((cyclopropylmethyl) carbamoyl)-2-((((isopropoxycarbonyl)oxy)methoxy) carbonyl)pyridin-3-yl)-4-methoxy-5-vinylbenzoic acid (78c)

Oxidation of ((isopropoxycarbonyl)oxy)methyl 6-((cyclopropylmethyl)carbamoyl)-3-(2-formyl-5-methoxy-4-vinylphenyl)picolinate (78b) (2.71 g, 5.46 mmol) using the procedure as reported in step 11 of scheme 1 gave after workup 2-(6-((cyclopropylmethyl)carbamoyl)-2-((((isopropoxycarbonyl)oxy)methoxy)carbonyl)pyridin-3-yl)-4-methoxy-5-vinylbenzoic acid (78c) (2.60 g, 5.07 mmol, 93% yield) as a white solid; $^1$H NMR (300 MHz, DMSO-$d_6$) δ 12.57 (s, 1H, $D_2O$ exchangeable), 8.66 (t, J=6.1 Hz, 1H), 8.22 (d, J=8.0 Hz, 1H), 8.11 (s, 1H), 7.96 (d, J=8.0 Hz, 1H), 6.98 (dd, J=17.8, 11.3 Hz, 1H), 6.88 (s, 1H), 5.91 (dd, J=17.8, 1.4 Hz, 1H), 5.72 (d, J=2.5 Hz, 2H), 5.39 (dd, J=11.2, 1.4 Hz, 1H), 4.73 (hept, J=6.4 Hz, 1H), 3.85 (s, 3H), 3.29-3.16 (m, 2H), 1.22 (d, J=6.2 Hz, 6H), 1.15 (d, J=3.6 Hz, 1H), 0.53-0.40 (m, 2H), 0.34-0.23 (m, 2H); MS (ES+): 513.5 (M+1), 535.5 (M+Na); MS (ES−): 511.5 (M−1).

Step-3: Preparation of ((isopropoxycarbonyl)oxy) methyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate (78d)

Compound (78d) was prepared from 2-(6-((cyclopropylmethyl)carbamoyl)-2-((((isopropoxycarbonyl)oxy)

methoxy)carbonyl)pyridin-3-yl)-4-methoxy-5-vinylbenzoic acid (78c) (0.56 g, 1.1 mmol) using EDCI (0.32 g, 1.64 mmol) and hexyl ((4-aminophenyl)(imino)methyl)carbamate (36a) (0.43 g, 1.64 mmol) in DMF (15 mL) and Pyridine (5 mL) according to the procedure reported in step 4 of scheme 2. This gave after workup and purification by flash column chromatography (Two separate columns: silica gel, 40 g, eluting with ethyl acetate in hexanes from 0 to 100%; third column: EZ-PREP, C-18 column, 30 g, eluting with 0.1% aq HCl in water and acetonitrile from 0-100%]) ((isopropoxycarbonyl)oxy)methyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (78d) (0.110 g, 0.145 mmol, 13% yield) as a white solid; $^1$H NMR (300 MHz, DMSO-$d_6$) δ 12.32 (bs, 1H, D$_2$O exchangeable), 11.23 (bs, 1H, D$_2$O exchangeable), 10.92 (s, 1H), 10.36 (bs, 1H, D$_2$O exchangeable), 8.64 (t, J=6.0 Hz, 1H), 8.22 (d, J=7.9 Hz, 1H), 8.09-7.97 (m, 2H), 7.92-7.67 (m, 4H), 7.19-6.81 (m, 2H), 6.10 (d, J=17.8 Hz, 1H), 5.85-5.58 (m, 2H), 5.44 (d, J=11.4 Hz, 1H), 4.89-4.58 (m, 1H), 4.26 (t, J=6.5 Hz, 2H), 3.88 (s, 3H), 3.28-3.13 (m, 2H), 1.75-1.56 (m, 2H), 1.44-1.22 (m, 6H), 1.19 (d, J=6.2 Hz, 6H), 1.17-1.02 (m, 1H), 0.92-0.82 (m, 3H), 0.54-0.37 (m, 2H), 0.36-0.17 (m, 2H); MS (ES+): 758.7 (M+1); MS (ES−): 792.6 (M+Cl); Analysis calculated for: C$_{40}$H$_{47}$N$_5$O$_{10}$.H$_2$O.HCl: C, 59.14; H, 6.20; Cl, 4.36; N, 8.62; found: C, 59.20; H, 6.27; Cl, 4.20; N, 8.57.

Scheme 79

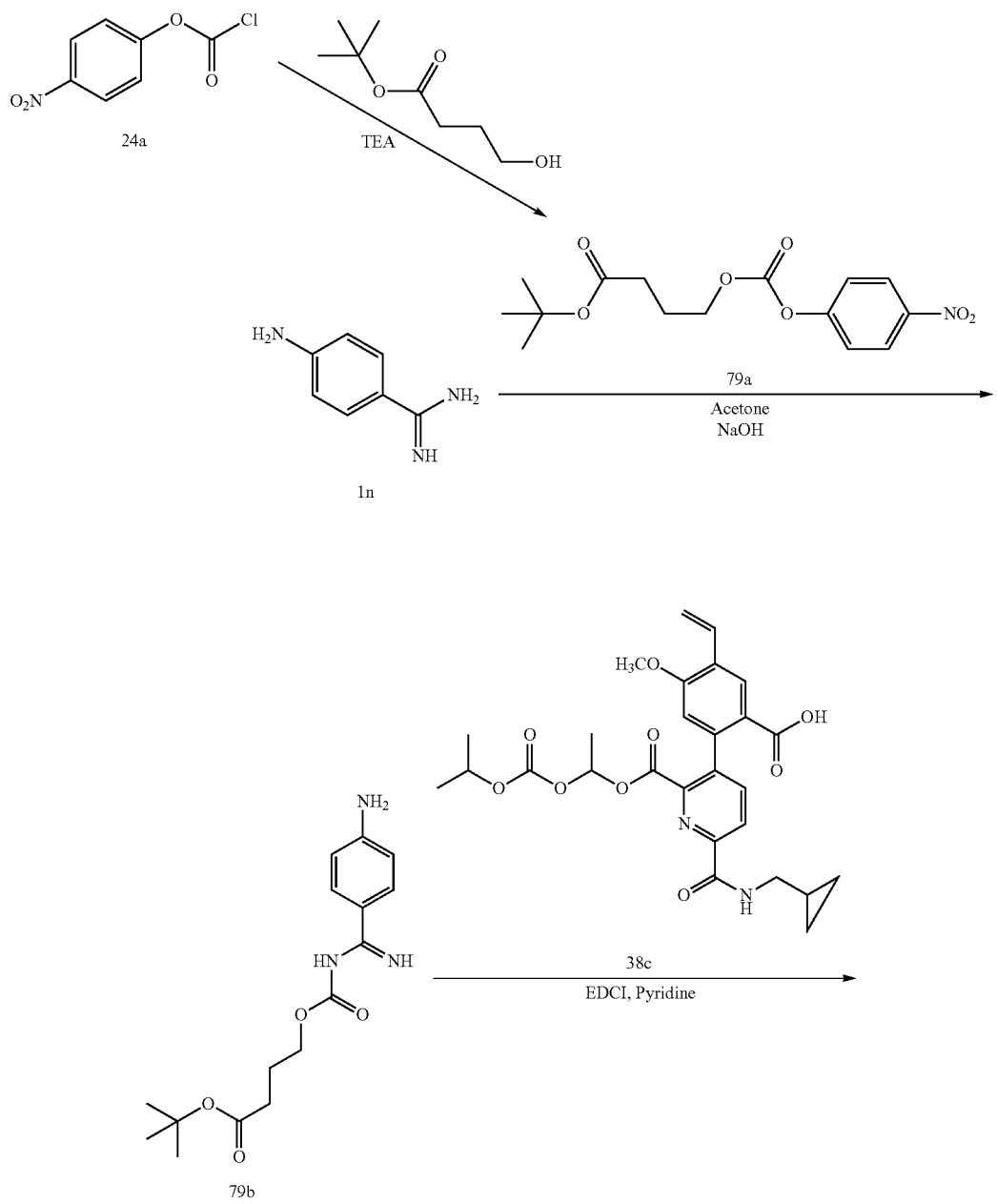

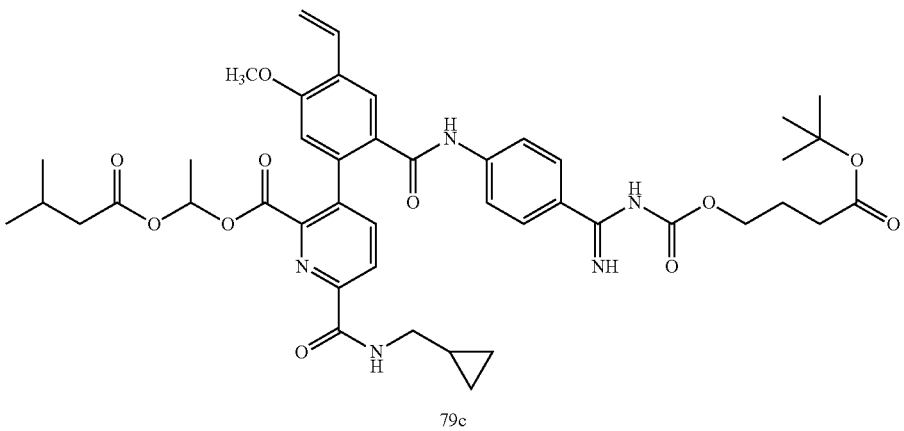

79c

Preparation of 1-((isopropoxycarbonyl)oxy)ethyl 3-(2-((4-(N-((4-(tert-butoxy)-4-oxobutoxy)carbonyl)carbamimidoyl)phenyl)carbamoyl)-5-methoxy-4-vinylphenyl)-6-((cyclopropylmethyl)carbamoyl) picolinate (79c)

Step-1: Preparation of tert-butyl 4-(((4-nitrophenoxy)carbonyl)oxy)butanoate (79a)

Compound (79a) was prepared according to the procedure described in step 1 of scheme 24 from 4-nitrophenyl chloroformate (5.19 g, 24.97 mmol) in THF (50 mL) using tert-butyl 4-hydroxybutanoate (4 g, 24.97 mmol) and triethylamine (7.66 mL, 54.9 mmol). This gave after workup and purification by flash column chromatography (silica gel, eluting with EtOAc in hexane from 0-50%) tert-butyl 4-(((4-nitrophenoxy)carbonyl)oxy)butanoate (79a) (5.16 g, 64% yield) as a clear oil; $^1$H NMR (300 MHz, DMSO-$d_6$) δ 8.37-8.21 (m, 2H), 7.64-7.43 (m, 2H), 4.26 (t, J=6.5 Hz, 2H), 2.34 (t, J=7.2 Hz, 2H), 2.00-1.78 (m, 2H), 1.40 (s, 9H).

Step-2: Preparation of tert-butyl 4-((((4-aminophenyl)(imino)methyl)carbamoyl)oxy)butanoate (79b)

Compound (79b) was prepared from 4-aminobenzimidamide dihydrochloride (1n) (2.47 g, 11.88 mmol) in acetone/water (26 mL, 12:1 ratio), using NaOH (0.97 g, 24.35 mmol) and tert-butyl 4-(((4-nitrophenoxy)carbonyl)oxy)butanoate (79a) (4.25 g, 13.06 mmol) according to the procedure reported in step 4 of scheme 23. This gave after workup and purification by flash column chromatography (silica gel 24 g, eluting with EtOAc/MeOH (9:1) in hexane from 0-70%) tert-butyl 4-((((4-aminophenyl)(imino)methyl)carbamoyl)oxy)butanoate (79b) (1.66 g, 5.17 mmol, 43.5% yield) as a yellow solid; $^1$H NMR (300 MHz, DMSO-$d_6$) δ 9.14 (s, 1H), 8.63 (s, 1H), 7.83-7.64 (m, 2H), 6.62-6.40 (m, 2H), 5.86 (s, 2H), 3.98 (t, J=6.6 Hz, 2H), 2.28 (t, J=7.3 Hz, 2H), 1.81 (p, J=6.9 Hz, 2H), 1.40 (s, 9H); MS (ES+) 322.5 (M+1), 344.5 (M+Na); (ES−) 356.5 (M+Cl).

Step-3: Preparation of 1-((isopropoxycarbonyl)oxy)ethyl 3-(2-((4-(N-((4-(tert-butoxy)-4-oxobutoxy)carbonyl)carbamimidoyl)phenyl)carbamoyl)-5-methoxy-4-vinylphenyl)-6-((cyclopropylmethyl)carbamoyl)picolinate (79c)

Compound (79c) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (1.0 g, 1.9 mmol) using EDCI (0.55 g, 2.85 mmol) and tert-butyl 4-((((4-aminophenyl)(imino)methyl)carbamoyl)oxy)butanoate (79b) (0.67 g, 2.09 mmol) in DMF (20 mL) and pyridine (4 mL) according to the procedure reported in step 4 of scheme 2. This gave after workup and purification by flash column chromatography [silica gel (24 g), eluting with EtOAc/MeOH (9:1) in hexane from 0-60%] and prep-HPLC [eluting with CH$_3$CN in water (containing 0.1% HCl) from 0-100%] 1-((isopropoxycarbonyl)oxy)ethyl 3-(2-((4-(N-((4-(tert-butoxy)-4-oxobutoxy)carbonyl)carbamimidoyl)phenyl)carbamoyl)-5-methoxy-4-vinylphenyl)-6-((cyclopropylmethyl)carbamoyl)picolinate (79c) (128 mg, 0.154 mmol, 8.12% yield) as a white solid; $^1$H NMR (300 MHz, DMSO-$d_6$) δ 10.74 (d, J=24.7 Hz, 1H), 10.32 (brs, 1H, D$_2$O exchangeable), 8.61 (d, J=30.0 Hz, 1H), 8.22 (d, J=8.1 Hz, 1H), 8.08-7.95 (m, 2H), 7.88-7.68 (m, 4H), 7.12-6.92 (m, 2H), 6.63 (q, J=5.3 Hz, 1H), 6.07 (d, J=17.6 Hz, 1H), 5.45 (d, J=11.4 Hz, 1H), 4.79-4.60 (m, 1H), 4.26 (t, J=6.1 Hz, 2H), 3.89 (s, 3H), 3.27-3.14 (m, 2H), 2.37 (t, J=7.4 Hz, 2H), 1.89 (p, J=6.9 Hz, 2H), 1.40 (s, 9H), 1.23-1.07 (m, 12H), 0.48-0.39 (m, 2H), 0.30-0.22 (m, 2H); MS (ES+) 830.8 (M+1); (ES−) 864.9 (M+Cl).

Scheme 80
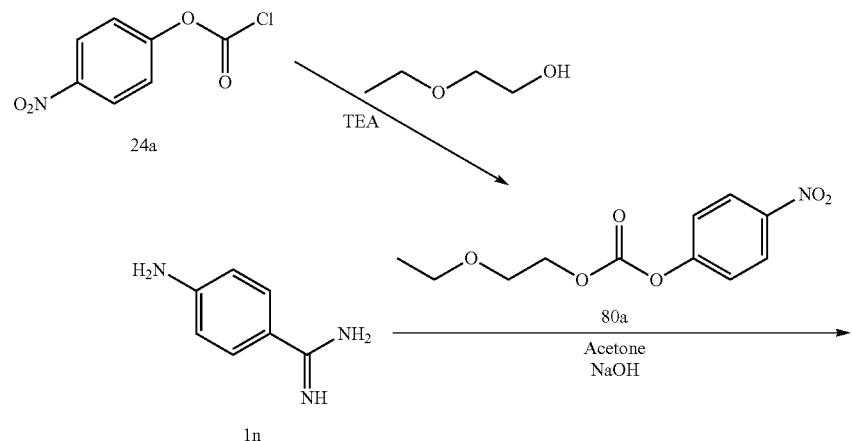
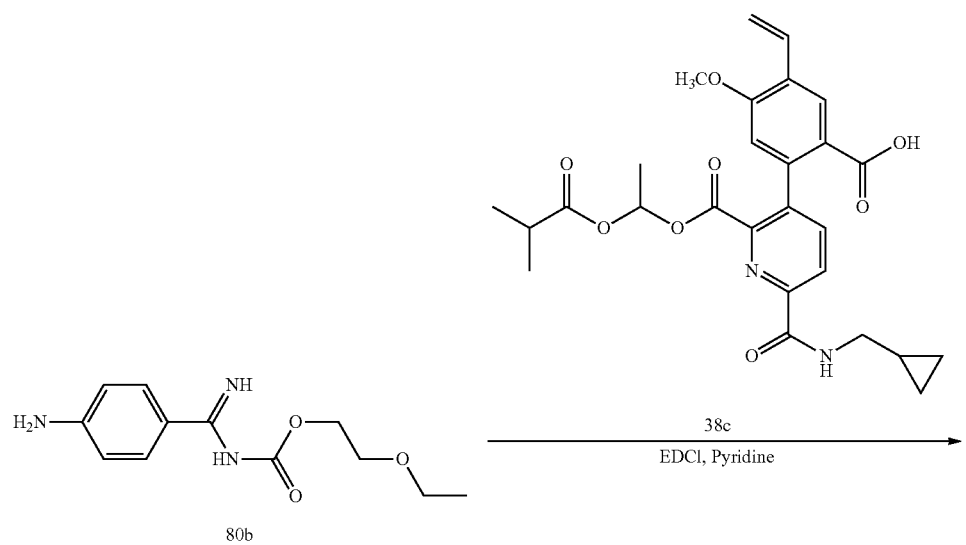
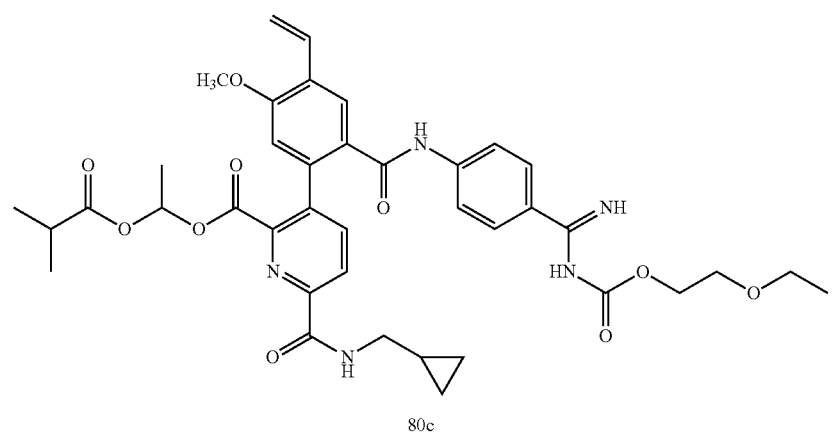

Preparation of 1-(isobutyryloxy)ethyl 6-((cyclopropylmethyl)carbamoyl)-3-(2-((4-(N-((2-ethoxyethoxy)carbonyl)carbamimidoyl)phenyl)carbamoyl)-5-methoxy-4-vinylphenyl)picolinate (80c)

Step-1: Preparation of 2-ethoxyethyl (4-nitrophenyl) carbonate (80a)

Compound (80a) was prepared according to the procedure described in step 1 of scheme 24 from 4-nitrophenyl chloroformate (6.11 g, 29.4 mmol) in THF (50 mL) using 2-ethoxyethanol (3 mL, 31.0 mmol) and triethylamine (9.49 mL, 68.1 mmol). This gave after workup 2-ethoxyethyl (4-nitrophenyl) carbonate (80a) (7.53 g, 95% yield) as a brown syrup which can be used as such in next step without further purification; $^1$H NMR (300 MHz, DMSO-$d_6$) δ 8.40-8.23 (m, 2H), 7.65-7.50 (m, 2H), 4.41-4.30 (m, 2H), 3.72-3.60 (m, 2H), 3.48 (p, J=7.1 Hz, 2H), 1.13 (t, J=7.0 Hz, 3H).

Step-2: Preparation of 2-ethoxyethyl ((4-aminophenyl)(imino)methyl)carbamate (80b)

Compound (80b) was prepared from 4-aminobenzimidamide dihydrochloride (1n) (6.11 g, 29.4 mmol) in acetone (100 mL), using 1 M aqueous NaOH solution (61.7 mL, 61.7 mmol) and a solution of -ethoxyethyl (4-nitrophenyl) carbonate (80a) (7.5 g, 29.4 mmol) in acetone (25 mL) according to the procedure reported in step 4 of scheme 23. This gave after workup and purification by flash column chromatography (silica gel, 80 g eluting with ethyl acetate and hexanes 0 to 100%) 2-ethoxyethyl ((4-aminophenyl)(imino)methyl)carbamate (80b) (7.0 g, 95% yield) as a brown solid; $^1$H NMR (300 MHz, DMSO-$d_6$) δ 9.13 (s, 1H), 8.65 (s, 1H), 7.87-7.54 (m, 2H), 6.67-6.36 (m, 2H), 5.86 (s, 2H), 4.13-4.05 (m, 2H), 3.61-3.52 (m, 2H), 3.46 (q, J=7.0 Hz, 2H), 1.12 (t, J=7.0 Hz, 3H); MS (ES+) 252.3 (M+1), (ES−) 250.4 (M−1).

Step-3: Preparation of 1-(isobutyryloxy)ethyl 6-((cyclopropylmethyl)carbamoyl)-3-(2-((4-(N-((2-ethoxyethoxy)carbonyl)carbamimidoyl)phenyl)carbamoyl)-5-methoxy-4-vinylphenyl)picolinate (80c)

Compound (80c) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.5 g, 0.98 mmol) using EDCI (0.28 g, 1.47 mmol) and 2-ethoxyethyl ((4-aminophenyl)(imino)methyl)carbamate (80b) (0.31 g, 1.23 mmol) in DMF (3 mL) and Pyridine (3 mL) according to the procedure reported in step 4 of scheme 2. This gave after workup and purification by flash column chromatography [silica gel 25 g, eluting with EtOAc/MeOH (9:1) in hexane from 0-60%] followed by lyophilization 1-(isobutyryloxy)ethyl 6-((cyclopropylmethyl)carbamoyl)-3-(2-((4-(N-((2-ethoxyethoxy)carbonyl)carbamimidoyl)phenyl)carbamoyl)-5-methoxy-4-vinylphenyl)picolinate hydrochloride (80c) (0.25 g, 34% yield) as a white solid; $^1$H NMR (300 MHz, DMSO-$d_6$) δ 10.63-10.38 (m, 1H), 9.29-8.73 (m, 2H, D$_2$O exchangeable), 8.67-8.47 (m, 1H), 8.22 (d, J=8.0 Hz, 1H), 7.99 (s, 2H), 7.93 (d, J=8.7 Hz, 2H), 7.74-7.60 (m, 2H), 7.10-6.94 (m, 2H), 6.73 (s, 1H), 6.05 (d, J=17.9 Hz, 1H), 5.44 (d, J=11.5 Hz, 1H), 4.11 (t, J=4.8 Hz, 2H), 3.88 (s, 3H), 3.57 (t, J=4.8 Hz, 2H), 3.45 (q, J=7.1 Hz, 2H), 3.29-3.14 (m, 2H), 2.49-2.37 (m, 1H), 1.17 (d, J=5.3 Hz, 3H), 1.11 (t, J=7.0 Hz, 3H), 1.05-0.91 (m, 7H), 0.49-0.39 (m, 2H), 0.31-0.23 (m, 2H); MS (ES+) 766.7 (M+Na).

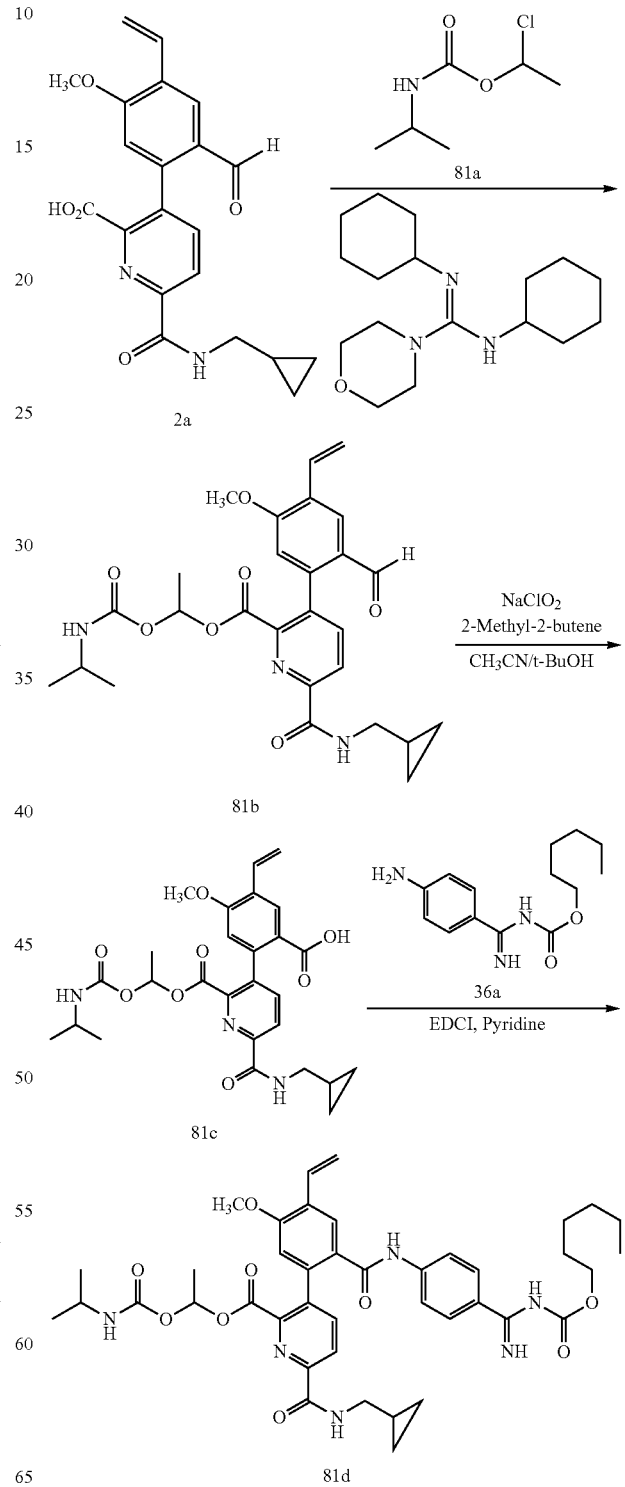

Scheme 81

Preparation of 1-((isopropylcarbamoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (81d)

Step-1: Preparation of 1-((isopropylcarbamoyl)oxy)ethyl 6-((cyclopropylmethyl)carbamoyl)-3-(2-formyl-5-methoxy-4-vinylphenyl)picolinate (81b)

Compound (81b) was prepared according to the procedure reported in step 1 of scheme 8 from 6-(Cyclopropylmethylcarbamoyl)-3-(2-formyl-5-methoxy-4-vinylphenyl)picolinic acid (2a) (1.0 g, 2.63 mmol) in DMF (5 mL) using N,N'-Dicyclohexyl-4-morpholinecarboxamidine (0.88 g, 3.02 mmol) and 1-chloroethyl isopropylcarbamate (81a) (1.08 g, 6.57 mmol, prepared according to the procedure reported by Dugar, Sundeep et al; in PCT Int. Appl., 2012137225). This gave after workup and purification by flash column chromatography (silica gel 40 g, eluting with ethyl acetate/Hexanes, 0-100%) 1-((isopropylcarbamoyl)oxy)ethyl 6-((cyclopropylmethyl)carbamoyl)-3-(2-formyl-5-methoxy-4-vinylphenyl)picolinate (81b) (0.76 g, 57% yield) as a yellow syrup; $^1$H NMR (300 MHz, DMSO-$d_6$) δ 9.70 and 9.65 (2s, 1H), 8.68 (d, J=3.6 Hz, 1H), 8.25 (dd, J=8.1, 5.8 Hz, 1H), 8.12 (d, J=5.8 Hz, 1H), 8.07 (d, J=8.0 Hz, 1H), 7.33 (dd, J=25.3, 7.6 Hz, 1H), 7.07-6.91 (m, 2H), 6.68 (dd, J=5.7, 1.7 Hz, 1H), 6.00 (d, J=17.8 Hz, 1H), 5.48-5.36 (m, 1H), 3.91 (d, J=4.4 Hz, 3H), 3.51 (dt, J=12.8, 6.3 Hz, 1H), 3.23 (dd, J=13.4, 7.0 Hz, 2H), 1.18-1.03 (m, 4H), 1.05-0.92 (m, 6H), 0.52-0.38 (m, 2H), 0.33-0.21 (m, 2H).

Step-2: Preparation of 2-(6-((cyclopropylmethyl)carbamoyl)-2-((1-((isopropylcarbamoyl)oxy)ethoxy)carbonyl)pyridin-3-yl)-4-methoxy-5-vinylbenzoic acid (81c)

Oxidation of Preparation of 1-((isopropylcarbamoyl)oxy)ethyl 6-((cyclopropylmethyl)carbamoyl)-3-(2-formyl-5-methoxy-4-vinylphenyl)picolinate (81b) (0.73 g, 1.43 mmol) using the procedure as reported in step 11 of scheme 1 gave after workup 2-(6-((cyclopropylmethyl)carbamoyl)-2-((1-((isopropylcarbamoyl)oxy)ethoxy)carbonyl)pyridin-3-yl)-4-methoxy-5-vinylbenzoic acid (81c) (0.7 g, 93% yield) as a yellow solid; MS (ES+) 548.3 (M+Na), (ES−) 524.3 (M−1).

Step-3: Preparation of 1-((isopropylcarbamoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (81d)

Compound (81d) was prepared from 2-(6-((cyclopropylmethyl)carbamoyl)-2-((1-((isopropylcarbamoyl)oxy)ethoxy)carbonyl)pyridin-3-yl)-4-methoxy-5-vinylbenzoic acid (13c) ((0.69 g, 1.31 mmol) using EDCI (0.302 g, 1.575 mmol) and hexyl ((4-aminophenyl)(imino)methyl)carbamate (36a) (0.346 g, 1.313 mmol) in DMF (2 mL) and Pyridine (2 mL) according to the procedure reported in step 4 of scheme 2. This gave after workup and purification by flash column chromatography (silica gel, 24 g, eluting with 9:1 mixture of EtOAc and methanol in hexanes 0 to 100%) 1-((isopropylcarbamoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (81d) (0.088 g, 9% yield) as a light yellow powder; $^1$H NMR (300 MHz, DMSO-$d_6$) δ 10.63-10.37 (m, 1H), 9.36-8.79 (m, 2H, $D_2O$ exchangeable), 8.68-8.41 (m, 1H), 8.21 (d, J=8.0 Hz, 1H), 8.05-7.92 (m, 4H), 7.91 (s, 1H), 7.75-7.57 (m, 2H), 7.38 (s, 1H), 7.10-6.95 (m, 2H), 6.77-6.65 (m, 1H), 6.05 (d, J=18.0 Hz, 1H), 5.44 (d, J=11.4 Hz, 1H), 3.99 (t, J=6.7 Hz, 2H), 3.89 (s, 3H), 3.61-3.42 (m, 1H), 3.28-3.18 (m, 2H), 1.68-1.48 (m, 2H), 1.39-1.21 (m, 6H), 1.21-1.03 (m, 4H), 1.05-0.91 (m, 6H), 0.91-0.80 (m, 2H), 0.51-0.39 (m, 2H), 0.32-0.21 (m, 2H); MS (ES+) 771.8 (M+1), 793.7 (M+Na), (ES−) 805.9 (M+Cl).

Scheme 82

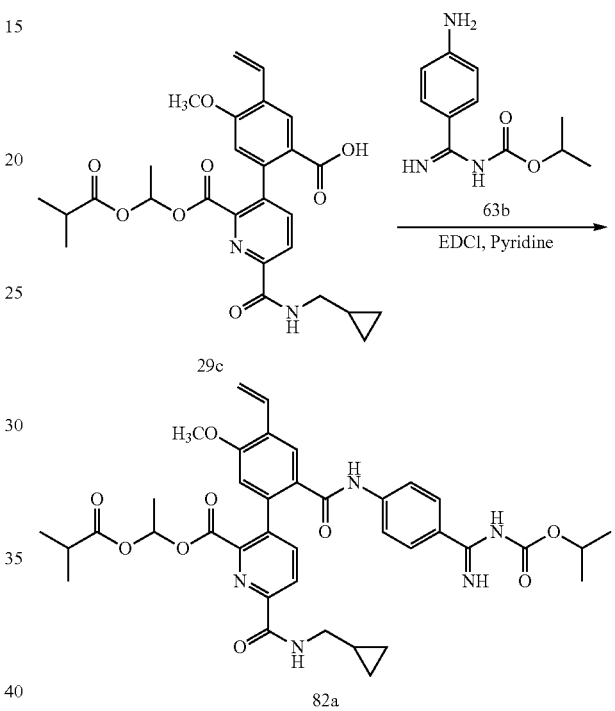

Preparation of 1-(isobutyryloxy)ethyl 6-((cyclopropylmethyl)carbamoyl)-3-(2-((4-(N-(isopropoxycarbonyl)carbamimidoyl)phenyl)carbamoyl)-5-methoxy-4-vinylphenyl)picolinate (82a)

Compound (82a) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (1.1 g, 2.16 mmol) using EDCI (0.62 g, 3.23 mmol) and isopropyl ((4-aminophenyl)(imino)methyl)carbamate (63b) (0.57 g, 2.59 mmol) in DMF (17 mL) and Pyridine (8 mL) according to the procedure reported in step-4 of scheme-2. This gave after workup and purification by flash column chromatography [silica gel (12 g), eluting with EtOAc/MeOH (9:1) in hexane from 0-60%] then prep HPLC [eluting with $CH_3CN$ in water (containing with 0.1% HCl) from 0-100%] followed by lyophilization 1-(isobutyryloxy)ethyl 6-((cyclopropylmethyl)carbamoyl)-3-(2-((4-(N-(isopropoxycarbonyl)carbamimidoyl)phenyl)carbamoyl)-5-methoxy-4-vinylphenyl)picolinate (82a) (65 mg, 4% yield) as an white solid; $^1$H NMR (300 MHz, DMSO-$d_6$) δ 10.67 (d, J=20.0 Hz, 1H, $D_2O$ exchangeable), 10.28 (s, 1H, $D_2O$ exchangeable), 8.63 (d, J=28.2 Hz, 1H, $D_2O$ exchangeable), 8.22 (d, J=8.0 Hz, 1H), 8.07-7.91 (m, 2H), 7.84-7.66 (m, 4H), 7.12-6.93 (m, 2H), 6.73 (d, J=5.3 Hz, 1H), 6.13-5.93 (m, 1H), 5.45 (d, J=11.7 Hz, 1H), 5.10-4.95 (m, 1H), 3.88 (s, 3H), 2.46-2.38 (m, 2H), 1.32 (d, J=6.2 Hz, 6H), 1.17 (d, J=5.4 Hz, 3H), 1.11-0.94 (m, 7H), 0.49-0.38 (m, 2H), 0.30-0.21 (m, 2H); MS (ES+) 730.7 (M+1); Analysis calculated for: $C_{38}H_{43}N_5O_9 \cdot 2H_2O \cdot 3HCl$: C, 58.03; H, 5.96; N, 8.90; found: C, 57.94; H, 6.13; N, 8.92.
Scheme 83
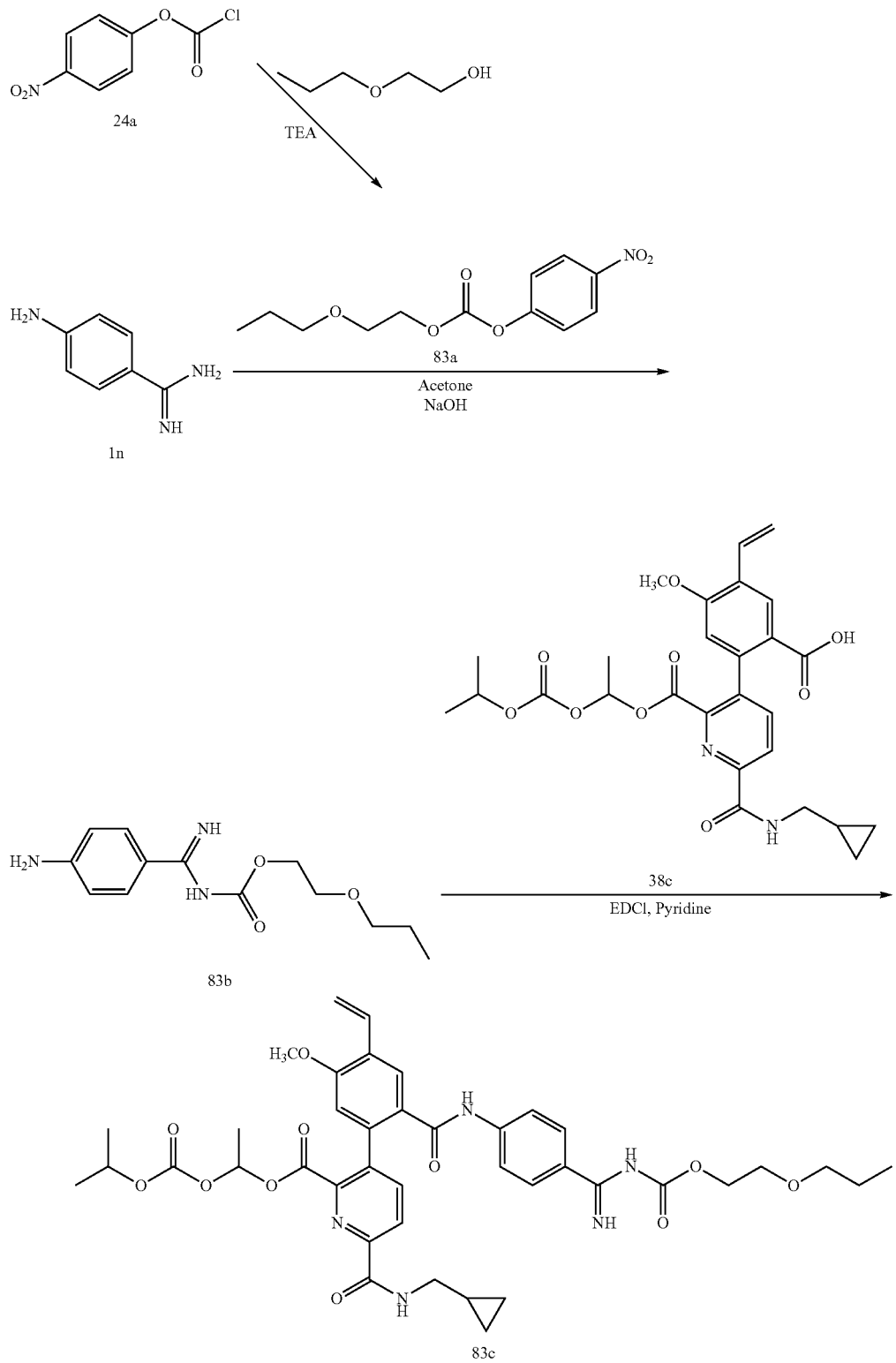

313

Preparation of 1-((isopropoxycarbonyl)oxy)ethyl 6-((cyclopropylmethyl)carbamoyl)-3-(5-methoxy-2-((4-(N-((2-propoxyethoxy)carbonyl)carbamimidoyl)phenyl)carbamoyl)-4-vinylphenyl)picolinate (83c)

Step-1: Preparation of 4-nitrophenyl (2-propoxyethyl) carbonate (83a)

Compound (83a) was prepared according to the procedure described in step 1 of scheme 24 from 4-nitrophenyl chloroformate (10 g, 48.1 mmol) in THF (150 mL) using 2-propoxyethanol (5.51 g, 52.9 mmol) and triethylamine (14.76 mL, 106 mmol). This gave after workup 4-nitrophenyl (2-propoxyethyl) carbonate (83a) (7.2 g, 56% yield) which can be used as such in next step without further purification; $^1$H NMR (300 MHz, DMSO-$d_6$) δ 8.36-8.26 (m, 2H), 7.60-7.51 (m, 2H), 4.41-4.30 (m, 2H), 3.70-3.61 (m, 2H), 3.39 (t, J=6.6 Hz, 2H), 1.58-1.45 (m, 2H), 0.86 (t, J=7.4 Hz, 3H).

Step-2: Preparation of 2-propoxyethyl ((4-aminophenyl)(imino)methyl)carbamate (83b)

Compound (80b) was prepared from 4-aminobenzimidamide dihydrochloride (1n) ((4.92 g, 23.63 mmol) in acetone/water (26 mL, 12:1), using sodium hydroxide (1.94 g, 48.5 mmol) and 4-nitrophenyl (2-propoxyethyl) carbonate (83a) (7.0 g, 26.0 mmol) according to the procedure reported in step 4 of scheme 23. This gave after workup and purification by flash column chromatography [silica gel, 24 g eluting with EtOAc/MeOH (9:1) in hexane from 0-70%] 2-propoxyethyl ((4-aminophenyl)(imino)methyl)carbamate (83b) (1.66 g, 44% yield) as a yellow solid. $^1$H NMR (300 MHz, DMSO-$d_6$) δ 9.10 (s, 1H), 8.64 (s, 1H), 7.82-7.64 (m, 2H), 6.60-6.43 (m, 2H), 5.85 (s, 2H), 4.13-4.03 (m, 2H), 3.61-3.50 (m, 2H), 3.37-3.31 (m, 2H), 1.58-1.41 (m, 2H), 0.86 (t, J=7.4 Hz, 3H); MS (ES−) 264.5 (M−1).

Step-3: Preparation of 1-((isopropoxycarbonyl)oxy)ethyl 6-((cyclopropylmethyl)carbamoyl)-3-(5-methoxy-2-((4-(N-((2-propoxyethoxy)carbonyl)carbamimidoyl)phenyl)carbamoyl)-4-vinylphenyl)picolinate (83c)

Compound (83c) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (1.0 g, 1.90 mmol) using EDCI (0.55 g, 2.85 mmol) and 2-propoxyethyl ((4-aminophenyl)(imino)methyl)carbamate (83b) (0.55 g, 2.09 mmol) in DMF (3 mL) and Pyridine (3 mL) according to the procedure reported in step 4 of scheme 2. This gave after workup and purification by flash column chromatography [silica gel (24 g), eluting with EtOAc/MeOH (9:1) in hexane from 0-60%] then prep HPLC [C18 column, eluting with CH$_3$CN in water (containing with 0.1% HCl) from 0-100%] followed by lyophilization 1-((isopropoxycarbonyl)oxy)ethyl 6-((cyclopropylmethyl)carbamoyl)-3-(5-methoxy-2-((4-(N-((2-propoxyethoxy)carbonyl)carbamimidoyl)phenyl)carbamoyl)-4-vinylphenyl)picolinate (83c) (26 mg, 2% yield) as a white solid; $^1$H NMR (300 MHz, DMSO-$d_6$) δ 12.47 (brs, 1H, D$_2$O exchangeable), 10.69 (d, J=25.6 Hz, 1H, D$_2$O exchangeable), 10.17 br (s, 1H, D$_2$O exchangeable), 8.61 (d, J=29.6 Hz, 1H, D$_2$O exchangeable), 8.22 (d, J=8.0 Hz, 1H), 8.07-7.96 (m, 2H), 7.86-7.69 (m, 4H), 7.15-6.93 (m, 2H), 6.63 (q, J=5.3 Hz, 1H), 6.06 (dd, J=17.7, 1.5 Hz, 1H), 5.45 (d, J=10.7 Hz, 1H), 4.79-4.60 (m, 1H), 4.42-4.25 (m, 2H), 3.89 (s, 3H), 3.71-3.57 (m, 2H), 3.27-3.15 (m, 3H), 1.51 (q, J=7.0 Hz, 2H), 1.26-1.00 (m, 12H), 0.86 (t, J=7.4 Hz, 3H), 0.48-0.39 (m, 2H), 0.33-0.23 (m, 2H); MS (ES+) 774.7 (M+1); (ES−) 808.8 (M+Cl); Analysis calculated for C$_{40}$H$_{47}$N$_5$O$_{10}$·HCl·1.25H$_2$O: C, 57.69; H, 6.11; N, 8.41; found: C, 57.77; H, 5.98; N, 8.31.

Scheme 84

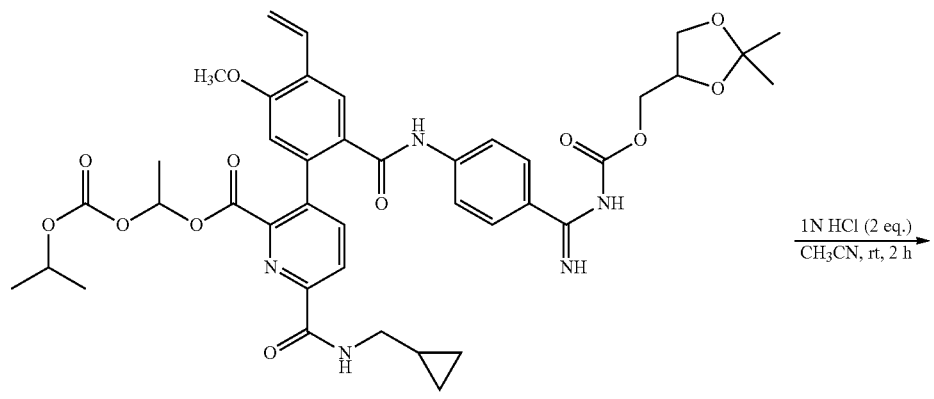

77c

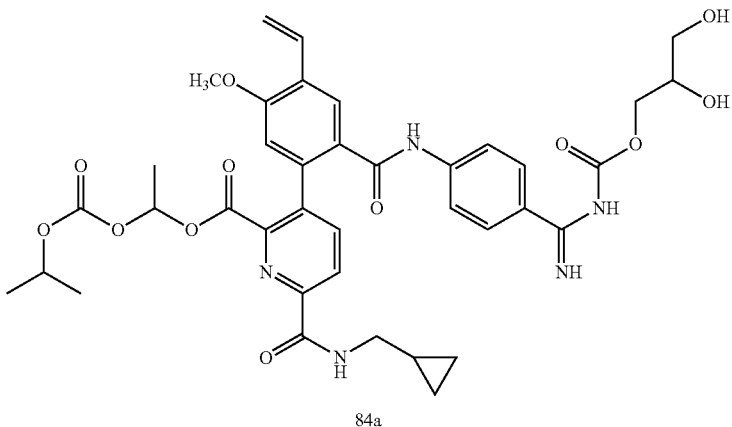

84a

Preparation of 1-((isopropoxycarbonyl)oxy)ethyl 6-((cyclopropylmethyl)carbamoyl)-3-(2-((4-(N-((2,3-dihydroxypropoxy)carbonyl)carbamimidoyl)phenyl)carbamoyl)-5-methoxy-4-vinylphenyl)picolinate (84a)

To a stirred solution of 1-((isopropoxycarbonyl)oxy)ethyl 6-((cyclopropylmethyl)carbamoyl)-3-(2-((4-(N-(((2,2-dimethyl-1,3-dioxolan-4-yl)methoxy)carbonyl)carbamimidoyl)phenyl)carbamoyl)-5-methoxy-4-vinylphenyl)picolinate (77c) (0.15 g, 0.19 mmol) in acetonitrile (5 mL) was added 1 N aq. HCl (0.37 mL, 0.37 mmol), continued stirring for 2 h. Excess solvent was evaporated under reduced pressure. The residue obtained was purified by flash column chromatography [EZ-PREP, C-18 column, 30 g, eluting with 0.1% aqueous HCl in water and acetonitrile from 0-100%], desired tubes were combined and lyophilized to furnish 1-((isopropoxycarbonyl)oxy)ethyl 6-((cyclopropylmethyl)carbamoyl)-3-(2-((4-(N-((2,3-dihydroxypropoxy)carbonyl)carbamimidoyl)phenyl)carbamoyl)-5-methoxy-4-vinylphenyl)picolinate (84a) (0.079 g, 55% yield) as a white solid; $^1$H NMR (300 MHz, DMSO-d$_6$) δ 11.15 & 12.5 (2bs, 1H, D$_2$O exchangeable), 10.85 & 10.78 (2s, 1H), 10.36 (bs, 1H, D$_2$O exchangeable), 8.66 & 8.56 (2bs, 1H), 8.22 (d, J=8.0 Hz, 1H), 8.10-7.93 (m, 2H), 7.88-7.56 (m, 4H), 7.12-6.96 (m, 2H), 6.63 (q, J=5.3 Hz, 1H), 6.09 (d, J=17.8 Hz, 1H), 5.44 (d, J=11.5 Hz, 1H), 4.78-4.63 (m, 1H), 4.33 (dd, J=11.0, 3.7 Hz, 1H), 4.18 (dd, J=11.1, 6.5 Hz, 1H), 3.89 (s, 3H), 3.82-3.70 (m, 1H), 3.54-3.36 (m, 2H), 3.27-3.18 (m, 2H), 1.23-1.09 (m, 10H), 0.49-0.38 (m, 2H), 0.33-0.21 (m, 2H); $^1$H NMR (300 MHz, DMSO-d$_6$/D$_2$O) δ 10.67 & 10.63 (2s, 1H), 9.08-8.93 & 8.93-8.80 (2m, 1H), 8.25-8.15 (m, 1H), 8.05-7.88 (m, 2H), 7.81-7.58 (m, 4H), 7.09-6.84 (m, 2H), 6.60 (q, J=5.3 Hz, 1H), 6.00 (d, J=17.8 Hz, 1H), 5.43 (d, J=11.5 Hz, 1H), 4.75-4.56 (m, 1H), 4.30 (dd, J=11.2, 3.6 Hz, 1H), 4.24-4.12 (m, 1H), 3.83 (s, 3H), 3.80-3.72 (m, 1H), 3.49-3.33 (m, 2H), 3.28-3.07 (m, 2H), 1.27-0.99 (m, 10H), 0.51-0.34 (m, 2H), 0.31-0.14 (m, 2H); MS (ES+): 762.6 (M+1); MS (ES−): 796.5 (M+Cl); Analysis calculated for: C$_{38}$H$_{43}$N$_5$O$_{12}$.2H$_2$O.1HCl C, 54.58; H, 5.76; Cl, 4.51; N, 8.33; found: C, 54.71; H, 5.80; Cl, 4.25; N, 8.39.

Scheme 85

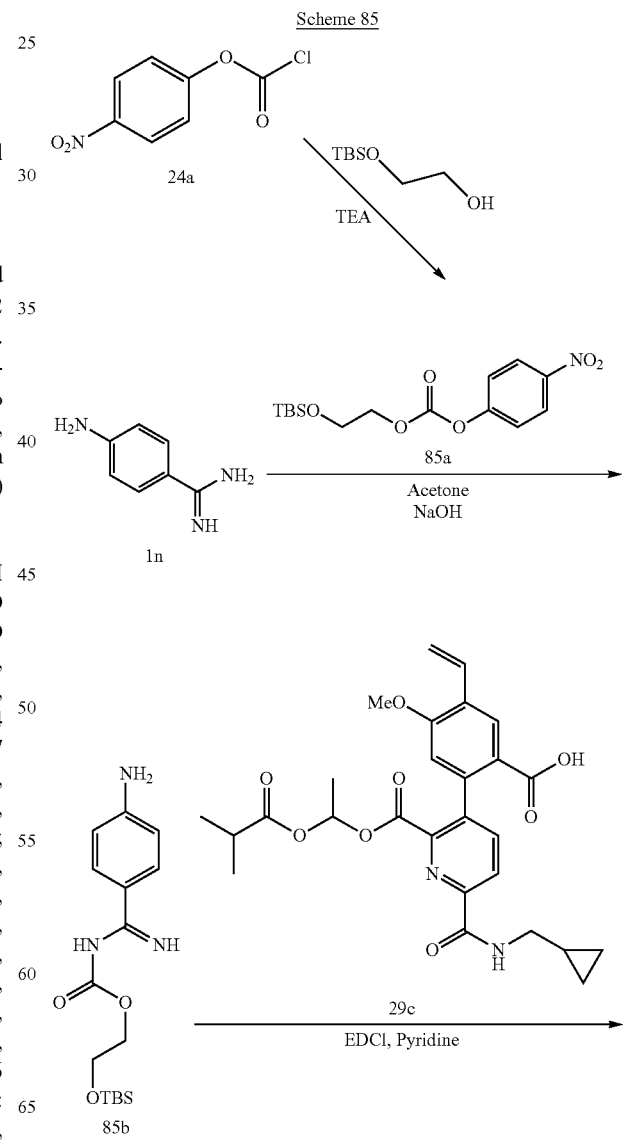

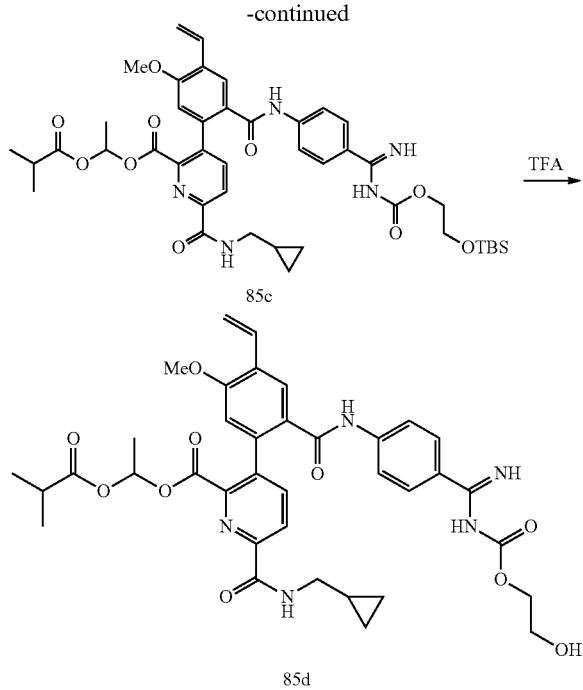

Preparation of 1-(isobutyryloxy)ethyl 6-((cyclopropylmethyl)carbamoyl)-3-(2-((4-(N-((2-hydroxyethoxy)carbonyl)carbamimidoyl)phenyl)carbamoyl)-5-methoxy-4-vinylphenyl)picolinate (85d)

Step-1: Preparation of 2-((tert-butyldimethylsilyl)oxy)ethyl (4-nitrophenyl) carbonate (85a)

Compound (85a) was prepared according to the procedure described in step 1 of scheme 24 from 4-nitrophenyl chloroformate (24a) (1.09 g, 5.39 mmol) in THF (40 mL) using 2-(tert-butyldimethylsilyloxy)ethanol (1 g, 5.67 mmol) and triethylamine (0.95 mL, 6.81 mmol). This gave after workup 2-((tert-butyldimethylsilyl)oxy)ethyl (4-nitrophenyl) carbonate (85a) (1.65 g, 85% yield) as a light orange solid which can be used as such in next step without further purification.

Step-2: Preparation of 2-((tert-butyldimethylsilyl)oxy)ethyl ((4-aminophenyl)(imino)methyl)carbamate (85b)

Compound (85b) was prepared from 4-aminobenzimidamide dihydrochloride (1n) 1.01 g, 4.83 mmol) in acetone (30 mL), water (5 mL) using 6 M aqueous NaOH solution (2.01 mL, 12.08 mmol) and a solution of 2-((tert-butyldimethylsilyl)oxy)ethyl (4-nitrophenyl) carbonate (85a) (1.65 g, 4.83 mmol) in acetone (10 mL) according to the procedure reported in step 4 of scheme 23. This gave after workup and purification by flash column chromatography [silica gel 24 g, MeOH:EtOAc (9:1) in hexanes 0 to 100% as eluents] 2-((tert-butyldimethylsilyl)oxy)ethyl ((4-aminophenyl)(imino)methyl)carbamate (85b) (1.05 g, 64% yield) as a pasty mass; $^1$H NMR (300 MHz, DMSO-$d_6$) δ 9.11 (s, 1H), 8.63 (s, 1H), 7.75 (d, J=8.7 Hz, 2H), 6.60-6.50 (m, 2H), 5.85 (s, 2H), 4.08-3.97 (m, 2H), 3.84-3.72 (m, 2H), 0.86 (s, 9H), 0.06 (s, 6H); MS (ES−) 372.4 (M+Cl).

Step-3: Preparation of 1-(isobutyryloxy)ethyl 3-(2-((4-(N-((2-((tert-butyldimethylsilyl)oxy)ethoxy)carbonyl)carbamimidoyl)phenyl)carbamoyl)-5-methoxy-4-vinylphenyl)-6-((cyclopropylmethyl)carbamoyl)picolinate (85c)

Compound (85c) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.45 g, 0.88 mmol) using EDCI (0.20 g, 1.06 mmol) and 2-((tert-butyldimethylsilyl)oxy)ethyl ((4-aminophenyl)(imino)methyl)carbamate (85b) (0.30 g, 0.88 mmol) in DMF (5 mL) and Pyridine (2 mL) according to the procedure reported in step 4 of scheme 2. This gave after workup and purification by flash column chromatography [silica gel 12 g, EtOAc in hexanes 0 to 100% as eluents] 1-(isobutyryloxy)ethyl 3-(2-((4-(N-((2-((tert-butyldimethylsilyl)oxy)ethoxy)carbonyl)carbamimidoyl)phenyl)carbamoyl)-5-methoxy-4-vinylphenyl)-6-((cyclopropylmethyl)carbamoyl)picolinate (85c) (0.20 g, 27% yield) as a white powder; $^1$H NMR (300 MHz, DMSO-$d_6$) δ 10.62-10.40 (m, 1H), 9.29-8.79 (m, 2H), 8.67-8.43 (m, 1H), 8.22 (d, J=8.0 Hz, 1H), 8.08-7.59 (m, 6H), 7.13-6.95 (m, 2H), 6.82-6.65 (m, 1H), 6.05 (dd, J=17.8, 1.5 Hz, 1H), 5.51-5.39 (m, 1H), 4.06 (dd, J=6.0, 4.2 Hz, 2H), 3.88 (s, 3H), 3.79 (dd, J=6.0, 4.3 Hz, 2H), 3.28-3.16 (m, 2H), 2.47-2.28 (m, 1H), 1.28-0.89 (m, 10H), 0.86 (s, 9H), 0.50-0.38 (m, 2H), 0.32-0.24 (m, 2H), 0.05 (s, 6H).

Step-4: Preparation of 1-(isobutyryloxy)ethyl 6-((cyclopropylmethyl)carbamoyl)-3-(2-((4-(N-((2-hydroxyethoxy)carbonyl)carbamimidoyl)phenyl)carbamoyl)-5-methoxy-4-vinylphenyl)picolinate (85d)

Compound (85d) was prepared from 1-(isobutyryloxy)ethyl 3-(2-((4-(N-((2-((tert-butyldimethylsilyl)oxy)ethoxy)carbonyl)carbamimidoyl)phenyl)carbamoyl)-5-methoxy-4-vinylphenyl)-6-((cyclopropylmethyl)carbamoyl)picolinate (85c) (0.19 g, 0.23 mmol) in dichloromethane (2 mL) using 2,2,2-trifluoroacetic acid (0.18 mL, 2.29 mmol) according to the procedure reported in Step-4 of scheme 8. This gave after workup and purification by prep-HPLC [C18 column, eluting with ACN in water (containing 0.1% HCl) from 0-100%], followed by lyophilization 1-(isobutyryloxy)ethyl 6-((cyclopropylmethyl)carbamoyl)-3-(2-((4-(N-((2-hydroxyethoxy)carbonyl)carbamimidoyl)phenyl)carbamoyl)-5-methoxy-4-vinylphenyl)picolinate (85d) (0.075 g, 46% yield) white solid; $^1$H NMR (300 MHz, DMSO-$d_6$) δ 12.49 (s, 1H), 11.13 (s, 1H), 10.90-10.63 (m, 1H), 10.37 (s, 1H), 8.73-8.45 (m, 1H), 8.22 (d, J=8.0 Hz, 1H), 8.11-7.89 (m, 2H), 7.89-7.68 (m, 4H), 7.11-6.95 (m, 2H), 6.80-6.67 (m, 1H), 6.07 (d, J=17.8 Hz, 1H), 5.45 (dd, J=11.3, 1.4 Hz, 1H), 4.30 (t, J=4.8 Hz, 2H), 3.88 (s, 3H), 3.68 (t, J=4.9 Hz, 2H), 3.29-3.15 (m, 2H), 2.47-2.33 (m, 1H), 1.18 (d, J=5.4 Hz, 3H), 1.16-1.01 (m, 1H), 1.04-0.92 (m, 6H), 0.49-0.40 (m, 2H), 0.31-0.23 (m, 2H); MS (ES+) 716.7 (M+1), MS (ES−) 750.7 (M+Cl).

Scheme 86
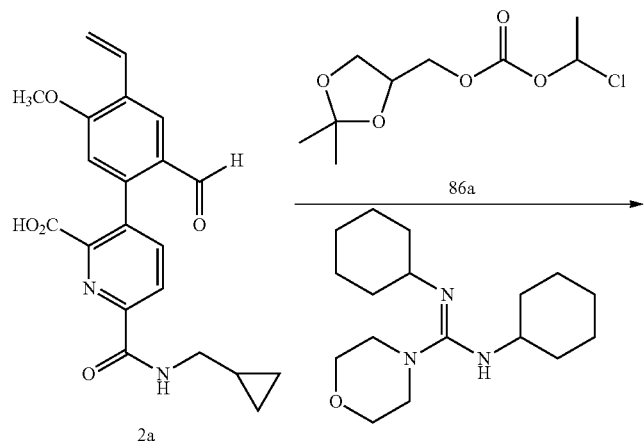
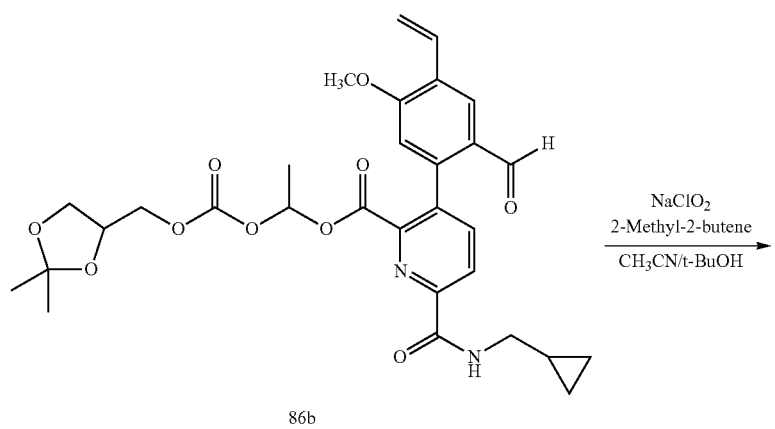
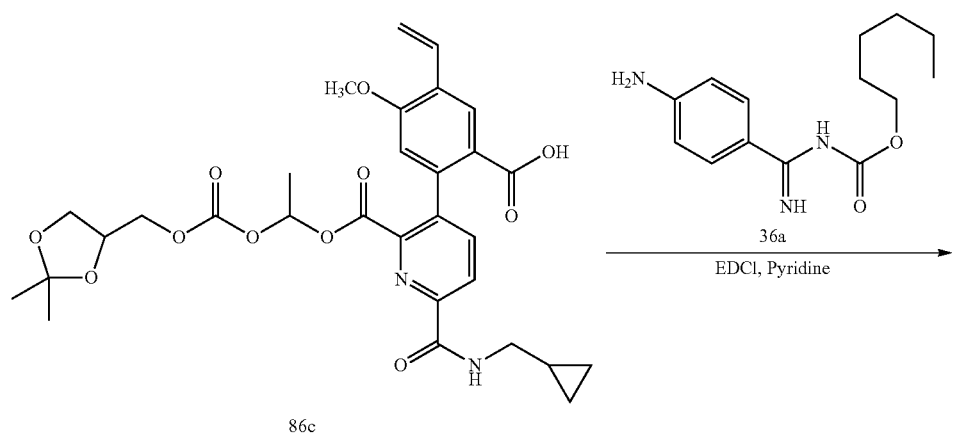

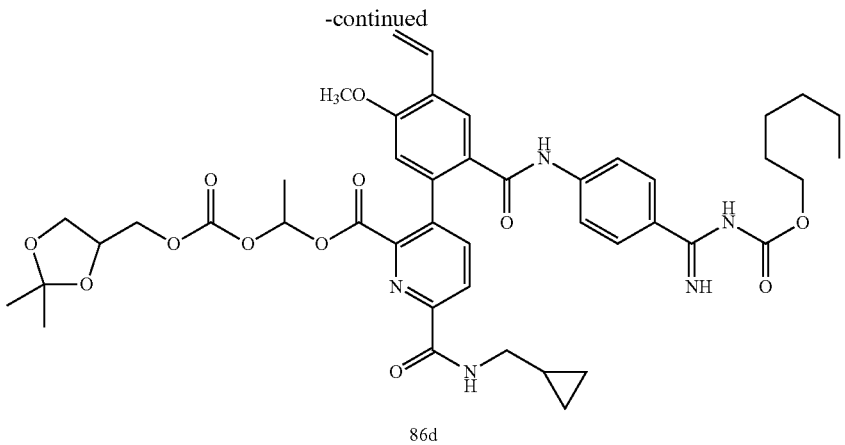

86d

Preparation of 1-(((((2,2-dimethyl-1,3-dioxolan-4-yl) methoxy)carbonyl)oxy)ethyl 6-((cyclopropylmethyl) carbamoyl)-3-(2-((4-(N-((hexyloxy)carbonyl)carbamimidoyl)phenyl)carbamoyl)-5-methoxy-4-vinylphenyl)picolinate (86d)

Step-1: Preparation of 1-((((2,2-dimethyl-1,3-dioxolan-4-yl)methoxy)carbonyl)oxy)ethyl 6-((cyclopropylmethyl)carbamoyl)-3-(2-formyl-5-methoxy-4-vinylphenyl)picolinate (86b)

Compound (86b) was prepared according to the procedure reported in step 1 of scheme 8 from 6-(Cyclopropylmethylcarbamoyl)-3-(2-formyl-5-methoxy-4-vinylphenyl)picolinic acid (2a) (3.04 g, 8.0 mmol) in DMF (80 mL) using N,N'-Dicyclohexyl-4-morpholinecarboxamidine (2.93 g, 10.0 mmol) and 1-chloroethyl ((2,2-dimethyl-1,3-dioxolan-4-yl)methyl) carbonate (86a) (2.86 g, 12.0 mmol, prepared according to the procedure reported by Ascher, Gerd and Thirring, Klaus, in PCT Int. Appl., 2004067536). This gave after workup and purification by flash column chromatography (silica gel 80 g, eluting with ethyl acetate/hexanes from 0-100%) 1-((((2,2-dimethyl-1,3-dioxolan-4-yl)methoxy)carbonyl)oxy)ethyl 6-((cyclopropylmethyl)carbamoyl)-3-(2-formyl-5-methoxy-4-vinylphenyl)picolinate (86b) (3.48 g, 75% yield) as a yellow wax; $^1$H NMR (300 MHz, DMSO-d$_6$) δ 9.49-9.37 (m, 1H), 8.53-8.36 (m, 1H), 8.00 (dd, J=8.0, 1.7 Hz, 1H), 7.87 (d, J=2.1 Hz, 1H), 7.81 (d, J=8.0 Hz, 1H), 6.86-6.64 (m, 2H), 6.44-6.27 (m, 1H), 5.75 (d, J=17.7 Hz, 1H), 5.18 (dd, J=11.4, 1.3 Hz, 1H), 4.04-3.83 (m, 2H), 3.82-3.68 (m, 2H), 3.68-3.60 (m, 3H), 3.47-3.33 (m, 1H), 3.05-2.92 (m, 2H), 1.15-0.75 (m, 10H), 0.31-0.13 (m, 2H), 0.08--0.06 (m, 2H); MS (ES+): 583.5 (M+1), 605.5 (M+Na).

Step-2: Preparation of 2-(6-((cyclopropylmethyl) carbamoyl)-2-((1-((((2,2-dimethyl-1,3-dioxolan-4-yl)methoxy)carbonyl)oxy)ethoxy)carbonyl)pyridin-3-yl)-4-methoxy-5-vinylbenzoic acid (86c)

Oxidation of 1-((((2,2-dimethyl-1,3-dioxolan-4-yl) methoxy)carbonyl)oxy)ethyl 6-((cyclopropylmethyl)carbamoyl)-3-(2-formyl-5-methoxy-4-vinylphenyl)picolinate (86b) (3.21 g, 5.51 mmol) using the procedure as reported in step 11 of scheme 1 gave after workup 2-(6-((cyclopropylmethyl)carbamoyl)-2-((1-((((2,2-dimethyl-1,3-dioxolan-4-yl)methoxy)carbonyl)oxy)ethoxy)carbonyl)pyridin-3-yl)-4-methoxy-5-vinylbenzoic acid (86c) (3.19 g, 97% yield) as a white solid; $^1$H NMR (300 MHz, DMSO-d$_6$) δ 12.6 (bs, 1H, D$_2$O exchangeable), 8.66 (s, 1H), 8.22 (d, J=8.0 Hz, 1H), 8.12 (s, 1H), 7.96 (dd, J=8.0, 1.0 Hz, 1H), 6.98 (dd, J=17.8, 11.2 Hz, 1H), 6.87 (s, 1H), 6.69-6.55 (m, 1H), 5.92 (dd, J=17.8, 1.5 Hz, 1H), 5.39 (d, J=11.3 Hz, 1H), 4.23 (d, J=8.1 Hz, 2H), 4.12-3.92 (m, 2H), 3.85 (s, 3H), 3.65 (dd, J=8.5, 5.9 Hz, 1H), 3.33-3.18 (m, 2H), 1.37-1.11 (m, 10H), 0.54-0.41 (m, 2H), 0.34-0.20 (m, 2H); MS (ES+): 599.6 (M+1), 621.6 (M+Na); MS (ES−): 597.7 (M−1).

Step-3: Preparation of 1-((((2,2-dimethyl-1,3-dioxolan-4-yl)methoxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (86d)

Compound (86d) was prepared from 2-(6-((cyclopropylmethyl)carbamoyl)-2-((1-((((2,2-dimethyl-1,3-dioxolan-4-yl)methoxy)carbonyl)oxy)ethoxy)carbonyl)pyridin-3-yl)-4-methoxy-5-vinylbenzoic acid (86c) (1.45 g, 2.42 mmol) using EDCI (0.7 g, 3.63 mmol) and hexyl ((4-aminophenyl)(imino)methyl)carbamate (36a) (0.64 g, 2.42 mmol) in DMF (15 mL) and Pyridine (5 mL) according to the procedure reported in step 4 of scheme 2. This gave after workup and purification by flash column chromatography (Two separate columns: [EZ-PREP, C-18 column, 30 g, eluting with 0.1% aqueous HCl in water and acetonitrile from 0-100%]; second column: silica gel, 40 g, eluting with ethyl acetate in hexanes from 0 to 100%]) 1-((((2,2-dimethyl-1,3-dioxolan-4-yl) methoxy)carbonyl)oxy)ethyl 6-((cyclopropylmethyl)carbamoyl)-3-(2-((4-(N-((hexyloxy)carbonyl)carbamimidoyl) phenyl)carbamoyl)-5-methoxy-4-vinylphenyl)picolinate (86d) (0.23 g, 11% yield) as a white solid; $^1$H NMR (300 MHz, DMSO-d$_6$) δ 10.55 & 10.48 (2bs, 1H), 9.12 & 8.93 (2bs, 2H, D$_2$O exchangeable), 8.66 & 8.58 (2bs, 1H), 8.23 (d, J=8.0 Hz, 1H), 8.12-7.83 (m, 4H), 7.80-7.57 (m, 2H), 7.15-6.90 (m, 2H), 6.75-6.48 (m, 1H), 6.06 (dd, J=17.7, 1.5 Hz, 1H), 5.44 (d, J=11.4 Hz, 1H), 4.28-4.14 (m, 1H), 4.11-3.92 (m, 3H), 3.89 (s, 3H), 3.63 (dd, J=8.3, 6.0 Hz, 1H), 3.23 (s, 2H), 1.72-1.53 (m, 2H), 1.43-1.02 (m, 18H), 1.00-0.77 (m, 3H), 0.56-0.39 (m, 2H), 0.34-0.22 (m, 2H); MS (ES+): 844.8 (M+1); Analysis calculated for: $C_{44}H_{53}N_5O_{12}$·0.5H$_2$O: C, 61.96; H, 6.38; N, 8.21; found: C, 62.08; H, 6.24; N, 8.10.

Scheme 87

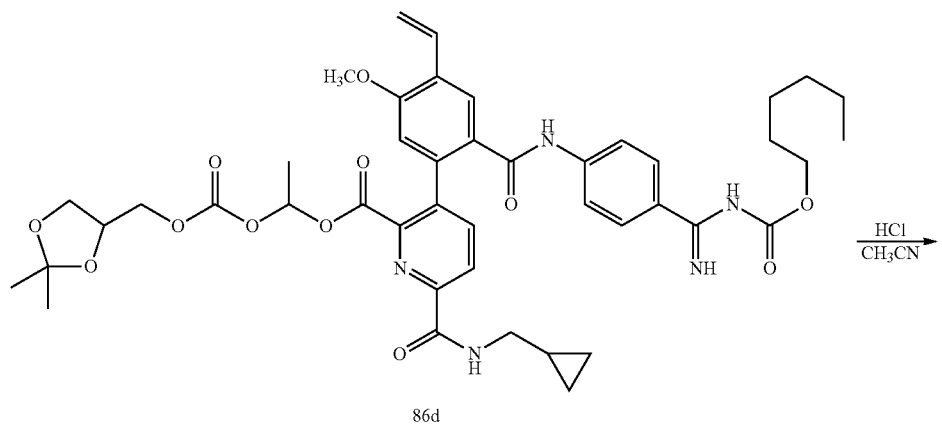

86d

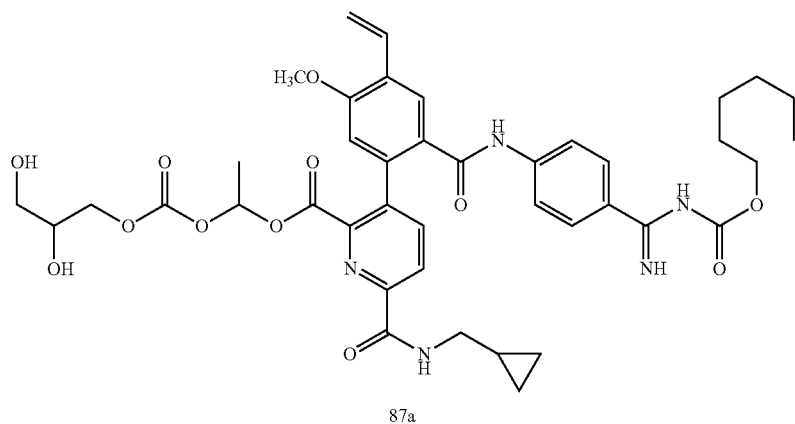

87a

Preparation of 1-(((((2,2-dimethyl-1,3-dioxolan-4-yl)methoxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (87a)

Hydrolysis of 1-(((((2,2-dimethyl-1,3-dioxolan-4-yl)methoxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (86d)

(0.17 g, 0.2 mmol) in acetonitrile (5 mL) using 1 N aq. HCl (0.201 mL, 0.201 mmol), according to the procedure reported in scheme 84 gave after workup and purification by flash column chromatography [EZ-PREP, C-18 column, 30 g, eluting with 0.1% aqueous HCl in water and acetonitrile from 0-100%], followed by lyophilization 1-(((((2,2-dimethyl-1,3-dioxolan-4-yl)methoxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (87a) (0.067 g, 0.083 mmol, 41% yield) as a white solid; $^1$H NMR (300 MHz, DMSO-$d_6$) δ 12.03 & 11.06 (2bs, 1H, D$_2$O exchangeable), 10.80 & 10.72 (2s, 1H), 10.34 (bs, 1H, D$_2$O exchangeable), 8.69 & 8.57 (2s, 1H), 8.23 (d, J=8.0 Hz, 1H), 8.11-7.92 (m, 2H), 7.77 (d, J=6.5 Hz, 4H), 7.15-6.92 (m, 2H), 6.63 (q, J=5.3 Hz, 1H), 6.07 (d, J=17.8 Hz, 1H), 5.44 (d, J=11.4 Hz, 1H), 4.90 (bs, 1H, D$_2$O exchangeable), 4.25 (t, J=6.5 Hz, 2H), 4.18-3.96 (m, 1H), 3.89 (s, 3H), 3.67-3.57 (m, 1H), 3.37-3.13 (m, 4H, observed after D$_2$O exchange), 1.78-1.56 (m, 2H), 1.51-0.95 (m, 10H), 0.96-0.78 (m, 3H), 0.53-0.36 (m, 2H), 0.34-0.16 (m, 2H); MS (ES+): 804.7 (M+1); MS (ES−): 838.9 (M+Cl); Analysis calculated for: C$_{41}$H$_{49}$N$_5$O$_{12}$.2H$_2$O HCl: C, 56.19; H, 6.21; Cl, 4.05; N, 7.99; found: C, 56.28; H, 6.01; Cl, 4.02; N, 7.93.

Scheme 88

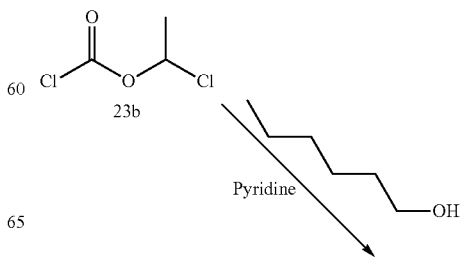

23b

Pyridine

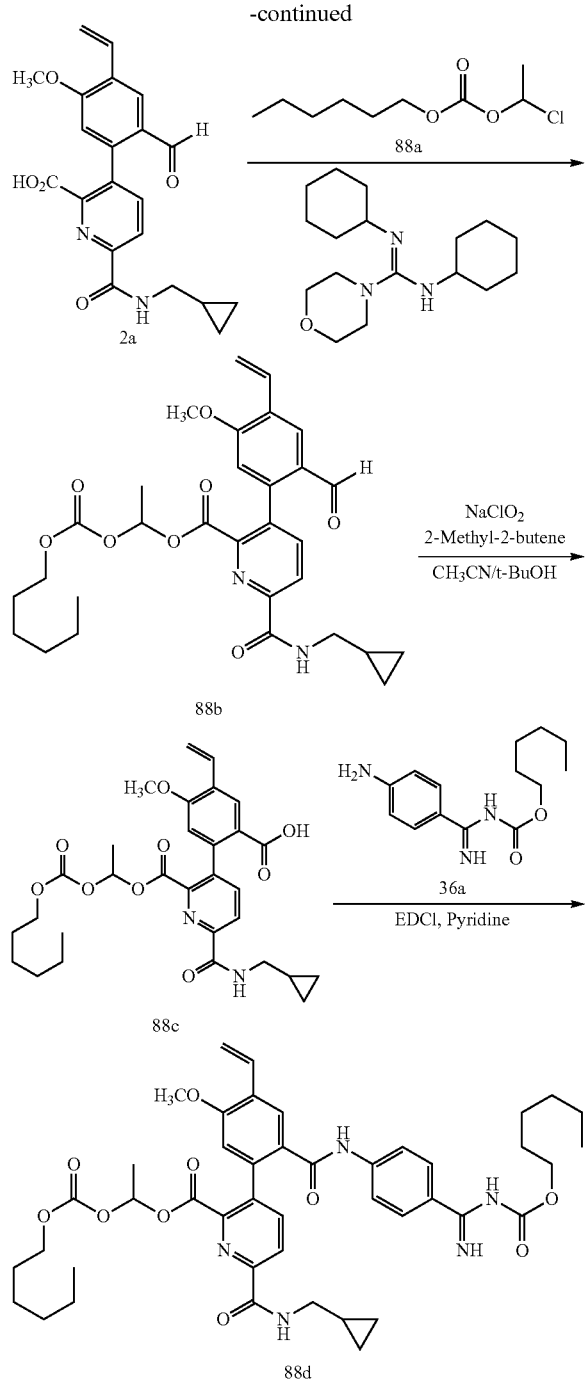

overnight. Solid obtained was filtered-off, water (150 mL) was added to the filtrate, layers were separated. Organic layer was dried, filtered, evaporated to dryness to afford 1-chloroethyl hexyl carbonate (88a) (9.88 g, 97% yield) as clear oil; $^1$H NMR (300 MHz, DMSO-$d_6$) δ 6.50 (q, J=5.7 Hz, 1H), 4.16 (td, J=6.5, 0.9 Hz, 2H), 1.76 (d, J=5.7 Hz, 3H), 1.68-1.53 (m, 1H), 1.45-1.15 (m, 7H), 0.93-0.79 (m, 3H).

Step-2: Preparation of 1-(((hexyloxy)carbonyl)oxy) ethyl 6-((cyclopropylmethyl)carbamoyl)-3-(2-formyl-5-methoxy-4-vinylphenyl)picolinate (88b)

Compound (88b) was prepared according to the procedure reported in step 1 of scheme 8 from 6-(Cyclopropylmethylcarbamoyl)-3-(2-formyl-5-methoxy-4-vinylphenyl)picolinic acid (2a) (3.04 g, 8.0 mmol) in DMF (5 mL) using N,N'-Dicyclohexyl-4-morpholinecarboxamidine (2.93 g, 10.0 mmol) and 1-chloroethyl hexyl carbonate (88a) (2.5 g, 12.0 mmol). This gave after workup and purification by flash column chromatography (silica gel 25 g, eluting with ethyl acetate/hexanes from 0-50%) 1-(((hexyloxy)carbonyl)oxy) ethyl 6-((cyclopropylmethyl)carbamoyl)-3-(2-formyl-5-methoxy-4-vinylphenyl)picolinate (88b) (3.91 g, 88% yield) as a yellow wax; $^1$H NMR (300 MHz, DMSO-$d_6$) δ 9.68 (s, 1H), 8.80-8.62 (m, 1H), 8.26 (dd, J=8.0, 1.2 Hz, 1H), 8.13 (s, 1H), 8.07 (dd, J=8.0, 0.8 Hz, 1H), 7.13-6.91 (m, 2H), 6.67-6.58 (m, 1H), 6.01 (dd, J=17.8, 1.1 Hz, 1H), 5.53-5.31 (m, 1H), 4.09-3.95 (m, 2H), 3.90 (d, J=3.7 Hz, 3H), 3.27-3.22 (m, 2H), 1.69-1.42 (m, 2H), 1.36-1.03 (m, 10H), 0.94-0.71 (m, 3H), 0.54-0.39 (m, 2H), 0.36-0.19 (m, 2H); MS (ES+): 575.5 (M+Na); MS (ES−): 551.7 (M−1).

Step-3: Preparation of 2-(6-((cyclopropylmethyl) carbamoyl)-2-((1-(((hexyloxy)carbonyl)oxy)ethoxy) carbonyl)pyridin-3-yl)-4-methoxy-5-vinylbenzoic acid (88c)

Oxidation of 1-(((hexyloxy)carbonyl)oxy)ethyl 6-((cyclopropylmethyl)carbamoyl)-3-(2-formyl-5-methoxy-4-vinylphenyl)picolinate (88b) (3.86 g, 6.98 mmol) using the procedure as reported in step 11 of scheme 1 gave after workup 2-(6-((cyclopropylmethyl)carbamoyl)-2-((1-(((hexyloxy) carbonyl)oxy)ethoxy)carbonyl)pyridin-3-yl)-4-methoxy-5-vinylbenzoic acid (88c) (3.15 g, 79% yield) as a white solid; $^1$H NMR (300 MHz, DMSO-$d_6$) δ 12.66 (bs, 1H, D$_2$O exchangeable), 8.64 (bs, 1H), 8.21 (d, J=8.0 Hz, 1H), 8.12 (s, 1H), 7.95 (d, J=8.0 Hz, 1H), 6.98 (dd, J=17.8, 11.3 Hz, 1H), 6.86 (s, 1H), 6.71-6.53 (m, 1H), 5.91 (dd, J=17.8, 1.5 Hz, 1H), 5.38 (dd, J=11.3, 1.4 Hz, 1H), 4.12-3.96 (m, 2H), 3.85 (s, 3H), 3.29-3.17 (m, 2H), 1.66-1.46 (m, 2H), 1.35-1.02 (m, 10H), 0.95-0.72 (m, 3H), 0.54-0.39 (m, 2H), 0.35-0.21 (m, 2H); MS (ES+): 591.6 (M+Na); MS (ES−): 567.6 (M−1).

Step-4: Preparation of 1-(((hexyloxy)carbonyl)oxy) ethyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate (88d)

Compound (88d) was prepared from 2-(6-((cyclopropylmethyl)carbamoyl)-2-((1-(((hexyloxy)carbonyl)oxy) ethoxy)carbonyl)pyridin-3-yl)-4-methoxy-5-vinylbenzoic acid (88c) (1.3 g, 2.29 mmol) using EDCI (0.66 g, 3.43 mmol) and hexyl ((4-aminophenyl)(imino)methyl)carbamate (36a) (0.60 g, 2.29 mmol) in DMF (30 mL) and Pyridine (10 mL) according to the procedure reported in step 4 of Preparation of 1-(((hexyloxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (88d)

Step-1: Preparation of 1-chloroethyl hexyl carbonate (88a)

To a ice-cold solution of hexan-1-ol (6.14 mL, 48.9 mmol) in DCM (100 mL) and pyridine (4.35 mL, 53.8 mmol) was added 1-chloroethyl chloroformate (23b) (5.28 mL, 48.9 mmol) and allowed to warm to room temperature scheme 2. This gave after workup and purification by flash column chromatography [EZ-Prep, C-18 column, 50 g, eluting with 0.1% aq HCl in water and acetonitrile from 0-100%] followed by lyophilization 1-(((hexyloxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (88d) (0.787 g, 0.967 mmol, 42% yield) as a white solid; $^1$H NMR (300 MHz, DMSO-$d_6$) δ 12.32 & 11.09 (2bs, 1H, D$_2$O exchangeable), 10.78 & 10.74 (2s, 1H), 10.36 (bs, 1H, D$_2$O exchangeable), 8.66 & 8.57 (2s, 1H), 8.22 (d, J=8.0 Hz, 1H), 8.09-7.94 (m, 2H), 7.92-7.65 (m, 4H), 7.16-6.92 (m, 2H), 6.81-6.48 (m, 1H), 6.08 (d, J=17.8 Hz, 1H), 5.45 (d, J=11.4 Hz, 1H), 4.26 (t, J=6.6 Hz, 2H), 4.15-3.94 (m, 2H), 3.89 (s, 3H), 3.31-3.16 (m, 2H), 1.78-1.61 (m, 2H), 1.58-1.46 (m, 2H), 1.46-0.98 (m, 16H), 0.96-0.75 (m, 6H), 0.53-0.37 (m, 2H), 0.35-0.21 (m, 2H); MS (ES+): 814.8 (M+1), 836.8 (M+Na); Analysis: calculated for: C$_{44}$H$_{55}$N$_5$O$_{10}$.2H$_2$O.HCl: C, 59.62; H, 6.82; Cl, 4.00; N, 7.90; found: C, 59.77; H, 6.53; Cl, 3.84; N, 8.05.

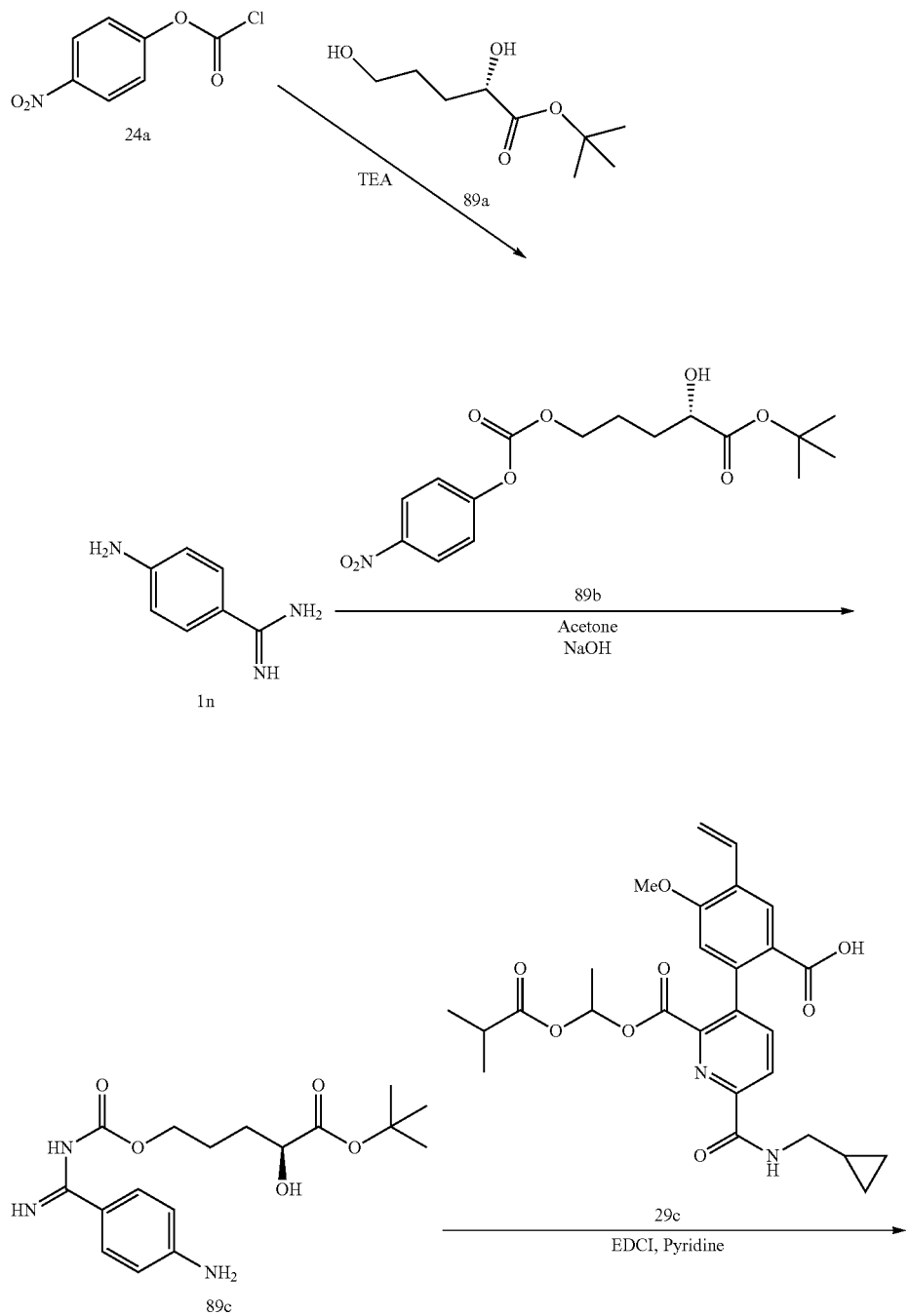

Scheme 89

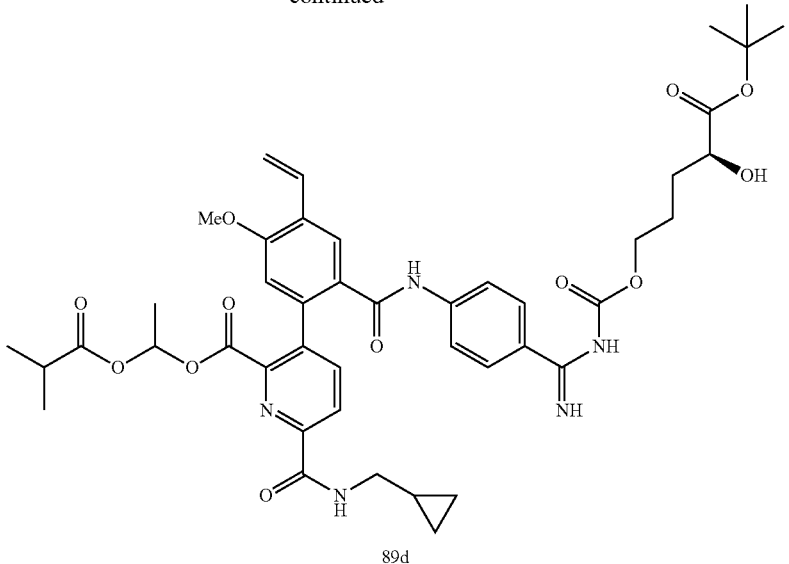

89d

Preparation of 1-(isobutyryloxy)ethyl 3-(2-((4-(N—((((S)-5-(tert-butoxy)-4-hydroxy-5-oxopentyl)oxy)carbonyl)carbamimidoyl)phenyl)carbamoyl)-5-methoxy-4-vinylphenyl)-6-((cyclopropylmethyl)carbamoyl)picolinate (89d)

Step-1: Preparation of (S)-tert-butyl 2-hydroxy-5-(((4-nitrophenoxy)carbonyl)oxy)pentanoate (89b)

Compound (89b) was prepared according to the procedure described in step 1 of scheme 24 from 4-nitrophenyl chloroformate (24a) (0.44 g, 2.13 mmol) in DCM (20 mL) using (S)-tert-butyl 2,5-dihydroxypentanoate (89a) (0.45 g, 2.36 mmol, prepared according to the procedure reported by Zhang, Dan-Wei et al; in Tetrahedron, 65(48), 9997-10001; 2009) and pyridine (0.91 mL, 2.36 mmol). This gave after workup (S)-tert-butyl 2-hydroxy-5-(((4-nitrophenoxy)carbonyl)oxy)pentanoate (89b) (0.32 g, 38% yield) as a brown syrup which can be used as such in next step without further purification; $^1$H NMR (300 MHz, DMSO-$d_6$) δ 8.40-8.24 (m, 2H), 7.64-7.44 (m, 2H), 5.30 (d, J=5.8 Hz, 1H, $D_2O$ exchangeable), 4.26 (t, J=6.0 Hz, 2H), 3.94 (dt, J=6.2, 4.0 Hz, 1H), 1.85-1.56 (m, 4H), 1.42 (s, 9H).

Step-2: Preparation of (S)-tert-butyl 5-((((4-aminophenyl)(imino)methyl)carbamoyl)oxy)-2-hydroxypentanoate (89c)

Compound (89c) was prepared from 4-aminobenzimidamide dihydrochloride (1n) (0.2 g, 0.96 mmol) in acetone (30 mL), using NaOH solution (1M solution, 7.3 mL, 7.3 mmol) and a solution (S)-tert-butyl 2-hydroxy-5-(((4-nitrophenoxy)carbonyl)oxy)pentanoate (89b) (0.31 g, 0.87 mmol) in acetone (30 mL) according to the procedure reported in step 4 of scheme 23. This gave after workup and purification by flash column chromatography (silica gel, 12 g eluting with ethyl acetate and hexanes 0 to 100%) (S)-tert-butyl 5-((((4-aminophenyl)(imino)methyl)carbamoyl)oxy)-2-hydroxypentanoate (89c) (0.2 g, 64% yield) as a yellow solid; $^1$H NMR (300 MHz, DMSO-$d_6$) δ 9.15 (s, 1H, $D_2O$ exchangeable), 8.63 (s, 1H, $D_2O$ exchangeable), 7.87-7.58 (m, 2H), 6.65-6.45 (m, 2H), 5.85 (s, 2H, $D_2O$ exchangeable), 5.23 (d, J=5.8 Hz, 1H), 4.06-3.92 (m, 2H), 3.90 (dd, J=6.0, 3.4 Hz, 1H), 1.73-1.50 (m, 4H), 1.41 (s, 9H).

Step-3: Preparation of 11-(isobutyryloxy)ethyl 3-(2-((4-(N—((((S)-5-(tert-butoxy)-4-hydroxy-5-oxopentyl)oxy)carbonyl)carbamimidoyl)phenyl)carbamoyl)-5-methoxy-4-vinylphenyl)-6-((cyclopropylmethyl)carbamoyl)picolinate (89d)

Compound (89d) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.26 g, 0.51 mmol) using EDCI (0.19 g, 0.61 mmol) and (S)-tert-butyl 5-((((4-aminophenyl)(imino)methyl)carbamoyl)oxy)-2-hydroxypentanoate (89c) (0.18 g, 0.51 mmol) in DMF (1 mL) and Pyridine (1 mL) according to the procedure reported in step 4 of scheme 2. This gave after workup and purification by flash column chromatography [silica gel 12 g, eluting with EtOAc/MeOH (9:1) in hexane from 0-60%] followed by flash column chromatography (C18, 26 g) eluting with 0.1% HCl and acetonitrile followed by lyophilization afforded 1-(isobutyryloxy)ethyl 3-(2-((4-(N—((((S)-5-(tert-butoxy)-4-hydroxy-5-oxopentyl)oxy)carbonyl)carbamimidoyl)phenyl)carbamoyl)-5-methoxy-4-vinylphenyl)-6-((cyclopropylmethyl)carbamoyl)picolinate (89d) (0.25 g, 58% yield) as a white solid; $^1$H NMR (300 MHz, DMSO-$d_6$) δ 12.61-12.13 (m, 1H, $D_2O$ exchangeable), 11.36-10.98 (m, 1H, $D_2O$ exchangeable), 10.83-10.59 (m, 1H), 10.53-10.19 (m, 1H, $D_2O$ exchangeable), 8.71-8.43 (m, 1H), 8.22 (d, J=8.0 Hz, 1H), 8.07-7.96 (m, 2H), 7.82-7.73 (m, 4H), 7.11-6.94 (m, 2H), 6.80-6.63 (m, 1H), 6.07 (d, J=17.8 Hz, 1H), 5.45 (d, J=11.5 Hz, 1H), 4.38-4.20 (m, 1H), 4.03-3.75 (m, 5H), 3.29-3.08 (m, 2H), 2.46-2.39 (m, 1H), 1.85-1.56 (m, 4H), 1.41 (s, 9H), 1.18 (d, J=5.2 Hz, 3H), 1.12-1.03 (m, 1H), 1.03-0.91 (m, 6H), 0.51-0.38 (m, 2H), 0.33-0.21 (m, 2H); MS (ES+) 844.8 (M+1), 866.8 (M+Na).

Scheme 90

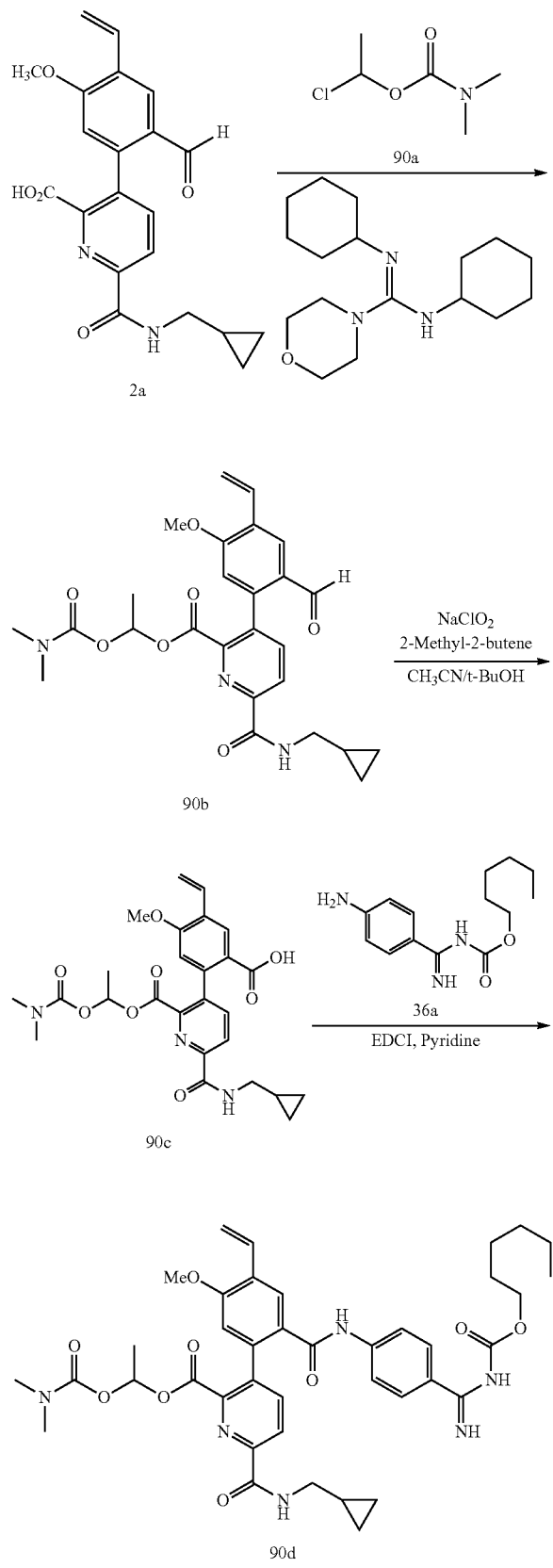

Preparation of 1-((dimethylcarbamoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (90d)

Step-1: Preparation of 1-((dimethylcarbamoyl)oxy) ethyl 6-((cyclopropylmethyl)carbamoyl)-3-(2-formyl-5-methoxy-4-vinylphenyl)picolinate (90b)

Compound (90b) was prepared according to the procedure reported in step 1 of scheme 8 from 6-(Cyclopropylmethylcarbamoyl)-3-(2-formyl-5-methoxy-4-vinylphenyl)picolinic acid (2a) (1.0 g, 2.63 mmol) in DMF (5 mL) using N,N'-Dicyclohexyl-4-morpholinecarboxamidine (0.89 g, 3.02 mmol) and 1-chloroethyl dimethylcarbamate (90a) 1.0 g, 6.57 mmol; CAS #92600-24-3). This gave after workup and purification by flash column chromatography (silica gel 125 g, eluting with ethyl acetate/Hexanes, 0-100%) 1-((dimethylcarbamoyl)oxy)ethyl 6-((cyclopropylmethyl)carbamoyl)-3-(2-formyl-5-methoxy-4-vinylphenyl)picolinate (16b) (0.73 g, 56% yield) as a yellow syrup; MS (ES+) 518.5 (M+Na).

Step-2: Preparation of 2-(6-((cyclopropylmethyl) carbamoyl)-2-((1-((dimethylcarbamoyl)oxy)ethoxy) carbonyl)pyridin-3-yl)-4-methoxy-5-vinylbenzoic acid (90c)

Oxidation of 1-((dimethylcarbamoyl)oxy)ethyl 6-((cyclopropylmethyl)carbamoyl)-3-(2-formyl-5-methoxy-4-vinylphenyl)picolinate (90b) (0.71 g, 1.43 mmol) using the procedure as reported in step 11 of scheme 1 gave after workup 2-(6-((cyclopropylmethyl)carbamoyl)-2-((1-((dimethylcarbamoyl)oxy)ethoxy)carbonyl)pyridin-3-yl)-4-methoxy-5-vinylbenzoic acid (90c) (0.81 g, 110% yield) as a yellow solid; MS (ES+0 534.3 (M+Na), (ES−) 510.4 (M−1).

Step-3: Preparation of 1-((dimethylcarbamoyl)oxy) ethyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate (90d)

Compound (90d) was prepared from 2-(6-((cyclopropylmethyl)carbamoyl)-2-((1-((dimethylcarbamoyl)oxy)ethoxy)carbonyl)pyridin-3-yl)-4-methoxy-5-vinylbenzoic acid (90c) (0.8 g, 1.56 mmol) using EDCI (0.36 g, 1.87 mmol) and hexyl ((4-aminophenyl)(imino)methyl)carbamate (36a) (0.412 g, 1.564 mmol) in DMF (3 mL) and Pyridine (3 mL) according to the procedure reported in step 4 of scheme 2. This gave after workup and purification by flash column chromatography (silica gel, 12 g, eluting with ethyl acetate in hexanes from 0 to 100%) followed by flash column chromatography (C18, 26 g) eluting with 0.1% HCl and acetonitrile followed by lyophilization afforded 1-((dimethylcarbamoyl)oxy)ethyl 6-((cyclopropylmethyl)carbamoyl)-3-(2-((4-(N-((hexyloxy)carbonyl)carbamimidoyl)phenyl) carbamoyl)-5-methoxy-4-vinylphenyl)picolinate hydrochloride (90d) (0.029 g, 3% yield) as a white solid; $^1$H NMR (300 MHz, DMSO-$d_6$) δ 10.58 (s, 1H), 8.74-8.59 (m, 1H), 8.61-8.46 (m, 1H), 8.21 (d, J=8.0 Hz, 1H), 8.07-7.91 (m, 2H), 7.86-7.70 (m, 4H), 7.12-6.96 (m, 2H), 6.77-6.59 (m, 1H), 6.06 (d, J=17.9 Hz, 1H), 5.45 (d, J=11.6 Hz, 1H), 4.28-4.14 (m, 2H), 3.89 (s, 3H), 3.29-3.15 (m, 2H), 2.80-2.62 (m, 6H), 1.73-1.57 (m, 2H), 1.42-1.25 (m, 7H), 1.26-1.13 (m, 2H), 1.13-1.01 (m, 1H), 0.94-0.83 (m, 3H), 0.50-0.38 (m, 2H), 0.33-0.21 (m, 2H); MS (ES+) 757.6 (M+1), (ES−) 791.6 (M+Cl); Analysis calculated for: $C_{40}H_{48}N_6O_9 \cdot HCl \cdot 2H_2O$: C, 57.93; H, 6.44; N, 10.13; found: C, 57.87; H, 6.23; N, 9.97.

Scheme 91

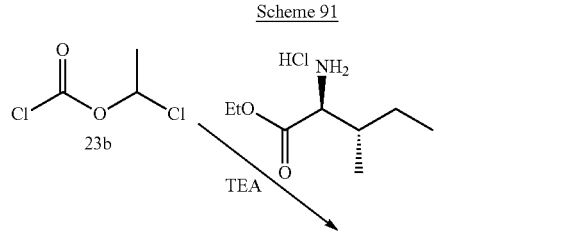

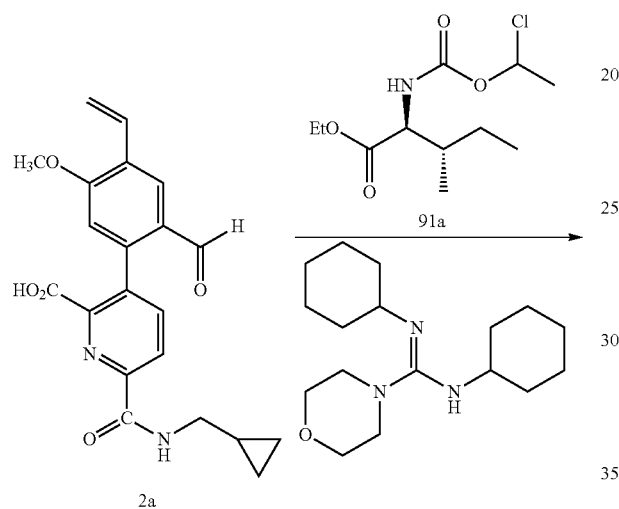

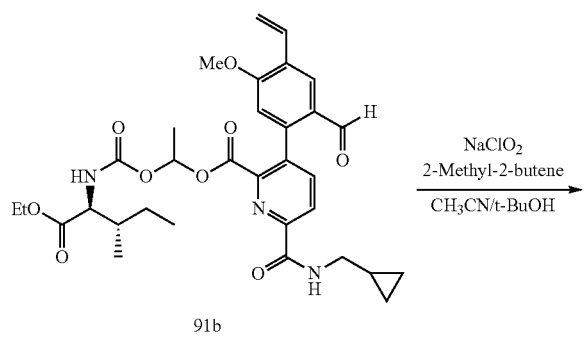

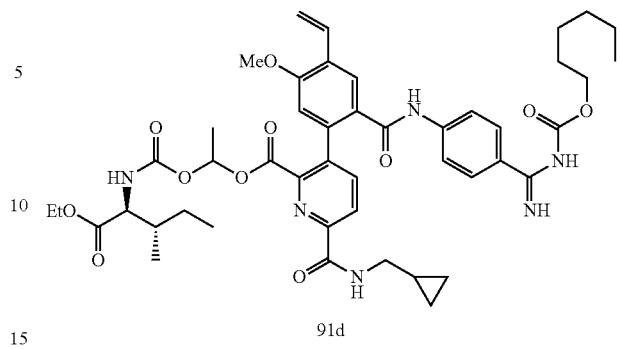

Preparation of 1-(((((2S,3S)-1-ethoxy-3-methyl-1-oxopentan-2-yl)carbamoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (91d)

Step-1: Preparation of (2S,3S)-ethyl 2-(((1-chloroethoxy)carbonyl)amino)-3-methylpentanoate (91a)

Compound (91a) was prepared according to the procedure described in step 1 of scheme 88 from (2S,3S)-ethyl 2-amino-3-methylpentanoate hydrochloride (3.0 g, 15.33 mmol) and 1-chloroethyl carbonochloridate (23b) (2.56 mL, 23.00 mmol) in THF (50 mL) using triethylamine (8.55 mL, 61.3 mmol). This gave after workup (2S,3S)-ethyl 2-(((1-chloroethoxy)carbonyl)amino)-3-methylpentanoate (91a) (4.5 g, 110% yield) which was used such in next step without further purification. $^1$H NMR (300 MHz, DMSO-$d_6$) δ 8.14 (d, J=8.1 Hz, 1H), 6.64-6.48 (m, 1H), 4.24-3.98 (m, 2H), 4.00-3.87 (m, 1H), 3.31-3.10 (m, 2H), 1.90-1.63 (m, 4H), 1.48-1.30 (m, 1H), 1.25-1.13 (m, 3H), 1.07 (td, J=7.0, 3.7 Hz, 2H), 0.93-0.72 (m, 3H); MS (ES−) 300.4 (M+Cl).

Step-2: Preparation of 1-(((((2S,3S)-1-ethoxy-3-methyl-1-oxopentan-2-yl)carbamoyl)oxy)ethyl 6-((cyclopropylmethyl)carbamoyl)-3-(2-formyl-5-methoxy-4-vinylphenyl)picolinate (91b)

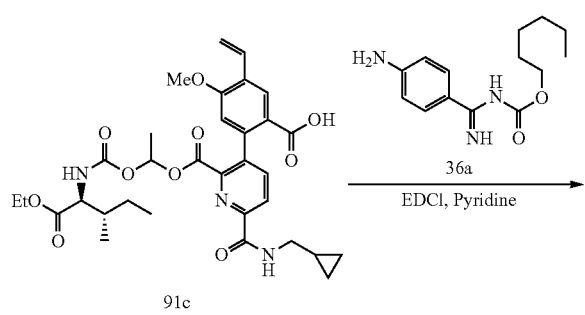

Compound (91b) was prepared according to the procedure reported in step 1 of scheme 8 from 6-(Cyclopropylmethylcarbamoyl)-3-(2-formyl-5-methoxy-4-vinylphenyl)picolinic acid (2a) (3.0 g, 7.89 mmol) in DMF (30 mL) using N,N'-Dicyclohexyl-4-morpholinecarboxamidine (3.47 g, 11.83 mmol) and (2S,3S)-ethyl 2-((1-chloroethoxy)carbonylamino)-3-methylpentanoate (91a) (3.14 g, 11.83 mmol). This gave after workup and purification by flash column chromatography (silica gel 125 g, eluting with ethyl acetate/Hexanes, 0-100%) 1-(((((2S,3S)-1-ethoxy-3-methyl-1-oxopentan-2-yl)carbamoyl)oxy)ethyl 6-((cyclopropylmethyl)carbamoyl)-3-(2-formyl-5-methoxy-4-vinylphenyl)

picolinate (91b) (313 mg, 7% yield) as a yellow thick syrup; $^1$H NMR (300 MHz, DMSO-d$_6$) δ 9.74-9.58 (m, 1H), 8.66 (s, 1H), 8.32-8.18 (m, 1H), 8.16-8.03 (m, 2H), 7.98-7.73 (m, 1H), 7.13-6.87 (m, 2H), 6.74-6.59 (m, 1H), 6.14 (d, J=8.0 Hz, 1H), 6.00 (d, J=17.8 Hz, 1H), 5.44 (d, J=11.3 Hz, 1H), 3.91 (d, J=9.8 Hz, 3H), 3.28-3.16 (m, 2H), 1.90-1.58 (m, 1H), 1.56-1.28 (m, 2H), 1.24-1.02 (m, 6H), 0.89-0.70 (m, 9H), 0.56-0.39 (m, 2H), 0.34-0.20 (m, 2H); MS (ES+) 610.6 (M+1), 632.5 (M+Na).

Step-3: Preparation of 2-(2-(((7S)-7-((S)-sec-butyl)-3-methyl-5,8-dioxo-2,4,9-trioxa-6-azaundecan-1-oyl)-6-((cyclopropylmethyl)carbamoyl)pyridin-3-yl)-4-methoxy-5-vinylbenzoic acid (91c)

Oxidation of 1-(((((2S,3S)-1-ethoxy-3-methyl-1-oxopentan-2-yl)carbamoyl)oxy)ethyl 6-((cyclopropylmethyl)carbamoyl)-3-(2-formyl-5-methoxy-4-vinylphenyl)picolinate (91b) (0.30 g, 0.49 mmol) using the procedure as reported in step 11 of scheme 1 gave after workup 2-(2-((7S)-7-((S)-sec-butyl)-3-methyl-5,8-dioxo-2,4,9-trioxa-6-azaundecan-1-oyl)-6-((cyclopropylmethyl)carbamoyl)pyridin-3-yl)-4-methoxy-5-vinylbenzoic acid (91c) (0.31 g, 100%) as a yellow solid; MS (ES+) 648.5 (M+Na), 624.5 (M−1).

Step-4: Preparation of 1-(((((2S,3S)-1-ethoxy-3-methyl-1-oxopentan-2-yl)carbamoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (91d)

Compound (91d) was prepared from 2-(6-((cyclopropylmethyl)carbamoyl)-2-((1-(((hexyloxy)carbonyl)oxy)ethoxy)carbonyl)pyridin-3-yl)-4-methoxy-5-vinylbenzoic acid (88c) (0.30 g, 0.48 mmol) using EDCI (0.14 g, 0.73 mmol) and hexyl ((4-aminophenyl)(imino)methyl)carbamate (36a) (0.18 g, 0.68 mmol) in DMF (2 mL) and Pyridine (2 mL) according to the procedure reported in step 4 of scheme 2. This gave after workup and purification by flash column chromatography (silica gel, 25 g, eluting with a 9:1 mixture of ethyl acetate and methanol in hexanes from 0 to 100%) 1-(((((2S,3S)-1-ethoxy-3-methyl-1-oxopentan-2-yl)carbamoyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (91d) (0.065 g, 15% yield) as a white solid; $^1$H NMR (300 MHz, DMSO-d$_6$) δ 10.89-10.65 (m, 1H, D$_2$O exchangeable), 9.28 (s, 2H, D$_2$O exchangeable), 9.05 (s, 2H, D$_2$O exchangeable), 8.73-8.39 (m, 4H, 3H D$_2$O exchangeable), 8.24 (d, J=8.0 Hz, 1H), 8.13-7.96 (m, 2H), 7.90-7.71 (m, 4H), 7.12-6.94 (m, 2H), 6.87 (q, J=5.3 Hz, 1H), 6.17-6.01 (m, 1H), 5.45 (d, J=11.4 Hz, 1H), 3.89 (d, J=2.8 Hz, 3H), 3.80 (s, 1H), 3.24 (s, 2H), 1.95-1.67 (m, 1H), 1.44-0.97 (m, 6H), 0.93-0.67 (m, 6H), 0.52-0.39 (m, 2H), 0.35-0.20 (m, 2H); MS (ES+) 671.5 (M+1), 693.4 (M+Na); Analysis: calculated for: C$_{46}$H$_{58}$N$_6$O$_{11}$.0.5H$_2$O: C, 62.78; H, 6.76; N, 9.55. Found: C, 62.81; H, 6.78; N, 9.13.

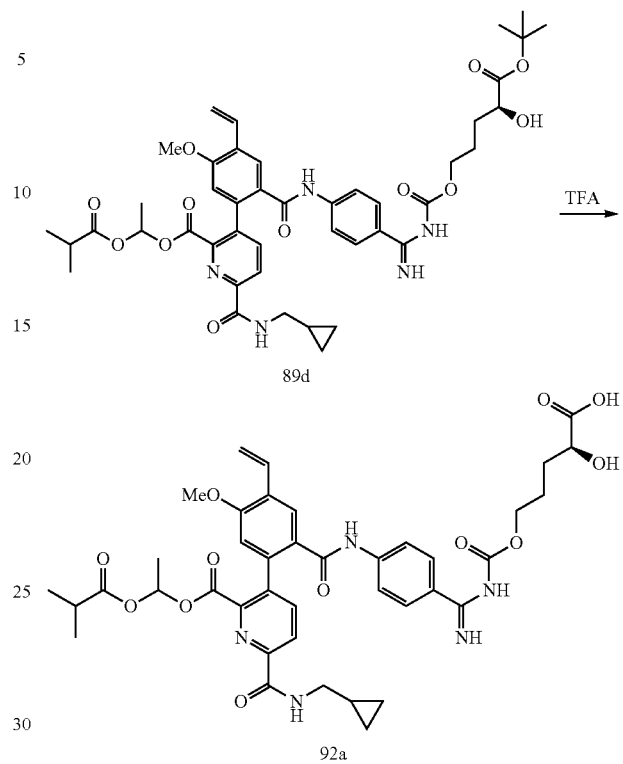

Scheme 92

Preparation of (2S)-5-((((4-(2-(6-((cyclopropylmethyl)carbamoyl)-2-((1-(isobutyryloxy)ethoxy)carbonyl)pyridin-3-yl)-4-methoxy-5-vinylbenzamido)phenyl)(imino)methyl)carbamoyl)oxy)-2-hydroxypentanoic acid (92a)

Compound (92a) was prepared from 1-(isobutyryloxy)ethyl 3-(2-((4-(N—((((S)-5-(tert-butoxy)-4-hydroxy-5-oxopentyl)oxy)carbonyl)carbamimidoyl)phenyl)carbamoyl)-5-methoxy-4-vinylphenyl)-6-((cyclopropylmethyl)carbamoyl)picolinate (89c) (0.1 g, 0.12 mmol) in dichloromethane (10 mL) using 2,2,2-trifluoroacetic acid (0.18 mL, 2.37 mmol). This gave after workup and purification by flash column chromatography (C18, 26 g) eluting with aqueous 0.1% HCl and acetonitrile 0-100%, followed by lyophilization (2S)-5-((((4-(2-(6-((cyclopropylmethyl)carbamoyl)-2-((1-(isobutyryloxy)ethoxy)carbonyl)pyridin-3-yl)-4-methoxy-5-vinylbenzamido)phenyl)(imino)methyl)carbamoyl)oxy)-2-hydroxypentanoic acid (92a) (0.041 g, 44% yield) hydrochloride salt as a white solid. $^1$H NMR (300 MHz, DMSO-d$_6$) δ 10.69 (d, J=22.0 Hz, 1H), 8.57 (d, J=25.8 Hz, 1H), 8.22 (d, J=8.0 Hz, 1H), 8.11-7.92 (m, 2H), 7.77 (s, 4H), 7.14-6.90 (m, 2H), 6.74 (d, J=5.8 Hz, 1H), 6.06 (d, J=17.9 Hz, 1H), 5.45 (d, J=11.5 Hz, 1H), 4.41-4.17 (m, 2H), 4.06-3.94 (m, 1H), 3.88 (s, 3H), 3.29-3.15 (m, 2H), 2.43 (p, J=1.9 Hz, 1H), 1.84-1.73 (m, 3H), 1.69-1.51 (m, 1H), 1.18 (d, J=5.3 Hz, 3H), 1.14-1.01 (m, 1H), 1.05-0.92 (m, 6H), 0.49-0.40 (m, 2H), 0.31-0.21 (m, 2H); MS (ES+) 788.7 (M+1); Analysis calculated for: C$_{40}$H$_{45}$N$_5$O$_{12}$.HCl.2H$_2$O: C, 55.84; H, 5.86; Cl, 4.12; N, 8.14; found: C, 55.56; H, 5.70; Cl, 4.11; N, 8.06.

Scheme 93

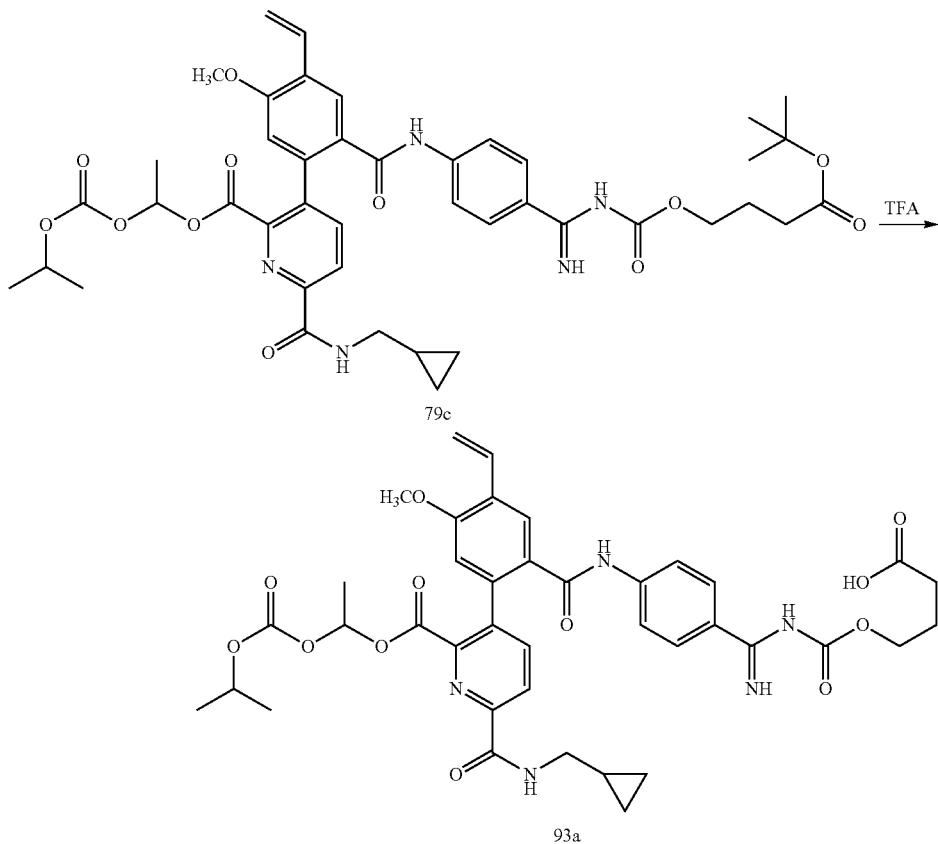

Preparation of (4-(((((4-(2-(6-(((cyclopropylmethyl)carbamoyl)-2-((1-((isopropoxycarbonyl)oxy)ethoxy)carbonyl)pyridin-3-yl)-4-methoxy-5-vinylbenzamido)phenyl)(imino)methyl)carbamoyl)oxy)butanoic acid (93a)

Compound (93a) was prepared from 1-((isopropoxycarbonyl)oxy)ethyl 3-(2-((4-(N-((4-(tert-butoxy)-4-oxobutoxy)carbonyl)carbamimidoyl)phenyl)carbamoyl)-5-methoxy-4-vinylphenyl)-6-((cyclopropylmethyl)carbamoyl)picolinate (79c) (70 mg, 0.084 mmol) in dichloromethane (20 mL) using 2,2,2-trifluoroacetic acid (0.260 mL, 3.37 mmol). This gave after workup and purification twice by preparative reverse phase HPLC chromatography (C18, 26 g) eluting with aqueous 0.1% HCl and acetonitrile 0-100%, followed by lyophilization (4-(((((4-(2-(6-(((cyclopropylmethyl)carbamoyl)-2-((1-((isopropoxycarbonyl)oxy)ethoxy)carbonyl)pyridin-3-yl)-4-methoxy-5-vinylbenzamido)phenyl)(imino)methyl)carbamoyl)oxy)butanoic acid (93a) (26 mg, 40% yield) as a white solid; $^1$H NMR (300 MHz, DMSO-$d_6$) δ 12.19 (s, 1H, D$_2$O exchangeable), 10.62 (d, J=21.9 Hz, 1H, D$_2$O exchangeable), 8.60 (d, J=26.5 Hz, 1H, D$_2$O exchangeable), 8.32-8.20 (m, 1H), 8.09-7.95 (m, 3H), 7.93-7.81 (m, 2H), 7.79-7.59 (m, 3H), 7.10-6.95 (m, 2H), 6.67-6.50 (m, 1H), 6.06 (d, J=17.8 Hz, 1H), 5.52-5.36 (m, 2H), 4.78-4.59 (m, 1H), 4.19-4.02 (m, 2H), 3.89 (s, 3H), 3.24-3.16 (m, 2H), 2.38-2.27 (m, 2H), 1.92-1.77 (m, 2H), 1.24-1.08 (m, 11H), 0.51-0.38 (m, 2H), 0.35-0.21 (m, 2H); MS (ES+) 774.8 (M+1); 796.5 (M+Na); Analysis calculated for: $C_{39}H_{43}N_5O_{12}$·HCl·2.75H$_2$O: C, 54.48; H, 5.80; Cl, 4.12; N, 8.15; found: C, 54.58; H, 5.46; Cl, 3.99; N, 8.01.

Scheme 94

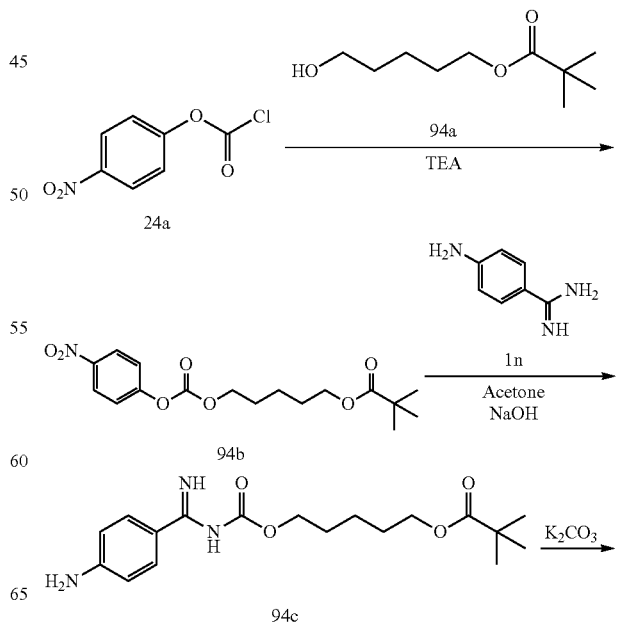

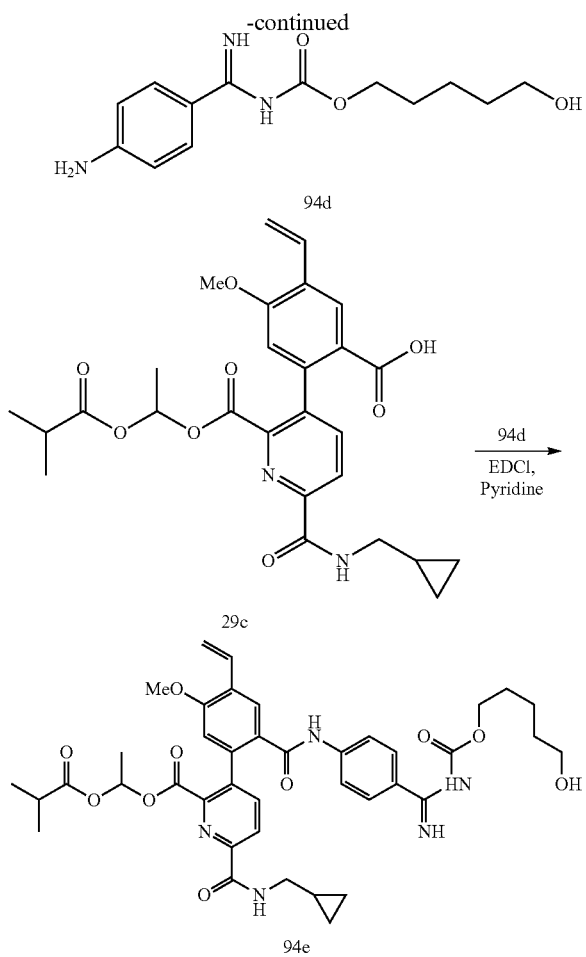

Preparation of 1-(isobutyryloxy)ethyl 6-((cyclopropylmethyl)carbamoyl)-3-(2-((4-(N-(((5-hydroxypentyl)oxy)carbonyl)carbamimidoyl)phenyl)carbamoyl)-5-methoxy-4-vinylphenyl)picolinate (94e)

Step-1: Preparation of 5-(((4-nitrophenoxy)carbonyl)oxy)pentyl pivalate (94b)

Compound (89b) was prepared according to the procedure described in step 1 of scheme 24 from 4-nitrophenyl chloroformate (24a) (3.41 g, 16.92 mmol) in DCM (50 mL) using 5-hydroxypentyl pivalate (94a) (3.19 mL, 16.92 mmol, Prepared according to the literature procedure described by J. R. Al Dulayymi et al; in Tetrahedron 62 (2006) 11867-11880) and triethylamine (5.89 mL, 42.3 mmol). This gave after workup 5-(((4-nitrophenoxy)carbonyl)oxy)pentyl pivalate (94b) (5.30 g, 89% yield) as a brown syrup which was used as such in next step without further purification; $^1$H NMR (300 MHz, DMSO-$d_6$) δ 8.32 (dd, J=9.4, 2.5 Hz, 2H), 7.63-7.50 (m, 2H), 4.26 (t, J=6.5 Hz, 2H), 4.02 (q, J=6.5 Hz, 2H), 1.81-1.64 (m, 2H), 1.61 (ddd, J=10.5, 8.2, 5.5 Hz, 2H), 1.50-1.36 (m, 2H), 1.14 (d, J=2.4 Hz, 9H); MS (ES−) 388.4 (M+Cl).

Step-2: Preparation of 5-((((4-aminophenyl)(imino)methyl)carbamoyl)oxy)pentyl pivalate (94c)

Compound (94c) was prepared from 4-aminobenzimidamide dihydrochloride (1n) (3.06 g, 14.72 mmol) in acetone (30 mL), using NaOH aqueous solution (1 N, 30.9 mL, 30.9 mmol) and a solution of 5-(((4-nitrophenoxy)carbonyl)oxy)pentyl pivalate (94b) (5.2 g, 14.72 mmol) in acetone (30 mL) according to the procedure reported in step 4 of scheme 23. This gave after workup and purification by flash column chromatography (silica gel, 40 g eluting with ethyl acetate and hexanes 0 to 100%) 5-((((4-aminophenyl)(imino)methyl)carbamoyl)oxy)pentyl pivalate (94c) (3.00 g, 58% yield) as a brown syrup; $^1$H NMR (300 MHz, DMSO-$d_6$) δ 9.13 (s, 1H, $D_2O$ exchangeable), 8.62 (s, 1H, $D_2O$ exchangeable), 7.85-7.60 (m, 2H), 6.67-6.45 (m, 2H), 5.84 (s, 2H, $D_2O$ exchangeable), 4.00 (dt, J=11.0, 6.4 Hz, 4H), 1.68-1.54 (m, 4H), 1.39 (qd, J=7.8, 7.2, 4.3 Hz, 2H), 1.13 (s, 9H); MS (ES+) 350.4 (M+1), 372.4 (M+Na), (ES−) 348.4 (M−1).

Step-3: Preparation of 5-hydroxypentyl ((4-aminophenyl)(imino)methyl)carbamate (94d)

To a stirred solution of 5-((((4-aminophenyl)(imino)methyl)carbamoyl)oxy)pentyl pivalate (94c) (2.1 g, 6.01 mmol) in methanol (30 mL) was added potassium carbonate (0.21 g, 1.5 mmol) at room temperature and stirred for 1 hr. The reaction mixture was concentrated in vacuum and the residue was suspended in ethyl acetate (100 mL). The ethyl acetate layer was washed with water (2×50 mL), brine (50 mL), dried, filtered and concentrated in vacuum. The residue obtained was purified by flash column chromatography (silica gel, 40 g eluting with a 9:1 mixture of ethyl acetate and methanol in hexanes) to afford 5-hydroxypentyl ((4-aminophenyl)(imino)methyl)carbamate (94d) (0.4 mg, 25% yield) as a brown syrup; $^1$H NMR (300 MHz, DMSO-$d_6$) δ 9.15 (s, 1H, $D_2O$ exchangeable), 8.64 (s, 1H, $D_2O$ exchangeable), 7.74 (d, J=8.6 Hz, 2H), 6.54 (d, J=8.4 Hz, 2H), 5.84 (s, 2H, $D_2O$ exchangeable), 4.39 (t, J=5.1 Hz, 1H, $D_2O$ exchangeable), 3.98 (q, J=7.2, 6.7 Hz, 2H), 1.57 (q, J=7.0 Hz, 2H), 1.50-1.24 (m, 6H); MS (ES−) 264.5 (M−1).

Step-4: Preparation of 1-(isobutyryloxy)ethyl 6-((cyclopropylmethyl)carbamoyl)-3-(2-((4-(N-(((5-hydroxypentyl)oxy)carbonyl)carbamimidoyl)phenyl)carbamoyl)-5-methoxy-4-vinylphenyl)picolinate (94e)

Compound (94e) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.75 g, 1.47 mmol) using EDCI (0.34 g, 1.76 mmol) and 5-hydroxypentyl ((4-aminophenyl)(imino)methyl)carbamate (94d) (0.39 g, 1.47 mmol) in DMF (2 mL) and Pyridine (2 mL) according to the procedure reported in step 4 of scheme 2. This gave after workup and purification by flash column chromatography [silica gel 40 g, eluting with EtOAc/MeOH (9:1) in hexane from 0-60%] 1-(isobutyryloxy)ethyl 6-((cyclopropylmethyl)carbamoyl)-3-(2-((4-(N-(((5-hydroxypentyl)oxy)carbonyl)carbamimidoyl)phenyl)carbamoyl)-5-methoxy-4-vinylphenyl)picolinate (94e) (125 mg, 11% yield) as a yellow solid; $^1$H NMR (300 MHz, DMSO-$d_6$) δ 10.68-10.24 (m, 1H, $D_2O$ exchangeable), 9.31-8.74 (m, 2H, $D_2O$ exchangeable), 8.66-8.43 (m, 1H), 8.22 (d, J=8.1 Hz, 1H), 7.99 (s, 2H), 7.92 (d, J=8.6 Hz, 2H), 7.75-7.55 (m, 2H), 7.12-6.92 (m, 2H), 6.73 (s, 1H), 6.05 (dd, J=17.8, 1.6 Hz, 1H), 5.44 (dd, J=11.2, 1.5 Hz, 1H), 4.38 (t, J=5.1 Hz, 1H, $D_2O$ exchangeable), 3.99 (t, J=6.6 Hz, 2H), 3.88 (s, 3H), 3.43-3.35 (m, 2H), 3.27-3.19 (m, 2H), 2.49-2.32 (m, 1H), 1.59 (p, J=6.8 Hz, 2H), 1.52-1.28 (m, 4H), 1.17 (d, J=5.4 Hz, 3H), 1.14-1.05 (m, 1H), 1.06-0.90 (m, 6H), 0.51-0.39 (m, 2H), 0.32-0.21 (m, 2H); MS (ES+) 758.715 (M+1), 780.723

(M+Na); HPLC: t=4.40 min, 94.93%; Analysis calculated for: $C_{40}H_{47}N_5O_{10} \cdot H_2O$: C, 61.92; H, 6.37; N, 9.03. Found: C, 62.19; H, 6.18; N, 8.87.

Scheme 95

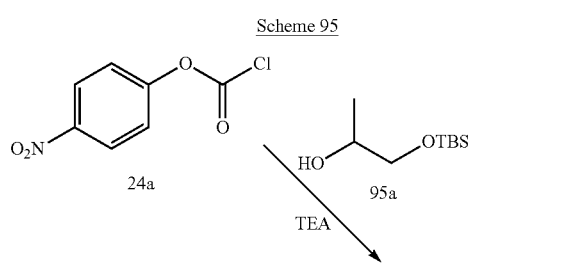

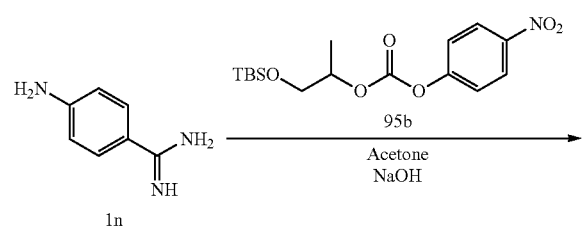

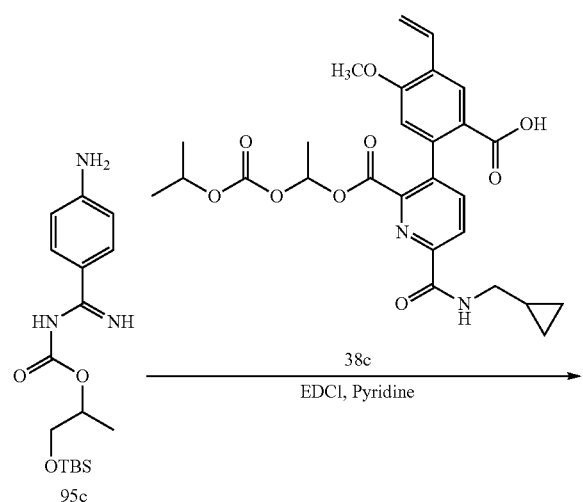

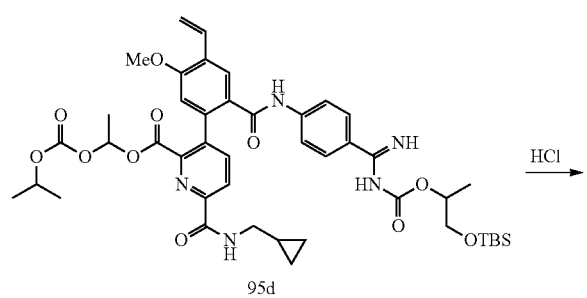

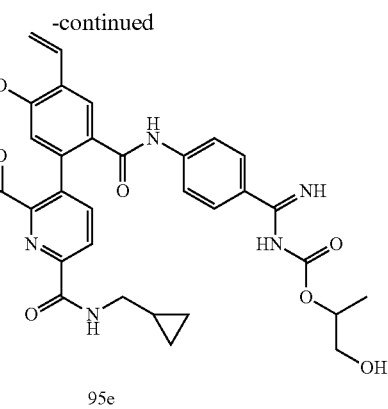

Preparation of 1-((isopropoxycarbonyl)oxy)ethyl 6-((cyclopropylmethyl)carbamoyl)-3-(2-((4-(N-(((1-hydroxypropan-2-yl)oxy)carbonyl)carbamimidoyl)phenyl)carbamoyl)-5-methoxy-4-vinylphenyl)picolinate (95e)

Step-1: Preparation of 1-((tert-butyldimethylsilyl)oxy)propan-2-ol (95a)

To a solution of propane-1,2-diol (8.6 g, 113 mmol) in anhydrous DCM (120 mL) at 0° C. was added imidazole (7.69 g, 113 mmol) and a solution of TBS-Cl (17.03 g, 113 mmol) in dichloromethane. The mixture was allowed to warm to room temperature and diluted with DCM and water. The organic layer was separated washed with water, brine, dried, filtered and concentrated in vacuum to give 1-((tert-butyldimethylsilyl)oxy)propan-2-ol (95a) (19.2 g, 89% yield) as a clear oil, which was used as such in next step without further purification; $^1$H NMR (300 MHz, DMSO-$d_6$) δ 4.47 (d, J=4.6 Hz, 1H, $D_2O$ exchangeable), 3.63-3.52 (m, 1H), 3.47 (dd, J=9.8, 5.3 Hz, 1H), 3.27 (dd, J=9.8, 6.4 Hz, 1H), 1.01 (d, J=6.2 Hz, 3H), 0.86 (s, 9H), 0.02 (s, 6H); MS (ES+) 213.4 (M+Na); (ES−) 189.3 (M−1).

Step-2: Preparation 1-((tert-butyldimethylsilyl)oxy)propan-2-yl (4-nitrophenyl) carbonate (95b)

Compound (95b) was prepared according to the procedure described in step 1 of scheme 24 from 4-nitrophenyl chloroformate (24a) (10.04 g, 48.3 mmol) in THF (150 mL) using 1-((tert-butyldimethylsilyl)oxy)propan-2-ol (95a) (9.2 g, 48.3 mmol) and triethylamine (14.82 mL, 106 mmol). This gave after workup 1-((tert-butyldimethylsilyl)oxy)propan-2-yl (4-nitrophenyl) carbonate (95b) (9.3 g, 54% yield) as a clear oil, which was used as such in next step without further purification. $^1$H NMR (300 MHz, DMSO-$d_6$) δ 8.40-8.17 (m, 2H), 7.59-7.42 (m, 2H), 4.97-4.46 (m, 1H), 3.81-3.61 (m, 2H), 1.27 (d, J=6.4 Hz, 3H), 0.86 (s, 9H), 0.05 (d, J=1.7 Hz, 6H); MS (ES+) 378.5 (M+Na).

Step-3: Preparation of 1-((tert-butyldimethylsilyl)oxy)propan-2-yl ((4-aminophenyl)(imino)methyl)carbamate (95c)

Compound (85b) was prepared from 4-aminobenzimidamide dihydrochloride (1n) (3.73 g, 17.90 mmol) in acetone/$H_2O$ (26 mL, Ratio: 12:1) using sodium hydroxide (1.468 g, 36.7 mmol) and 1-((tert-butyldimethylsilyl)oxy)propan-2-yl (4-nitrophenyl) carbonate (95b) (7 g, 19.69 mmol) according to the procedure reported in step 4 of scheme 23. This gave after workup and purification by flash column chromatography [silica gel 24 g, eluting with 0-100% MeOH:EtOAc (9:1) in hexanes] 1-((tert-butyldimethylsilyl)oxy)propan-2-yl ((4-aminophenyl)(imino)methyl)carbamate (95c) (3.2 g, 9.10 mmol, 50.8% yield) as a semisolid. $^1$H NMR (300 MHz, DMSO-$d_6$) δ 9.07 (brs, 1H, $D_2O$ exchangeable), 8.54 (brs, 1H, $D_2O$ exchangeable), 7.75-7.59 (m, 2H), 6.56-6.40 (m, 2H), 5.78 (s, 2H, $D_2O$ exchangeable), 4.77-4.56 (m, 1H), 3.67-3.56 (m, 1H), 3.56-3.45 (m, 1H), 1.10 (d, J=6.4 Hz, 3H), 0.80 (s, 9H), −0.01 (d, J=3.3 Hz, 6H); MS (ES+) 352.6 (M+1); (ES−) 350.6 (M−1).

Step-4: Preparation of 1-((isopropoxycarbonyl)oxy) ethyl 3-(2-((4-(N-(((1-((tert-butyldimethylsilyl)oxy) propan-2-yl)oxy)carbonyl)carbamimidoyl)phenyl) carbamoyl)-5-methoxy-4-vinylphenyl)-6-((cyclopropylmethyl)carbamoyl)picolinate (95d)

Compound (95d) was prepared from 2-(6-((cyclopropylmethyl)carbamoyl)-2-((1-((isopropoxycarbonyl)oxy) ethoxy)carbonyl)pyridin-3-yl)-4-methoxy-5-vinylbenzoic acid (38c) (1 g, 1.9 mmol) using EDCI (0.47 g, 2.47 mmol) and 1-((tert-butyldimethylsilyl)oxy)propan-2-yl ((4-aminophenyl)(imino)methyl)carbamate (95c) (0.73 g, 2.09 mmol) in DMF (50 mL) and Pyridine (10 mL) according to the procedure reported in step 4 of scheme 2. This gave after workup and purification by flash column chromatography [silica gel, eluting with EtOAc/MeOH (9:1) in hexane from 0-60%] then preparative HPLC [eluting with $CH_3CN$ in water (containing with 0.1% HCl) from 0-100%] followed by lyophilization 1-(isobutyryloxy)ethyl 1-((isopropoxycarbonyl)oxy)ethyl 3-(2-((4-(N-(((1-((tert-butyldimethylsilyl) oxy)propan-2-yl)oxy)carbonyl)carbamimidoyl)phenyl)carbamoyl)-5-methoxy-4-vinylphenyl)-6-((cyclopropylmethyl) carbamoyl)picolinate (95d) (0.36 mg, 22% yield) as a white solid; $^1$H NMR (300 MHz, DMSO-$d_6$) δ 10.49 (d, J=22.7 Hz, 1H, $D_2O$ exchangeable), 9.02 (s, 1H, $D_2O$ exchangeable), 8.54 (s, 1H, $D_2O$ exchangeable), 8.22 (d, J=8.0 Hz, 1H), 8.08-7.85 (m, 5H), 7.74-7.59 (m, 2H), 7.11-6.94 (m, 2H), 6.63 (q, J=5.2 Hz, 1H), 6.05 (d, J=18.1 Hz, 1H), 5.44 (d, J=11.9 Hz, 1H), 4.83-4.61 (m, 2H), 3.89 (s, 3H), 3.69-3.56 (m, 2H), 3.27-3.17 (m, 2H), 1.20-1.08 (m, 13H), 0.85 (s, 9H), 0.49-0.39 (m, 2H), 0.31-0.22 (m, 2H), 0.05 (d, J=3.1 Hz, 6H); MS (ES+) 861.3 (M+1);

Step-5: Preparation of 1-((isopropoxycarbonyl)oxy) ethyl 6-((cyclopropylmethyl)carbamoyl)-3-(2-((4-(N-(((1-hydroxypropan-2-yl)oxy)carbonyl)carbamimidoyl)phenyl)carbamoyl)-5-methoxy-4-vinylphenyl)picolinate (95e)

To a solution of 1-((isopropoxycarbonyl)oxy)ethyl 3-(2-((4-(N-(((1-((tert-butyldimethylsilyl)oxy)propan-2-yl)oxy) carbonyl)carbamimidoyl)phenyl)carbamoyl)-5-methoxy-4-vinylphenyl)-6-((cyclopropylmethyl)carbamoyl)picolinate (95d) (0.32 g, 0.37 mmol) in DCM (15 mL) was added HCl (4N in dioxane, 0.93 mL, 3.72 mmol) and stirred at room temperature for 3 h. The reaction mixture was concentrated in vacuum and purified twice by prep HPLC [eluting with $CH_3CN$ in water (containing with 0.1% HCl) from 0-100%] to give 1-((isopropoxycarbonyl)oxy)ethyl 6-((cyclopropylmethyl)carbamoyl)-3-(2-((4-(N-(((1-hydroxypropan-2-yl) oxy)carbonyl)carbamimidoyl)phenyl)carbamoyl)-5-methoxy-4-vinylphenyl)picolinate (95e) (21 mg, 8% yield) as a white solid; $^1$H NMR (300 MHz, DMSO-$d_6$) δ 12.41 (brs, 1H, $D_2O$ exchangeable), 11.16 (brs, 1H, $D_2O$ exchangeable), 10.84 (d, J=15.2 Hz, 1H, $D_2O$ exchangeable), 10.36 (s, 1H, $D_2O$ exchangeable), 8.61 (d, J=28.6 Hz, 1H, $D_2O$ exchangeable), 8.22 (d, J=8.0 Hz, 1H), 8.10-7.96 (m, 2H), 7.87-7.66 (m, 4H), 7.11-6.96 (m, 2H), 6.63 (q, J=5.3 Hz, 1H), 6.10 (d, J=17.8 Hz, 1H), 5.44 (d, J=11.4 Hz, 1H), 5.03-4.88 (m, 1H), 4.71 (p, J=6.3 Hz, 1H), 3.89 (s, 3H), 3.60-3.51 (m, 2H), 3.27-3.17 (m, 2H), 1.27 (d, J=6.4 Hz, 3H), 1.23-1.04 (m, 11H), 0.49-0.40 (m, 2H), 0.31-0.23 (m, 2H); MS (ES+) 746.7 (M+1); (ES−) 780.8 (M+Cl); Analysis calculated for $C_{38}H_{43}N_5O_{11}HCl.2H_2O$: C, 55.78; H, 5.91; N, 8.56; found: C, 55.59; H, 5.91; N, 8.54.

Scheme 96

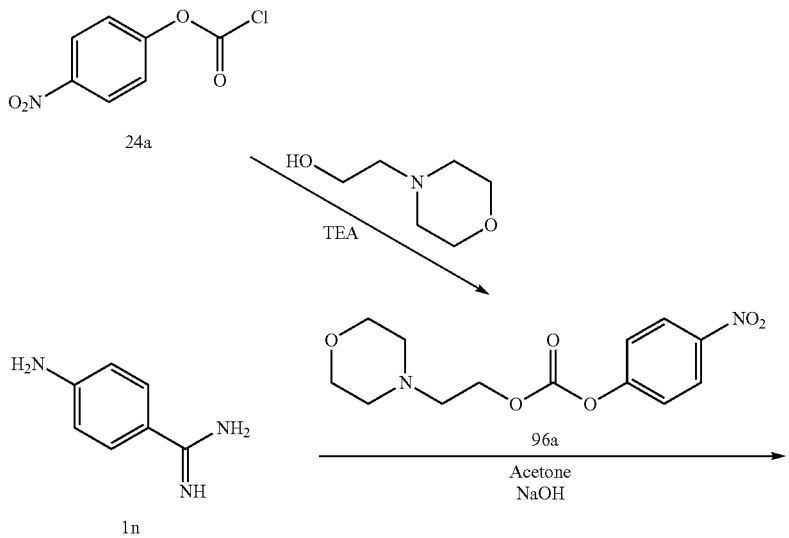

-continued
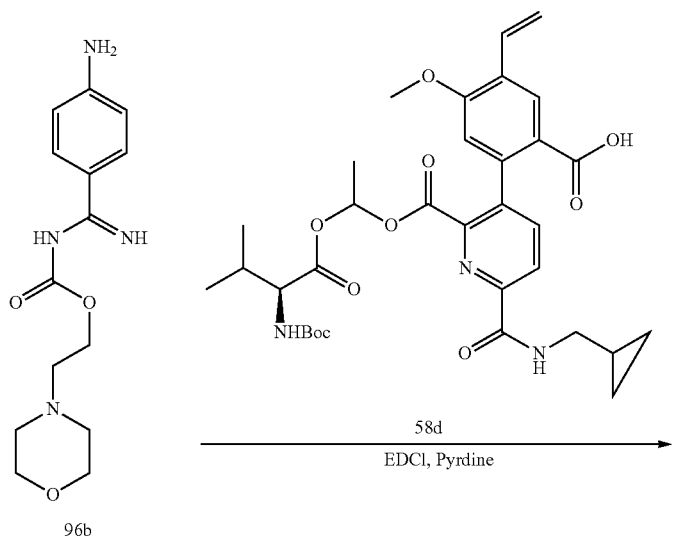
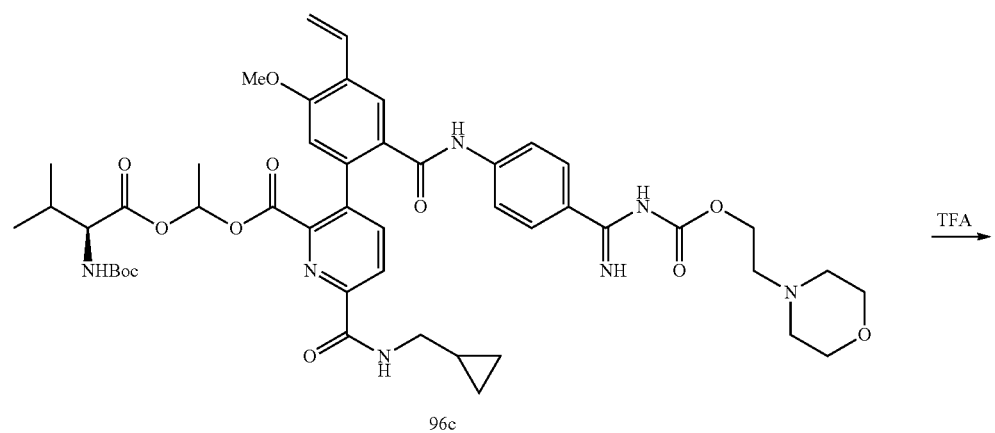
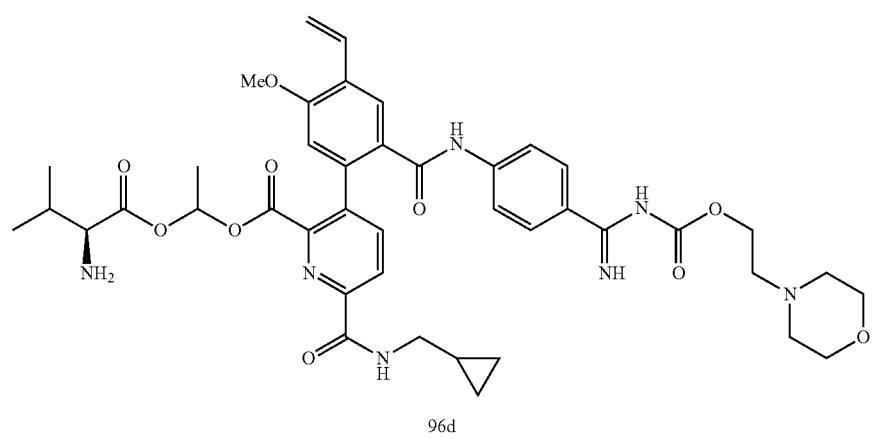 [SMILES: C=Cc1cc(C(=O)Nc2ccc(C(=N)NC(=O)OCCN3CCOCC3)cc2)c(-c2ccc(C(=O)NCC3CC3)nc2C(=O)OC(C)OC(=O)[C@@H](N)C(C)C)cc1OC]

Preparation of 1-(((S)-2-amino-3-methylbutanoyl)oxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (96d)

Step-1: Preparation of 2-morpholinoethyl (4-nitrophenyl) carbonate (96a)

Compound (96a) was prepared according to the procedure described in step 1 of scheme 24 from 4-nitrophenyl chloroformate (24a) (2 g, 9.92 mmol) in THF (100 mL) using 2-morpholinoethanol (1.367 g, 10.42 mmol) and triethylamine (2.77 mL, 19.84 mmol). This gave after workup 2-morpholinoethyl (4-nitrophenyl) carbonate (96a) (2.8 g, 9.45 mmol, 95% yield) as thick dark orange syrup; $^1$H NMR (300 MHz, DMSO-$d_6$) δ 8.35-8.30 (m, 2H), 7.59-7.53 (m, 2H), 4.35 (t, J=5.5 Hz, 2H), 3.56 (q, J=7.0, 5.9 Hz, 4H), 2.64 (t, J=5.5 Hz, 2H), 2.47-2.40 (m, 4H).

Step-2: Preparation 2-morpholinoethyl ((4-aminophenyl)(imino)methyl)carbamate (96b)

Compound (85b) was prepared from 4-aminobenzimidamide dihydrochloride (1n) (1.5 g, 7.21 mmol) in acetone/H$_2$O (40 mL, Ratio: 3:1) using sodium hydroxide (0.634 g, 15.86 mmol) and a solution of 2-morpholinoethyl (4-nitrophenyl) carbonate (96a) (2.78 g, 9.37 mmol) in acetone (30 mL) according to the procedure reported in step 4 of scheme 23. This gave after workup and purification by flash column chromatography [silica gel 24 g, eluting with 0-100% EtOAc in hexanes] 2-morpholinoethyl ((4-aminophenyl)(imino)methyl)carbamate (96b) (0.7 g, 33% yield) as a light orange solid. $^1$H NMR (300 MHz, DMSO-$d_6$) δ 9.09 (s, 1H), 8.61 (s, 1H), 7.79-7.69 (m, 2H), 6.60-6.51 (m, 2H), 5.85 (s, 2H), 4.09 (t, J=5.9 Hz, 2H), 3.61-3.52 (m, 4H), 2.54 (t, J=6.0 Hz, 2H), 2.46-2.35 (m, 4H); MS (ES+) 585.6 (2M+1), MS (ES−) 291.4 (M−1), 327.5 (M+Cl).

Step-3: Preparation of 1-(((S)-2-((tert-butoxycarbonyl)amino)-3-methylbutanoyl)oxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (96c)

Compound (96c) was prepared from 2-(6-((cyclopropylmethyl)carbamoyl)-2-((6S)-6-isopropyl-3,10,10-trimethyl-5,8-dioxo-2,4,9-trioxa-7-azaundecan-1-oyl)pyridin-3-yl)-4-methoxy-5-vinylbenzoic acid (58d) (0.3 g, 0.47 mmol) using EDCI (0.11 g, 0.56 mmol) and 2-morpholinoethyl ((4-aminophenyl)(imino)methyl)carbamate (96b) (0.14 g, 0.47 mmol) in DMF (4 mL) and Pyridine (1 mL) according to the procedure reported in step 4 of scheme 2. This gave after workup and purification by flash column chromatography [silica gel 24 g, eluting with EtOAc/MeOH (9:1) in hexane from 0-100%] then preparative HPLC [eluting with CH$_3$CN in water (containing with 0.1% HCl) from 0-100%] 1-(((S)-2-((tert-butoxycarbonyl)amino)-3-methylbutanoyl)oxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (96c) (0.19 g, 44% yield) as a white powder; MS (ES+) 936.8 (M+Na), MS (ES−) 949.0 (M+Cl).

Step-4: Preparation of 1-(((S)-2-amino-3-methylbutanoyl)oxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (96d)

Compound (96d) was prepared from 1-(((S)-2-((tert-butoxycarbonyl)amino)-3-methylbutanoyl)oxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (96c) (0.19 g, 0.21 mmol) in dichloromethane (2 mL) using 2,2,2-trifluoroacetic acid (0.24 mL, 3.12 mmol). This gave after workup and purification by reverse phase column chromatography [silica gel 26 g, Acetonitrile in 0.1% HCl in water as eluents, 0 to 50%] followed by lyophilization 1-(((S)-2-amino-3-methylbutanoyl)oxy)ethyl 6-((cyclopropylmethyl)carbamoyl)-3-(5-methoxy-2-((4-(N-((2-morpholinoethoxy)carbonyl)carbamimidoyl)phenyl)carbamoyl)-4-vinylphenyl)picolinate (96d) (0.12 g, 71% yield) hydrochloride salt as a white solid; $^1$H NMR (300 MHz, DMSO-$d_6$) δ 10.95 (s, 1H), 10.85-10.51 (m, 2H), 8.67-8.34 (m, 4H), 8.24 (d, J=7.9 Hz, 1H), 8.10-7.96 (m, 2H), 7.94-7.62 (m, 4H), 7.12-6.96 (m, 2H), 6.93-6.82 (m, 1H), 6.09 (dd, J=17.9, 5.7 Hz, 1H), 5.45 (d, J=11.4 Hz, 1H), 4.71-4.43 (m, 3H), 3.90 (s, 9H), 3.70-3.00 (m, 6H), 2.19-1.95 (m, 1H), 1.37-0.99 (m, 4H), 0.98-0.75 (m, 6H), 0.53-0.39 (m, 2H), 0.34-0.22 (m, 2H); MS (ES+) 814.9 (M+1), MS (ES−) 849.6 (M+Cl);

Scheme 97

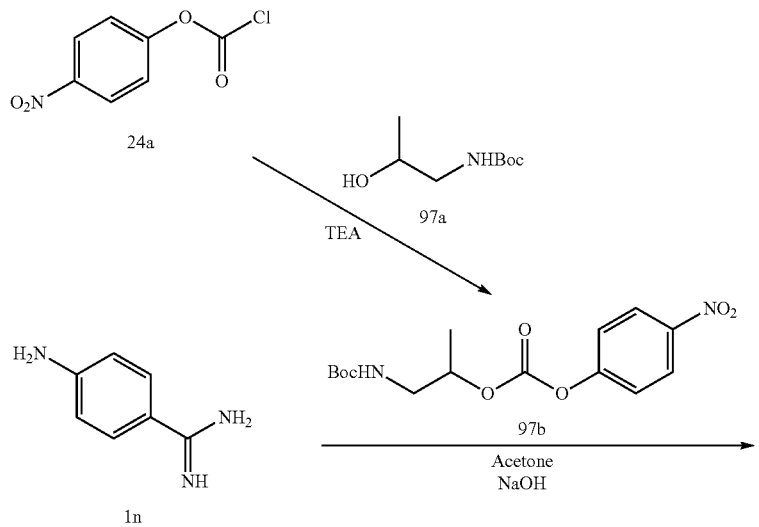

-continued
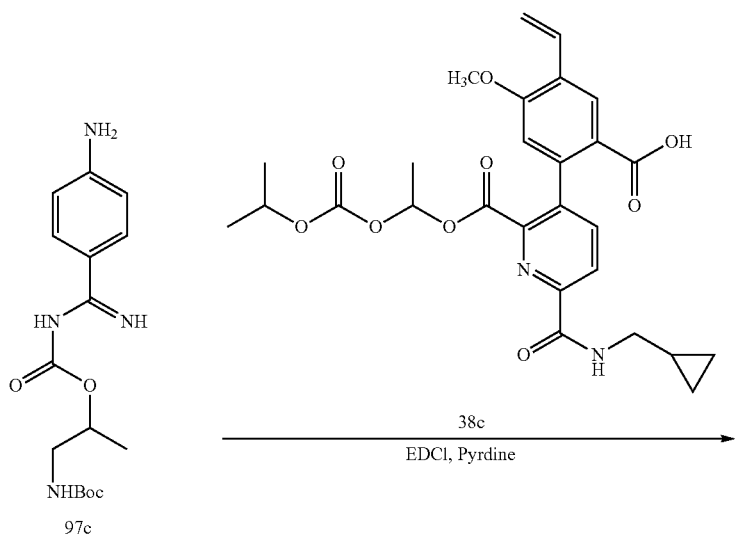
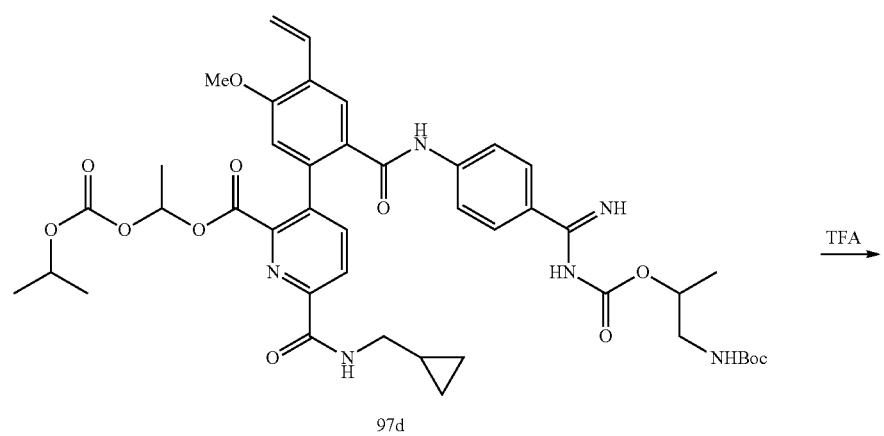

Preparation of 1-((isopropoxycarbonyl)oxy)ethyl 3-(2-((4-(N-(((1-aminopropan-2-yl)oxy)carbonyl) carbamimidoyl)phenyl)carbamoyl)-5-methoxy-4-vinylphenyl)-6-((cyclopropylmethyl)carbamoyl) picolinate (97e)

Step-1: Preparation of tert-butyl (2-(((4-nitrophenoxy)carbonyl)oxy)propyl)carbamate (97b)

Compound (97b) was prepared according to the procedure described in step 1 of scheme 24 from 4-nitrophenyl chloroformate (24a) (3.79 g, 18.26 mmol) in THF (100 mL) using tert-butyl 2-hydroxypropylcarbamate (97a) (3.2 g, 18.26 mmol) and triethylamine (5.60 mL, 40.2 mmol). This gave after workup and purification by flash column chromatography (silica gel, eluting with EtOAc in hexane from 0-50%) tert-butyl (2-(((4-nitrophenoxy)carbonyl)oxy)propyl)carbamate (97b) (5 g, 80% yield) as yellow oil; $^1$H NMR (300 MHz, DMSO-$d_6$) δ 8.42-8.20 (m, 2H), 7.64-7.43 (m, 2H), 7.17 (t, J=6.0 Hz, 1H), 4.89-4.68 (m, 1H), 3.36-3.26 (m, 1H), 3.18-3.04 (m, 1H), 1.38 (s, 9H), 1.26 (d, J=6.4 Hz, 3H); MS (ES+) 363.4 (M+Na); (ES−) 375.4 (M+Cl).

Step-2: Preparation 1-((tert-butoxycarbonyl)amino)propan-2-yl ((4-aminophenyl)(imino)methyl)carbamate (97c)

Compound (97c) was prepared from 4-aminobenzimidamide dihydrochloride (1n) (3.06 g, 14.69 mmol) in acetone/H$_2$O (26 mL, Ratio: 12:1) using sodium hydroxide (1.21 g, 30.1 mmol) and tert-butyl (2-(((4-nitrophenoxy)carbonyl)oxy)propyl)carbamate (97b) according to the procedure reported in step 4 of scheme 23. This gave after workup and purification by flash column chromatography [(silica gel, 12 g) eluting with ethyl acetate/MeOH (9:1) in hexanes from 0 to 100%] 1-((tert-butoxycarbonyl)amino)propan-2-yl ((4-aminophenyl)(imino)methyl)carbamate (97c) (2.23 g, 45% yield) as a white solid; $^1$H NMR (300 MHz, DMSO-$d_6$) δ 9.13 (brs, 1H, D$_2$O exchangeable), 8.63 (brs, 1H, D$_2$O exchangeable), 7.75 (dd, J=8.7, 1.5 Hz, 2H), 6.95 (t, J=5.8 Hz, 1H), 6.63-6.44 (m, 2H), 5.85 (s, 2H, D$_2$O exchangeable), 4.71 (q, J=6.2 Hz, 1H), 3.15-2.91 (m, 2H), 1.37 (s, 9H), 1.12 (d, J=6.3 Hz, 3H); MS (ES+) 337.5 (M+1).

Step-3: Preparation of 1-((isopropoxycarbonyl)oxy) ethyl 3-(2-((4-(N-(((1-((tert-butoxycarbonyl)amino) propan-2-yl)oxy)carbonyl)carbamimidoyl)phenyl) carbamoyl)-5-methoxy-4-vinylphenyl)-6-((cyclopropylmethyl)carbamoyl)picolinate (97d)

Compound (97d) was prepared from 2-(6-((cyclopropylmethyl)carbamoyl)-2-((1-((isopropoxycarbonyl)oxy) ethoxy)carbonyl)pyridin-3-yl)-4-methoxy-5-vinylbenzoic acid (38c) (1 g, 1.90 mmol) using EDCI (0.47 g, 2.47 mmol) and 1-((tert-butoxycarbonyl)amino)propan-2-yl ((4-aminophenyl)(imino)methyl)carbamate (97c) (0.64 g, 1.90 mmol) in DMF/pyridine (60 mL, 4:2) according to the procedure reported in step 4 of scheme 2. This gave after workup and purification by flash column chromatography [silica gel (24 g), eluting with EtOAc/MeOH (9:1) in hexane from 0-60%] 1-((isopropoxycarbonyl)oxy)ethyl 3-(2-((4-(N-(((1-((tert-butoxycarbonyl)amino)propan-2-yl)oxy)carbonyl)carbamimidoyl)phenyl)carbamoyl)-5-methoxy-4-vinylphenyl)-6-((cyclopropylmethyl)carbamoyl)picolinate (97d) (89 mg, 6% yield) as a white solid. MS (ES+) 845.8 (M+1).

Step-4: Preparation of 1-((isopropoxycarbonyl)oxy) ethyl 3-(2-((4-(N-(((1-aminopropan-2-yl)oxy)carbonyl)carbamimidoyl)phenyl)carbamoyl)-5-methoxy-4-vinylphenyl)-6-((cyclopropylmethyl)carbamoyl) picolinate (97e)

Compound (97e) was prepared from 1-((isopropoxycarbonyl)oxy)ethyl 3-(2-((4-(N-(((1-((tert-butoxycarbonyl)amino)propan-2-yl)oxy)carbonyl)carbamimidoyl)phenyl)carbamoyl)-5-methoxy-4-vinylphenyl)-6-((cyclopropylmethyl)carbamoyl)picolinate (97d) (85 mg, 0.10 mmol) in dichloromethane (10 mL) using 2,2,2-trifluoroacetic acid (0.16 mL, 2.01 mmol). This gave after workup and purification by reverse phase column chromatography [silica gel 26 g, Acetonitrile in 0.1% HCl in water as eluents, 0 to 50%] followed by lyophilization 1-((isopropoxycarbonyl)oxy)ethyl 3-(2-((4-(N-(((1-aminopropan-2-yl)oxy)carbonyl)carbamimidoyl)phenyl)carbamoyl)-5-methoxy-4-vinylphenyl)-6-((cyclopropylmethyl)carbamoyl)picolinate (97e) (35 mg, 47% yield) as a white solid; $^1$H NMR (300 MHz, DMSO-$d_6$) δ 10.80 (d, J=22.2 Hz, 1H, D$_2$O exchangeable), 10.30 (brs, 1H, D$_2$O exchangeable), 8.61 (d, J=28.8 Hz, 1H, D$_2$O exchangeable), 8.35 (s, 3H, D$_2$O exchangeable), 8.25-8.15 (m, 1H), 8.06-7.95 (m, 2H), 7.92-7.63 (m, 5H), 7.11-6.94 (m, 2H), 6.63 (q, J=5.3 Hz, 1H), 6.07 (d, J=17.7 Hz, 1H), 5.45 (d, J=11.6 Hz, 1H), 5.20-5.03 (m, 1H), 4.77-4.60 (m, 1H), 3.89 (s, 3H), 3.28-2.99 (m, 4H), 1.36 (d, J=6.4 Hz, 2H), 1.26-1.05 (m, 12H), 0.50-0.38 (m, 2H), 0.31-0.22 (m, 2H); MS (ES$^+$) 745.7 (M+1); 767.6 (M+Na); (ES$^-$) 779.8 (M+Cl); Analysis calculated for C$_{38}$H$_{44}$N$_6$O$_{10}$.2HCl.4H$_2$O: C, 51.29; H, 6.12; Cl, 7.97; N, 9.45; found: C, 51.11; H, 5.83; Cl, 7.94; N, 9.39.

Scheme 98

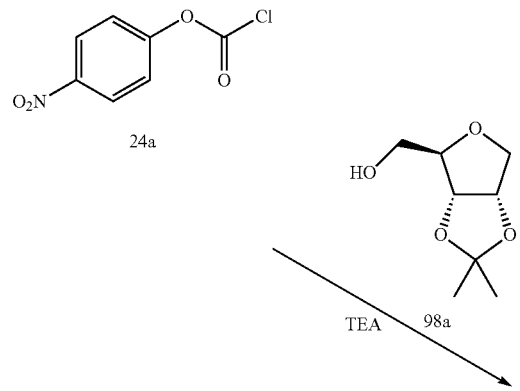

-continued
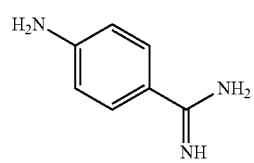
1n
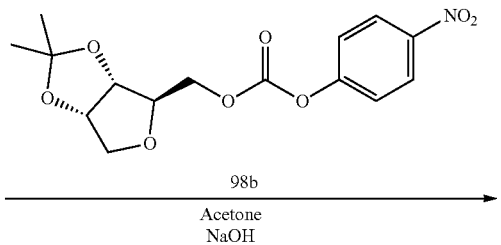
98b
Acetone
NaOH
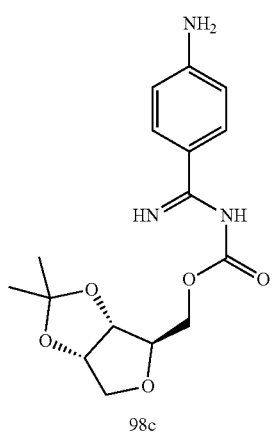
98c
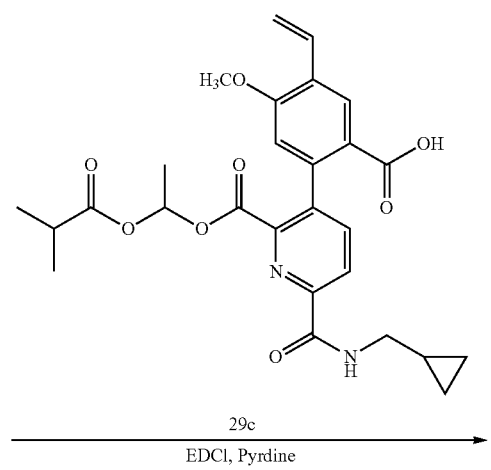
29c
EDCl, Pyrdine
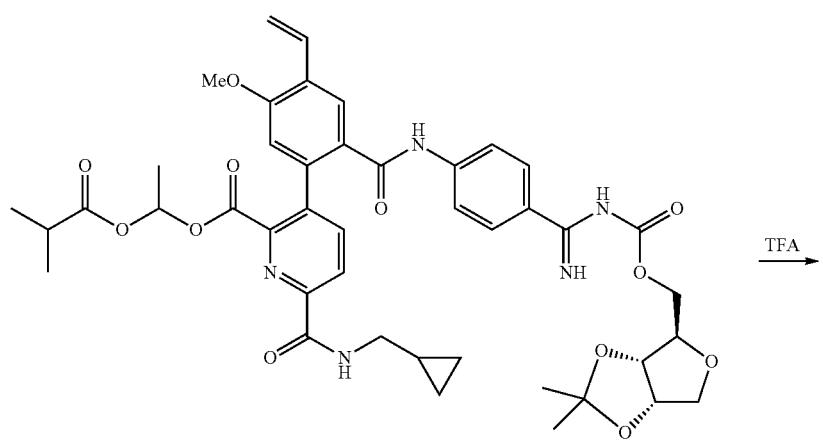
98d
TFA
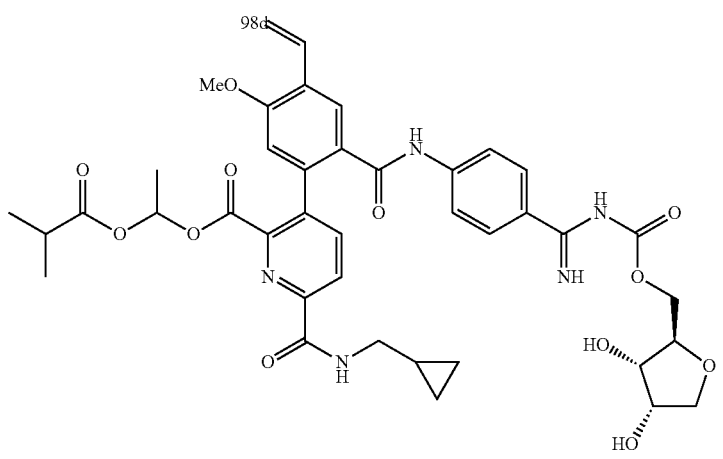
98e Preparation of 1-(isobutyryloxy)ethyl 6-((cyclopropylmethyl)carbamoyl)-3-(2-((4-(N-((((2R,3S,4S)-3,4-dihydroxytetrahydrofuran-2-yl)methoxy)carbonyl)carbamimidoyl)phenyl)carbamoyl)-5-methoxy-4-vinylphenyl)picolinate (98e)

Step-1: Preparation of ((3aR,4R,6aS)-2,2-dimethyltetrahydrofuro[3,4-d][1,3]dioxol-4-yl)methyl (4-nitrophenyl) carbonate (98b)

Compound (98b) was prepared according to the procedure described in step 1 of scheme 24 from 4-nitrophenyl chloroformate (24a) (0.17 g, 0.86 mmol) in THF (10 mL) using ((3aR,4R,6aS)-2,2-dimethyltetrahydrofuro[3,4-d][1,3]dioxol-4-yl)methanol (98a) (0.15 g, 0.86 mmol) and triethylamine (0.18 mL, 1.29 mmol). This gave after workup ((3aR,4R,6aS)-2,2-dimethyltetrahydrofuro[3,4-d][1,3]dioxol-4-yl)methyl (4-nitrophenyl) carbonate (98b) (0.25 g, 86% yield) as thick dark orange syrup which was used as such for next step.

Step-2: Preparation ((3aR,4R,6aS)-2,2-dimethyltetrahydrofuro[3,4-d][1,3]dioxol-4-yl)methyl ((4-aminophenyl)(imino)methyl)carbamate (98c)

Compound (98c) was prepared from 4-aminobenzimidamide dihydrochloride (1n) (0.15 g, 0.71 mmol) in acetone (10 mL) using 6 N aqueous sodium hydroxide (0.26 mL, 1.56 mmol) and a solution of ((3aR,4R,6aS)-2,2-dimethyltetrahydrofuro[3,4-d][1,3]dioxol-4-yl)methyl (4-nitrophenyl) carbonate (98b) (0.24 g, 0.71 mmol) in acetone (5 mL) according to the procedure reported in step 4 of scheme 23. This gave after workup and purification by flash column chromatography [(silica gel, 12 g) eluting with ethyl acetate/MeOH (9:1) in hexanes from 0 to 100%] ((3 aR,4R,6aS)-2,2-dimethyltetrahydrofuro[3,4-d][1,3]dioxol-4-yl)methyl ((4-aminophenyl)(imino)methyl)carbamate (98c) (0.08 g, 34% yield) as a colorless foam. $^1$H NMR (300 MHz, CDCl$_3$) δ 7.74 (d, J=8.6 Hz, 2H), 6.67 (d, J=8.6 Hz, 2H), 4.89 (dd, J=5.4, 3.3 Hz, 1H), 4.82-4.73 (m, 1H), 4.35 (t, J=5.2 Hz, 1H), 4.20 (t, J=5.5 Hz, 2H), 4.05-3.98 (m, 2H), 1.52 (s, 3H), 1.34 (s, 3H).

Step-3: Preparation of 1-(isobutyryloxy)ethyl 6-((cyclopropylmethyl)carbamoyl)-3-(2-((4-(N-((((3aR,4R,6aS)-2,2-dimethyltetrahydrofuro[3,4-d][1,3]dioxol-4-yl)methoxy)carbonyl)carbamimidoyl)phenyl)carbamoyl)-5-methoxy-4-vinylphenyl)picolinate (98d)

Compound (98d) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (0.12 g, 0.23 mmol) using EDCI (0.04 g, 0.21 mmol) and ((3aR,4R,6aS)-2,2-dimethyltetrahydrofuro[3,4-d][1,3]dioxol-4-yl)methyl ((4-aminophenyl)(imino)methyl)carbamate (98c) (0.07 g, 0.21 mmol) in DMF (2 mL) and pyridine (1 mL) according to the procedure reported in step 4 of scheme 2. This gave after workup and purification by flash column chromatography [silica gel (24 g), eluting with EtOAc/MeOH (9:1) in hexane from 0-100%] 1-(isobutyryloxy)ethyl 6-((cyclopropylmethyl)carbamoyl)-3-(2-((4-(N-((((3aR,4R,6aS)-2,2-dimethyltetrahydrofuro[3,4-d][1,3]dioxol-4-yl)methoxy)carbonyl)carbamimidoyl)phenyl)carbamoyl)-5-methoxy-4-vinylphenyl)picolinate (98d) (0.08 g, 46% yield) as a white powder; MS (ES+) 828.6 (M+1), 850.6 (M+Na).

Step-4: Preparation of 1-(isobutyryloxy)ethyl 6-((cyclopropylmethyl)carbamoyl)-3-(2-((4-(N-((((2R,3S,4S)-3,4-dihydroxytetrahydrofuran-2-yl)methoxy)carbonyl)carbamimidoyl)phenyl)carbamoyl)-5-methoxy-4-vinylphenyl)picolinate (98e)

Compound (98e) was prepared from 1-(isobutyryloxy)ethyl 6-((cyclopropylmethyl)carbamoyl)-3-(2-((4-(N-((((3aR,4R,6aS)-2,2-dimethyltetrahydrofuro[3,4-d][1,3]dioxol-4-yl)methoxy)carbonyl)carbamimidoyl)phenyl)carbamoyl)-5-methoxy-4-vinylphenyl)picolinate (98d) (0.08 g, 0.097 mmol) in dichloromethane (2 mL) using 2,2,2-trifluoroacetic acid (0.074 mL, 0.97 mmol). This gave after workup and purification by reverse phase column chromatography [silica gel 26 g, Acetonitrile in 0.1% HCl in water as eluents, 0 to 50%] followed by lyophilization 1-(isobutyryloxy)ethyl 6-((cyclopropylmethyl)carbamoyl)-3-(2-((4-(N-((((2R,3S,4S)-3,4-dihydroxytetrahydrofuran-2-yl)methoxy)carbonyl)carbamimidoyl)phenyl)carbamoyl)-5-methoxy-4-vinylphenyl)picolinate (98e) (0.042 g, 0.053 mmol, 55.2% yield) as a white solid; $^1$H NMR (300 MHz, DMSO-d$_6$) δ 12.66-12.23 (m, 1H), 11.30-11.04 (m, 1H), 10.84-10.63 (m, 1H), 10.50-10.26 (m, 1H), 8.67-8.44 (m, 1H), 8.27-8.17 (m, 1H), 8.09-7.94 (m, 2H), 7.77 (s, 4H), 7.13-6.96 (m, 2H), 6.80-6.68 (m, 1H), 6.06 (d, J=17.9 Hz, 1H), 5.45 (d, J=11.4 Hz, 1H), 4.46 (d, J=11.8 Hz, 1H), 4.23 (dd, J=11.5, 5.3 Hz, 1H), 4.03 (t, J=3.9 Hz, 1H), 3.97-3.78 (m, 7H), 3.57 (ddd, J=11.6, 8.1, 4.3 Hz, 2H), 3.29-3.15 (m, 2H), 2.47-2.30 (m, 1H), 1.17 (s, 3H), 1.15-0.98 (m, 1H), 1.04-0.90 (m, 6H), 0.50-0.39 (m, 2H), 0.32-0.21 (m, 2H); MS (ES+) 788.7 (M+1).

Scheme 99

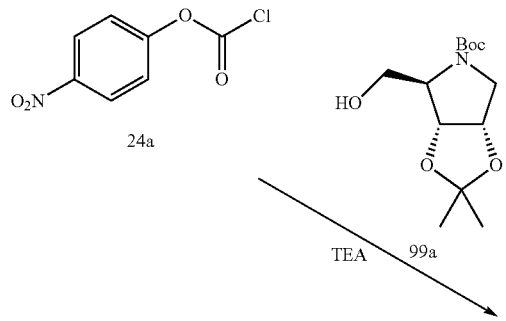

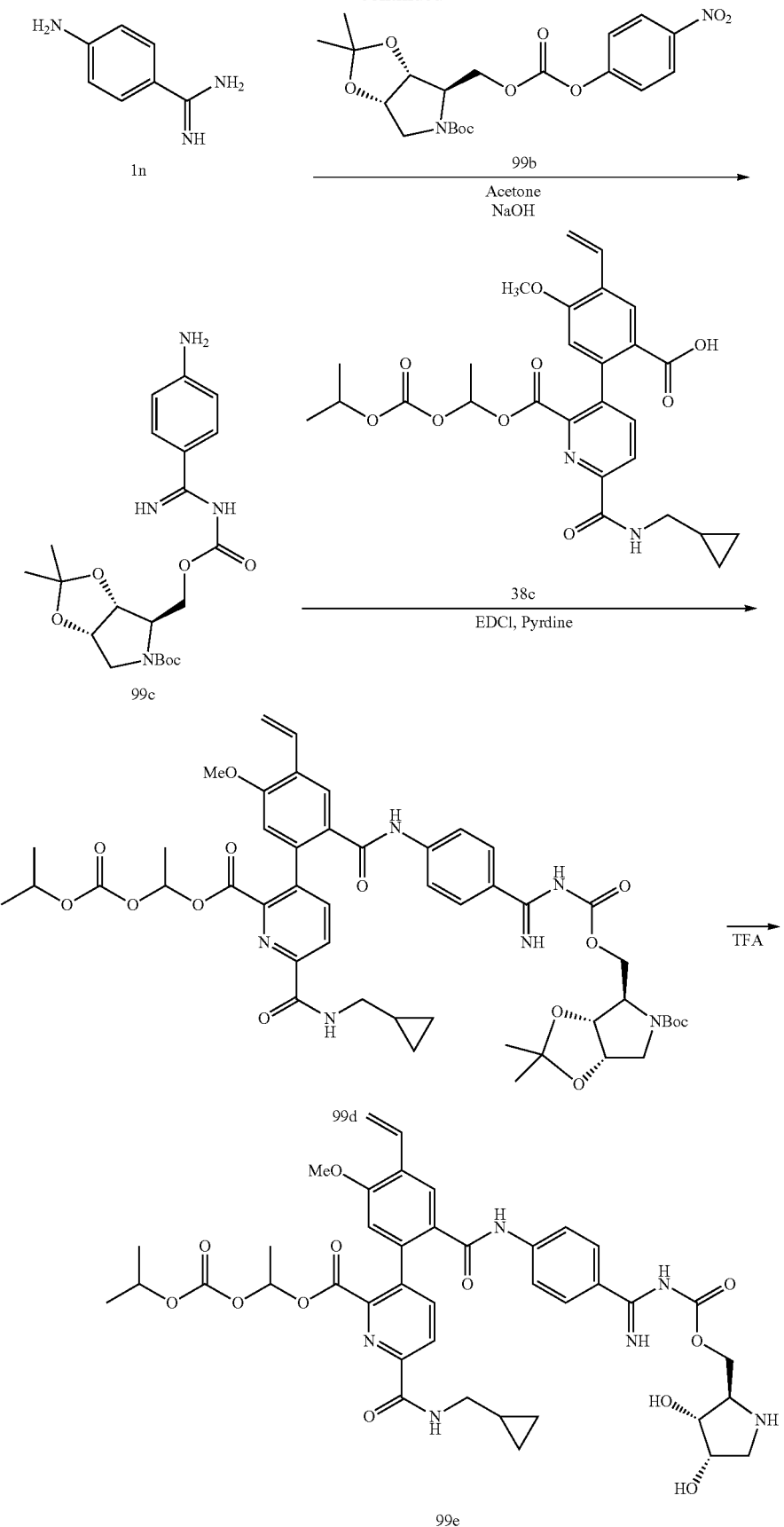

Preparation of 1-((isopropoxycarbonyl)oxy)ethyl 6-((cyclopropylmethyl)carbamoyl)-3-(2-((4-(N-((((2R,3R,4S)-3,4-dihydroxypyrrolidin-2-yl)methoxy)carbonyl)carbamimidoyl)phenyl)carbamoyl)-5-methoxy-4-vinylphenyl)picolinate (99e)

Step-1: Preparation of (3aR,4R,6aS)-tert-butyl 2,2-dimethyl-4-((((4-nitrophenoxy)carbonyl)oxy)methyl)dihydro-3aH-[1,3]dioxolo[4,5-c]pyrrole-5(4H)-carboxylate (99b)

Compound (99b) was prepared according to the procedure described in step 1 of scheme 24 from 4-nitrophenyl chloroformate (24a) (1.94 g, 9.33 mmol) in THF (30 mL) using (3 aR,4R,6aS)-tert-butyl 4-(hydroxymethyl)-2,2-dimethyldihydro-3aH-[1,3]dioxolo[4,5-c]pyrrole-5(4H)-carboxylate (99a) (2.55 g, 9.33 mmol, CAS #154905-24-5) and triethylamine (2.86 mL, 20.52 mmol). This gave after workup and purification by flash column chromatography [silica gel 80 g, eluting with ethyl acetate in hexanes from 0-30%](3 aR,4R,6aS)-tert-butyl 2,2-dimethyl-4-((((4-nitrophenoxy)carbonyl)oxy)methyl)dihydro-3aH-[1,3]dioxolo[4,5-c]pyrrole-5(4H)-carboxylate (99b) (1.79 g, 944% yield) as a yellow solid; $^1$H NMR (300 MHz, DMSO-d$_6$) δ 8.41-8.28 (m, 2H), 7.66-7.49 (m, 2H), 4.80-4.56 (m, 2H), 4.38-4.09 (m, 3H), 3.66 (t, J=11.9 Hz, 1H), 3.50-3.25 (m, 1H), 1.40 (s, 9H), 1.35 (s, 3H), 1.26 (s, 3H); MS (ES+): 461.4 (M+Na).

Step-2: Preparation (3aR,4R,6aS)-tert-butyl 4-(((((4-aminophenyl)(imino)methyl)carbamoyl)oxy)methyl)-2,2-dimethyldihydro-3aH-[1,3]dioxolo[4,5-c]pyrrole-5(4H)-carboxylate (99c)

Compound (99c) was prepared from 4-aminobenzimidamide dihydrochloride (1n) (1.01 g, 4.84 mmol) in acetone/water (40 mL) using sodium hydroxide (0.37 g, 9.29 mmol) and (3 aR,4R,6aS)-tert-butyl 4-(hydroxymethyl)-2,2-dimethyldihydro-3aH-[1,3]dioxolo[4,5-c]pyrrole-5(4H)-carboxylate (99a) (1.77 g, 4.04 mmol) according to the procedure reported in step 4 of scheme 23. This gave after workup and purification by flash column chromatography [silicagel, 80 g, eluting with ethyl acetate in hexanes from 0 to 100%](3 aR,4R,6aS)-tert-butyl 4-(((((4-aminophenyl)(imino)methyl)carbamoyl)oxy)methyl)-2,2-dimethyldihydro-3aH-[1,3]dioxolo[4,5-c]pyrrole-5(4H)-carboxylate (99c) (1.33 g, 3.06 mmol, 76% yield) as a yellow solid; $^1$H NMR (300 MHz, DMSO-d$_6$) δ 9.15 (s, 1H), 8.71 (s, 1H), 7.77 (d, J=8.5 Hz, 2H), 6.71-6.35 (m, 2H), 5.88 (s, 2H), 4.80-4.69 (m, 1H), 4.63 (t, J=6.6 Hz, 1H), 4.18-3.91 (m, 3H), 3.60 (t, J=13.8 Hz, 1H), 3.48-3.28 (m, 1H), 1.39 (d, J=5.4 Hz, 9H), 1.35 (s, 3H), 1.25 (s, 3H); MS (ES-): 433.5 (M-1).

Step-3: Preparation of (3aR,4R,6aS)-tert-butyl 4-(((((4-(2-(6-((cyclopropylmethyl)carbamoyl)-2-((1-((isopropoxycarbonyl)oxy)ethoxy)carbonyl)pyridin-3-yl)-4-methoxy-5-vinylbenzamido)phenyl)(imino)methyl)carbamoyl)oxy)methyl)-2,2-dimethyldihydro-3aH-[1,3]dioxolo[4,5-c]pyrrole-5(4H)-carboxylate (99d)

Compound (99d) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (1.00 g, 1.90) using EDCI (0.55 g, 2.85 mmol) and (3aR,4R,6aS)-tert-butyl 4-(((((4-aminophenyl)(imino)methyl)carbamoyl)oxy)methyl)-2,2-dimethyldihydro-3aH-[1,3]dioxolo[4,5-c]pyrrole-5(4H)-carboxylate (99c) (0.83 g, 1.90 mmol) in DMF (30 mL) and pyridine (10 mL) according to the procedure reported in step 4 of scheme 2. This gave after workup and purification by flash column chromatography [silica gel 40 g, eluting with methanol in DCM from 0-100%] (3aR,4R,6aS)-tert-butyl 4-(((((4-(2-(6-((cyclopropylmethyl)carbamoyl)-2-((1-((isopropoxycarbonyl)oxy)ethoxy)carbonyl)pyridin-3-yl)-4-methoxy-5-vinylbenzamido)phenyl)(imino)methyl)carbamoyl)oxy)methyl)-2,2-dimethyldihydro-3aH-[1,3]dioxolo[4,5-c]pyrrole-5(4H)-carboxylate (99d) (0.446 g, 0.473 mmol, 24.90% yield) as a white solid; $^1$H NMR (300 MHz, DMSO-d$_6$) δ 12.14 (s, 1H), 10.68-10.35 (m, 1H), 10.10 (s, 1H), 8.54-8.21 (m, 1H), 7.96 (d, J=8.0 Hz, 1H), 7.86-7.65 (m, 2H), 7.67-7.32 (m, 4H), 6.90-6.61 (m, 2H), 6.37 (q, J=5.3 Hz, 1H), 5.81 (d, J=17.8 Hz, 1H), 5.18 (d, J=11.5 Hz, 1H), 4.60-4.51 (m, 1H), 4.50-4.32 (m, 2H), 4.04 (s, 2H), 3.99-3.81 (m, 1H), 3.63 (s, 3H), 3.43-3.14 (m, 2H), 3.03-2.86 (m, 2H), 1.19-1.03 (m, 11H), 1.02-0.72 (m, 14H), 0.27-0.11 (m, 2H), 0.07--0.07 (m, 2H); MS (ES+): 943.9 (M+1); MS (ES-): 977.9 (M+Cl).

Step-4: Preparation of 1-((isopropoxycarbonyl)oxy)ethyl 6-((cyclopropylmethyl)carbamoyl)-3-(2-((4-(N-((((2R,3R,4S)-3,4-dihydroxypyrrolidin-2-yl)methoxy)carbonyl)carbamimidoyl)phenyl)carbamoyl)-5-methoxy-4-vinylphenyl)picolinate (99e)

Compound (99e) was prepared from (3aR,4R,6aS)-tert-butyl 4-(((((4-(2-(6-((cyclopropylmethyl)carbamoyl)-2-((1-((isopropoxycarbonyl)oxy)ethoxy)carbonyl)pyridin-3-yl)-4-methoxy-5-vinylbenzamido)phenyl)(imino)methyl)carbamoyl)oxy)methyl)-2,2-dimethyldihydro-3aH-[1,3]dioxolo[4,5-c]pyrrole-5(4H)-carboxylate (99d) (0.20 g, 0.22 mmol) in dichloromethane (10 mL) using 2,2,2-trifluoroacetic acid (0.33 mL, 4.31 mmol). This gave after workup and purification by reverse phase column chromatography [EZ-PREP, C-18 column, 40 g, eluting with 0.1% aq HCl in water and in acetonitrile from 0-50%] followed by lyophilization 1-((isopropoxycarbonyl)oxy)ethyl 6-((cyclopropylmethyl)carbamoyl)-3-(2-((4-(N-((((2R,3R,4S)-3,4-dihydroxypyrrolidin-2-yl)methoxy)carbonyl)carbamimidoyl)phenyl)carbamoyl)-5-methoxy-4-vinylphenyl)picolinate (99e) (0.029 mmol, 13% yield) as a white solid; $^1$H NMR (300 MHz, DMSO-d$_6$) δ 11.15-10.49 (m, 1H), 9.82 (bs, 1H, D$_2$O exchangeable), 9.44 (bs, 1H, D$_2$O exchangeable), 8.76-8.50 (m, 1H), 8.22 (d, J=8.0 Hz, 1H), 8.10-7.97 (m, 2H), 7.92-7.69 (m, 6H), 7.16-6.91 (m, 2H), 6.63 (q, J=5.3 Hz, 1H), 6.07 (d, J=17.9 Hz, 1H), 5.45 (d, J=11.5 Hz, 1H), 4.77-4.66 (m, 1H), 4.64-4.40 (m, 2H), 4.12 (s, 1H), 4.04-3.96 (m, 1H), 3.89 (s, 3H), 3.71-3.01 (m, 6H), 1.37-0.91 (m, 10H), 0.51-0.39 (m, 2H), 0.35-0.21 (m, 2H); MS (ES+): 803.6 (M+1); MS (ES-): 837.6 (M+Cl); Analysis calculated for: C$_{40}$H$_{46}$N$_6$O$_{12}$.3H$_2$O.2.5HCl: C, 50.68; H, 5.79; N, 8.86; found: C, 50.85; H, 5.70; N, 8.97.

Scheme 100
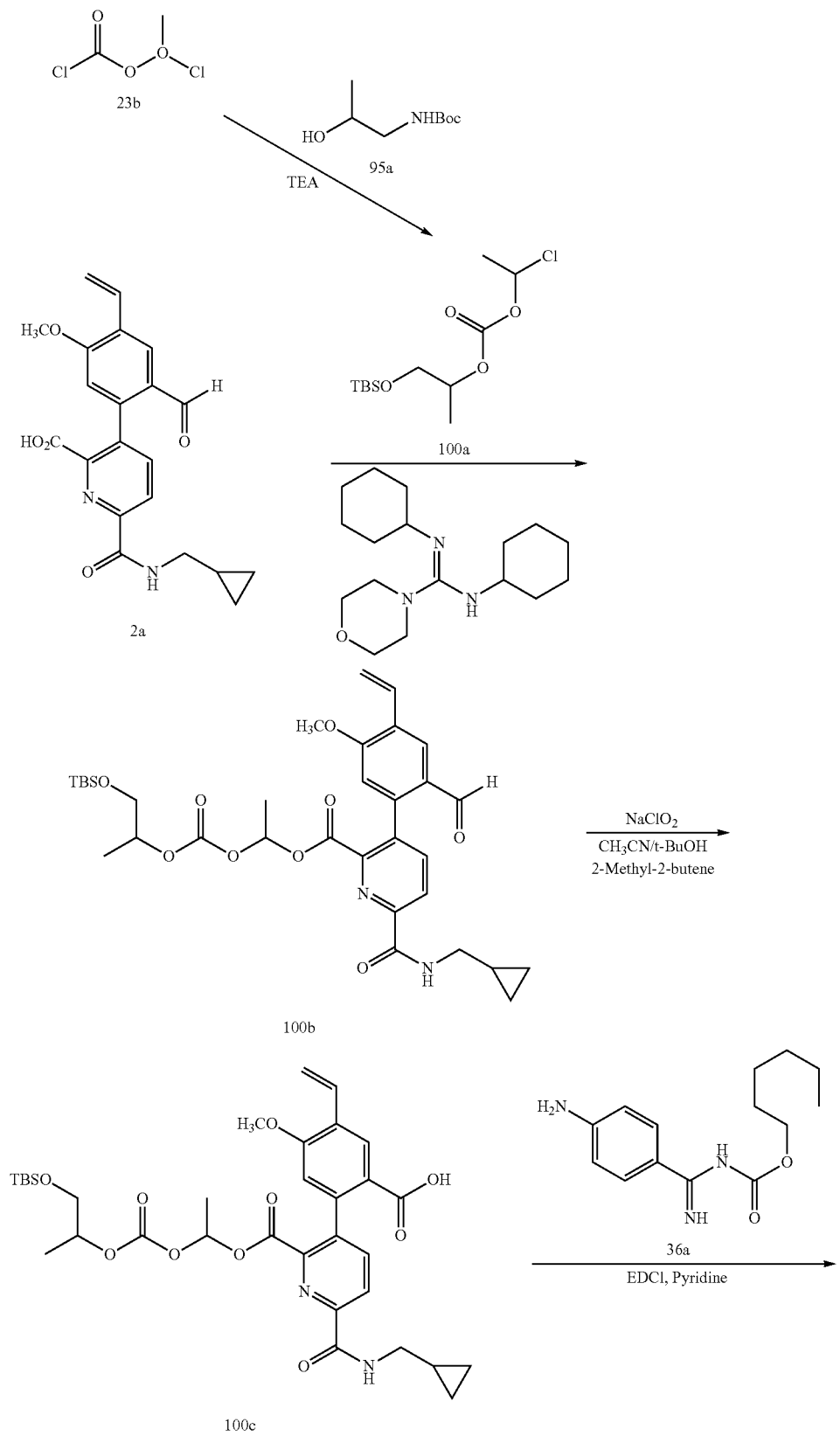

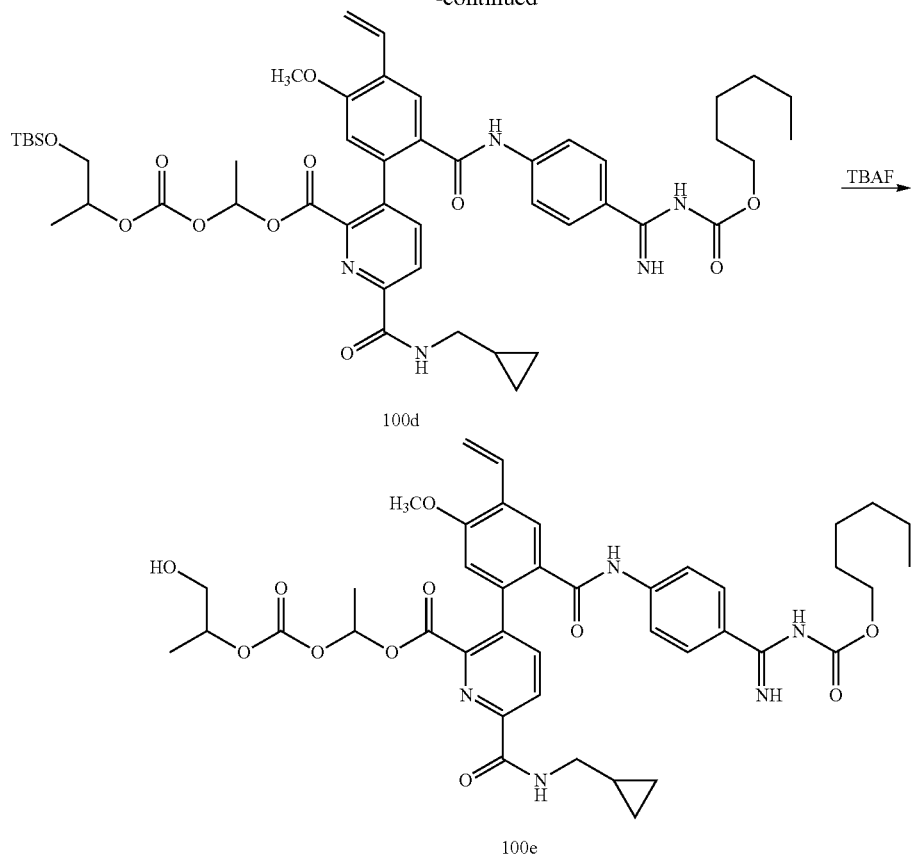

Preparation of 1-((((1-hydroxypropan-2-yl)oxy)carbonyl)oxy)ethyl 6-((cyclopropylmethyl)carbamoyl)-3-(2-((4-(N-((hexyloxy)carbonyl)carbamimidoyl) phenyl)carbamoyl)-5-methoxy-4-vinylphenyl) picolinate (100e)

Step-1: Preparation of 1-((tert-butyldimethylsilyl) oxy)propan-2-yl (1-chloroethyl) carbonate (100a)

Compound (100a) was prepared according to the procedure described in step 1 of scheme 88 from 1-((tert-butyldimethylsilyl)oxy)propan-2-ol (95a) (2.5 g, 13.13 mmol) and 1-chloroethyl carbonochloridate (23b) (1.417 mL, 13.13 mmol) in DCM (50 mL) using pyridine (1.2 mL). This gave after workup 1-((tert-butyldimethylsilyl)oxy)propan-2-yl (1-chloroethyl) carbonate (100a) (3.81 g, 98% yield) as a clear oil which was used such in next step without further purification. $^1$H NMR (300 MHz, DMSO-d$_6$) δ 6.60-6.31 (m, 1H), 4.90-4.55 (m, 1H), 3.78-3.47 (m, 2H), 1.71 (dd, J=5.7, 2.8 Hz, 3H), 1.16 (dd, J=6.5, 4.4 Hz, 3H), 0.85-0.78 (m, 9H), 0.02--0.02 (m, 6H).

Step-2: Preparation of 2,2,3,3,6-pentamethyl-8-oxo-4,7,9-trioxa-3-silaundecan-10-yl 6-((cyclopropylmethyl)carbamoyl)-3-(2-formyl-5-methoxy-4-vinylphenyl)picolinate (100b)

Compound (100b) was prepared according to the procedure reported in step 1 of scheme 8 from 6-(Cyclopropyl-methylcarbamoyl)-3-(2-formyl-5-methoxy-4-vinylphenyl) picolinic acid (2a) (2.09 g, 5.50 mmol) in DMF (50 mL) using N,N'-Dicyclohexyl-4-morpholinecarboxamidine (2.02 g, 6.88 mmol) and 1-((tert-butyldimethylsilyl)oxy)propan-2-yl (1-chloroethyl) carbonate (100a) (1.633 g, 5.50 mmol). This gave after workup and purification by flash column chromatography (silica gel 80 g, eluting with ethyl acetate/hexanes from 0-100%) 2,2,3,3,6-pentamethyl-8-oxo-4,7,9-trioxa-3-silaundecan-10-yl 6-((cyclopropylmethyl)carbamoyl)-3-(2-formyl-5-methoxy-4-vinylphenyl)picolinate (100b) (1.781 g, 51% yield) as a yellow wax; $^1$H NMR (300 MHz, DMSO-d$_6$) δ 9.71-9.64 (m, 1H), 8.80-8.53 (m, 1H), 8.30-8.22 (m, 1H), 8.18-7.98 (m, 2H), 7.13-6.81 (m, 2H), 6.74-6.41 (m, 1H), 5.99 (d, J=17.8 Hz, 1H), 5.43 (dd, J=11.3, 1.4 Hz, 1H), 4.81-4.52 (m, 2H), 4.01-3.79 (m, 3H), 3.70-3.48 (m, 1H), 3.23 (s, 2H), 1.33-0.97 (m, 7H), 0.90-0.64 (m, 9H), 0.51-0.39 (m, 2H), 0.36-0.23 (m, 2H), 0.10--0.15 (m, 6H); MS (ES-): 639.7 (M-1).

Step-3: Preparation of 2-(6-((cyclopropylmethyl) carbamoyl)-2-(3,7,10,10,11,11-hexamethyl-5-oxo-2,4,6,9-tetraoxa-10-siladodecan-1-oyl)pyridin-3-yl)-4-methoxy-5-vinylbenzoic acid (100c)

Oxidation of 2,2,3,3,6-pentamethyl-8-oxo-4,7,9-trioxa-3-silaundecan-10-yl 6-((cyclopropylmethyl)carbamoyl)-3-(2-formyl-5-methoxy-4-vinylphenyl)picolinate (100b) (1.7 g, 2.65 mmol) using the procedure as reported in step 11 of scheme 1 gave after workup 2-(6-((cyclopropylmethyl)carbamoyl)-2-(3,7,10,10,11,11-hexamethyl-5-oxo-2,4,6,9-tetraoxa-10-siladodecan-1-oyl)pyridin-3-yl)-4-methoxy-5-vinylbenzoic acid (100c) (1.719 g, 2.62 mmol, 99% yield) as a white solid. Compound was pure enough to continue to next step; $^1$H NMR (300 MHz, DMSO-d$_6$) δ 12.57 (s, 1H), 8.61 (s, 1H), 8.22 (d, J=8.0 Hz, 1H), 8.12 (s, 1H), 7.96 (d, J=8.0 Hz, 1H), 7.15-6.77 (m, 2H), 6.69-6.50 (m, 1H), 5.91 (d, J=17.8 Hz, 1H), 5.39 (d, J=11.3 Hz, 1H), 4.78-4.59 (m, 1H), 3.85 (s, 3H), 3.70-3.49 (m, 1H), 3.30-3.14 (m, 2H), 1.22-1.08 (m, 8H), 0.83 & 0.77 (2s, 9H), 0.52-0.38 (m, 2H), 0.33-0.22 (m, 2H), 0.04--0.07 (m, 6H); MS (ES+): 679.7 (M+1); MS (ES−): 655.7 (M−1).

Step-4: Preparation of 2,2,3,3,6-pentamethyl-8-oxo-4,7,9-trioxa-3-silaundecan-10-yl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (100d)

Compound (100d) was prepared from 2-(6-((cyclopropylmethyl)carbamoyl)-2-(3,7,10,10,11,11-hexamethyl-5-oxo-2,4,6,9-tetraoxa-10-siladecan-1-oyl)pyridin-3-yl)-4-methoxy-5-vinylbenzoic acid (100c) (1.00 g, 1.52 mmol) using EDCI (0.44 g, 2.28 mmol) and hexyl ((4-aminophenyl)(imino)methyl)carbamate (36a) (0.40 g, 1.52 mmol) in DMF (15 mL) and Pyridine (5 mL) according to the procedure reported in step 4 of scheme 2. This gave after workup 2,2,3,3,6-pentamethyl-8-oxo-4,7,9-trioxa-3-silaundecan-10-yl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (100d) (1.3 g, 95% yield) as a white solid, which was used as such in the next step; MS (ES+): 902.9 (M+1); MS (ES−): 937.1 (M+Cl).

Step-5: Preparation of 1-((((1-hydroxypropan-2-yl)oxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (100e)

To a stirred solution of 2,2,3,3,6-pentamethyl-8-oxo-4,7,9-trioxa-3-silaundecan-10-yl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (100d) (1.25 g, 1.39 mmol) in THF (30 mL) at 0° C. was added TBAF (0.54 g, 2.078 mmol) and warmed to room temperature over a period of 2 h. The residue was diluted with aqueous NH$_4$Cl (75 mL) and extracted with ethyl acetate (2×150 mL). The combined organic layers were dried, filtered, evaporated to dryness. The residue obtained was purified by flash column chromatography [silica gel 24 g, eluting with ethyl acetate in hexanes from 0-100%] to furnish to furnish 1-((((1-hydroxypropan-2-yl)oxy)carbonyl)oxy)ethyl 6-((cyclopropylmethyl)carbamoyl)-3-(2-((4-(N-((hexyloxy)carbonyl)carbamimidoyl)phenyl)carbamoyl)-5-methoxy-4-vinylphenyl)picolinate (100e) (0.028 g, 3% yield) as a white solid; $^1$H NMR (300 MHz, DMSO-d$_6$) δ 10.64-10.33 (m, 1H), 9.00 (bs, 2H, D$_2$O exchangeable), 8.76-8.46 (m, 1H), 8.26-8.20 (m, 1H), 8.08-7.88 (m, 4H), 7.71-7.56 (m, 2H), 7.16-6.90 (m, 2H), 6.79-6.43 (m, 1H), 6.05 (dd, J=17.7, 1.5 Hz, 1H), 5.44 (d, J=11.5 Hz, 1H), 4.90 (t, J=5.8 Hz, 1H, D$_2$O exchangeable), 4.70-4.50 (m, 1H), 4.12-3.94 (m, 2H), 3.95-3.78 (m, 3H), 3.43-3.35 (m, 1H), 3.27-3.15 (m, 2H), 1.67-1.49 (m, 2H), 1.41-1.01 (m, 12H), 0.92-0.75 (m, 5H), 0.54-0.37 (m, 2H), 0.33-0.20 (m, 2H); MS (ES+): 788.6 (M+1), 810.8 (M+Na); Analysis calculated for C$_{41}$H$_{49}$N$_5$O$_{11}$.1.25H$_2$O: C, 60.77; H, 6.41; N, 8.64. Found: C, 60.87; H, 6.89; N, 8.30.

Scheme 101

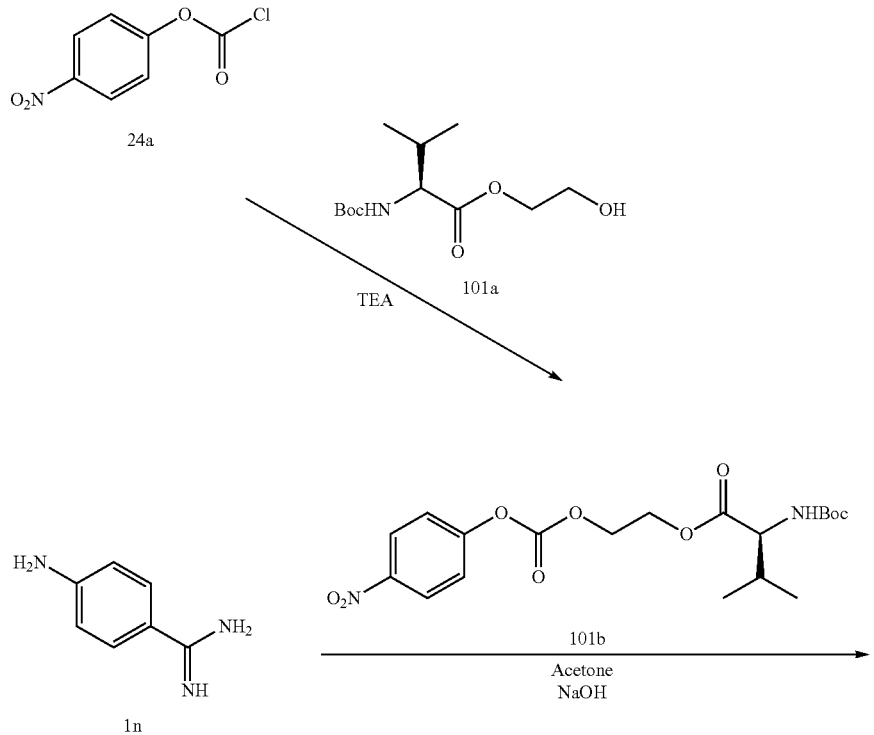

-continued
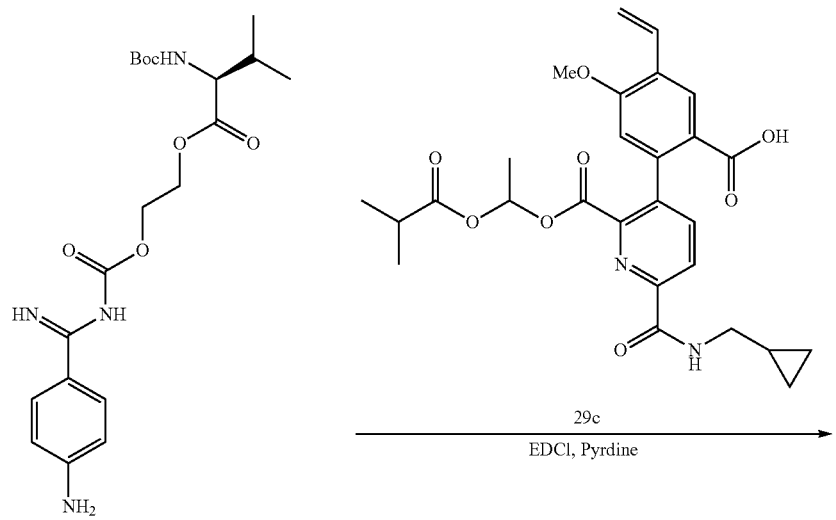
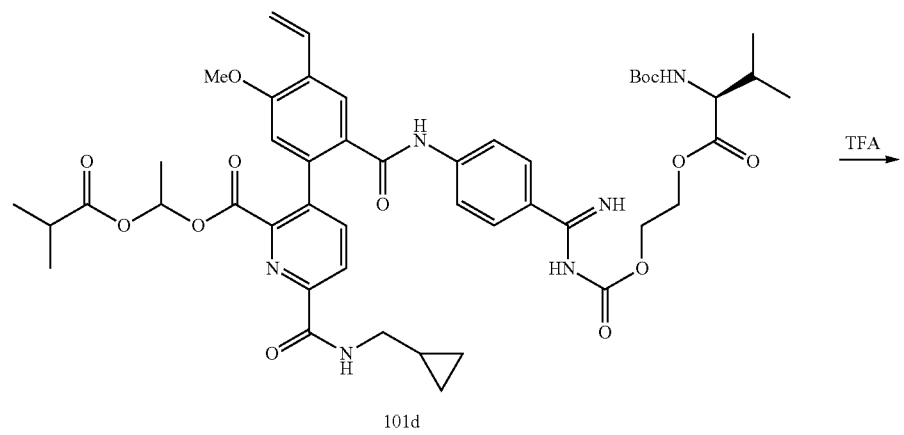
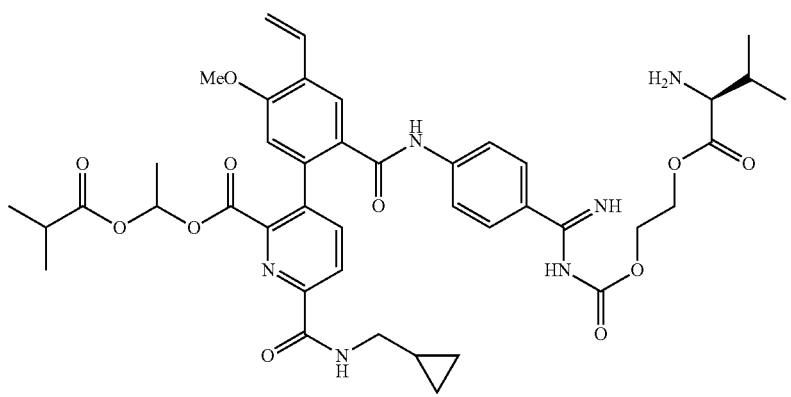

Preparation of 1-(isobutyryloxy)ethyl 3-(2-((4-(N-((2-(((S)-2-amino-3-methylbutanoyl)oxy)ethoxy) carbonyl)carbamimidoyl)phenyl)carbamoyl)-5-methoxy-4-vinylphenyl)-6-((cyclopropylmethyl) carbamoyl)picolinate (101e)

Step-1: Preparation of (S)-2-(((4-nitrophenoxy)carbonyl)oxy)ethyl 2-((tert-butoxycarbonyl)amino)-3-methylbutanoate (101b)

Compound (101b) was prepared according to the procedure described in step 1 of scheme 24 from 4-nitrophenyl chloroformate (24a) (1.27 g, 6.31 mmol) in THF (50 mL) using (S)-2-hydroxyethyl 2-((tert-butoxycarbonyl)amino)-3-methylbutanoate (101a) (1.5 g, 5.74 mmol, Prepared according to the literature procedure described by Albrecht, Wolfgang et al; in PCT Int. Appl, 2014096425) and triethylamine (3.20 mL, 22.96 mmol). This gave after workup (S)-2-(((4-nitrophenoxy)carbonyl)oxy)ethyl 2-((tert-butoxycarbonyl)amino)-3-methylbutanoate (101b) (2.30 g, 94% yield) as a brown syrup which was used as such in next step without further purification; MS (ES+): 449.5 (M+Na).

Step-2: Preparation of (S)-2-((((4-aminophenyl) (imino)methyl)carbamoyl)oxy)ethyl 2-((tert-butoxycarbonyl)amino)-3-methylbutanoate (101c)

Compound (101c) was prepared from 4-aminobenzimidamide dihydrochloride (1n) (1.45 g, 6.99 mmol) in acetone (30 mL), using NaOH solution (1 N solution, 14.8 mL, 14.8 mmol) and a solution of (S)-2-(((4-nitrophenoxy)carbonyl) oxy)ethyl 2-((tert-butoxycarbonyl)amino)-3-methylbutanoate (101b) (2.98 g, 6.99 mmol) in acetone (30 mL) according to the procedure reported in step 4 of scheme 23. This gave after workup and purification by flash column chromatography (silica gel, 40 g eluting with ethyl acetate and hexanes 0 to 100%) (S)-2-((((4-aminophenyl)(imino)methyl)carbamoyl)oxy)ethyl 2-((tert-butoxycarbonyl)amino)-3-methylbutanoate (101c) (1.11 g, 38% yield) as a brown solid; $^1$H NMR (300 MHz, DMSO-$d_6$) δ 9.13 (s, 1H, $D_2O$ exchangeable), 8.69 (s, 1H, $D_2O$ exchangeable), 7.75 (d, J=8.6 Hz, 2H), 6.66-6.45 (m, 2H), 5.87 (s, 2H, $D_2O$ exchangeable), 4.25 (d, J=40.7 Hz, 4H), 3.85 (dd, J=8.1, 6.3 Hz, 1H), 1.37 (s, 9H), 0.88 (s, 3H), 0.85 (s, 3H); MS (ES+) 423.6 (M+1), (ES−) 457.7 (M+Cl).

Step-3: Preparation of 1-(isobutyryloxy)ethyl 6-((cyclopropylmethyl)carbamoyl)-3-(2-((4-(N—((S)-7-isopropyl-11,11-dimethyl-6,9-dioxo-2,5,10-trioxa-8-azadodecan-1-oyl)carbamimidoyl)phenyl) carbamoyl)-5-methoxy-4-vinylphenyl)picolinate (101d)

Compound (101d) was prepared from 2-(6-((cyclopropylmethyl)carbamoyl)-2-((1-(isobutyryloxy)ethoxy)carbonyl) pyridin-3-yl)-4-methoxy-5-vinylbenzoic acid (29c) (1.21 g, 2.36 mmol) using EDCI (0.545 g, 2.84 mmol) and (S)-2-((((4-aminophenyl)(imino)methyl)carbamoyl)oxy)ethyl 2-((tert-butoxycarbonyl)amino)-3-methylbutanoate (101c) (1.0 g, 2.37 mmol) in DMF (5 mL) and Pyridine (5 mL) according to the procedure reported in step 4 of scheme 2. This gave after workup and purification by flash column chromatography [silica gel 40 g, eluting with EtOAc/MeOH (9:1) in hexane from 0-100%] of 1-(isobutyryloxy)ethyl 6-((cyclopropylmethyl)carbamoyl)-3-(2-((4-(N—((S)-7-isopropyl-11,11-dimethyl-6,9-dioxo-2,5,10-trioxa-8-azadodecan-1-oyl)carbamimidoyl)phenyl)carbamoyl)-5-methoxy-4-vinylphenyl)picolinate (101d) (0.41 g, 19% yield) as a yellow solid; $^1$H NMR (300 MHz, DMSO-$d_6$) δ 10.51 (d, J=23.9 Hz, 1H, $D_2O$ exchangeable), 9.32-9.09 (m, 1H, $D_2O$ exchangeable), 8.99 (s, 1H, $D_2O$ exchangeable), 8.56 (d, J=26.9 Hz, 1H), 8.22 (d, J=8.0 Hz, 1H), 8.09-7.83 (m, 5H), 7.70 (d, J=8.7 Hz, 1H), 7.18 (d, J=8.1 Hz, 1H), 7.10-6.96 (m, 2H), 6.74 (s, 1H), 6.05 (dd, J=17.8, 1.5 Hz, 1H), 5.49-5.37 (m, 1H), 4.42-4.30 (m, 1H), 4.31-4.07 (m, 3H), 3.88 (d, J=4.8 Hz, 3H), 3.23 (s, 2H), 2.43 (d, J=1.7 Hz, 1H), 2.13-1.88 (m, 1H), 1.37 (d, J=2.1 Hz, 9H), 1.30 (s, OH), 1.22-1.13 (m, 3H), 1.11 (d, J=6.8 Hz, 1H), 1.04-0.92 (m, 6H), 0.91-0.78 (m, 6H), 0.51-0.40 (m, 2H), 0.33-0.23 (m, 2H); MS (ES+) 915.9 (M+1), 937.8 (M+Na).

Step-4: Preparation of 1-(isobutyryloxy)ethyl 3-(2-((4-(N-((2-(((S)-2-amino-3-methylbutanoyl)oxy) ethoxy)carbonyl)carbamimidoyl)phenyl)carbamoyl)-5-methoxy-4-vinylphenyl)-6-((cyclopropylmethyl) carbamoyl)picolinate (101e)

Compound (101e) was prepared from 1-(isobutyryloxy) ethyl 6-((cyclopropylmethyl)carbamoyl)-3-(2-((4-(N—((S)-7-isopropyl-11,11-dimethyl-6,9-dioxo-2,5,10-trioxa-8-azadodecan-1-oyl)carbamimidoyl)phenyl)carbamoyl)-5-methoxy-4-vinylphenyl)picolinate (101d) (0.39 g, 0.43 mmol) in dichloromethane (10 mL) using 2,2,2-trifluoroacetic acid (0.65 mL, 8.52 mmol) according to the procedure reported in Step-4 of scheme 8. This gave after workup and purification by flash column chromatography (C18, 100 g) eluting with 0.1% HCl and acetonitrile followed by lyophilization 1-(isobutyryloxy)ethyl-3-(2-((4-(N-((2-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinate hydrochloride (19e) (0.075 g, 22% yield) as a white solid; $^1$H NMR (300 MHz, DMSO-$d_6$) δ 12.51 (s, 1H, $D_2O$ exchangeable), 11.30 (s, 1H, $D_2O$ exchangeable), 10.81 (d, J=13.2 Hz, 1H), 10.41 (s, 1H, $D_2O$ exchangeable), 8.65 (s, 3H, $D_2O$ exchangeable), 8.62-8.47 (m, 1H, $D_2O$ exchangeable), 8.22 (d, J=8.0 Hz, 1H), 8.12-7.93 (m, 2H), 7.90-7.64 (m, 4H), 7.15-6.89 (m, 2H), 6.82-6.63 (m, 1H), 6.09 (d, J=17.7 Hz, 1H), 5.45 (d, J=11.4 Hz, 1H), 4.71-4.26 (m, 4H), 3.94-3.84 (m, 4H), 3.32-3.09 (m, 2H), 2.50-2.34 (m, 1H), 2.31-2.10 (m, 1H), 1.23-1.14 (m, 3H), 1.14-1.09 (m, 1H), 1.10-0.83 (m, 12H), 0.53-0.39 (m, 2H), 0.33-0.21 (m, 2H); MS (ES+) 815.8 (M+1).

Scheme 102
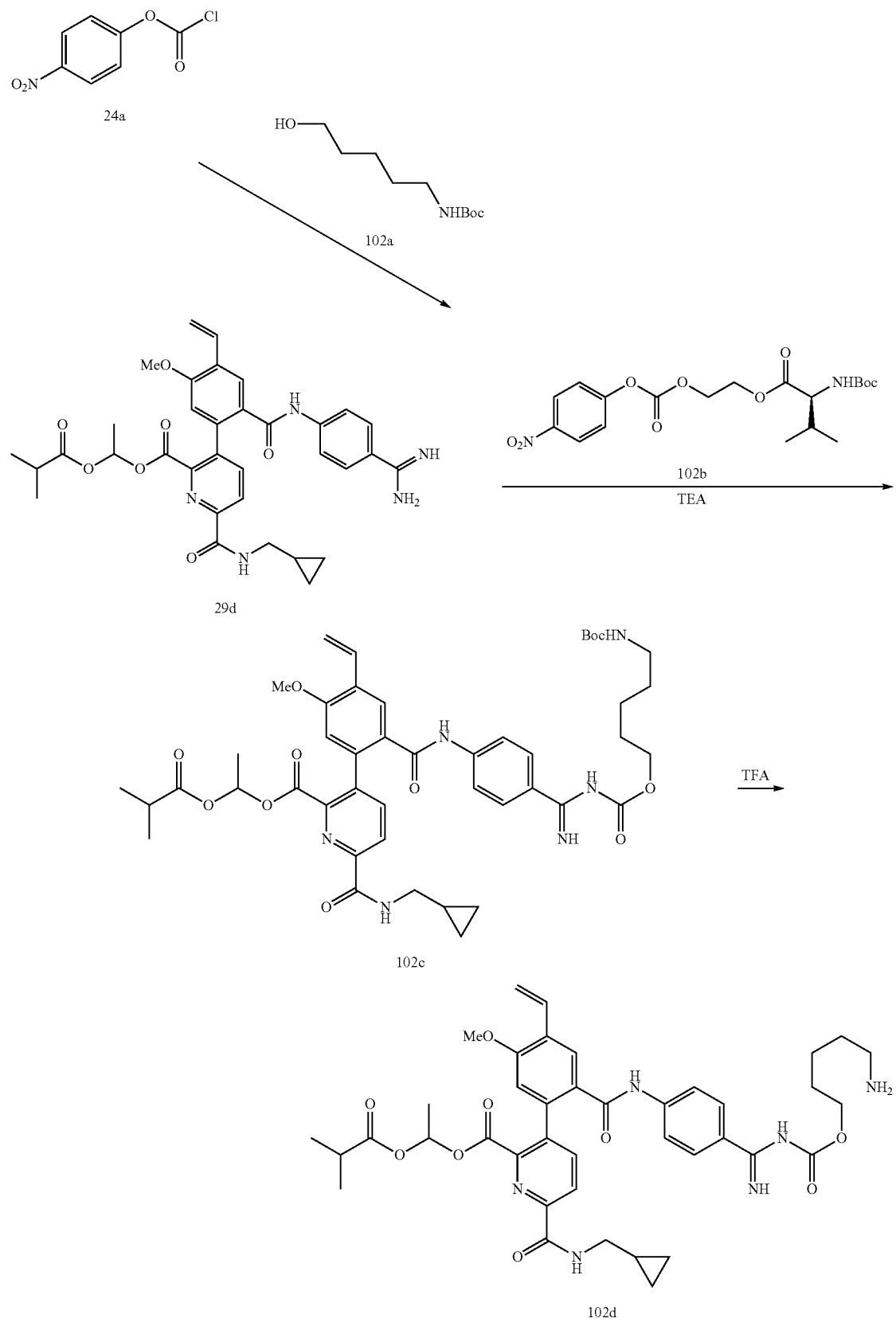

Preparation of 1-(isobutyryloxy)ethyl 3-(2-((4-(N-(((5-aminopentyl)oxy)carbonyl)carbamimidoyl)phenyl)carbamoyl)-5-methoxy-4-vinylphenyl)-6-((cyclopropylmethyl)carbamoyl)picolinate (102d)

Step-1: Preparation of tert-butyl (5-(((4-nitrophenoxy)carbonyl)oxy)pentyl)carbamate (102b)

Compound (102b) was prepared according to the procedure described in step 1 of scheme 24 from 4-nitrophenyl chloroformate (24a)(1.98 g, 9.84 mmol) in THF (30 mL) using tert-butyl (5-hydroxypentyl)carbamate (102a) (2.0 g, 9.84 mmol) and triethylamine (4.11 mL, 29.5 mmol). This gave after workup tert-butyl (5-(((4-nitrophenoxy)carbonyl)oxy)pentyl)carbamate (102b) (1.2 g, 33% yield) as a brown syrup which was used as such in next step without further purification; $^1$H NMR (300 MHz, DMSO-d$_6$) δ 8.39-8.23 (m, 2H), 7.64-7.37 (m, 2H), 6.83 (td, J=15.6, 14.0, 5.8 Hz, 1H), 4.24 (t, J=6.5 Hz, 2H), 2.90 (dq, J=12.7, 6.5 Hz, 2H), 1.37 (d, J=1.1 Hz, 15H); MS (ES−) 403.5 (M+Cl).

Step-2: Preparation of 1-(isobutyryloxy)ethyl 3-(2-((4-(N-(((5-((tert-butoxycarbonyl)amino)pentyl)oxy)carbonyl)carbamimidoyl)phenyl)carbamoyl)-5-methoxy-4-vinylphenyl)-6-((cyclopropylmethyl)carbamoyl)picolinate (102c)

Compound (102c) was prepared according to the procedure described in step 1 of scheme 24 from 1-(isobutyryloxy)ethyl 3-(2-((4-carbamimidoylphenyl)carbamoyl)-5-methoxy-4-vinylphenyl)-6-((cyclopropylmethyl)carbamoyl)picolinate (29d) (0.5 g, 0.797 mmol) in DMF using tert-butyl (5-(((4-nitrophenoxy)carbonyl)oxy)pentyl)carbamate (102b) (0.44 g, 1.20 mmol) and triethylamine (0.33 mL, 2.39 mmol). This gave after workup and purification by flash column chromatography [(silica gel, 12 g eluting with a 9:1 mixture of ethyl acetate and methanol in hexanes (0 to 100%)] 1-(isobutyryloxy)ethyl 3-(2-((4-(N-(((5-((tert-butoxycarbonyl)amino)pentyl)oxy)carbonyl)carbamimidoyl)phenyl)carbamoyl)-5-methoxy-4-vinylphenyl)-6-((cyclopropylmethyl)carbamoyl)picolinate (102c) (74 mg, 11% yield) as a white solid; MS (ES+) 857.6 (M+1).

Step-3: Preparation of 1-(isobutyryloxy)ethyl 3-(2-((4-(N-(((5-aminopentyl)oxy)carbonyl)carbamimidoyl)phenyl)carbamoyl)-5-methoxy-4-vinylphenyl)-6-((cyclopropylmethyl)carbamoyl)picolinate (102d)

Compound (102d) was prepared from 1-(isobutyryloxy)ethyl 3-(2-((4-(N-(((5-((tert-butoxycarbonyl)amino)pentyl)oxy)carbonyl)carbamimidoyl)phenyl)carbamoyl)-5-methoxy-4-vinylphenyl)-6-((cyclopropylmethyl)carbamoyl)picolinate (102c) (0.07 g, 0.082 mmol) in dichloromethane (5 mL) using 2,2,2-trifluoroacetic acid (0.126 mL, 1.63 mmol) according to the procedure reported in Step-4 of scheme 8. This gave after workup and purification by flash column chromatography (C18, 100 g) eluting with 0.1% aqueous HCl and acetonitrile followed by lyophilization 1-(isobutyryloxy)ethyl 3-(2-((4-(N-(((5-aminopentyl)oxy)carbonyl)carbamimidoyl)phenyl)carbamoyl)-5-methoxy-4-vinylphenyl)-6-((cyclopropylmethyl)carbamoyl)picolinate hydrochloride (102d) (0.037 g, 55% yield) as a white solid; $^1$H NMR (300 MHz, DMSO-d$_6$) δ 10.73 (d, J=17.1 Hz, 1H), 8.58 (d, J=24.9 Hz, 1H), 8.22 (d, J=8.1 Hz, 1H), 8.13-7.63 (m, 9H, 3H D$_2$O exchangeable), 7.12-6.94 (m, 2H), 6.74 (d, J=5.5 Hz, 1H), 6.07 (d, J=17.9 Hz, 1H), 5.45 (d, J=11.5 Hz, 1H), 4.25 (s, 2H), 3.89 (s, 3H), 3.23 (m, 2H), 2.77 (m, 2H), 2.44 (m, 1H), 1.77-1.52 (m, 4H), 1.43 (m, 2H), 1.18 (s, 3H), 1.15-1.03 (m, 1H), 1.05-0.88 (m, 6H), 0.49-0.39 (m, 2H), 0.32-0.22 (m, 2H); MS (ES+) 757.8 (M+1), (ES−) 791.9 (M+Cl); Analysis calculated for; C$_{40}$H$_{48}$N$_6$O$_9$.2HCl.3.5H$_2$O: C, 53.81; H, 6.43; N, 9.41; found: C, 53.34; H, 6.41; N, 9.38.

Scheme 103

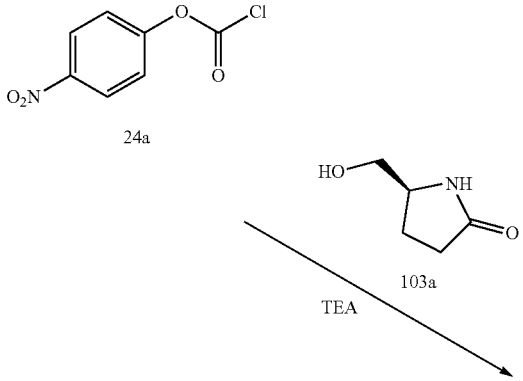

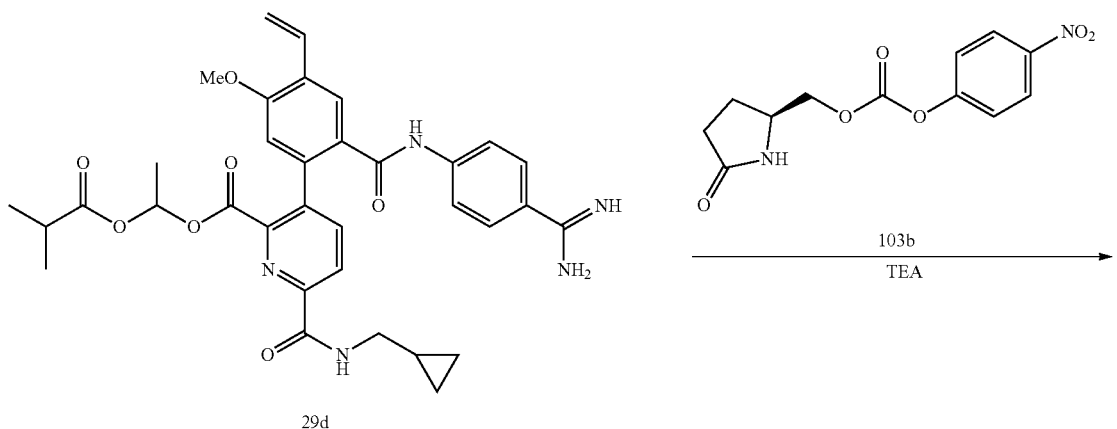

Preparation of 1-(isobutyryloxy)ethyl 6-((cyclopropylmethyl)carbamoyl)-3-(5-methoxy-2-((4-(N—((((S)-5-oxopyrrolidin-2-yl)methoxy)carbonyl)carbamimidoyl)phenyl)carbamoyl)-4-vinylphenyl) picolinate (103c)

Step-1: Preparation of (S)-4-nitrophenyl ((5-oxopyrrolidin-2-yl)methyl) carbonate (103b)

Compound (103b) was prepared according to the procedure described in step 1 of scheme 24 from 4-nitrophenyl chloroformate (24a) (0.88 g, 4.34 mmol) in THF (20 mL) using (S)-5-(hydroxymethyl)pyrrolidin-2-one (103a) (0.5 g, 4.34 mmol) and triethylamine (0.6 mL, 4.34 mmol). This gave after workup (S)-4-nitrophenyl ((5-oxopyrrolidin-2-yl)methyl) carbonate (103b) (1.1 g, 3.93 mmol, 90% yield) as pasty mass which was used as such in next step without purification; $^1$H NMR (300 MHz, DMSO-d$_6$) δ 8.37-8.28 (m, 2H), 7.91 (s, 1H), 7.62-7.52 (m, 2H), 4.20 (d, J=5.3 Hz, 2H), 3.94-3.81 (m, 1H), 2.25-2.02 (m, 3H), 1.88-1.63 (m, 1H).

Step-2: Preparation 1-(isobutyryloxy)ethyl 6-((cyclopropylmethyl)carbamoyl)-3-(5-methoxy-2-((4-(N—((((S)-5-oxopyrrolidin-2-yl)methoxy)carbonyl)carbamimidoyl)phenyl)carbamoyl)-4-vinylphenyl) picolinate (103c)

Compound (103c) was prepared according to the procedure described in step 1 of scheme 24 from 1-(isobutyryloxy)ethyl 3-(2-(4-carbamimidoylphenylcarbamoyl)-5-methoxy-4-vinylphenyl)-6-(cyclopropylmethylcarbamoyl) picolinate (29d) (0.4 g, 0.637 mmol) in DMF (3 mL) using TEA (0.178 mL, 1.28 mmol) and (S)-4-nitrophenyl ((5-oxopyrrolidin-2-yl)methyl) carbonate (103b) (0.27 g, 0.96 mmol). This gave after workup and purification by flash column chromatography [silica gel 12 g, MeOH-EtOAc (9:1) in hexanes 0 to 100% as eluents] 1-(isobutyryloxy) ethyl 6-((cyclopropylmethyl)carbamoyl)-3-(5-methoxy-2-((4-(N—((((S)-5-oxopyrrolidin-2-yl)methoxy)carbonyl)carbamimidoyl)phenyl)carbamoyl)-4-vinylphenyl)picolinate (103c) (0.065 g, 13% yield) as a white powder; $^1$H NMR (300 MHz, DMSO-d$_6$) δ 10.63-10.41 (m, 1H), 9.38-8.88 (m, 2H), 8.68-8.45 (m, 1H), 8.22 (d, J=8.0 Hz, 1H), 8.06-7.89 (m, 3H), 7.80 (s, 1H), 7.77-7.60 (m, 3H), 7.12-6.96 (m, 2H), 6.80-6.69 (m, 1H), 6.10-6.00 (m, 1H), 5.48-5.40 (m, 1H), 4.05-3.88 (m, 2H), 3.88 (s, 3H), 3.82-3.72 (m, 1H), 3.29-3.16 (m, 2H), 2.78-1.99 (m, 4H), 1.86-1.70 (m, 1H), 1.17 (d, J=5.4 Hz, 3H), 1.16-1.03 (m, 1H), 1.05-0.92 (m, 6H), 0.51-0.39 (m, 2H), 0.32-0.23 (m, 2H); MS (ES+) 769.7 (M+1); Analysis calculated for $C_{40}H_{44}N_6O_{10} \cdot 2H_2O$: C, 59.69; H, 6.01; N, 10.44; found: C, 59.61; H, 5.82; N, 10.42.

temperature, diluted with water (20 mL), acidified with 1 N HCl and extracted with ethyl acetate (2×50 mL). The combined organic layers were washed with brine (50 mL), dried, filtered and evaporated in vacuum. The residue obtained was purified by flash column chromatography [EZ-PREP, C-18 column, 50 g, eluting with 0.1% aq. HCl in water and in acetonitrile from 0-50%], and lyophilized to Scheme 104

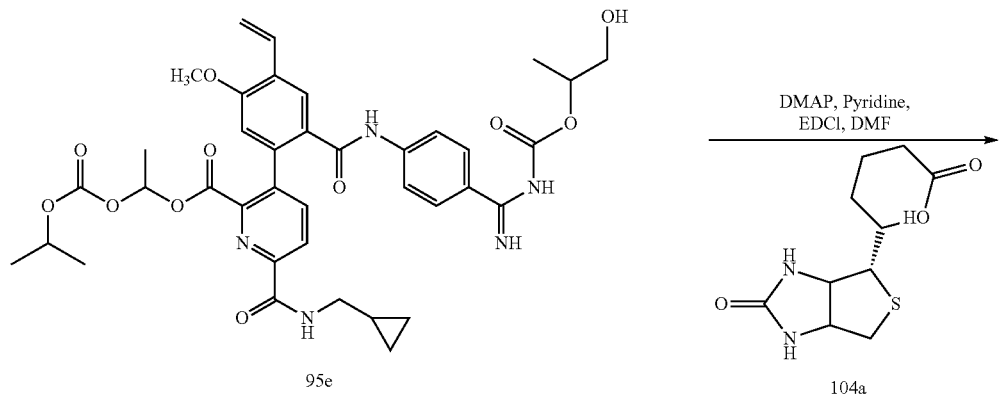

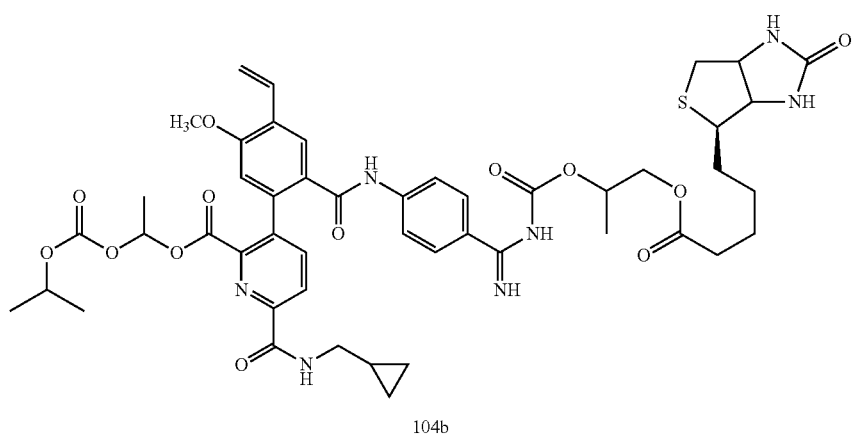

Preparation of 1-((isopropoxycarbonyl)oxy)ethyl 6-((cyclopropylmethyl)carbamoyl)-3-(5-methoxy-2-((4-(N-(((1-((5-((4R)-2-oxohexahydro-1H-thieno[3,4-d]imidazol-4-yl)pentanoyl)oxy)propan-2-yl)oxy)carbonyl)carbamimidoyl)phenyl)carbamoyl)-4-vinylphenyl)picolinate (104b)

To a solution of 1-(isopropoxycarbonyloxy)ethyl 6-(cyclopropylmethylcarbamoyl)-3-(2-(4-(N-((1-hydroxypropan-2-yloxy)carbonyl)carbamimidoyl)phenylcarbamoyl)-5-methoxy-4-vinylphenyl)picolinate (95e) (0.13 g, 0.178 mmol) and 5-((4S)-2-oxohexahydro-1H-thieno[3,4-d]imidazol-4-yl)pentanoic acid D(+) (biotin) (104a) (0.065 g, 0.27 mmol) in DMF (6 mL) was added DMAP (4.36 mg, 0.036 mmol), pyridine (2 mL) and EDCI (0.051 g, 0.268 mmol). The reaction mixture was stirred overnight at room furnish 1-((isopropoxycarbonyl)oxy)ethyl 6-((cyclopropylmethyl)carbamoyl)-3-(5-methoxy-2-((4-(N-(((1-((5-((4R)-2-oxohexahydro-1H-thieno[3,4-d]imidazol-4-yl)pentanoyl)oxy)propan-2-yl)oxy)carbonyl)carbamimidoyl)phenyl)carbamoyl)-4-vinylphenyl)picolinate (104b) (0.019 g, 0.020 mmol, 11% yield) as a white solid; $^1$H NMR (300 MHz, DMSO-$d_6$) δ 12.4 (bs, 1H, $D_2O$ exchangeable), 10.84-10.48 (m, 1H), 10.2 (bs, 1H, $D_2O$ exchangeable), 8.77-8.41 (m, 1H), 8.31-8.11 (m, 1H), 8.10-7.88 (m, 2H), 7.89-7.55 (m, 5H), 7.18-6.86 (m, 2H), 6.71-6.55 (m, 1H), 6.52-6.22 (m, 2H, $D_2O$ exchangeable), 6.05 (d, J=17.8 Hz, 1H), 5.44 (d, J=11.0 Hz, 1H), 5.14 (s, 1H), 4.71 (s, 1H), 4.47-4.04 (m, 4H), 3.88 (d, J=5.1 Hz, 3H), 3.32-2.95 (m, 3H), 2.77 (s, 1H), 2.55-2.45 (m, 2H), 2.43-2.17 (m, 2H), 1.70-0.93 (m, 17H), 0.54-0.36 (m, 2H), 0.34-0.17 (m, 2H); MS (ES+): 972.7 (M+1).

Scheme 105

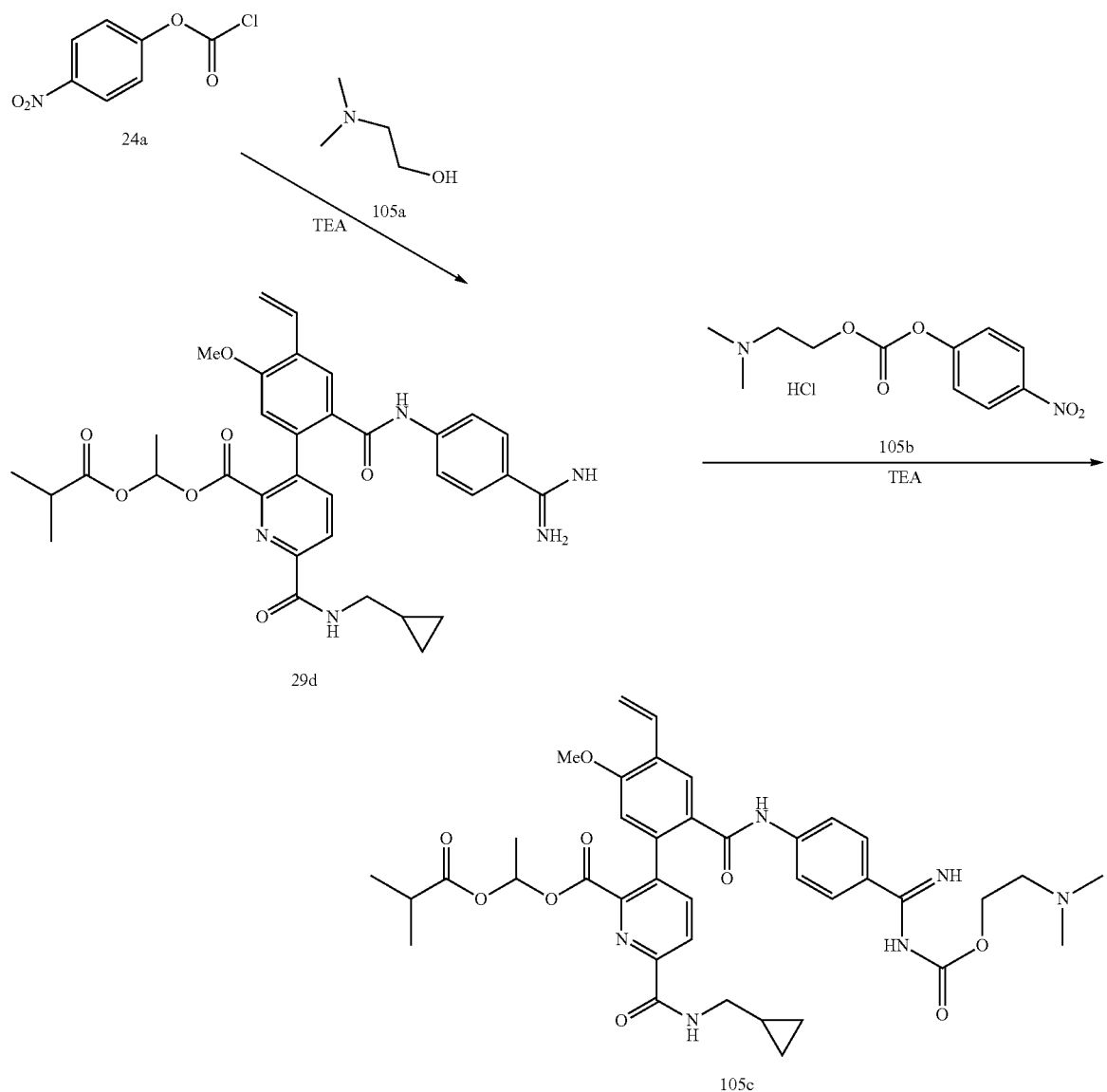

Preparation of 1-(isobutyryloxy)ethyl 6-((cyclopropylmethyl)carbamoyl)-3-(2-((4-(N-((2-(dimethylamino)ethoxy)carbonyl)carbamimidoyl)phenyl)carbamoyl)-5-methoxy-4-vinylphenyl)picolinate (105c)

Step-1: Preparation of 2-(dimethylamino)ethyl (4-nitrophenyl) carbonate hydrochloride (105b)

To a solution of 2-(dimethylamino)ethanol (105a) (1 g, 11.22 mmol) in THF (40 mL) was added 4-nitrophenyl carbonochloridate (24a) (2.261 g, 11.22 mmol) in portions at 0° C. (ice-water bath) under argon atmosphere. The reaction mixture was stirred at room temperature for 3 h, diluted with EtOAc (30 mL) and stirred for few minutes. The solid obtained was collected by filtration, washed with EtOAc (2×4 mL) and dried in vacuum to afford 2-(dimethylamino) ethyl 4-nitrophenyl carbonate hydrochloride (105b) (2.22 g, 7.64 mmol, 68.1% yield) as a white solid; $^1$H NMR (300 MHz, DMSO-$d_6$) δ 8.17-8.06 (m, 2H), 7.03-6.90 (m, 2H), 3.71 (s, 2H), 3.17-3.06 (m, 2H), 2.76 (s, 6H).

Step-2: Preparation 1-(isobutyryloxy)ethyl 6-((cyclopropylmethyl)carbamoyl)-3-(2-((4-(N-((2-(dimethylamino)ethoxy)carbonyl)carbamimidoyl)phenyl)carbamoyl)-5-methoxy-4-vinylphenyl)picolinate (105c)

Compound (105c) was prepared according to the procedure described in step 1 of scheme 24 from 1-(isobutyryloxy)ethyl 3-(2-(4-carbamimidoylphenylcarbamoyl)-5-methoxy-4-vinylphenyl)-6-(cyclopropylmethylcarbamoyl) picolinate (29d) (0.4 g, 0.64 mmol) in DMF (3 mL) using TEA 0.27 mL, 1.91 mmol) and 2-(dimethylamino)ethyl (4-nitrophenyl) carbonate hydrochloride (105b) (0.28 g, 0.96 mmol). This gave after workup and purification by reverse phase column chromatography [C18, 26 g, Acetonitrile and water (0.1% HCl) 0 to 50% as eluents] 1-(isobutyryloxy)ethyl 6-((cyclopropylmethyl)carbamoyl)-3-(2-((4-(N-((2-(dimethylamino)ethoxy)carbonyl)carbamimidoyl)phenyl)carbamoyl)-5-methoxy-4-vinylphenyl)picolinate (105c) (0.04 g, 9% yield) hydrochloride salt as a white powder; $^1$H NMR (300 MHz, DMSO-$d_6$) δ 10.90-10.60 (m, 1H), 8.70-8.47 (m, 1H), 8.22 (d, J=8.0 Hz, 1H), 8.10-7.93 (m, 2H), 7.91-7.70 (m, 4H), 7.16-6.95 (m, 2H), 6.80-6.67 (m, 1H), 6.15-5.99 (m, 1H), 5.51-5.38 (m, 1H), 4.68-4.51 (m, 2H), 3.96-3.83 (m, 3H), 3.52-3.39 (m, 2H), 3.29-3.16 (m, 2H), 2.83 (s, 3H), 2.81 (s, 3H), 2.47-2.29 (m, 1H), 1.23-1.14 (m, 3H), 1.14-1.03 (m, 1H), 1.05-0.92 (m, 6H), 0.51-0.38 (m, 2H), 0.33-0.21 (m, 2H); MS (ES+) 743.7 (M+1), 765.7 (M+Na).
Scheme 106
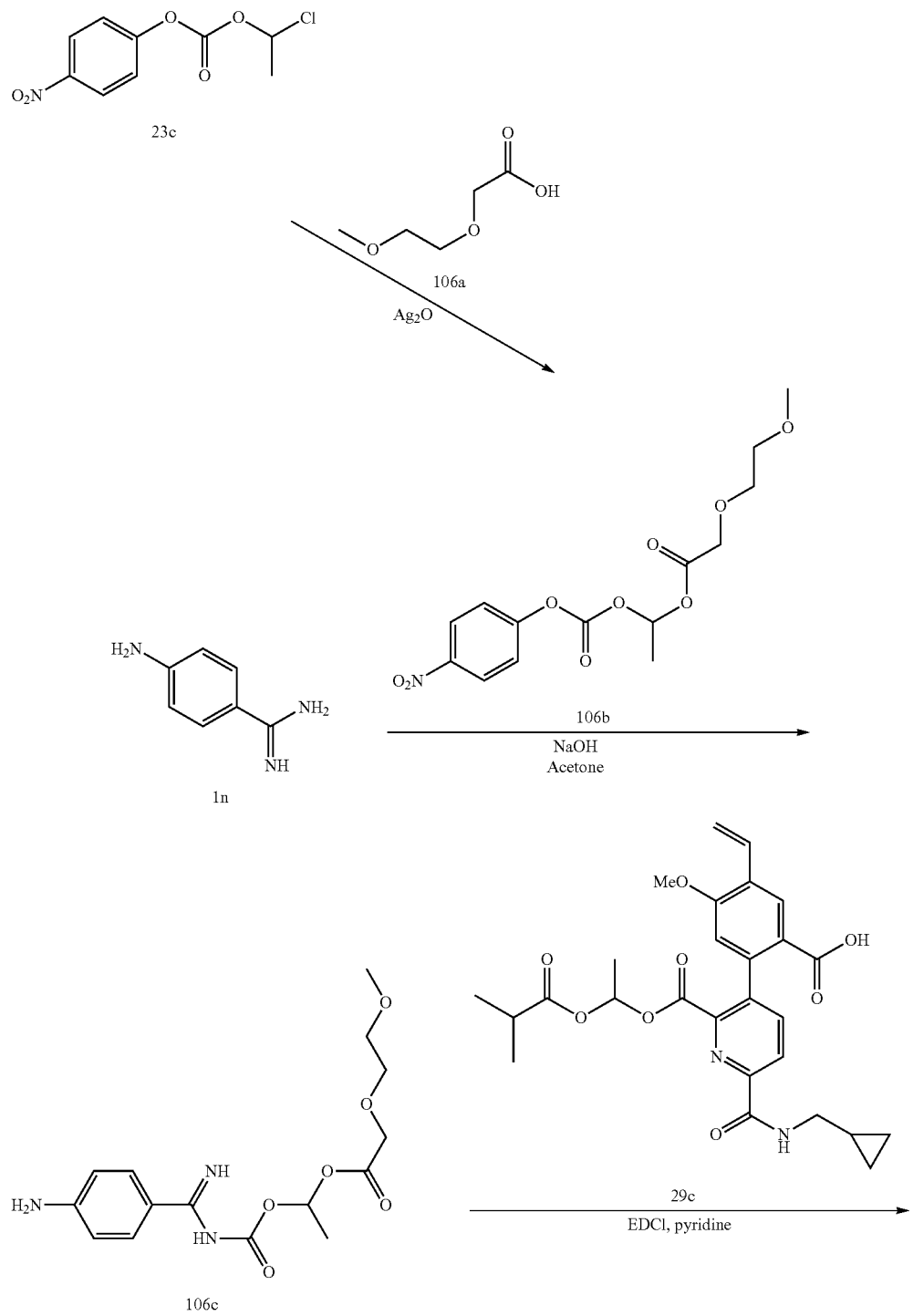

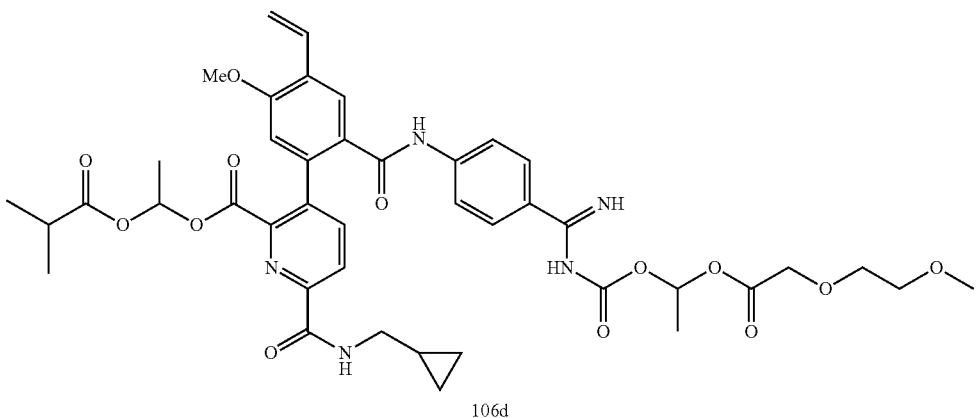 [SMILES: C=Cc1cc(C(=O)Nc2ccc(C(=N)NC(=O)OC(C)OC(=O)COCCOC)cc2)c(-c2ccc(C(=O)NCC3CC3)nc2C(=O)OC(C)OC(=O)C(C)C)cc1OC]

106d

Preparation of 1-(isobutyryloxy)ethyl 6-((cyclopropylmethyl)carbamoyl)-3-(5-methoxy-2-((4-(N-(3-methyl-5-oxo-2,4,7,10-tetraoxaundecan-1-oyl)carbamimidoyl)phenyl)carbamoyl)-4-vinylphenyl)picolinate (106d)

Step-1: Preparation of 1-(((4-nitrophenoxy)carbonyl)oxy)ethyl 2-(2-methoxyethoxy)acetate (106b)

Compound (106b) was prepared according to the procedure reported in step 1 of scheme 33 from 1-chloroethyl (4-nitrophenyl) carbonate (23a) (5 g, 20.36 mmol), 2-(2-methoxyethoxy)acetic acid (106a) (6.94 mL, 61.1 mmol) and silver oxide (4.72 g, 20.36 mmol). This gave after workup and purification by flash column chromatography [silica gel 120 g, eluting with EtOAc in hexane 0-100%] 1-(((4-nitrophenoxy)carbonyl)oxy)ethyl 2-(2-methoxyethoxy)acetate (106b) (5.84 g, 84% yield). $^1$H NMR (300 MHz, DMSO-d$_6$) δ 8.41-8.27 (m, 2H), 7.69-7.50 (m, 2H), 6.82 (q, J=5.4 Hz, 1H), 4.22 (d, J=1.3 Hz, 2H), 3.61 (dd, J=9.9, 5.8 Hz, 2H), 3.50-3.40 (m, 2H), 3.24 (s, 3H), 1.56 (d, J=5.4 Hz, 3H); MS (ES+) 366.2 (M+Na).

Step-2: Preparation of 1-((((4-aminophenyl)(imino)methyl)carbamoyl)oxy)ethyl 2-(2-methoxyethoxy)acetate (106c)

Compound (106c) was prepared from 4-aminobenzimidamide dihydrochloride (1n) (3.4 g, 16.34 mmol) in acetone (75 mL), NaOH (1 N solution, 34.3 mL, 34.3 mmol) and 1-(((4-nitrophenoxy)carbonyl)oxy)ethyl 2-(2-methoxyethoxy)acetate (106b) (5.61 g, 16.34 mmol) according to the procedure reported in step 4 of scheme 23. This gave after workup and purification by flash column chromatography [silica gel 125 g, eluting with EtOAc/MeOH (9:1) in hexane from 0-70%] 1-((((4-aminophenyl)(imino)methyl)carbamoyl)oxy)ethyl 2-(2-methoxyethoxy)acetate (106c) (1.42 g, 26% yield) as a brown syrup; $^1$H NMR (300 MHz, DMSO-d$_6$) δ 9.17 (s, 1H, D$_2$O exchangeable), 8.87 (s, 1H, D$_2$O exchangeable), 7.87-7.69 (m, 2H), 6.84 (q, J=5.4 Hz, 1H), 6.67-6.40 (m, 2H), 5.94 (s, 2H, D$_2$O exchangeable), 4.11 (s, 2H), 3.61-3.52 (m, 2H), 3.43 (dd, J=5.8, 3.6 Hz, 2H), 3.22 (s, 3H), 1.44 (d, J=5.4 Hz, 3H); MS (ES+) 340.3 (M+1), 362.4 (M+Na), (ES−) 338.3 (M−1).

Step-3: Preparation of 1-(isobutyryloxy)ethyl 6-((cyclopropylmethyl)carbamoyl)-3-(5-methoxy-2-((4-(N-(3-methyl-5-oxo-2,4,7,10-tetraoxaundecan-1-oyl)carbamimidoyl)phenyl)carbamoyl)-4-vinylphenyl)picolinate (106d)

Compound (106d) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (1.84 g, 3.62 mmol) using EDCI (1.04 g, 5.42 mmol) and 1-((((4-aminophenyl)(imino)methyl)carbamoyl)oxy)ethyl 2-(2-methoxyethoxy)acetate (106c) (1.35 g, 3.98 mmol) in DMF (3 mL) and Pyridine (3 mL) according to the procedure reported in step 4 of scheme 2. This gave after workup and purification by flash column chromatography [first column: silica gel (80 g), eluting with EtOAc/MeOH (9:1) in hexane from 0-100%, second column: silica gel, (40 g), eluting with methanol in dichloromethane 0-10%] followed by lyophilization 1-(isobutyryloxy)ethyl 6-((cyclopropylmethyl)carbamoyl)-3-(5-methoxy-2-((4-(N-(3-methyl-5-oxo-2,4,7,10-tetraoxaundecan-1-oyl)carbamimidoyl)phenyl)carbamoyl)-4-vinylphenyl)picolinate (106d) (1.9 g, 63% yield) as a white solid; $^1$H NMR (300 MHz, DMSO-d$_6$) δ 10.53 (d, J=23.7 Hz, 1H, D$_2$O exchangeable), 9.23 (d, J=14.0 Hz, 2H, D$_2$O exchangeable), 8.56 (d, J=27.1 Hz, 1H), 8.22 (d, J=8.0 Hz, 1H), 8.07-7.88 (m, 4H), 7.68 (s, 2H), 7.11-6.96 (m, 2H), 6.84 (q, J=5.4 Hz, 1H), 6.74 (s, 1H), 6.05 (dd, J=17.8, 1.6 Hz, 1H), 5.51-5.33 (m, 1H), 4.12 (s, 2H), 3.88 (s, 3H), 3.62-3.53 (m, 2H), 3.48-3.38 (m, 2H), 3.22 (s, 5H), 2.48-2.30 (m, 1H), 1.45 (d, J=5.4 Hz, 3H), 1.21-1.13 (m, 3H), 1.15-1.06 (m, 1H), 1.05-0.90 (m, 6H), 0.50-0.38 (m, 2H), 0.32-0.23 (m, 2H); MS (ES+) 832.4 (M+1), 854.7 (M+Na); Analysis calculated for: $C_{42}H_{49}N_5O_{13}$ $(H_2O)_{1.25}$: C, 59.04; H, 6.08; N, 8.20; found: C, 59.03; H, 5.94; N, 8.04.

Scheme 107
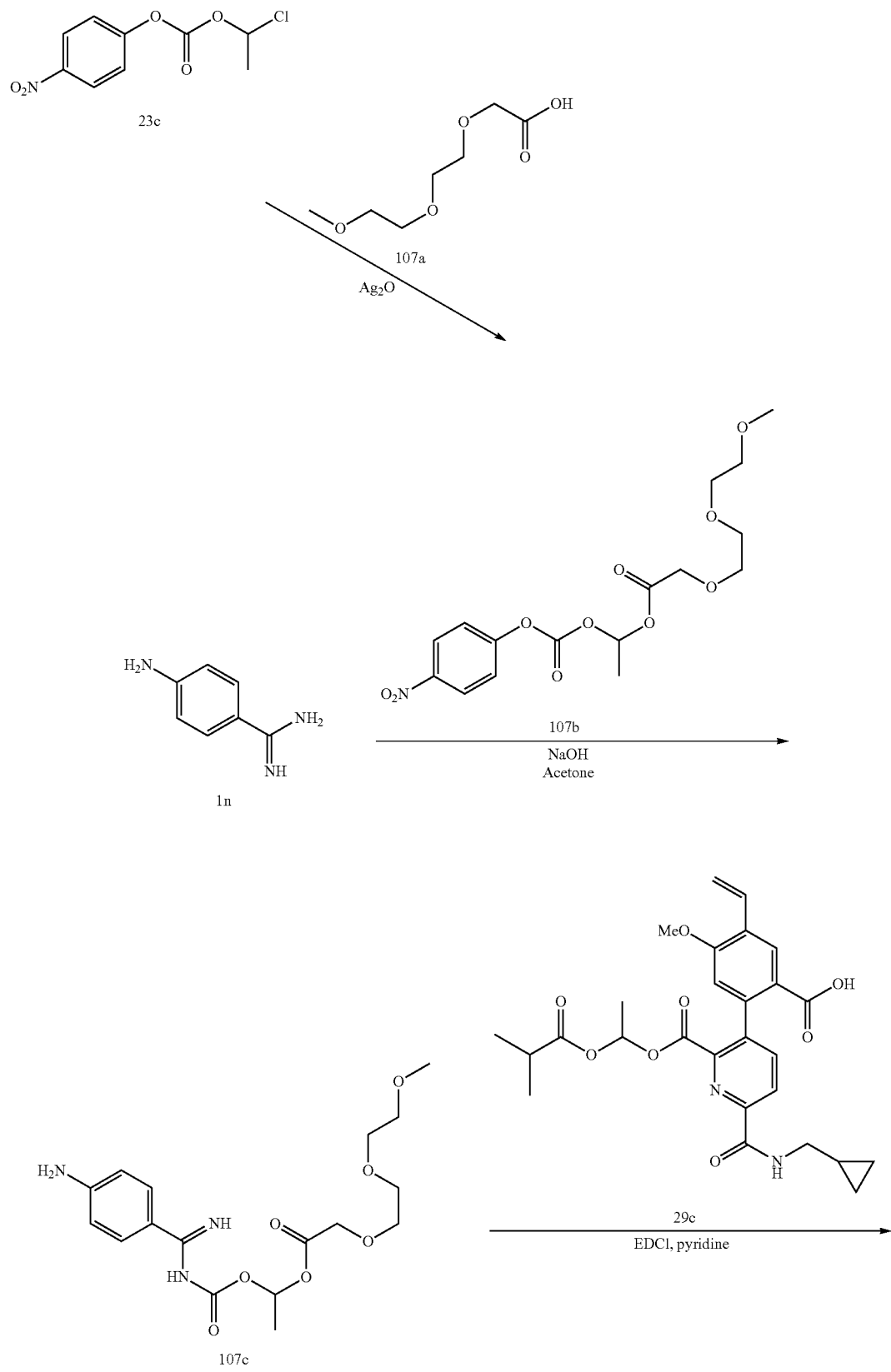

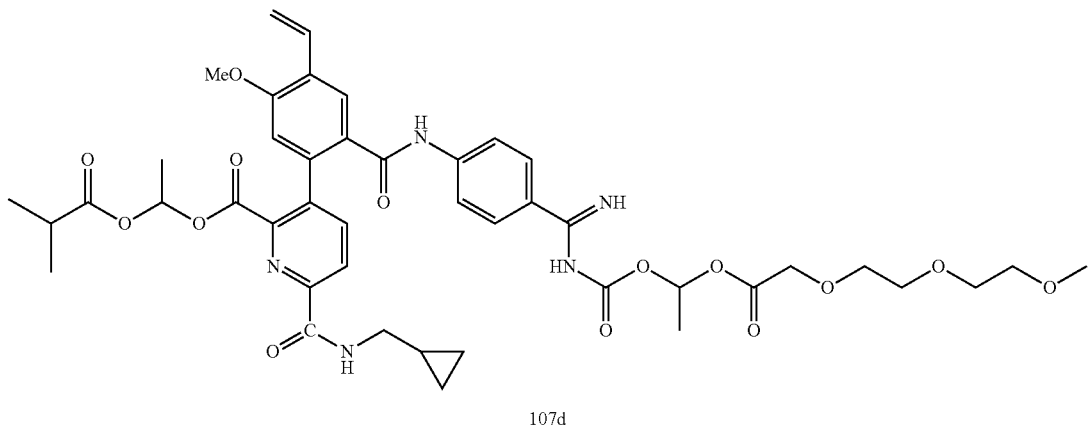 [SMILES: C=Cc1cc(C(=O)Nc2ccc(C(=N)NC(=O)OC(C)OC(=O)COCCOCCOC)cc2)c(-c2ccc(C(=O)NCC3CC3)nc2C(=O)OC(C)OC(=O)C(C)C)cc1OC]

107d

Preparation of 1-(isobutyryloxy)ethyl 6-((cyclopropylmethyl)carbamoyl)-3-(5-methoxy-2-((4-(N-(3-methyl-5-oxo-2,4,7,10,13-pentaoxatetradecan-1-oyl)carbamimidoyl)phenyl)carbamoyl)-4-vinylphenyl)picolinate (107d)

Step-1: Preparation of 1-(((4-nitrophenoxy)carbonyl)oxy)ethyl 2-(2-(2-methoxyethoxy)ethoxy)acetate (107b)

Compound (107b) was prepared according to the procedure reported in step 1 of scheme 33 from 1-chloroethyl (4-nitrophenyl) carbonate (23c) (5 g, 20.36 mmol), 2-(2-(2-methoxyethoxy)ethoxy)acetic acid (107a) (9.37 mL, 10.88 mmol) and silver oxide (4.72 g, 20.36 mmol). This gave after workup and purification by flash column chromatography [silica gel 120 g, eluting with EtOAc in hexane 0-100%] 1-(((4-nitrophenoxy)carbonyl)oxy)ethyl 2-(2-(2-methoxyethoxy)ethoxy)acetate (107b) (5.65 g, 71% yield). $^1$H NMR (300 MHz, DMSO-d$_6$) δ 8.42-8.27 (m, 2H), 7.65-7.53 (m, 2H), 6.83 (p, J=5.4, 5.0 Hz, 1H), 4.24 (d, J=1.3 Hz, 2H), 3.65-3.57 (m, 2H), 3.57-3.47 (m, 4H), 3.47-3.38 (m, 2H), 3.24 (d, J=1.4 Hz, 3H), 1.57 (d, J=5.4 Hz, 3H); MS (ES+) 410.3 (M+Na).

Step-2: Preparation of 1-(((((4-aminophenyl)(imino)methyl)carbamoyl)oxy)ethyl 2-(2-(2-methoxyethoxy)ethoxy)acetate (107c)

Compound (107c) was prepared from 4-aminobenzimidamide dihydrochloride (1n) (2.9 g, 13.94 mmol) in acetone (60 mL), NaOH (1 N solution, 29.3 mL, 29.3 mmol) and 1-(((4-nitrophenoxy)carbonyl)oxy)ethyl 2-(2-(2-methoxyethoxy)ethoxy)acetate (107b) (5.4 g, 13.94 mmol) in acetone (20 mL) according to the procedure reported in step 4 of scheme 23. This gave after workup and purification by flash column chromatography [silica gel (125 g), eluting with EtOAc/MeOH (9:1) in hexane from 0-70%] 1-(((((4-aminophenyl)(imino)methyl)carbamoyl)oxy)ethyl 2-(2-(2-methoxyethoxy)ethoxy)acetate (107c) (1.2 g, 22.45% yield) as a brown syrup. $^1$H NMR (300 MHz, DMSO-d$_6$) δ 9.17 (s, 1H, D$_2$O exchangeable), 8.87 (s, 1H, D$_2$O exchangeable), 7.82-7.70 (m, 2H), 6.84 (q, J=5.4 Hz, 1H), 6.59-6.50 (m, 2H), 5.93 (s, 2H, D$_2$O exchangeable), 4.12 (s, 2H), 3.57 (dd, J=6.5, 3.5 Hz, 2H), 3.56-3.44 (m, 4H), 3.46-3.36 (m, 2H), 3.22 (s, 3H), 1.44 (d, J=5.4 Hz, 3H); MS (ES+) 384.3 (M+1), (ES−) 382.4 (M−1).

Step-3: Preparation of 1-(isobutyryloxy)ethyl 6-((cyclopropylmethyl)carbamoyl)-3-(5-methoxy-2-((4-(N-(3-methyl-5-oxo-2,4,7,10,13-pentaoxatetradecan-1-oyl)carbamimidoyl)phenyl)carbamoyl)-4-vinylphenyl)picolinate (107d)

Compound (107d) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (1.53 g, 3.00 mmol) using EDCI (0.86 g, 4.50 mmol) and 1-(((((4-aminophenyl)(imino)methyl)carbamoyl)oxy)ethyl 2-(2-(2-methoxyethoxy)ethoxy)acetate (107c) (1.15 g, 3.00 mmol) in DMF (3 mL) and Pyridine (3 mL) according to the procedure reported in step 4 of scheme 2. This gave after workup and purification by flash column chromatography [first column: silica gel (80 g), eluting with EtOAc/MeOH (9:1) in hexane from 0-100%; second column: silica gel, (40 g), eluting with methanol in dichloromethane 0-10%] followed by lyophilization 1-(isobutyryloxy)ethyl 6-((cyclopropylmethyl)carbamoyl)-3-(5-methoxy-2-((4-(N-(3-methyl-5-oxo-2,4,7,10,13-pentaoxatetradecan-1-oyl)carbamimidoyl)phenyl)carbamoyl)-4-vinylphenyl)picolinate (107d) (1.51 g, 56% yield) as a white solid; $^1$H NMR (300 MHz, DMSO-d$_6$) δ 10.53 (d, J=25.5 Hz, 1H, D$_2$O exchangeable), 9.22 (d, J=25.3 Hz, 2H, D$_2$O exchangeable), 8.57 (d, J=28.1 Hz, 1H), 8.23 (d, J=8.0 Hz, 1H), 7.97 (d, J=17.7 Hz, 4H), 7.80-7.56 (m, 2H), 7.10-6.95 (m, 2H), 6.83-6.68 (m, 2H), 6.17-5.94 (m, 1H), 5.44 (d, J=11.4 Hz, 1H), 3.89 (s, 3H), 3.22 (d, J=6.4 Hz, 2H), 2.61-2.30 (m, 2H), 1.43 (d, J=5.4 Hz, 3H), 1.17 (s, 3H), 1.05 (dd, J=7.0, 5.3 Hz, 6H), 1.05-0.88 (m, 7H), 0.50-0.40 (m, 2H), 0.32-0.23 (m, 2H); MS (ES+) 786.7 (M+1), 808.7 (M+Na), (ES−) 784.8 (M−1); Analysis calculated for: $C_{44}H_{53}N_5O_{14} \cdot H_2O$: C, 59.12; H, 6.20; N, 7.83; found; C, 59; 0.24; H, 6.14; N, 7.72.

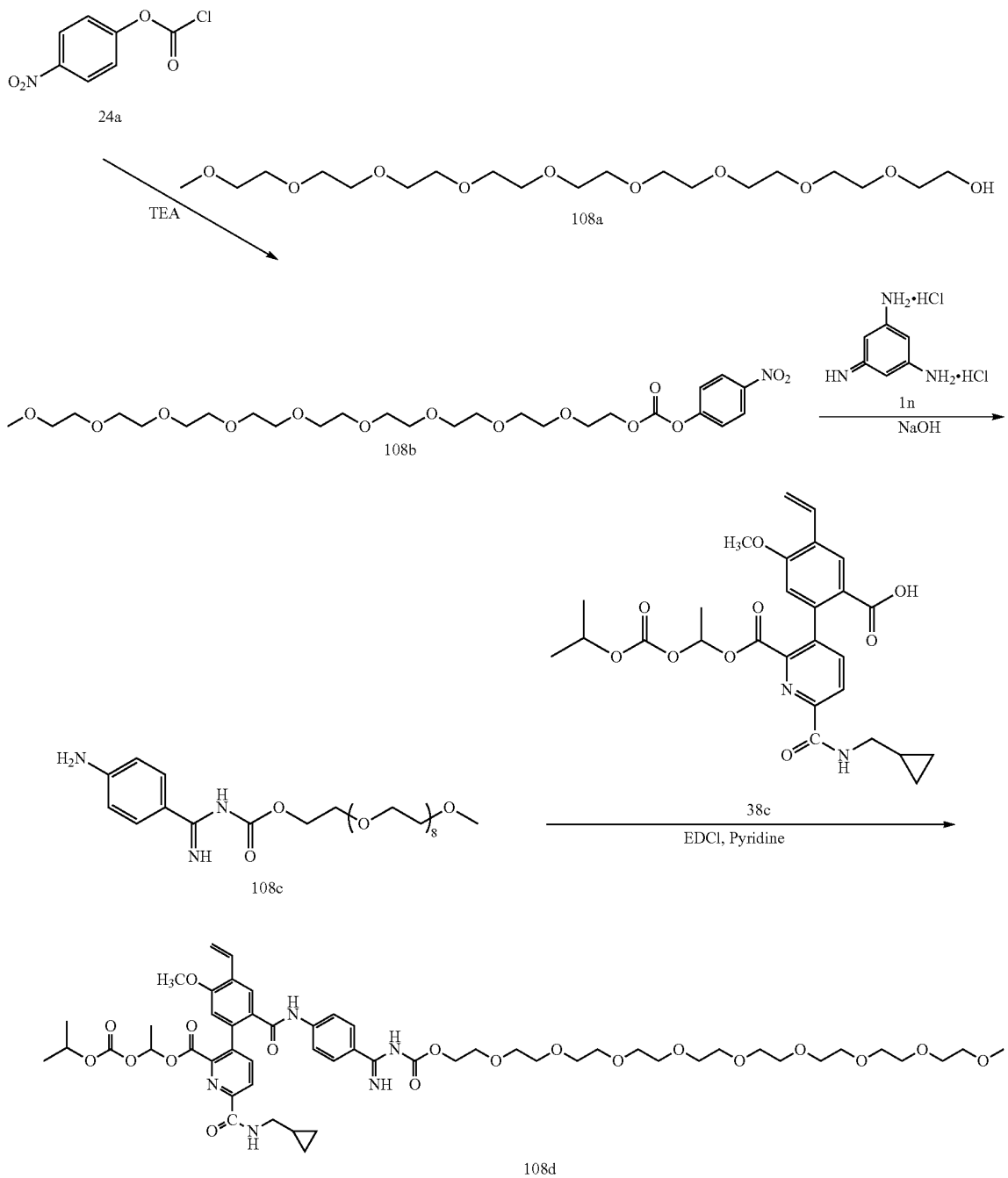

Preparation of 1-((isopropoxycarbonyl)oxy)ethyl 3-(2-((4-(N-(2,5,8,11,14,17,20,23,26,29-decaoxatriacontan-1-oyl)carbamimidoyl)phenyl)carbamoyl)-5-methoxy-4-vinylphenyl)-6-((cyclopropylmethyl)carbamoyl)picolinate (108d)

Step-1: Preparation of 4-nitrophenyl 2,5,8,11,14,17,20,23,26-nonaoxaoctacosan-28-yl carbonate (108b)

Compound (108b) was prepared according to the procedure described in step 1 of scheme 24 from 4-nitrophenyl chloroformate (24a) (0.53 g, 2.57 mmol) in THF (8 mL) using 2,5,8,11,14,17,20,23,26-nonaoxaoctacosan-28-ol (108a) (1.00 g, 2.33 mmol) and triethylamine (0.72 mL, 5.13 mmol). This gave after workup and purification by flash column chromatography [silica gel 80 g, eluting with ethyl acetate in hexanes from 0-30%] 1-((isopropoxycarbonyl)oxy)ethyl 3-(2-((4-(N-(2,5,8,11,14,17,20,23,26,29-decaoxatriacontan-1-oyl)carbamimidoyl)phenyl)carbamoyl)-5-methoxy-4-vinylphenyl)-6-((cyclopropylmethyl)carbamoyl)picolinate (108b) (1.11 g, 1.870 mmol, 80% yield) as a thick yellow oil; $^1$H NMR (300 MHz, DMSO-$d_6$) δ 8.42-8.26 (m, 2H), 7.66-7.46 (m, 2H), 4.42-4.30 (m, 2H), 3.77-3.67 (m, 2H), 3.62-3.37 (m, 32H), 3.23 (s, 3H); MS (ES+): 616.6 (M+Na).

Step-2: Preparation (2,5,8,11,14,17,20,23,26-nonaoxaoctacosan-28-yl ((4-aminophenyl)(imino)methyl)carbamate (108c)

Compound (108c) was prepared from 4-aminobenzimidamide dihydrochloride (1n) (0.46 g, 2.22 mmol) in acetone/water (20 mL) using sodium hydroxide (0.17 g, 4.26 mmol) and 4-nitrophenyl 2,5,8,11,14,17,20,23,26-nonaoxaoctacosan-28-yl carbonate (108b) (1.1 g, 1.85 mmol) according to the procedure reported in step 4 of scheme 23. This gave after workup and purification by flash column chromatography [silica gel, 24 g, eluting with ethyl acetate in hexanes from 0 to 100%] (2,5,8,11,14,17,20,23,26-nonaoxaoctacosan-28-yl ((4-aminophenyl)(imino)methyl)carbamate (108c) (0.24 g, 22% yield) as a yellow solid; $^1$H NMR (300 MHz, DMSO-$d_6$) δ 9.12 (bs, 1H, $D_2O$ exchangeable), 8.64 (bs, 1H, $D_2O$ exchangeable), 7.88-7.62 (m, 2H), 6.69-6.35 (m, 2H), 5.86 (bs, 2H, $D_2O$ exchangeable), 4.09 (t, J=4.8 Hz, 2H), 3.61 (t, J=4.8 Hz, 2H), 3.56-3.40 (m, 32H), 3.23 (s, 3H); MS (ES+): 590.7 (M+1).

Step-3: Preparation of 1-((isopropoxycarbonyl)oxy)ethyl 3-(2-((4-(N-(2,5,8,11,14,17,20,23,26,29-decaoxatriacontan-1-oyl)carbamimidoyl)phenyl)carbamoyl)-5-methoxy-4-vinylphenyl)-6-((cyclopropylmethyl)carbamoyl)picolinate (108d)

Compound (108d) was prepared from 2-(6-((cyclopropylmethyl)carbamoyl)-2-((1-((isopropoxycarbonyl)oxy)ethoxy)carbonyl)pyridin-3-yl)-4-methoxy-5-vinylbenzoic acid (38c) (0.25 g, 0.47) using EDCI (0.11 g, 0.59 mmol) and (2,5,8,11,14,17,20,23,26-nonaoxaoctacosan-28-yl ((4-aminophenyl)(imino)methyl)carbamate (108c) (0.23 g, 0.39 mmol) in DMF (10 mL) and pyridine (5 mL) according to the procedure reported in step 4 of scheme 2. This gave after workup and purification by flash column chromatography [Three separate columns: EZ-PREP, C-18 column, 30 g, eluting with 0.1% aqueous HCl in water and in acetonitrile from 0-100%] followed by lyophilization 1-((isopropoxycarbonyl)oxy)ethyl 3-(2-((4-(N-(2,5,8,11,14,17,20,23,26,29-decaoxatriacontan-1-oyl)carbamimidoyl)phenyl)carbamoyl)-5-methoxy-4-vinylphenyl)-6-((cyclopropylmethyl)carbamoyl)picolinate (108d) (0.032 g, 7% yield) as a hygroscopic white solid; $^1$H NMR (300 MHz, DMSO-$d_6$) δ 10.97 (s, 1H), 10.68-10.39 (m, 1H), 8.75-8.47 (m, 1H), 8.22 (d, J=8.0 Hz, 1H), 8.05-7.93 (m, 1H), 7.92-7.79 (m, 2H), 7.78-7.60 (m, 2H), 7.16-6.90 (m, 2H), 6.71-6.56 (m, 1H), 6.05 (d, J=17.7 Hz, 1H), 5.44 (d, J=11.3 Hz, 1H), 4.82-4.59 (m, 1H), 4.35-4.17 (m, 2H), 3.89 (s, 3H), 3.71-3.60 (m, 2H), 3.59-3.37 (m, 34H), 3.22 (s, 3H), 1.28-1.03 (m, 10H), 0.51-0.36 (m, 2H), 0.34-0.17 (m, 2H); MS (ES+): 1121.7 (M+Na).

Scheme 109

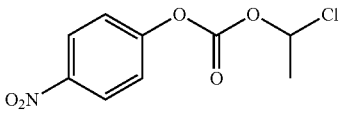

23c

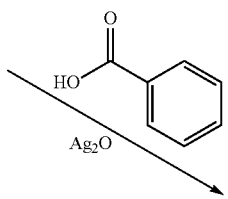

Ag$_2$O

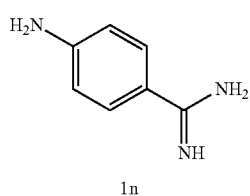

1n

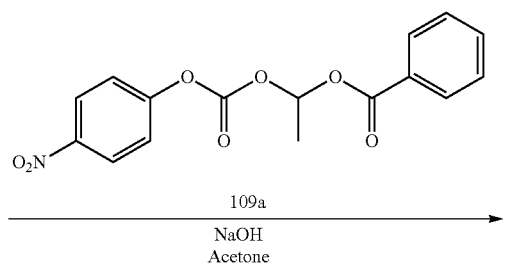

109a
NaOH
Acetone

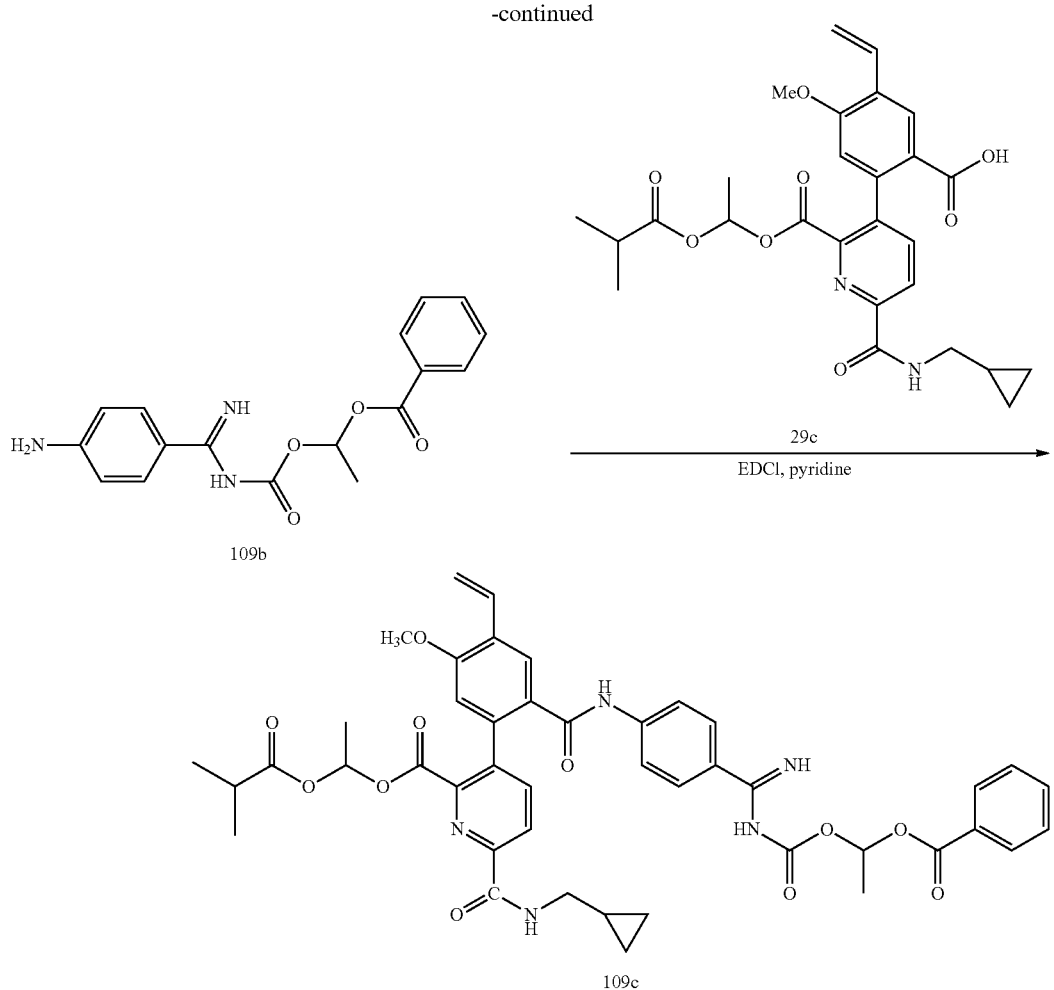

Preparation of 1-(isobutyryloxy)ethyl 3-(2-((4-(N-((1-(benzoyloxy)ethoxy)carbonyl)carbamimidoyl)phenyl)carbamoyl)-5-methoxy-4-vinylphenyl)-6-((cyclopropylmethyl)carbamoyl)picolinate (109c)

Step-1: Preparation of 1-(((4-nitrophenoxy)carbonyl)oxy)ethyl benzoate (109a)

Compound (109a) was prepared according to the procedure reported in step 1 of scheme 33 from 1-chloroethyl (4-nitrophenyl) carbonate (23c) (4.08 g, 16.61 mmol), benzoic acid (6.09 g, 49.8 mmol), and silver oxide (3.85 g, 16.61 mmol). This gave after workup and purification by flash column chromatography [silica gel 120 g, eluting with ethyl acetate in hexanes (0 to 20 to 100%)] 1-(((4-nitrophenoxy)carbonyl)oxy)ethyl benzoate (109a) (2.82 g, 51% yield) as a thick clear oil; MS (ES+): 354.3 (M+Na);

Step-2: Preparation of 1-((((4-aminophenyl)(imino)methyl)carbamoyl)oxy)ethyl benzoate (109b)

Compound (109b) was prepared from 4-aminobenzimidamide dihydrochloride (1n) (1.76 g, 8.45 mmol) in acetone (50 mL), NaOH (1 N solution, 17.75 mL, 17.75 mmol) and 1-(((4-nitrophenoxy)carbonyl)oxy)ethyl benzoate (109a) (2.80 g, 8.45 mmol) according to the procedure reported in step 4 of scheme 23. This gave after workup and purification by flash column chromatography [silica gel 40 g, eluting with ethyl acetate in hexanes from 0-100%]1-((((4-aminophenyl)(imino)methyl)carbamoyl)oxy)ethyl benzoate (109b) (1.24 g, 45% yield) as a yellow solid; $^1$H NMR (300 MHz, DMSO-$d_6$) δ 9.18 (s, 1H, D$_2$O exchangeable), 8.86 (s, 1H, D$_2$O exchangeable), 7.96 (d, J=6.8 Hz, 2H), 7.77 (d, J=8.6 Hz, 2H), 7.72-7.64 (m, 1H), 7.54 (t, J=7.6 Hz, 2H), 7.03 (q, J=5.4 Hz, 1H), 6.54 (d, J=8.7 Hz, 2H), 5.93 (s, 2H, D$_2$O exchangeable), 1.57 (d, J=5.4 Hz, 3H); MS (ES+): 328.3 (M+1); 350.3 (M+Na); MS (ES−): 362.1 (M+Cl).

Step-3: Preparation of 1-(isobutyryloxy)ethyl 3-(2-((4-(N-((1-(benzoyloxy)ethoxy)carbonyl)carbamimidoyl)phenyl)carbamoyl)-5-methoxy-4-vinylphenyl)-6-((cyclopropylmethyl)carbamoyl)picolinate (109c)

Compound (109c) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (2.25 g, 4.40 mmol) using EDCI (1.05 g, 5.50 mmol) and 1-((((4-aminophenyl)(imino)methyl)carbamoyl)oxy)ethyl benzoate (109b) (1.20 g, 3.67 mmol) in DMF (20 mL) and Pyridine (10 mL) according to the procedure reported in step 4 of scheme 2. This gave after workup and purification by flash column chromatography [silica gel 40 g, eluting with ethyl acetate/methanol (9:1) in hexanes from 0-100%] 1-(isobutyryloxy)ethyl 3-(2-((4-(N-((1-(benzoyloxy)ethoxy)carbonyl)carbamimidoyl)phenyl)carbamoyl)-5-methoxy-4-vinyl-phenyl)-6-((cyclopropylmethyl)carbamoyl)picolinate (109c) (1.21 g, 40% yield) as a white solid. $^1$H NMR (300 MHz, DMSO-d$_6$) δ 10.57 & 10.49 (2s, 1H, D$_2$O exchangeable), 9.26 (s, 1H, D$_2$O exchangeable), 9.19 (s, 1H, D$_2$O exchangeable), 8.61 & 8.52 (2s, 1H), 8.22 (d, J=8.1 Hz, 1H), 8.10-7.83 (m, 6H), 7.77-7.61 (m, 3H), 7.53 (t, J=7.7 Hz, 2H), 7.16-6.92 (m, 3H), 6.87-6.60 (m, 1H), 6.06 (d, J=17.7 Hz, 1H), 5.44 (d, J=11.4 Hz, 1H), 3.89 (s, 3H), 3.29-3.16 (m, 2H), 2.46-2.29 (m, 1H), 1.58 (d, J=5.4 Hz, 3H), 1.29-0.86 (m, 10H), 0.54-0.38 (m, 2H), 0.32-0.19 (m, 2H); MS (ES+): 842.4 (M+Na); MS (ES−): 818.6 (M−1); Analysis calculated for: C$_{44}$H$_{45}$N$_5$O$_{11}$·H$_2$O: C, 63.07; H, 5.65; N, 8.36; found: C, 63.46; H, 5.61; N, 8.24.

Scheme 110

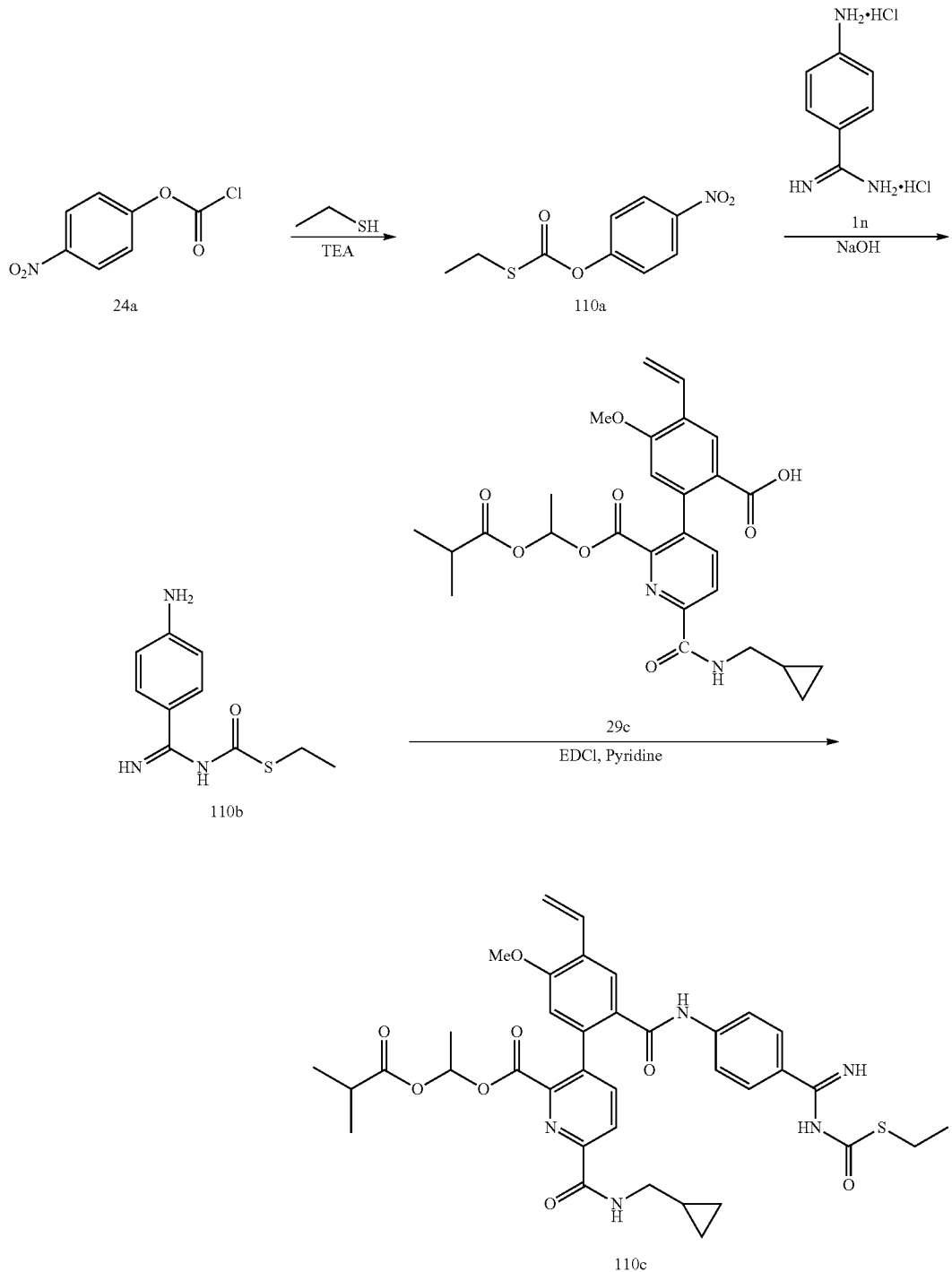

Preparation of 1-(isobutyryloxy)ethyl 6-((cyclopropylmethyl)carbamoyl)-3-(2-((4-(N-((ethylthio)carbonyl)carbamimidoyl)phenyl)carbamoyl)-5-methoxy-4-vinylphenyl)picolinate (110c)

Step-1: Preparation of S-ethyl O-(4-nitrophenyl) carbonothioate (110a)

Compound (110a) was prepared according to the procedure described in step 1 of scheme 24 from 4-nitrophenyl chloroformate (24a) (13.38 g, 64.4 mmol) in THF (150 mL) using ethanethiol (4 g, 64.4 mmol) and triethylamine (19.74 mL, 142 mmol). This gave after workup and purification by flash column chromatography [silica gel, eluting with EtOAc in hexane from 0-50% %] 1-(isobutyryloxy)ethyl 6-((cyclopropylmethyl)carbamoyl)-3-(2-((4-(N-((ethylthio)carbonyl)carbamimidoyl)phenyl)carbamoyl)-5-methoxy-4-vinylphenyl)picolinate (110c) (10 g, 68% yield) as clear yellow oil, which was used in the next step without further purification. $^1$H NMR (300 MHz, DMSO-$d_6$) δ 8.42-8.19 (m, 2H), 7.64-7.44 (m, 2H), 2.99 (q, J=7.3 Hz, 2H), 1.31 (t, J=7.3 Hz, 3H).

Step-2: Preparation S-ethyl (4-aminophenyl)(imino)methylcarbamothioate 110b Compound (110b) was prepared from 4-aminobenzimidamide dihydrochloride (1n) (5 g, 24.03 mmol) in acetone/H$_2$O (52 mL, Ratio: 12:1, v/v) using sodium hydroxide (2.018 g, 50.5 mmol) and S-ethyl O-(4-nitrophenyl) carbonothioate (110a) (8.19 g, 36.0 mmol) according to the procedure reported in step 4 of scheme 23. This gave after workup and purification by flash column chromatography [silica gel (40 g), eluting with EtOAc/MeOH (9:1) in hexane from 0-70%] S-ethyl (4-aminophenyl)(imino)methylcarbamothioate 110b) (4.2 g, 18.81 mmol, 78% yield) as a yellow solid; $^1$H NMR (300 MHz, DMSO-$d_6$) δ 9.25 (s, 1H, D$_2$O exchangeable), 8.74 (s, 1H, D$_2$O exchangeable), 7.80-7.65 (m, 2H), 6.63-6.48 (m, 2H), 5.94 (s, 2H, D$_2$O exchangeable), 2.73 (q, J=7.3 Hz, 2H), 1.21 (t, J=7.3 Hz, 3H); MS (ES$^+$) 224.2 (M+1), 246.3 (M+Na); (ES$^-$) 222.2 (M−1).

Step-3: Preparation of 1-(isobutyryloxy)ethyl 6-((cyclopropylmethyl)carbamoyl)-3-(2-((4-(N-((ethylthio)carbonyl)carbamimidoyl)phenyl)carbamoyl)-5-methoxy-4-vinylphenyl)picolinate (110c)

Compound (110c) was prepared from 2-(6-((cyclopropylmethyl)carbamoyl)-2-((1-(isobutyryloxy)ethoxy)carbonyl) pyridin-3-yl)-4-methoxy-5-vinylbenzoic acid (29c) (3.40 g, 6.65 mmol) using EDCI (1.74 g, 9.07 mmol) and S-ethyl (4-aminophenyl)(imino)methylcarbamothioate 110b) (1.35 g, 6.05 mmol) in DMF (15 mL) and pyridine (15 mL) according to the procedure reported in step 4 of scheme 2. This gave after workup and purification by flash column chromatography twice by [silica (120 g) eluting with EtOAc/MeOH (9:1) in hexane from 0 to 50%] then further twice by [silica (120 g), eluting with MeOH in DCM from 0-15%] 1-(isobutyryloxy)ethyl 6-((cyclopropylmethyl)carbamoyl)-3-(2-((4-(N-((ethylthio)carbonyl)carbamimidoyl) phenyl)carbamoyl)-5-methoxy-4-vinylphenyl)picolinate (110c) (1.59 g, 37% yield) as a white solid; $^1$H NMR (300 MHz, DMSO-$d_6$) δ 10.53 (d, J=24.9 Hz, 1H, D$_2$O exchangeable), 9.31 (s, 1H, D$_2$O exchangeable), 9.05 (s, 1H, D$_2$O exchangeable), 8.56 (d, J=29.8 Hz, 1H, D$_2$O exchangeable), 8.22 (d, J=8.0 Hz, 1H), 7.95 (d, J=25.3 Hz, 4H), 7.77-7.57 (m, 2H), 7.10-6.94 (m, 2H), 6.80-6.65 (m, 1H), 6.05 (dd, J=17.7, 1.5 Hz, 1H), 5.44 (d, J=12.0 Hz, 1H), 3.88 (s, 3H), 3.23 (t, J=6.4 Hz, 2H), 2.75 (q, J=7.3 Hz, 2H), 2.48-2.30 (m, 1H), 1.27-1.13 (m, 6H), 1.12-1.05 (m, 1H), 1.02-0.91 (m, 6H), 0.49-0.39 (m, 2H), 0.31-0.20 (m, 2H); MS (ES+) 715.3 (M+1), 738.3 (M+Na), 714.6 (M−1) 750.3 (M+Cl).

Scheme 111

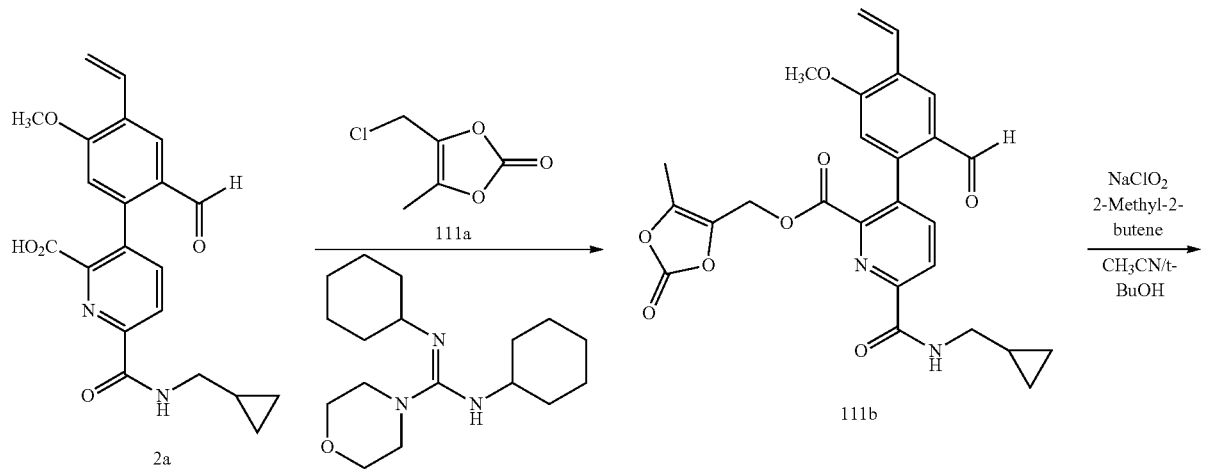

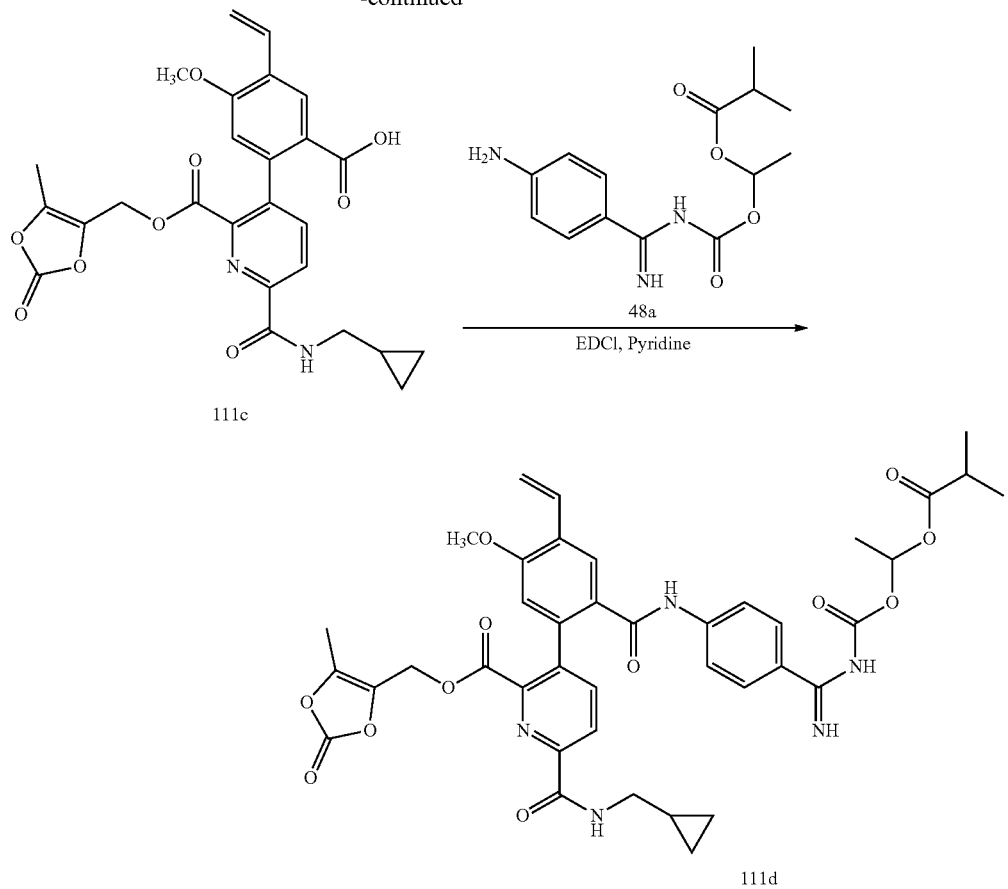

Preparation of (5-methyl-2-oxo-1,3-dioxol-4-yl) methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl) picolinate (111d)

Step-1: Preparation of (5-methyl-2-oxo-1,3-dioxol-4-yl)methyl 6-((cyclopropylmethyl)carbamoyl)-3-(2-formyl-5-methoxy-4-vinylphenyl)picolinate (111b)

Compound (111b) was prepared according to the procedure reported in step 1 of scheme 8 from 6-(Cyclopropylmethylcarbamoyl)-3-(2-formyl-5-methoxy-4-vinylphenyl) picolinic acid (2a) (3 g, 7.89 mmol) in DMF (30 mL) using N,N'-Dicyclohexyl-4-morpholinecarboxamidine (2.78 g, 9.46 mmol) and 4-(chloromethyl)-5-methyl-1,3-dioxol-2-one (111a) (1.76 g, 11.83 mmol). This gave after workup and purification by flash column chromatography [silica gel 40 g, MeOH:EtOAc (9:1) in hexanes as eluents, 0 to 100%] (5-methyl-2-oxo-1,3-dioxol-4-yl)methyl 6-((cyclopropylmethyl)carbamoyl)-3-(2-formyl-5-methoxy-4-vinylphenyl)picolinate (111b) (3.4 g, 6.90 mmol, 88% yield) as a colorless foam; $^1$H NMR (300 MHz, DMSO-$d_6$) δ 9.63 (s, 1H), 8.76 (t, J=6.0 Hz, 1H), 8.26 (d, J=8.0 Hz, 1H), 8.14-8.01 (m, 2H), 7.06-6.85 (m, 2H), 5.98 (dd, J=17.8, 1.4 Hz, 1H), 5.44 (dd, J=11.2, 1.3 Hz, 1H), 5.08-4.88 (m, 2H), 3.87 (s, 3H), 3.22 (p, J=6.7 Hz, 2H), 1.99 (d, J=1.5 Hz, 3H), 1.16-1.00 (m, 1H), 0.50-0.40 (m, 2H), 0.32-0.24 (m, 2H).

Step-2: Preparation of 2-(6-((cyclopropylmethyl) carbamoyl)-2-(((5-methyl-2-oxo-1,3-dioxol-4-yl) methoxy)carbonyl)pyridin-3-yl)-4-methoxy-5-vinylbenzoic acid (111c)

Oxidation of (5-methyl-2-oxo-1,3-dioxol-4-yl)methyl 6-((cyclopropylmethyl)carbamoyl)-3-(2-formyl-5-methoxy-4-vinylphenyl)picolinate (111b) (3.4 g, 6.90 mmol) using the procedure as reported in step 11 of scheme 1 gave after workup 2-(6-((cyclopropylmethyl)carbamoyl)-2-(((5-methyl-2-oxo-1,3-dioxol-4-yl)methoxy)carbonyl)pyridin-3-yl)-4-methoxy-5-vinylbenzoic acid (111c) (3.3 g, 94% yield) as a light yellow solid; $^1$H NMR (300 MHz, DMSO-$d_6$) δ 12.55 (s, 1H), 8.68 (t, J=6.1 Hz, 1H), 8.21 (d, J=8.0 Hz, 1H), 8.05 (s, 1H), 7.97 (d, J=8.0 Hz, 1H), 7.03-6.82 (m, 2H), 5.96-5.84 (m, 1H), 5.43-5.34 (m, 1H), 5.05-4.87 (m, 2H), 3.83 (s, 3H), 3.22 (q, J=6.2 Hz, 2H), 1.99 (s, 3H), 1.19-1.13 (m, 1H), 0.50-0.39 (m, 2H), 0.31-0.24 (m, 2H); MS (ES+) 531.3 (M+23), MS (ES−) 507.2 (M−1).

Step-3: Preparation of (5-methyl-2-oxo-1,3-dioxol-4-yl)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (111d)

Compound (111d) was prepared from 2-(6-((cyclopropylmethyl)carbamoyl)-2-(((5-methyl-2-oxo-1,3-dioxol-4-yl)methoxy)carbonyl)pyridin-3-yl)-4-methoxy-5-vinylbenzoic acid (111c) (0.52 g, 1.02 mmol) using EDCI (0.196 g, 1.02 mmol) and 1-((((4-aminophenyl)(imino)methyl)carbamoyl)oxy)ethyl isobutyrate (48a) (0.3 g, 1.02) in DMF (15 mL) and Pyridine (5 mL) according to the procedure reported in step 4 of scheme 2. This gave after workup and purification by flash column chromatography [silica gel 24 g, using MeOH:EtOAc (9:1) in hexanes 0 to 100% as eluents] (5-methyl-2-oxo-1,3-dioxol-4-yl)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (111d) (0.13 g, 0.166 mmol, 16.22% yield) as a white solid; $^1$H NMR (300 MHz, DMSO-$d_6$) δ 10.44 (s, 1H), 9.35-9.09 (m, 2H), 8.64 (t, J=6.1 Hz, 1H), 8.20 (d, J=8.0 Hz, 1H), 8.03-7.88 (m, 4H), 7.63 (d, J=8.7 Hz, 2H), 7.09-6.91 (m, 2H), 6.77 (q, J=5.3 Hz, 1H), 6.11-5.97 (m, 1H), 5.43 (d, J=11.4 Hz, 1H), 4.97 (d, J=2.8 Hz, 2H), 3.85 (s, 3H), 3.28-3.14 (m, 3H), 2.01 (s, 3H), 1.43 (d, J=5.4 Hz, 3H), 1.06 (dd, J=7.0, 5.3 Hz, 7H), 0.49-0.39 (m, 2H), 0.32-0.21 (m, 2H); MS (ES+) 784.5 (M+1).

Scheme 112

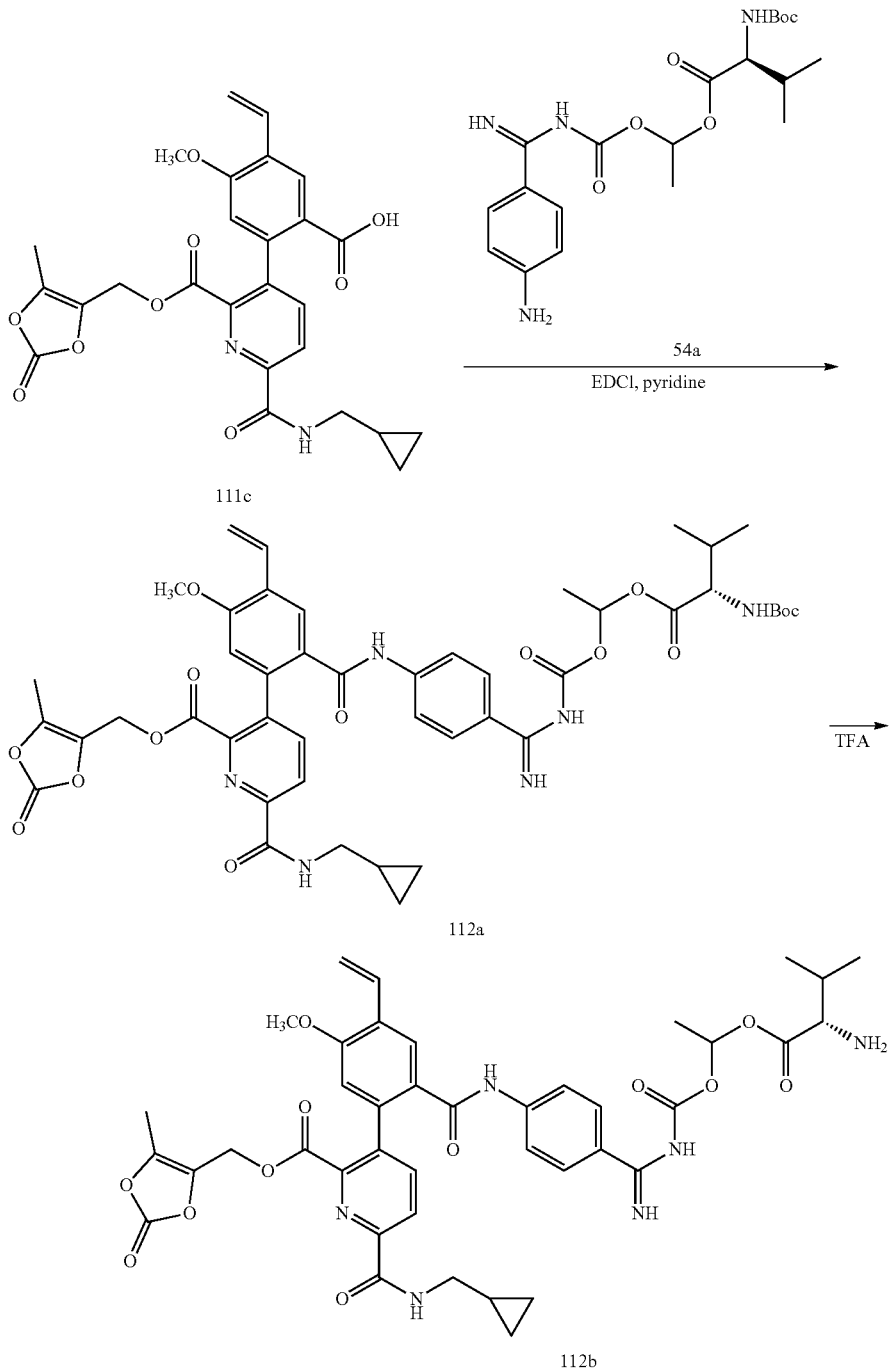

403

Preparation of (5-methyl-2-oxo-1,3-dioxol-4-yl)methyl 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinate (112b)

Step-1: Preparation of (5-methyl-2-oxo-1,3-dioxol-4-yl)methyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinate (112a)

Compound (112a) was prepared from 2-(6-((cyclopropylmethyl)carbamoyl)-2-(((5-methyl-2-oxo-1,3-dioxol-4-yl)methoxy)carbonyl)pyridin-3-yl)-4-methoxy-5-vinylbenzoic acid (111c) (0.7 g, 1.38 mmol) using EDCI (0.26 g, 1.38 mmol) and (2S)-1-((((4-aminophenyl)(imino)methyl)carbamoyl)oxy)ethyl 2-((tert-butoxycarbonyl)amino)-3-methylbutanoate (54a) (0.58 g, 1.38 mmol) in DMF (10 mL) and Pyridine (5 mL) according to the procedure reported in step 4 of scheme 2. This gave after workup and purification by flash column chromatography [silica gel 12 g, using MeOH:EtOAc (9:1) in hexanes 0 to 100% as eluents] ((5-methyl-2-oxo-1,3-dioxol-4-yl)methyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinate (112a) (0.4 g, 32% yield) as a gummy solid; MS (ES+) 913.7 (M+1), MS (ES−) 947.6 (M+Cl);

404

Step-2: Preparation of (5-methyl-2-oxo-1,3-dioxol-4-yl)methyl 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinate (112b)

Compound (112b) was prepared from (5-methyl-2-oxo-1,3-dioxol-4-yl)methyl 6-((cyclopropylmethyl)carbamoyl)-3-(2-((4-(N-((6S)-6-isopropyl-3,10,10-trimethyl-5,8-dioxo-2,4,9-trioxa-7-azaundecan-1-oyl)carbamimidoyl)phenyl)carbamoyl)-5-methoxy-4-vinylphenyl)picolinate (112a) (0.4 g, 0.44 mmol) in dichloromethane (3 mL) using 2,2,2-trifluoroacetic acid (0.68 mL, 8.76 mmol) according to the procedure reported in Step-4 of scheme 8. This gave after workup and purification by reverse phase column chromatography [silica gel 26 g, Acetonitrile in 0.1% HCl in water as eluents, 0 to 50%] followed by lyophilization (5-methyl-2-oxo-1,3-dioxol-4-yl)methyl 3-(2-((4-(N-((1-(((S)-2-amino-3-methylbutanoyl)oxy)ethoxy)carbonyl)carbamimidoyl)phenyl)carbamoyl)-5-methoxy-4-vinylphenyl)-6-((cyclopropylmethyl)carbamoyl)picolinate (112b) (0.13 g, 37% yield) HCl salt as a light orange solid; $^1$H NMR (300 MHz, DMSO-$d_6$) δ 10.63 (s, 1H), 10.21-9.61 (m, 2H), 8.64 (t, J=6.1 Hz, 1H), 8.60-8.48 (m, 3H), 8.20 (d, J=8.0 Hz, 1H), 8.05-7.91 (m, 2H), 7.84 (d, J=8.5 Hz, 2H), 7.72 (d, J=8.7 Hz, 2H), 7.10-6.90 (m, 3H), 6.13-5.97 (m, 1H), 5.52-5.37 (m, 1H), 4.98 (bs, 2H), 4.04-3.50 (m, 2H), 3.85 (s, 3H), 3.29-3.14 (m, 2H), 2.27-2.09 (m, 1H), 2.02 (s, 3H), 1.56 (d, J=5.4 Hz, 3H), 1.15-1.02 (m, 1H), 1.03-0.89 (m, 6H), 0.50-0.36 (m, 2H), 0.32-0.19 (m, 2H); MS (ES+) 813.5 (M+1), MS (ES−) 847.5 (M+Cl).

Scheme 113

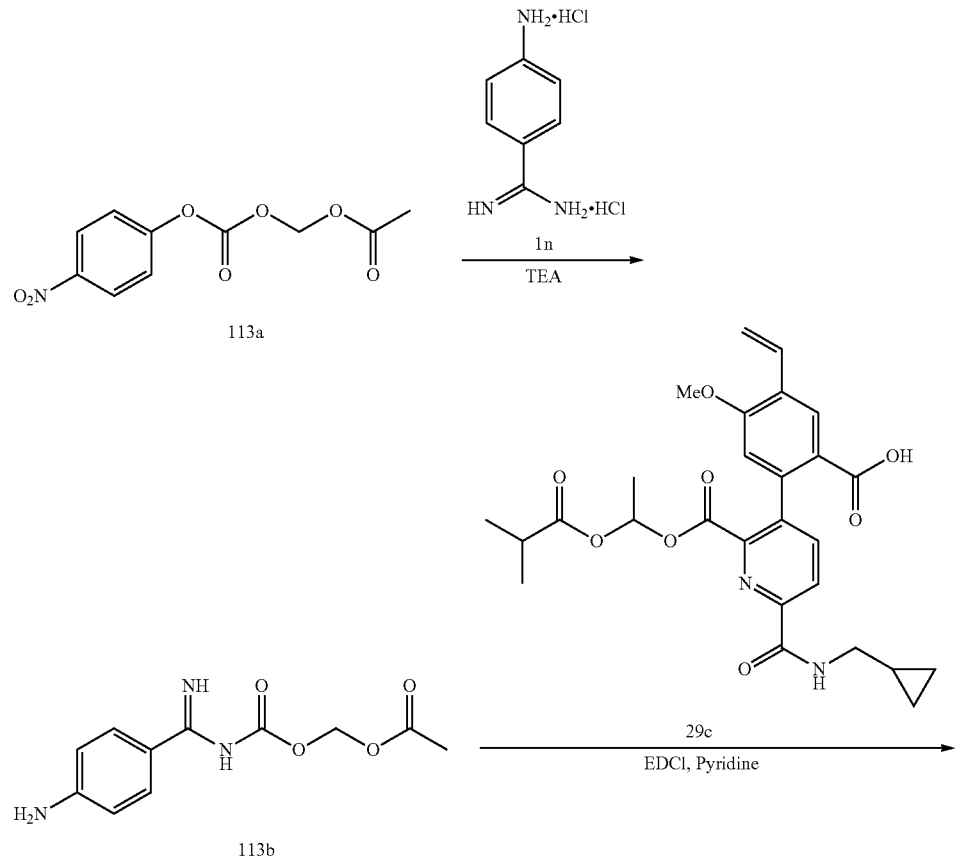

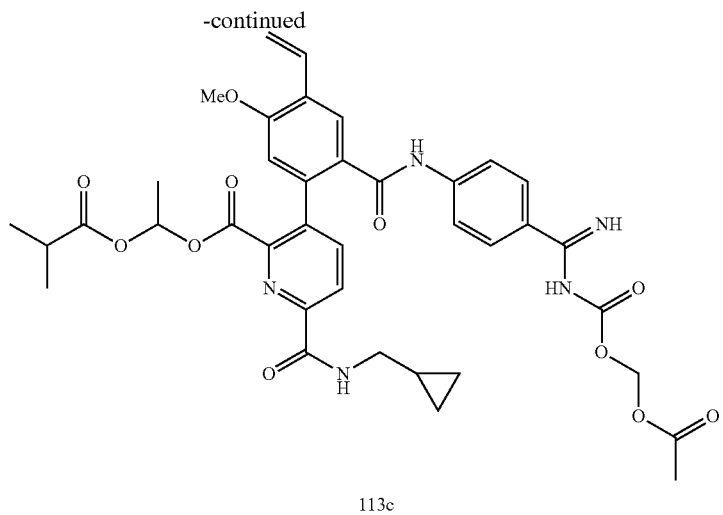

113c

Preparation of 1-(isobutyryloxy)ethyl 3-(2-((4-(N-((acetoxymethoxy)carbonyl)carbamimidoyl)phenyl)carbamoyl)-5-methoxy-4-vinylphenyl)-6-((cyclopropylmethyl)carbamoyl)picolinate (113c)

Step-1: Preparation of ((((4-aminophenyl)(imino)methyl)carbamoyl)oxy)methyl acetate (113b)

Compound (113b) was prepared according to the procedure described in step 1 of scheme 24 from 4-aminobenzimidamide dihydrochloride (1n) (2.6 g, 12.49 mmol) in DMF (5 mL) using (((4-nitrophenoxy)carbonyl)oxy)methyl acetate (113a) (3.51 g, 13.74 mmol, prepared according to the procedure reported by Alexander, Jose; in Eur. Pat. Appl., 167451) and triethylamine (5.22 mL, 37.5 mmol). This gave after workup and purification by flash column chromatography [silica gel 40 g, MeOH-EtOAc (9:1) in hexanes 0 to 80% as eluents] ((((4-aminophenyl)(imino)methyl)carbamoyl)oxy)methyl acetate (113b) (2.1 g, 67% yield) as a light orange solid; $^1$H NMR (300 MHz, DMSO-$d_6$) δ 9.16 (s, 1H), 8.89 (s, 1H), 7.78 (d, J=8.7 Hz, 2H), 6.61-6.51 (m, 2H), 5.94 (s, 2H), 5.69 (s, 2H), 2.06 (s, 3H).

Step-2: Preparation 1-(isobutyryloxy)ethyl 3-(2-((4-(N-((acetoxymethoxy)carbonyl)carbamimidoyl)phenyl)carbamoyl)-5-methoxy-4-vinylphenyl)-6-((cyclopropylmethyl)carbamoyl)picolinate (113c)

Compound (113c) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (2.44 g, 4.78 mmol) using EDCI (0.92 g, 4.78 mmol) and ((((4-aminophenyl)(imino)methyl)carbamoyl)oxy)methyl acetate (113b) (1.2 g, 4.78 mmol) in DMF (20 mL) and pyridine (8 mL) according to the procedure reported in step 4 of scheme 2. This gave after workup and purification by flash column chromatography [silica gel 40 g, MeOH-EtOAc (9:1) in hexanes 0 to 100% as eluents] 1-(isobutyryloxy)ethyl 3-(2-((4-(N-((acetoxymethoxy)carbonyl)carbamimidoyl)phenyl)carbamoyl)-5-methoxy-4-vinylphenyl)-6-((cyclopropylmethyl)carbamoyl)picolinate (113c) (1.62 g, 46% yield) as a white powder; $^1$H NMR (300 MHz, DMSO-$d_6$) δ 10.64-10.41 (m, 1H), 9.22 (s, 2H), 8.67-8.44 (m, 1H), 8.22 (d, J=8.0 Hz, 1H), 8.06-7.88 (m, 4H), 7.77-7.58 (m, 2H), 7.15-6.94 (m, 2H), 6.74 (s, 1H), 6.05 (d, J=17.7 Hz, 1H), 5.71 (s, 2H), 5.44 (d, J=11.4 Hz, 1H), 3.88 (s, 3H), 3.29-3.18 (m, 2H), 2.44-2.29 (m, 1H), 2.06 (s, 3H), 1.23-0.89 (m, 10H), 0.52-0.38 (m, 2H), 0.32-0.23 (m, 2H); MS (ES+) 744.0 (M+1), 767.0 (M+Na).

Scheme 114

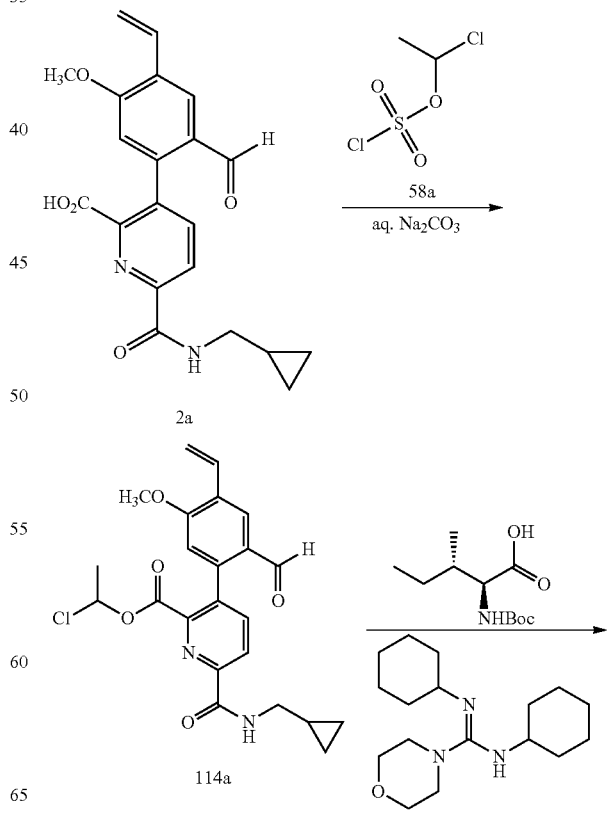

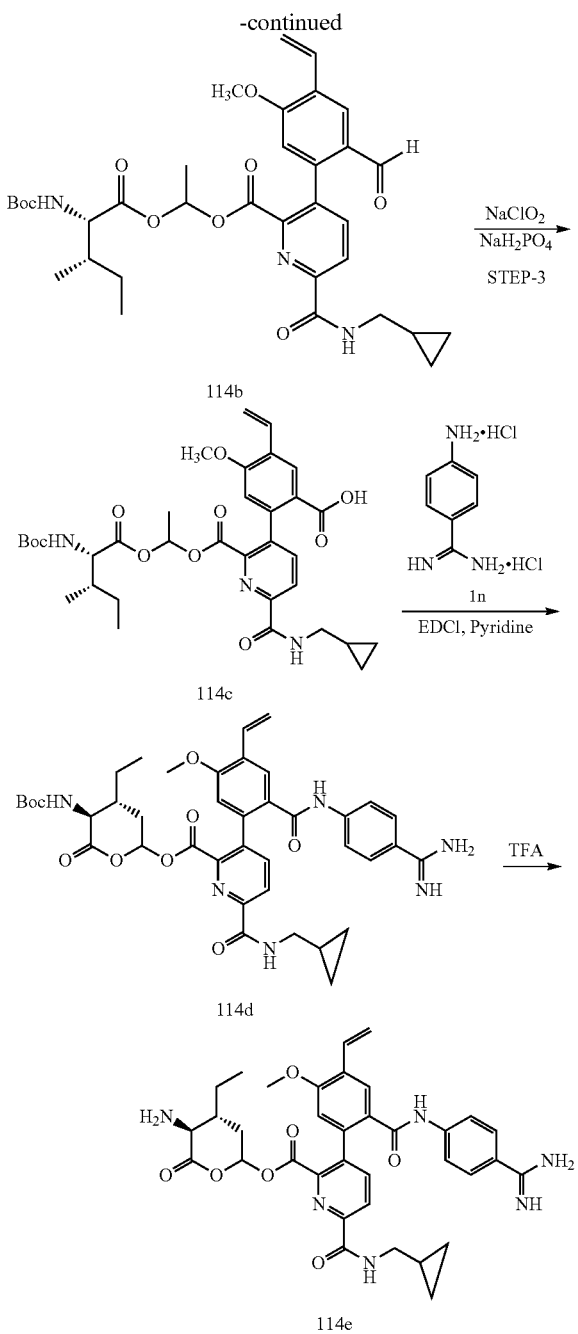

Preparation of (((2S,3S)-2-amino-3-methylpentanoyl)oxy)methyl 3-(2-((4-carbamimidoylphenyl)carbamoyl)-5-methoxy-4-vinylphenyl)-6-((cyclopropylmethyl)carbamoyl)picolinate (114e)

Step-1: Preparation of 1-chloroethyl 6-((cyclopropylmethyl)carbamoyl)-3-(2-formyl-5-methoxy-4-vinylphenyl)picolinate (114a)

Compound (114a) was prepared according to the procedure reported in step 1 of scheme 37 from 6-(cyclopropylmethylcarbamoyl)-3-(2-formyl-5-methoxy-4-vinylphenyl) picolinic acid (2a) (4 g, 10.52 mmol) in EtOAc (60 mL), water (60 mL) using tetra butyl ammonium hydrogen sulfate (0.36 g, 1.05 mmol) and 1-chloroethyl sulfochloridate (2.353 g, 13.14 mmol). This gave after workup 1-chloroethyl 6-((cyclopropylmethyl)carbamoyl)-3-(2-formyl-5-methoxy-4-vinylphenyl)picolinate (114a) (4.6 g, 99% yield) as light brown syrup; $^1$H NMR (300 MHz, DMSO-$d_6$) δ 9.71 (d, J=1.6 Hz, 1H), 8.73 (td, J=6.2, 2.4 Hz, 1H), 8.28 (dt, J=8.0, 2.2 Hz, 1H), 8.16 (s, 1H), 8.10 (dd, J=8.0, 2.0 Hz, 1H), 7.10-6.91 (m, 2H), 6.54 (qd, J=5.7, 3.1 Hz, 1H), 6.00 (dd, J=17.8, 1.4 Hz, 1H), 5.44 (d, J=11.3 Hz, 1H), 3.90 (s, 3H), 3.30-3.19 (m, 2H), 1.46 (dd, J=5.7, 3.4 Hz, 3H), 1.18-1.05 (m, 1H), 0.54-0.37 (m, 2H), 0.34-0.22 (m, 2H); MS (ES+) 465.3 (M+Na), (ES−) 477.2 (M+Cl).

Step-2: Preparation of 1-(((2S,3S)-2-((tert-butoxycarbonyl)amino)-3-methylpentanoyl)oxy)ethyl 6-((cyclopropylmethyl)carbamoyl)-3-(2-formyl-5-methoxy-4-vinylphenyl)picolinate (114b)

Compound (114b) was prepared according to the procedure reported in step 1 of scheme 8 from 1-chloroethyl 6-((cyclopropylmethyl)carbamoyl)-3-(2-formyl-5-methoxy-4-vinylphenyl)picolinate (114a) (4.5 g, 10.16 mmol) in DMF (25 mL) using N,N'-Dicyclohexyl-4-morpholinecarboxamidine (3.73 g, 12.7 mmol) and Boc-L isoleucine (2.82 g, 12.19 mmol). This gave after workup and purification by flash column chromatography (silica gel 40 g, eluting with ethyl acetate/Hexanes, 0-100%) 1-(((2S,3S)-2-((tert-butoxycarbonyl)amino)-3-methylpentanoyl)oxy)ethyl 6-((cyclopropylmethyl)carbamoyl)-3-(2-formyl-5-methoxy-4-vinylphenyl)picolinate (114b) (2.84 g, 44% yield) as a light yellow solid; $^1$H NMR (300 MHz, DMSO-$d_6$) δ 9.74-9.63 (m, 1H), 8.71-8.48 (m, 1H), 8.33-8.23 (m, 1H), 8.14 (d, J=5.3 Hz, 1H), 8.08 (d, J=8.0 Hz, 1H), 7.29-7.09 (m, 1H), 7.11-6.85 (m, 2H), 6.82-6.62 (m, 1H), 6.01 (d, J=17.8 Hz, 1H), 5.44 (d, J=11.3 Hz, 1H), 3.95-3.87 (m, 3H), 3.79 (d, J=6.1 Hz, 1H), 3.25 (s, 3H), 1.35 (d, J=3.8 Hz, 9H), 1.25 (dd, J=12.3, 7.2 Hz, 3H), 1.17 (dd, J=10.1, 6.0 Hz, 3H), 0.74 (td, J=15.5, 13.4, 9.6 Hz, 6H), 0.53-0.37 (m, 2H), 0.37-0.21 (m, 2H); MS (ES+) 660.4 (M+Na).

Step-3: Preparation of 2-(2-((6S)-6-((S)-sec-butyl)-3,10,10-trimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (114c)

Oxidation of 1-(((2S,3S)-2-((tert-butoxycarbonyl)amino)-3-methylpentanoyl)oxy)ethyl 6-((cyclopropylmethyl)carbamoyl)-3-(2-formyl-5-methoxy-4-vinylphenyl)picolinate (114b) (2.1 g, 3.29 mmol) using the procedure as reported in step 11 of scheme 1 gave after workup 2-(2-((6S)-6-((S)-sec-butyl)-3,10,10-trimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (114c) (2.51 g, 117% yield) as a yellow solid; MS (ES+) 654.3 (M+1), 676.4 (M+Na), (ES−) 652.5 (M−1).

Step-4: Preparation of 1-(((2S,3S)-2-((tert-butoxycarbonyl)amino)-3-methylpentanoyl)oxy)ethyl 3-(2-((4-carbamimidoylphenyl)carbamoyl)-5-methoxy-4-vinylphenyl)-6-((cyclopropylmethyl)carbamoyl) picolinate (114d)

Compound (114d) was prepared from 2-(2-((S)-6-((S)-sec-butyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (23c) (2.5 g, 3.82 mmol) using EDCI (1.5 equiv.) and hexyl 4-aminobenzimidamide dihydrochloride (1n) (0.915 g, 4.4 mmol) in DMF (5 mL) and Pyridine (5 mL) according to the procedure reported in step 4 of scheme 2. This gave after workup 1-(((2S,3S)-2-((tert-butoxycarbonyl)amino)-3-methylpentanoyl)oxy)ethyl 3-(2-((4-carbamimidoylphenyl)carbamoyl)-5-methoxy-4-vinylphenyl)-6-((cyclopropylmethyl)carbamoyl)picolinate (114d) (2.25 g, 73% yield) which was used in next step without further purification; MS (ES+) 771.5 (M+1), (ES−) 805.6 (M+Cl).

Step-5: Preparation of 1-(((2S,3S)-2-amino-3-methylpentanoyl)oxy)ethyl 3-(2-((4-carbamimidoylphenyl)carbamoyl)-5-methoxy-4-vinylphenyl)-6-((cyclopropylmethyl)carbamoyl)picolinate (114e)

Compound (114e) was prepared from (((2S,3S)-2-((tert-butoxycarbonyl)amino)-3-methylpentanoyl)oxy)methyl 3-(2-((4-carbamimidoylphenyl)carbamoyl)-5-methoxy-4-vinylphenyl)-6-((cyclopropylmethyl)carbamoyl)picolinate (114d) (2.21 g, 2.74 mmol) in dichloromethane (20 mL) using 2,2,2-trifluoroacetic acid (4.22 mL, 54.7 mmol) according to the procedure reported in Step-4 of scheme 8. This gave after workup and purification by flash column chromatography (C18, 26 g) eluting with 0.1% HCl and acetonitrile followed by lyophilization 1-(((2S,3S)-2-amino-3-methylpentanoyl)oxy)ethyl 3-(2-((4-carbamimidoylphenyl)carbamoyl)-5-methoxy-4-vinylphenyl)-6-((cyclopropylmethyl)carbamoyl)picolinate (114e) (0.960 g, 47.2% yield) as a light brown solid. $^1$H NMR (300 MHz, DMSO-$d_6$) δ 10.89-10.65 (m, 1H, $D_2O$ exchangeable), 9.28 (s, 2H, $D_2O$ exchangeable), 9.05 (s, 2H, $D_2O$ exchangeable), 8.73-8.39 (m, 4H, 3H $D_2O$ exchangeable), 8.24 (d, J=8.0 Hz, 1H), 8.13-7.96 (m, 2H), 7.90-7.71 (m, 4H), 7.12-6.94 (m, 2H), 6.87 (q, J=5.3 Hz, 1H), 6.17-6.01 (m, 1H), 5.45 (d, J=11.4 Hz, 1H), 3.89 (d, J=2.8 Hz, 3H), 3.80 (s, 1H), 3.24 (s, 2H), 1.95-1.67 (m, 1H), 1.44-0.97 (m, 6H), 0.93-0.67 (m, 6H), 0.52-0.39 (m, 2H), 0.35-0.20 (m, 2H); MS (ES+) 671.5 (M+1), 693.4 (M+Na); Analysis calculated for: $C_{36}H_{42}N_6O_7$·2HCl·4$H_2O$: C, 53.01; H, 6.43; N, 10.30; Cl, 8.69; found; C, 53.10; H, 6.28; N, 10.38; Cl, 8.61.

Scheme 115

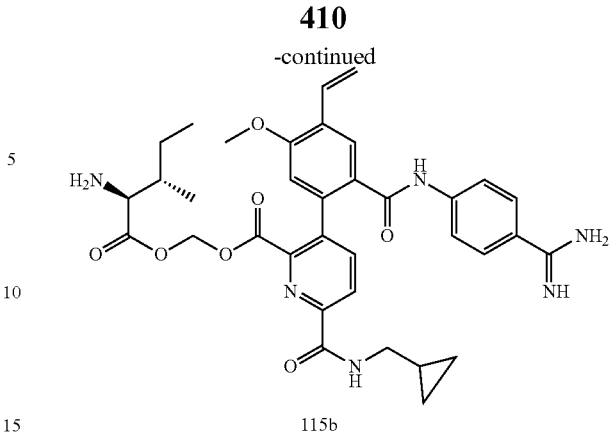

Preparation of (((2S,3S)-2-amino-3-methylpentanoyl)oxy)methyl 3-(2-((4-carbamimidoylphenyl)carbamoyl)-5-methoxy-4-vinylphenyl)-6-((cyclopropylmethyl)carbamoyl)picolinate (115b)

Step-1: Preparation of (((2S,3S)-2-((tert-butoxycarbonyl)amino)-3-methylpentanoyl)oxy)methyl 3-(2-((4-carbamimidoylphenyl)carbamoyl)-5-methoxy-4-vinylphenyl)-6-((cyclopropylmethyl)carbamoyl)picolinate (115a)

Compound (15a) was prepared from 2-(2-((S)-6-((S)-sec-butyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (62b) (3.0 g, 4.69 mmol) using EDCI (1.5 equiv.) and hexyl 4-aminobenzimidamide dihydrochloride (1n) (1.12 g, 5.39 mmol) in DMF (5 mL) and Pyridine (5 mL) according to the procedure reported in step 4 of scheme 2. This gave after workup and purification by combiflash (silica gel, 80 g) eluting with methanol in dichloromethane 0 to 20%) (((2S,3S)-2-((tert-butoxycarbonyl)amino)-3-methylpentanoyl)oxy)methyl 3-(2-((4-carbamimidoylphenyl)carbamoyl)-5-methoxy-4-vinylphenyl)-6-((cyclopropylmethyl)carbamoyl)picolinate (115a) (2.25 g, 73% yield) as a white solid; $^1$H NMR (300 MHz, DMSO-$d_6$) δ 10.77 (s, 1H), 9.23 (s, 2H), 9.03 (s, 2H), 8.42 (s, 1H), 8.24 (d, J=8.0 Hz, 1H), 8.02 (d, J=22.7 Hz, 2H), 7.79 (s, 4H), 7.28 (d, J=7.7 Hz, 1H), 7.12-6.93 (m, 2H), 6.06 (d, J=17.8 Hz, 1H), 5.96-5.61 (m, 2H), 5.45 (d, J=11.4 Hz, 1H), 3.90 (s, 3H), 3.87-3.82 (m, 1H), 3.28-3.18 (m, 2H), 1.75-1.55 (m, 1H), 1.42-1.19 (m, 10H), 1.10 (dq, J=13.5, 7.4, 6.8 Hz, 2H), 0.73 (t, J=7.1 Hz, 6H), 0.51-0.39 (m, 2H), 0.32-0.20 (m, 2H); MS (ES+) 757.5 (M+1).

Step-2: Preparation of (((2S,3S)-2-amino-3-methylpentanoyl)oxy)methyl 3-(2-((4-carbamimidoylphenyl)carbamoyl)-5-methoxy-4-vinylphenyl)-6-((cyclopropylmethyl)carbamoyl)picolinate (115b)

Compound (115b) was prepared from (((2S,3S)-2-((tert-butoxycarbonyl)amino)-3-methylpentanoyl)oxy)methyl 3-(2-((4-carbamimidoylphenyl)carbamoyl)-5-methoxy-4-vinylphenyl)-6-((cyclopropylmethyl)carbamoyl)picolinate (115a) (1.15 g, 1.45 mmol) in dichloromethane (20 mL) using 2,2,2-trifluoroacetic acid (2.23 mL, 29.0 mmol) according to the procedure reported in Step-4 of scheme 8. This gave after workup and purification by flash column chromatography (C18, 26 g) eluting with 0.1% HCl and acetonitrile followed by lyophilization (((2S,3S)-2-amino- 3-methylpentanoyl)oxy)methyl 3-(2-((4-carbamimidoylphenyl)carbamoyl)-5-methoxy-4-vinylphenyl)-6-((cyclopropylmethyl)carbamoyl)picolinate (115b) (0.370 g, 35% yield) as a white solid. $^1$H NMR (300 MHz, DMSO-d$_6$) δ 10.80 (s, 1H, D$_2$O exchangeable), 9.26 (s, 2H, D$_2$O exchangeable), 8.99 (s, 2H, D$_2$O exchangeable), 8.52 (d, J=29.4 Hz, 4H, 3H D$_2$O exchangeable), 8.25 (d, J=8.0 Hz, 1H), 8.04 (d, J=12.3 Hz, 2H), 7.80 (s, 4H), 7.15-6.94 (m, 2H), 6.09 (d, J=18.0 Hz, 1H), 5.90 (d, J=35.2 Hz, 2H), 5.45 (d, J=11.4 Hz, 1H), 3.90 (d, J=4.8 Hz, 4H), 3.22 (d, J=8.3 Hz, 2H), 1.83 (s, 1H), 1.43-1.24 (m, 1H), 1.24-0.98 (m, 2H), 0.88-0.69 (m, 6H), 0.44 (dd, J=7.0, 5.2 Hz, 2H), 0.28 (t, J=4.9 Hz, 2H); MS (ES+) 657.4 (M+1), 679.4 (M+Na), (ES−) 691.5 (M+Cl); Analysis calculated for MF: C$_{35}$H$_{40}$N$_6$O$_7$·2HCl·3H$_2$O: C, 53.64; H, 6.17; N, 10.72; Cl, 9.05; found: C, 53.30; H, 6.17; N, 10.67; Cl, 9.07.

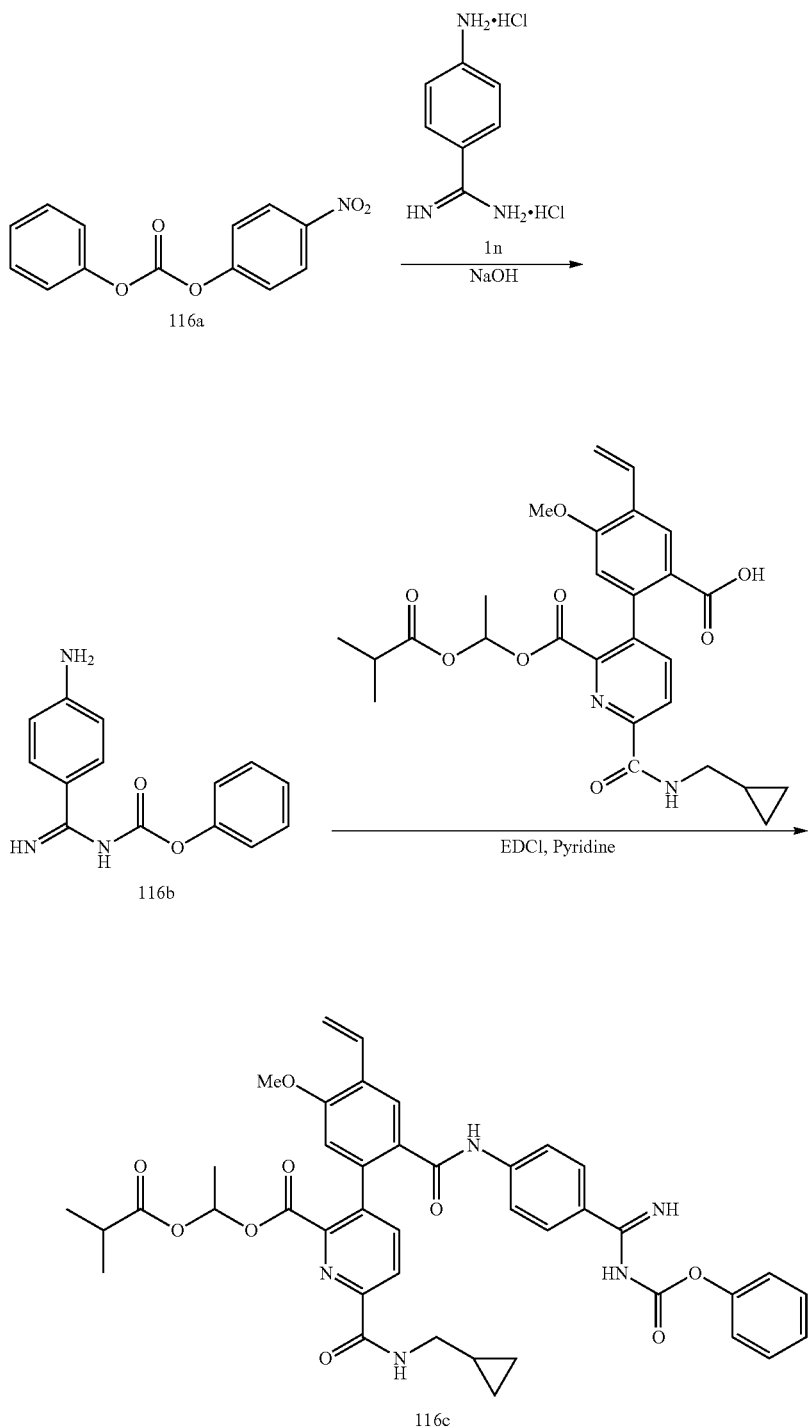

Scheme 116

Preparation of 1-(isobutyryloxy)ethyl 6-((cyclopropylmethyl)carbamoyl)-3-(5-methoxy-2-((4-(N-(phenoxycarbonyl)carbamimidoyl)phenyl)carbamoyl)-4-vinylphenyl)picolinate (116c)

Step-1: Preparation of phenyl ((4-aminophenyl)(imino)methyl)carbamate (116b)

Compound (116b) was prepared according to the procedure reported in step 4 of scheme 23 from 4-aminobenzimidamide dihydrochloride (1n) (6 g, 28.8 mmol) in acetone/H$_2$O (52 mL, Ratio: 12:1, v/v) using sodium hydroxide (2.42 g, 60.6 mmol) and 4-nitrophenyl phenyl carbonate (116a) (11.21 g, 43.3 mmol, prepared according to the procedure reported by Urn, Ik-Hwan et al; in Bulletin of the Chemical Society of Japan, 85(9), 1007-1013; 2012). This gave after workup and purification by flash column chromatography [first column: silica gel (80 g), eluting with DMA80 in DCM from 0-50%; second column: silica gel (80 g), eluting with EtOAc/MeOH (9:1) in hexane from 0-100%] phenyl ((4-aminophenyl)(imino)methyl)carbamate (116b) (1.75 g, 24% yield) as a yellow solid. $^1$H NMR (300 MHz, DMSO-d$_6$) δ 9.11 (s, 1H, D$_2$O exchangeable), 8.88 (s, 1H, D$_2$O exchangeable), 7.79 (d, J=8.5 Hz, 2H), 7.44-7.21 (m, 2H), 7.22-7.00 (m, 3H), 6.56 (d, J=8.6 Hz, 2H), 5.95 (s, 2H, D$_2$O exchangeable); MS (ES+) 256.3 (M+1); 278.3 (M+Na).

Step-2: Preparation of 1-(isobutyryloxy)ethyl 6-((cyclopropylmethyl)carbamoyl)-3-(5-methoxy-2-((4-(N-(phenoxycarbonyl)carbamimidoyl)phenyl)carbamoyl)-4-vinylphenyl)picolinate (116c)

Compound (110c) was prepared from 2-(6-((cyclopropylmethyl)carbamoyl)-2-((1-(isobutyryloxy)ethoxy)carbonyl)pyridin-3-yl)-4-methoxy-5-vinylbenzoic acid (29c) (2.97 g, 5.82 mmol) using EDCI (1.52 g, 7.93 mmol) and phenyl ((4-aminophenyl)(imino)methyl)carbamate (116b) (1.35 g, 6.05 mmol) in DMF (15 mL) and pyridine (15 mL) according to the procedure reported in step 4 of scheme 2. This gave after workup and purification by flash column chromatography [first column: silica (24 g), eluting with EtOAc/MeOH (9:1) in hexane from 0-40%; second column: prep-HPLC [C18 column, eluting with CH$_3$CN in water (containing 0.1% HCl) from 0-100%] 1-(isobutyryloxy)ethyl 6-((cyclopropylmethyl)carbamoyl)-3-(5-methoxy-2-((4-(N-(phenoxycarbonyl)carbamimidoyl)phenyl)carbamoyl)-4-vinylphenyl)picolinate (116c) (192 mg, 0.257 mmol, 4.86% yield) as a white solid; $^1$H NMR (300 MHz, DMSO-d$_6$) δ 10.71 (d, J=19.9 Hz, 1H, D$_2$O exchangeable), 10.13 (s, 1H, D$_2$O exchangeable), 8.58 (d, J=26.3 Hz, 1H, D$_2$O exchangeable), 8.23 (d, J=8.0 Hz, 1H), 8.02 (s, 2H), 7.95-7.65 (m, 5H), 7.55-7.39 (m, 2H), 7.37-7.20 (m, 3H), 7.07-6.94 (m, 2H), 6.74 (d, J=6.7 Hz, 1H), 6.07 (d, J=17.8 Hz, 1H), 5.45 (d, J=11.4 Hz, 1H), 3.89 (s, 3H), 3.28-3.17 (m, 2H), 2.46-2.32 (m, 1H), 1.18 (d, J=5.3 Hz, 3H), 1.14-1.05 (m, 1H), 1.03-0.95 (m, 6H), 0.51-0.39 (m, 2H), 0.33-0.21 (m, 2H); MS (ES$^+$) 748.4 (M+1), 770.4 (M+Na), 782.4 (M+Cl); Analysis calculated for C$_{41}$H$_{41}$N$_5$O$_9$.1.75H$_2$O.HCl C, 60.36; H, 5.62; Cl, 4.35; N, 8.58. Found: C, 60.54; H, 5.63; Cl, 3.98; N, 8.58.

Scheme 117

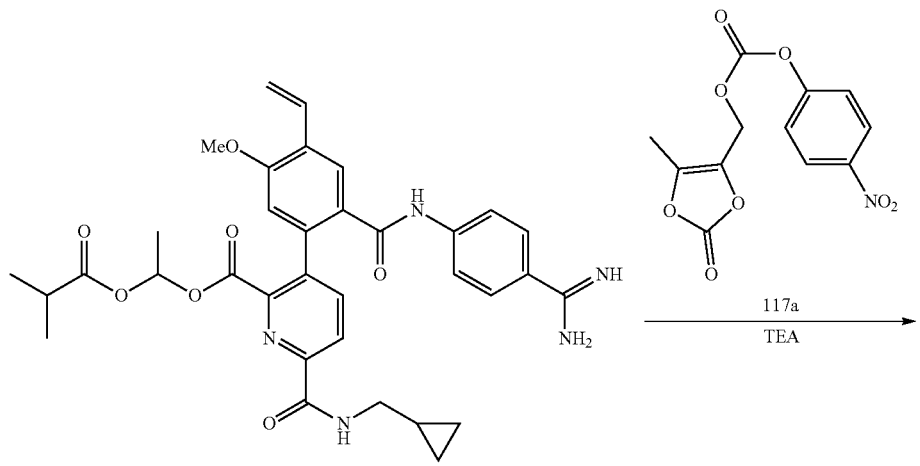

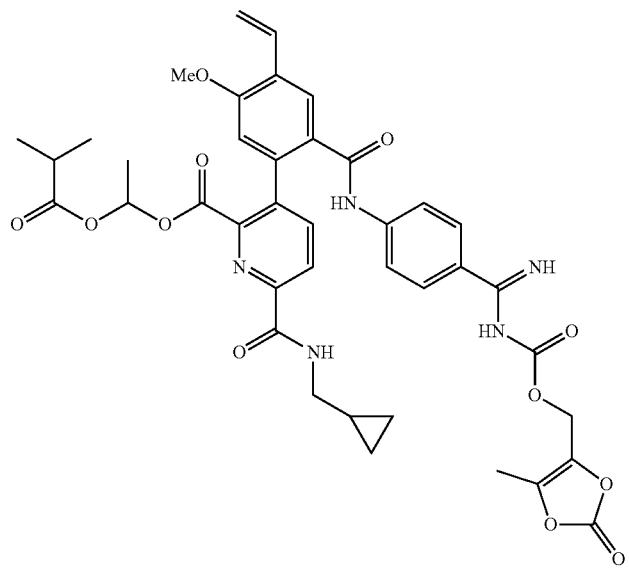

117b

Preparation of 1-(isobutyryloxy)ethyl 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinate (117b)

To a solution of 1-(isobutyryloxy)ethyl 3-(2-(4-carbamimidoylphenylcarbamoyl)-5-methoxy-4-vinylphenyl)-6-(cyclopropylmethylcarbamoyl)picolinate (29d) (0.3 g, 0.478 mmol) in DMF (5 mL) was added TEA (0.133 mL, 0.956 mmol), (5-methyl-2-oxo-1,3-dioxol-4-yl)methyl 4-nitrophenyl carbonate (117a) (0.169 g, 0.574 mmol; prepared according to the procedure reported by Rabmathullah, Syed M. et al; in Journal of Medicinal Chemistry, 42(19), 3994-4000; 1999) and stirred at room temperature for 2 h. Mixture was poured into water (100 mL) and resultant suspension extracted with EtOAc (2×80 mL). The combined organics were washed with brine, dried, filtered, concentrated in vacuum and purified by flash column chromatography [silica gel 12 g, MeOH-EtOAc (9:1) in hexanes 0 to 80% as eluents] to afford 1-(isobutyryloxy)ethyl 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinate (117b) (0.16 g, 43% yield) as a white powder; $^1$H NMR (300 MHz, DMSO-$d_6$) δ 10.63-10.42 (m, 1H), 9.25-9.00 (m, 2H), 8.66-8.46 (m, 1H), 8.22 (d, J=8.0 Hz, 1H), 8.06-7.59 (m, 6H), 7.11-6.95 (m, 2H), 6.81-6.67 (m, 1H), 6.11-6.00 (m, 1H), 5.44 (d, J=11.3 Hz, 1H), 4.92 (s, 2H), 3.88 (s, 3H), 3.27-3.18 (m, 2H), 2.46-2.30 (m, 1H), 2.17 (s, 3H), 1.21-0.90 (m, 10H), 0.49-0.39 (m, 2H), 0.30-0.24 (m, 2H); MS (ES+) 784.5 (M+1); Analysis calculated for $C_{40}H_{41}N_5O_{12} \cdot H_2O$; C, 59.92; H, 5.41; N, 8.73; found C, 60.11; H, 5.46; N, 8.66.

Scheme 118

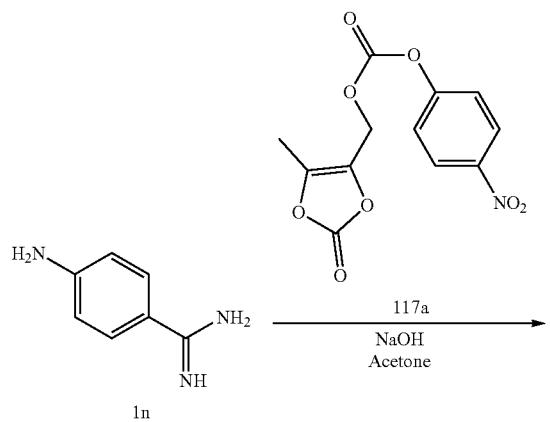

-continued
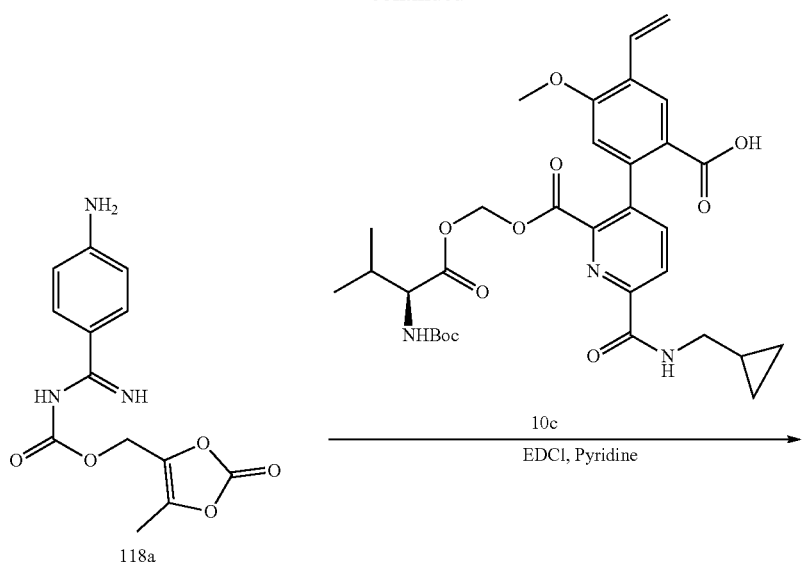
118a
10c
EDCl, Pyridine
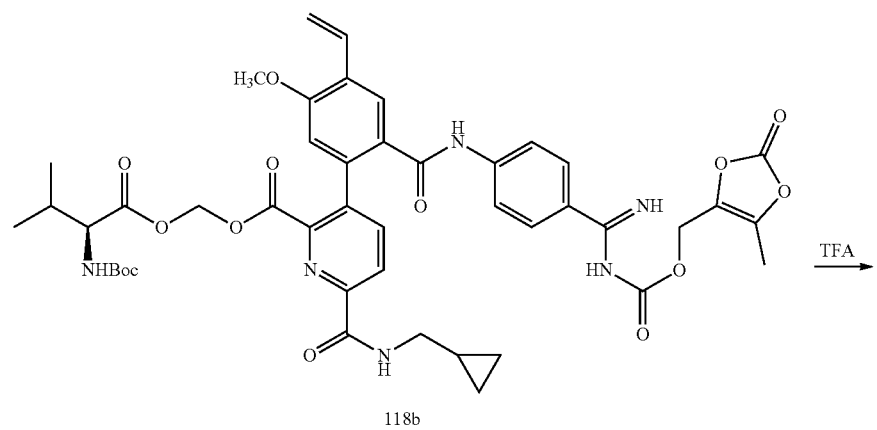
118b
TFA
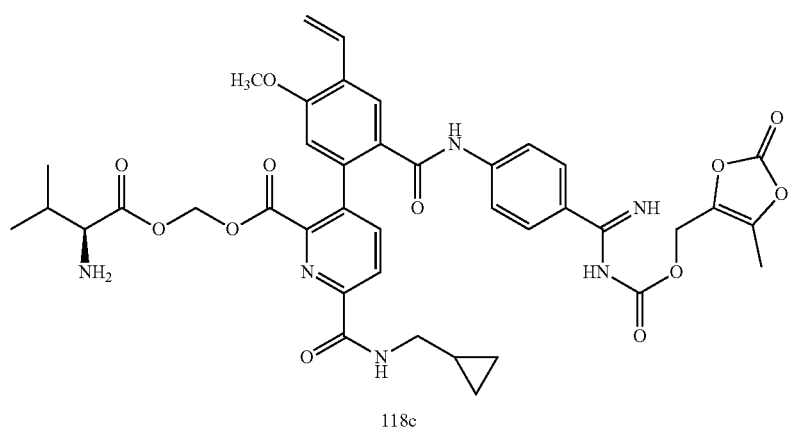
118c

Preparation of (S)-((2-amino-3-methylbutanoyl)oxy) methyl 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinate (118c)

Step-1: Preparation of (5-methyl-2-oxo-1,3-dioxol-4-yl)methyl ((4-aminophenyl)(imino)methyl)carbamate (118b)

Compound (118b) was prepared from 4-aminobenzimidamide dihydrochloride (1n) (4.09 g, 19.65 mmol) in acetone (60 mL), water (20 mL) using sodium hydroxide (1.73 g, 43.2 mmol) and (5-methyl-2-oxo-1,3-dioxol-4-yl)methyl (4-nitrophenyl) carbonate (117a) (5.8 g, 19.65 mmol) according to the procedure reported in step 4 of scheme 23. This gave after workup and purification by flash column chromatography [silica gel, 80 g, eluting with ethyl acetate in hexanes from 0 to 100%] (5-methyl-2-oxo-1,3-dioxol-4-yl)methyl ((4-aminophenyl)(imino)methyl)carbamate (118b) (1.8 g, 32% yield) as a solid; MS (ES+) 314.3 (M+Na), MS (ES−) 290.3 (M−1).

Step-2: Preparation (S)-((2-((tert-butoxycarbonyl)amino)-3-methylbutanoyl)oxy)methyl 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl) picolinate (118b)

Compound (118b) was prepared from (S)-2-(6-((cyclopropylmethyl)carbamoyl)-2-(6-isopropyl-10,10-dimethyl-5,8-dioxo-2,4,9-trioxa-7-azaundecan-1-oyl)pyridin-3-yl)-4-methoxy-5-vinylbenzoic acid (10c) (0.8 g, 1.28 mmol) using EDCI (0.25 g, 1.28 mmol) and ((5-methyl-2-oxo-1,3-dioxol-4-yl)methyl ((4-aminophenyl)(imino)methyl)carbamate (118b) (0.37 g, 1.28 mmol) in DMF (8 mL) and pyridine (3 mL) according to the procedure reported in step 4 of scheme 2. This gave after workup and purification by flash column chromatography [silica gel 12 g, using MeOH:EtOAc (9:1) in hexanes 0 to 100% as eluents](S)-((2-((tert-butoxycarbonyl)amino)-3-methylbutanoyl)oxy)methyl 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinate (118b) (0.32 g, 0.356 mmol, 27.8% yield) as a gummy solid; MS (ES+) 899.5 (M+1), 921.6 (M+Na).

Step-3: Preparation of (S)-((2-amino-3-methylbutanoyl)oxy)methyl 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinate (118c)

Compound (118a) was prepared from ((S)-((2-((tert-butoxycarbonyl)amino)-3-methylbutanoyl)oxy)methyl 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinate (118b) (0.32 g, 0.36 mmol) in dichloromethane (5 mL) using 2,2,2-trifluoroacetic acid (0.55 mL, 7.12 mmol). This gave after workup and purification by reverse phase column chromatography [EZ-PREP, C-18 column, 26 g, eluting with 0.1% aqueous HCl in water and in acetonitrile from 0-50%] followed by lyophilization (S)-((2-amino-3-methylbutanoyl)oxy)methyl 6-((cyclopropylmethyl)carbamoyl)-3-(5-methoxy-2-((4-(N-(((5-methyl-2-oxo-1,3-dioxol-4-yl)methoxy)carbonyl)carbamimidoyl)phenyl)carbamoyl)-4-vinylphenyl)picolinate (118c) (0.11 g, 39% yield) as a light orange solid; $^1$H NMR (300 MHz, DMSO-$d_6$) δ 10.77 (s, 1H), 8.65-8.41 (m, 5H), 8.25 (d, J=8.0 Hz, 1H), 8.09-7.97 (m, 2H), 7.88-7.71 (m, 4H), 7.11-6.96 (m, 2H), 6.15-6.03 (m, 1H), 6.03-5.71 (m, 2H), 5.51-5.41 (m, 1H), 5.15 (s, 2H), 3.97-3.83 (m, 4H), 3.29-3.15 (m, 2H), 2.21 (s, 3H), 2.15-2.00 (m, 1H), 1.16-0.99 (m, 1H), 0.87 (d, J=6.9 Hz, 6H), 0.50-0.41 (m, 2H), 0.32-0.23 (m, 2H); MS (ES+) 799.5 (M+1), MS (ES−) 833.6 (M+Cl); Analysis calculated for $C_{40}H_{42}N_6O_{12}\cdot 2HCl\cdot 3H_2O$; C, 51.90; H, 5.44; N, 9.08; Cl, 7.66; found C, 51.50; H, 5.50; N, 9.04; Cl, 7.38.

Scheme 119

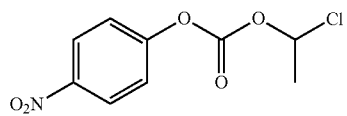

23c

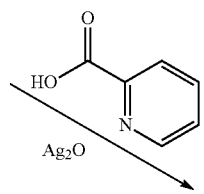

Ag$_2$O

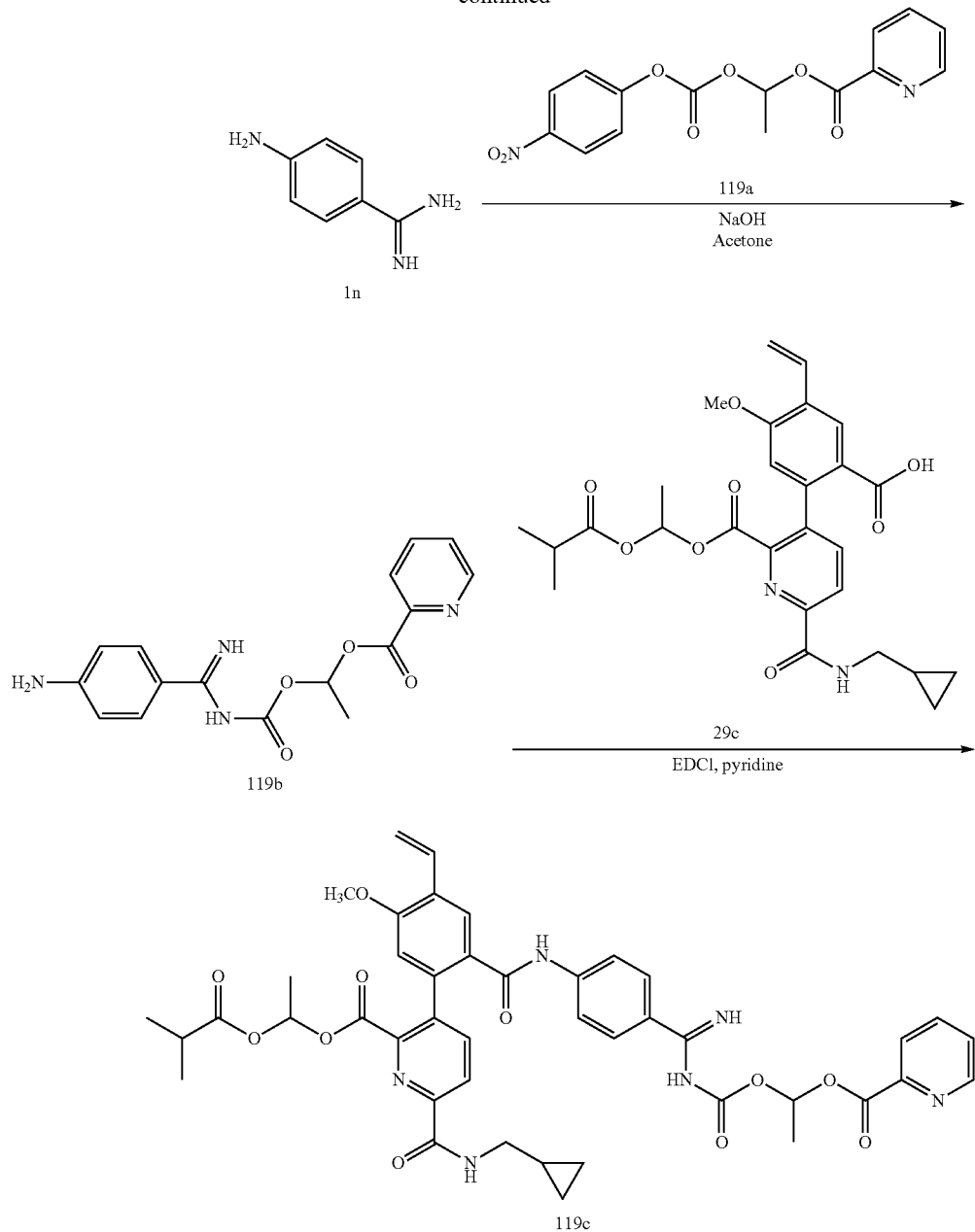

Preparation of 1-(isobutyryloxy)ethyl 3-(2-((4-(N-((1-(benzoyloxy)ethoxy)carbonyl)carbamimidoyl)phenyl)carbamoyl)-5-methoxy-4-vinylphenyl)-6-((cyclopropylmethyl)carbamoyl)picolinate (119c)

Step-1: Preparation of 1-(((4-nitrophenoxy)carbonyl)oxy)ethyl benzoate (119a)

Compound (109a) was prepared according to the procedure reported in step 1 of scheme 33 from 1-chloroethyl (4-nitrophenyl) carbonate (23c) (20 g, 81 mmol), picolinic acid (30.1 g, 244 mmol), and silver oxide (18.87 g, 81 mmol). This gave after workup and purification by flash column chromatography [silica gel 120 g, eluting with ethyl acetate in hexanes from 0-100%] to furnish 1-((4-nitrophenoxy)carbonyloxy)ethyl picolinate (119a) (2.53 g, 9% yield) as a clear thick oil; $^1$H NMR (300 MHz, DMSO-$d_6$) δ 8.82-8.73 (m, 1H), 8.42-8.26 (m, 2H), 8.19-8.10 (m, 1H), 8.05 (td, J=7.7, 1.7 Hz, 1H), 7.76-7.68 (m, 1H), 7.64-7.56 (m, 2H), 7.05 (q, J=5.4 Hz, 1H), 1.71 (d, J=5.4 Hz, 3H); MS (ES+): 355.2 (M+Na).

Step-2: Preparation of 1-(((((4-aminophenyl)(imino)methyl)carbamoyl)oxy)ethyl benzoate (119b)

Compound (119b) was prepared from 4-aminobenzimidamide dihydrochloride (1n) (1.685 g, 8.10 mmol) in acetone (25 mL), NaOH (1 N solution, 17.00 mL, 17.00 mmol) and 1-((4-nitrophenoxy)carbonyloxy)ethyl picolinate (119a)

(2.69 g, 8.10 mmol) according to the procedure reported in step 4 of scheme 23. This gave after workup 1-((4-aminophenyl)(imino)methylcarbamoyloxy)ethyl picolinate (119b) (1.72 g, 65% yield) as a yellow solid; $^1$H NMR (300 MHz, DMSO-$d_6$) δ 9.18 (bs, 1H, $D_2O$ exchangeable), 8.88 (s, 1H, $D_2O$ exchangeable), 8.73 (d, J=4.7 Hz, 1H), 8.15-7.95 (m, 2H), 7.78 (d, J=8.4 Hz, 2H), 7.67 (t, J=6.1 Hz, 1H), 7.16-6.97 (m, 1H), 6.54 (d, J=8.3 Hz, 2H), 5.95 (bs, 2H, $D_2O$ exchangeable), 1.58 (d, J=5.4 Hz, 3H); MS (ES+): 351.2 (M+Na); MS (ES−): 363.3 (M+Cl).

Step-3: Preparation of 1-(isobutyryloxy)ethyl 6-(cyclopropylmethylcarbamoyl)-3-(5-methoxy-2-(4-(N-((1-(picolinoyloxy)ethoxy)carbonyl)carbamimidoyl)phenylcarbamoyl)-4-vinylphenyl)picolinate (119c)

Compound (119c) was prepared from 2-(6-(cyclopropylmethylcarbamoyl)-2-((1-(isobutyryloxy)ethoxy)carbonyl)pyridin-3-yl)-4-methoxy-5-vinylbenzoic acid (29c) (3.13 g, 6.14 mmol) (2.25 g, 4.40 mmol) using EDCI (1.05 g, 5.50 mmol) and 1-((4-aminophenyl)(imino)methylcarbamoyloxy)ethyl picolinate (119b) (1.68 g, 5.12 mmol) in DMF (30 mL) and Pyridine (15 mL) according to the procedure reported in step 4 of scheme 2. This gave after workup and purification by flash column chromatography [silica gel 80 g, eluting with ethyl acetate/methanol (9:1) in hexanes from 0-100%] 1-(isobutyryloxy)ethyl 6-(cyclopropylmethylcarbamoyl)-3-(5-methoxy-2-(4-(N-((1-(picolinoyloxy)ethoxy)carbonyl)carbamimidoyl)phenylcarbamoyl)-4-vinylphenyl)picolinate (119c) (0.69 g, 16% yield) as an off-white solid; $^1$H NMR (300 MHz, DMSO-$d_6$) δ 10.65-10.38 (m, 1H, $D_2O$ exchangeable), 9.42-9.05 (m, 1H), 8.74 (t, J=5.7 Hz, 1H), 8.68-8.44 (m, 1H, $D_2O$ exchangeable), 8.22 (d, J=8.0 Hz, 1H), 8.15-7.90 (m, 6H), 7.85 (d, J=8.4 Hz, 1H), 7.74-7.57 (m, 3H), 7.15-6.92 (m, 3H), 6.74 (s, 1H), 6.05 (d, J=17.8 Hz, 1H), 5.44 (d, J=11.4 Hz, 1H), 3.89 (s, 3H), 3.29-3.16 (m, 2H), 2.46-2.29 (m, 1H), 1.62 (dd, J=17.2, 5.4 Hz, 3H), 1.29-0.86 (m, 10H), 0.51-0.39 (m, 2H), 0.34-0.23 (m, 2H); MS (ES+): 821.4 (M+1), 843.3 (M+Na); MS (ES−): 820.6 (M−1).

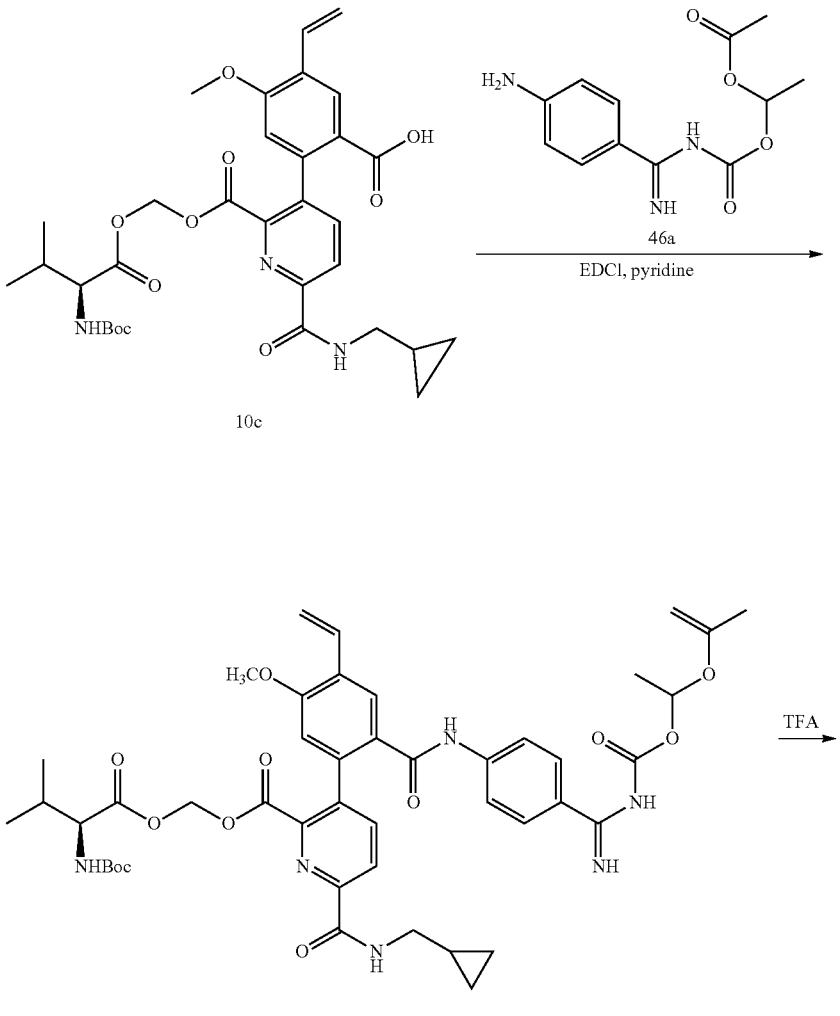

Scheme 120

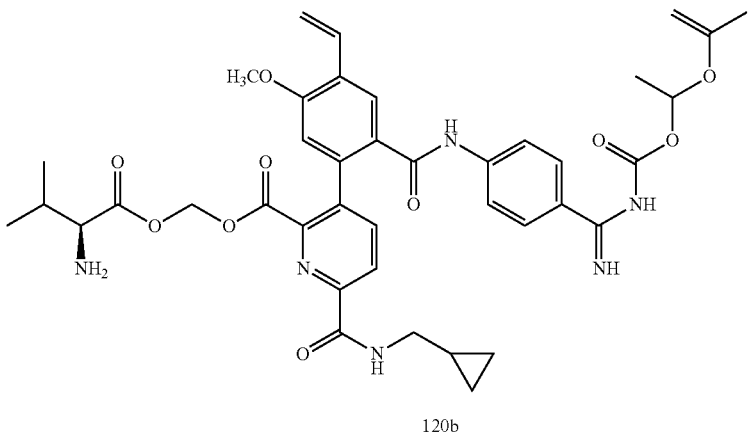

120b

Preparation of (((S)-2-amino-3-methylbutanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (120b)

Step-1: Preparation of (((S)-2-((tert-butoxycarbonyl)amino)-3-methylbutanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (120a)

Compound (120a) was prepared from (S)-2-(6-((cyclopropylmethyl)carbamoyl)-2-(6-isopropyl-10,10-dimethyl-5,8-dioxo-2,4,9-trioxa-7-azaundecan-1-oyl)pyridin-3-yl)-4-methoxy-5-vinylbenzoic acid (10c) (3 g, 4.79 mmol) using EDCI (1.1 g, 5.75 mmol) and 1-((((4-aminophenyl)(imino)methyl)carbamoyl)oxy)ethyl acetate (46a) (1.27 g, 4.79 mmol) in DMF (20 mL) and pyridine (7 mL) according to the procedure reported in step 4 of scheme 2. This gave after workup and purification by flash column chromatography [silica gel 40 g, using MeOH:EtOAc (9:1) in hexanes 0 to 100% as eluents] (((S)-2-((tert-butoxycarbonyl)amino)-3-methylbutanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (120a) (2.84 g, 68% yield) as a colorless foam; $^1$H NMR (300 MHz, DMSO-$d_6$) δ 10.56 (s, 1H), 9.32-9.08 (m, 2H), 8.51-8.36 (m, 1H), 8.24 (d, J=8.0 Hz, 1H), 8.02 (d, J=8.0 Hz, 1H), 7.95 (d, J=8.9 Hz, 3H), 7.68 (d, J=8.6 Hz, 2H), 7.25 (d, J=7.8 Hz, 1H), 7.14-6.94 (m, 2H), 6.76 (q, J=5.4 Hz, 1H), 6.05 (d, J=17.8 Hz, 1H), 5.95-5.57 (m, 2H), 5.44 (d, J=11.4 Hz, 1H), 3.89 (s, 3H), 3.82 (t, J=7.1 Hz, 1H), 3.28-3.16 (m, 2H), 1.99 (s, 3H), 1.97-1.85 (m, 1H), 1.43 (d, J=5.4 Hz, 3H), 1.33 (s, 9H), 1.14-0.99 (m, 1H), 0.79 (d, J=6.8 Hz, 6H), 0.52-0.39 (m, 2H), 0.31-0.21 (m, 2H); MS (ES+) 873.5 (M+1), 871.6 (M−1).

Step-2: Preparation (((S)-2-amino-3-methylbutanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (120b)

Compound (120b) was prepared from (((S)-2-((tert-butoxycarbonyl)amino)-3-methylbutanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (120a) (2.8 g, 3.21 mmol) in dichloromethane (30 mL) using 2,2,2-trifluoroacetic acid (3.71 mL, 48.1 mmol). This gave after workup and purification by reverse phase column chromatography [C18, 130 g, eluting with 0.1% aqueous HCl in water and in acetonitrile from 0-50%] followed by lyophilization HCl salt of (((S)-2-amino-3-methylbutanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (120b) (0.81 g, 31% yield) as a white powder; $^1$H NMR (300 MHz, DMSO-$d_6$) δ 10.77 (s, 1H), 8.65-8.40 (m, 4H), 8.25 (d, J=8.0 Hz, 1H), 8.03 (d, J=9.7 Hz, 2H), 7.88-7.70 (m, 4H), 7.11-6.95 (m, 2H), 6.90-6.78 (m, 1H), 6.08 (d, J=17.7 Hz, 1H), 6.03-5.72 (m, 3H), 5.45 (d, J=11.4 Hz, 1H), 3.89 (s, 3H), 3.31-3.15 (m, 2H), 2.07 (s, 3H), 1.50 (d, J=5.7 Hz, 3H), 1.16-1.00 (m, 1H), 0.87 (d, J=6.9 Hz, 6H), 0.51-0.40 (m, 2H), 0.31-0.23 (m, 2H); MS (ES+) 773.4 (M+1), MS (ES−) 807.5 (M+Cl).

Scheme 121
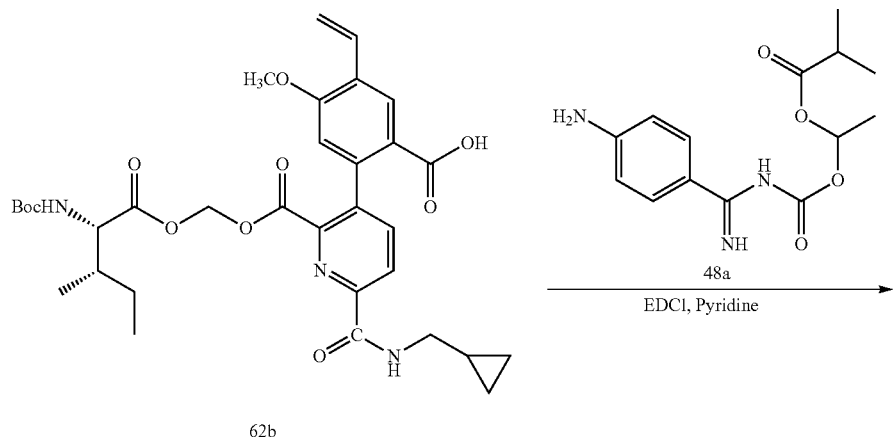
62b
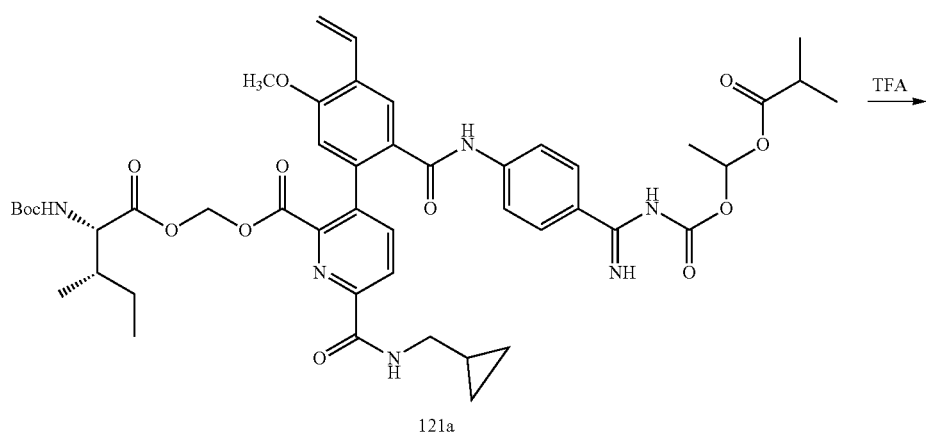
121a
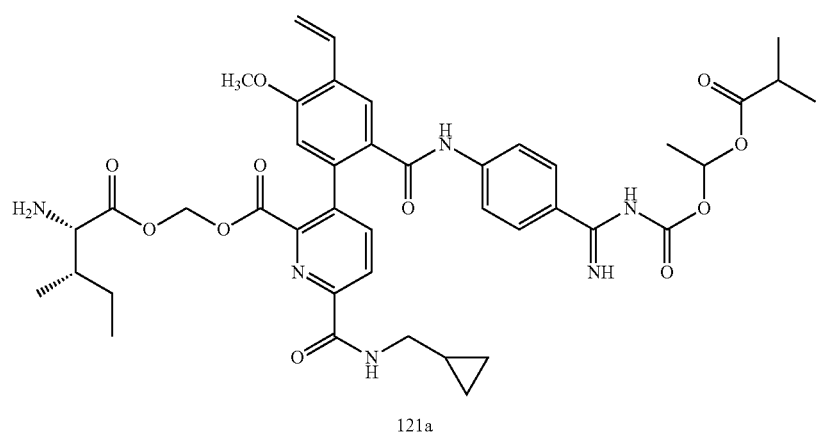
121a

Preparation of (((2S,3S)-2-amino-3-methylpentanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (121b)

Step-1: Preparation of (((2S,3S)-2-((tert-butoxycarbonyl)amino)-3-methylpentanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (121a)

Compound (121a) was prepared from 2-(2-((S)-6-((S)-sec-butyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (62b) (4.0 g, 6.25 mmol) using EDCI (1.8 g, 9.38 mmol) and 1-((((4-aminophenyl)(imino)methyl)carbamoyl)oxy)ethyl isobutyrate (48a) 2.12 g, 7.19 mmol) in DMF (5 mL) and Pyridine (5 mL) according to the procedure reported in step 4 of scheme 2. This gave after workup (((2S,3S)-2-((tert-butoxycarbonyl)amino)-3-methylpentanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (121a) (3.05 g, 53.3% yield) as a white solid; $^1$H NMR (300 MHz, DMSO-$d_6$) δ 10.58 (s, 1H), 9.22 (d, J=26.0 Hz, 2H), 8.42 (s, 1H), 8.24 (d, J=8.0 Hz, 1H), 8.03 (d, J=8.1 Hz, 1H), 7.95 (d, J=8.3 Hz, 3H), 7.74-7.62 (m, 3H), 7.27 (d, J=7.8 Hz, 1H), 7.10-6.97 (m, 2H), 6.77 (q, J=5.4 Hz, 1H), 6.05 (d, J=17.7 Hz, 1H), 5.92-5.56 (m, 2H), 5.44 (d, J=11.5 Hz, 1H), 3.94-3.80 (m, 4H), 3.23 (s, 2H), 1.65 (s, 1H), 1.43 (d, J=5.4 Hz, 3H), 1.38-1.21 (m, 9H), 1.17-0.97 (m, 9H), 0.82-0.63 (m, 6H), 0.53-0.37 (m, 2H), 0.34-0.18 (m, 2H); MS (ES+) 915.6 (M+1), 937.5 (M+Na).

Step-2: Preparation of (((2S,3S)-2-amino-3-methylpentanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (121b)

Compound (121b) was prepared from (((2S,3S)-2-((tert-butoxycarbonyl)amino)-3-methylpentanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (121a) (3.0 g, 3.28 mmol) in dichloromethane (20 mL) using 2,2,2-trifluoroacetic acid (5.5 mL, 65.6 mmol) according to the procedure reported in Step-4 of scheme 8. This gave after workup and purification by reverse phase column chromatography [C18, 275 g, acetonitrile in 0.1% HCl in water as eluents, 0 to 50%] followed by lyophilization (((2S,3S)-2-amino-3-methylpentanoyl)oxy)methyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (121b) (1.35 g, 46.4% yield) dihydrochloride salt as a white powder; $^1$H NMR (300 MHz, DMSO-$d_6$) δ 10.79 (s, 1H, $D_2O$ exchangeable), 10.36-9.61 (m, 1H, $D_2O$ exchangeable), 9.16 (d, J=69.0 Hz, 1H, $D_2O$ exchangeable), 8.78-8.57 (m, 4H, $D_2O$ exchangeable), 8.51-8.38 (m, 1H), 8.25 (d, J=8.0 Hz, 1H), 8.04 (d, J=7.6 Hz, 2H), 7.89-7.66 (m, 4H), 7.12-6.95 (m, 2H), 6.90-6.75 (m, 1H), 6.24-6.01 (m, 1H), 6.02-5.66 (m, 2H), 5.54-5.29 (m, 1H), 3.89 (s, 4H), 3.23 (s, 2H), 2.64-2.52 (m, 1H), 1.96-1.76 (m, 1H), 1.59-1.44 (m, 3H), 1.44-1.27 (m, 1H), 1.27-1.12 (m, 1H), 1.12-0.97 (m, 7H), 0.95-0.65 (m, 6H), 0.54-0.37 (m, 2H), 0.37-0.20 (m, 2H); 1H NMR (300 MHz, DMSO-$d_6$-$D_2O$) δ 8.23 (d, J=8.0 Hz, 1H), 8.01 (d, J=8.1 Hz, 1H), 7.93 (d, J=5.4 Hz, 1H), 7.84-7.58 (m, 4H), 7.09-6.93 (m, 2H), 6.78 (dq, J=22.3, 5.4 Hz, 1H), 6.02 (dd, J=17.8, 1.6 Hz, 1H), 5.96-5.81 (m, 1H), 5.83-5.66 (m, 1H), 5.44 (d, J=11.4 Hz, 1H), 3.91 (d, J=3.8 Hz, 1H), 3.85 (s, 3H), 3.27-3.10 (m, 2H), 2.59-2.51 (m, 1H), 1.84-1.72 (m, 1H), 1.55-1.42 (m, 3H), 1.39-1.22 (m, 1H), 1.21-1.10 (m, 1H), 1.11-0.96 (m, 7H), 0.83-0.67 (m, 6H), 0.50-0.38 (m, 2H), 0.31-0.18 (m, 2H); MS (ES+) 815.5 (M+1); CHN calculated for $C_{42}H_{50}N_6O_{11}$·1.75HCl·3$H_2O$: C, 54.08; H, 6.24; Cl, 6.65; N, 9.01. Found: C, 54.07; H, 5.91; Cl, 6.80; N, 8.99.

Scheme 122

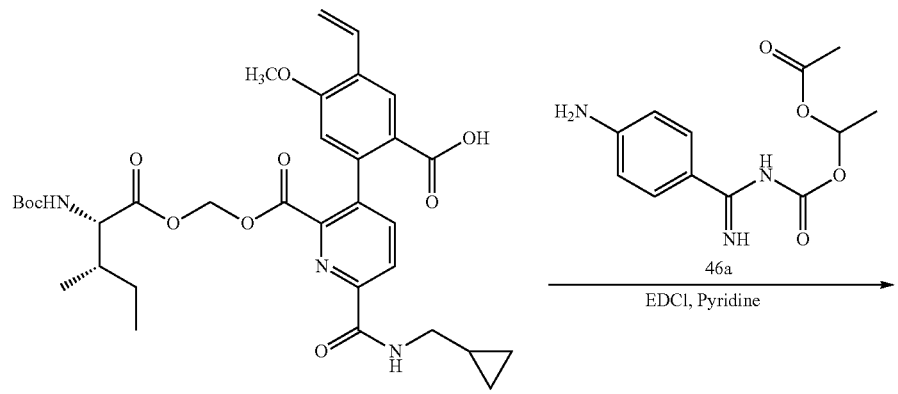

62b

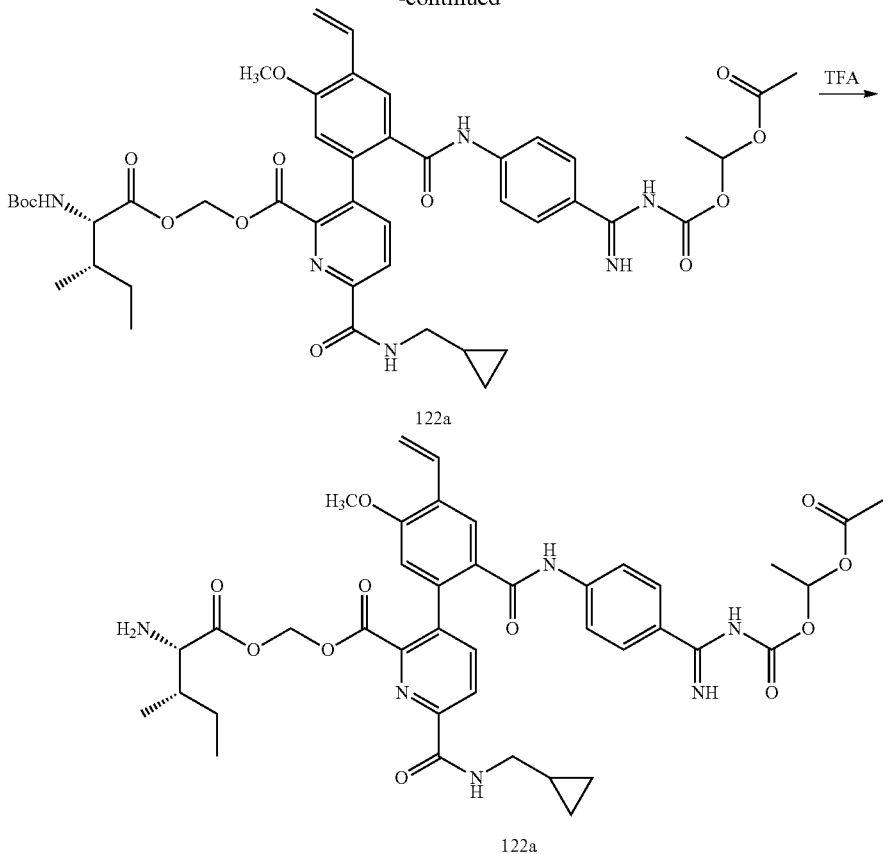

122a

122a

Preparation of ((((2S,3S)-2-amino-3-methylpentanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (122b)

Step-1: Preparation of ((((2S,3S)-2-((tert-butoxycarbonyl)amino)-3-methylpentanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (122a)

Compound (122a) was prepared from 2-(2-((S)-6-((S)-sec-butyl)-10,10-dimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (62b) (3.0 g, 4.69 mmol) using EDCI (1.35 g, 7.03 mmol) and 1-((((4-aminophenyl)(imino)methyl)carbamoyl)oxy)ethyl acetate (46a) (1.43 g, 5.39 mmol) in DMF (5 mL) and Pyridine (5 mL) according to the procedure reported in step 4 of scheme 2. This gave after workup (((2S,3S)-2-((tert-butoxycarbonyl)amino)-3-methylpentanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (122a) (2.65 g, 64% yield) as a white solid; $^1$H NMR (300 MHz, DMSO-$d_6$) δ 10.57 (s, 1H, D$_2$O exchangeable), 9.22 (d, J=24.0 Hz, 2H, D$_2$O exchangeable), 8.43 (s, 1H), 8.24 (d, J=8.0 Hz, 1H), 8.09-7.86 (m, 4H), 7.68 (d, J=8.6 Hz, 2H), 7.27 (d, J=7.7 Hz, 1H), 7.15-6.97 (m, 2H), 6.76 (q, J=5.4 Hz, 1H), 6.05 (d, J=17.8 Hz, 1H), 5.97-5.58 (m, 2H), 5.44 (d, J=11.4 Hz, 1H), 3.95-3.77 (m, 4H), 3.29-3.07 (m, 2H), 2.02 (s, 3H), 1.65 (s, 1H), 1.43 (d, J=5.4 Hz, 3H), 1.37-1.21 (m, 10H), 1.20-0.99 (m, 2H), 0.72 (q, J=7.2 Hz, 6H), 0.52-0.40 (m, 2H), 0.32-0.21 (m, 2H); MS (ES+) 887.5 (M+1), 909.5 (M+Na).

Step-2: Preparation of ((((2S,3S)-2-amino-3-methylpentanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (122b)

Compound (122b) was prepared from ((((2S,3S)-2-((tert-butoxycarbonyl)amino)-3-methylpentanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (122a) (2.5 g, 2.82 mmol) in dichloromethane (20 mL) using 2,2,2-trifluoroacetic acid (4.34 mL, 56.4 mmol) according to the procedure reported in Step-4 of scheme 8. This gave after workup and purification by reverse phase column chromatography [C18, 275 g, acetonitrile in 0.1% HCl in water as eluents, 0 to 50%] followed by lyophilization (((2S,3S)-2-amino-3-methylpentanoyl)oxy)methyl 3-(2-((4-(N-((1-acetoxyethoxy)carbonyl)carbamimidoyl)phenyl)carbamoyl)-5-methoxy-4-vinylphenyl)-6-((cyclopropylmethyl)carbamoyl)picolinate (122b) (350 mg, 15.78% yield) dihydrochloride salt as a white powder; $^1$H NMR (300 MHz, DMSO-$d_6$) δ 10.84-10.52 (m, 1H, D$_2$O exchangeable), 9.08 (d, J=93.4 Hz, 1H, D$_2$O exchangeable), 8.65-8.39 (m, 4H, D$_2$O exchangeable), 8.25 (d, J=8.0 Hz, 1H), 8.09-7.95 (m, 2H), 7.90-7.64 (m, 4H), 7.10-6.94 (m, 3H), 6.87-6.71 (m, 1H), 6.07 (d, J=17.8 Hz, 1H), 6.01-5.64 (m, 2H), 5.45 (d, J=11.5 Hz, 1H), 3.95 (s, 1H), 3.89 (s, 3H), 3.23 (s, 2H), 2.06 (s, 3H), 1.90-1.75 (m, 1H), 1.48 (d, J=5.4 Hz, 3H), 1.43-1.25 (m, 1H), 1.24-0.98 (m, 2H), 0.87-0.80 (m, 3H), 0.80-0.72 (m, 3H), 0.50-0.41 (m, 2H), 0.31-0.24 (m, 2H); $^1$H NMR (300 MHz, DMSO-d$_6$-D$_2$O) δ 8.61-8.49 (m, 1H), 8.24 (d, J=8.1 Hz, 1H), 8.02 (d, J=8.3 Hz, 1H), 7.95 (d, J=4.5 Hz, 1H), 7.80 (dd, J=8.9, 2.2 Hz, 2H), 7.76-7.62 (m, 2H), 7.10-6.94 (m, 2H), 6.87-6.70 (m, 1H), 6.03 (d, J=17.8 Hz, 1H), 5.98-5.82 (m, 1H), 5.82-5.68 (m, 1H), 5.45 (d, J=11.4 Hz, 1H), 3.94 (d, J=3.6 Hz, 1H), 3.87 (s, 3H), 3.30-3.14 (m, 2H), 2.04 (s, 3H), 1.86-1.72 (m, 1H), 1.47 (t, J=5.8 Hz, 3H), 1.39-1.22 (m, 1H), 1.21-0.99 (m, 2H), 0.79 (d, J=6.9 Hz, 3H), 0.77-0.68 (m, 3H), 0.49-0.40 (m, 2H), 0.29-0.21 (m, 2H); MS (ES+) 787.4 (M+1); Analysis calculated for C$_{40}$H$_{46}$N$_6$O$_{11}$.2HCl.3H$_2$O: C, 52.58; H, 5.96; Cl, 7.76; N, 9.20. Found: C, 52.48; H, 5.91; Cl, 7.52; N, 9.25.
Scheme 123
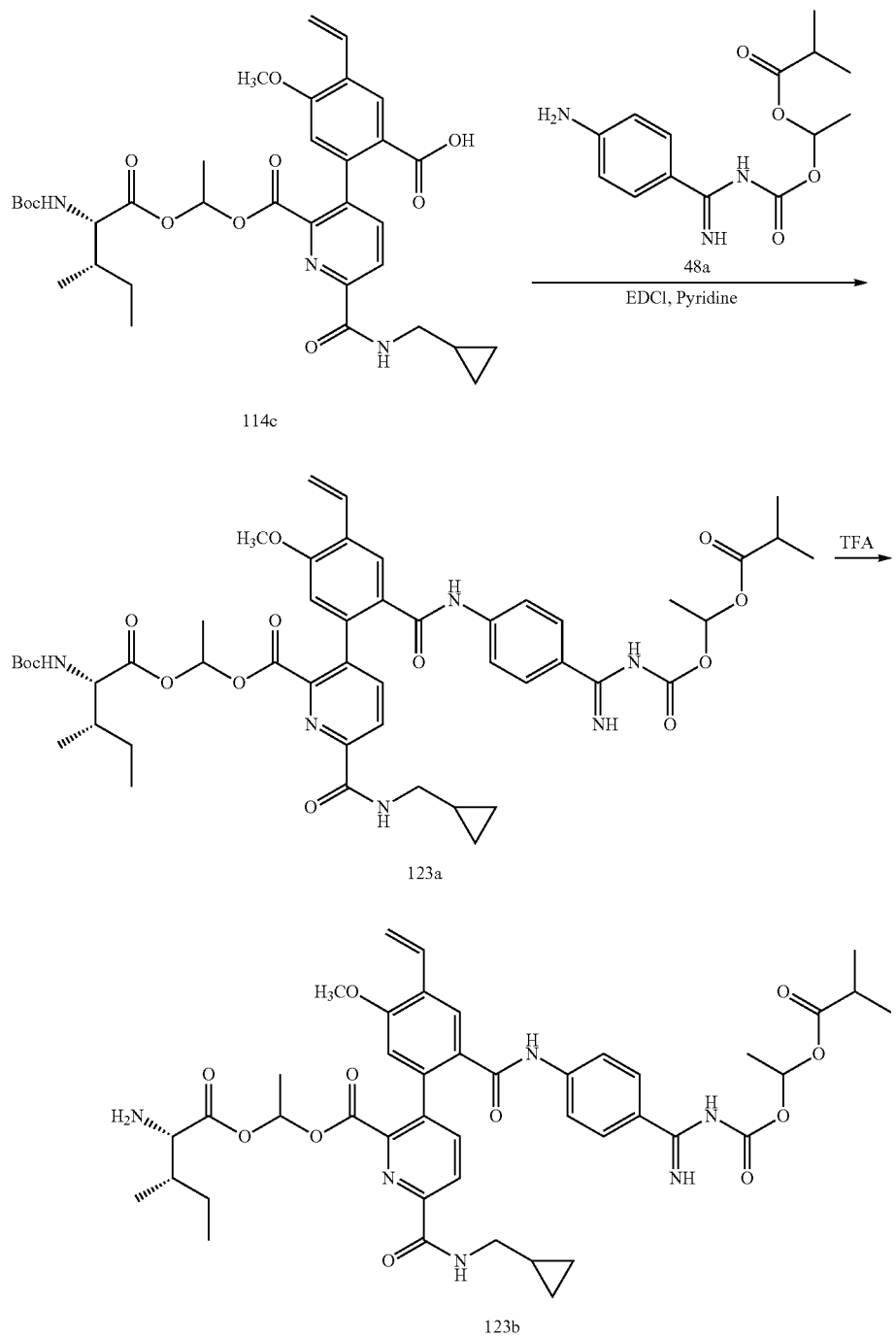

Preparation of 1-(((2S,3S)-2-amino-3-methylpentanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (123b)

Step-1: Preparation of 1-(((2S,3S)-2-((tert-butoxycarbonyl)amino)-3-methylpentanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (123a)

Compound (123a) was prepared from 2-(2-(((6S)-6-((S)-sec-butyl)-3,10,10-trimethyl-5,8-dioxo-2,4,9-trioxa-7-azaundecan-1-oyl)-6-((cyclopropylmethyl)carbamoyl)pyridin-3-yl)-4-methoxy-5-vinylbenzoic acid (114c) (5.3 g, 8.11 mmol) using EDCI (2.31 g, 12.16 mmol) and 1-((((4-aminophenyl)(imino)methyl)carbamoyl)oxy)ethyl isobutyrate (48a) (2.73 g, 9.32 mmol) in DMF (7 mL) and Pyridine (5 mL) according to the procedure reported in step 4 of scheme 2. This gave after workup and purification by flash column chromatography, 1-(((2S,3S)-2-((tert-butoxycarbonyl)amino)-3-methylpentanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (123a) (4.42 g, 59% yield) as a white solid; $^1$H NMR (300 MHz, DMSO-d$_6$) δ 10.49 (d, J=37.5 Hz, 1H, D$_2$O exchangeable), 9.20 (d, J=21.3 Hz, 2H, D$_2$O exchangeable), 8.43 (s, 1H), 8.23 (d, J=8.0 Hz, 1H), 8.05-7.86 (m, 4H), 7.68 (s, 2H), 7.16 (s, 1H), 7.11-6.96 (m, 2H), 6.77 (q, J=5.2 Hz, 2H), 6.05 (d, J=17.7 Hz, 1H), 5.44 (d, J=11.4 Hz, 1H), 3.90 (s, 3H), 3.81 (t, J=7.2 Hz, 1H), 3.24 (s, 2H), 1.65 (s, 1H), 1.43 (d, J=5.4 Hz, 3H), 1.40-1.26 (m, 9H), 1.28-0.98 (m, 13H), 0.74 (q, J=8.9, 8.1 Hz, 6H), 0.51-0.39 (m, 2H), 0.33-0.19 (m, 2H); MS (ES+) 930.5 (M+1).

Step-2: Preparation of 1-(((2S,3S)-2-amino-3-methylpentanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (123b)

Compound (123b) was prepared from 1-(((2S,3S)-2-((tert-butoxycarbonyl)amino)-3-methylpentanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (123a) (4.4 g, 4.74 mmol) in dichloromethane (30 mL) using 2,2,2-trifluoroacetic acid (7.3 mL, 95 mmol) according to the procedure reported in Step-4 of scheme 8. This gave after workup and purification by reverse phase column chromatography [C18, 275 g, acetonitrile in 0.1% HCl in water as eluents, 0 to 50%], followed by lyophilization 1-(((2S,3S)-2-amino-3-methylpentanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (123b) (1.8 g, 46% yield) dihydrochloride salt as a white powder; $^1$H NMR (300 MHz, DMSO-d$_6$) δ 10.76 (d, J=18.5 Hz, 1H, D$_2$O exchangeable), 10.45-9.69 (m, 1H, D$_2$O exchangeable), 9.14 (d, J=70.4 Hz, 1H, D$_2$O exchangeable), 8.57 (s, 3H, D$_2$O exchangeable), 8.42 (t, J=6.2 Hz, 1H), 8.24 (d, J=8.0 Hz, 1H), 8.10-7.98 (m, 2H), 7.88-7.66 (m, 4H), 7.13-6.96 (m, 2H), 6.93-6.79 (m, 2H), 6.10 (dd, J=17.7, 5.9 Hz, 1H), 5.45 (d, J=11.4 Hz, 1H), 3.96-3.85 (m, 4H), 3.24 (s, 2H), 2.65-2.45 (m, 1H), 1.94-1.69 (m, 1H), 1.52 (d, J=5.4 Hz, 3H), 1.45-1.22 (m, 3H), 1.25-0.99 (m, 9H), 0.92-0.68 (m, 6H), 0.52-0.40 (m, 2H), 0.34-0.21 (m, 2H); MS (ES+) 829.5 (M+1), 851.4 (M+Na), (ES−) 863.6 (M+Cl).

Scheme 124

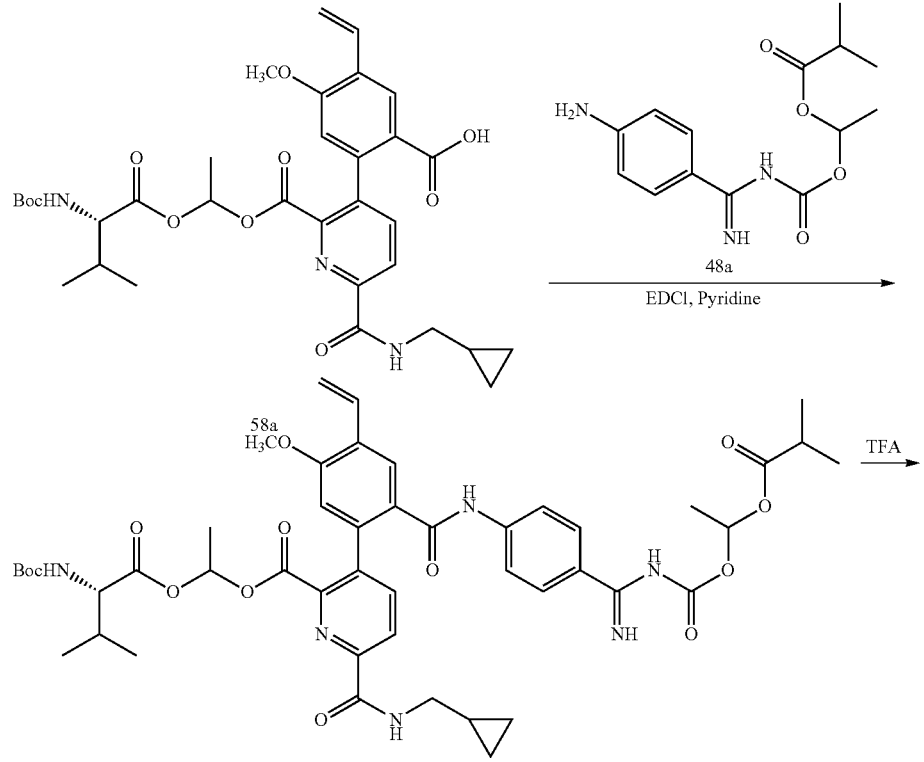

124a

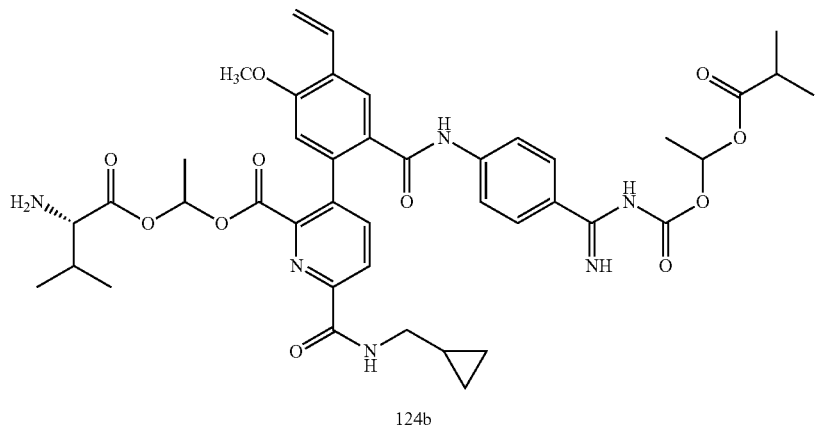

124b

Step-2: Preparation of 1-(((S)-2-amino-3-methylbutanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (124b)

Compound (124b) was prepared from 1-(((S)-2-((tert-butoxycarbonyl)amino)-3-methylbutanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (124a) (2 g, 2.18 mmol) in dichloromethane (20 mL) using 2,2,2-trifluoroacetic acid (2.53 mL, 32.8 mmol) according to the procedure reported in Step-4 of scheme 8. This gave after workup and purification by reverse phase column chromatography [C18, 150 g, acetonitrile in 0.1% HCl in water as eluents, 0 to 50%] followed by lyophilization 1-(((S)-2-amino-3-methylbutanoyl)oxy)ethyl 6-((cyclopropylmethyl)carbamoyl)-3-(2-((4-(N-((1-(isobutyryloxy)ethoxy)carbonyl)carbamimidoyl)phenyl)carbamoyl)-5-methoxy-4-vinylphenyl)picolinate (124b) (0.65 g, 33.5% yield) dihydrochloride salt as a white powder; $^1$H NMR (300 MHz, DMSO-$d_6$) δ 10.75 (s, 1H), 10.27-9.91 (m, 2H), 8.72-8.34 (m, 4H), 8.24 (d, J=7.9 Hz, 1H), 8.11-7.97 (m, 2H), 7.89-7.71 (m, 4H), 7.12-6.97 (m, 2H), 6.93-6.77 (m, 2H), 6.10 (dd, J=17.4, 5.3 Hz, 1H), 5.45 (d, J=11.4 Hz, 1H), 3.98-3.80 (m, 4H), 3.24 (s, 2H), 2.65-2.52 (m, 1H), 2.08 (s, 1H), 1.51 (d, J=5.5 Hz, 3H), 1.34-1.00 (m, 10H), 0.97-0.76 (m, 6H), 0.53-0.38 (m, 2H), 0.34-0.22 (m, 2H); MS (ES+) 815.5 (M+1), MS (ES−) 849.5 (M+Cl).

Scheme 125

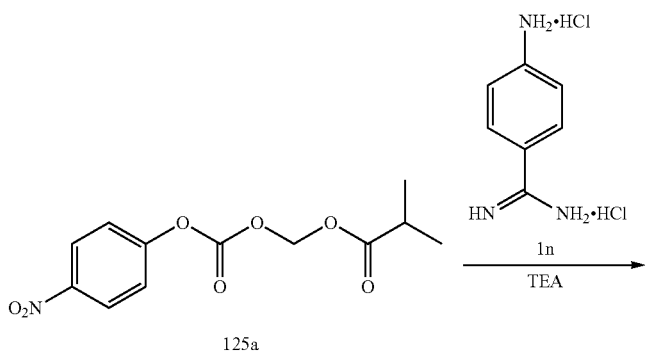

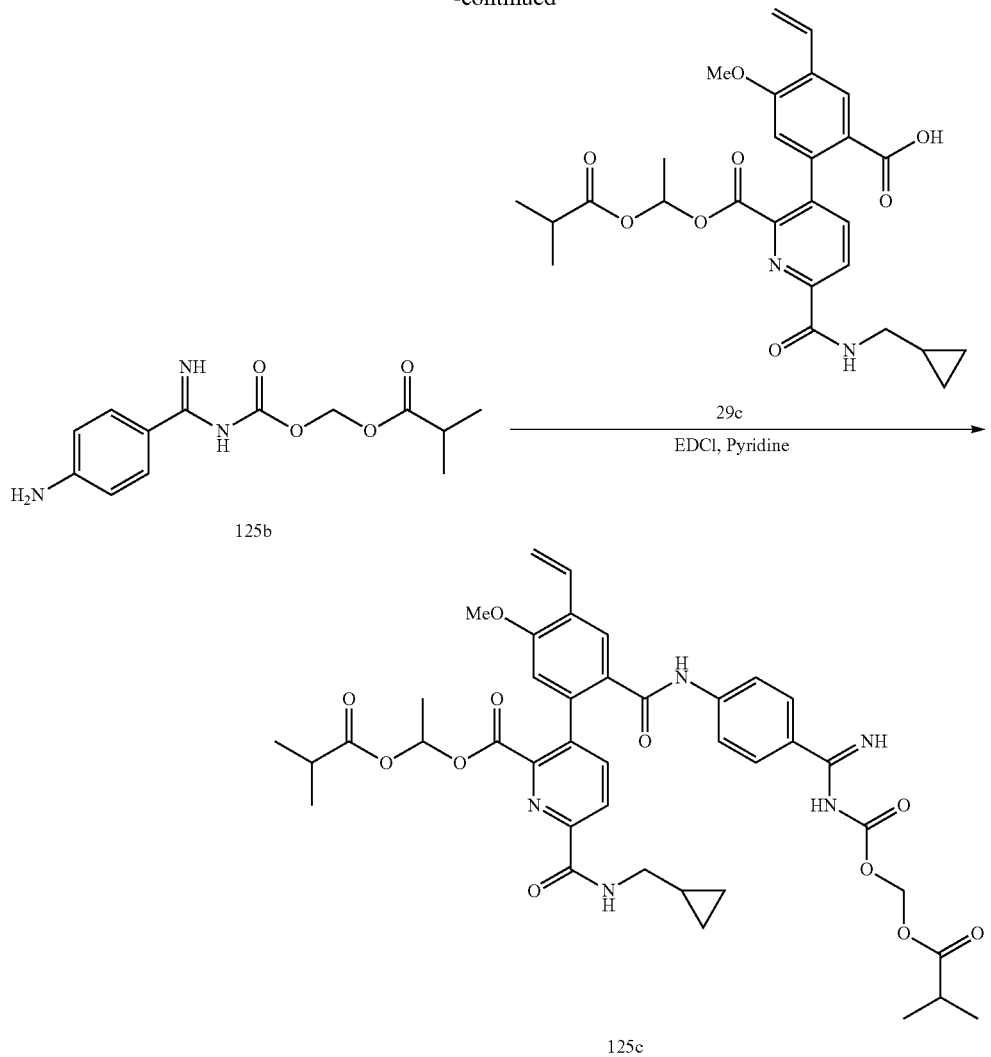

Preparation of 1-(isobutyryloxy)ethyl 6-((cyclopropylmethyl)carbamoyl)-3-(2-((4-(N-(((isobutyryloxy)methoxy)carbonyl)carbamimidoyl)phenyl)carbamoyl)-5-methoxy-4-vinylphenyl)picolinate (125c)

Step-1: (((((4-aminophenyl)(imino)methyl)carbamoyl)oxy)methyl isobutyrate (125b)

Compound (125b) was prepared according to the procedure described in step 1 of scheme 24 from 4-aminobenzimidamide dihydrochloride (1n) (2.3 g, 11.05 mmol) in DMF (10 mL) using (((4-nitrophenoxy)carbonyl)oxy) methyl isobutyrate (125a) (3.76 g, 13.26 mmol, prepared according to the procedure reported by Chrusciel, Robert A. et al; in PCT Int. Appl., 2015120062) and triethylamine (5.22 mL, 37.5 mmol). This gave after workup and purification by flash column chromatography [silica gel 40 g, eluting with MeOH-EtOAc (9:1) in hexanes 0 to 80%] (((((4-aminophenyl)(imino)methyl)carbamoyl)oxy)methyl isobutyrate (125b) (0.2 g, 6.5% yield) as a light orange solid; $^1$H NMR (300 MHz, DMSO-$d_6$) δ 9.16 (s, 1H), 8.88 (s, 1H), 7.82-7.72 (m, 2H), 6.55 (d, J=8.7 Hz, 2H), 5.92 (s, 2H), 5.72 (s, 2H), 2.62-2.52 (m, 1H), 1.09 (d, J=7.0 Hz, 6H).

Step-2: Preparation 1-(isobutyryloxy)ethyl 6-((cyclopropylmethyl)carbamoyl)-3-(2-((4-(N-(((isobutyryloxy)methoxy)carbonyl)carbamimidoyl)phenyl) carbamoyl)-5-methoxy-4-vinylphenyl)picolinate (125c)

Compound (125c) was prepared from 2-(6-((cyclopropylmethyl)carbamoyl)-2-((1-(isobutyryloxy)ethoxy)carbonyl) pyridin-3-yl)-4-methoxy-5-vinylbenzoic acid (29c) (0.4 g, 0.78 mmol) using EDCI (0.16 g, 0.86 mmol) and (((4-aminophenyl)(imino)methyl)carbamoyl)oxy)methyl isobutyrate (125b) (0.2 g, 0.71 mmol) in DMF (3 mL) and pyridine (1 mL) according to the procedure reported in step 4 of scheme 2. This gave after workup and purification by flash column chromatography [silica gel 12 g, MeOH-EtOAc (9:1) in hexanes 0 to 100% as eluents] 1-(isobutyryloxy)ethyl 6-((cyclopropylmethyl)carbamoyl)-3-(2-((4-(N-(((isobutyryloxy)methoxy)carbonyl)carbamimidoyl)phenyl) carbamoyl)-5-methoxy-4-vinylphenyl)picolinate (125c) (0.14 g, 25% yield) as a white powder; $^1$H NMR (300 MHz, DMSO-$d_6$) δ 10.62-10.36 (m, 1H), 9.21 (s, 2H), 8.70-8.41 (m, 1H), 8.22 (d, J=8.0 Hz, 1H), 8.07-7.89 (m, 4H), 7.79-7.59 (m, 2H), 7.12-6.92 (m, 2H), 6.74 (d, J=5.8 Hz, 1H), 6.05 (dd, J=17.7, 1.6 Hz, 1H), 5.73 (s, 2H), 5.44 (dd, J=11.2, 1.5 Hz, 1H), 3.88 (s, 3H), 3.24 (t, J=6.6 Hz, 2H), 2.64-2.52 (m, 1H), 2.46-2.29 (m, 1H), 1.18 (d, J=5.4 Hz, 3H), 1.09 (d, J=7.0 Hz, 6H), 1.04-0.92 (m, 7H), 0.52-0.40 (m, 2H), 0.32-0.24 (m, 2H); MS (ES+) 772.4 (M+1), 794.3 (M+Na), MS (ES−) 806.5 (M+Cl).

Example 126: Bioavailability of Prodrugs of Kallikrein Inhibitors

Plasma pharmacokinetics of compounds was determined using three male Sprague Dawley rats following a single oral dose administration. All animals were placed in a rat metabolic cage, isolated, and fasted approximately 15 hours prior to dosing. Identifying markers were placed on each animal. Each animal was weighed prior to dose administration. Animals were administered orally with a solution formulation of test compound either in water or a combination of water/propylene glycol, at a dose of 10 mg/kg. Gavage needles were attached to syringes and filled with appropriate amount of test article to be dosed. Blood samples (approximately 500 µL) were collected from three rats at pre-dose (time 0), 0.5, 1, 2, 4, 8, 12 and 24 hr, respectively, depending on study duration. Samples were collected into labeled micro centrifuge tubes containing (heparin solution) as an anticoagulant. Plasma was immediately harvested from the blood by centrifugation at 14,000 rpm for 3 min at 4° C., and stored below −70° C. until bioanalysis. Individual plasma samples were analyzed for the parent compound, 3-[2-(4-carbamimidoyl-phenylcarbamoyl)-5-methoxy-4-vinyl-phenyl]-6-(cyclopropylmethyl-carbamoyl)-pyridine-2-carboxylic acid. As shown in Table-1, the test compounds yielded varying degrees of exposure to the parent compound. The test compounds generally provided for improved bioavailability of the parent compound as compared to dosing of the parent compound in aqueous solutions.

TABLE 1

$AUC_{0\text{-}last\ hour}$ (area under the curve) after a single oral (10 mg/kg) dose administration to male Sprague Dawley rats. [A = 0-1,000 ng/mL; B = 1,001-10,000 ng/mL; C > 10,000 ng/mL].

| Example | study duration | AUC (hr · ng/mL) |
|---|---|---|
| 100e | 8 h | B |
| 101e | 8 h | A |
| 102d | 8 h | A |
| 103c | 8 h | A |
| 104d | 8 h | A |
| 10e | 12 h | B |
| 117b | 8 h | B |
| 118c | 8 h | A |
| 14d | 12 h | A |
| 15d | 12 h | A |
| 18e | 8 h | A |
| 18f | 8 h | A |
| 18g | 8 h | A |
| 19d | 12 h | A |
| 1o | 8 h | A |
| 20b | 8 h | A |
| 22d | 8 h | A |
| 23e | 8 h | B |
| 23f | 12 h | B |
| 24c | 8 h | A |
| 29d | 12 h | B |
| 2d | 12 h | A |
| 31b | 12 h | B |

TABLE 1-continued $AUC_{0\text{-}last\ hour}$ (area under the curve) after a single oral (10 mg/kg) dose administration to male Sprague Dawley rats. [A = 0-1,000 ng/mL; B = 1,001-10,000 ng/mL; C > 10,000 ng/mL].

| Example | study duration | AUC (hr · ng/mL) |
|---|---|---|
| 32c | 12 h | B |
| 33c | 12 h | B |
| 34a | 8 h | B |
| 35a | 8 h | B |
| 36b | 8 h | C |
| 37e | 8 h | B |
| 39a | 8 h | C |
| 41a | 8 h | B |
| 42a | 8 h | C |
| 43a | 8 h | C |
| 44b | 8 h | A |
| 45b | 8 h | A |
| 47a | 8 h | B |
| 48b | 8 h | C |
| 49a | 8 h | B |
| 50d | 8 h | B |
| 51b | 8 h | A |
| 52b | 8 h | A |
| 54c | 8 h | B |
| 55b | 8 h | B |
| 56b | 8 h | C |
| 57a | 8 h | B |
| 58f | 8 h | B |
| 59b | 8 h | B |
| 60c | 8 h | B |
| 61d | 8 h | A |
| 62d | 8 h | B |
| 63c | 8 h | C |
| 64b | 8 h | B |
| 65c | 8 h | B |
| 66c | 8 h | B |
| 68a | 8 h | B |
| 69d | 8 h | A |
| 6a | 8 h | A |
| 70d | 8 h | B |
| 71a | 8 h | A |
| 72a | 8 h | B |
| 73d | 8 h | A |
| 74e | 8 h | B |
| 75c | 8 h | B |
| 77c | 8 h | B |
| 80c | 8 h | C |
| 81d | 8 h | A |
| 83c | 8 h | B |
| 84a | 8 h | A |
| 85d | 8 h | A |
| 87a | 8 h | B |
| 90d | 8 h | A |
| 91d | 8 h | A |
| 92a | 8 h | A |
| 94e | 8 h | B |
| 95e | 8 h | B |
| 96d | 8 h | A |
| 97e | 8 h | A |
| 98e | 8 h | A |
| 99e | 8 h | A |
| 9c | 8 h | A |

INCORPORATION BY REFERENCE

All of the U.S. patents and U.S. published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound having the structure of formula (I) or a pharmaceutically acceptable salt thereof:

(I)

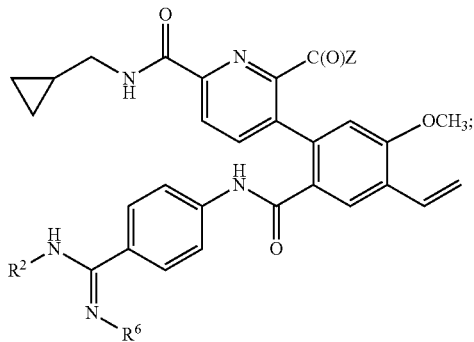

wherein, independently for each occurrence:
Z represents $OR^1$ or NH(OH);
$R^1$ represents

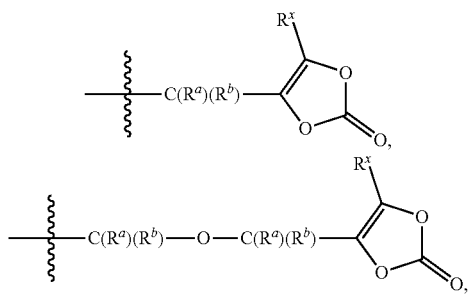

—$C(R^a)(R^b)$—O—C(O)-M-$R^3$, or $(C_2-C_6)$alkyl optionally substituted by hydroxyl or heterocycloalkyl;
$R^a$ represents H or $(C_1-C_6)$alkyl;
$R^b$ represents H or $(C_1-C_6)$alkyl;
$R^x$ represents H or $(C_1-C_6)$alkyl;
M is a bond or represents O, S, NH, or $N(CH_3)$;
$R^2$ represents H, —OH, —$C(O)OR^4$, —$C(O)SR^4$, —C(O)O—$[C(R^c)(R^d)]_n$—O—C(O)-L-$R^5$, or

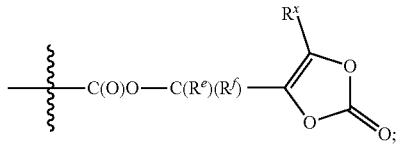

$R^6$ represents H, OH, —$C(O)OR^4$, —$C(O)SR^4$, —C(O)O—$[C(R^c)(R^d)]_n$ O—C(O)-L-$R^5$, or

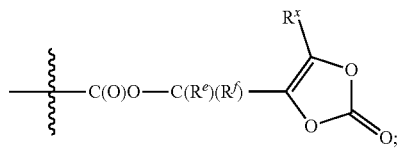

or $R^2$ and $R^6$, taken together with the atoms to which they are attached, form an optionally substituted 1,2,4-oxadiazol-5-one group;

L, independently for each occurrence, is a bond or represents O, S, NH, or $N(CH_3)$;

$R^c$, $R^d$, $R^e$, and $R^f$ each independently for each occurrence represent H or $(C_1-C_6)$alkyl;

$R^3$ represents $(C_1-C_6)$alkyl, aralkyl, or cycloalkyl, optionally substituted with one or more substituents each independently selected from the group consisting of amino, hydroxyl, optionally substituted heterocycloalkyl, —C(O)OH, and —C(O)O($(C_1-C_6)$alkyl);

$R^4$, independently for each occurrence, represents $(C_1-C_6)$alkyl, cycloalkyl, heterocycloalkyl, aryl, or heteroaryl, optionally substituted with one or more substituents each independently selected from the group consisting of —C(O)OH, —C(O)O($(C_1-C_6)$alkyl), $(C_1-C_6)$alkoxy, hydroxyl, oxo, heterocycloalkyl, amino, $(C_1-C_6)$alkylamino, di($(C_1-C_6)$alkyl)amino, and silyl ether;

$R^5$, independently for each occurrence, represents $(C_1-C_6)$alkyl, aryl, or heteroaryl, optionally substituted with one or more substituents each independently selected from the group consisting of amino, heterocycloalkyl, $(C_1-C_6)$alkoxy optionally substituted by $(C_1-C_6)$alkoxy or a polyether chain; and n represents 1 or 2;

provided that at least one of $R^2$ and $R^6$ is not H; and provided that if Z is $OR^1$ and $R^1$ is ethyl or 2-(morpholino)ethyl, then $R^4$ is not hexyl or butyl.

2. The compound of claim 1, wherein $R^1$ represents

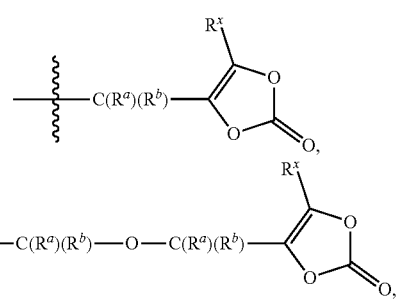

or —$C(R^a)(R^b)$—O—C(O)-M-$R^3$.

3. The compound of claim 1, wherein $R^a$ and $R^b$ each independently represent H or methyl.

4. The compound of claim 1, wherein $R^1$ represents —$C(R^a)(R^b)$—O—C(O)-M-$R^3$, and M is a bond or O.

5. The compound of claim 4, wherein $R^3$ represents $(C_1-C_6)$alkyl, $(C_3-C_5)$alkyl, cycloalkyl, aralkyl optionally substituted with —$NH_2$, $(C_1-C_6)$alkyl substituted with —$NH_2$ or —OH, or $(C_3-C_5)$alkyl substituted with —$NH_2$ or —OH.

6. The compound of claim 1, wherein $R^1$ represents

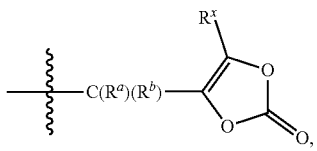

and $R^x$ represents H or methyl; or
wherein $R^1$ represents $(C_2\text{-}C_6)$alkyl optionally substituted with hydroxyl.

7. The compound of claim 1, wherein:
(a) $R^2$ represents H and $R^6$ represents OH;
(b) $R^2$ represents —C(O)OR$^4$;
(c) $R^2$ represents —C(O)O—[C(R$^c$)(R$^d$)]$_n$—O—C(O)-L-R$^5$; or
(d) $R^2$ and $R^6$, taken together with the atoms to which they are attached, form a 1,2,4-oxadiazol-5-one group.

8. The compound of claim 7, wherein $R^2$ represents —C(O)OR$^4$;
and $R^4$ represents ethyl, isopropyl, hexyl, or $(C_1\text{-}C_6)$alkyl substituted with amino, hydroxy, or $(C_1\text{-}C_6)$alkoxy;
optionally wherein $R^6$ represents H.

9. The compound of claim 7, wherein $R^2$ represents —C(O)O—[C(R$^c$)(R$^d$)]$_n$—O—C(O)-L-R$^5$, and n is 1; and at least one of R$^c$ and R$^d$ is H or at least one of R$^c$ and R$^d$ is methyl;
optionally wherein $R^6$ represents H.

10. The compound of claim 9, wherein L is a bond, and/or wherein $R^5$ represents $(C^1\text{-}C^4)$alkyl optionally substituted by amino.

11. The compound of claim 1, wherein:
if $R^1$ is —CH$_2$—O—C(O)—CH(iPr)NH$_2$, then $R^2$ is not —C(O)O(ethyl); and
if $R^1$ is —CH$_2$—O—C(O)—CH(iBu)NH$_2$, then $R^2$ is not —C(O)O(hexyl).

12. The compound of claim 1 selected from the following table:

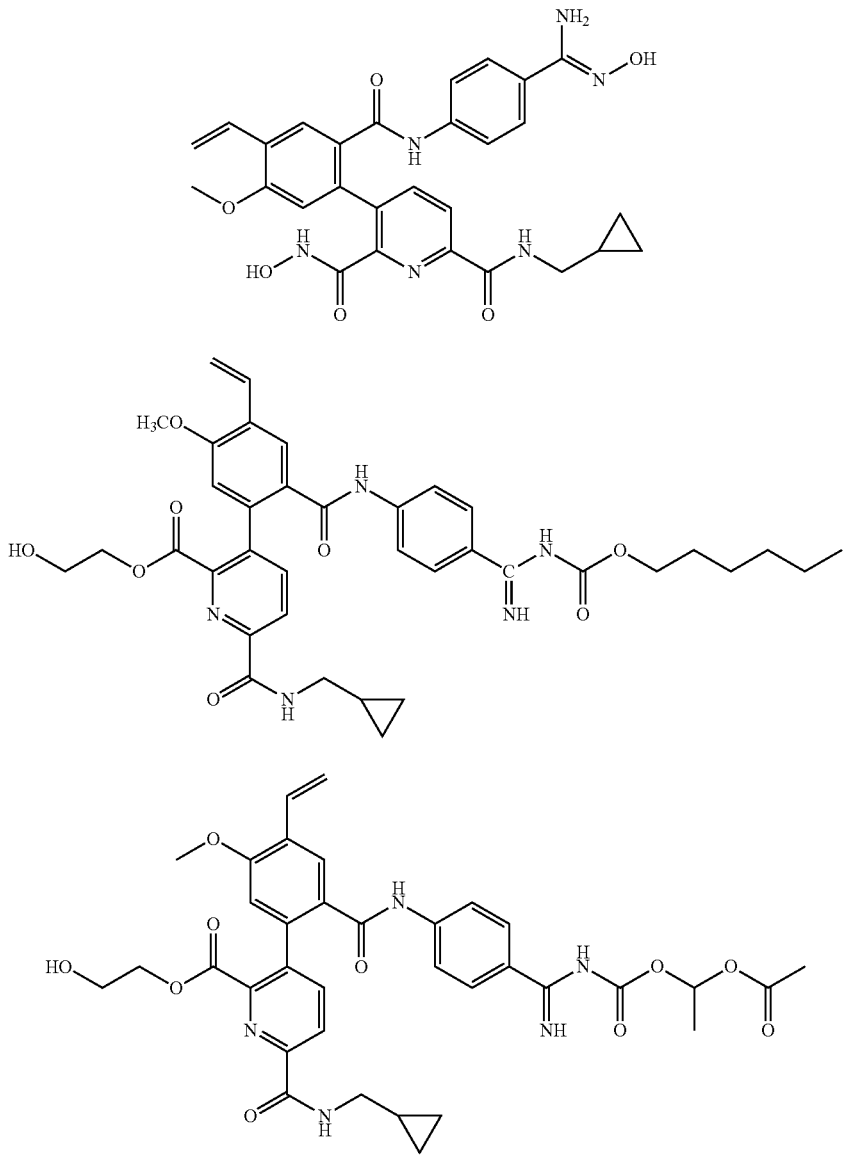

-continued
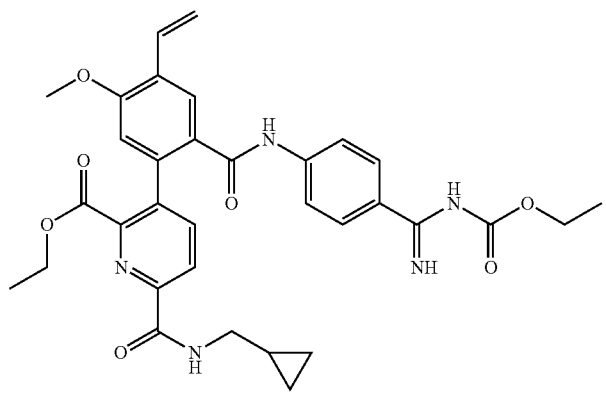 [SMILES: C=Cc1cc(C(=O)Nc2ccc(C(=N)NC(=O)OCC)cc2)c(-c2ccc(C(=O)NCC3CC3)nc2C(=O)OCC)cc1OC]
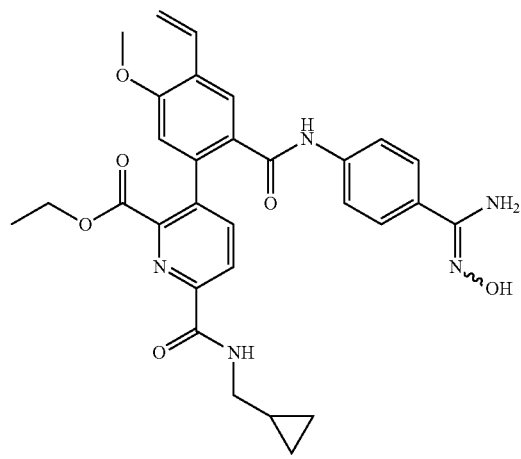 [SMILES: C=Cc1cc(C(=O)Nc2ccc(C(N)=NO)cc2)c(-c2ccc(C(=O)NCC3CC3)nc2C(=O)OCC)cc1OC]
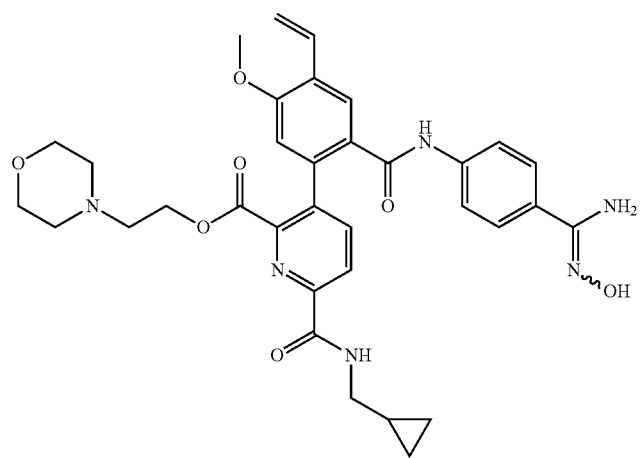 [SMILES: C=Cc1cc(C(=O)Nc2ccc(C(N)=NO)cc2)c(-c2ccc(C(=O)NCC3CC3)nc2C(=O)OCCN2CCOCC2)cc1OC]

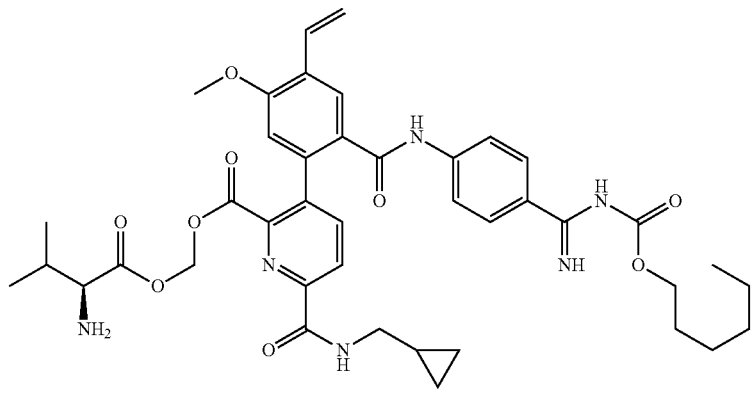 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)C(C)C)cc1OC]
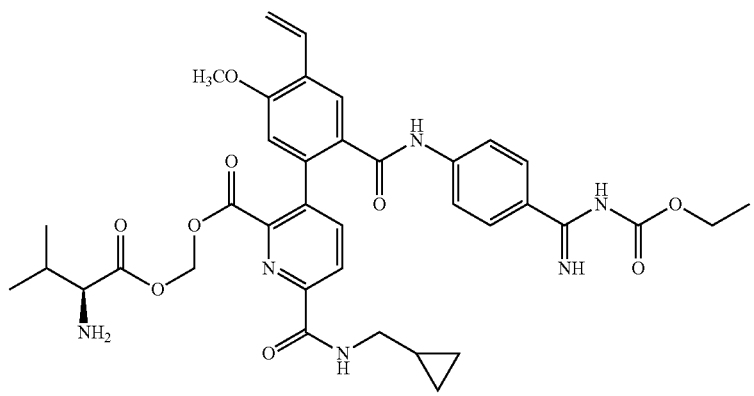 [SMILES: C=Cc1cc(C(=O)Nc2ccc(C(=N)NC(=O)OCC)cc2)c(-c2ccc(C(=O)NCC3CC3)nc2C(=O)OCOC(=O)[C@@H](N)C(C)C)cc1OC]
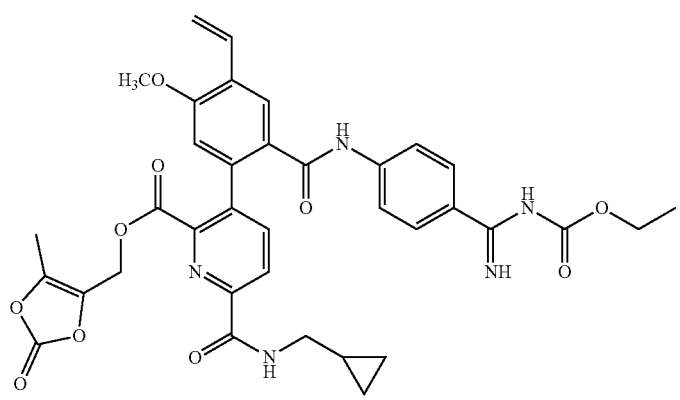 [SMILES: C=Cc1cc(C(=O)Nc2ccc(C(=N)NC(=O)OCC)cc2)c(-c2ccc(C(=O)NCC3CC3)nc2C(=O)OCc2oc(=O)oc2C)cc1OC]
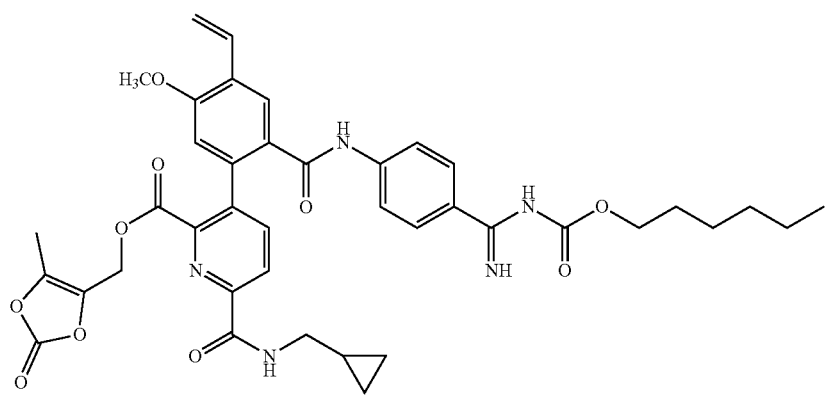 [SMILES: C=Cc1cc(C(=O)Nc2ccc(C(=N)NC(=O)OCCCCCC)cc2)c(-c2ccc(C(=O)NCC3CC3)nc2C(=O)OCc2oc(=O)oc2C)cc1OC]

-continued
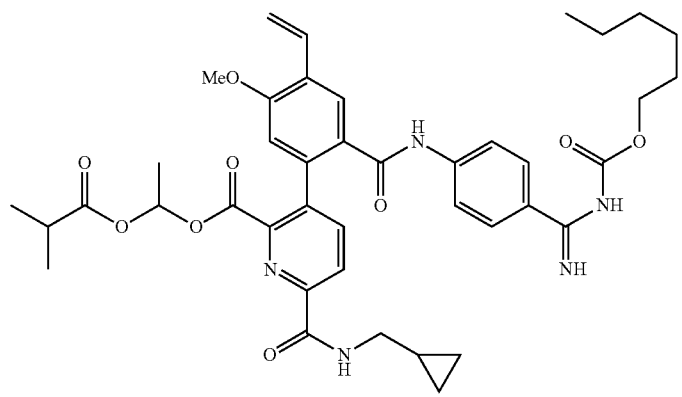 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)C(C)C)cc1OC]
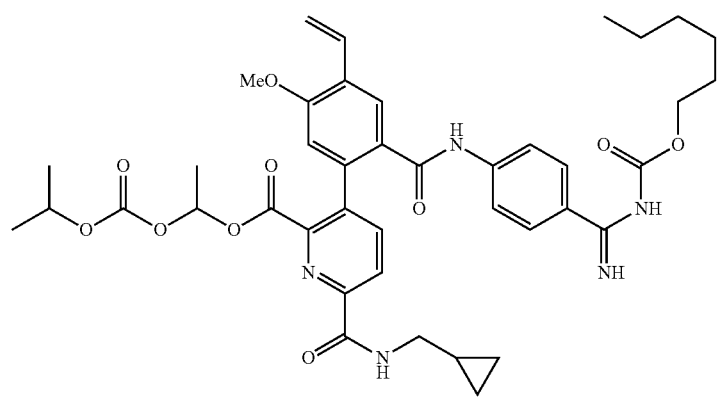 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)OC(C)C)cc1OC]
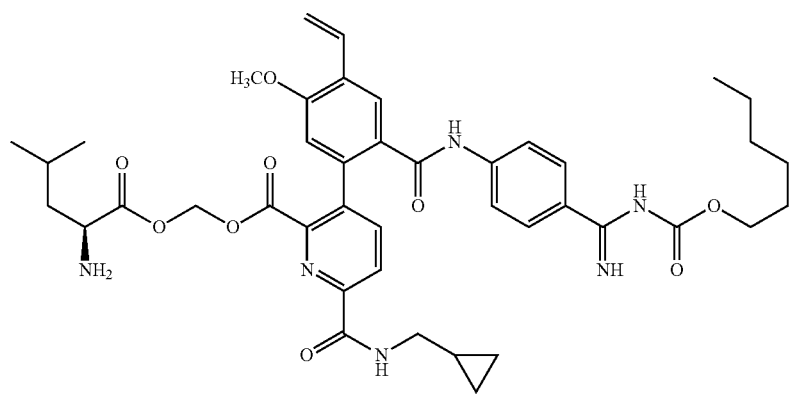 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)CC(C)C)cc1OC]
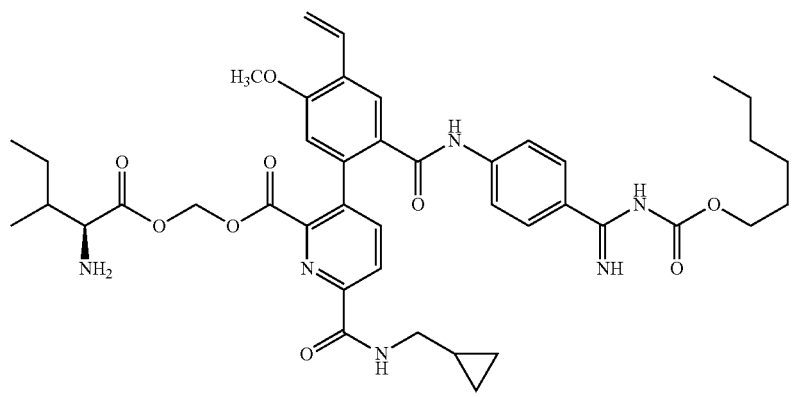 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)C(C)CC)cc1OC]

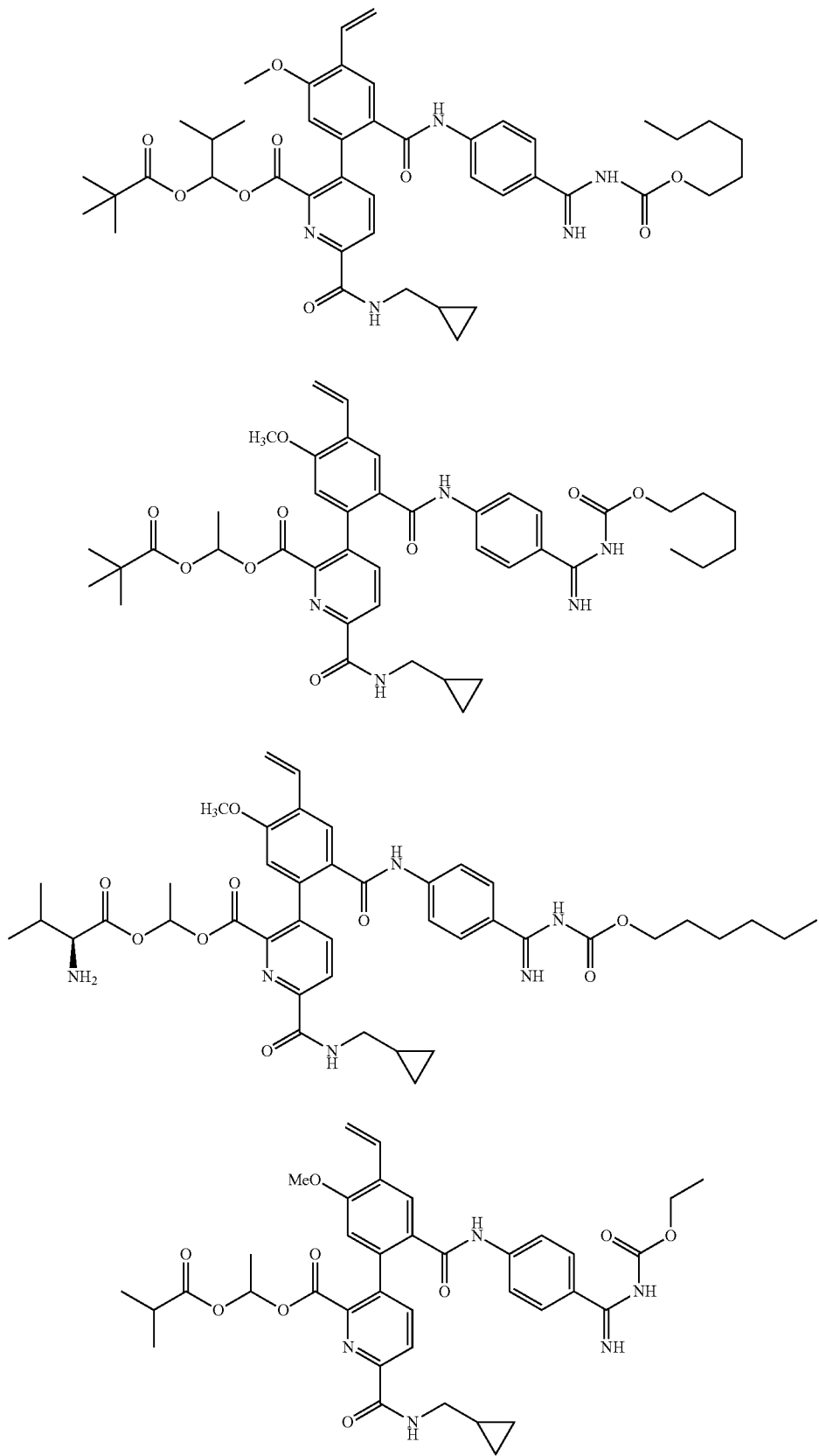

-continued
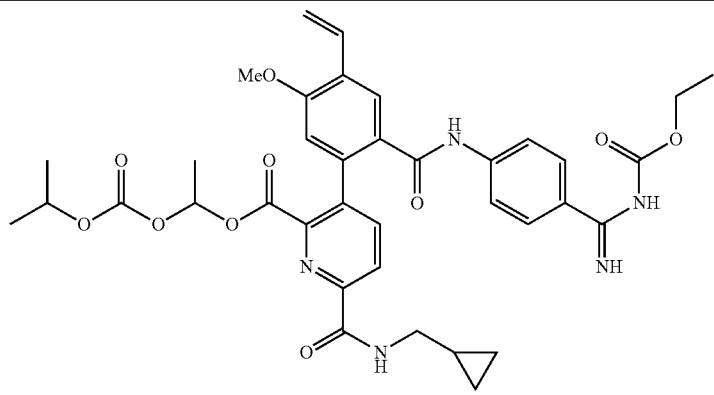
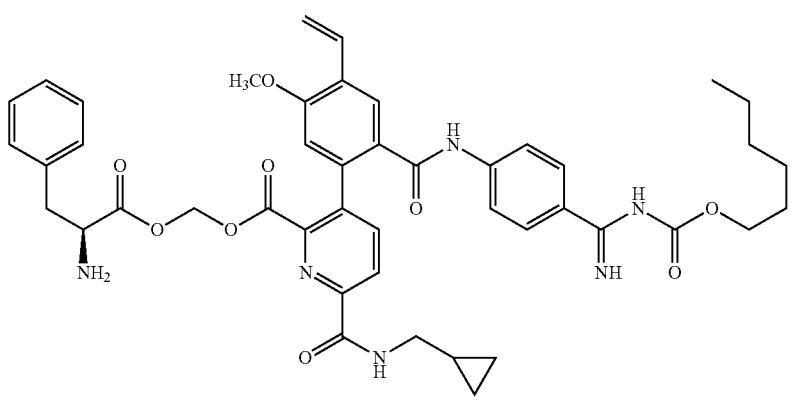 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)Cc2ccccc2)cc1OC]
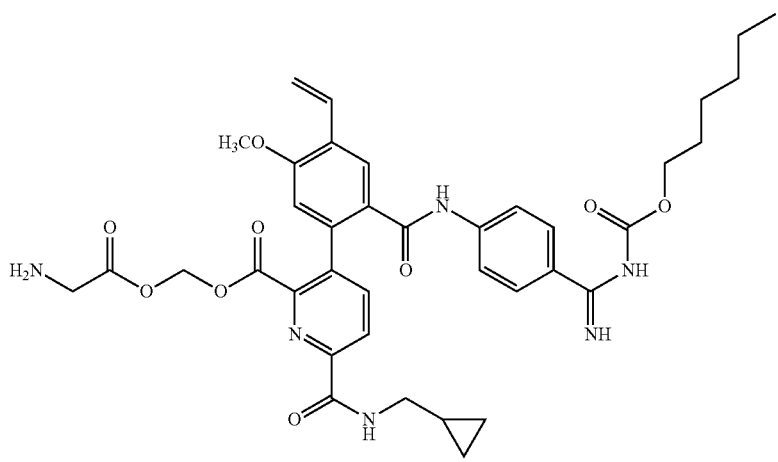 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)CN)cc1OC]
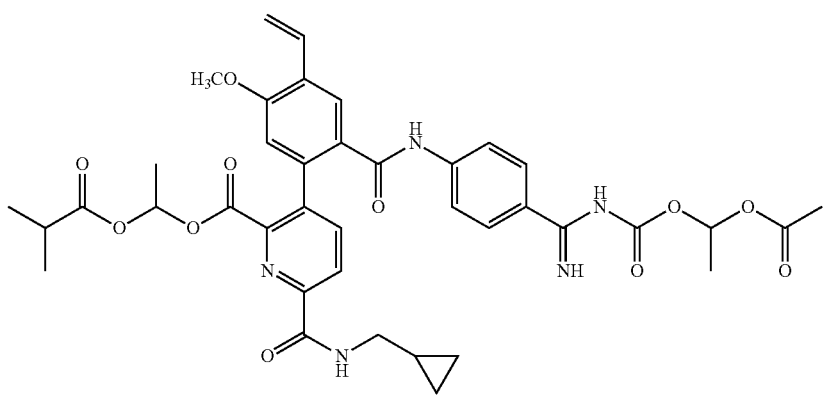 [SMILES: C=Cc1cc(C(=O)Nc2ccc(C(=N)NC(=O)OC(C)OC(C)=O)cc2)c(-c2ccc(C(=O)NCC3CC3)nc2C(=O)OC(C)OC(=O)C(C)C)cc1OC]

-continued
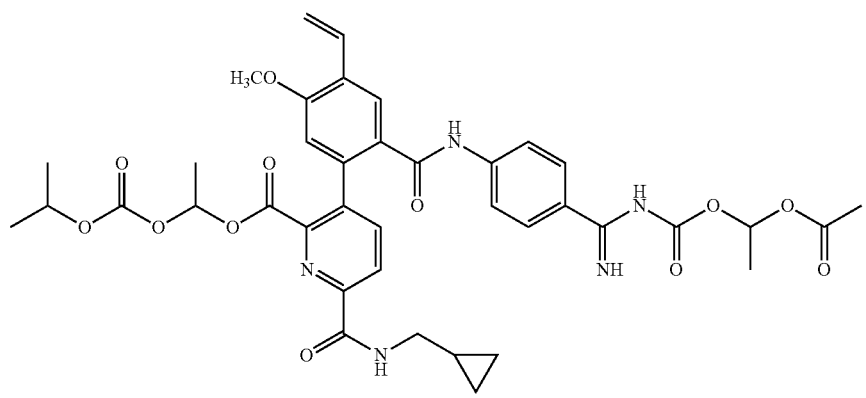 [SMILES: C=Cc1cc(C(=O)Nc2ccc(C(=N)NC(=O)OC(C)OC(C)=O)cc2)c(-c2ccc(C(=O)NCC3CC3)nc2C(=O)OC(C)OC(=O)OC(C)C)cc1OC]
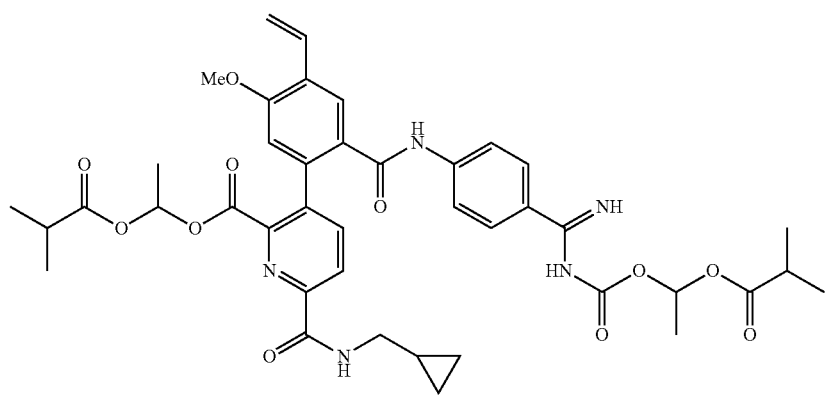 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OC(C)OC(=O)C(C)C)cc1OC]
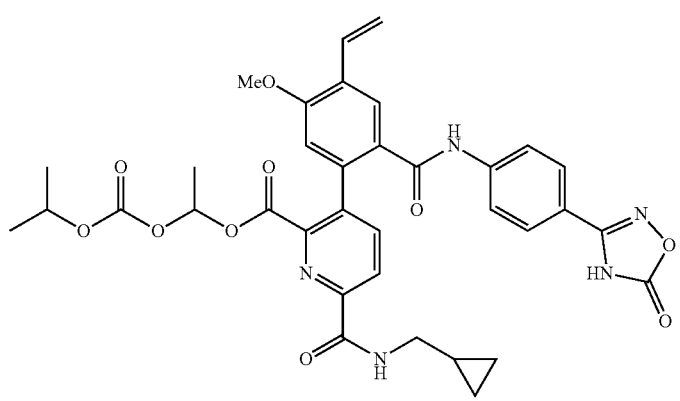 [SMILES: C=Cc1cc(C(=O)Nc2ccc(-c3noc(=O)[nH]3)cc2)c(-c2ccc(C(=O)NCC3CC3)nc2C(=O)OC(C)OC(=O)OC(C)C)cc1OC]
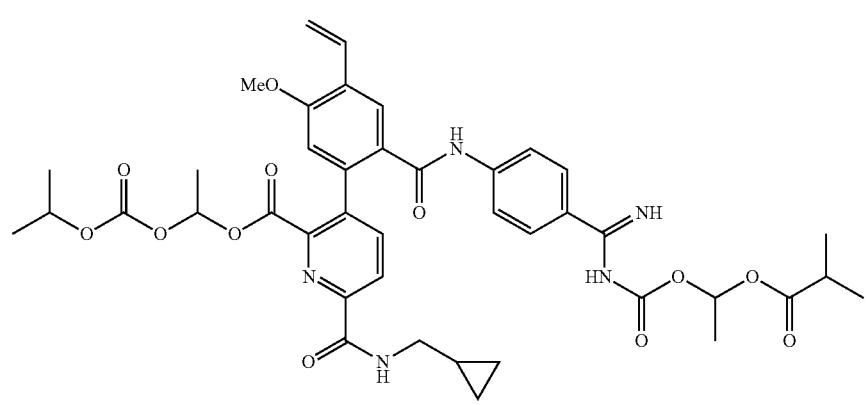 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OC(C)OC(=O)OC(C)C)cc1OC]

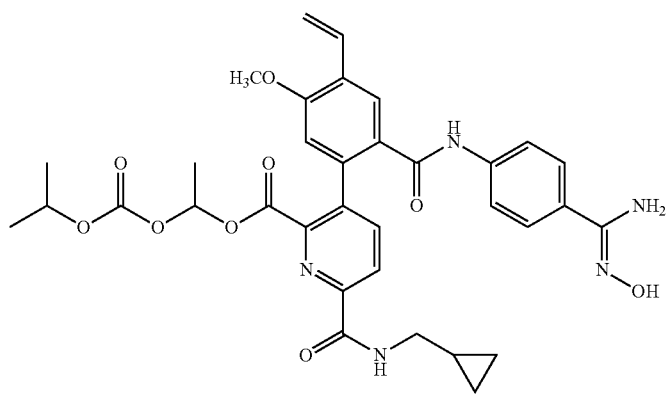 [SMILES: C=Cc1cc(C(=O)Nc2ccc(/C(N)=N/O)cc2)c(-c2ccc(C(=O)NCC3CC3)nc2C(=O)OC(C)OC(=O)OC(C)C)cc1OC]
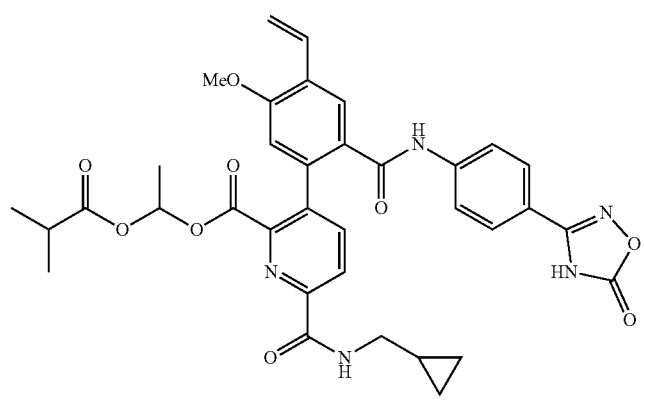 [SMILES: C=Cc1cc(C(=O)Nc2ccc(-c3noc(=O)[nH]3)cc2)c(-c2ccc(C(=O)NCC3CC3)nc2C(=O)OC(C)OC(=O)C(C)C)cc1OC]
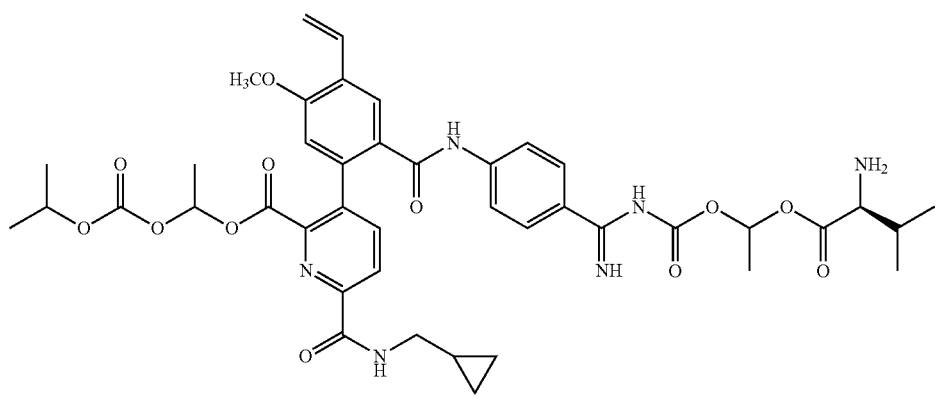 [SMILES: C=Cc1cc(C(=O)Nc2ccc(C(=N)NC(=O)OC(C)OC(=O)[C@@H](N)C(C)C)cc2)c(-c2ccc(C(=O)NCC3CC3)nc2C(=O)OC(C)OC(=O)OC(C)C)cc1OC]
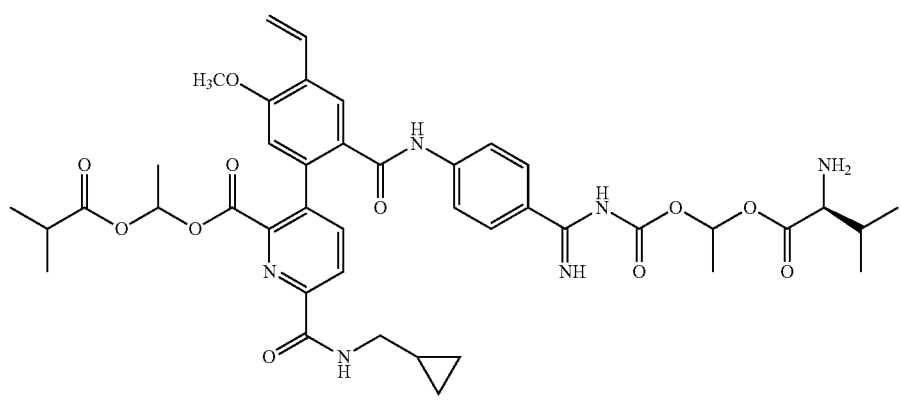 [SMILES: C=Cc1cc(C(=O)Nc2ccc(C(=N)NC(=O)OC(C)OC(=O)[C@@H](N)C(C)C)cc2)c(-c2ccc(C(=O)NCC3CC3)nc2C(=O)OC(C)OC(=O)C(C)C)cc1OC]

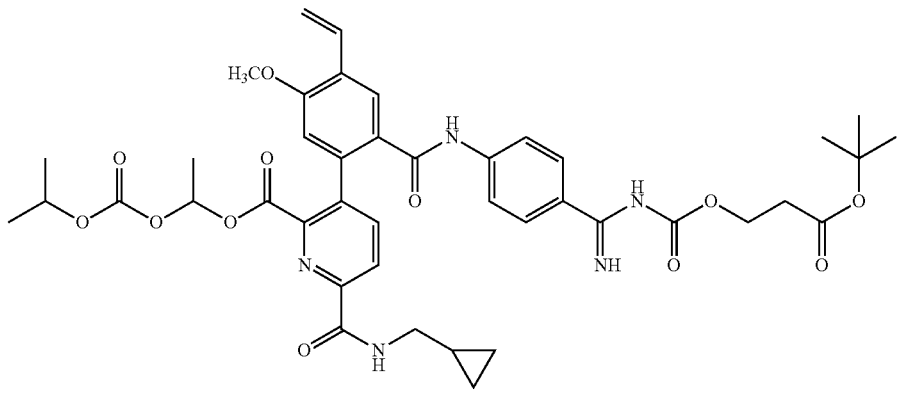 [SMILES: C=Cc1cc(C(=O)Nc2ccc(C(=N)NC(=O)OCCC(=O)OC(C)(C)C)cc2)c(-c2ccc(C(=O)NCC3CC3)nc2C(=O)OC(C)OC(=O)OC(C)C)cc1OC]
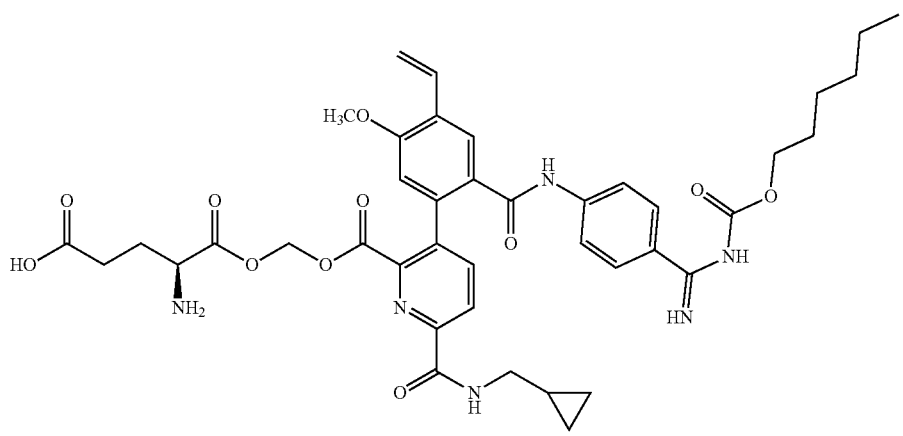 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)CCC(=O)O)cc1OC]
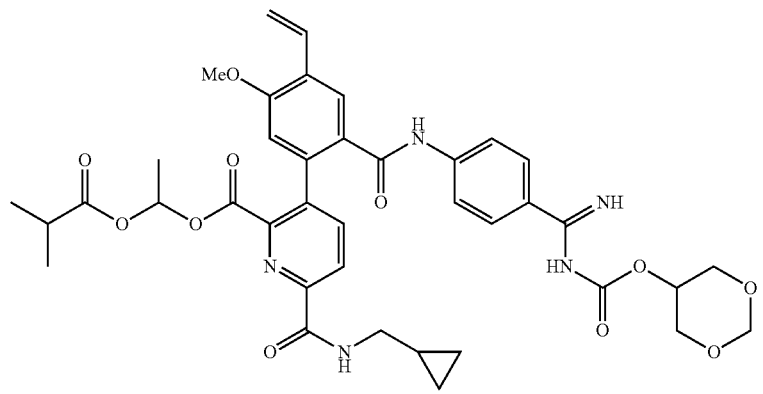 [SMILES: C=Cc1cc(C(=O)Nc2ccc(C(=N)NC(=O)OC3COCOC3)cc2)c(-c2ccc(C(=O)NCC3CC3)nc2C(=O)OC(C)OC(=O)C(C)C)cc1OC]
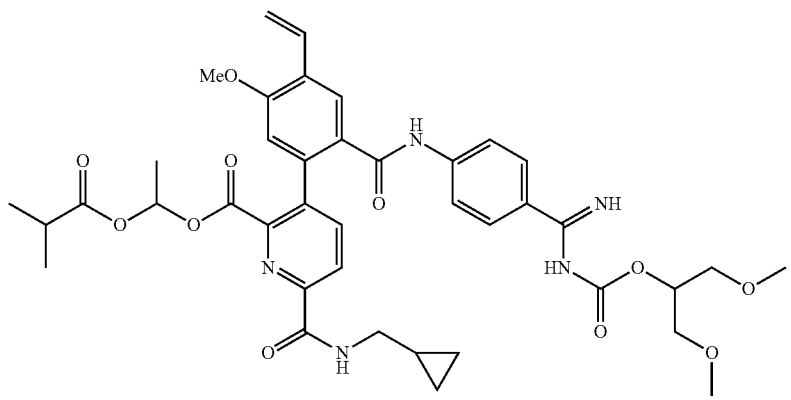 [SMILES: C=Cc1cc(C(=O)Nc2ccc(C(=N)NC(=O)OC(COC)COC)cc2)c(-c2ccc(C(=O)NCC3CC3)nc2C(=O)OC(C)OC(=O)C(C)C)cc1OC]

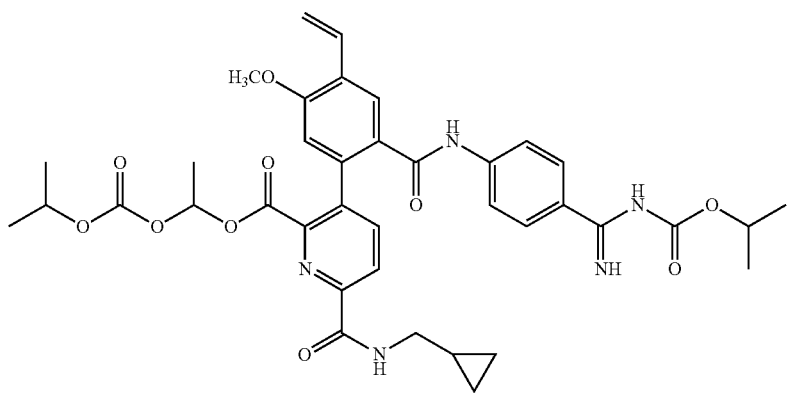 [SMILES: C=Cc1cc(C(=O)Nc2ccc(C(=N)NC(=O)OC(C)C)cc2)c(-c2ccc(C(=O)NCC3CC3)nc2C(=O)OC(C)OC(=O)OC(C)C)cc1OC]
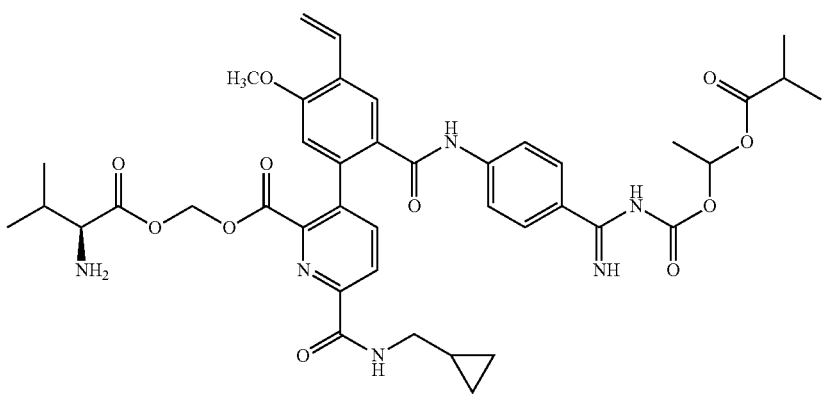 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OCOC(=O)[C@@H](N)C(C)C)cc1OC]
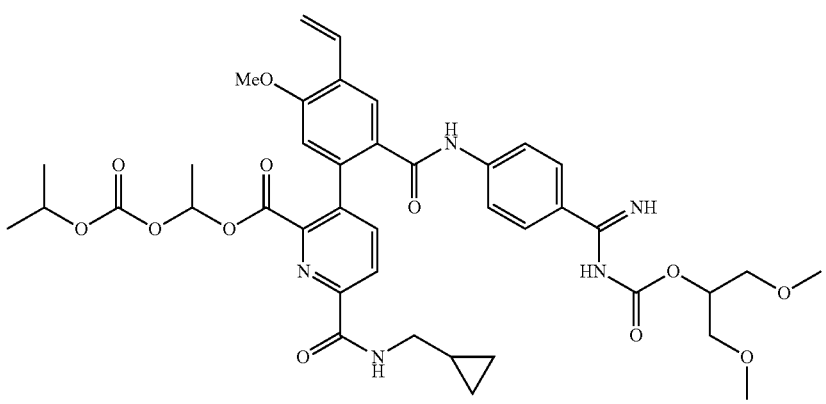 [SMILES: C=Cc1cc(C(=O)Nc2ccc(C(=N)NC(=O)OC(COC)COC)cc2)c(-c2ccc(C(=O)NCC3CC3)nc2C(=O)OC(C)OC(=O)OC(C)C)cc1OC]
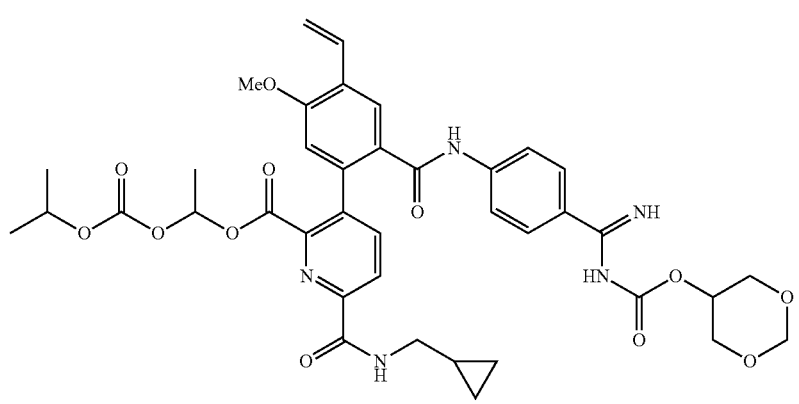 [SMILES: C=Cc1cc(C(=O)Nc2ccc(C(=N)NC(=O)OC3COCOC3)cc2)c(-c2ccc(C(=O)NCC3CC3)nc2C(=O)OC(C)OC(=O)OC(C)C)cc1OC]

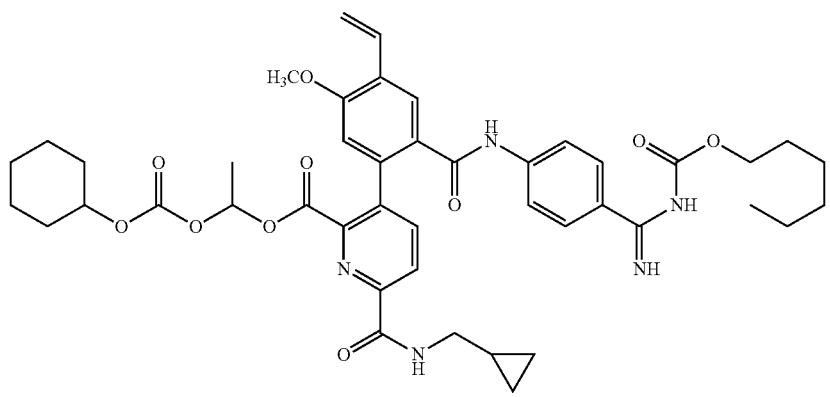 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)OC2CCCCC2)cc1OC]
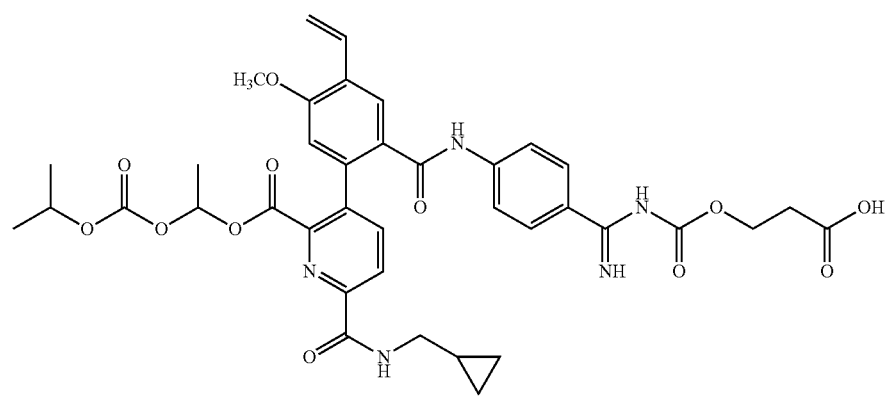 [SMILES: C=Cc1cc(C(=O)Nc2ccc(C(=N)NC(=O)OCCC(=O)O)cc2)c(-c2ccc(C(=O)NCC3CC3)nc2C(=O)OC(C)OC(=O)OC(C)C)cc1OC]
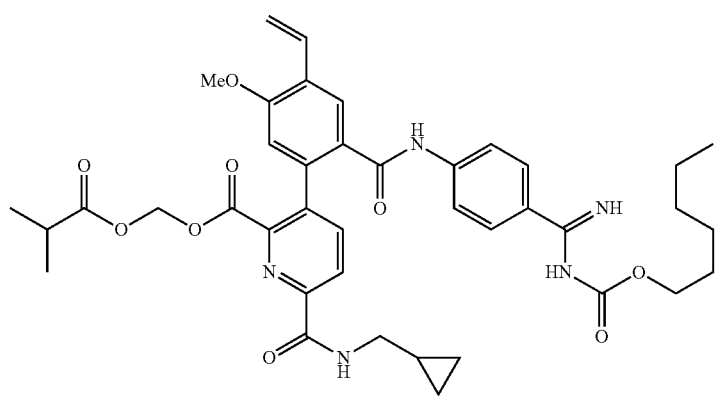 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)C(C)C)cc1OC]
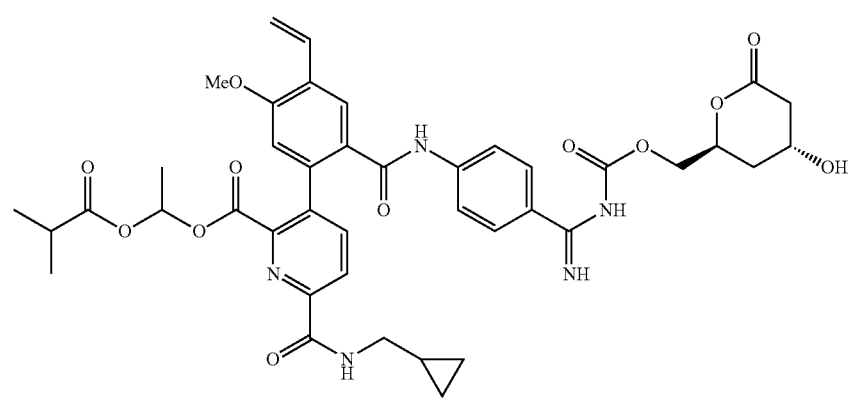 [SMILES: C=Cc1cc(C(=O)Nc2ccc(C(=N)NC(=O)OC[C@@H]3C[C@@H](O)CC(=O)O3)cc2)c(-c2ccc(C(=O)NCC3CC3)nc2C(=O)OC(C)OC(=O)C(C)C)cc1OC]

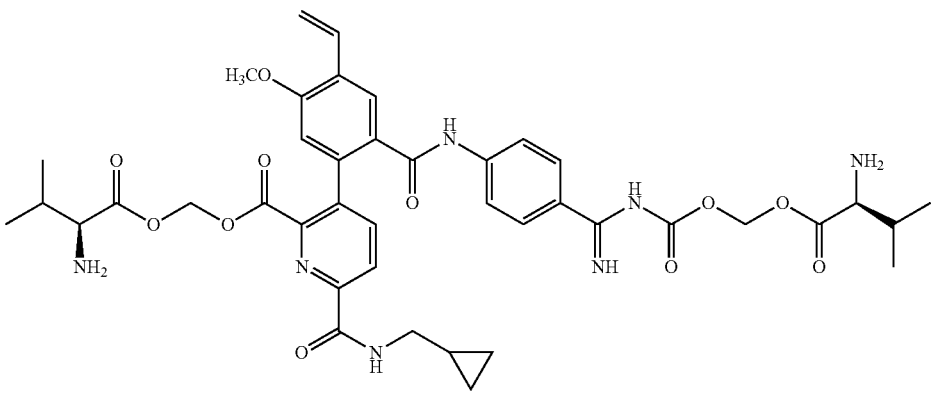 [SMILES: C=Cc1cc(C(=O)Nc2ccc(C(=N)NC(=O)OCOC(=O)[C@@H](N)C(C)C)cc2)c(-c2ccc(C(=O)NCC3CC3)nc2C(=O)OCOC(=O)[C@@H](N)C(C)C)cc1OC]
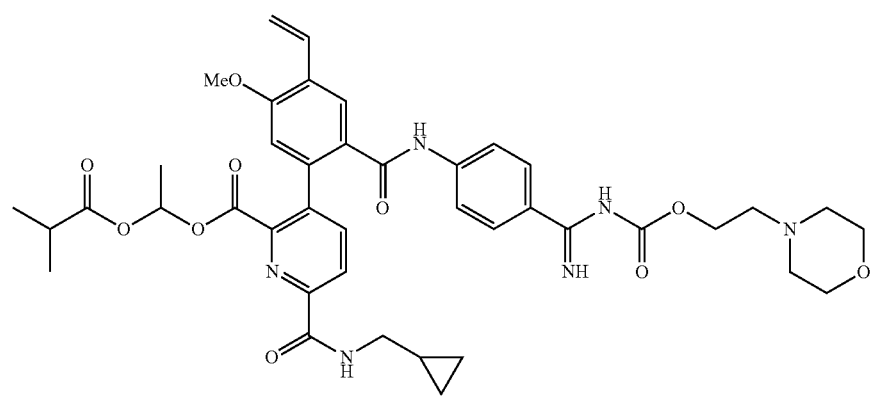 [SMILES: C=Cc1cc(C(=O)Nc2ccc(C(=N)NC(=O)OCCN3CCOCC3)cc2)c(-c2ccc(C(=O)NCC3CC3)nc2C(=O)OC(C)OC(=O)C(C)C)cc1OC]
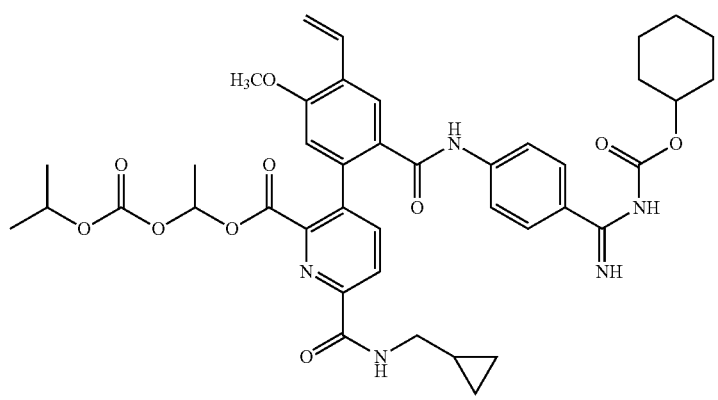 [SMILES: C=Cc1cc(C(=O)Nc2ccc(C(=N)NC(=O)OC3CCCCC3)cc2)c(-c2ccc(C(=O)NCC3CC3)nc2C(=O)OC(C)OC(=O)OC(C)C)cc1OC]
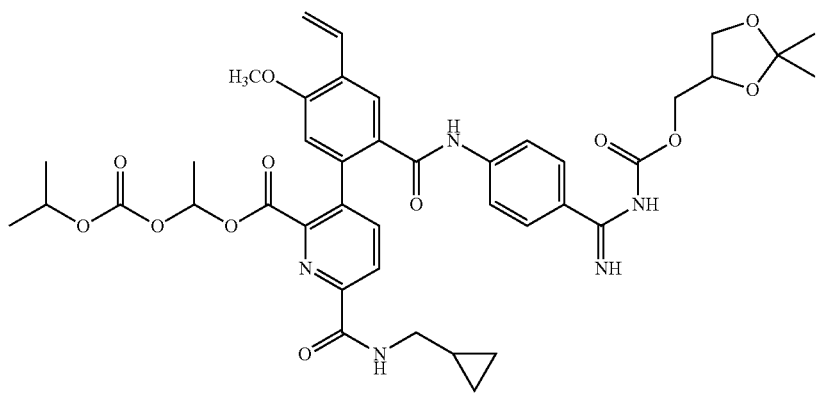 [SMILES: C=Cc1cc(C(=O)Nc2ccc(C(=N)NC(=O)OCC3COC(C)(C)O3)cc2)c(-c2ccc(C(=O)NCC3CC3)nc2C(=O)OC(C)OC(=O)OC(C)C)cc1OC]

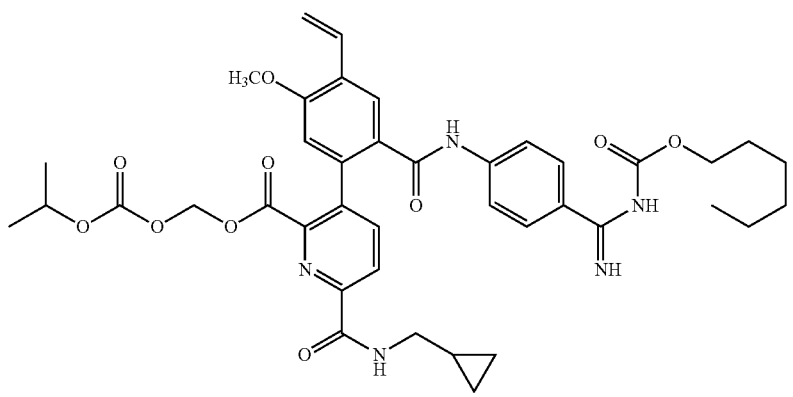 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)OC(C)C)cc1OC]
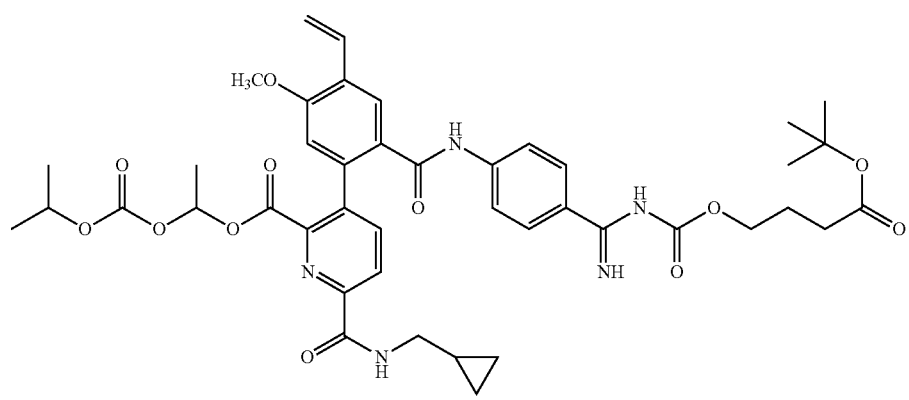 [SMILES: C=Cc1cc(C(=O)Nc2ccc(C(=N)NC(=O)OCCCC(=O)OC(C)(C)C)cc2)c(-c2ccc(C(=O)NCC3CC3)nc2C(=O)OC(C)OC(=O)OC(C)C)cc1OC]
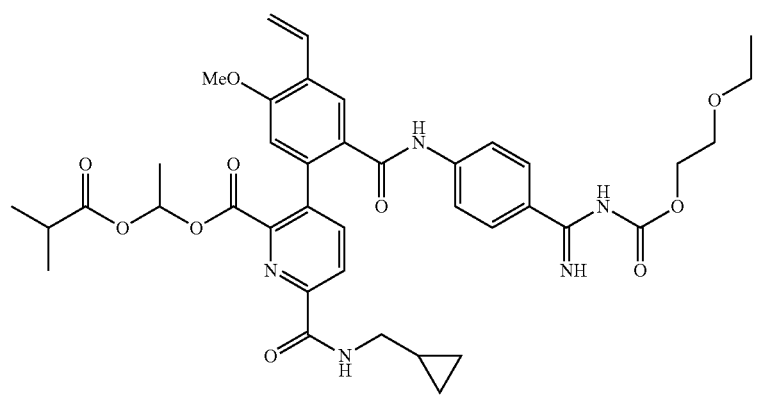 [SMILES: C=Cc1cc(C(=O)Nc2ccc(C(=N)NC(=O)OCCOCC)cc2)c(-c2ccc(C(=O)NCC3CC3)nc2C(=O)OC(C)OC(=O)C(C)C)cc1OC]
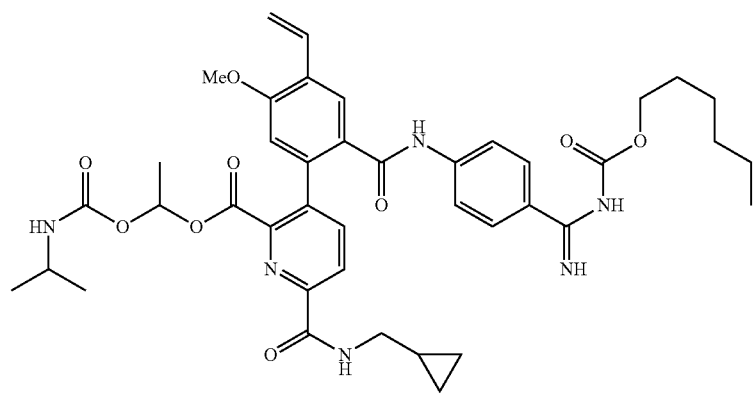 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)NC(C)C)cc1OC]

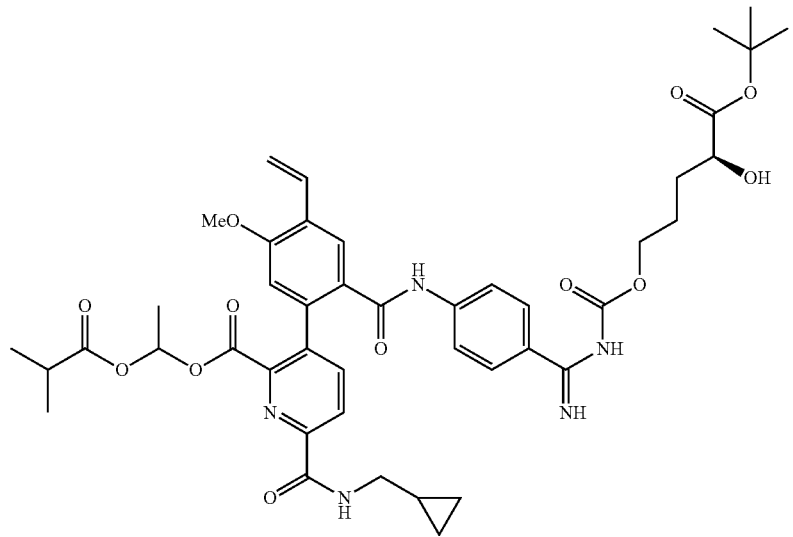 [SMILES: C=Cc1cc(C(=O)Nc2ccc(C(=N)NC(=O)OCCC[C@H](O)C(=O)OC(C)(C)C)cc2)c(-c2ccc(C(=O)NCC3CC3)nc2C(=O)OC(C)OC(=O)C(C)C)cc1OC]
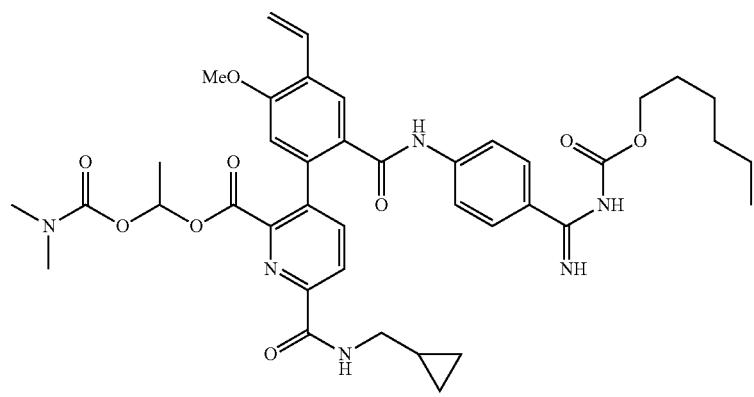 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)N(C)C)cc1OC]
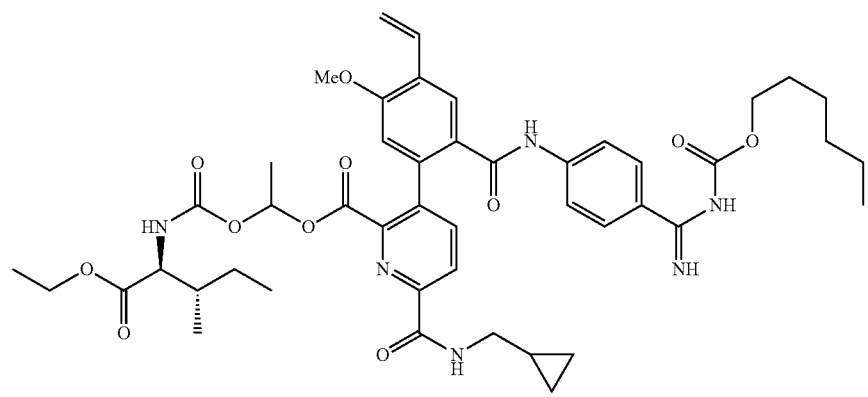 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)N[C@H](C(=O)OCC)[C@@H](C)CC)cc1OC]

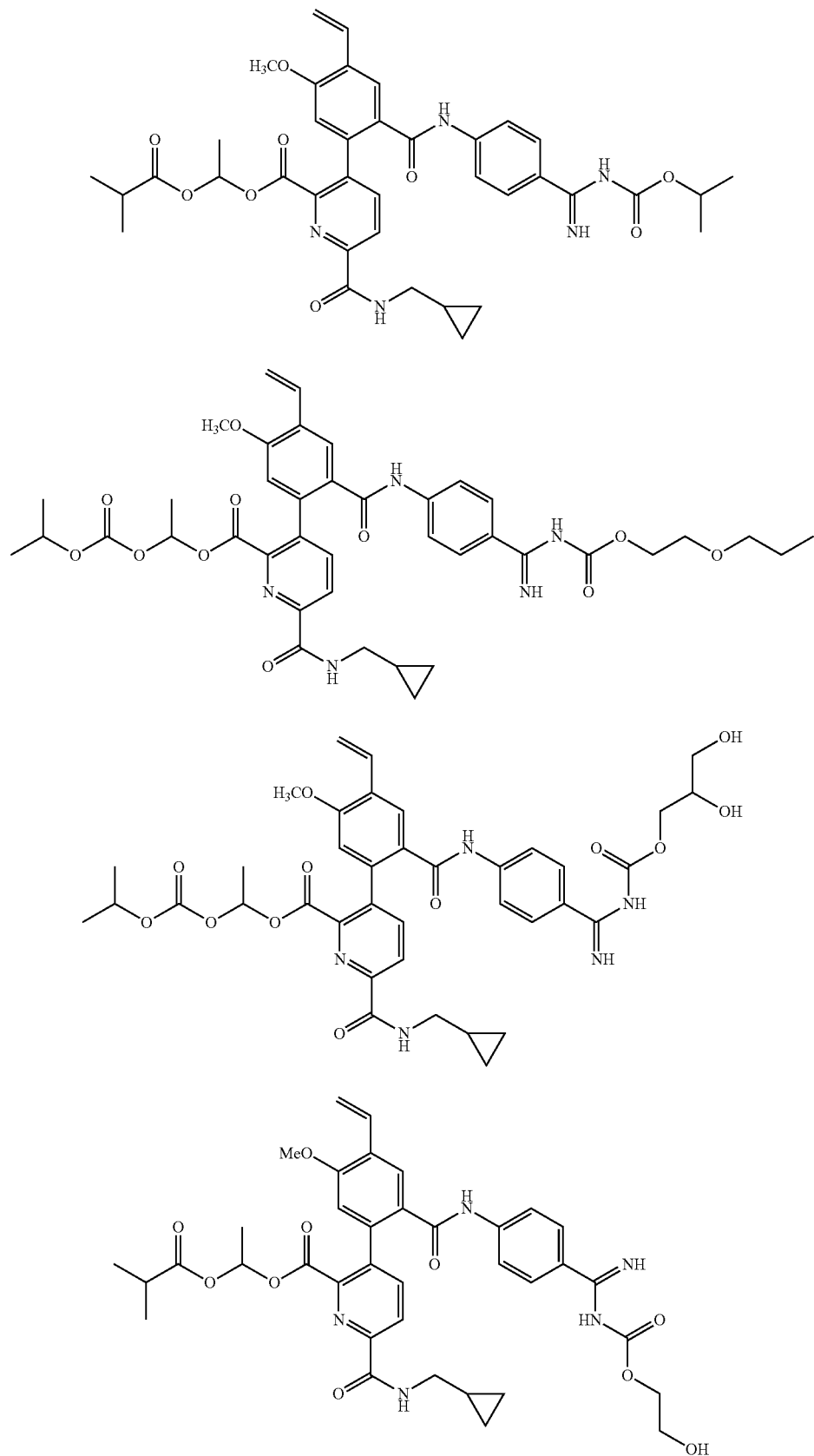

-continued
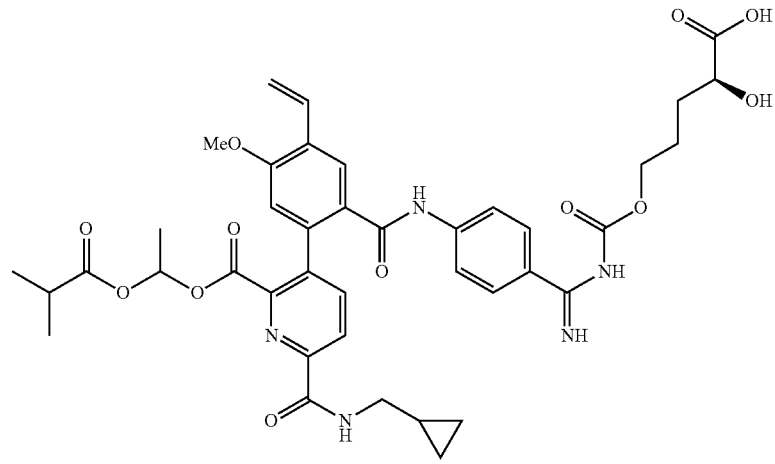 [SMILES: C=Cc1cc(C(=O)Nc2ccc(C(=N)NC(=O)OCCC[C@H](O)C(=O)O)cc2)c(-c2ccc(C(=O)NCC3CC3)nc2C(=O)OC(C)OC(=O)C(C)C)cc1OC]
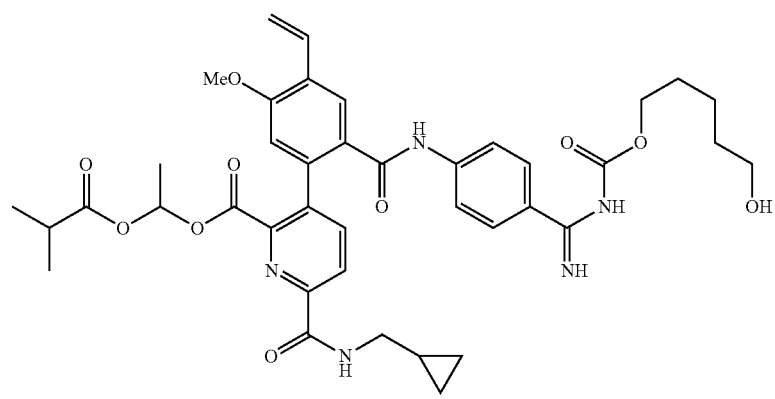 [SMILES: C=Cc1cc(C(=O)Nc2ccc(C(=N)NC(=O)OCCCCCO)cc2)c(-c2ccc(C(=O)NCC3CC3)nc2C(=O)OC(C)OC(=O)C(C)C)cc1OC]
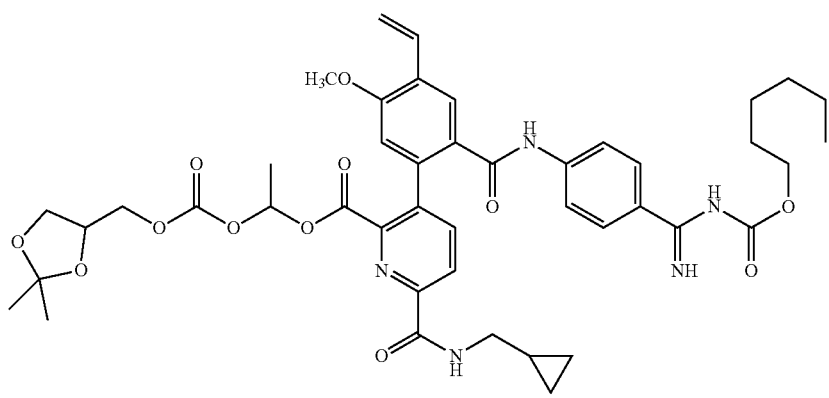 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)OCC2COC(C)(C)O2)cc1OC]
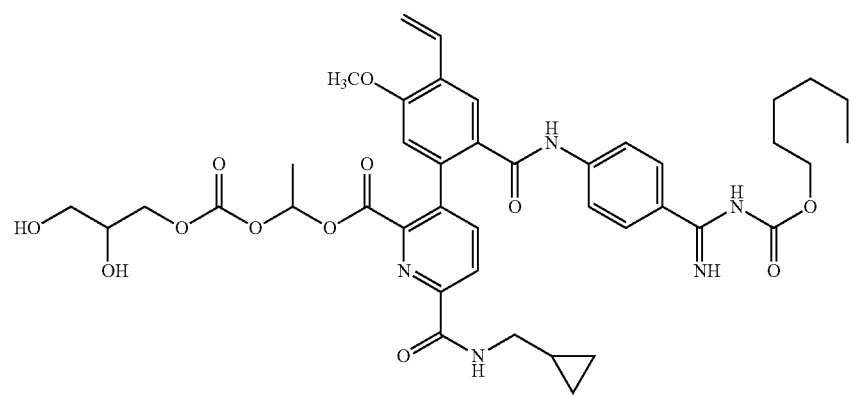 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)OCC(O)CO)cc1OC]

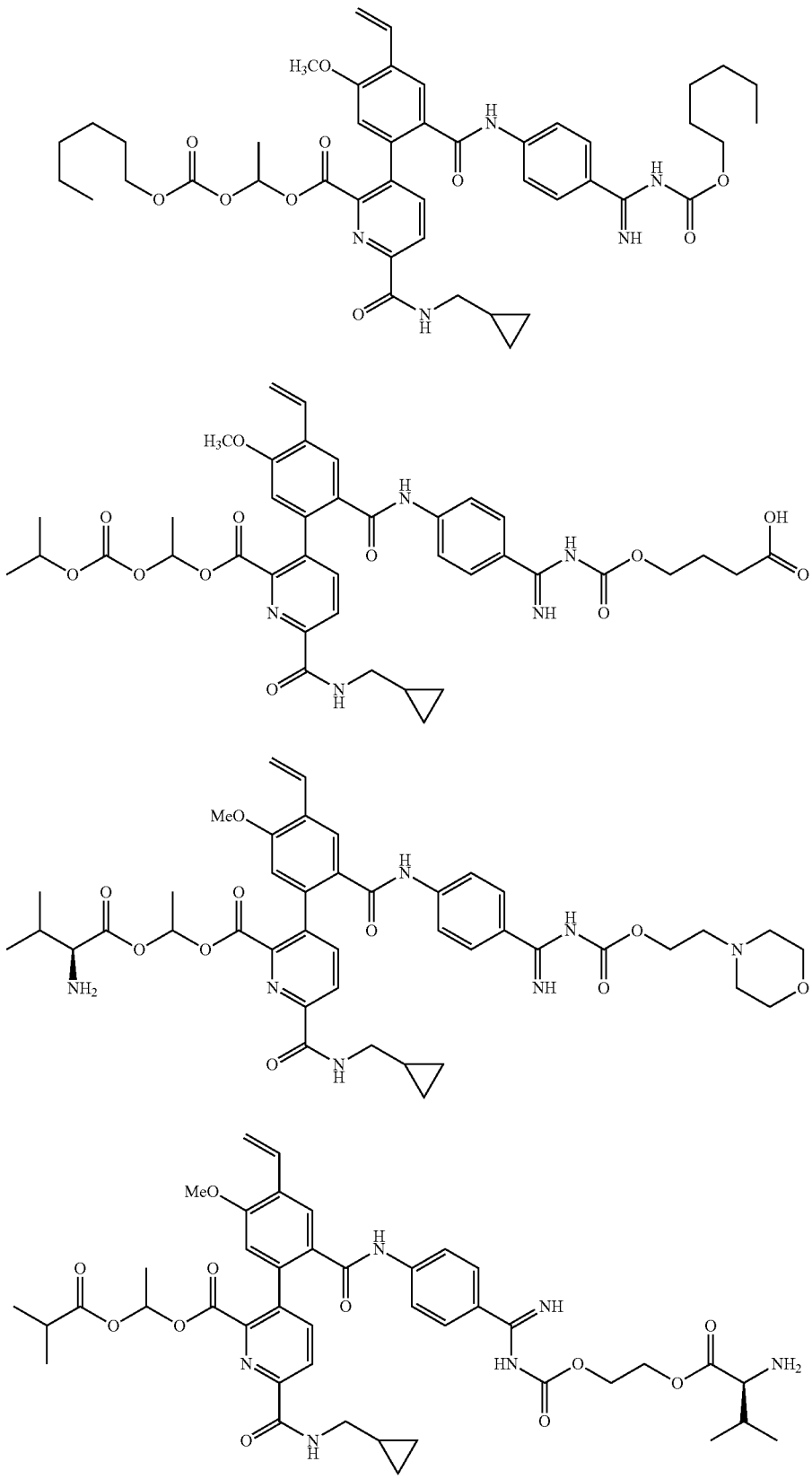

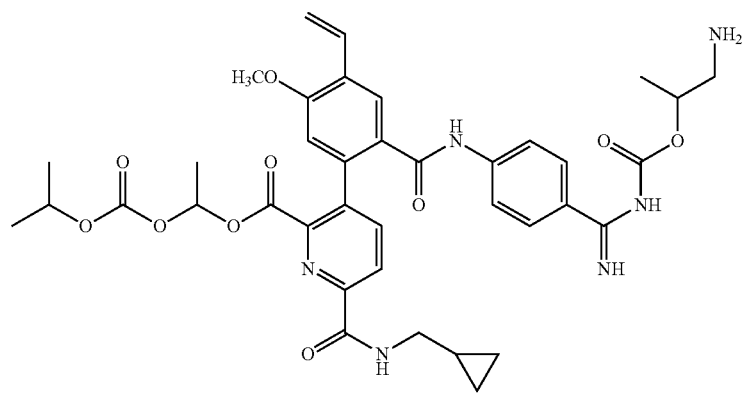 [SMILES: C=Cc1cc(C(=O)Nc2ccc(C(=N)NC(=O)OC(C)CN)cc2)c(-c2ccc(C(=O)NCC3CC3)nc2C(=O)OC(C)OC(=O)OC(C)C)cc1OC]
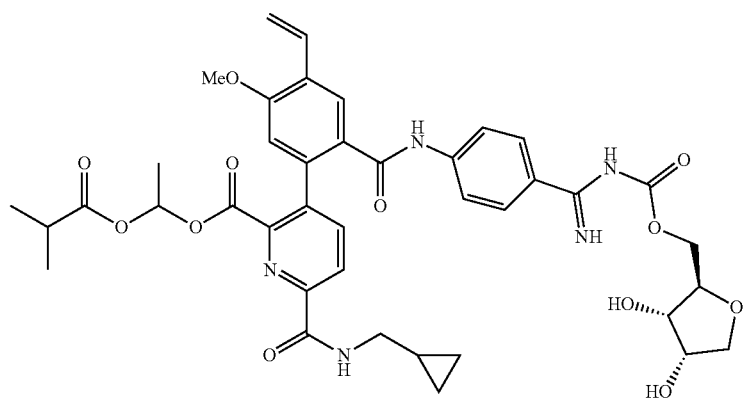 [SMILES: C=Cc1cc(C(=O)Nc2ccc(C(=N)NC(=O)OC[C@H]3OC[C@H](O)[C@@H]3O)cc2)c(-c2ccc(C(=O)NCC3CC3)nc2C(=O)OC(C)OC(=O)C(C)C)cc1OC]
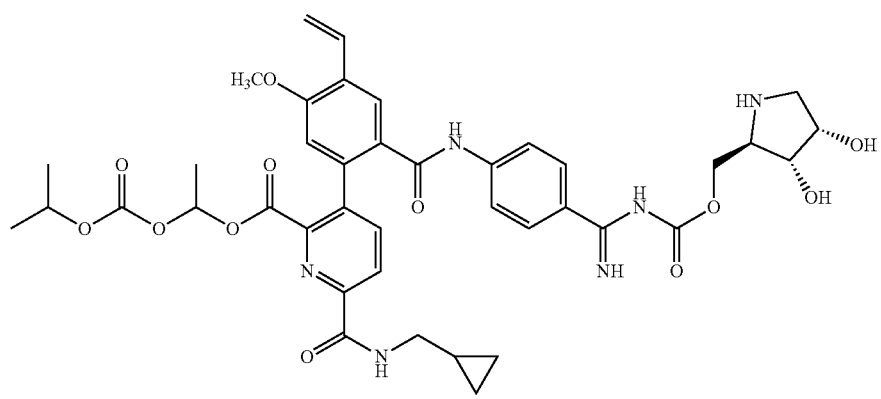 [SMILES: C=Cc1cc(C(=O)Nc2ccc(C(=N)NC(=O)OC[C@H]3NC[C@H](O)[C@@H]3O)cc2)c(-c2ccc(C(=O)NCC3CC3)nc2C(=O)OC(C)OC(=O)OC(C)C)cc1OC]
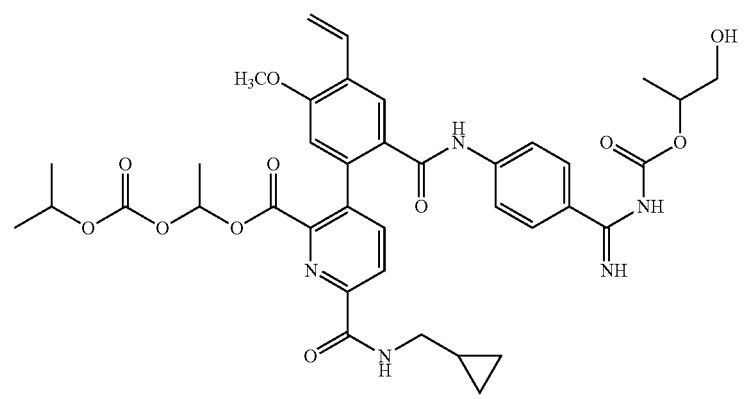 [SMILES: C=Cc1cc(C(=O)Nc2ccc(C(=N)NC(=O)OC(C)CO)cc2)c(-c2ccc(C(=O)NCC3CC3)nc2C(=O)OC(C)OC(=O)OC(C)C)cc1OC]

-continued
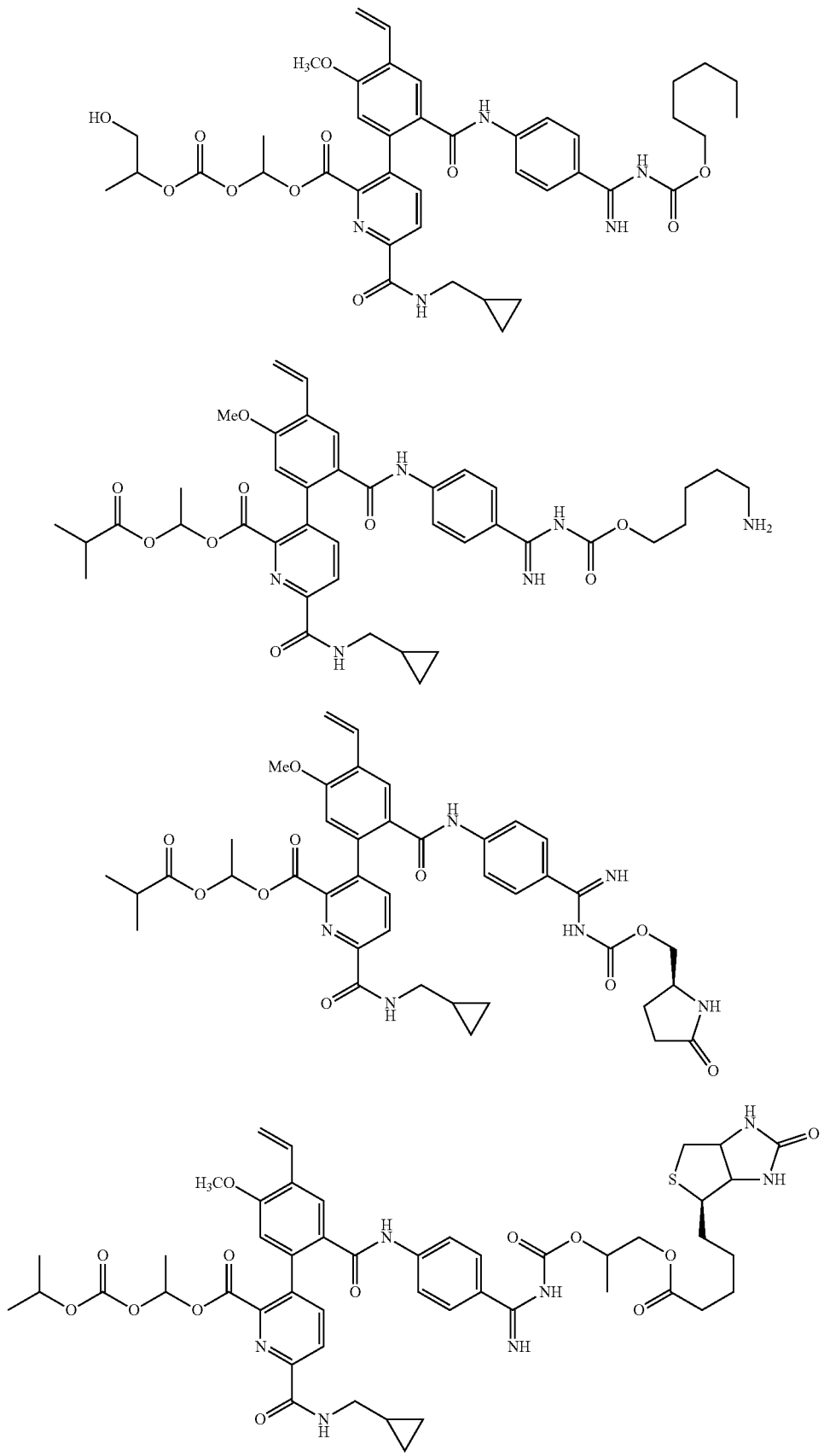

-continued
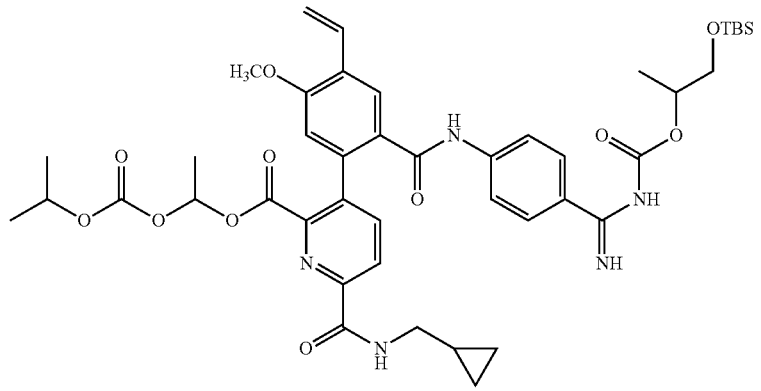 [SMILES: C=Cc1cc(C(=O)Nc2ccc(C(=N)NC(=O)OC(C)CO[Si](C)(C)C(C)(C)C)cc2)c(-c2ccc(C(=O)NCC3CC3)nc2C(=O)OC(C)OC(=O)OC(C)C)cc1OC]
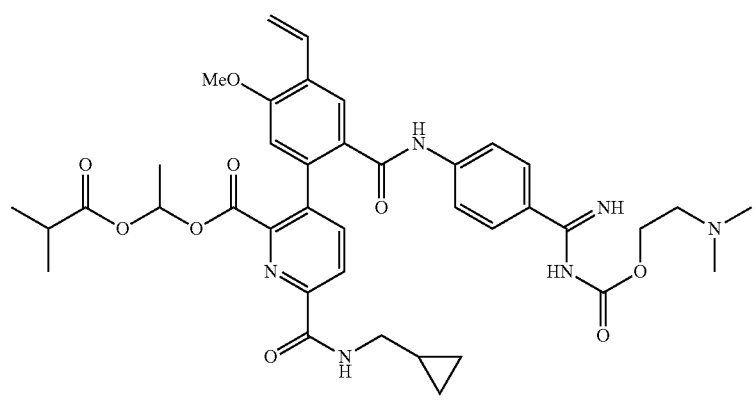 [SMILES: C=Cc1cc(C(=O)Nc2ccc(C(=N)NC(=O)OCCN(C)C)cc2)c(-c2ccc(C(=O)NCC3CC3)nc2C(=O)OC(C)OC(=O)C(C)C)cc1OC]
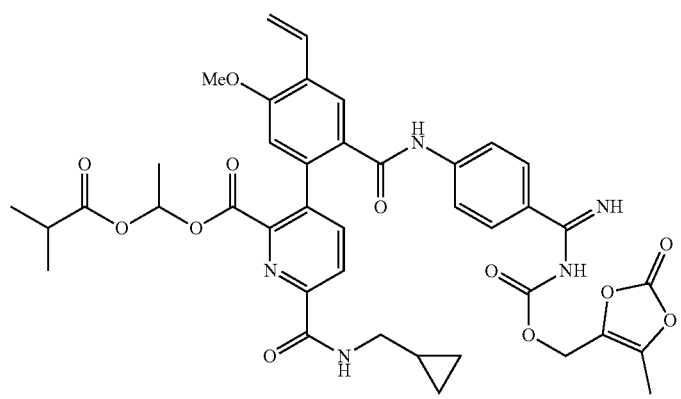 [SMILES: C=Cc1cc(C(=O)Nc2ccc(C(=N)NC(=O)OCc3oc(=O)oc3C)cc2)c(-c2ccc(C(=O)NCC3CC3)nc2C(=O)OC(C)OC(=O)C(C)C)cc1OC]
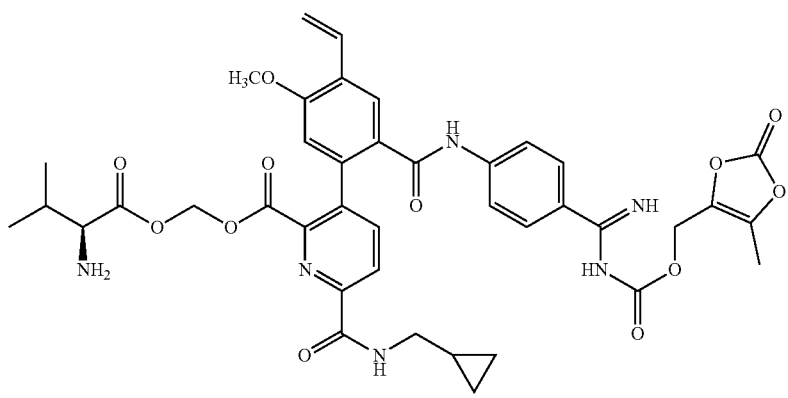 [SMILES: C=Cc1cc(C(=O)Nc2ccc(C(=N)NC(=O)OCc3oc(=O)oc3C)cc2)c(-c2ccc(C(=O)NCC3CC3)nc2C(=O)OCOC(=O)[C@@H](N)C(C)C)cc1OC]

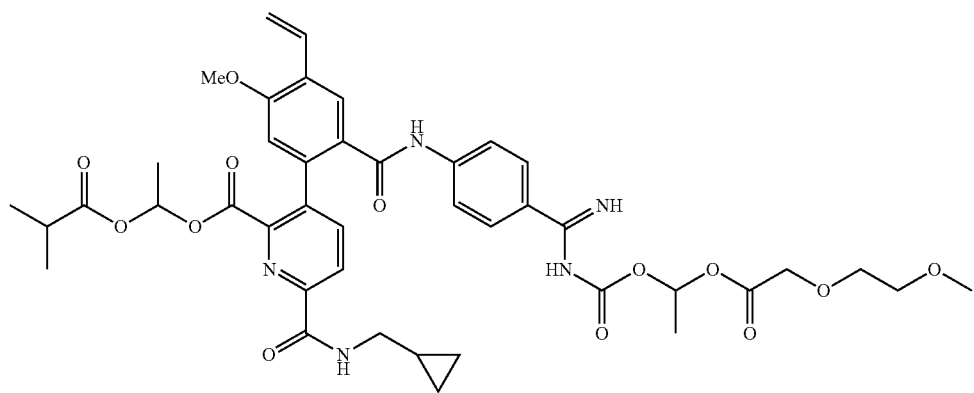 [SMILES: C=Cc1cc(C(=O)Nc2ccc(C(=N)NC(=O)OC(C)OC(=O)COCCOC)cc2)c(-c2ccc(C(=O)NCC3CC3)nc2C(=O)OC(C)OC(=O)C(C)C)cc1OC]
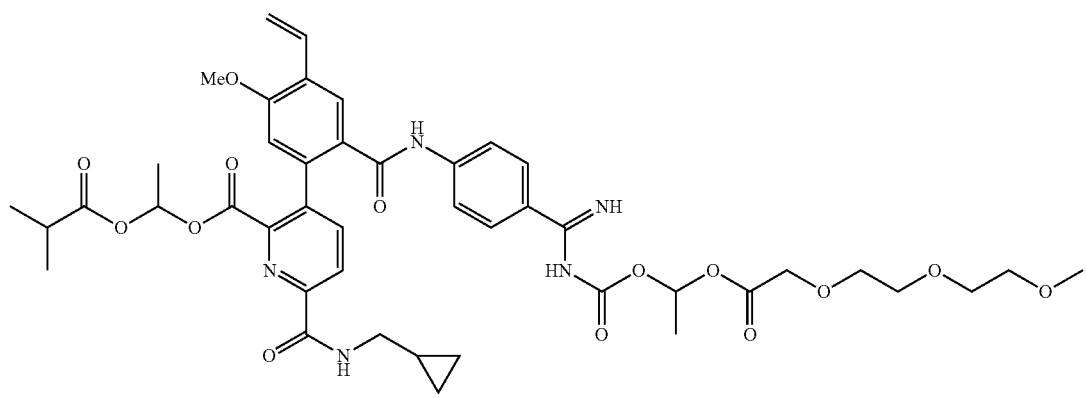 [SMILES: C=Cc1cc(C(=O)Nc2ccc(C(=N)NC(=O)OC(C)OC(=O)COCCOCCOC)cc2)c(-c2ccc(C(=O)NCC3CC3)nc2C(=O)OC(C)OC(=O)C(C)C)cc1OC]
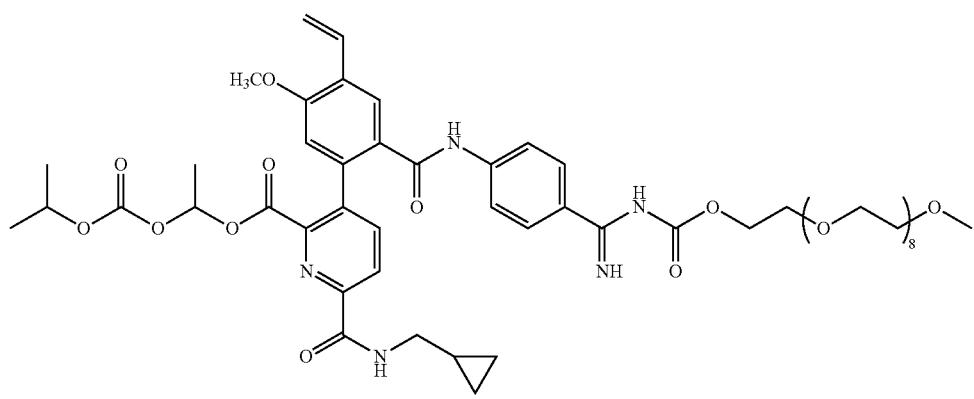
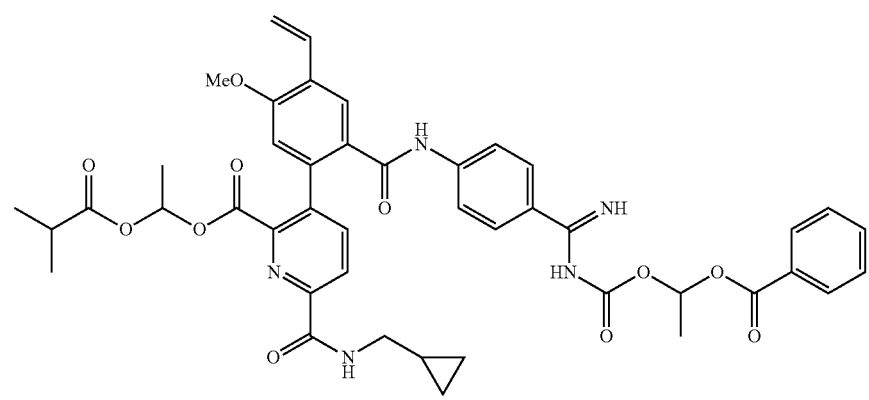 [SMILES: C=Cc1cc(C(=O)Nc2ccc(C(=N)NC(=O)OC(C)OC(=O)c3ccccc3)cc2)c(-c2ccc(C(=O)NCC3CC3)nc2C(=O)OC(C)OC(=O)C(C)C)cc1OC]

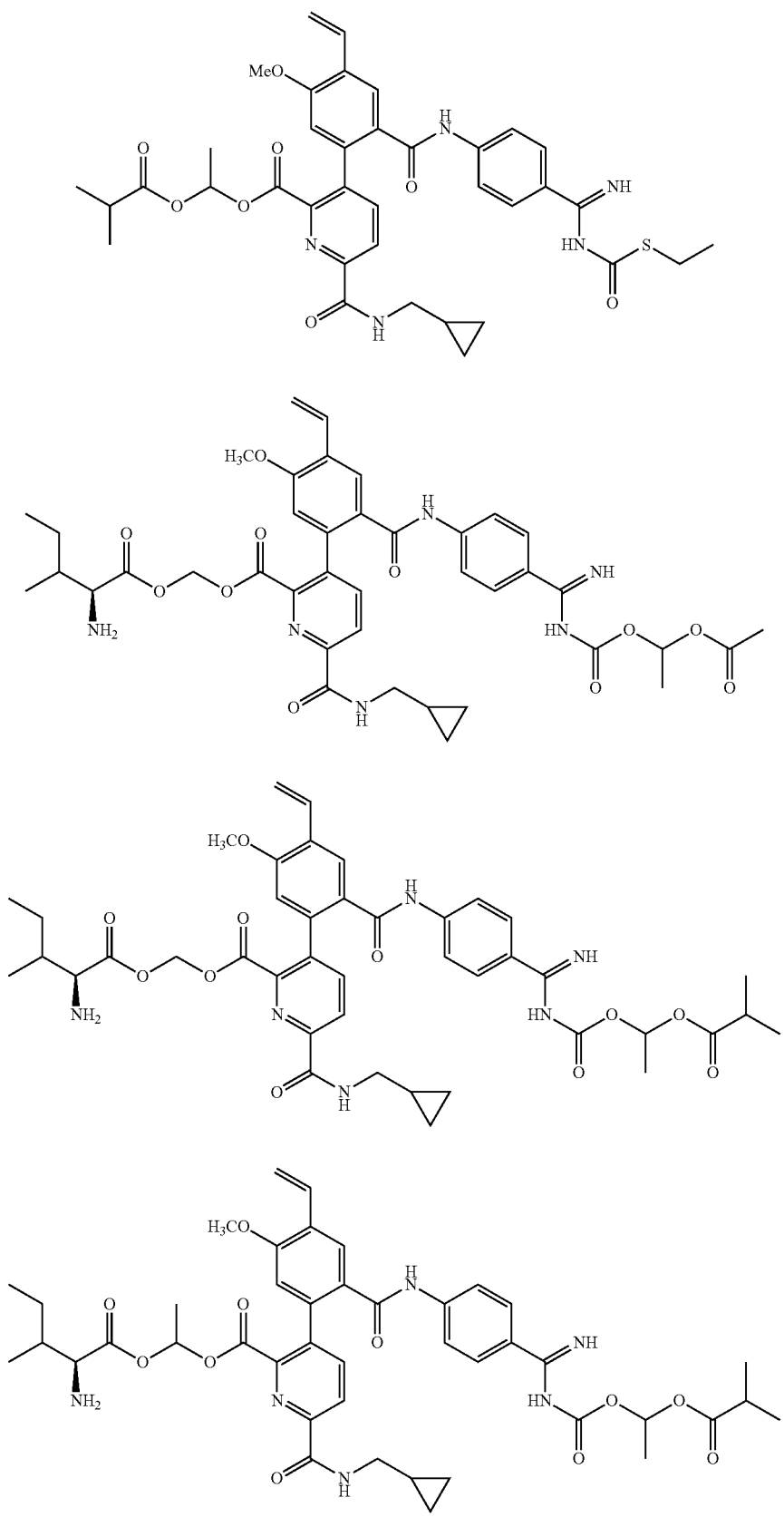

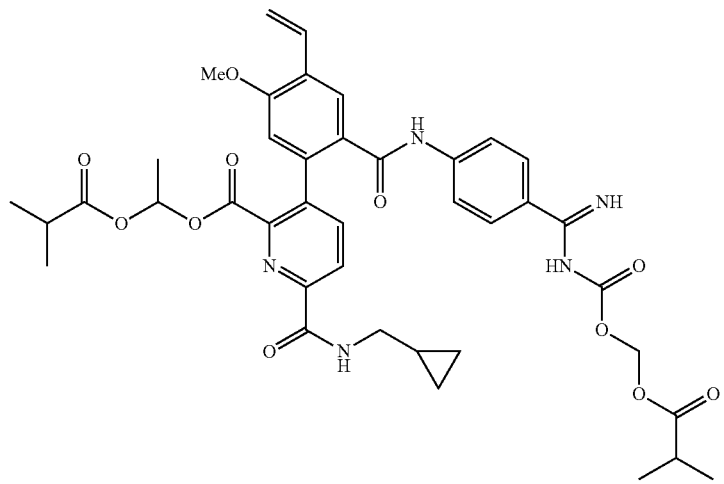 [SMILES: C=Cc1cc(C(=O)Nc2ccc(C(=N)NC(=O)OCOC(=O)C(C)C)cc2)c(-c2ccc(C(=O)NCC3CC3)nc2C(=O)OC(C)OC(=O)C(C)C)cc1OC]
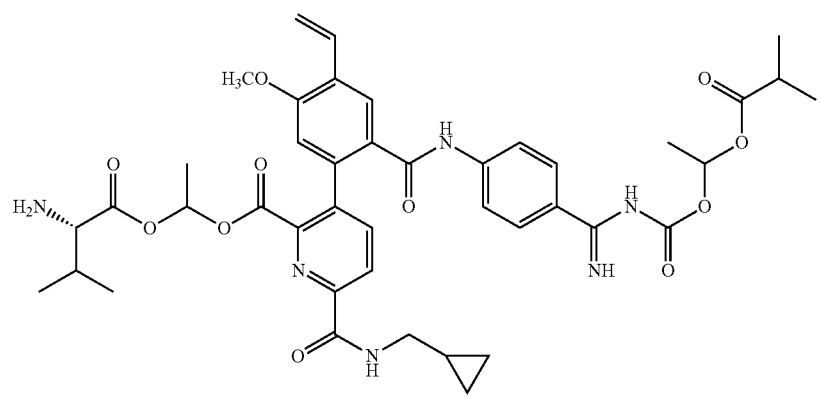 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OC(C)OC(=O)[C@@H](N)C(C)C)cc1OC]
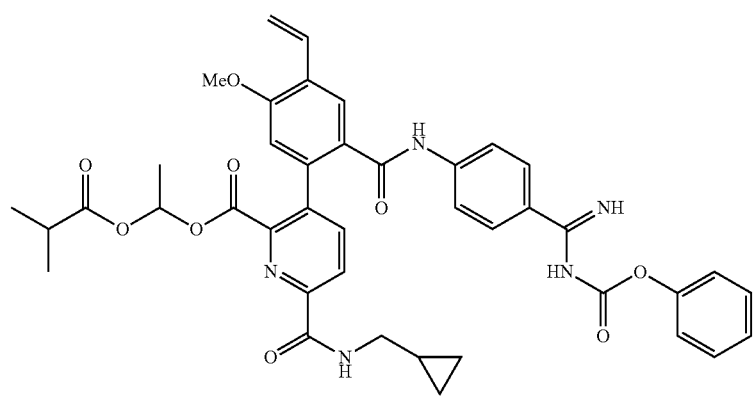 [SMILES: C=Cc1cc(C(=O)Nc2ccc(C(=N)NC(=O)Oc3ccccc3)cc2)c(-c2ccc(C(=O)NCC3CC3)nc2C(=O)OC(C)OC(=O)C(C)C)cc1OC]

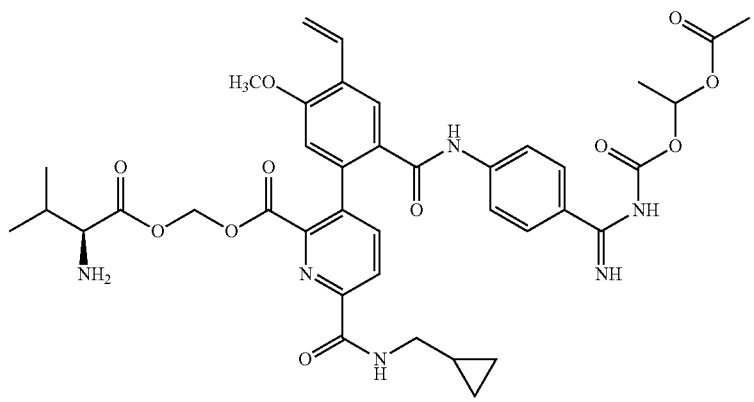 [SMILES: C=Cc1cc(C(=O)Nc2ccc(C(=N)NC(=O)OC(C)OC(C)=O)cc2)c(-c2ccc(C(=O)NCC3CC3)nc2C(=O)OCOC(=O)[C@@H](N)C(C)C)cc1OC]
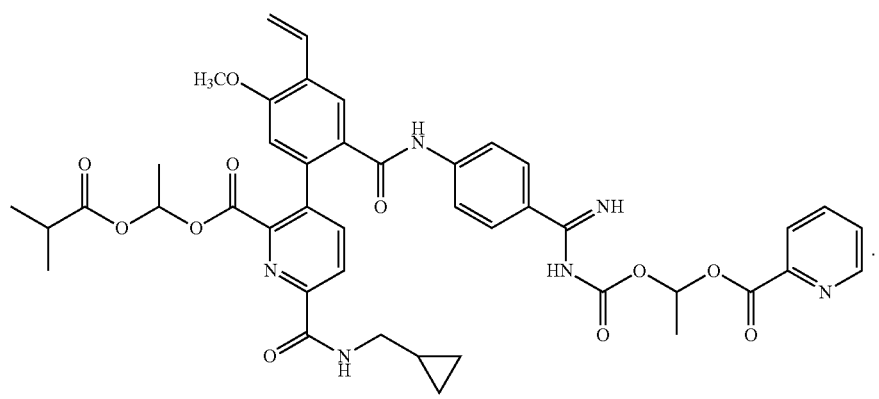 [SMILES: C=Cc1cc(C(=O)Nc2ccc(C(=N)NC(=O)OC(C)OC(=O)c3ccccn3)cc2)c(-c2ccc(C(=O)NCC3CC3)nc2C(=O)OC(C)OC(=O)C(C)C)cc1OC]
13. The compound of claim 12 selected from the following table:
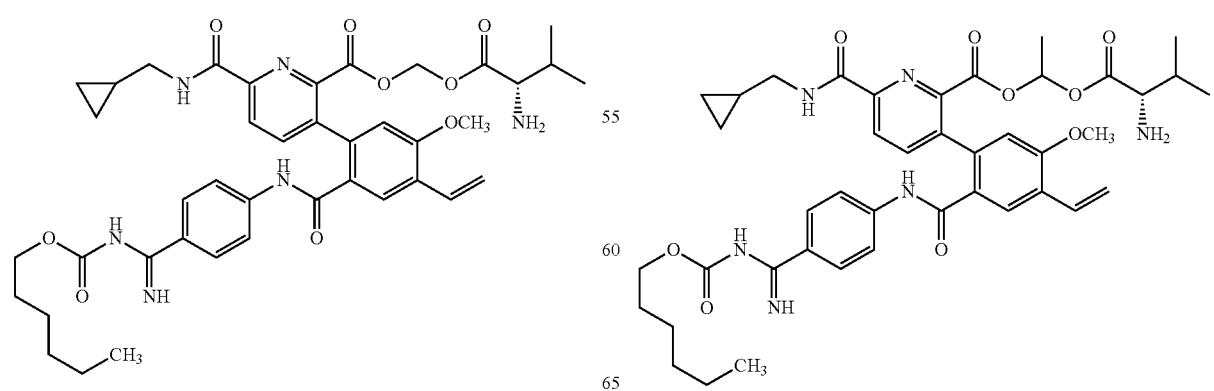

493
-continued
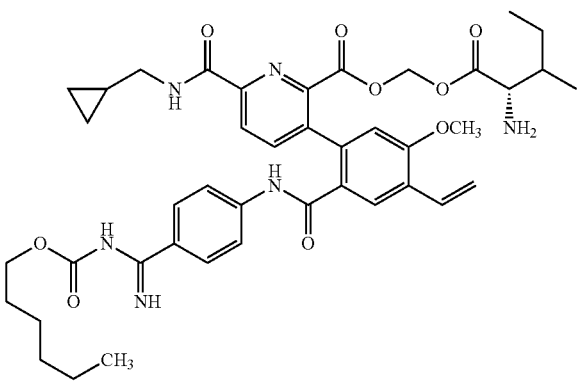 [SMILES: C=Cc1cc(C(=O)Nc2ccc(C(=N)NC(=O)OCCCCCC)cc2)c(-c2ccc(C(=O)NCC3CC3)nc2C(=O)OCOC(=O)[C@@H](N)C(C)CC)cc1OC]
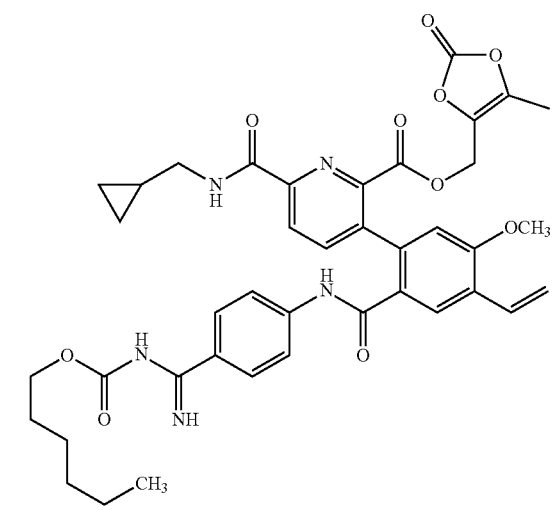 [SMILES: C=Cc1cc(C(=O)Nc2ccc(C(=N)NC(=O)OCCCCCC)cc2)c(-c2ccc(C(=O)NCC3CC3)nc2C(=O)OCc2oc(=O)oc2C)cc1OC]
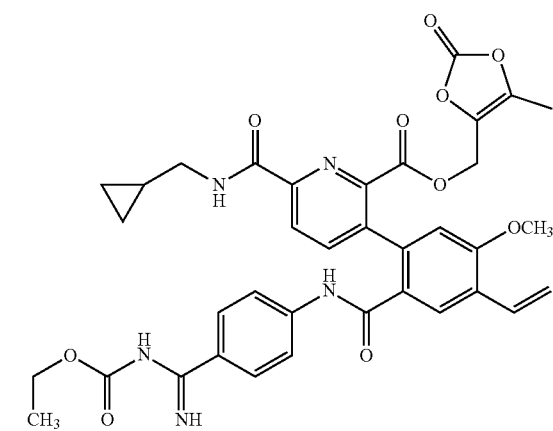 [SMILES: C=Cc1cc(C(=O)Nc2ccc(C(=N)NC(=O)OCC)cc2)c(-c2ccc(C(=O)NCC3CC3)nc2C(=O)OCc2oc(=O)oc2C)cc1OC]
494
-continued
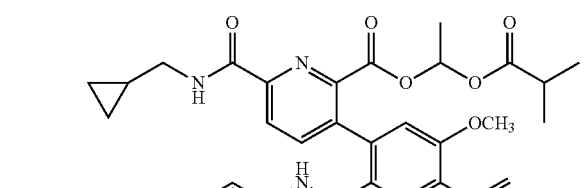
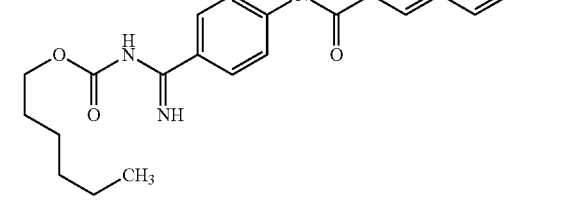
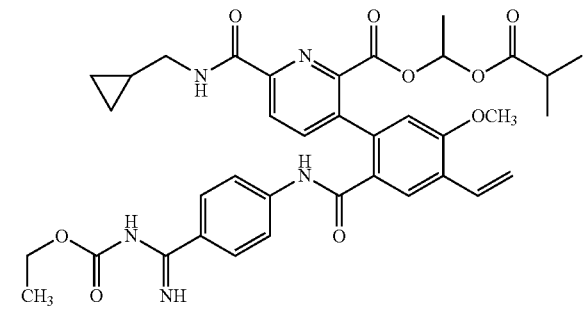 [SMILES: C=Cc1cc(C(=O)Nc2ccc(C(=N)NC(=O)OCC)cc2)c(-c2ccc(C(=O)NCC3CC3)nc2C(=O)OC(C)OC(=O)C(C)C)cc1OC]
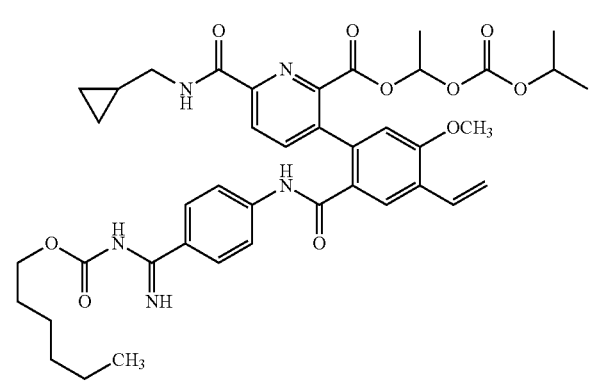 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)OC(C)C)cc1OC]
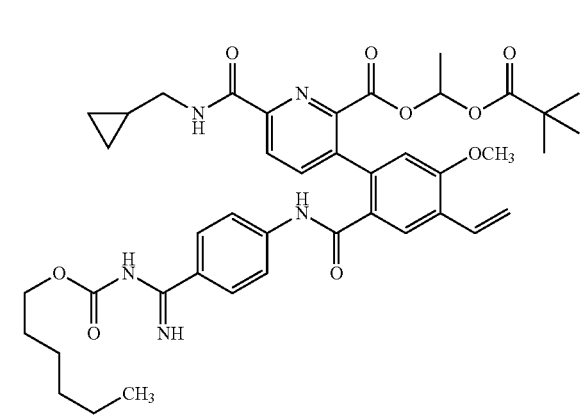 [SMILES: C=Cc1cc(C(=O)Nc2ccc(C(=N)NC(=O)OCCCCCC)cc2)c(-c2ccc(C(=O)NCC3CC3)nc2C(=O)OC(C)OC(=O)C(C)(C)C)cc1OC]

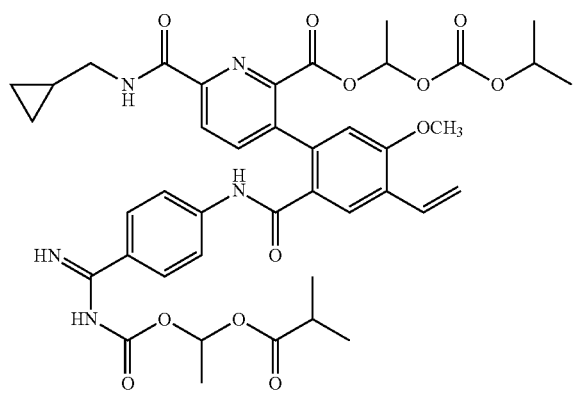 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)OC(C)OC(=O)OC(C)C)cc1OC]

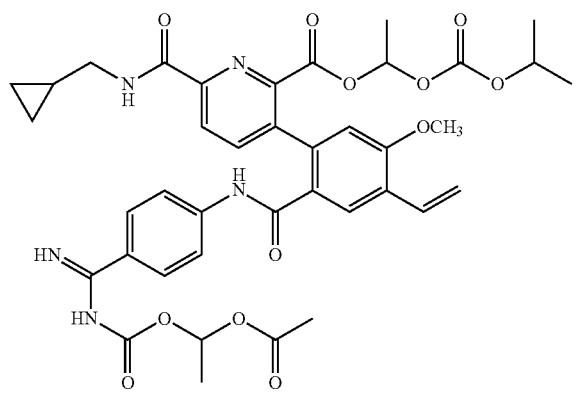 [SMILES: C=Cc1cc(C(=O)Nc2ccc(C(=N)NC(=O)OC(C)OC(C)=O)cc2)c(-c2ccc(C(=O)NCC3CC3)nc2C(=O)OC(C)OC(=O)OC(C)C)cc1OC]

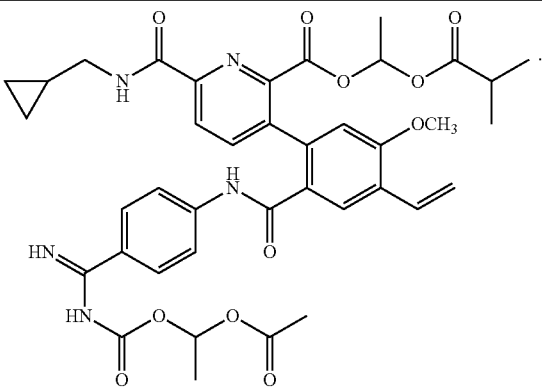

14. A compound having the structure of formula (II) or a pharmaceutically acceptable salt thereof:

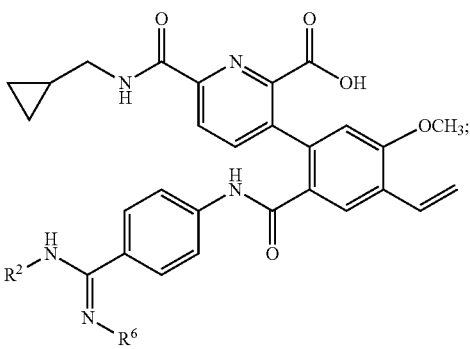

wherein, independently for each occurrence:

$R^2$ represents H, —OH, —C(O)OR$^4$, —C(O)SR$^4$, —C(O)O—[C(R$^c$)(R$^d$)]$_n$—O—C(O)-L-R$^5$, or

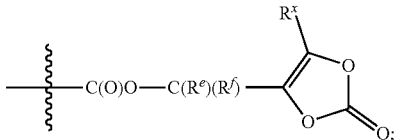

$R^6$ represents H, OH, —C(O)OR$^4$, —C(O)SR$^4$, —C(O)O—[C(R$^c$)(R$^d$)]$_n$—O—C(O)-L-R$^5$, or

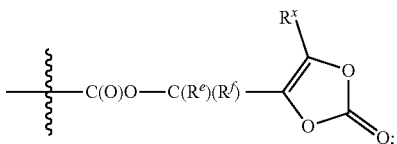

or $R^2$ and $R^6$, taken together with the atoms to which they are attached, form an optionally substituted 1,2,4-oxadiazol-5-one group;

L, independently for each occurrence, is a bond or represents O, S, NH, or N(CH$_3$);

$R^c$, $R^d$, $R^e$, and $R^f$ each independently for each occurrence represent H or (C$_1$-C$_6$)alkyl;

$R^4$, independently for each occurrence, represents (C$_1$-C$_6$)alkyl, cycloalkyl, heterocycloalkyl, aryl, or heteroaryl, optionally substituted with one or more substituents each independently selected from the group consisting of —C(O)OH, —C(O)O((C$_1$-C$_6$)alkyl), (C$_1$-

$C_6$)alkoxy, hydroxyl, oxo, heterocycloalkyl, amino, ($C_1$-$C_6$)alkylamino, di(($C_1$-$C_6$)alkyl)amino, and silyl ether;

$R^5$, independently for each occurrence, represents ($C_1$-$C_6$)alkyl, aryl, or heteroaryl, optionally substituted with one or more substituents each independently selected from the group consisting of amino, heterocycloalkyl, ($C_1$-$C_6$)alkoxy optionally substituted by ($C_1$-$C_6$)alkoxy or a polyether chain; and n represents 1 or 2;

provided that at least one of $R^2$ and $R^6$ is not H; and the compound of formula (II) is not

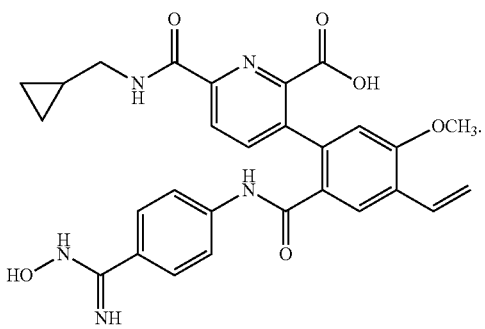 [SMILES: C=Cc1cc(C(=O)Nc2ccc(C(=N)NO)cc2)c(-c2ccc(C(=O)NCC3CC3)nc2C(=O)O)cc1OC]

15. The compound of claim 14, wherein $R^2$ represents —C(O)O$R^4$ or —C(O)O—[C($R^c$)($R^d$)]$_n$—O—C(O)-L-$R^5$, optionally wherein $R^6$ represents H.

16. The compound of claim 15, wherein $R^2$ represents —C(O)O$R^4$; and $R^4$ represents ethyl, isopropyl, hexyl, or $R^4$ represents ($C_1$-$C_6$)alkyl substituted with amino, hydroxy, or ($C_1$-$C_6$)alkoxy.

17. The compound of claim 15, wherein $R^2$ represents —C(O)O—[C($R^c$)($R^d$)]$_n$O—C(O)-L-$R^5$, and n is 1; and at least one of $R^c$ and $R^d$ is H or at least one of $R^c$ and $R^d$ is methyl.

18. The compound of claim 17, wherein L is a bond, and/or wherein $R^5$ represents ($C_1$-$C_6$)alkyl, optionally substituted by amino.

19. The compound of claim 14, wherein $R^2$ and $R^6$, taken together with the atoms to which they are attached, form a 1,2,4-oxadiazol-5-one group.

20. The compound of claim 14 selected from the following table:

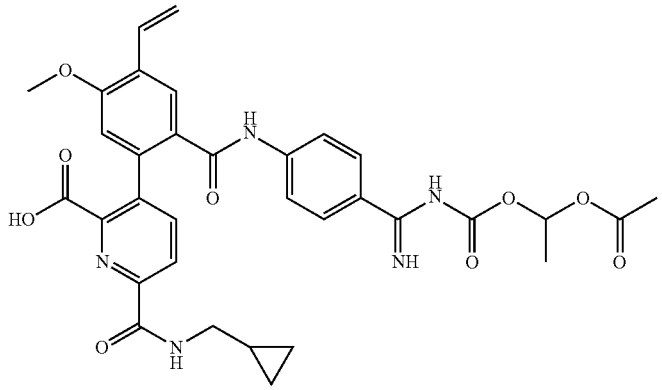 [SMILES: C=Cc1cc(C(=O)Nc2ccc(C(=N)NC(=O)OC(C)OC(C)=O)cc2)c(-c2ccc(C(=O)NCC3CC3)nc2C(=O)O)cc1OC]

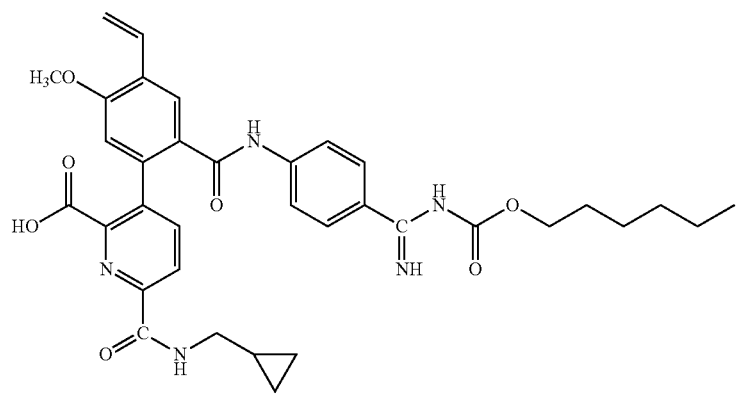 [SMILES: C=Cc1cc(C(=O)Nc2ccc(C(=N)NC(=O)OCCCCCC)cc2)c(-c2ccc(C(=O)NCC3CC3)nc2C(=O)O)cc1OC]

-continued
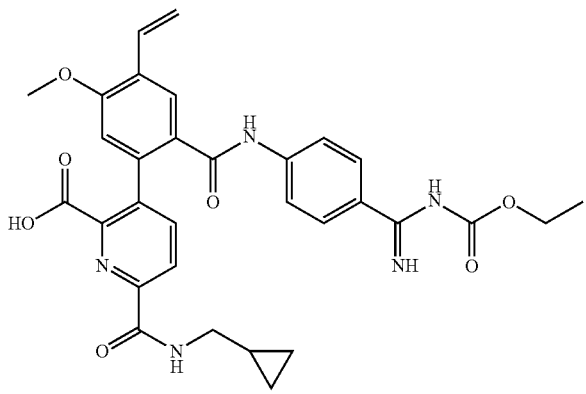 [SMILES: C=Cc1cc(C(=O)Nc2ccc(C(=N)NC(=O)OCC)cc2)c(-c2ccc(C(=O)NCC3CC3)nc2C(=O)O)cc1OC]
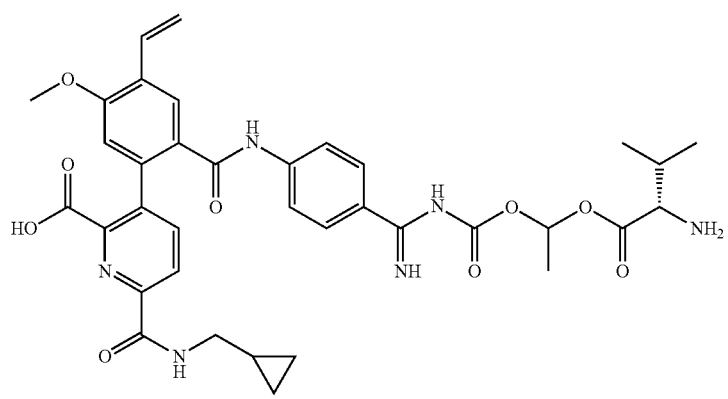 [SMILES: C=Cc1cc(C(=O)Nc2ccc(C(=N)NC(=O)OC(C)OC(=O)[C@@H](N)C(C)C)cc2)c(-c2ccc(C(=O)NCC3CC3)nc2C(=O)O)cc1OC]
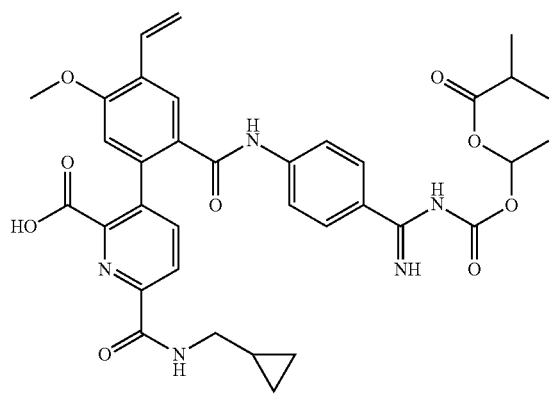 [SMILES: C=Cc1cc(C(=O)Nc2ccc(C(=N)NC(=O)OC(C)OC(=O)C(C)C)cc2)c(-c2ccc(C(=O)NCC3CC3)nc2C(=O)O)cc1OC]
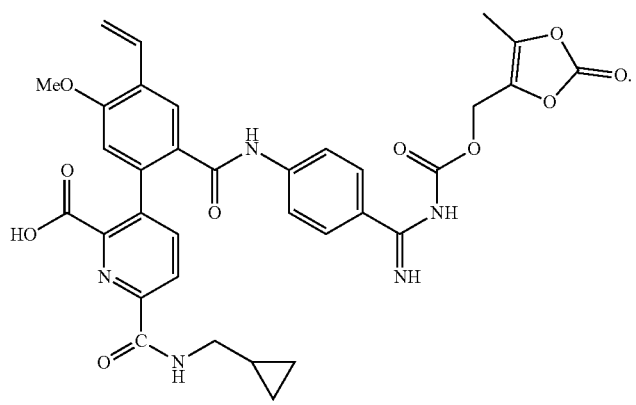 [SMILES: C=Cc1cc(C(=O)Nc2ccc(C(=N)NC(=O)OCc3oc(=O)oc3C)cc2)c(-c2ccc(C(=O)NCC3CC3)nc2C(=O)O)cc1OC]

21. A compound having the structure of formula (III) or a pharmaceutically acceptable salt thereof:

(III)

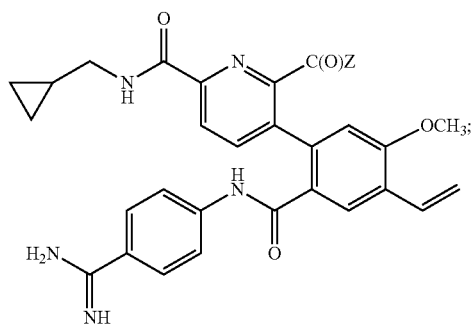

wherein, independently for each occurrence:
Z represents $OR^1$ or NH(OH);
$R^1$ represents

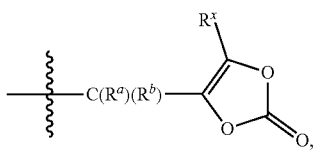

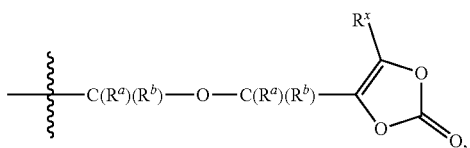

—$C(R^a)(R^b)$—O—C(O)-M-$R^3$, or ($C_2$-$C_6$)alkyl optionally substituted by hydroxyl or heterocycloalkyl;

$R^a$ represents H or ($C_1$-$C_6$)alkyl;
$R^b$ represents H or ($C_1$-$C_6$)alkyl;
$R^x$ represents H or ($C_1$-$C_6$)alkyl;
M is a bond or represents O, S, NH, or N($CH_3$);
$R^3$ represents ($C_1$-$C_6$)alkyl, aralkyl, or cycloalkyl, optionally substituted with one or more substituents each independently selected from the group consisting of amino, hydroxyl, optionally substituted heterocycloalkyl, —C(O)OH, and —C(O)O(($C_1$-$C_6$)alkyl);

provided that the compound of formula (III) is not selected from the following table:

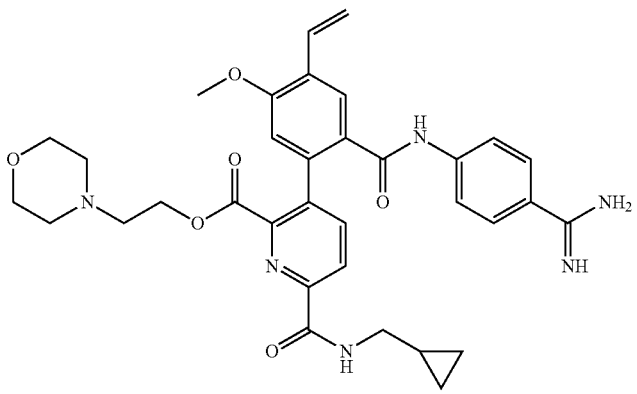 [SMILES: C=Cc1cc(C(=O)Nc2ccc(C(=N)N)cc2)c(-c2ccc(C(=O)NCC3CC3)nc2C(=O)OCCN2CCOCC2)cc1OC]

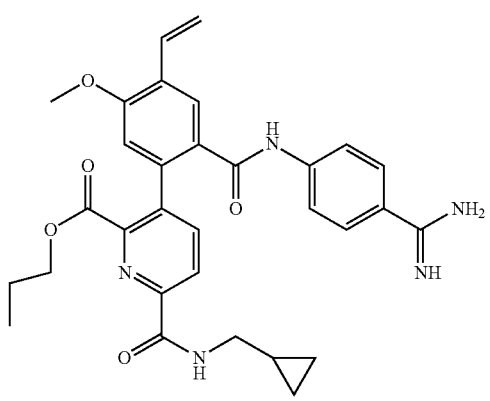 [SMILES: C=Cc1cc(C(=O)Nc2ccc(C(=N)N)cc2)c(-c2ccc(C(=O)NCC3CC3)nc2C(=O)OCCC)cc1OC]

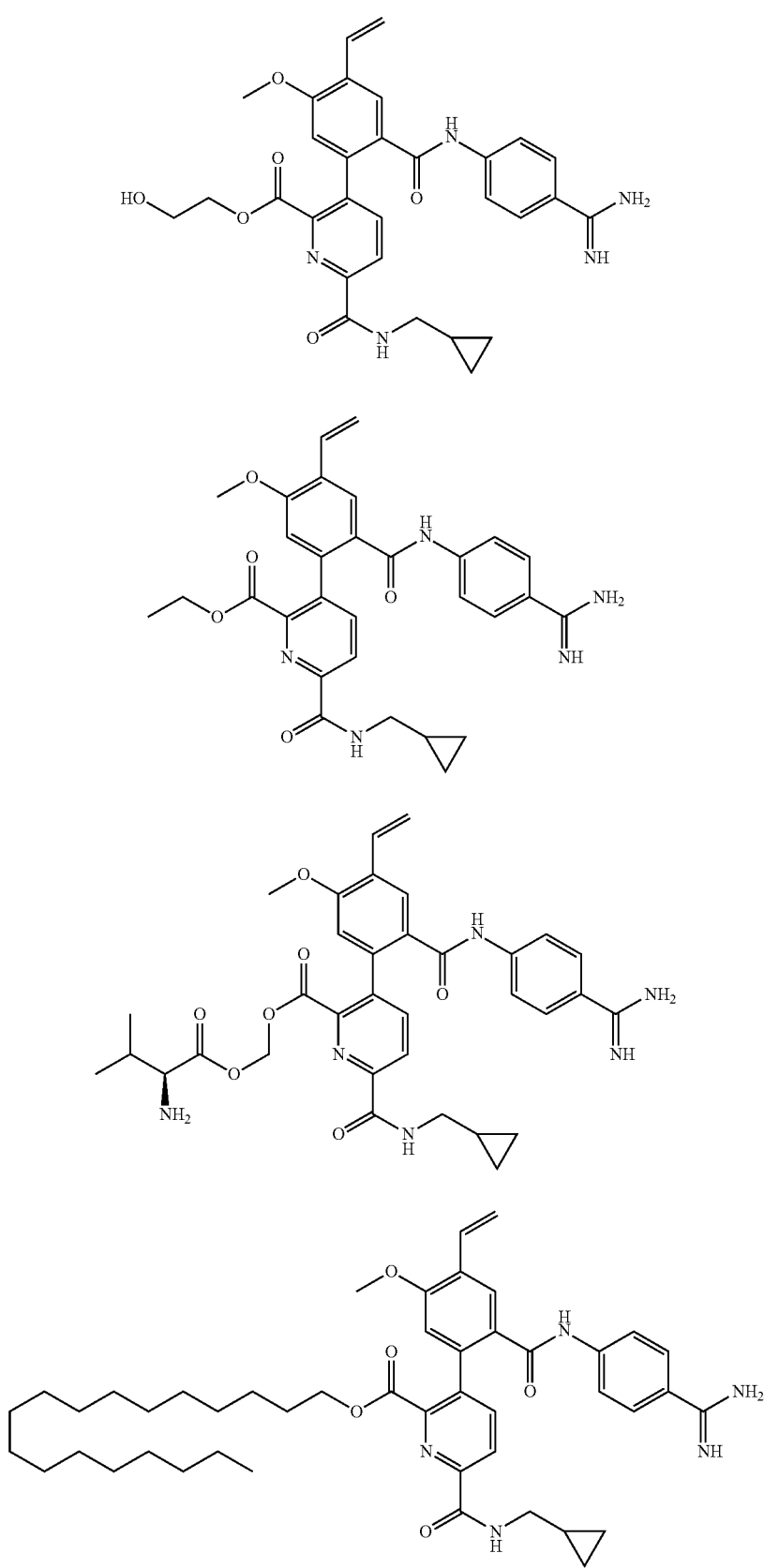

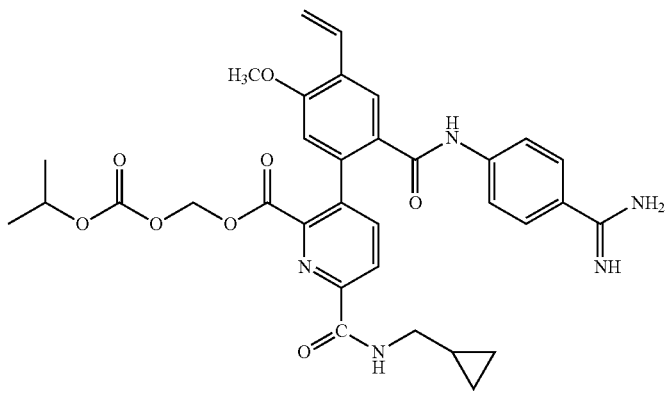 [SMILES: C=Cc1cc(C(=O)Nc2ccc(C(=N)N)cc2)c(-c2ccc(C(=O)NCC3CC3)nc2C(=O)OCOC(=O)OC(C)C)cc1OC]
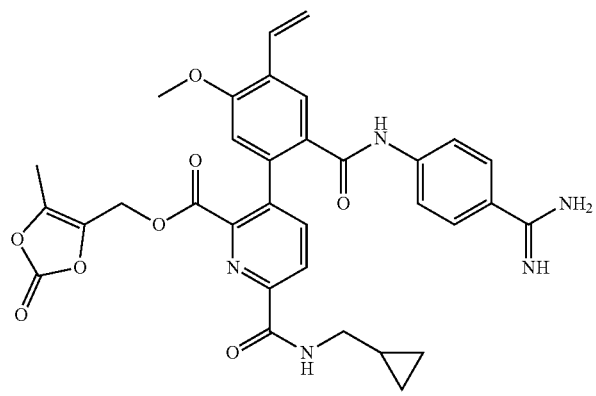 [SMILES: C=Cc1cc(C(=O)Nc2ccc(C(=N)N)cc2)c(-c2ccc(C(=O)NCC3CC3)nc2C(=O)OCc2oc(=O)oc2C)cc1OC]
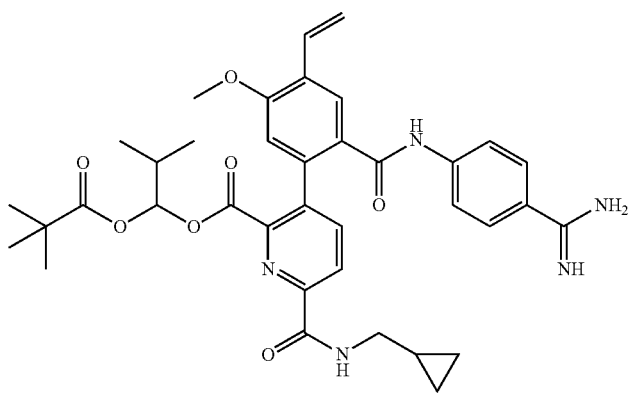 [SMILES: C=Cc1cc(C(=O)Nc2ccc(C(=N)N)cc2)c(-c2ccc(C(=O)NCC3CC3)nc2C(=O)OC(OC(=O)C(C)(C)C)C(C)C)cc1OC]
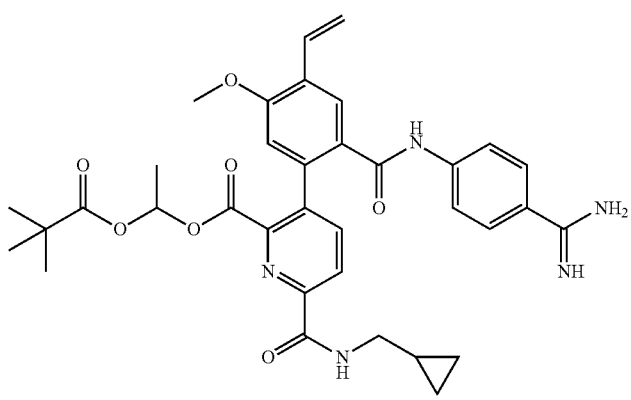 [SMILES: C=Cc1cc(C(=O)Nc2ccc(C(=N)N)cc2)c(-c2ccc(C(=O)NCC3CC3)nc2C(=O)OC(C)OC(=O)C(C)(C)C)cc1OC]

-continued

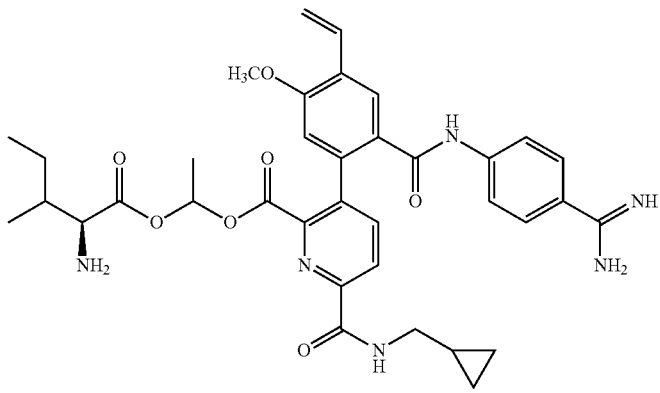 [SMILES: C=Cc1cc(C(=O)Nc2ccc(C(=N)N)cc2)c(-c2ccc(C(=O)NCC3CC3)nc2C(=O)OC(C)OC(=O)[C@@H](N)C(C)CC)cc1OC]

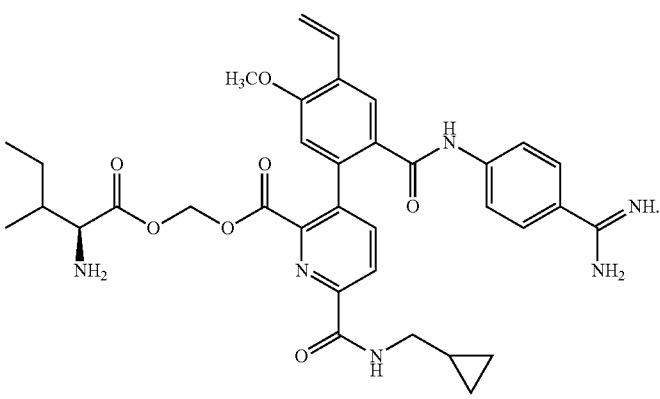 [SMILES: C=Cc1cc(C(=O)Nc2ccc(C(=N)N)cc2)c(-c2ccc(C(=O)NCC3CC3)nc2C(=O)OCOC(=O)[C@@H](N)C(C)CC)cc1OC]

22. The compound of claim 21, wherein $R^1$ represents

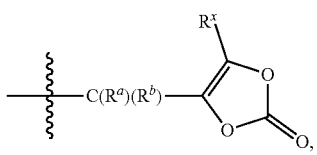

or, —C($R^a$)($R^b$)—O—C(O)-M-$R^3$.

23. The compound of claim 21, wherein $R^a$ and $R^b$ each independently represent H or methyl.

24. The compound of claim 21, wherein $R^1$ represents —C($R^a$)($R^b$)—O—C(O)-M-$R^3$, and M is a bond or O.

25. The compound of claim 24, wherein $R^3$ represents ($C_1$-$C_6$)alkyl, ($C_3$-$C_5$) alkyl, cycloalkyl, aralkyl optionally substituted with —$NH_2$, ($C_1$-$C_6$)alkyl substituted with —$NH_2$ or —OH, or ($C_3$-$C_5$)alkyl substituted with —$NH_2$ or —OH.

26. The compound of claim 21, wherein $R^1$ represents

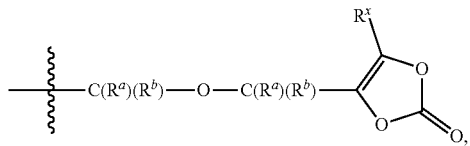

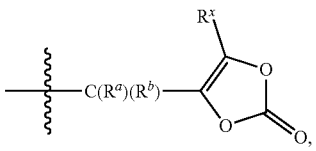

and $R^x$ represents H or methyl, or wherein $R^1$ represents ($C_3$-$C_6$)alkyl optionally substituted with hydroxyl.

27. The compound of claim 21 selected from the following table:

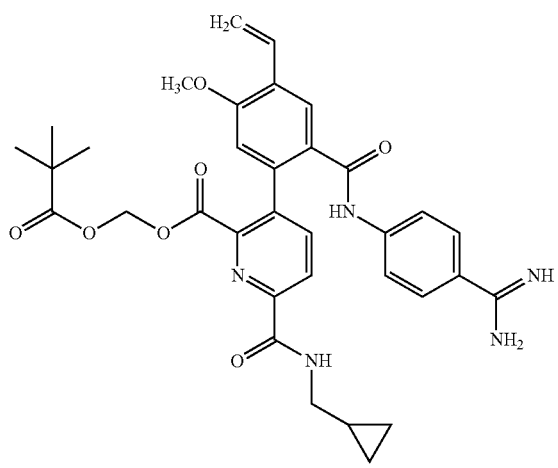 [SMILES: C=Cc1cc(C(=O)Nc2ccc(C(=N)N)cc2)c(-c2ccc(C(=O)NCC3CC3)nc2C(=O)OCOC(=O)C(C)(C)C)cc1OC]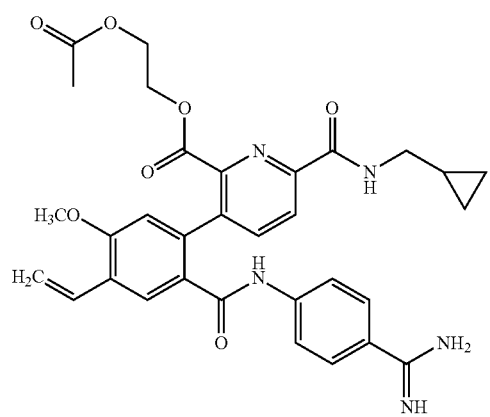 [SMILES: C=Cc1cc(C(=O)Nc2ccc(C(=N)N)cc2)c(-c2ccc(C(=O)NCC3CC3)nc2C(=O)OCCOC(C)=O)cc1OC]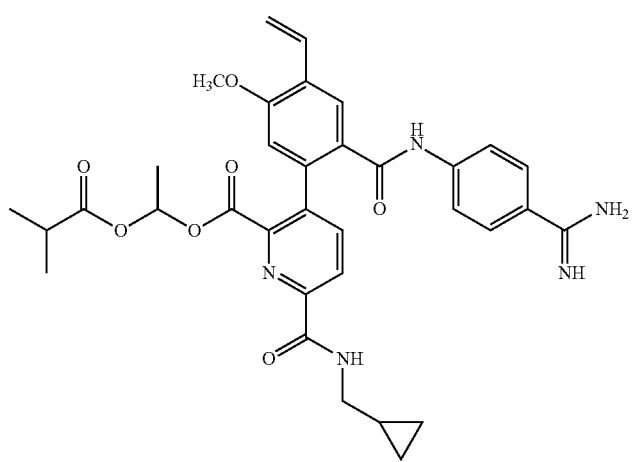 [SMILES: C=Cc1cc(C(=O)Nc2ccc(C(=N)N)cc2)c(-c2ccc(C(=O)NCC3CC3)nc2C(=O)OC(C)OC(=O)C(C)C)cc1OC]

-continued
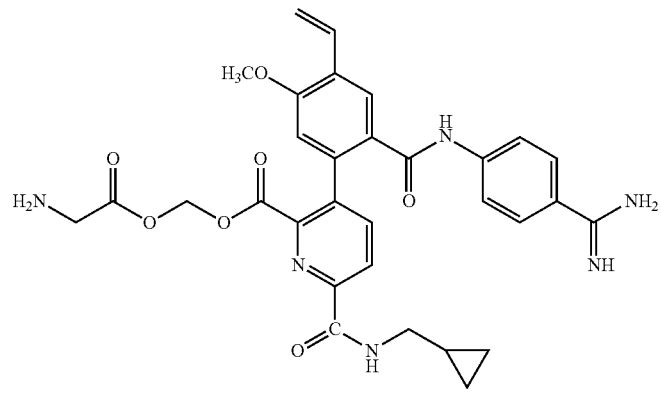 [SMILES: C=Cc1cc(C(=O)Nc2ccc(C(=N)N)cc2)c(-c2ccc(C(=O)NCC3CC3)nc2C(=O)OCOC(=O)CN)cc1OC]
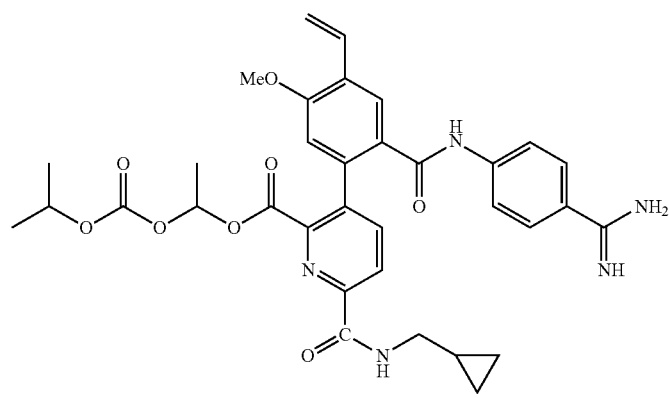 [SMILES: C=Cc1cc(C(=O)Nc2ccc(C(=N)N)cc2)c(-c2ccc(C(=O)NCC3CC3)nc2C(=O)OC(C)OC(=O)OC(C)C)cc1OC]
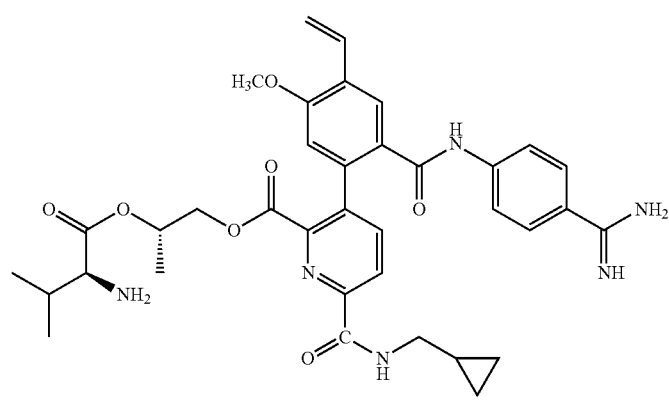 [SMILES: C=Cc1cc(C(=O)Nc2ccc(C(=N)N)cc2)c(-c2ccc(C(=O)NCC3CC3)nc2C(=O)OC[C@H](C)OC(=O)[C@@H](N)C(C)C)cc1OC]
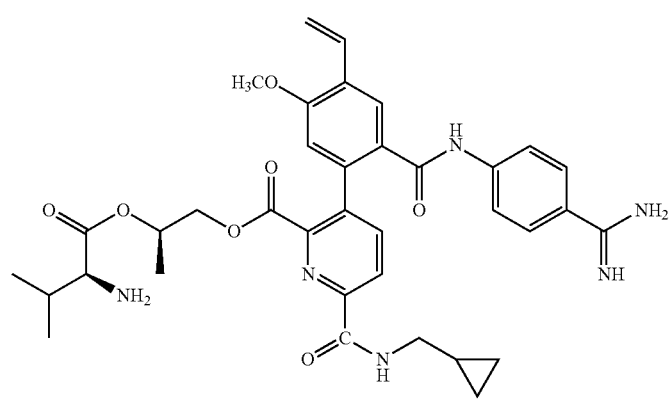 [SMILES: C=Cc1cc(C(=O)Nc2ccc(C(=N)N)cc2)c(-c2ccc(C(=O)NCC3CC3)nc2C(=O)OC[C@@H](C)OC(=O)[C@@H](N)C(C)C)cc1OC]

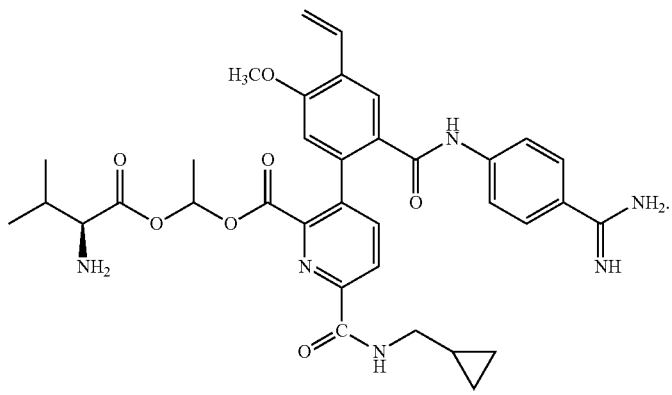 [SMILES: C=Cc1cc(C(=O)Nc2ccc(C(=N)N)cc2)c(-c2ccc(C(=O)NCC3CC3)nc2C(=O)OC(C)OC(=O)[C@@H](N)C(C)C)cc1OC]

28. A method of treating acquired angioedema or hereditary angioedema, comprising administering to a subject in need thereof a therapeutically effective amount of a compound of claim 1.

29. A method of treating a disease or condition associated with aberrant activity of kallikrein, comprising administering to a subject in need thereof a therapeutically effective amount of a compound of claim 1.

30. A method of inhibiting blood coagulation, comprising administering to a subject in need thereof an effective amount of a compound of claim 1.

* * * * *